US008431565B2

(12) United States Patent
Beckett et al.

(10) Patent No.: US 8,431,565 B2
(45) Date of Patent: *Apr. 30, 2013

(54) SUBSTITUTED IMIDAZOHETEROCYCLES

(75) Inventors: R. Paul Beckett, Yorktown Heights, NY (US); Richard Foster, Bude (GB); Christelle Henault, Bude (GB); Janet L. Ralbovsky, Shelton, CT (US); Carla M. Gauss, White Plains, NY (US); Gary R. Gustafson, Ridgefield, CT (US); Robert Zhiyong Luo, New City, NY (US); Ann-Marie Campbell, Monroe, CT (US); Tatiana E. Shelekhin, Ridgefield, CT (US); Mary-Margaret E. Zablocki, Fairfield, CT (US)

(73) Assignee: Cara Therapeutics, Inc., Shelton, CT (US)

( * ) Notice: Subject to any disclaimer, the term of this patent is extended or adjusted under 35 U.S.C. 154(b) by 943 days.

This patent is subject to a terminal disclaimer.

(21) Appl. No.: 12/337,683

(22) Filed: Dec. 18, 2008

(65) Prior Publication Data

US 2009/0149450 A1    Jun. 11, 2009

Related U.S. Application Data

(63) Continuation-in-part of application No. 12/142,846, filed on Jun. 20, 2008, now Pat. No. 7,517, 874.

(60) Provisional application No. 60/936,754, filed on Jun. 21, 2007, provisional application No. 60/994,422, filed on Sep. 19, 2007, provisional application No. 61/008,395, filed on Dec. 19, 2007.

(51) Int. Cl.
*A61K 31/519* (2006.01)
*C07D 487/04* (2006.01)
*A61P 25/02* (2006.01)

(52) U.S. Cl.
USPC ...... 514/211.08; 514/249; 514/221; 544/230; 544/350; 540/543; 540/568

(58) Field of Classification Search .................. 540/573, 540/268; 514/221, 211.08
See application file for complete search history.

(56) References Cited

U.S. PATENT DOCUMENTS

| 5,753,648 | A | 5/1998 | Albright et al. |
| 6,936,619 | B2 | 8/2005 | Blagg et al. |
| 6,960,595 | B2 | 11/2005 | Pinto et al. |
| 2005/0124607 | A1 | 6/2005 | Chin et al. |
| 2006/0166973 | A1 | 7/2006 | McKenna et al. |
| 2007/0004736 | A1 | 1/2007 | Kubo et al. |
| 2007/0043057 | A1 | 2/2007 | Matteucci et al. |
| 2007/0093501 | A1 | 4/2007 | Kubo et al. |
| 2007/0191337 | A1 | 8/2007 | Ivashchenko et al. |
| 2007/0219181 | A1 | 9/2007 | Kimura et al. |

FOREIGN PATENT DOCUMENTS

| FR | 2617478 A1 | 1/1989 |
| JP | 07101959 A | 4/1995 |
| JP | 08325234 A | 12/1996 |
| RU | 2281947 C1 | 5/2005 |
| WO | 02053558 A1 | 7/2002 |
| WO | 03/068776 A1 | 8/2003 |
| WO | 2006/027226 A1 | 3/2006 |
| WO | 2006/087147 A2 | 8/2006 |
| WO | 2007/117180 A1 | 10/2007 |
| WO | 2007/136603 A2 | 11/2007 |
| WO | 2007/139992 A2 | 12/2007 |
| WO | 2008/017932 A2 | 2/2008 |
| WO | WO 2008157751 | * 12/2008 |

OTHER PUBLICATIONS

Vippagunta, S.R., (Adv. Drug. Delivery Rev., 2001, 48, pp. 3-26).*
Vippagunta et al. (Adv. Drug Delivery Reviews, 2001, v.43. pp. 3-26).
T. G. Mural Dhar, "Synthesis and SAR of p38a MAP kinase inhibitors based on heterobicyclic scaffolds", Bioorganic & Medicinal Chemistry Letters (journal); Sep. 15, 2007; pp. 5019-5024, vol. 17, issue 18, Elsevier Science Ltd., England.
Masashige Yamauchi and Masaichiro Masui; "Synthesis of 6,7,8,9-Tetrahydro-5H-imidazo [1,5-a] [1,4] Diazepines"; Chemistry and Industry (journal), 1976, pp. 31-32; Faculty of Pharmaceutical Sciences, Osaka University, Yamada-Kami Suita-Shi Osaka, Japan.
Masashige Yamauchi and Masaichiro Masui; "Reactivity of 2,4 (5)-Dialkylimidazoles. Synthesis of 6,7,8,9-Tetrahydro-5H-imidazo [1,5-a] [1,4] diazepine Derivatives", vol. 24, No. 7, pp. 1480-1484, Chemical & pharmaceutical bulletin (journal), Jul. 25, 1976; Faculty of Pharmaceutical Sciences, Osaka University, Osaka Japan.
Ariamala Gopalsamy* and Mengxiao Shi; "Novel Synthetic Approach to 6, 7-Dihydro-5H-imidazo[1,5-a]-pyrazin-8-ones", Organic Letters (journal) 2003, vol. 5, No. 21, pp. 3907-3909; Chemical and Screening Sciences, Wyeth Research, Pearl River, New York 10965.
Alexey P. Ilyin, Sergey E. Tkachenko, et al; "Synthesis of Annelated Azaheterocycles Containing a 5-Carbamoylpyrazin-3-one Fragment by a Modification of the Four-Component Ugi Reaction", Eur. Journal Org. Chem. 2005, pp. 4670-4679; Wiley-VCH Verlag GmbH & Co. KGaA, Weinheim, Germany.

* cited by examiner

*Primary Examiner* — Susanna Moore
(74) *Attorney, Agent, or Firm* — Algis Anilionis; F. Chau & Associates LLC

(57) ABSTRACT

The present invention provides substituted imidazoheterocyclic compounds having the structure of formula I

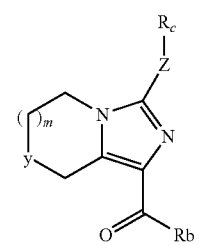

(I)

Also provided are pharmaceutically acceptable salts, acid salts, hydrates, solvates and stereoisomers of the compounds of formula I. The compounds are useful as modulators of cannabinoid receptors and for the prophylaxis and treatment of cannabinoid receptor-associated diseases and conditions, such as pain, inflammation and pruritis.

22 Claims, 3 Drawing Sheets

SUBSTITUTED IMIDAZOHETEROCYCLES

RELATED APPLICATIONS

This application claims the benefit of U.S. applications with Ser. Nos. 60/936,754, filed Jun. 21, 2007; 60/994,422, filed Sep. 19, 2007; 61/008,395, filed Dec. 19, 2007; and 12/142,846, now U.S. Pat. No. 7,517,874, as a continuation-in-part (CIP), filed Jun. 20, 2008, the specifications of which are hereby incorporated by reference in their entireties.

FIELD OF THE INVENTION

The invention relates to substituted imidazoheterocycles, and more particularly to substituted tetrahydroimidazo[1,5-α]pyrazine and substituted tetrahydro-5H-imidazo[1,5-α][1,4]diazepine compounds and their use in the prophylaxis and treatment of cannabinoid receptor-associated diseases, disorders and conditions, such as pain, inflammation and pruritis.

BACKGROUND OF THE INVENTION

Classical cannabinoids such as the marijuana-derived compound $\Delta^9$-tetra-hydrocannabinol, ($\Delta^9$-THC) exert their pharmacological effects through interaction with specific members of the G-protein coupled receptor (GPCR) family. To date, two cannabinoid receptors have been cloned and characterized: CB1, a receptor found in the mammalian brain and to a lesser extent in peripheral tissues; and CB2, a receptor found primarily in the peripheral tissues, particularly in cells of the immune system. Several endogenous ligands for these cannabinoid receptors, known as endocannabinoids, have been identified. For a review see Hanus, L. O., *Discovery and isolation of anandamide and other endocannabinoids*, Chem. Biodivers. (2007) 8:1828-41.

Compounds that are modulators of one or both of the cannabinoid receptors have been shown to produce a variety of pharmacological effects that may be of therapeutic benefit in humans (see, for example, Mackie, K., *Cannabinoid receptors as therapeutic targets*, Ann. Rev. Pharmacol. Toxicol. (2006) 46: 101-122; Pertwee, R. G., *The therapeutic potential of drugs that target cannabinoid receptors or modulate the tissue levels or actions of endocannabinoids*, AAPS J. (2005) 7:E625-654). The cannabinoid receptor modulator can be an agonist, an inverse agonist or a neutral antagonist, and may interact at the same (orthosteric) site as the endogenous ligand, or at a different (allosteric) site.

Activation of the CB1 receptor in the brain is believed to mediate undesirable psychotropic effects associated with $\Delta^9$-THC and other centrally acting cannabinoid ligands. As a result, there has been considerable interest in developing compounds that possess high affinity and selectivity for the CB2 receptor (see for example, Raitio, K. H. et al., *Targeting the Cannabinoid CB2 Receptor: Mutations, Modelling and Development of selective CB2 ligands*, Curr. Med. Chem. (2005) 12: 1217-37). CB2 receptor agonists have shown efficacy in preclinical models of neuropathic and inflammatory pain and may also find application in cancer, multiple sclerosis, osteoporosis, Alzheimer's disease, liver disease and diabetes (Mackie, K.; Ross R A; CB2 *cannabinoid receptors: new vistas*, Br. J. Pharmacol. (2008) 153: 177-78 and references cited therein). There is an ongoing need to identify new CB2 ligands that exhibit greater receptor selectivity, improved drug-like properties and, for some indications, restriction to the periphery with low or minimal effects on the central nervous system (CNS).

SUMMARY OF THE INVENTION

The present invention provides compounds having the structure of formula I and pharmaceutically acceptable salts, acid salts, hydrates, solvates and stereoisomers of the compounds of formula I:

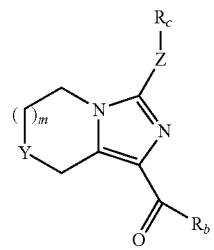

Formula I

Also provided are mixtures of stereoisomers of compounds of formula I.

In the compounds of formula I, Y is $NR_a$ or $N^+R_1R_2X^-$, wherein $X^-$ is an anionic counterion; m is an integer equal to 1, 2 or 3; and Z is a bond or a bivalent linking group chosen from —$(CH_2)_p$—, —CH=CH—, —C≡C—, —CONH— and —CO—; wherein p is an integer from one to six.

The radical $R_a$ is chosen from hydrogen, alkyl having from one to eight carbon atoms, alkenyl and alkynyl each having from three to six carbon atoms; cycloalkyl or cycloalkenyl each having from three to eight ring carbon atoms; aryl; —$SO_2R_3$, —$COR_3$, —$CONR_3R_4$, —$CSNR_3R_4$, —$COOR_3$, and —$(CH_2)_q$-heterocyclyl; wherein q is zero or an integer from one to four. The alkyl, cycloalkyl, cycloalkenyl, aryl and heterocyclyl moieties of $R_a$ are each optionally substituted with from one to four groups independently chosen from halo, hydroxyl, oxo, amino, nitro, cyano, carboxyl, —$COR_3$, trifluoromethoxy, trifluoromethyl, alkyl having from one to six carbon atoms, alkoxy having from one to four carbon atoms, cycloalkyl having three to eight ring carbon atoms and phenyl.

The radical $R_b$ is bonded through the carbonyl of formula I and is chosen from alkyl having from one to eight carbon atoms, alkenyl having from two to eight carbon atoms, aryl, —$NR_5R_6$,

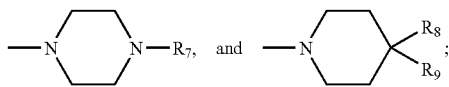

wherein the alkyl, alkenyl and aryl of $R_b$ are each optionally substituted with one to three substituents independently chosen from alkyl having from one to four carbon atoms, alkenyl having from two to four carbon atoms, cycloalkyl having from three to six carbon atoms, alkoxy having from one to four carbon atoms, aryl, and four-, five-, six-, seven-, eight- and nine-membered heterocyclyl, halo, hydroxyl, amino, cyano and nitro.

The radical $R_c$ is chosen from halo, alkyl having from one to six carbon atoms, alkenyl having from two to six carbon atoms, alkynyl having from two to six carbon atoms, cycloalkyl having from three to ten carbon atoms, cycloalkenyl having from three to eight carbon atoms, alkoxy having from one to four carbon atoms, aryl, and four-, five-, six-, seven-, eight- and nine-membered heterocyclyl; wherein the alkenyl, alkynyl, cycloalkyl, cycloalkenyl, aryl, four-, five-, six-, seven-, eight- and nine-membered heterocyclyl of $R_c$, are optionally substituted with one to five substituents independently chosen from alkyl, alkoxy, haloalkyl, and haloalkoxy each having from one to four carbon atoms, cycloalkyl having from three to six carbon atoms, cycloalkenyl having from four to eight carbon atoms, halo, hydroxyl, amino, (A)(A')(A")(A''')aryl, (A)(A')(A")(A''')heterocyclyl, —$NR_{14}R_{15}$, —$(CH_2)_pNR_{14}R_{15}$, cyano, nitro, oxo, —$COOR_{14}$, —$SOR_{16}$, —$SO_2R_{16}$, —$SO_2NR_{14}R_{15}$, —$NR_{15}SO_2R_{16}$, —$COR_{14}$, —$CONR_{14}R_{15}$ and —$NR_{15}COR_{16}$; wherein (A), (A'), (A") and (A''') are each an independently chosen from hydrogen, halo and alkyl having from one to four carbon atoms; and each heterocyclyl of the (A)(A')(A")(A''')heterocyclyl is independently chosen from four-, five-, six-, seven-, eight- and nine-membered heterocyclyl.

The substituents, $R_1$ and $R_2$ are each independently an alkyl radical having from one to four carbon atoms.

The substituents, $R_3$ and $R_4$, when either or both are present, are each independently chosen from hydrogen, alkyl having from one to six carbon atoms, alkenyl having from three to six carbon atoms, alkynyl having from three to six carbon atoms, cycloalkyl having from three to eight ring carbon atoms, cycloalkenyl having from three to eight ring carbon atoms, aryl and four-, five-, six-, seven-, eight- and nine-membered heterocyclyl. The alkyl, alkenyl, alkynyl and cycloalkyl of $R_3$ and $R_4$ are each optionally substituted with one to three substituents independently chosen from alkyl having from one to six carbon atoms, haloalkyl having from one to six carbon atoms, cycloalkyl having from three to eight ring carbon atoms, alkoxy having from one to four carbon atoms, acyl having from one to four carbon atoms, aryl, five-, six-, seven-, eight-, nine- and ten-membered heterocyclyl, amino, nitro, cyano, hydroxyl, carboxyl, oxo, and halo. Alternatively, $R_3$ and $R_4$ taken together with the nitrogen atom to which they are bonded form a four-membered, five-membered, six-membered, seven-membered or eight-membered heterocyclyl moiety.

The substituent, $R_5$ is chosen from hydrogen, alkyl chain of one to eight carbon atoms and haloalkyl having from one to four carbon atoms; wherein the alkyl and haloalkyl are optionally substituted with from one to four substituents independently chosen from alkoxy having from one to four carbon atoms, hydroxyl, amino, oxo and cyano.

The substituent, $R_6$ is chosen from the following: hydrogen, —$CR_{10}R_{11}R_{12}$, —$CR_{10}R_{11}COR_{13}$, alkyl having from one to eight carbon atoms, cycloalkyl having from three to ten ring carbon atoms, aryl, haloaryl and $(CH_2)_q$-linked heterocyclyl having a four-, five-, six-, seven-, eight-, nine- or ten-membered moiety; wherein the alkyl, cycloalkyl, aryl, and heterocyclyl are optionally substituted with from one to five substituents independently chosen from alkyl having one to four carbon atoms, aryl, halo, hydroxyl, amino, -cyano, nitro, alkoxy having one to four carbon atoms, hydroxyalkyl having one to four carbon atoms, —$COR_{13}$, —$CONHCH_3$, —$SO_2R_{11}$, —$SO_2NR_8R_9$, and five-, six-, seven-, eight-, nine- and ten-membered heterocyclyl.

Alternatively, $R_5$ and $R_6$ taken together with the nitrogen atom to which they are bonded can form a five-, six-, seven- or eight-, nine- or ten-membered heterocyclyl, which is optionally substituted with one to two substituents independently chosen from alkyl having from one to four carbon atoms, haloalkyl having from one to four carbon atoms, halo, oxo, —$CONR_1R_2$ and five-, six-, seven- or eight-, nine- or ten-membered heterocyclyl.

The substituent, $R_7$ is chosen from —$COR_3$, —$COOR_3$, —$SO_2R_3$, and five-, six- and seven-membered heterocyclyl.

The substituents, $R_8$ and $R_9$ are independently chosen from hydrogen; alkyl, hydroxyalkyl, alkylaminoalkyl, alkoxyalkyl and cyanoalkyl, each having from one to six carbon atoms; haloalkyl having from one to four carbon atoms, aminoacyl having from one to four carbon atoms, alkyl-$NHSO_2CH_3$ having from one to six carbon atoms, alkoxy having from one to four carbon atoms, alkenyl chain having two to four carbon atoms, cycloalkyl having from three to six ring carbon atoms, aryl; —$(CH_2)_q$-linked five-, six-, seven-, eight- nine- and ten-membered (B)(B')heterocyclyl, halo, hydroxyl, alkoxy or alkyl having from one to four carbon atoms, amido, amino, cyano or nitro. The substituents (B) and (B') are each independently hydrogen, hydroxyl, alkyl or hydroxyalkyl having from one to four carbon atoms.

In the first of two alternatives, $R_8$ and $R_9$, taken together with the nitrogen atom to which they are bonded, form a four-, five-, six, seven-, eight-, nine or ten-membered heterocyclyl moiety, or an eight-, nine- or ten-membered spirobicyclic heterocyclyl moiety, which heterocyclyl moiety is optionally substituted with from one to three substituents independently chosen from alkyl or haloalkyl having from one to four carbon atoms, halo, oxo, —$(CH_2)_q$—OH, —$(CH_2)_q$—CN, $COOR_1$, $SO_2CH_3$, acyl having from one to four carbon atoms and aryl. In the second of two alternatives, $R_8$ and $R_9$, taken together with the carbon atom to which they are bonded, form a carbocycle, which carbocycle is optionally substituted with from one to three substituents independently chosen from alkyl having from one to four carbon atoms, halo, hydroxyl, oxo and aryl.

The substituent, $R_{10}$ is chosen from hydrogen and alkyl having from one to eight carbon atoms.

The substituent, $R_{11}$ is chosen from: hydrogen, alkyl having from one to eight carbon atoms, alkenyl having from two to six carbon atoms, an alkynyl chain having two to four carbon atoms, cycloalkyl having from three to ten ring carbon atoms, aryl, five-, six-, seven- and eight-membered monocyclic heterocyclyl and nine-membered and ten-membered bicyclic heterocyclyl; wherein the alkyl, alkenyl, alkynyl, cycloalkyl, aryl and heterocyclyl of $R_{11}$ are optionally substituted with from one to three substituents independently chosen from alkyl having from one to four carbon atoms, cycloalkyl having from three to six carbon atoms, aryl, 5-, 6-, 7- and 8-membered monocyclic heterocyclyl, 9- and 10-membered bicyclic heterocyclyl, halo, hydroxyl, alkoxy having from one to four carbon atoms, amino, guanidino, cyano, amino, oxo, —$COOR_{10}$, —$CONR_8R_9$, —$SO_2NR_8R_9$, —$SR_{10}$, —$SOR_1$ and —$SO_2R_1$.

The substituent, $R_{12}$ is chosen from hydrogen, alkyl having from one to eight carbon atoms, and hydroxyalkyl having from one to six carbon atoms.

The substituent, $R_{13}$ is chosen from —$OR_{10}$ and —$NR_8R_9$.

The substituents, $R_{14}$ and $R_{15}$ are each independently hydrogen, alkyl having from one to four carbon atoms or aryl; and $R_{16}$ is $C_1$-$C_4$ alkyl or aryl.

Alternatively, substituents, $R_{14}$ and $R_{15}$ taken together with the nitrogen atom to which they are bonded form a five-, six-, seven-, eight-, nine- and ten-membered heterocyclyl moiety.

In formula I, when $R_c$ is heterocyclyl, then a ring carbon atom of the heterocyclyl moiety is directly bonded to Z, or in the case where Z is a bond, to the imidazolyl carbon atom to which Z is bonded.

The many embodiments of the compounds of formula I of the invention exhibit useful properties related to their activities as ligands of cannabinoid receptors and the biological consequences of binding to these receptors.

In particular embodiments of the invention, the compounds of formula I bind one or more cannabinoid receptors, such as without limitation, CB1 and CB2. Such compounds include those that can be classified as agonists, partial agonists or inverse agonists for a particular cannabinoid receptor and in certain embodiments these compounds exhibit selectivity for the CB2 receptor over the CB1 receptor. In one aspect, the cannabinoid receptor is a mammalian cannabinoid receptor, such as a human cannabinoid receptor, which can be, including but not limited to, a human CB1 or a human CB2 receptor.

The invention also provides pharmaceutical compositions useful for the prophylaxis and treatment of a CB2-associated and/or CB1-associated disease or condition. The pharmaceutical compositions include a compound of formula I and a pharmaceutically acceptable vehicle, diluent, excipient or carrier.

The invention further provides a method of prophylaxis or treatment of a CB2-associated disease or condition by administering a compound of formula I or a pharmaceutically acceptable salt, acid salt hydrate, solvate, stereoisomer, or mixture of stereoisomers thereof. In another embodiment, the invention provides a method of prophylaxis or treatment of a CB2-associated and/or CB1-associated disease, disorder or condition by administering a compound of formula I or a pharmaceutically acceptable salt, acid salt hydrate, solvate, stereoisomer or mixture of stereoisomers thereof. Such CB2-associated diseases or conditions and CB1-associated and CB2-associated diseases, disorders and conditions include, without limitation, pain and inflammation, wherein such pain can be inflammatory pain, visceral pain, neuropathic pain or hyperalgesia. Each of these types of pain can present as acute or chronic pain.

DETAILED DESCRIPTION OF THE INVENTION

Figure 1:
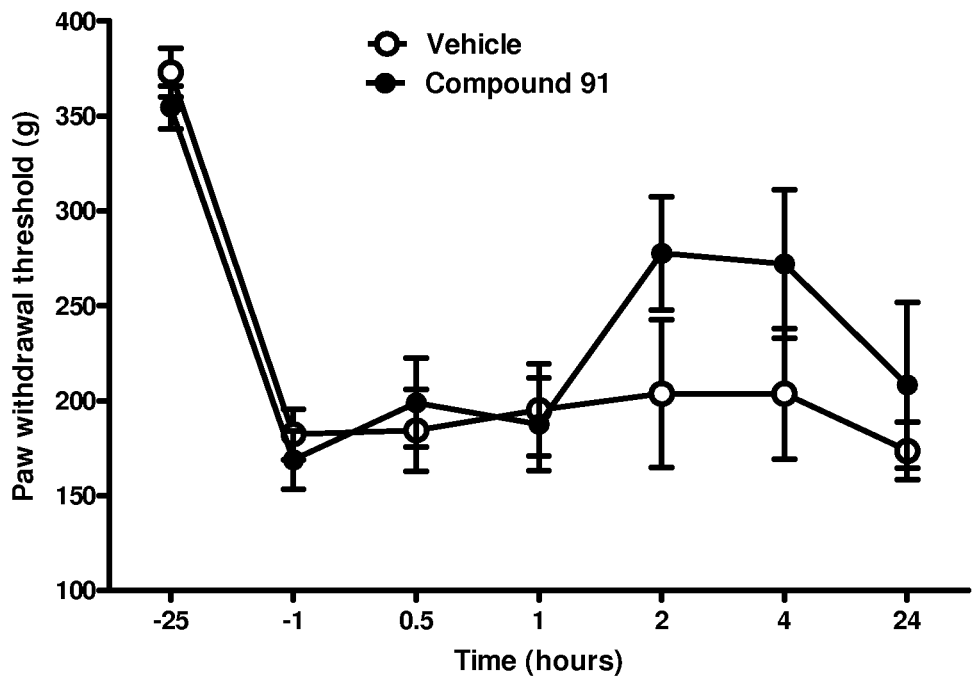
FIG. 1 shows the anti-hyperalgesic effect of intraperitoneal administration of compound 91 on paw withdrawal threshold (in grams) after intrapaw administration of Freund's Complete Adjuvant (CFA) as compared to vehicle alone over a twenty-four hour period after CFA injection.

The following definitions elucidate the meaning of the listed terms a used in this specification:

Alkyl—a saturated branched or straight chain monovalent hydrocarbon radical of a specified number of carbon atoms. Thus, the term alkyl includes, but is not limited to, methyl, ethyl, propyl, isopropyl, n-butyl, t-butyl. A chain of one to six carbon atoms is also herein interchangeably designated as $C_1$-$C_6$ alkyl; a chain of three to six carbon atoms can be alternatively designated as $C_3$-$C_6$ alkyl and so on.

Alkenyl—refers to branched or straight chain hydrocarbon radical having at least one double bond between two carbon atoms. It should be noted that in an alkenyl substituted nitrogen, the unsaturated carbon atom cannot be bound directly to the nitrogen atom, i.e. there must be at least one unsaturated carbon (—$CH_2$— or —CR'R"—) intervening between the nitrogen atom and the nearest unsaturated carbon atom.

Alkynyl—refers to branched or straight chain hydrocarbon radical having at least one triple bond between two carbon atoms. It should be noted that in an alkynyl substituted nitrogen, the unsaturated carbon atom cannot be bound directly to the nitrogen atom, i.e. there must be at least one unsaturated carbon (—$CH_2$— or —CR'R"—) intervening between the nitrogen atom and the nearest unsaturated carbon atom.

Haloalkyl—an alkyl group having one or more hydrogen atoms substituted with a halogen atom, each independently chosen such that a haloalkyl group having more than one halogen atom can be a mixed haloalkyl, such as for instance, 2-fluoro, 2-chloroethyl, or perhalo as in trifluoromethyl.

Alkoxy—refers to an (alkyl)$_a$-O-(alkyl)$_b$ substituent group wherein a is zero or an integer, and b is an integer and the alkyl group is as defined above. So that for instance alkoxy can be and without limitation, —O-methyl, O-ethyl, —O-propyl, —(CH$_2$)$_a$O-methyl, —(CH$_2$)$_a$O-ethyl, —(CH$_2$)$_a$—O-propyl, and so forth.

Cycloalkyl—a saturated monocyclic, polycyclic or bridged hydrocarbon ring system radical or linking group. In a substituted cycloalkyl ring, the substituent is bonded to ring carbon atom replacing a hydrogen atom. The term $C_3$-$C_{10}$ cycloalkyl is herein used to designate a ring of three to ten carbon atoms, or a ring of three of more carbon atoms with the remaining carbon atoms forming one or more alkyl substituents of the ring. Similarly, a $C_3$-$C_7$ cycloalkyl designates a saturated or partially unsaturated carbocycle, although not all the designated number of carbon atoms are necessarily ring carbon atoms. Cycloalkyl typically includes, but is not limited to, cyclopropyl, cyclobutyl, cyclopentyl, cyclohexyl, cyclohexenyl, cycloheptyl and cyclooctyl. However, $C_{10}$ cycloalkyl includes 1,3,3-trimethylbicyclo[2.2.1]heptyl, wherein seven of the ten designated carbon atoms form the seven-membered bicyclo-carbocycle and the remaining three are methyl substituents.

Cycloalkenyl—partially unsaturated monocyclic, polycyclic or bridged hydrocarbon ring system radical or linking group having at least one double bond between two carbon atoms. In a substituted cycloalkenyl ring, the substituent is bonded to ring carbon atom replacing a hydrogen atom. The term $C_3$-$C_{10}$ cycloalkenyl is herein used to designate a ring of three to ten carbon atoms, or a ring of three or more carbon atoms with the remaining carbon atoms forming one or more alkyl substituents of the ring. Similarly, $C_3$-$C_7$ cycloalkenyl designates as partially unsaturated carbocycle, although not all the designated number of carbon atoms are necessarily ring carbon atoms. Cycloalkenyl typically includes, but is not limited to, cyclopentenyl, cyclohexenyl, cycloheptenyl.

Heterocyclyl—a saturated, partially unsaturated or unsaturated monocyclic, polycyclic or bridged hydrocarbon ring system radical or linking group, wherein at least one ring carbon atom has been replaced with a heteroatom selected from nitrogen, oxygen and sulfur. A heterocyclyl moiety system further includes a ring system having one, two, three or four nitrogen ring atoms, or a ring system having zero, one, two or three nitrogen ring atoms and one oxygen or sulfur ring atom. The heterocyclic ring system can include more than one ring heteroatom, wherein one heteroatom is nitrogen and the other is selected from nitrogen, oxygen and sulfur. A heterocyclyl moiety is derived by the removal of one hydrogen atom from a single carbon or nitrogen ring atom. Heterocyclyl includes, but is not limited to, furyl, thienyl, 2H-pyrrole, 2-pyrrolinyl, 3-pyrrolinyl, pyrrolidinyl, pyrrolyl, 1,3-dioxolanyl, oxazolyl, thiazolyl, imidazolyl, 2-imidazolinyl, imidazolidinyl, 2-pyrazolinyl, pyrazolidinyl, pyrazolyl, isoxazolyl, isothiazolyl, oxadiazolyl, triazolyl, thiadiazolyl, tetrazolyl, 2H-pyranyl, 4H-pyranyl, pyridinyl, piperidinyl, 1,4-dioxanyl, morpholinyl, 1,4-dithianyl, thiomorpholinyl, pyridazinyl, pyrimidinyl, pyrazinyl, piperazinyl, azepanyl, diazepinyl, indolizinyl, indolyl, isoindolyl, 3H-indolyl, indolinyl, benzo[b]furyl, benzo[b]thienyl, 1H-indazolyl, benzimidazolyl, benzothiazolyl, purinyl, 4H-quinolizinyl, quinolinyl, isoquinolinyl, cinnolinyl, phthalzinyl, quinazolinyl, quinoxalinyl, 1,8-napthyridinyl, pteridinyl, quinuclidinyl.

Heterocyclyl—as used herein, also includes an aromatic heterocycle such as pyrrolyl, pyrazolyl, imidazolyl, triazolyl, oxazolyl, isoxazolyl, thiazolyl, isothiazolyl, furyl, thienyl, pyridyl, pyrazinyl, pyrimidinyl, and can be optionally substituted by alkyl. Arylalkyl—an optionally substituted aryl group attached to the end carbon atom of $C_1$-$C_4$ alkyl group. As used herein "heterocyclyl" also includes bicyclic heterocyclyl moieties in which one or both rings are heterocyclic, such as for example, but not limited to imidazopyrazinyl, benzofuranyl, benzodioxolyl, benzothiophenyl, and quinolinyl.

Aryl—an unsaturated, π-electron conjugated monocyclic or polycyclic hydrocarbon ring system radical or linking group of six, eight, ten or fourteen carbon atoms. An aryl radical is derived by the removal of one hydrogen atom from a single carbon ring atom. Aryl includes, but is not limited to, phenyl, naphthalenyl, azulenyl, anthracenyl.

Aminosulfonylalkyl—a radical of the formula —$NHSO_2$-alkyl.

Sulfonylaminoalkyl—a linking group of the formula —$SO_2$NH-alkyl- or a radical of the formula —$SO_2$N(alkyl)$_2$.

Alkylcarbamoyl—a linking group of the formula -alkyl-C(O)NH— or a radical of the formula -alkyl-C(O)$NH_2$.

Carbamoylalkyl—a linking group of the formula —NHC(O)-alkyl- or a radical of the formula —NHC(O)-alkyl.

Halogen—fluoro, chloro, bromo or iodo.

Carboxyl—a radical of the formula —COOH.

Hydroxyl—a radical of the formula —OH.

Cyano—a radical of the formula —C≡N.

Oxo—a radical of the formula =O in which the oxygen atom is double bonded.

Amino—a radical of the formula —$NH_2$ or a linking group having the formula —NH—.

Aminoalkyl—a radical of the formula —NH-alkyl or —N(alkyl)$_2$.

As used herein, the terms: compound, salt, polymorph, isomer, solvate are also interchangeably referred to in the plural form (i.e. compounds, salts, polymorphs, isomers and solvates).

The compounds of the present invention can contain one or more stereogenic centers, depending upon the location and nature of the various substituents desired. These stereogenic centers may be present in the (R) or (S) configuration, resulting in racemic mixtures and/or diastereomeric mixtures. Substituents on a partially or fully saturated ring may also be present in either cis or trans form. All such configurations (including enantiomers and diastereomers) of the compounds described or exemplified herein, are contemplated within the scope of the present invention. Compounds of the invention can also exist as individual stereoisomers or as mixtures in varying ratios (e.g. enantiomerically enriched or racemates). Enantiomeric mixtures of the compounds may be partially or fully resolved through standard purification and/or separation techniques known in the art, including but not limited to chiral chromatography (e.g. chiral derivatized solid phase), formation and separation of diastereomeric salts (e.g. tartaric acid salts or camphorsulfonic acid salts), or enzymatic separation. Diastereomeric mixtures can be separated by techniques well known in the art, based on their physical and/or chemical differences, or by methods described above.

In this specification, salts of a compound of formula I refers to a complex of the compound with an inorganic or organic counter ion or counter ions. For examples, see Handbook of Pharmaceutical Salts: Properties, Selection and Use; Stahl P. H., Wermuth, C. G., Eds.; John Wiley and Sons, 2002. Pharmaceutically useful salts include those obtained by treating the compound, functioning as a base, with an inorganic or organic acid to form a salt or salts. Additional pharmaceutically useful salts include those obtained by treating the compound, functioning as an acid, with an inorganic or organic base to form a salt or salts. Other pharmaceutically useful salts include those obtained by treatment of basic nitrogen-containing groups with such agents as alkyl halides such as chlorides or bromides to form a quaternary ammonium a salt or salts.

As used herein, the term "solvates" describes a complex wherein the compound is coordinated with a proportional amount of a solvent molecule. Specific solvates, wherein the solvent is water, is referred to as hydrates. Combinations of a drug and propylene glycol (1,2-propanediol) have been used to form pharmaceutical drug solvates. See for example U.S. Pat. No. 3,970,651. Other suitable solvates are hydrates of drug compounds. Such hydrates include hydrates which either have comparable activity or hydrates which are converted back to the active compound following administration.

The compounds of the present invention described and exemplified herein modulate a signal that regulates a biological activity, by modulating the activity of a cannabinoid receptor. Modulation of a cannabinoid receptor can be effected by a compound of the present invention acting as an agonist, a partial agonist, inverse agonist or an antagonist upon binding at a cannabinoid receptor such as CB2 and/or CB1. The modulation of a cannabinoid receptor can be activation by compound of the present invention acting an agonist. Alternatively, the modulation of a cannabinoid receptor can be inhibition or deactivation by an antagonist. One particular signal regulated by CB2 is the intracellular concentration of cyclic adenosine monophosphate (cAMP).

The term 'agonist' as used herein means a molecule that produces a physiological response by activating a receptor.

The term 'inverse agonist' as used herein means a molecule that tends to reverse the effect of an agonist. Current theory holds that this occurs due to the higher affinity of the inverse agonist for binding the inactive conformation over the active conformation of the receptor.

The term 'antagonist' as used herein means a molecule that binds a receptor and thereby interferes with the interaction of an agonist and its cognate receptor, or blocks the constitutive activity of the receptor.

The term 'neutral antagonist' as used herein means a molecule that binds a receptor with equal affinity for the active and inactive conformations and thereby inhibits receptor activity by competing with an agonist.

The compounds of the present invention have the structure of formula I:

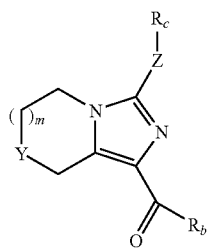

Formula I

In particular embodiments of the invention, Y is an amino-radical, $NR_a$ or a quaternary amino radical $N^+R_1R_2$ with an anionic counterion $X^-$. The anionic counterion $X^-$ can be any anionic counterion, such as for instance, an inorganic counterion such as chloride, or an organic counterion such as succinate; and m is an integer equal to 1, 2 or 3, such that the Y-containing ring includes six, seven or eight ring atoms fused to the imidazole ring. Z is a bond or a bivalent linking group chosen from —$(CH_2)_p$—, —CH=CH—, —C≡C—, —CONH— and —CO—; wherein p is an integer from 1 to 6.

The compounds have the structure of formula I, wherein $R_a$ is hydrogen or a substituent chosen from $C_1$-$C_8$ alkyl, $C_3$-$C_6$ alkenyl, $C_3$-$C_6$ alkynyl, aryl, $C_3$-$C_8$ cycloalkyl, $C_3$-$C_8$ cycloalkenyl, —$SO_2R_3$, —$COR_3$, —$CONR_3R_4$, —$CSNR_3R_4$, —$COOR_3$, and —$(CH_2)_q$-linked-heterocyclyl; wherein q is zero or an integer from one to four. The alkyl, cycloalkyl, cycloalkenyl, aryl and heterocyclyl substituents of $R_a$ are optionally substituted with from one to four groups, each independently chosen from halo, hydroxyl, oxo, amino, nitro, cyano, carboxyl, —$COR_3$, $C_1$-$C_6$ alkyl, $C_1$-$C_4$ alkoxy, $C_3$-$C_8$ cycloalkyl, phenyl, trifluoromethoxy and trifluoromethyl. In one embodiment when $R_a$ is —$SO_2R_3$, then $R_3$ is not hydrogen.

In the compounds having the structure of formula I, $R_b$ is a radical bonded through the carbonyl to the imidazolyl ring. $R_b$ is chosen from $C_1$-$C_8$ alkyl, $C_2$-$C_8$ alkenyl, aryl, —$NR_5R_6$, 4-$R_7$-substituted piperazinyl, and 4—$R_8$,4—$R_9$-substituted piperidinyl; wherein the alkyl, alkenyl and aryl are optionally substituted with from one to three groups chosen independently from the following: $C_1$-$C_4$ alkyl, $C_2$-$C_4$ alkenyl, $C_2$-$C_6$ alkynyl, $C_3$-$C_{10}$ cycloalkyl, $C_1$-$C_4$ alkoxy, aryl, five-membered, six-membered and seven-membered heterocyclyl, halo, hydroxyl, amino, cyano and nitro.

In formula I, the radical $R_c$ is chosen from the following: halo, $C_1$-$C_6$ alkyl, $C_2$-$C_6$ alkenyl, $C_2$-$C_6$ alkynyl, $C_3$-$C_{10}$ cycloalkyl, $C_3$-$C_8$ cycloalkenyl, $C_1$-$C_4$ alkoxy, aryl, and five-membered, six-membered, seven-membered and eight-membered monocyclic heterocyclyl, nine-membered and ten-membered bicyclic heterocyclyl. The alkyl, alkenyl, alkynyl, cycloalkyl, cycloalkenyl, aryl and heterocyclyl of $R_c$ are optionally substituted with from one to five substituents independently chosen from $C_1$-$C_4$ alkyl, $C_1$-$C_4$ alkoxy, $C_1$-$C_4$ haloalkyl, $C_1$-$C_4$ haloalkoxy, $C_3$-$C_6$ cycloalkyl, $C_4$-$C_8$ cycloalkenyl, halo, hydroxyl, oxo, amino, cyano, nitro, (A) (A')(A")(A''')aryl, (A)(A')(A")(A''')heterocyclyl, $NR_{14}R_{15}$, $(CH_2)_pNR_{14}R_{15}$, —$COOR_{14}$, $SOR_{14}$, $SO_2R_{14}$, $SO_2NR_{14}R_{15}$, $NR_{15}SO_2R_{16}$, $COR_{14}$, $CONR_{14}R_{15}$ and $NR_{15}COR_{16}$; wherein (A), (A'), (A") and (A''') are each independently chosen from hydrogen and $C_1$-$C_4$ alkyl; and each heterocyclyl of (A)(A')(A")(A''')heterocyclyl is independently chosen from five-membered, six-membered, seven-membered and eight-membered monocyclic heterocyclyl, nine-membered and ten-membered bicyclic heterocyclyl.

In formula I, when $R_c$ is heterocyclyl, the heterocyclyl moiety is directly bonded through a carbon atom of the heterocyclic ring or ring system to the radical Z, or if Z is a bond, to the imidazole ring of formula I.

The substituents, $R_1$ and $R_2$ are each $C_1$-$C_4$ alkyl. The substituents, $R_1$ and $R_2$ can be identical or different, branched or straight chain alkyl substituents.

The substituents, $R_3$ and $R_4$ are each independently chosen from the following: hydrogen, $C_1$-$C_6$ alkyl, $C_3$-$C_8$ alkenyl, $C_3$-$C_8$ alkynyl, $C_3$-$C_8$ cycloalkyl, $C_3$-$C_8$ cycloalkenyl, aryl, and heterocyclyl having from four to eight ring atoms. Each $R_3$ and $R_4$ can be optionally substituted with one to three groups independently chosen from $C_1$-$C_6$ alkyl, $C_1$-$C_6$ haloalkyl, $C_3$-$C_8$ cycloalkyl, $C_1$-$C_4$ alkoxy, $C_1$-$C_4$ acyl, aryl, five- to eight-membered monocyclic heterocyclyl, 9-, 10-membered bicyclic heterocyclyl, amino, nitro, cyano, hydroxyl, carboxyl, oxo, and halo. However, when $R_a$ is —$SO_2R_3$, then $R_3$ is not hydrogen.

Alternatively, $R_3$ and $R_4$ can be taken together with the nitrogen atom to which they are bonded to form a heterocyclyl moiety, wherein the heterocyclyl formed from $R_3$ and $R_4$ can be a four-membered heterocyclyl, a five-membered heterocyclyl, a six-membered heterocyclyl, a seven-membered heterocyclyl or an eight-membered heterocyclyl moiety.

The substituent, $R_5$ is hydrogen or a substituent chosen from the following: $C_1$-$C_4$ alkyl, and $C_1$-$C_4$ haloalkyl. The alkyl and haloalkyl of $R_5$ are optionally substituted with one to four substituents independently chosen from $C_1$-$C_4$ alkoxy, hydroxyl, amino and cyano.

The substituent, $R_6$ is hydrogen or a substituent chosen from the following: —$CR_{10}R_{11}R_{12}$, —$CR_{10}R_{11}COR_{13}$, $C_1$-$C_8$ alkyl, $C_3$-$C_{10}$ cycloalkyl, aryl, and heterocyclyl; wherein the alkyl, cycloalkyl, aryl, and 5-, 6-, 7-, 8-membered monocyclic heterocyclyl, and 9-, 10-membered bicyclic heterocyclyl can be optionally substituted by from one to three substituents independently selected from the group consisting of $C_1$-$C_4$ alkyl, aryl, halo, —OH, $C_1$-$C_4$ alkoxy, —$NH_2$, —CN, —$NO_2$.

Alternatively, the substituents, $R_5$ and $R_6$ taken together with the nitrogen atom to which they are bonded form a 5-, 6-, 7-, 8-membered monocyclic heterocyclyl, and 9-, 10-membered bicyclic heterocyclyl, which monocyclic heterocyclyl, or bicyclic heterocyclyl is optionally substituted with one or two substituents chosen from oxo and —$CONR_1R_2$.

The substituent, $R_7$ is selected from the following: —$COR_3$, —$CO_2R_3$, —$SO_2R_3$, and 5-, 6-, and 7-membered heterocyclyl.

The substituents, $R_8$ and $R_9$ are independently chosen from the following: hydrogen, $C_1$-$C_4$ alkyl, $C_1$-$C_4$ haloalkyl, $C_1$-$C_4$ alkoxyalkyl, $C_2$-$C_4$ alkenyl, $C_3$-$C_6$ cycloalkyl, aryl, 5-, 6-, 7-, 8-membered monocyclic heterocyclyl, 9-, 10-membered bicyclic heterocyclyl, halo, hydroxyl, $C_1$-$C_4$ alkoxy, amido, amino, cyano and nitro.

In a first alternative, the substituents, $R_8$ and $R_9$ taken together with the nitrogen atom to which they are bonded form a heterocyclyl moiety, which heterocyclyl moiety is optionally substituted with one to three substituents chosen from $C_1$-$C_4$ alkyl, halo, oxo and aryl.

In a second alternative, the substituents, $R_8$ and $R_9$ taken together with the carbon atom to which they are bonded form a carbocyclyl ring, which heterocyclyl moiety is optionally substituted with one to three substituents chosen from $C_1$-$C_4$ alkyl, halo, oxo and aryl.

The substituent, $R_{10}$ is hydrogen or $C_1$-$C_4$ alkyl; and the substituent, $R_{11}$ is chosen from hydrogen and $C_1$-$C_8$ alkyl, $C_2$-$C_6$ alkenyl, $C_2$-$C_4$ alkynyl, $C_3$-$C_{10}$ cycloalkyl, aryl, five-membered, six-membered, seven-membered and eight-membered monocyclic heterocyclyl, nine-membered and ten-membered bicyclic heterocyclyl; wherein the alkyl, alkenyl, alkynyl, cycloalkyl, aryl and 5 five-membered, six-membered, seven-membered and eight-membered monocyclic heterocyclyl, nine-membered and ten-membered bicyclic heterocyclyl of $R_{11}$ are each optionally substituted with one to three substituents independently chosen from $C_1$-$C_4$ alkyl, $C_3$-$C_6$ cycloalkyl, aryl, and five-membered, six-membered, seven-membered and eight-membered monocyclic heterocyclyl, nine-membered and ten-membered bicyclic heterocyclyl, halo, hydroxyl, $C_1$-$C_4$ alkoxy, amino, guanidino, cyano, nitro, oxo, —COOR$_{10}$, —CONR$_8$R$_9$, —SO$_2$NR$_8$R$_9$, —SR$_{10}$, —SOR$_1$, and —SO$_2$R$_1$.

The substituent, $R_{12}$ is chosen from hydrogen, $C_1$-$C_4$ alkyl and $C_1$-$C_4$ hydroxyalkyl; and the substituent, $R_{13}$ is chosen from —OR$_{10}$ and —NR$_8$R$_9$. The substituents, $R_{14}$, $R_{15}$ and $R_{16}$ are each independently hydrogen or $C_1$-$C_4$ alkyl; or alternatively, substituents, $R_{14}$ and $R_{15}$ taken together with the nitrogen atom to which they are bonded form a five-membered, six-membered, seven-membered and eight-membered monocyclic heterocyclyl, nine-membered and ten-membered bicyclic heterocyclyl moiety.

In one embodiment of the invention, in the compounds of formula I, Y is NR$_a$ or N$^+$R$_1$R$_2$X$^-$, wherein X$^-$ is a halide ion; and R$_a$ is chosen from the following: hydrogen, $C_1$-$C_6$ alkyl, cyclopropyl, —SO$_2$R$_3$, —COR$_3$, —CONR$_3$R$_4$, —CSNR$_3$R$_4$, —CO$_2$R$_3$, and —(CH$_2$)$_p$heterocyclyl, wherein p is zero or 1; and m is 1 or 2; and the alkyl, aryl and heterocyclyl of R$_a$ are each optionally substituted with halo, hydroxyl, cyclopropyl, acetyl or phenyl. In this embodiment, the substituent, $R_3$ is chosen from $C_1$-$C_5$ alkyl, cyclopropyl, five-membered heterocyclyl, six-membered heterocyclyl and aryl; wherein the aryl substituent of R$_a$ is optionally substituted with cyano, nitro, halo or trifluoromethyl.

In one particular aspect of this embodiment, the radical R$_a$ is hydrogen, $C_1$-$C_4$ alkyl, 4-fluorophenyl-sulfonyl, or —(CH$_2$)$_p$-pyrimidinyl, wherein the alkyl of R$_a$, is optionally substituted with cyclopropyl.

In another embodiment of the compounds of formula I, the radical R$_b$ is chosen from $C_1$-$C_6$ alkyl, $C_2$-$C_6$ alkenyl, NR$_5$R$_6$,

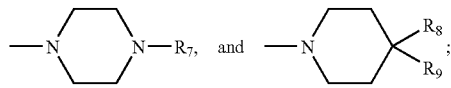

wherein the alkyl of R$_b$ is optionally substituted with aryl and $R_3$ is aryl and $R_5$ is hydrogen. The substituent, $R_6$ is chosen from the following: —CR$_{10}$R$_{11}$R$_{12}$, —CR$_{10}$R$_{11}$COR$_{13}$, $C_1$-$C_6$ alkyl, $C_3$-$C_{10}$ cycloalkyl, aryl, and five-membered, six-membered, seven-membered and eight-membered monocyclic heterocyclyl, nine-membered and ten-membered bicyclic heterocyclyl. The alkyl, cycloalkyl, aryl, and heterocyclyl substituents of $R_6$ are themselves optionally substituted with from one to three substituents independently chosen from: methyl, aryl, halo, and hydroxyl. Additionally, in this embodiment, the heterocyclyl of $R_6$ is optionally substituted with a single —CONHR$_1$R$_2$ substituent. The substituent, $R_7$ is either —COR$_3$ or a six-membered heterocyclyl. Substituents, $R_8$ and $R_9$ are independently chosen from: hydrogen, $C_1$-$C_4$ alkyl, $C_1$-$C_2$ haloalkyl, $C_1$-$C_3$ alkoxyalkyl, $C_3$-$C_4$ cycloalkyl, —CONH$_2$, five-membered monocyclic heterocyclyl, six-membered monocyclic heterocyclyl and nine-membered bicyclic heterocyclyl, and ten-membered bicyclic heterocyclyl; wherein the $C_1$-$C_4$ alkyl and five-, and six-membered monocyclic heterocyclyl of $R_8$ and $R_9$ are optionally substituted with a six-membered monocyclic heterocyclyl, or one or two methyl groups. Alternatively, $R_8$ and $R_9$ taken together with the atom to which they are bonded form a carbocyclic or heterocyclyl moiety, which carbocyclic or heterocyclyl moiety is optionally substituted with one to two substituents independently chosen from methyl, halo, oxo and aryl. The substituent, $R_{10}$ in this embodiment is either hydrogen or $C_1$-$C_4$ alkyl; and the substituent, $R_{11}$ is chosen from: hydrogen, $C_1$-$C_5$ alkyl, $C_3$-$C_{10}$ cycloalkyl, aryl, $C_1$-$C_4$ alkylaryl, and five-membered and six-membered monocyclic heterocyclyl; wherein the alkyl, cycloalkyl, aryl, and heterocyclyl of $R_{11}$ are optionally substituted with from one to three substituents independently chosen from $C_1$-$C_4$ alkyl, $C_3$-$C_6$ cycloalkyl, aryl, five-membered heterocyclyl, 6-membered heterocyclyl, and nine-membered bicyclic heterocyclyl, halo, hydroxyl, —COOR$_{10}$, —CONR$_8$R$_9$, and —SO$_2$NR$_8$R$_9$.

In one aspect of this embodiment, the radical, R$_b$ is NR$_5$CHR$_{11}$COR$_{13}$. In a particular example of the aspect wherein R$_b$ is NR$_5$CHR$_{11}$COR$_{13}$, the substituent, $R_5$ is hydrogen and $R_{13}$ is NR$_8$R$_9$. In another example of this aspect, the substituent, $R_8$ is hydrogen and $R_9$ is methyl. In a particular aspect of this embodiment, the radical, R$_b$ is —NHCH(tBu)CONHCH$_3$.

The invention provides another embodiment of the compounds of formula I, wherein m is an integer equal to 1 or 2 and radical, R$_c$ is chosen from the following: halo, $C_1$-$C_6$ alkyl, $C_2$-$C_6$ alkenyl, $C_3$-$C_7$ cycloalkyl, $C_3$-$C_7$ cycloalkenyl, aryl, five-membered heterocyclyl, six-membered heterocyclyl, seven-membered heterocyclyl and ten-membered bicyclic heterocyclyl. The alkyl, alkenyl, cycloalkyl, aryl and heterocyclyl of R$_c$ are optionally substituted with from one to three substituents independently chosen from $C_1$-$C_4$ alkyl, $C_1$-$C_4$ alkoxy, $C_1$-$C_4$ haloalkoxy, $C_1$-$C_4$ haloalkyl, $C_3$-$C_6$ cycloalkyl, aryl, five-membered heterocyclyl, six-membered heterocyclyl, seven-membered heterocyclyl, halo, hydroxyl, amino, —NR$_{14}$R$_{15}$, —(CH$_2$)$_p$NR$_{14}$R$_{15}$, cyano, nitro, oxo, —COOR$_{14}$, —SO$_2$R$_{14}$, —SO$_2$NR$_{14}$R$_{15}$, —NR$_{15}$SO$_2$R$_{16}$, —COR$_{14}$, —CONR$_{14}$R$_{15}$, and —NR$_{15}$COR$_{16}$.

In another embodiment of the compounds of formula I, Z is a bond, or Z is —(CH$_2$)$_p$, or —CH=CH—; and the radical R$_c$ is chosen from $C_3$-$C_8$ cycloalkyl, $C_3$-$C_8$ cycloalkenyl, phenyl, five-membered heterocyclyl and six-membered heterocyclyl, wherein the cycloalkyl, cycloalkenyl, phenyl and heterocyclyl of R$_c$ are optionally substituted with from one or two substituents independently chosen from $C_1$-$C_4$ alkyl, $C_1$-$C_4$ alkoxy, $C_3$-$C_6$ cycloalkyl, halo, trifluoromethoxy, trifluoromethyl, hydroxyl, cyano, and an additional optional independently selected halo substituent.

In one aspect of the above embodiment of the compounds of formula I, Z is a bond and the radical R$_c$ is optionally substituted phenyl, wherein the phenyl of R$_c$ is optionally substituted with from one or two substituents independently chosen from halo, methyl, methoxy, trifluoromethyl and cyano; and the phenyl of R$_c$ is further optionally substituted with an additional halo substituent. In a particular aspect of this embodiment, the radical R$_c$ is one of the following: phenyl, 3-chloro-4-methylphenyl, 2-chloro-4-fluorophenyl, 2-fluoro-4-chlorophenyl, 2-fluoro-4-bromophenyl, 2-fluoro-5-chlorophenyl, 2,4-difluorophenyl, 2,5-difluorophenyl, 3,5-difluorophenyl, 3,4-difluorophenyl, 2-fluoro-4-methylphenyl, 2-fluoro-5-methylphenyl, 2-fluoro-3-methoxyphenyl, 2-fluoro-4-methoxyphenyl, 2-fluoro-4-trifluoromethylphenyl, 2-fluoro-5-trifluoromethylphenyl, 3-cyano-4-fluorophenyl, 2-fluoro-4-methyl-5-chlorophenyl, 2,4-difluoro-5-chlorophenyl, 2,4,5-trifluorophenyl, 3,4,5-tri-fluorophenyl, 2,5-difluoro-4-methoxyphenyl, 2-fluorophenyl, 3-fluorophenyl, 4-fluorophenyl, 2-chlorophenyl, 3-chlorophenyl, 4-chlorophenyl, 3-methyl-4-fluorophenyl, 2-fluoro-3-chlorophenyl, 3-trifluoromethyl-phenyl, 3-methylphenyl, 3-fluoro-4-methylphenyl, 3-methyl-4-fluorophenyl, 3-chloro-4-fluorophenyl and 3-fluoro-4-chlorophenyl.

In a particular aspect of the above embodiment of the compounds of formula I, Z is a bond and the radical $R_c$ is chosen from phenyl, 2-fluoro-4-chlorophenyl, 2-fluoro-4-bromophenyl, 2,4-fluoro-5-chlorophenyl, and 2,4,5-trifluorophenyl.

In another aspect of the above embodiment of the compounds of formula I, Z is a bond and the radical $R_c$ is chosen from the following: $C_2-C_6$ alkyl, $C_2-C_8$ alkenyl, $C_3-C_8$ cycloalkyl, $C_3-C_8$ cycloalkenyl, five-membered heterocyclyl, and six-membered heterocyclyl. In this aspect of the above embodiment of the compounds of formula I, the alkyl, cycloalkyl, cycloalkenyl and heterocyclyl of $R_c$ are optionally substituted with from one to two substituents independently chosen from $C_1-C_4$ alkyl, methoxy, trifluoromethyl, $C_3-C_6$ cycloalkyl, halo, hydroxyl and cyano.

In a particular aspect of this embodiment, the radical $R_c$ is chosen from ethyl, n-propyl, isopropyl, 1,2-dimethylpropyl, isobutyl, 3,3-dimethylbutyl, n-pentyl, n-hexyl, 1-methyl-2,2,2-trifluoroethyl, cyclopropylethyl, ethenyl, propen-1-yl, propen-2-yl, 2-methylpropen-1-yl, 3,3-dimethylbut-2-en-2-yl, 2-methylpropen-1-yl, 1-penten-1-yl, 1-hexen-1-yl, 3-methoxypropyl, cyclopropyl, cyclopentyl, cyclopentenyl, cyclohexyl, 4-methylcyclohexyl, 4,4-difluorocyclohexyl, 1,4-dioxaspiro[4.5]dec-7-en-7-yl, cyclohexen-1-yl, 4-methylcyclohexen-1-yl, 4-tert-butyl-cyclohexen-1-yl, cycloheptyl, cyclohepten-1-yl, thiophen-3-ylethyl and 2-(thiophen-3-yl)ethen-1-yl.

In a particular aspect of the above embodiment of the compounds of formula I, the radical $R_c$ is chosen from dihydropyran-2-yl, tetrahydropyran-2-yl, dihydropyran-4-yl, piperidin-4-yl, pyridin-2-yl, 3,4-dihydropiperidin-4-yl, pyridin-3-yl, pyridin-4-yl, 3-fluoro-pyridin-4-yl, pyrimidin-5-yl, 1-methylpyrazol-4-yl, 3,5-dimethylisoxazol-4-yl, thiophen-2-yl, thiophen-3-yl, 4-methylthiophen-3-yl, furan-2-yl, 5-methylfuran-2-yl, furan-3-yl, thiazol-2-yl, benzofuran-2-yl, benzothiophen-3-yl, benzo[d][1,3]dioxol-5-yl and 2,3-dihydrobenzo[b][1,4]dioxin-6-yl.

The present invention further provides pharmaceutically acceptable salts, acids salts, solvates (including hydrates) and stereoisomers of the compounds having the structure of formula I. Also provided are mixtures of stereoisomers of the compounds having the structure of formula I wherein the mixture can include equal quantities of each stereoisomer, or the mixture can contain an excess of one stereoisomer over another.

In one embodiment of the invention, the compounds having the structure of formula I bind one or more cannabinoid receptors such as, without limitation the CB I or CB2 receptor.

Certain compounds of the invention exhibit an $EC_{50}$ for the CB1 receptor and/or the CB2 receptor of from about 0.1 nM to about 10 μM; or from about 1 nM to about 1 μM; or from about 5 nM to about 500 nM.

As used herein, a cannabinoid receptor-associated disease, condition or disorder is any disease, condition or disorder that is preventable or treatable by modulation of a cannabinoid receptor, such as and without limitation, CB2 or CB1. The modulation can be activation by an agonist, or inhibition by an inverse agonist. The cannabinoid receptor can be any mammalian cannabinoid receptor, such as but not limited to, a human cannabinoid receptor or a rat cannabinoid receptor. In one aspect, the compounds of the invention having the structure of formula I are cannabinoid receptor agonists that activate a cannabinoid receptor.

The cannabinoid receptor-associated disease, condition or disorder can be any cannabinoid receptor-associated disease, condition or disorder, such as and without limitation: pain, inflammation, immunomodulation and pruritis; and can also include osteoclastogenesis. The cannabinoid receptor-associated disease, condition or disorder can also be obesity.

The cannabinoid receptor-associated pain can be neuropathic pain, somatic pain, visceral pain, cutaneous pain, ocular pain, otic pain, diabetic pain, pain associated with inflammatory bowel disease or irritable bowel syndrome, breakthrough cancer pain, metastatic cancer pain, virally-induced pain (such as AIDS-associated pain), or chemotherapy-induced pain.

The cannabinoid receptor-associated inflammation can be otic or ocular inflammation due to any of a variety of causes; inflammation due to rheumatoid arthritis, eczema, atopic dermatitis, inflammatory bowel disease, irritable bowel syndrome, kidney dialysis, insect bites or the inflammation can be inflammation caused by autoimmunity.

The cannabinoid receptor-associated pruritis can be opioid-induced pruritis, where in the pruritis is caused by use or abuse of an opioid, such as morphine.

The cannabinoid receptor can be any mammalian cannabinoid receptor, such as but not limited to, a human cannabinoid receptor or a rat cannabinoid receptor. In one aspect, the compounds of the invention having the structure of formula I are cannabinoid receptor agonists that activate a cannabinoid receptor.

In some embodiments, a particular dose and route of administration of the compound can be chosen by a clinician to completely prevent or cure the disease, condition or disorder. In other embodiments a particular dose and route of administration of the compound chosen by the clinician ameliorates or reduces one or more symptoms of the disease, condition or disorder.

As used herein, "effective amount" or "sufficient amount" of the compound of the invention refers to an amount of the compound as described herein that may be therapeutically effective to inhibit, prevent, or treat a symptom of a particular disease, disorder, condition, or side effect.

As used herein, "pharmaceutically acceptable" refers to compounds, materials, compositions, and/or dosage forms which are, within the scope of sound medical judgment, suitable for contact with the tissues of human beings and animals without severe toxicity, irritation, allergic response, or other complications, commensurate with a benefit-to-risk ratio that is reasonable for the medical condition being treated.

As used herein, a "pharmaceutically acceptable salt" refers to a derivative of a compound wherein the parent compound is modified by making an acid or a base salt thereof. Examples of pharmaceutically acceptable salts include, but are not limited to, mineral or organic acid salts of basic residues such as amines; alkali or organic salts of acidic residues such as carboxylic acids and the like.

The pharmaceutically acceptable salts include the conventional non-toxic salts or the quaternary ammonium salts of the parent compound formed, for example, from non-toxic inorganic or organic acids. For instance, such conventional non-toxic salts include those derived from inorganic acids such as hydrochloric, hydrobromic, sulfuric, sulfamic, phosphoric, nitric acids and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic acids, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine. Thus, a pharmaceutically acceptable salt of a substituted imidazoheterocycle of the invention can be formed from any such compound having either acidic, basic or both functional groups. For example, a compound having a carboxylic acid group, may in the presence of a pharmaceutically suitable base, form a carboxylate anion paired with a cation such as a sodium or potassium cation. Similarly, a compound having an amine functional group may, in the presence of a pharmaceutically suitable acid such as HCl, form a salt.

Pharmaceutically acceptable carriers used in parenteral preparations of the compounds of formula I include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include sodium chloride for injection, Ringers solution for injection, isotonic dextrose for injection, sterile water for injection, dextrose and lactated Ringers solution for injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose.

Buffers include phosphate and citrate. Antioxidants include sodium bisulfite. Local anesthetics include procaine hydrochloride.

Suspending and dispersing agents include sodium carboxymethylcelluose, hydroxypropyl methylcellulose and polyvinylpyrrolidone.

Emulsifying agents include Polysorbate 80 (Tween 80). A sequestering or chelating agent of metal ions such as EDTA can also be incorporated. Pharmaceutical carriers also include ethyl alcohol, polyethylene glycol and propylene glycol for water miscible vehicles and the pH can be adjusted to a physiologically compatible pH by addition of sodium hydroxide, hydrochloric acid, citric acid or lactic acid.

The pharmaceutical compositions that include the compounds of formula I of the invention can be delivered or administered intravenously, transdermally, transmucosally, intranasally, subcutaneously, intramuscularly, orally or topically (such as for example to the eye). The compositions can be administered for prophylaxis or treatment of individuals suffering from, or at risk of a disease or a disorder. Prophylaxis is defined as a measure designed to preserve the health of an individual.

For therapeutic applications, a pharmaceutical composition is typically administered to a subject suffering from a disease, condition or disorder, in an amount sufficient to inhibit, prevent, or ameliorate the disease or disorder. An amount adequate to accomplish this is defined as a "therapeutically effective dose."

The pharmaceutical compositions of the invention can be administered to a mammal for prophylactic or therapeutic purposes in any of the above-described formulations and delivery modes. The mammal can be any mammal, such as a domesticated or feral mammal, or even a wild mammal. The mammal can be any mammal, such as for instance a primate, ungulate, canine or feline. For instance, and without limitation, the mammal can be a pet or companion animal, such as a dog or a cat; a high-value mammal such as a thoroughbred or show animal; a farm animal, such as a cow, a goat, a sheep or pig; or a primate such as an ape or monkey. In one embodiment, the mammalian cannabinoid receptor is a human cannabinoid receptor, such as a CB1 or a CB2 receptor.

Without wishing to be bound by any particular theory, it is believed that due to their ability to bind and modulate the activity of the CB1 receptor and/or the CB2 receptor, the compounds of the present invention are useful in the treatment of conditions or disorders that include, but are not limited to, inflammatory diseases such as rheumatoid arthritis, systemic lupus erythematosus, Crohn's disease, psoriasis, eczema, multiple sclerosis, diabetes and thyroiditis.

Certain compounds of the invention can also be used in the treatment of disorders that include, but are not limited to, pain (e.g. inflammatory pain, visceral pain, postoperative pain, cancer pain, neuropathic pain, musculoskeletal pain, dysmenorrhea, menstrual pain, migraine, headache); skin disorders (e.g. sunburn, dermatitis, pruritis); lung disorders (e.g. chronic obstructive pulmonary disease, cough, asthma, bronchitis); ophthalmic disorders (e.g. glaucoma, retinitis, reinopathies, uveitis, conjunctivitis); gastrointestinal disorders (e.g. ulcerative colitis, irritable bowel syndrome, coeliac disease, inflammatory bowel disease, gastroesophageal reflux disease, organ transplant, nausea, emesis); cardiovascular disorders (e.g. stroke, cardiac arrest, atherosclerosis, myocardial ischemia); neurodegenerative, neuroinflammatory or psychiatric disorders (e.g. senile dementia, Alzheimer's disease, vascular dementia, amyotrophic lateral sclerosis, neuroinflammation, tinnitus); bladder disorders (e.g. bladder hyper-reflexia, cystitis) and cancer, such as for instance, lymphoblastic leukemia and lymphoma, acute myelogenous leukemia, chronic lymphocytic leukemia, glioma, skin cancer, breast cancer, prostate cancer, liver cancer, kidney cancer, lung cancer, pancreatic cancer.

In addition, certain compounds of the invention can be used to modulate bone formation and/or resorption for treating conditions including, but not limited to, ankylosing spondylitis, gout, arthritis associated with gout, osteoarthritis and osteoporosis. Certain compounds of the invention can also be used for the treatment of neuropathic pain including but not limited to diabetic neuropathy, fibromyalgia, lower back pain, sciatica, pain from physical trauma, cancer, amputation, toxins or chronic inflammatory conditions. The compounds of the invention and their pharmaceutically acceptable salts can be administered in a standard manner, for example orally, parentarally, sublingually, dermally, transdermally, rectally, or via inhalation, or by buccal, nasal, ocular or otic administration.

General Methods

All reactions involving moisture sensitive compounds were carried out under an anhydrous nitrogen or argon atmosphere. All reagents were purchased from commercial sources and used without further purification. Unless otherwise noted, the starting materials used in the examples were obtained from readily available commercial sources or synthesized by standard methods known to those skilled in the art of organic synthesis. Reactions performed under microwave irradiation conditions were carried out in a Biotage Initiator® 60 microwave system (Charlottesville, Va.; model no. 10986-22V) with a 300 Watt magnetron. Normal phase chromatography and reverse phase chromatography was performed on an ISCO CombiFlash® Companion®, CombiFlash® Companion/TS® system (Teledyne Isco, Inc., Lincoln, Nebr.) or ISCO CombiFlash® Sq 16x. Reverse phase chromatography was also performed on a Waters Autopurification System with 3100 Mass Detector. The HPLC column was a Waters XBridge C18 5 μm OBD 19×150 mm; eluents were A: water with 0.1% formic acid and B: acetonitrile with 0.1% formic acid. Gradient elution was from 5% B-95% B. The total run time was 13 minutes. Mass spectra (MS) data were acquired on the Waters SQ Detector/3100 Mass detector using electrospray techniques or a Waters ZQ mass spectrometer with a Waters 600 HPLC pump and a 2487 UV detector and a 1525u binary LC pump with integrated degasser.

Compounds were also characterized by their LCMS-Electrospray/chemical ionization mass spectra (LC ESCI-MS) on one of the following systems:

(1) Waters HPLC-MS system (Waters Corp., Milford, Mass.) equipped with a 2767 Sample Manager, 2545 Binary Gradient Module, SFO System Fluidics Organizer, 2996 Photodiode Array Detector and 3100 Mass Detector. Data were collected across a range of wavelengths from 220-280 nm in positive ESCI mode. Spectra were scanned from 100-1400 atomic mass units (amu). The HPLC column was a Waters XBridge C18 3.5 μm 4.6×30 mm; eluents were A: water with 0.1% formic acid and B: acetonitrile with 0.1% formic acid. Gradient elution was from 5% B-95% B over 2.3 minutes with an initial hold of 0.2 minutes and a final hold at 95% B of 0.5 minutes. The total run time was four minutes.

(2) Waters (Waters Corporation, Milford, Mass.) HPLC-MS system equipped with an Acquity Sample Manager, Acquity Binary Solvent Manager, Acquity Photodiode Array Detector, Acquity Evaporative Light Scattering Detector and SQ Detector. Data were collected at 220 nm and 254 nm and in positive electrospray-chemical ionization mode. The HPLC column used was a Waters Acquity HPLC BEH C18 1.7 um 2.1×50 mm. Spectra were scanned from 100-1400 amu. The eluents were A: water with 0.1% formic acid and B: acetonitrile with 0.1% formic acid. Gradient elution from 5% B to 95% B over 0.8 minutes was used with a final hold at 95% B of 0.2 minutes at a flow rate of 0.8 milliliters per minute. Total run time was 1.5 minutes.

Nuclear magnetic resonance spectra were recorded using a Bruker Avance spectrometer (DPX400 Shielded), a Jeol ECX 400 MHz spectrometer or a Bruker Avance III (400 MHz shielded) spectrometer equipped with a Gradient Multinuclear Broadband Fluorine Observe (BBFO) probe. Spectra were acquired in the indicated solvent. Chemical shifts (δ) are given in ppm (parts per million upfield or downfield from TMS defined as 0 ppm). Coupling constants J are in hertz (Hz). Peak shapes in the NMR spectra are indicated by symbols 'q' (quartet), 't' (triplet), 'd' (doublet), 's' (singlet), 'br s' (broad singlet), 'br' (broad) 'm' (multiplet) and 'br d' (broad doublet).

Abbreviations used herein:

| Abbreviations used herein: | |
|---|---|
| AcOH | Acetic acid |
| Boc | tert-butyloxycarbonyl |
| Celite | Diatomaceous earth |
| DAST | (Diethylamino)sulfur trifluoride |
| DBU | 1,8-Diazabicyclo[5,4,0]undec-7-ene |
| DCM | Dichloromethane |
| DIPEA | N,N-Diisopropylethylamine |
| DMF | Dimethylformamide |
| DCE | Dichloroethane |
| DIEA | N,N-Diisopropylethylamine |
| EDCI | N-(3-dimethylaminopropyl)-N'-ethylcarbodiimide |
| eq. | Equivalent |
| EtOAc | Ethyl acetate |
| HBTU | O-(Benzotriazol-1-yl)-N,N,N',N'-tetramethyluronium hexafluorophosphate |
| HCl | Hydrochloric acid |
| HOAc | Acetic acid |
| HOBt | N-hydroxybenzotriazole |
| iPrOH | Isopropanol |
| KH | Potassium hydride |
| LiOH | Lithium hydroxide |
| MeCN | Acetonitrile |
| MeOH | Methanol |
| NBS | N-bromosuccinimide |
| NCS | N-chlorosuccinimide |
| Pd-(dppf)Cl$_2$ | Dichloro[1,1'-bis(diphenylphosphino)ferrocene] palladium (II) |
| Pd(Ph$_3$P)$_4$ | Tetrakis(triphenylphosphine) palladium(0) |
| Ph$_3$P | Triphenylphosphine |
| TBAI | Tetrabutylammonium iodide |
| TBTU | O-(Benzotriazol-1-yl)-N,N,N',N'-tetramethyluronium tetrafluoroborate |
| t-BuLi | tert-Butyl lithium |
| TEA | Triethylamine |
| TFA | Trifluoroacetic acid |
| THF | Tetrahydrofuran |

Scheme 1

General Synthetic Schemes

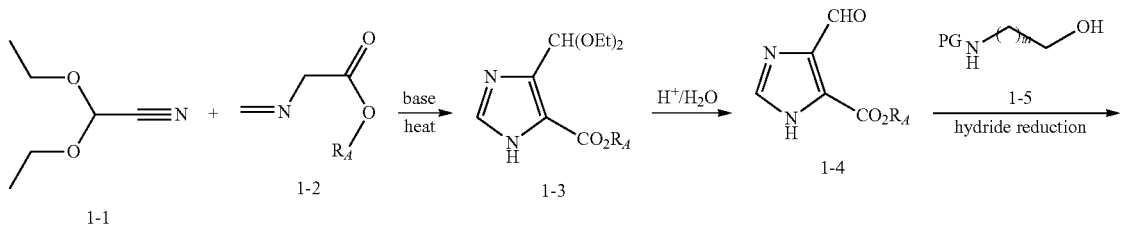

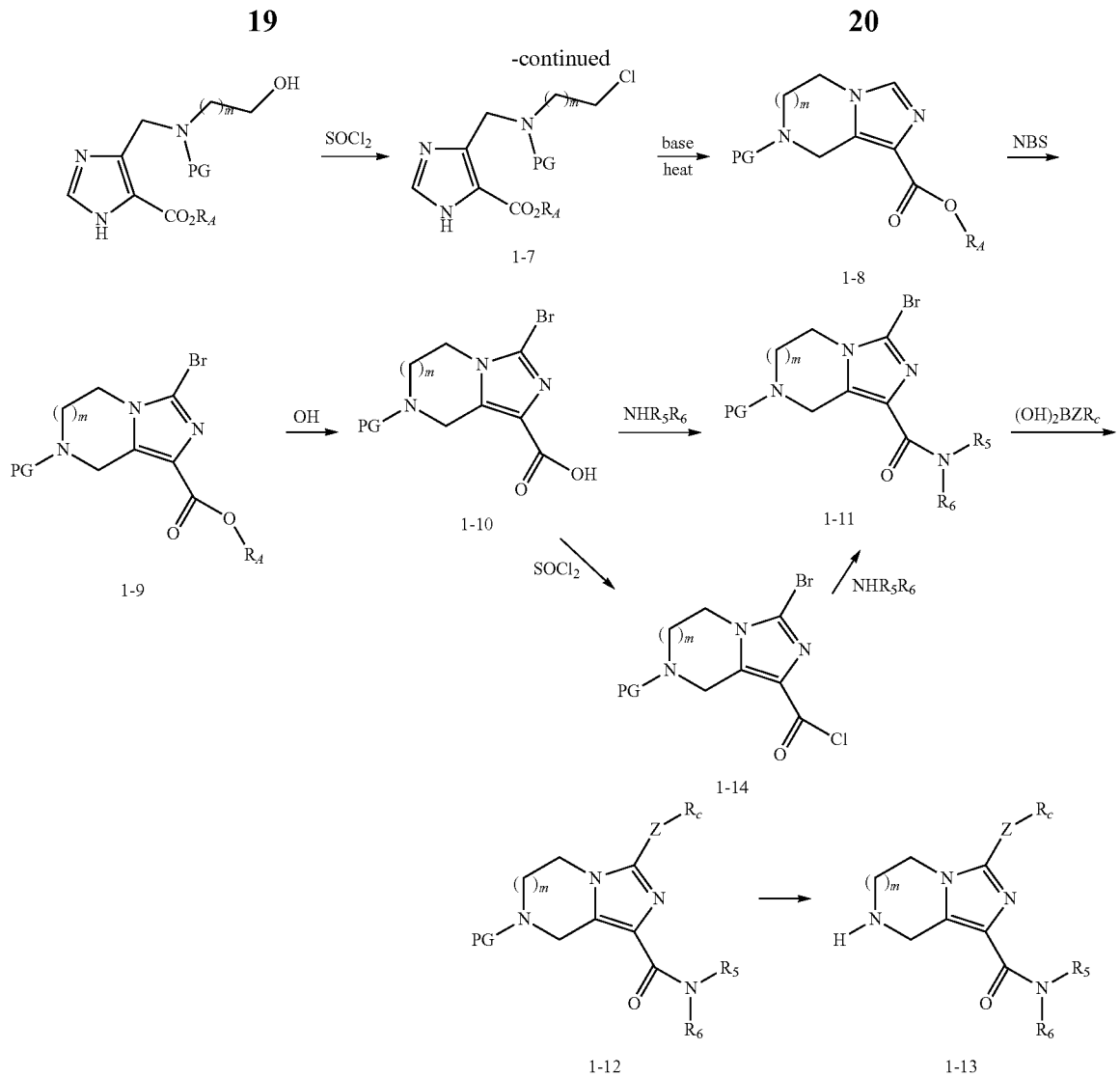

$R_A$ = Me, Ethyl
m = 1, 2

$R_A$ = Me, Ethyl
m = 1, 2

Diethoxyacetonitrile (Compound 1-1) reacts with a 3-iminopropionate ester 1-2 to provide the acetal 1-3. The acetal is converted to the aldehyde 1-4 in acidic conditions such as in the presence of acetic acid. Reductive amination of 1-4 with 1-5 using an appropriately protected hydroxylamine (1-5, PG=protecting group, such as benzyl), provides 1-6.

Conversion of the alcohol to a chloride, 1-7, is accomplished by reaction with a chlorinating reagent such as thionyl chloride. Upon heating with the appropriate base, the compound of formula 1-7 cyclizes to 1-8. Bromination of 1-8 using NBS or bromine provides ester 1-9. (Alternatively, chlorination of 1-8 is accomplished by reacting with NCS).

Hydrolysis of the ester to the acid 1-10 using, for example, a base such as lithium hydroxide followed by coupling of an amine to the acid using a coupling reagent such as EDCI or TBTU or HBTU yields the desired amide 1-11. Alternatively, treatment of acid 1-10 with a chlorination reagent such as thionyl chloride provides acid chloride 1-14 which is then treated with an amine to provide compound of formula 1-11.

Coupling of the bromide 1-11 with a boronic acid under Suzuki reaction conditions gives 1-12. The protecting group is then removed using conditions appropriate to the particular protecting group, to provide compound 1-13. See Protective Groups in Organic Synthesis. 2nd Ed. Greene, Theodora W.; Wuts, Peter G. M. USA. (1991), 473 pp. Publisher: John Wiley and Sons, Inc., New York, N.Y.

In scheme 2, below, treatment of a compound of formula 2-1 with an isothiocyanate or an isocyanate (for example 2-fluorophenylisocyanate) provides 2-2. Alternatively, the amine 2-1 is acylated with a chloroformate derivative or an acid chloride, or sulfonylated with a sulfonyl chloride under basic conditions (such as triethylamine) to give 2-3, 2-4 or 2-5, respectively. In another alternative, the amine of 2-1 is treated with a carboxylic acid using a coupling reagent such as EDCI to provide 2-4.

Reductive amination of 2-1 with an aldehyde or ketone in the presence of a hydride source such as sodium triacetoxyborohydride provides 2-6. Treatment of a compound of formula 2-1 with 1-ethoxycyclopropoxy)trimethylsilane provides a compound of formula 2-7. In still another alternative, compound 2-1 is treated with a halogenated heterocycle such as 2-chloropyrimidine to provide 2-8.

Scheme 2

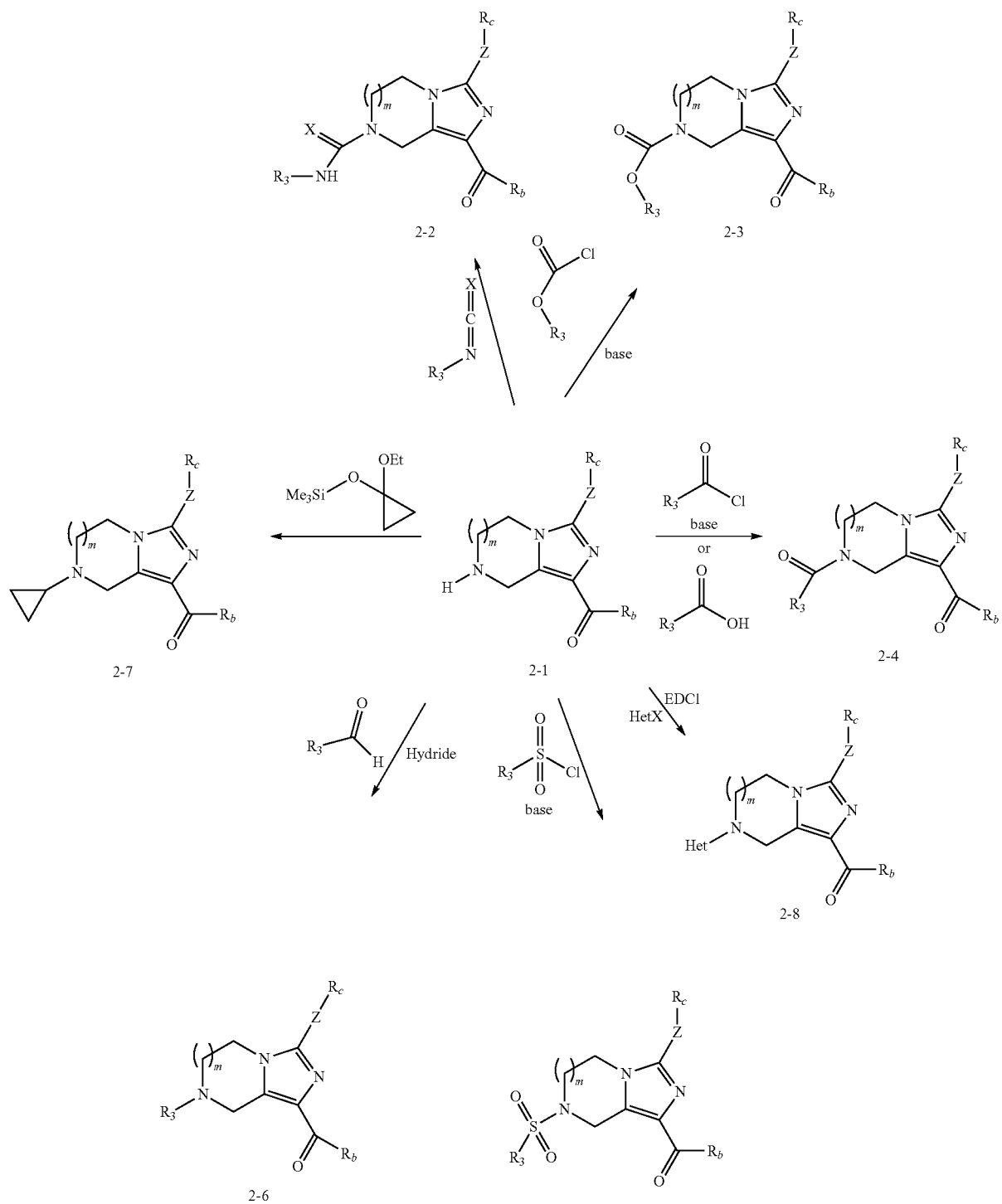

X = O, S
m = 1, 2
Het = heterocyle

As shown in scheme 3, below, intermediate 3-1 is reacted with a diborane such as bis(pinacolato)diboron using an appropriate metal catalyst (such as Pd-(dppf)Cl₂ or Pd(Ph₃P)₄) to give 3-2, which in turn, is treated with an alkyl or aryl halide such as benzyl bromide to provide 3-3. Alternatively, intermediate 3-1 is reacted with a boronic acid or boronic pinacol ester (for example phenylboronic acid) using an appropriate metal catalyst such as palladium acetate or Pd(Ph₃P)₄ to provide 3-4.

Scheme 3

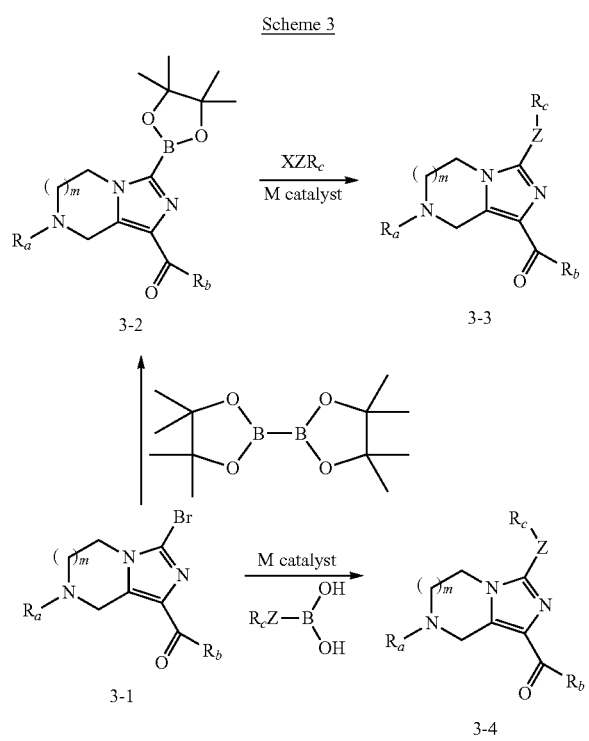

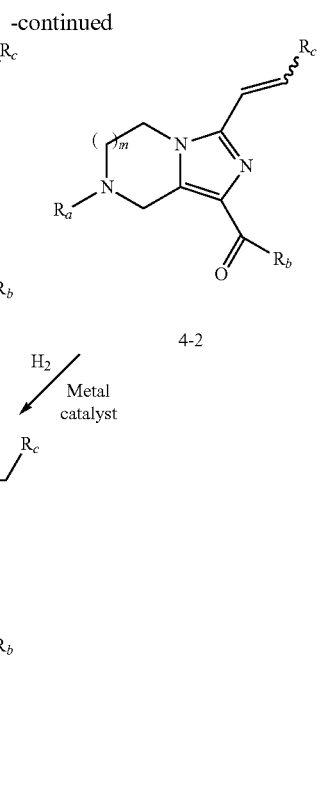

Scheme 4

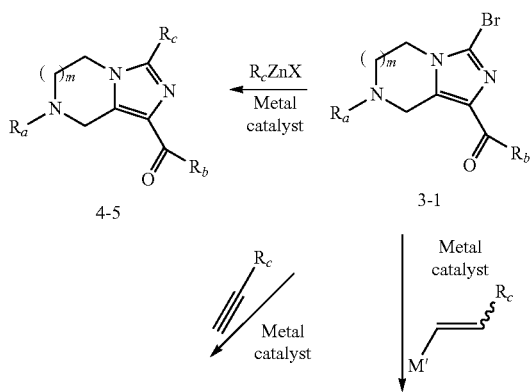

Treatment of a compound of formula 3-1 with a vinyl tin or borane using an appropriate metal catalyst (such as Pd-(dppf)Cl$_2$ or Pd(Ph$_3$P)$_4$) provides compound 4-2. Alternatively, intermediate 3-1 is reacted with a substituted alkyne such as ethynyl benzene or 3-ethynyl pyridine using an appropriate metal catalyst such as, for instance, CuI with triphenylphosphine and a base for example K$_2$CO$_3$ to provide 4-3. Treatment of a compound of formula 4-2 with hydrogen gas under pressure in the presence of a metal catalyst such as palladium on carbon provides compound 4-4. Treatment of 3-1 with an organozinc compound such as 2-thiazolyl bromide in the presence of a catalyst such as Pd-(dppf)Cl$_2$ or PdCl$_2$(Ph$_3$P)$_2$ and CuI provides a compound of formula 4-5.

Scheme 5

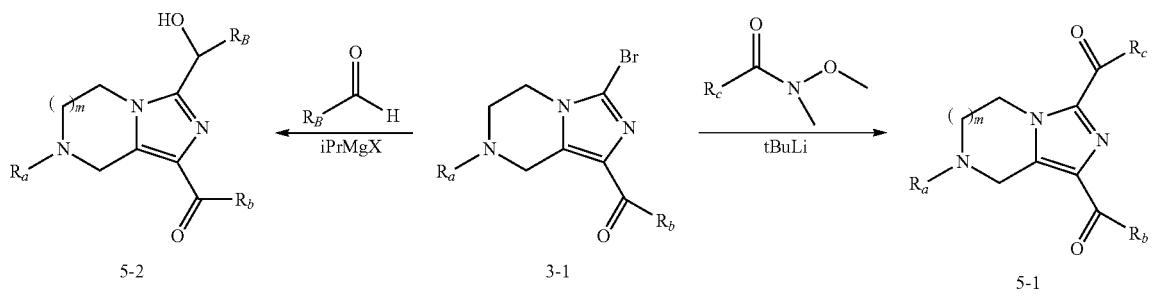

Treatment of a compound of formula 3-1 with a base such as tert-butyl lithium or isopropyl magnesium chloride followed by an electrophile such as a Weinreb amide or aldehyde provides compounds 5-1 and 5-2.

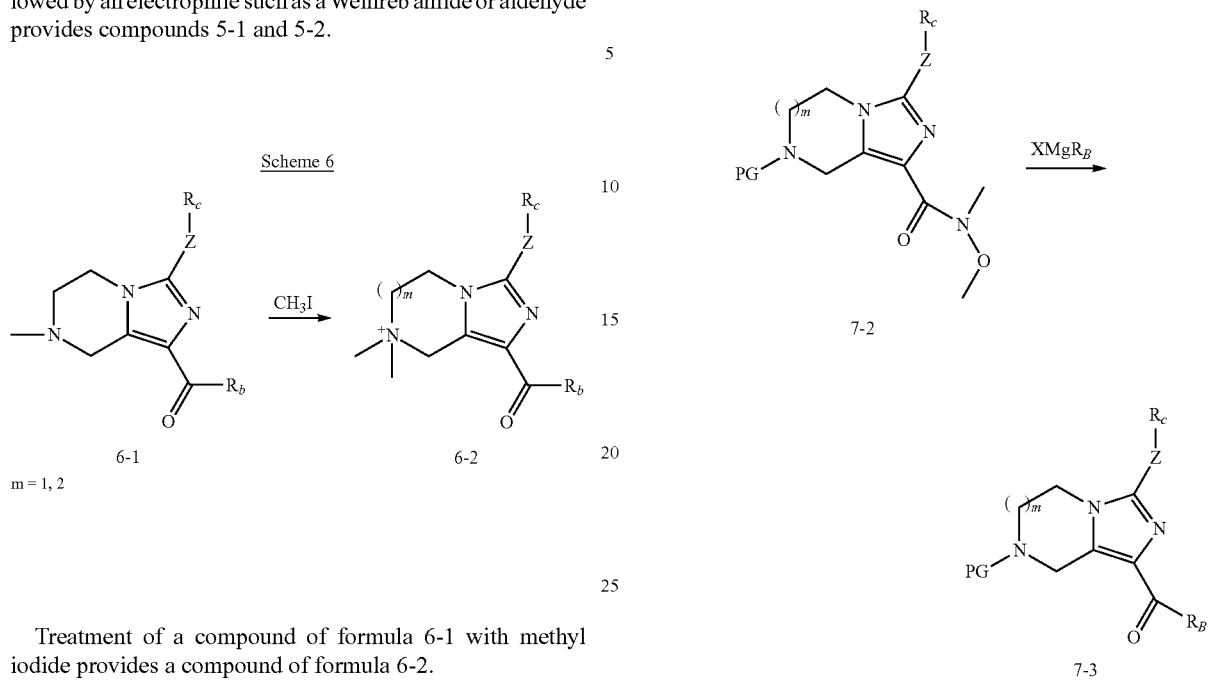

Treatment of a compound of formula 6-1 with methyl iodide provides a compound of formula 6-2.

Treatment of a compound of formula 7-1 with a Grignard reagent such as isopropyl magnesium chloride and N,O-dimethylhydroxylamine provides a compound of formula 7-2. Reaction of a Grignard reagent, such as neopentylmagnesium chloride, with compound 7-2 provides a compound of formula 7-3.

Treatment of a compound of formula 8-1 shown in Scheme 8, below, with an amino ester, such as methyl 2-amino-3,3-dimethylbutanoate, and a coupling reagent such as EDC or TBTU provides compound 8-2. Compound 8-2 is hydrolyzed with a base such as lithium hydroxide to provide the carboxylic acid 8-3.

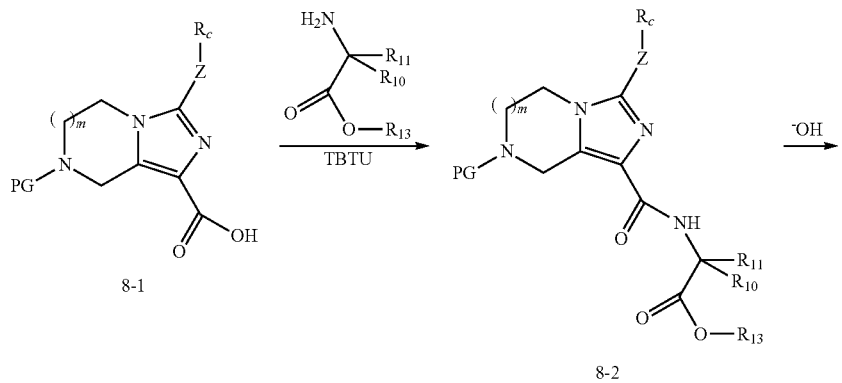

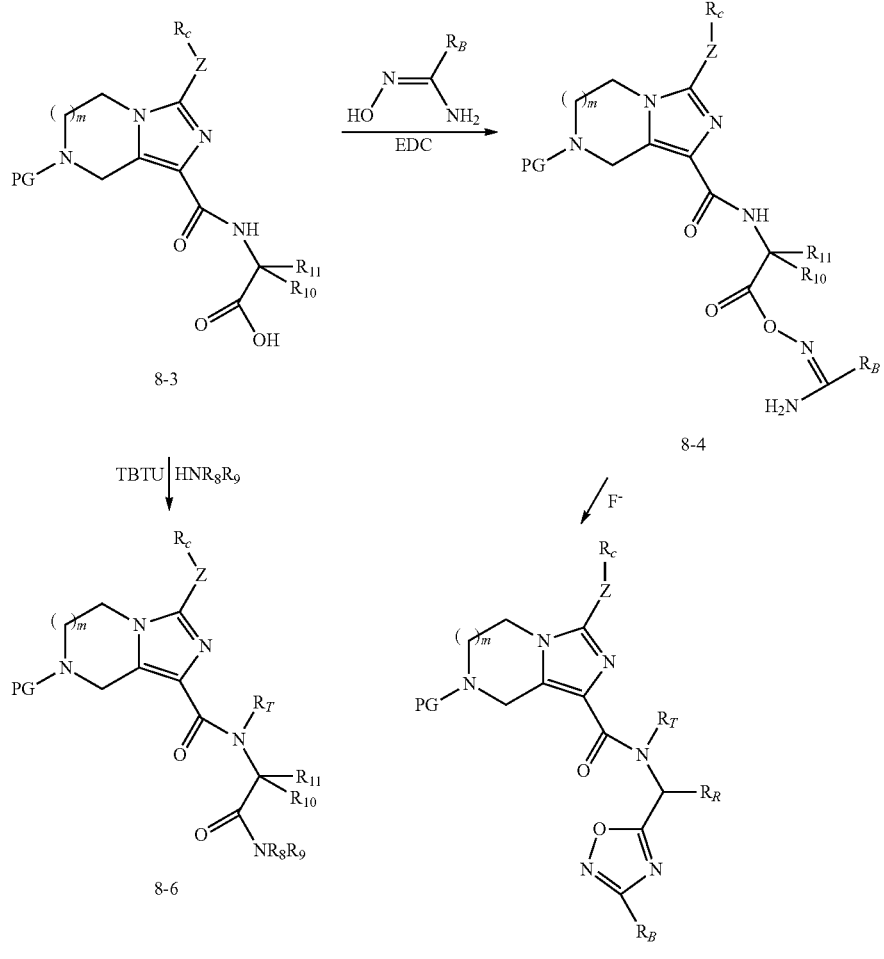

8-3

8-4

8-6

8-5 m = 1, 2
$R_B$ = alkyl, aryl

Treatment of compound 8-3 with an amidoxime derivative such as (Z)—N'-hydroxyacetimidamide provides 8-4 which upon reaction with fluoride anion (for example TBAF) yields compound 8-5. Alternatively, reacting a compound of formula 8-3 with an amine such as ethylamine using a coupling reagent such as TBTU or EDC provides a compound of formula 8-6.

Scheme 9

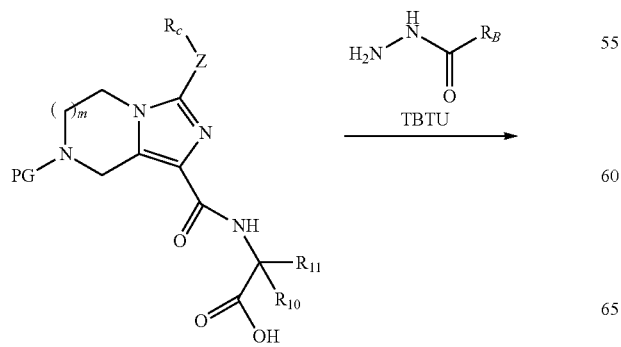

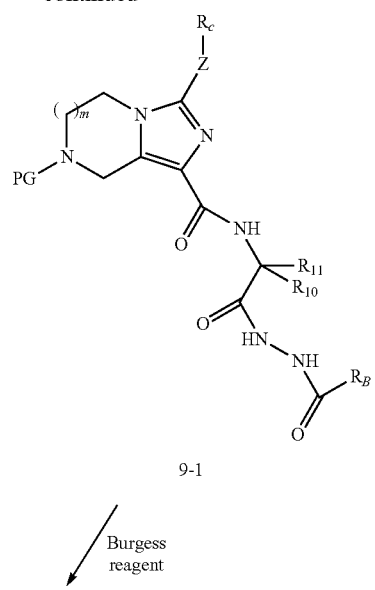

9-1

Burgess reagent

-continued

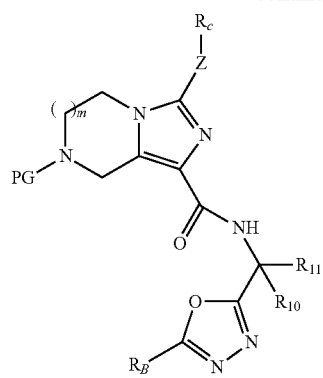

$R_B$ = alkyl, aryl

Treatment of compound 8-3 with a hydrazide such as acetohydrazide and a coupling reagent such as TBTU or EDC provides 9-1, which then provides 9-2 upon further treatment with Burgess reagent.

Scheme 10

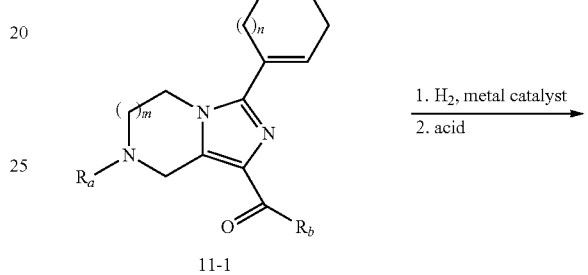

Treatment of a compound of formula 10-1 with an amine such as methylamine hydrochloride and a coupling reagent such as TBTU or EDC provides compound 10-2. Removal the protecting group (for example, a tert-butyloxycarbonyl group, removed with an acid, such at TFA) yields a compound of formula 10-3.

As shown in Scheme 11, below, treatment of a compound of formula 2-1 with a substituted boronic acid or dioxaborolane such as 1,4-dioxaspiro[4.5]dec-7-en-8-ylboronic acid provides a compound of formula 11-1. Reduction of the double bond with hydrogen gas using a metal catalyst such as palladium on carbon followed by treatment with acid such as hydrogen chloride gives compound of formula 11-2. Treatment of 11-2 with a fluorinating reagent such as DAST provides compound 11-3.

Scheme 11

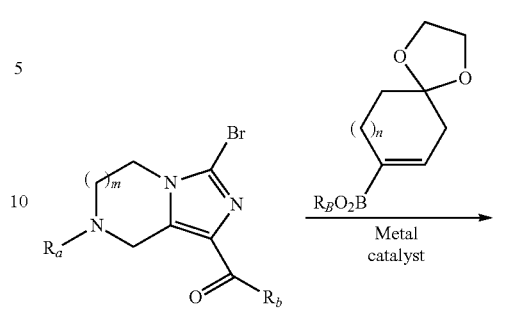

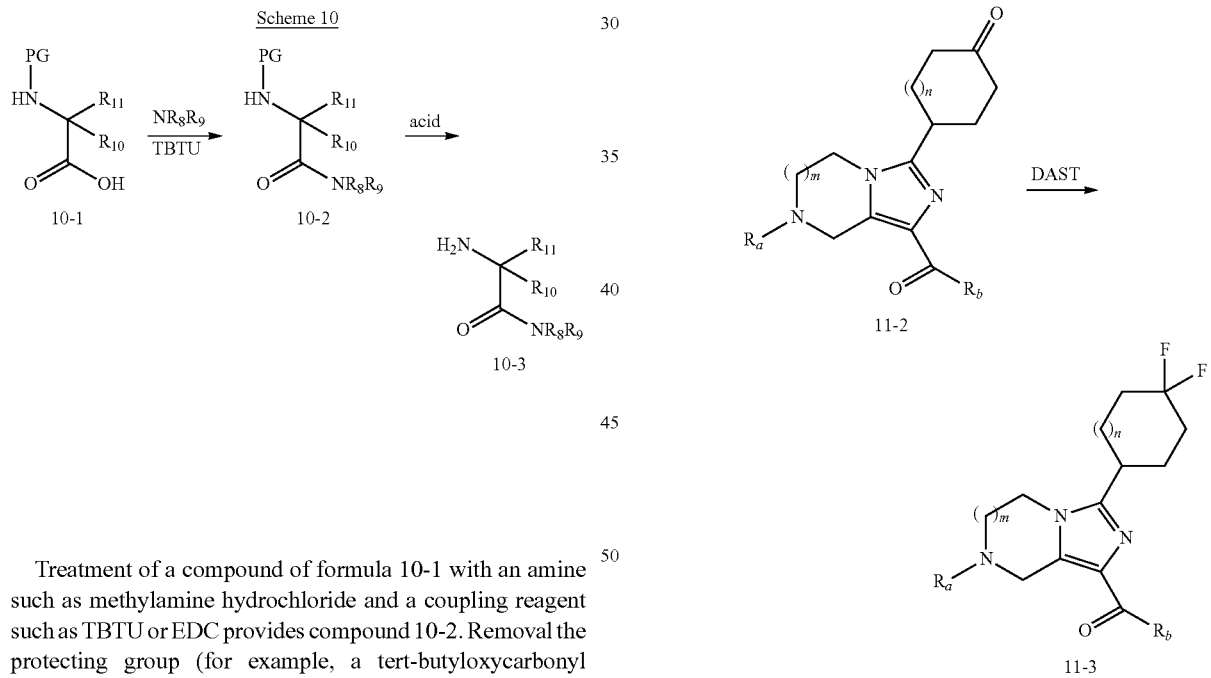

m = 1, 2 n = 0, 1, 2

Example 1

Preparation of (S)-tert-butyl 1-(3,3-dimethyl-1-(methylamino)-1-oxobutan-2-ylcarbamoyl)-3-phenyl-5,6-dihydroimidazo[1,5-a]pyrazine-7(8H)-carboxylate (Compound 1)

Step 1: Preparation of methyl 4-(diethoxymethyl)-1H-imidazole-5-carboxylate (Intermediate 1B). To a stirred suspension of 30-35% KH (7.90 g) in 40 mL anhydrous diglyme at −20° C. was added a solution of diethoxyacetonitrile (Intermediate 1A, 6.20 g, 46.6 mmol) and methyl isocyanoacetate (4.96 g, 65.2 mmol) in 25 mL of anhydrous diglyme. The resulting mixture was heated to 70-80° C. and stirred overnight. The mixture was cooled to room temperature and quenched with saturated NH$_4$Cl solution. DCM was added and the layers were separated. The mixture was further extracted with DCM. The combined organic extracts were dried over anhydrous MgSO$_4$, filtered and concentrated under reduced pressure to give brown oil. Cold ether was added to the residue and the resulting white precipitate was filtered, washed with cold ether and dried to give the desired product Intermediate 1B (5.65 g, 53%) as a white solid.

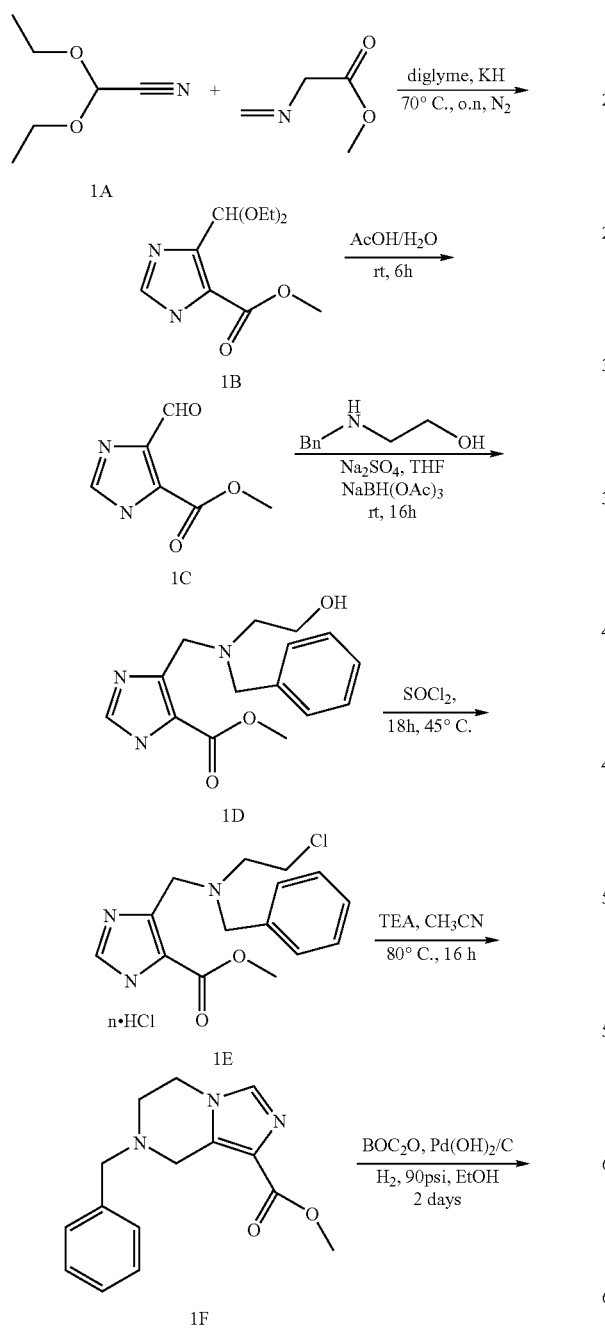

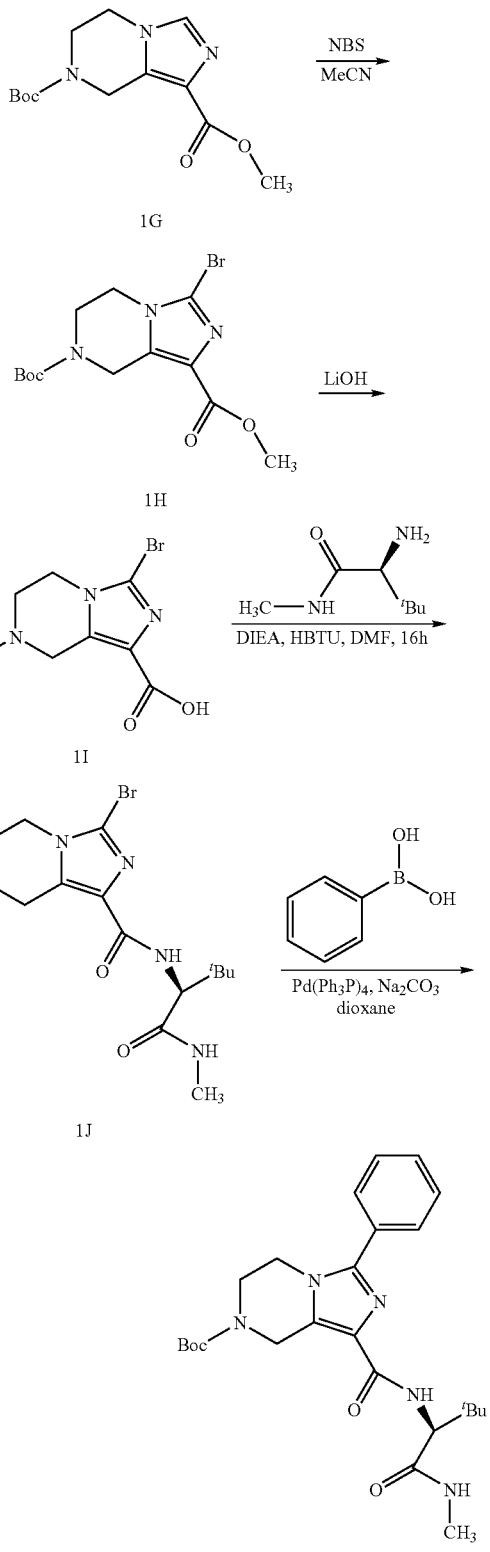

Step 2: Preparation of methyl 4-formyl-1H-imidazole-5-carboxylate (Intermediate 1C). To a solution of Intermediate 1B (5.65 g, 24.75 mmol) in water (12 mL) was added acetic acid (49 mL, 0.86 mol). The resulting mixture was stirred under nitrogen for 6 hours. The reaction mixture was azeotroped with toluene and dried under vacuum to give the desired aldehyde, Intermediate 1C in quantitative yield as a white solid, which was used in the next step without further purification.

Step 3: Preparation of methyl 4-((benzyl(2-hydroxyethyl)amino)methyl)-1H-imidazole-5-carboxylate (Intermediate 1D). To a stirred suspension of Intermediate 1C (3.20 g, 20.76 mmol) in dry THF (180 mL) was added anhydrous $Na_2SO_4$ (14.48 g, 192 mmol) and N-benzylethanolamine (3.70 g, 24.47 mmol). The resulting mixture was stirred at room temperature under nitrogen for 1 hour. Sodium triacetoxyborohydride (6.37 g, 28.5 mmol) was added portion-wise and the resulting mixture was stirred under nitrogen for 48 hours. The resulting mixture was quenched with water and neutralized with saturated $NaHCO_3$ solution. The mixture was extracted with DCM and the combined organic extracts were dried over anhydrous $Na_2SO_4$, filtered and concentrated. The crude mixture was purified using normal phase chromatography eluting with a 10-30% methanol/DCM gradient to provide Intermediate 1D as a white solid (5.80 g, 98%).

Step 4: Preparation of methyl 4-((benzyl(2-chloroethyl)amino)methyl)-1H-imidazole-5-carboxylate hydrochloride (Intermediate 1E). To a solution of Intermediate 1D (0.94 g, 3.24 mmol) in DCM (30 mL) was added thionyl chloride (0.95 mL, 12.96 mmol). The resulting mixture was stirred at 44° C. overnight and allowed to cool to ambient temperature. The mixture was concentrated under reduced pressure, azeotroped with acetonitrile and dried under vacuum overnight to give Intermediate 1E in quantitative yield as a white solid which was used in the next step without further purification.

Step 5: Preparation of methyl 7-benzyl-5,6,7,8-tetrahydroimidazo[1,5-a]pyrazine-1-carboxylate (Intermediate 1F). The chloride, Intermediate 1E (0.97 g, 3.15 mmol) was dissolved in acetonitrile (30 mL) and TEA (1.77 mL, 12.62 mmol) was added drop wise. The resulting mixture was stirred at 80° C. under nitrogen overnight. The mixture was allowed to cool, was filtered and the filtrate was concentrated. The residue was partitioned between DCM and saturated $NaHCO_3$ solution and the phases were separated. The aqueous phase was further extracted with DCM and combined organic extracts were dried over anhydrous $MgSO_4$, filtered and concentrated. The crude residue was purified using normal phase chromatography, eluting with a 0-40% methanol/DCM gradient to provide product Intermediate 1F (0.58 g, 66%) as a brown solid.

Step 6: Preparation of 7-tert-butyl 1-methyl 5,6-dihydroimidazo[1,5-a]pyrazine-1,7(8H)-dicarboxylate (Intermediate 1G). Under a nitrogen atmosphere, the product Intermediate 1F (3.70 g, 13.64 mmol) was dissolved in ethanol (180 mL) and di-tert-butyldicarbonate (3.87 g, 17.73 mmol) was added followed by DIEA (7.15 mL, 40.9 mmol) and 20% palladium hydroxide on carbon (1.92 g, 2.73 mmol). The resulting black suspension was stirred under a hydrogen atmosphere (90 psi) for 48 hours using a Parr hydrogenator. The mixture was filtered through a pad of celite and washed with methanol. The filtrate was concentrated, dissolved in ethyl acetate and washed with saturated $NaHCO_3$ solution and brine. The organic layer was dried over anhydrous $Na_2SO_4$, filtered and concentrated to give the desired product Intermediate 1G as a white solid (3.20 g, 83%) which was used in the next step without further purifications.

Step 7: Preparation of 7-tert-butyl 1-methyl 3-bromo-5,6-dihydroimidazo[1,5-a]pyrazine-1,7(8H)-dicarboxylate (Intermediate 1H). The Intermediate 1G (3.20 g, 11.38 mmol) was dissolved in acetonitrile and NBS (2.43 g, 13.65 mmol) was added. The reaction mixture was stirred at room temperature overnight. The mixture was concentrated and partitioned between ethyl acetate and water. The organic layer was washed with brine, dried over anhydrous $Na_2SO_4$, filtered and concentrated to give a yellow solid. The solid was dissolved in DCM and passed through a silica gel plug, eluting with 10% methanol in DCM to give product Intermediate 1H as a yellow solid (3.90 g, 95%).

Step 8: Preparation of 3-bromo-7-(tert-butoxycarbonyl)-5,6,7,8-tetrahydro-imidazo[1,5-a]pyrazine-1-carboxylic acid (Intermediate 1I). The product Intermediate 1H (0.85 g, 2.36 mmol) was dissolved in methanol (50 mL) and LiOH (0.79 g, 18.88 mmol) in water (10 mL) was added. The resulting solution was stirred at 50° C. overnight. The reaction mixture was concentrated, cooled on ice and brought to pH 3 using 1N HCl. The resulting white precipitate was filtered, washed with water and air dried to give the desired acid Intermediate 1I as a white solid (0.62 g, 76%).

Step 9: Preparation of (S)-tert-butyl 3-bromo-1-(3,3-dimethyl-1-(methylamino)-1-oxobutan-2-ylcarbamoyl)-5,6-dihydroimidazo[1,5-a]pyrazine-7(8H)-carboxylate (Intermediate 1J). Acid Intermediate 1I (0.62 g, 1.79 mmol) was dissolved in DMF and L-tert-Leucine methylamide (0.31 g, 2.14 mmol) was added followed by DIEA (0.94 mL, 5.37 mmol). The resulting mixture was stirred for 20 minutes, HBTU (0.75 g, 1.97 mmol) was added in one portion and the mixture was stirred overnight. The mixture was diluted with water and extracted with ethyl acetate. The organic layer was washed successively with water, then brine, and dried over anhydrous $Na_2SO_4$, filtered and concentrated. The residue was purified by normal phase chromatography, eluting with a 0-10% methanol/DCM gradient to provide product Intermediate 1J as an off-white solid (0.68 g, 80%).

Step 10: Preparation of (S)-tert-butyl 1-(3,3-dimethyl-1-(methylamino)-1-oxobutan-2-ylcarbamoyl)-3-phenyl-5,6-dihydroimidazo[1,5-a]pyrazine-7(8H)-carboxylate (Compound 1). Intermediate 1J (0.20 g, 0.42 mmol) was dissolved in dioxane (4 mL) and phenylboronic acid (0.10 g, 0.85 mmol) was added, followed by 2N $Na_2CO_3$ solution (0.70 mL, 1.39 mmol). The resulting mixture was degassed with nitrogen and tetrakis(triphenylphosphine) palladium(0) (0.073 g, 0.06 mmol) was added. The mixture was heated in a microwave reactor at 150° C. for 20 min. The reaction mixture was filtered through a celite pad, rinsed with methanol and the combined filtrate and washings were concentrated. The residue was purified by normal phase chromatography, eluting with 0-100% hexanes/ethyl acetate to provide Compound 1 as a yellow solid (0.15 g, 75%).

Example 2

Preparation of (S)—N-(3,3-dimethyl-1-(methylamino)-1-oxobutan-2-yl)-3-phenyl-5,6,7,8-tetrahydroimidazo[1,5-a]pyrazine-1-carboxamide (Compound 2)

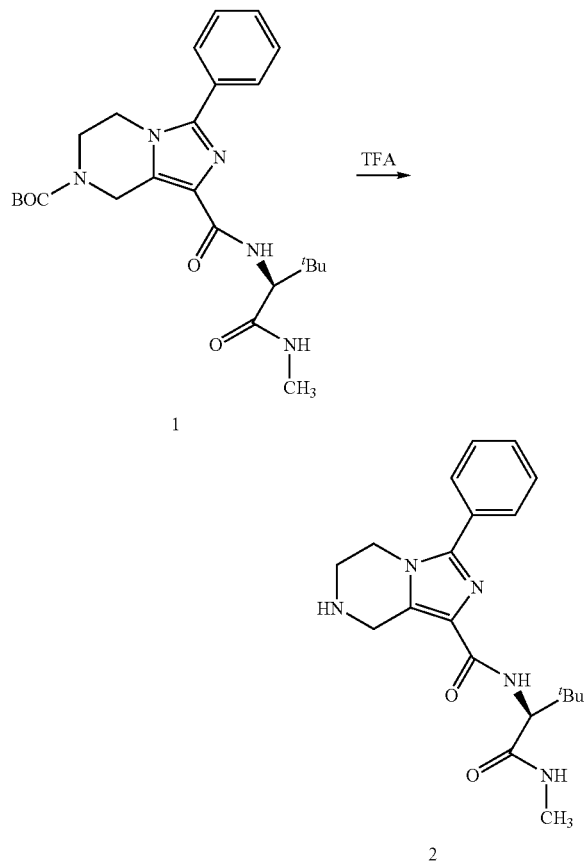

Compound 1 (150 mg, 0.32 mmol) was dissolved in DCM and TFA (0.25 mL, 3.20 mmol) was added. The resulting mixture was stirred overnight. The mixture was concentrated, diluted with DCM and washed with saturated NaHCO$_3$ solution. The filtrate was dried anhydrous Na$_2$SO$_4$, filtered and concentrated. The residue was purified by normal phase chromatography, eluting with 0-30% 1M methanolic ammonia/dichloro-methane to give desired product, Compound 2 as a white solid (0.10 g, 85%). MS: m/z 370.2 [M+H]$^+$. $^1$H-NMR (400 MHz, CD$_3$OD) δ: 1.05 (s, 9H), 2.76 (s, 3H), 3.16 (m, 2H), 4.11 (m, 2H), 4.37 (m, 3H), 7.53 (m, 3H), 7.71 (m, 2H).

Additional Compounds 3-21 were synthesized by the same procedure as described above except that alternative boronic acids were used in place of phenylboronic acid in the reaction with Intermediate 1J to form Intermediate 1. For example, Compound 18 was synthesized using 3-chlorophenyl boronic acid. These intermediates were then deprotected with TFA as described in Example 2 to form additional Compounds 3-21.

Additional compounds 22-29 were synthesized by the same procedure as described above (Examples 1 and 2) for Compound 2 except that in Example 1, alternative amines were used in place of L-tert-Leucine methylamide in the reaction with intermediate Intermediate 1I to form intermediate Intermediate 1J. For example, Compound 22 was synthesized in the same manner as Compound 2 except that (S)-2-amino-3,3-dimethylbutan-1-ol was used in place of L-tert-Leucine methylamide. Compound 23 was synthesized in the same manner as Compound 2 except that (R)-2-amino-3,3-dimethylbutan-1-ol was used in place of L-tert-Leucine methylamide. These resulting intermediates were deprotected with TFA, as described in Example 2, to form additional Compounds 22-29.

Example 3

Preparation of tert-butyl 3-phenyl-1-(1,3,3-trimethylbicyclo[2.2.1]heptan-2-ylcarbamoyl)-5,6-dihydroimidazo[1,5-a]pyrazine-7(8H)-carboxylate (Compound 30)

Step 1: Preparation of 7-tert-butyl 1-methyl 5,6-dihydroimidazo[1,5-a]pyrazine-1,7(8H)-dicarboxylate (Intermediate 1G). To a stirred suspension of 10% Pd/C (5.45 g) in ethanol (150 mL) under nitrogen a solution of Intermediate 1F (10.9 g, 40.17 mmol) and di-tert-butyl dicarbonate (10.85 g, 48.20 mmol) in ethanol (200 mL) was added drop-wise. The resulting mixture was stirred under hydrogen (90 psi) at 50° C. for 2 days. The reaction mixture was allowed to cool to room temperature. The catalyst was removed by filtration through Celite and washed with methanol and ethanol. The combined washings and filtrate were concentrated under reduced pressure to give the crude product, which was purified by column chromatography silica) eluting with ethyl acetate in hexane mixtures to give Intermediate 1G as a white solid at 80% yield. $^1$H-NMR (400 MHz, CDCl$_3$) δ: 1.49 (s, 9H), 3.83 (m, 2H), 3.89 (s, 3H), 4.05 (m, 2H), 4.90 (s, 2H), 7.45 (s, 1H). LCMS (+ESI) m/z 282.21 [M+H]$^+$.

Step 2: Preparation of 7-tert-butyl 1-methyl 3-bromo-5,6-dihydroimidazo[1,5-a]pyrazine-1,7(8H)-dicarboxylate (Intermediate 1H). To a stirred solution of Intermediate 1G (2 g, 7.11 mmol) in anhydrous acetonitrile (30 mL) at room temperature, NBS (1.30 g, 7.11 mmol) was added in one portion. The resulting mixture was stirred at room temperature in the dark for 24 hours. The solvent was removed under reduced pressure and the residue was diluted with ethyl acetate. A saturated aqueous solution of sodium sulfite was added and the biphasic mixture was stirred vigorously at room temperature for 30 minutes. The aqueous phase was separated and the organic layer was washed twice with brine, dried over anhydrous MgSO$_4$, filtered and evaporated under reduced pressure to give the crude product which was purified by column chromatography (silica), eluting with ethyl acetate/hexane mixtures to give Intermediate 1H as a white solid at 60% yield. $^1$H-NMR (400 MHz, CDCl$_3$) δ: 1.52 (s, 9H), 3.85 (m, 2H), 3.89 (s, 3H), 3.93 (m, 2H), 4.89 (s, 2H). LCMS (+ESI) m/z 362.16 [M+H]$^+$, 360.16 [M+H]$^+$.

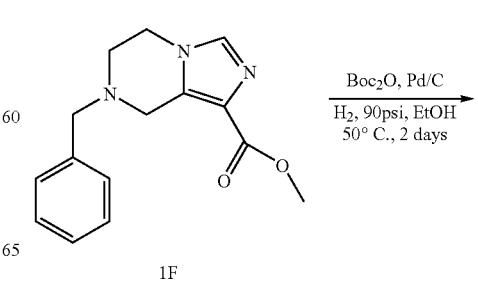

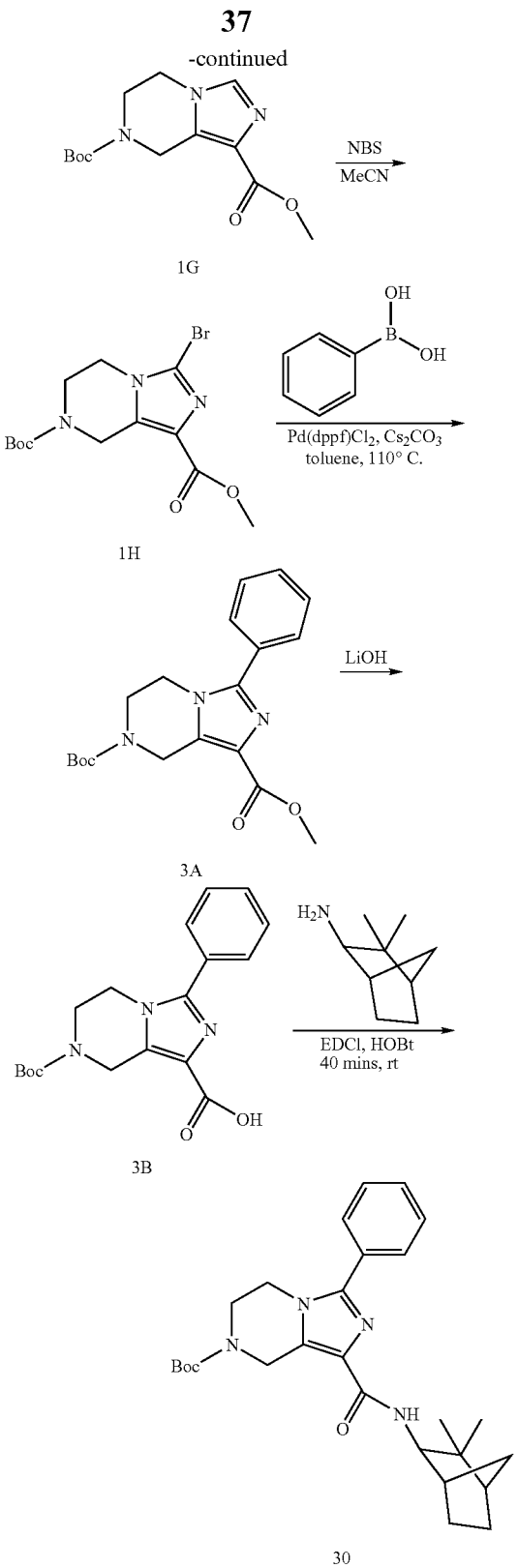

g, 16.65 mmol), [Pd-(dppf)Cl₂] (0.45 g, 10 mol %), and cesium carbonate (5.45 g, 16.65 mmol) was added toluene (anhydrous and de-gassed; 80 mL). The reaction mixture was heated to 110° C. while stirring under argon for 6 hours. After cooling to room temperature, saturated aqueous NaHCO₃ solution was added and the mixture was extracted three times with ethyl acetate. The combined extracts were dried over anhydrous MgSO₄, filtered and concentrated under reduced pressure to give the crude product. Purification by column chromatography (silica), eluting with ethyl acetate/hexane mixtures, provided Intermediate 3A as a white solid (70% yield). $^1$H-NMR (400 MHz, CDCl₃) δ: 1.52 (s, 9H), 3.79 (m, 2H), 3.93 (s, 3H), 4.12 (m, 2H), 5.00 (s, 2H), 7.43-7.47 (m, 3H), 7.63-7.66 (m, 2H). LCMS (+ESI) m/z 358.28 [M+H]⁺.

Step 4: Preparation of 7-(tert-butoxycarbonyl)-3-phenyl-5, 6,7,8-tetrahydro-imidazo[1,5-a]pyrazine-1-carboxylic acid (Intermediate 3B). To 7-tert-butyl 1-methyl 3-phenyl-5,6-dihydroimidazo[1,5-a]pyrazine-1,7(8H)-dicarboxylate (3A) (1.6 g, 4.47 mmol) in THF (50 mL) was added aqueous LiOH (0.7 g in 18.5 mL water) and ethanol (13 mL). The resulting mixture was stirred at room temperature for 2 days. The reaction mixture was concentrated under reduced pressure, diluted with water and acidified to pH 4 with 1N aqueous HCl solution. The aqueous suspension was extracted 3 times with ethyl acetate. The combined organic extracts were washed with brine, dried over anhydrous MgSO₄, filtered and concentrated under reduced pressure to give Intermediate 3B as a white solid in quantitative yield. The material was used in the next step without further purification. $^1$H-NMR (400 MHz, CDCl₃) δ: 1.52 (s, 9H), 3.81 (m, 2H), 4:14 (m, 2H), 5.02 (s, 2H), 7.46-7.51 (m, 3H), 7.62-7.68 (m, 2H). LCMS (+ESI) m/z 344.23 [M+H]⁺.

Step 5: Synthesis of Compound 30. To intermediate 3B (0.47 g, 1.36 mmol) in anhydrous DMF (20 mL) was added EDCI (0.415 g, 2.16 mmol), HOBt (0.238 g, 1.76 mmol) and TEA (0.35 g, 3.4 mmol). After 40 min, (1,3,3-trimethylbicyclo[2.2.1]hept-2-yl)amine hydrochloride (0.325 g, 1.66 mmol) was added and the reaction mixture was stirred overnight. The solvent was evaporated and the residue was diluted with ethyl acetate and washed with 1N aqueous HCl solution and brine. The organic layer was dried over anhydrous Na₂SO₄, filtered and concentrated under reduced pressure to give the crude product, which was purified by column chromatography (silica), eluting with ethyl acetate/hexane mixtures to give Compound 30 as a white solid (79% yield). $^1$H-NMR (400 MHz, CDCl₃) [as rotamers] δ: 0.87 (s, 3H), 1.10 (s, 3H), 1.16 (s, 3H), 1.20-1.26 (m, 2H), 1.48-1.51 (m, 2H), 1.51 (s, 9H), 1.62-1.73 (m, 2H), 1.79 (s, 1H), 3.70-3.80 (m, 3H), 4.11 (m, 2H), 5.07 (m, 2H), 7.28 (br, 1H), 7.43-7.51 (m, 3H), 7.62-7.66 (m, 2H). LCMS (+ESI) m/z 479.48 [M+H]⁺.

Compounds 31-38 were synthesized by the same procedure as detailed above for Compound 30 except that phenyl boronic acid or 4-chlorophenyl boronic acid was used in step 3 and 1,3,3-trimethylbicyclo[2.2.1]heptan-2-amine in step 5 was replaced with an alternative amine. For example, Compound 32 was prepared using aniline as the amine in step 5.

Step 3: Preparation of 7-tert-butyl 1-methyl 3-phenyl-5,6-dihydroimidazo[1,5-a]pyrazine-1,7(8H)-dicarboxylate (Intermediate 3A). To a round-bottomed flask charged with Intermediate 1H (2 g, 5.55 mmol), phenyl boronic acid (2.07

Example 4

Preparation of 3-Phenyl-N-(1,3,3-trimethylbicyclo[2.2.1]heptan-2-yl)-5,6,7,8-tetrahydro-imidazo[1,5-a]pyrazine-1-carboxamide HCl (Compound 39)

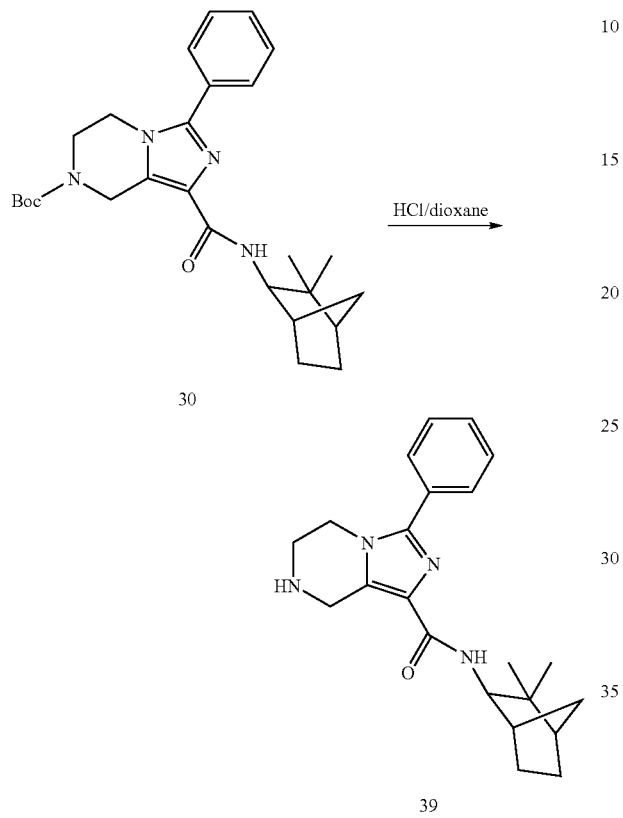

To a cooled (0° C.) and stirred solution of Compound 30 (0.5 g, 1.04 mmol) in dry DCM (10 mL) was added hydrogen chloride [4M in 1,4-dioxane] (5.2 mL, 20.8 mmol). The mixture was warmed to ambient temperature and left to stir overnight (with a calcium chloride drying tube). The reaction solvents were removed under reduced pressure, and the residue was azeotroped twice with methanol and diethyl ether to give the title compound as a white solid in quantitative yield. LCMS (+ESI) m/z 379.36 [M+H]$^+$.

Compounds 40-47 were prepared essentially as described above for the preparation of compound 39 except that Compound 30 was replaced with Compounds 31, 32, 33, 34, 35, 37, 38, and 36, respectively.

Example 5

Preparation of (S)—N-(3,3-dimethyl-1-(methylamino)-1-oxobutan-2-yl)-7-methyl-3-phenyl-5,6,7,8-tetrahydroimidazo[1,5-a]pyrazine-1-carboxamide (Compound 48)

Compound 2 (140 mg, 0.38 mmol) was dissolved in THF and cooled to 0° C. Formaldehyde solution (37% in water, 30 mL, 3.80 mmol) was added, followed by sodium triacetoxyborohydride (112 mg, 0.53 mmol) and acetic acid (27 mg, 0.45 mmol). The reaction mixture was brought to ambient temperature and stirred overnight.

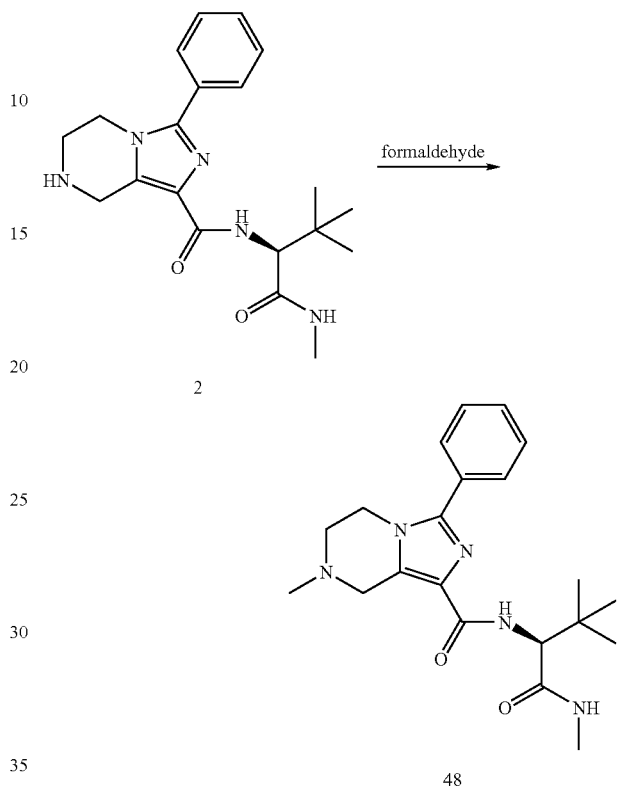

The reaction mixture was quenched with saturated NaHCO$_3$ solution and stirred for 10 minutes. The mixture was diluted with DCM and the organic layer was separated, washed with brine, and dried over anhydrous Na$_2$SO$_4$ and concentrated. The residue was purified by reverse phase chromatography, eluting with acetonitrile/water/0.5% acetic acid to provide the desired product, Compound 48 (84 mg, 58%) as a white solid. MS: m/z 384.24 [M+H]$^+$. $^1$H-NMR (400 MHz, CD$_3$OD) δ: 1.05 (s, 9H), 2.53 (s, 3H), 2.73 (s, 3H), 2.86 (m, 2H), 4.01 (dd, 2H), 4.18 (m, 2H), 4.32 (s, 1H), 7.52 (m, 3H), 7.71 (m, 2H).

Compound 49 was synthesized by the same procedure as described above for Compound 48, above, except that Compound 9 was used in place of Compound 2. Similarly, Compound 50 was synthesized by the same procedure as described above for Compound 48 except that Compound 26 was used in place of Compound 2. In a like manner, Compound 51 was synthesized by the same procedure as described above for Compound 48 except that compound 27 was used in place of Compound 2.

Compound 52 was synthesized by the same procedure as described above for Compound 48 except that Compound 26 was used in place of Compound 2 and isobutyraldehyde was used in place of formaldehyde. Similarly, compound 53 was synthesized by the same procedure as described above for Compound 48 except that compound 27 was used in place of Compound 2 and isobutyraldehyde was used in place of formaldehyde. Likewise, Compound 54 was synthesized by the same procedure as described above for Compound 48 except that a 3,3-dimethylbutanal (2 eq) was used instead of formaldehyde.

Compound 55 was synthesized by the same procedure as described above for Compound 48 except that pivaldehyde was used in place of formaldehyde. Similarly, Compound 56 was synthesized by the same procedure as described above for Compound 48 except that cyclopropane carboxaldehyde was used in place of formaldehyde. Likewise, Compound 57 was synthesized by the same procedure as described above for Compound 48 except that Compound 24 was used in place of Compound 2. Compound 58 was synthesized by the same procedure as described above for Compound 48 except that Compound 24 was used in place of Compound 2 and isobutyraldehyde was used in place of formaldehyde. Similarly, Compound 59 was synthesized by the same procedure as described above for Compound 48 except that Compound 22 was used in place of Compound 2. In a similar fashion, Compound 60 was synthesized by the same procedure as described above for Compound 2 except that Compound 22 was used in place of Compound 2 and isobutyraldehyde was used in place of formaldehyde.

Compound 61 was synthesized by the same procedure as described above for Compound 48 except that benzaldehyde (3 eq) was used in place of formaldehyde. Likewise, Compound 62 was synthesized by the same procedure as described above for Compound 48 except that pyrimidine-5-carbaldehyde (3 eq) was used in place of formaldehyde. Similarly, Compound 63 was synthesized by the same procedure as described above for Compound 48 except that nicotinaldehyde (3 eq) was used in place of formaldehyde. In a similar fashion, Compound 64 was synthesized by the same procedure as described above for Compound 48 except that furan-2-carbaldehyde (3 eq) was used in place of formaldehyde.

Compound 65 was synthesized by the same procedure as described above for Compound 48 except that 1-methyl-1H-pyrazole-5-carbaldehyde (3 eq) was used in place of formaldehyde. Similarly, Compound 66 was synthesized by the same procedure as described above for Compound 48 except that 1-methyl-1H-pyrazole-4-carbaldehyde (3 eq) was used in place of formaldehyde. Likewise, Compound 67 was synthesized by the same procedure as described above for Compound 48 except that Compound 23 was used in place of Compound 2.

Compound 68 was synthesized by the same procedure as described above for Compound 48 except that Compound 23 was used in place of Compound 2 and isobutyraldehyde was used in place of formaldehyde. Similarly, Compound 69 was synthesized by the same procedure as described above for Compound 48 except that Compound 25 was used in place of Compound 2. Likewise, Compound 70 was synthesized by the same procedure as described above for Compound 48 except that Compound 25 was used in place of Compound 2 and isobutyraldehyde was used in place of formaldehyde.

Compound 71 was synthesized by the same procedure as described above for Compound 48 except that 1-methyl-1H-pyrrole-2-carbaldehyde (3 eq) was used in place of formaldehyde. Similarly, Compound 72 was synthesized by the same procedure as described above for Compound 48 except that thiazole-2-carbaldehyde (3 eq) was used in place of formaldehyde. Likewise, Compound 73 was synthesized by the same procedure as described above for Compound 48 except that Compound 11 was used in place of Compound 2.

Compound 74 was synthesized by the same procedure as described above for Compound 48 except that Compound 11 was used in place of Compound 2 and cyclopropanecarbaldehyde was used in place of formaldehyde. Similarly, Compound 75 was synthesized by the same procedure as described above for Compound 48 except that Compound 20 was used in place of Compound 2. Likewise, Compound 76 was synthesized by the same procedure as described above for Compound 48 except that Compound 11 was used in place of Compound 2 and pyrimidine-5-carbaldehyde was used in place of formaldehyde.

Compound 77 was synthesized by the same procedure as described above for Compound 48 except that Compound 28 was used in place of 2 and pyrimidine-5-carbaldehyde was used in place of formaldehyde. Similarly, Compound 78 was synthesized by the same procedure as described above for Compound 48 except that Compound 28 was used in place of Compound 2. Likewise, Compound 79 was synthesized by the same procedure as described above for Compound 48 except that Compound 196 was used in place of Compound 2.

Compound 80 was synthesized by the same procedure as described above for Compound 48 except that Compound 196 was used in place of Compound 2 and isobutyraldehyde was used in place of formaldehyde. Similarly, Compound 81 was synthesized by the same procedure as described above for Compound 48 except that Compound 21 was used in place of Compound 2. Likewise, compound Compound 82 was synthesized by the same procedure as described above for Compound 48 except that Compound 29 was used in place of Compound 2.

Compound 83 was synthesized by the same procedure as described above for Compound 48 except that Compound 29 was used in place of Compound 2 and cyclopropanecarbaldehyde was used in place of formaldehyde. Similarly, Compound 84 was synthesized by the same procedure as described above for Compound 48 except that Compound 22 was used in place of Compound 2 and cyclopropanecarbaldehyde was used in place of formaldehyde. Likewise, Compound 85 was synthesized by the same procedure as described above for Compound 48 except that acetone was used in place of formaldehyde.

Compound 86 was synthesized by the same procedures as described above for Compound 48 except that in Example 1, step 9, (S)-methyl 2-amino-3,3-dimethylbutanoate was used in place of L-tert-Leucine methylamide. Similarly, Compound 87 was synthesized by the same procedure as described above for Compound 48 except that Compound 282 was used in place of Compound 2. Likewise, Compound 88 was synthesized by the same procedure as described above for Compound 48 except that compound Compound 282 was used in place of Compound 2 and cyclopropane-carbaldehyde was used in place of formaldehyde.

Compound 89 was synthesized by the same procedure as described above for Compound 48 except that Compound 282 was used in place of Compound 2 and acetone was used in place of formaldehyde. Similarly, Compound 90 was synthesized by the same procedure as described above for Compound 48 except that compound Compound 282 was used in place of Compound 2 and isobutyraldehyde was used in place of formaldehyde.

Example 6

Preparation of (S)—N-(3,3-dimethyl-1-(methylamino)-1-oxobutan-2-yl)-7-(ethylsulfonyl)-3-phenyl-5,6,7,8-tetrahydroimidazo[1,5-a]pyrazine-1-carboxamide (Compound 91)

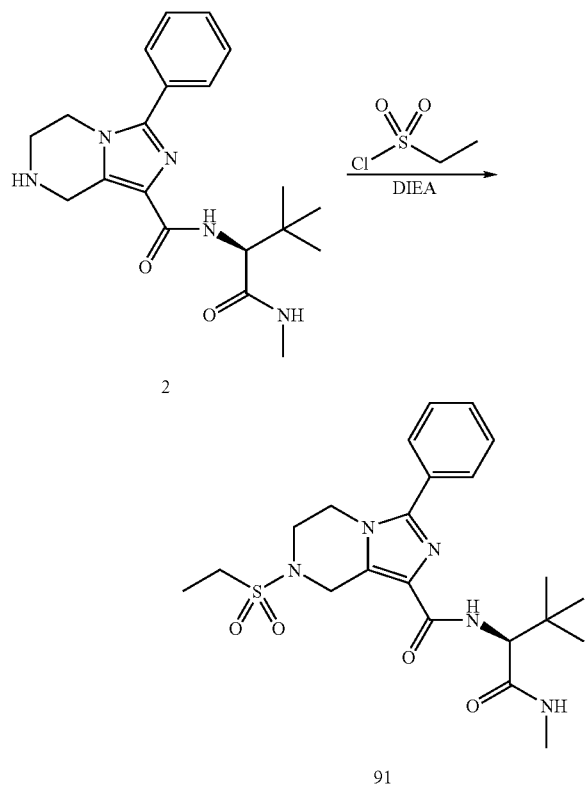

Compound 2 (150 mg, 0.41 mmol) was dissolved in DCM and cooled to 0° C. Ethanesulfonyl chloride (62.2 mg, 0.49 mmol) was added, followed by DIEA (0.21 mL, 1.22 mmol). The reaction mixture was allowed to warm to ambient temperature and stirred overnight. The mixture was diluted with DCM and washed with saturated NaHCO₃ solution. The organic layer was separated, washed with brine, dried over anhydrous Na₂SO₄ and concentrated. The residue was purified by normal phase chromatography eluting with 10-50% methanol/DCM gradient to provide Compound 91 as a white solid (0.13 g, 69%). MS: m/z 462.34 [M+H]⁺.

Compound 92 was synthesized by the same procedure as described above for Compound 91 except that methylsulfonyl chloride was used in place of ethanesulfonyl chloride. Similarly, Compound 93 was synthesized by the same procedure described above for Compound 91 except that 4-fluorobenzenesulfonyl chloride was used in place of ethanesulfonyl chloride. Likewise, Compound 94 was synthesized by the same procedure as described above for Compound 91 except that propane-2-sulfonylchloride was used in place of ethylsulfonylchloride.

Compound 95 was synthesized by the same procedure as described above for Compound 91 except that 2-methylpropane-1-sulfonylchloride was used in place of ethylsulfonylchloride. Similarly, Compound 96 was synthesized by the same procedure as described above for Compound 91 except that benzenesulfonyl chloride was used in place of ethylsulfonylchloride. Likewise, Compound 97 was synthesized by the same procedure as described above for Compound 91 except that 2-nitrobenzene-1-sulfonyl chloride was used in place of ethylsulfonylchloride.

Compound 98 was synthesized by the same procedure as described above for Compound 91 except that 2-fluorobenzene-1-sulfonylchloride was used in place of ethylsulfonylchloride. Similarly, Compound 99 was synthesized by the same procedure as described above for Compound 91 except that 3-fluorobenzene-1-sulfonyl chloride was used in place of ethylsulfonylchloride. Likewise, Compound 100 was synthesized by the same procedure as described above for Compound 91 except that cyclopropanesulfonyl chloride was used in place of ethylsulfonylchloride.

Compound 101 was synthesized by the same procedure as described above for Compound 91 except that Compound 22, was used in place of 2 and 4-fluorobenzene-1-sulfonylchloride was used in place of ethylsulfonylchloride. Similarly, Compound 102 was synthesized by the same procedure as described above for Compound 91 except that Compound 22, was used in place of Compound 2 and benzenesulfonylchloride was used in place of ethylsulfonylchloride. Likewise, Compound 103 was synthesized by the same procedure as described above for Compound 91 except that Compound 24, was used in place of Compound 2 and 4-fluorobenzene-1-sulfonylchloride was used in place of ethylsulfonylchloride.

Compound 104 was synthesized by the same procedure as described above for Compound 91 except that Compound 24, was used in place of Compound 2 and benzenesulfonylchloride was used in place of ethylsulfonylchloride. Similarly, Compound 105 was synthesized by the same procedure as described above for Compound 91 except that Compound 25, was used in place of Compound 2 and 4-fluorobenzene-1-sulfonyl-chloride was used in place of ethylsulfonylchloride. Likewise, Compound 106 was synthesized by the same procedure as described above for Compound 91 except that 4-chlorobenzene-1-sulfonylchloride was used in place of ethylsulfonylchloride.

Compound 107 was synthesized by the same procedure as described above for Compound 91 except that 4-trifluoromethylbenzene-1-sulfonylchloride was used in place of ethylsulfonylchloride. Similarly, Compound 108 was synthesized by the same procedure as described above for Compound 91 except that 4-cyanobenzene-1-sulfonyl chloride was used in place of ethylsulfonylchloride. Likewise, Compound 109 was synthesized by the same procedure as described above for Compound 91 except that Compound 11, was used in place of Compound 2 and 4-fluorobenzene-1-sulfonylchloride was used in place of ethylsulfonylchloride.

Compound 110 was synthesized by the same procedure as described above for Compound 91 except that (S)-amino-N-methylpropanamide was used in place of L-tert-leucine methylamide and 4-fluorobenzene-1-sulfonylchloride was used in place of ethylsulfonylchloride.

Example 7

Preparation of (R)—N-(1-cyclohexylethyl)-7-(ethyl-sulfonyl)-3-phenyl-5,6,7,8-tetrahydroimidazo[1,5-a]pyrazine-1-carboxamide (Compound 111)

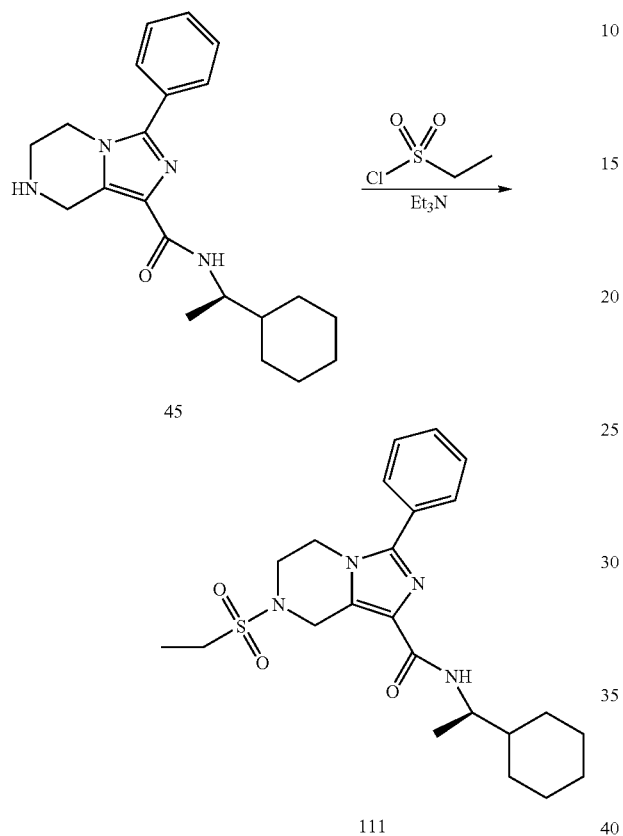

To Compound 45 (1 eq. in 1 mL of anhydrous DMF) was added TEA (5 eq.). An aliquot of ethylsulphonylchloride (1.2 eq. in 1 mL of anhydrous DMF) was then added to the vial which was sealed and stirred overnight at room temperature. The solvent was removed by centrifugal evaporation at reduced pressure. The residue was dissolved in DCM (2 mL), and washed sequentially with 10% $K_2CO_3$ solution (1 mL) and water (2×1 mL). The combined organic extracts were evaporated to dryness under reduced pressure. The desired product, Compound III, was isolated by mass directed LC. $^1$H-NMR (400 MHz, CDCl$_3$) δ: 1.00-1.29 (m, 5H), 1.18 (d, 3H, J=6.8), 1.38-1.46 (m, 1H), 1.40 (t, 3H, J=7.4), 1.60-1.68 (m, 1H), 1.70-1.85 (m, 4H), 3.15 (q, 2H, J=7.4), 3.69-3.73 (m, 2H), 3.94-4.02 (m, 1H), 4.16-4.20 (m, 2H), 5.01 (s, 2H), 6.94 (br d, 1H), 7.44-7.52 (m, 3H), 7.60-7.64 (m, 2H). LCMS (+ESI) m/z 445.15 [M+H]$^+$.

Compound 112 was synthesized by the same procedure as described above for Compound 111 except that Compound 39, was used in place of Compound 45. Compound 113 was synthesized by the same procedure as described above for Compound 111 except that Compound 40 was used in place of Compound 45. Compound 114 was synthesized by the same procedure as described above for Compound III except that Compound 41 was used in place of Compound 45.

Similarly, compounds 115-118 were synthesized by the same procedure as described above for compound 111 except that compounds 44, 42, 46 or 47, respectively, were used in place of compound 45.

Example 8

Preparation of 7-(cyclopropanecarbonyl)-3-phenyl-N-(1,3,3-trimethyl-bicyclo[2.2.1]heptan-2-yl)-5,6,7,8-tetrahydroimidazo[1,5-a]pyrazine-1-carboxamide (Compound 119)

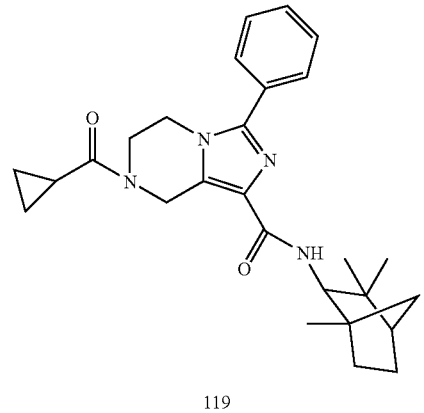

To a solution of cyclopropanecarboxylic acid (1.2 eq.) in anhydrous DMF (2 mL) was distributed EDCI (1.6 eq.), HOBt (1.3 eq.) and TEA (5 eq.). The vial was sealed and stirred for 40 minutes at room temperature. Compound 39 (1 eq. in 1 mL of anhydrous DMF) was added to the vial which was then sealed and stirred overnight at room temperature. The solvent was removed by centrifugal evaporation under reduced pressure. The residue was dissolved in DCM (2 mL), and washed sequentially with 10% $K_2CO_3$ solution (1 mL) and water (1 mL). The water wash was then re-extracted with DCM (0.5 mL), the combined organic extracts were evaporated to dryness under reduced pressure. The desired product, Compound 119, was isolated by mass directed LC. LCMS (+ESI) m/z 447.38 [M+H]+

Compounds 120-123 were prepared by the same procedure as described above for Compound 119 except that another carboxylic acid was used in place of cyclopropanecarboxylic acid. For example, Compound 122 was synthesized using furan-2-carboxylic acid.

Compound 124 was synthesized by the same procedure as described above for Compound 119 except that Compound 40 was used in place of Compound 39. Compound 125 was synthesized by the same procedure as described above for Compound 119 except that Compound 40 was used in place of Compound 39 and benzoic acid was used in place of cyclopropyl carboxylic acid.

Likewise, Compound 126 was synthesized by the same procedure except that Compound 1 was used in place of Compound 39. Similarly, Compound 127 was synthesized by substituting Compound 2 in place of Compound 39 and benzoic acid in place of cyclopropyl carboxylic acid. Likewise, Compound 128 was synthesized by the same procedure using Compound 2 in place of Compound 39 and furan-2-carboxylic acid in place of cyclopropyl carboxylic acid. Compound 129 was synthesized by the same procedure using Compound 41 in place of Compound 39.

Compound 130 was synthesized by the same procedure as described above for Compound 119 except that Compound 42 was used in place of Compound 39 and benzoic acid was used in place of cyclopropanecarboxylic acid. Similarly, Compound 131 was synthesized by the same procedure except that Compound 42 was used in place of Compound 39. Compound 132 was similarly synthesized by the same procedure using Compound 45 in place of Compound 39.

Compound 133 was synthesized by the same procedure as described above for Compound 119 except that Compound 45 was used in place of Compound 39 and pivalic acid was used in place of cyclopropanecarboxylic acid. In a like manner, Compound 134 was synthesized by using Compound 46 in place of Compound 39. Similarly, use of Compound 46 in place of Compound 39 and tetrahydrofuran-3-carboxylic acid in place of cyclopropanecarboxylic acid produced Compound 135.

Compound 136 was synthesized by the same procedure as described for the synthesis of Compound 119 except that Compound 47 was used in place of Compound 39.

Compound 137 was synthesized using the same procedure described for Compound 119 except that Compound 47 was used in place of Compound 39 and pivalic acid was used in place of cyclopropyl carboxylic acid. Similarly, use of Compound 47 in place of Compound 39 and furan-3-carboxylic acid in place of cyclopropyl carboxylic acid produced Compound 138. Compound 139 was synthesized by the same procedure except that Compound 45 was used in place of Compound 39 and tetrahydrofuran-3-carboxylic acid was used in place of cyclopropanecarboxylic acid.

Example 9

Preparation of (R)—N-(1-cyclohexylethyl)-7-(2-hydroxyethyl)-3-phenyl-5,6,7,8-tetrahydroimidazo[1,5-a]pyrazine-1-carboxamide (Compound 140)

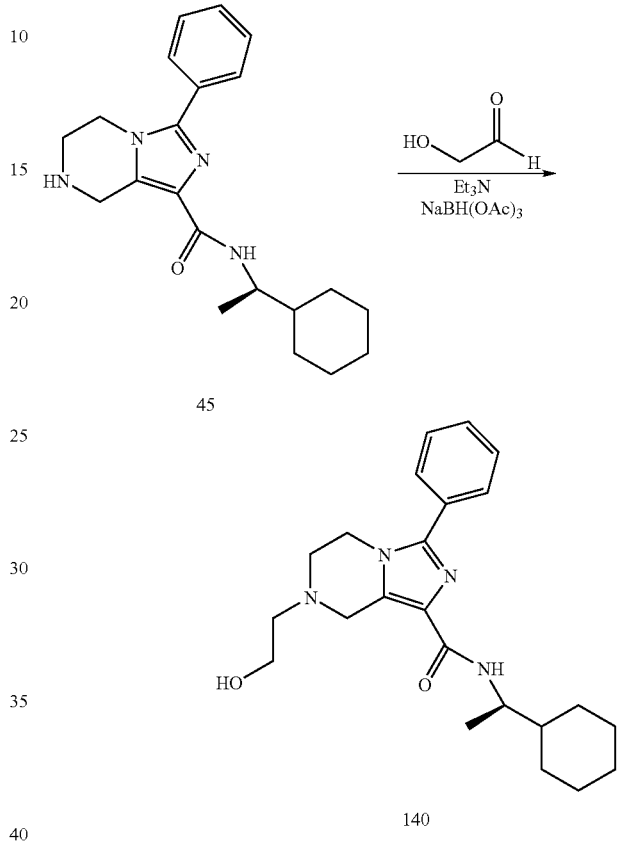

To the amine, Compound 45 (1 eq.) in anhydrous DCE (2 mL) was added TEA (5 eq.). 2-Hydroxyacetaldehyde (1.2 eq. in 1 mL of anhydrous DCE) was added to the vial, which was sealed and stirred for 1 hour at room temperature. Sodium triacetoxyborohydride (3 eq.) was added in portions and the vial was sealed and stirred overnight at room temperature. The solvent was removed by centrifugal evaporation under reduced pressure. Saturated sodium carbonate solution (1 mL) was added to the vial, which was then sealed and sonicated for approximately 20 min. DCM (2 mL) was added and the vial was sonicated for approximately 5 min. The organic layer was removed and the remaining aqueous layer was re-extracted with DCM (1 mL). The combined organic extracts were evaporated to dryness under reduced pressure. Compound 140, was purified by mass directed LC. LCMS (+ESI) m/z 397.18 [M+H]+.

Compound 141 was synthesized by the same procedure as described above for Compound 140 except that Compound 47 was used in place of Compound 45 and tetrahydrofuran-3-carboxaldehyde was used in place of 2-hydroxyacetaldehyde.

Compound 142 was synthesized by the same procedure as described above for Compound 140 except that Compound 39 was used in place of Compound 45 and isobutyraldehyde was used in place of 2-hydroxyacetaldehyde. Compound 143 was synthesized by the same procedure except that Compound 39 was used in place of Compound 45. Similarly, Compound 144 was synthesized by the same procedure except that Compound 39 was used in place of Compound 45 and acetaldehyde (10 eq.) was used in place of 2-hydroxyacetaldehyde.

Compound 145 was synthesized by the same procedure as described above for Compound 140 except that Compound 40, was used in place of Compound 45 and isobutyraldehyde was used instead of 2-hydroxyacetaldehyde. Likewise, Compound 146 was synthesized by the same procedure except that Compound 40 was used in place of Compound 45. Compound 147 was synthesized by the same procedure except that Compound 40 was used in place of Compound 45 and acetaldehyde (10 eq.) was used instead of 2-hydroxyacetaldehyde.

Compound 148 was synthesized by the same procedure as described above for Compound 140 except that Compound 2 was used in place of Compound 45 and isobutyraldehyde was used instead of 2-hydroxyacetaldehyde. Similarly, Compound 149 was synthesized by the same procedure as described above for Compound 140 except that Compound 2 was used in place of Compound 45 and acetaldehyde (10 eq.) was used instead of 2-hydroxyacetaldehyde.

Compound 150 was synthesized by the same procedure as described above for Compound 140 except that Compound 41 was used in place of Compound 45 and isobutyraldehyde was used instead of 2-hydroxyacetaldehyde. Similarly, Compound 151 was synthesized by the same procedure except that Compound 41 was used in place of Compound 45.

Compound 152 was synthesized by the same procedure as described above for compound 140 except that Compound 41 was used in place of Compound 45 and acetaldehyde (10 eq.) was used instead of 2-hydroxyacetaldehyde. Similarly, Compound 153 was synthesized by the same procedure except that Compound 2 was used in place of Compound 45. Likewise, Compound 154 was synthesized by the same procedure as described above for Compound 140 except that Compound 41 was used in place of Compound 45 and propionaldehyde was used instead of 2-hydroxyacetaldehyde.

Compound 155 was synthesized by the same procedure as described above for Compound 140 except that Compound 44 was used in place of Compound 45 and isobutyraldehyde was used instead of 2-hydroxyacetaldehyde. Similarly, Compound 156 was synthesized by the same procedure except that Compound 44 was used in place of Compound 45. Compound 157 was synthesized by the same procedure except that Compound 42 was used in place of Compound 45 and isobutyraldehyde was used in place of 2-hydroxyacetaldehyde.

Compound 158 was synthesized by the same procedure as described above for Compound 140 except that Compound 42 was used in place of Compound 45 and acetaldehyde (10 eq.) was used in place of 2-hydroxyacetaldehyde. Similarly, Compound 159 was synthesized by the same procedure except that Compound 42 was used in place of Compound 45. Likewise, Compound 160 was synthesized by the same procedure except that Compound 43 was used in place of Compound 45 and isobutyraldehyde was used in place of 2-hydroxyacetaldehyde.

Compound 161 was synthesized by the same procedure as described above for Compound 140 except that Compound 43 was used in place of Compound 45 and acetaldehyde (10 eq.) was used in place of 2-hydroxyacetaldehyde. Similarly, Compound 162 was synthesized by the same procedure as described above for Compound 140 except that Compound 43 was used in place of Compound 45. Likewise, Compound 163 was synthesized by the same procedure except that isobutyraldehyde was used in place of 2-hydroxyacetaldehyde.

Compound 164 was synthesized by the same procedure as described above for Compound 140 except that acetaldehyde (10 eq.) was used in place of 2-hydroxyacetaldehyde. Similarly, Compound 165 was synthesized by the same procedure except that Compound 47 was used in place of Compound 45 and isobutryaldehyde was used in place of 2-hydroxyacetaldehyde. Likewise, Compound 166 was synthesized by the same procedure except that Compound 47 was used in place of Compound 45.

Compound 167 was synthesized by the same procedure as described above for Compound 140 except that Compound 46 was used in place of Compound 45 and isobutryaldehyde was used in place of 2-hydroxyacetaldehyde. Similarly, Compound 168 was synthesized by the same procedure except that Compound 46 was used in place of Compound 45 and acetaldehyde (10 eq.) was used in place of 2-hydroxyacetaldehyde. Likewise, Compound 169 was synthesized by the same procedure except that Compound 46 was used in place of Compound 45.

Example 10

Preparation of (R)-7-acetyl-N-(1-cyclohexylethyl)-3-phenyl-5,6,7,8-tetrahydro-imidazo[1,5-a]pyrazine-1-carboxamide. (Compound 170)

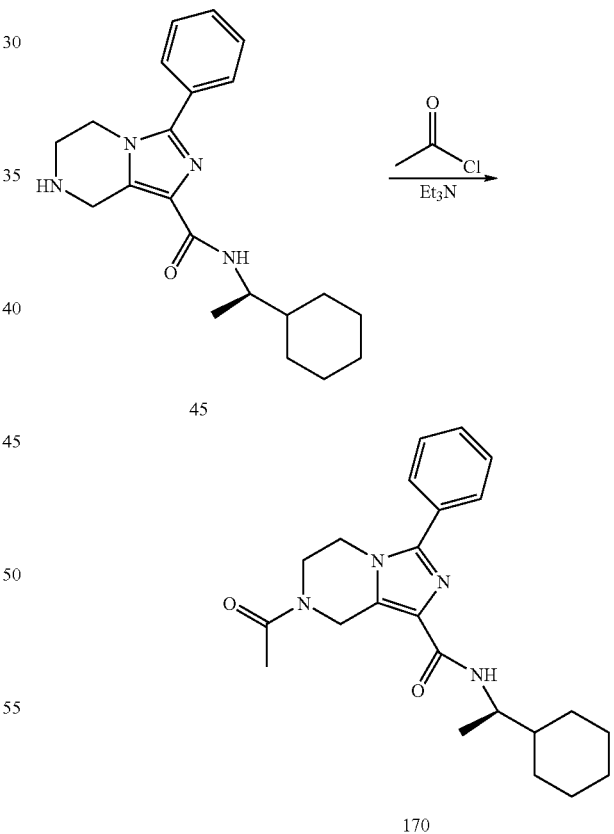

To Intermediate 45 (1 eq. in 1 mL of anhydrous DCM or DMF) was added TEA (5 eq.). An aliquot of acetyl chloride (1.2 eq. in 1 mL of anhydrous DCM or DMF) was added to the vial which was then sealed and stirred overnight at room temperature. The solvent was removed by centrifugal evaporation under reduced pressure. The residue was dissolved in DCM (2 mL) and washed sequentially with 2M $Na_2CO_3$ (1 mL) and water (1 mL). The water wash was then re-extracted with DCM (0.5 mL), the combined organic extracts and evaporated to dryness under reduced pressure. Compound 170 was purified by mass directed LC. MS: m/z 395.17 $[M+H]^+$.

Compound 171 was synthesized by the same procedure as described above for Compound 170 except that Compound 39 was used in place of Compound 45 and 2-isocyanatopropane was used in place of acetyl chloride. Compound 172 was synthesized by the same procedure as described above for Compound 170 except that Compound 40 was used in place of Compound 45. Similarly, Compound 173 was synthesized by the same procedure as described above for Compound 170, except that Compound 41 was used in place of Compound 45.

Compound 174 was synthesized by the same procedure as described above for Compound 170 except that Compound 2 was used in place of Compound 45. Similarly, Compound 175 was synthesized by the same procedure except that Compound 44 was used in place of Compound 45. In a similar fashion, Compound 176 was synthesized by the same procedure except that Compound 46 was used in place of Compound 45. Likewise, Compound 177 was synthesized by the same procedure except that Compound 47 was used in place of Compound 45. In a like manner, Compound 178 was synthesized by the same procedure except that Compound 39 was used in place of Compound 45 and that methylchloroformate was used in place of acetyl chloride.

Compound 179 was synthesized by the same procedure as described above for Compound 170 except that Compound 40 was used in place of Compound 45 and that methylchloroformate was used in place of acetyl chloride. Similarly, Compound 180 was synthesized by the same procedure except that Compound 2 was used in place of Compound 45 and methylchloroformate was used in place of acetyl chloride.

Compound 181 was synthesized by the same procedure as described above for Compound 170 except that Compound 41 was used in place of Compound 45 and that methylchloroformate was used in place of acetyl chloride. Similarly, Compound 182 was synthesized by the same procedure except that Compound 44 was used in place of Compound 45 and methylchloroformate was used in place of acetyl chloride. Likewise, Compound 183 was synthesized by the same procedure except that Compound 42 was used in place of Compound 45 and methylchloroformate was used in place of acetyl chloride.

Compound 184 was synthesized by the same procedure as described above for Compound 170 except that Compound 43 was used in place of Compound 45 and that methylchloroformate was used in place of acetyl chloride. Similarly, Compound 185 was synthesized by the same procedure except that methylchloroformate was used in place of acetyl chloride. Likewise, Compound 186 was synthesized by the same procedure except that Compound 46 was used in place of Compound 45 and methyl chloroformate was used in place of acetyl chloride. In a like manner, Compound 187 was synthesized by the same procedure except that Compound 47, was used in place of Compound 45 and that methylchloroformate was used in place of acetyl chloride.

Compound 188 was synthesized by the same procedure as described above for Compound 170 except that Compound 2 was used in place of Compound 45 and 3,3-dimethylbutanoyl chloride was used in place of acetyl chloride. Similarly, Compound 189 was synthesized by the same procedure except that compound 2, was used in place of compound 45 and propionyl chloride was used in place of acetyl chloride. Likewise, compound 190 was synthesized by the same procedure except that compound 2, was used in place of compound 45 and pivaloyl chloride was used in place of acetyl chloride.

Compound 191 was synthesized by the same procedure as described above for compound 170 except that compound 2 was used in place of compound 45 and isobutyryl chloride was used in place of acetyl chloride. Likewise, compound 192 was synthesized by the same procedure except that compound 2, was used in place of compound 45 and 2-isocyanato-2-methylpropane was used in place of acetyl chloride. Similarly, compound 193 was synthesized by the same procedure as described above for compound 170 except that compound 2 was used in place of compound 45 and 1-isocyanatopropane was used in place of acetyl chloride. In a like manner, compound 194 was synthesized by the same procedure except that compound 2, was used in place of compound 45 and that isocyanatobenezene was used in place of acetyl chloride.

Example 11

Preparation of (S)—N-(3,3-dimethyl-1-(methylamino)-1-oxobutan-2-yl)-3-phenyl-7-(propylcarbamothioyl)-5,6,7,8-tetrahydroimidazo[1,5-a]pyrazine-1-carboxamide (Compound 195)

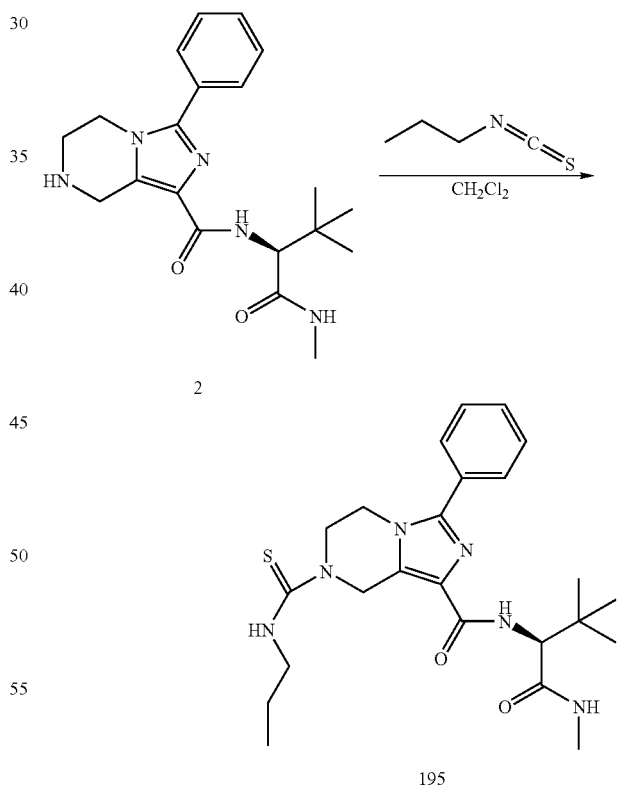

Compound 2 (see Examples 1 and 2, above) (0.0600 g, 0.162 mmol) was dissolved in 1 mL of dichloromethane. Propyl isothiocyanate (0.0195 g, 0.195 mmol) was added to the solution and the reaction mixture stirred at ambient temperature for 20 hours. The reaction mixture was diluted with DCM and washed successively with saturated aqueous $NaHCO_3$ solution, water and brine. The organic layer was dried over anhydrous Na$_2$SO$_4$ and concentrated to provide Compound 195 (0.056 g; 73%) as a light yellow solid. MS: m/z 471.41 [M+H]$^+$.

Example 12

Preparation of (S)—N-(1-(dimethylamino)-3,3-dimethyl-1-oxobutan-2-yl)-3-phenyl-5,6,7,8-tetrahydroimidazo[1,5-a]pyrazine-1-carboxamide (Compound 196)

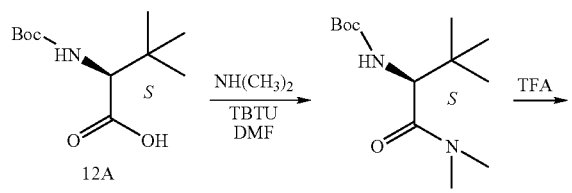

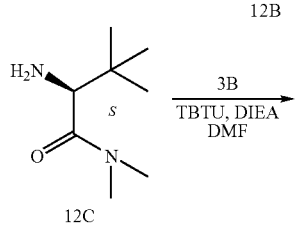

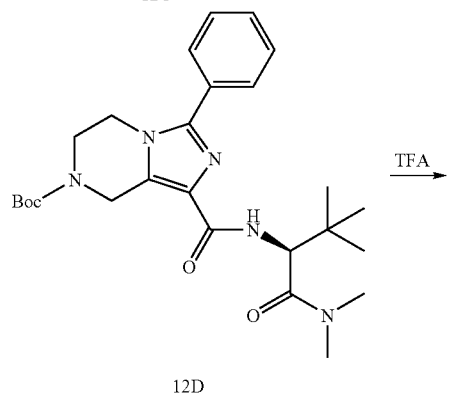

Step 1: Preparation of intermediate 12B. Intermediate 12A (0.2 g, 0.86 mmol) was dissolved in DMF (3 mL) at 0° C. Dimethylamine (2M solution in THF, 2.15 mL) was added, followed by HBTU (0.49 g, 1.29 mmol). The reaction mixture slowly warmed to ambient temperature and stirred overnight. The reaction mixture was concentrated under reduced pressure and diluted with ethyl acetate. The organic solution was washed several times with water and dried over anhydrous Na$_2$SO$_4$. The organic layer was concentrated to provide intermediate 2B which was used in the next step without further purification. MS: m/z 259.3 [M+H]$^+$.

Step 2: Preparation of Intermediate 12C. Intermediate 12B was dissolved in methylene chloride (1 mL) and TFA (1 mL). The reaction mixture stirred overnight at ambient temperature. The reaction mixture was concentrated to provide 12C (TFA salt) which was used in the next step without further purification.

Step 3: Preparation of Intermediate 12D. To intermediate 3B (0.3 g, 0.85 mmol) in DMF (3 mL) was added 12C (0.25 g, 1.58 mmol), DIEA (0.45 g, 3.5 mmol), and TBTU (0.3 g, 0.96 mmol). The reaction mixture stirred for 24 hours at ambient temperature. Water was added and the reaction mixture was extracted with methylene chloride. The organic layer was dried over anhydrous Na$_2$SO$_4$ and concentrated. The crude material was purified using normal phase chromatography (hexanes/ethyl acetate; 0-100% gradient) to provide intermediate 12D as an oil (0.31 g).

Step 4: Preparation of Compound 196. Intermediate 12D (0.31 g, 0.62 mmol) was dissolved in methylene chloride (2 mL) and 1 mL of TFA. The reaction mixture stirred for 2 hours at ambient temperature. The reaction mixture was concentrated and the residue was dissolved in methanol (2 mL). The solution was filtered through a sulfonic acid SPE column to remove excess TFA. The desired compound was obtained by adding 2N ammonia in methanol to the column. The eluate was concentrated to yield Compound 196 as a white solid (0.2 g). MS: m/z 384.27 [M+H]$^+$.

Example 13

Preparation of (S)-7-cyclopropyl-N-(3,3-dimethyl-1-(methylamino)-1-oxobutan-2-yl)-3-phenyl-5,6,7,8-tetrahydroimidazo[1,5-a]pyrazine-1-carboxamide (Compound 197)

Compound 2 (60 mg, 0.16 mmol) was dissolved in methanol and (1-ethoxycyclopropoxy)trimethylsilane (170 mg, 0.94 mmol) was added followed by sodium cyanoborohydride (46 mg, 0.73 mmol) and acetic acid (98 mg, 1.62 mmol). The reaction mixture was heated at 60° C. overnight, cooled down to room temperature, filtered and concentrated.

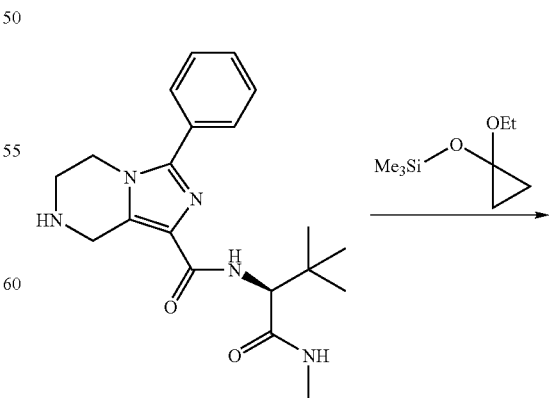

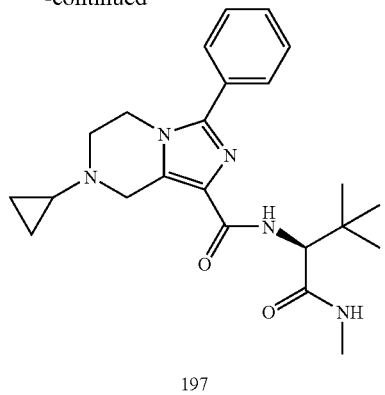

197

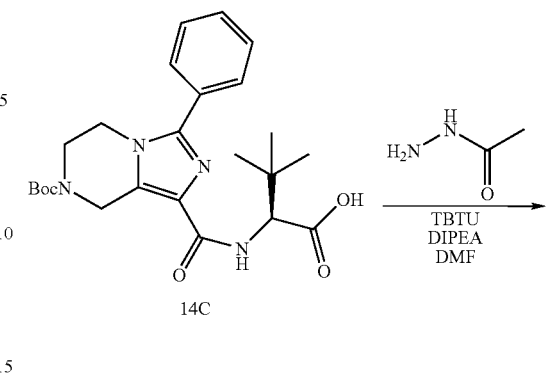

14C

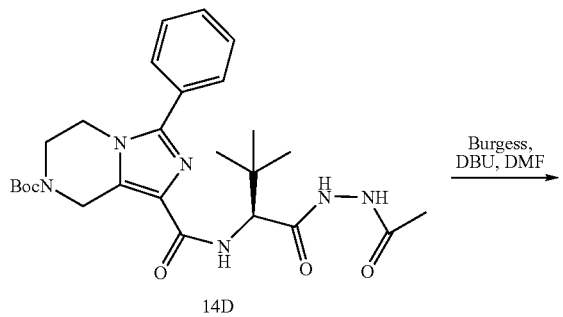

14D

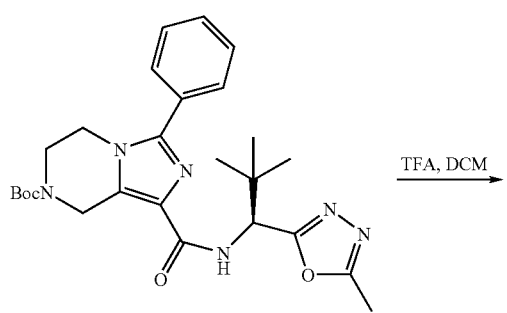

14E

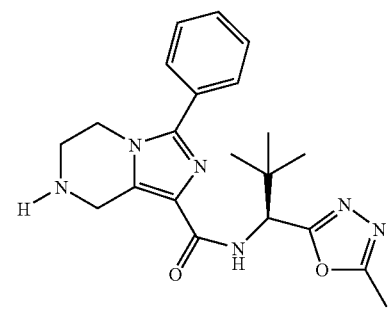

200

The residue was diluted with DCM and washed with 2N NaOH and brine, dried over anhydrous $Na_2SO_4$, filtered and concentrated. The crude mixture was purified using normal phase chromatography eluting with a 10-20% methanol/DCM gradient to provide Compound 197 as a white solid (35 mg, 51%). MS: m/z 410.17 [M+H]$^+$. $^1$H-NMR (400 MHz, DMSO-d$_6$) δ: 0.45 (m, 2H), 0.55 (m, 2H), 0.94 (s, 9H), 1.95 (m, 1H), 2.61 (d, 3H), 2.97 (m, 2H), 4.08 (d, 2H), 4.13 (t, 2H), 4.33 (d, 1H), 7.52 (m, 4H), 7.74 (m, 2H), 8.18 (m, 1H).

Compound 198 was synthesized in the same manner as compound 197 except that compound 282 was used in place of compound 2. Similarly, compound 199 was synthesized in the same manner as compound 197 except that compound 314 was used in place of compound 2.

Example 14

Preparation of (S)—N-(2,2-dimethyl-1-(5-methyl-1,3,4-oxadiazol-2-yl)propyl)-3-phenyl-5,6,7,8-tetrahydroimidazo[1,5-a]pyrazine-1-carboxamide (Compound 200) and (S)—N-(2,2-dimethyl-1-(5-methyl-1,3,4-oxadiazol-2-yl)propyl)-7-methyl-3-phenyl-5,6,7,8-tetrahydroimidazo[1,5-a]pyrazine-1-carboxamide (Compound 201)

Step 1: Synthesis of (S)-tert-butyl 1-(1-(2-acetylhydrazinyl)-3,3-dimethyl-1-oxobutan-2-ylcarbamoyl)-3-phenyl-5,6-dihydroimidazo[1,5-a]pyrazine-7(8H)-carboxylate (14D). Intermediate 14C (50 mg, 0.11 mmol) was dissolved in DMF (2 mL) in a 20 mL vial. Acetyl hydrazide (9 mg, 0.12 mmol) was added followed by DIPEA (38 μL, 0.22 mmol). The mixture was vortexed until homogeneous. TBTU (40 mg, 0.12 mmol) was added and the reaction was stirred for 3 hours, after which LC/MS showed that the starting material had been consumed. Saturated $NaHCO_3$ (2 mL) was added to quench and the reaction was extracted of EtOAc (2×2 mL). The organic layers were combined, dried with anhydrous $Na_2SO_4$, filtered and evaporated to provide Intermediate 14D as a light yellow oil (48 mg, 85% yield) which was used in the next step without further purification. LCMS (+ESI) m/z 513.3 [M+H]$^+$.

Step 2: Synthesis of (S)-tert-butyl 1-(2,2-dimethyl-1-(5-methyl-1,3,4-oxadiazol-2-yl)propylcarbamoyl)-3-phenyl-5,6-dihydroimidazo[1,5-a]pyrazine-7(8H)-carboxylate (14E). The intermediate 14D (48 mg, 94 μmol) was taken up in THF (1 mL) and added to a 2 mL microwave reaction vial. DBU (21 μL, 0.14 mmol) was added to the reaction, followed by the Burgess reagent (112 mg, 468 μmol). The vial was capped and the reaction mixture was heated to 150° C. for 5 minutes, after which some starting material still remained. Additional Burgess reagent (1 equiv) was added and the reaction was heated to 150° C. for 10 minutes. LC/MS showed that the starting material was consumed. The reaction was diluted with of saturated aqueous NaHCO$_3$ (1 mL) and EtOAc (2 mL). The organic layer was removed and the aqueous layer extracted with EtOAc (2 mL). The organic layers were combined, dried with anhydrous Na$_2$SO$_4$, filtered and evaporated. The residue was purified by Flash chromatography on silica using a gradient from 10% EtOAc/Hexanes to 60% EtOAc/Hexanes. This provided intermediate 14E as a clear oil (25 mg, 54% yield). LCMS (+ESI) m/z 495.3 [M+H]$^+$.

Step 3: Synthesis of Compound 200. The intermediate 14E (20 mg, 0.04 mmol) was taken up in 25% TFA in DCM (1 mL). The reaction was stirred for 1 hour after which it was found to be complete by LC/MS. The reaction mixture was neutralized (pH 7-8) by the addition of saturated aqueous NaHCO$_3$. The solution was extracted with DCM (3×1 mL). The combined organic extracts were dried with anhydrous Na$_2$SO$_4$, filtered and evaporated to provide Compound 200 which was used without further purification. LCMS (+ESI) m/z 395.0 [M+H]$^+$.

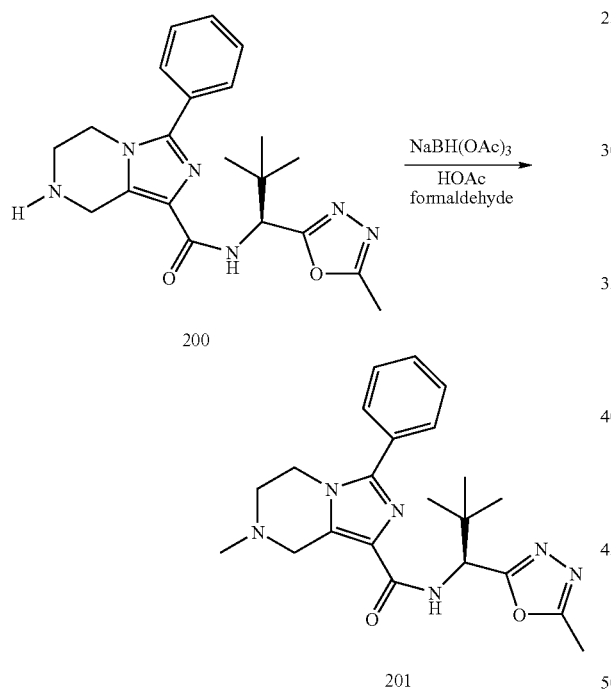

Compound 200 was taken up in THF (0.5 mL) and transferred to a 2 mL microwave vial equipped with a stir bar. Formaldehyde (36 µL, 0.4 mmol) was added followed by the HOAc (3 µL, 0.053 mmol). After mixing, sodium triacetoxyborohydride (13 mg, 0.061 mmol) was added. The vial was capped and the reaction was heated at 150° C. for 5 minutes. LC/MS showed that the reaction was about 70% complete. The reaction was heated at 160° C. for a further 5 minutes. The reaction was more than 90% complete by LC/MS, but other products were beginning to form, so the reaction was terminated. The reaction mixture was diluted with 2 mL of saturated aqueous NaHCO$_3$ and the solution was vortexed. The solution was extracted of DCM (3×1 mL). The combined organic extracts were dried with anhydrous Na$_2$SO$_4$, filtered and evaporated. The desired product, Compound 201, was obtained as a yellow oil (13 mg, 79% yield) by flash chromatography on silica using a gradient from 100% EtOAc to 5% MeOH in EtOAc. LCMS (+ESI) m/z 409.2 [M+H]$^+$.

Compound 202 was synthesized in the same manner as compound 201 except that isobutryaldehyde was used in place of formaldehyde.

Example 15

Preparation of (S)—N-(3,3-dimethyl-1-(methylamino)-1-oxobutan-2-yl)-7-methyl-3-(phenylethynyl)-5,6,7,8-tetrahydroimidazo[1,5-a]pyrazine-1-carboxamide (Compound 203)

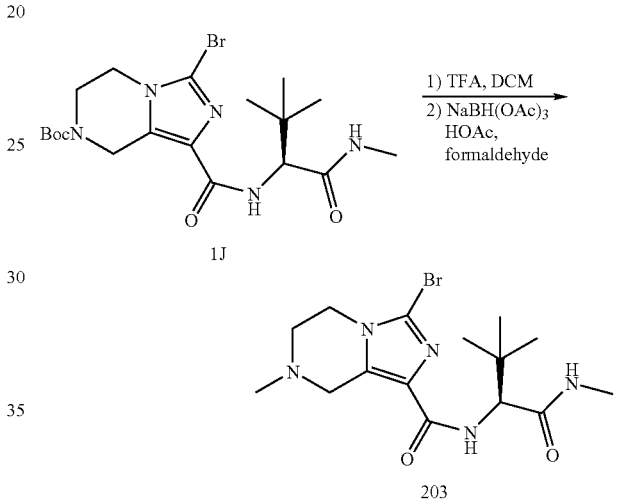

The intermediate 1J (80 mg, 0.16 mmol) was taken up in 25% TFA in DCM (2 mL). The reaction was stirred for 1 hour, after which it was found to be complete by LC/MS. The reaction mixture was neutralized (pH 7-8). by the addition of saturated aqueous NaHCO$_3$. The solution was extracted of DCM 3×1 mL. The combined organic layers were dried with anhydrous Na$_2$SO$_4$, filtered and evaporated. The residue was dissolved in THF (0.5 mL) and transferred to a 2 mL microwave vial equipped with a stirrer bar. Formaldehyde (144 µL, 1.6 mmol) was added, followed by the HOAc (12 µL, 0.21 mmol). After mixing everything together, the sodium triacetoxyborohydride (50 mg, 0.24 mmol) was added. The vial was capped and the reaction was heated at 160° C. for 5 minutes. LC/MS showed that the reaction was more than 90% complete by LC/MS. The reaction was diluted with saturated aqueous NaHCO$_3$ (2 mL) and the mixture was vortexed and extracted 3×1 mL of DCM. The combined organic layers were dried with anhydrous Na$_2$SO$_4$, filtered and evaporated. The desired product, Compound 203, was isolated as a yellow oil (51 mg, 78% yield) by Flash chromatography on silica using a gradient from 100% EtOAc to 5% MeOH in EtOAc. LCMS (+ESI) m/z 387.2 [M+H]$^+$.

Example 16

Preparation of (S)—N-(3,3-dimethyl-1-(methylamino)-1-oxobutan-2-yl)-7-methyl-3-(phenylethynyl)-5,6,7,8-tetrahydroimidazo[1,5-a]pyrazine-1-carboxamide (Compound 204)

Example 17

Preparation of (S)-7-methyl-N-(3-methyl-1-(methylamino)-1-oxobutan-2-yl)-3-phenyl-5,6,7,8-tetrahydroimidazo[1,5-a]pyrazine-1-carboxamide (Compound 206)

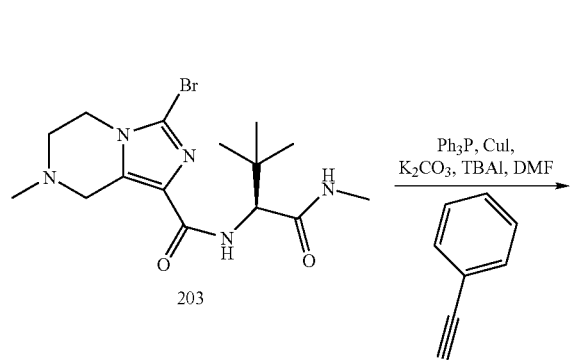

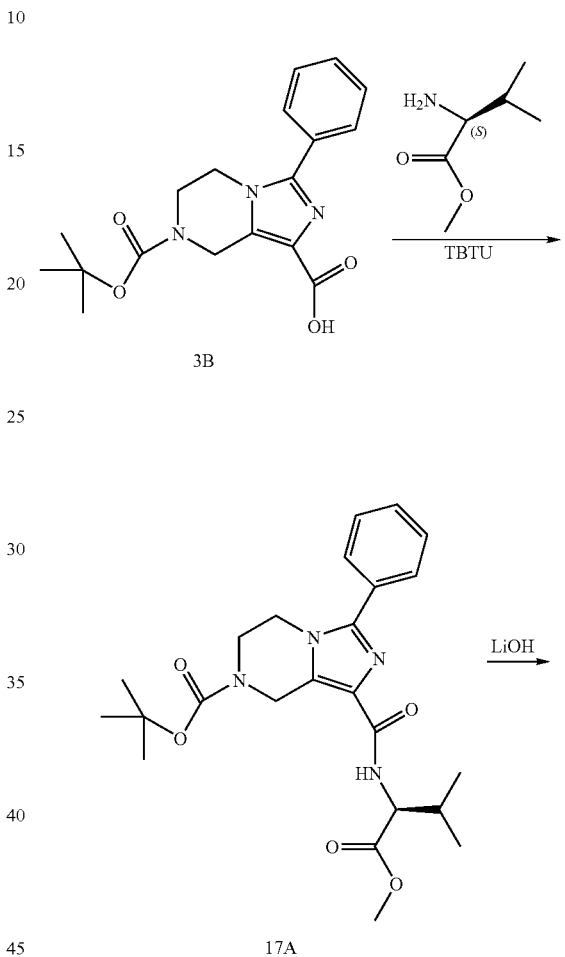

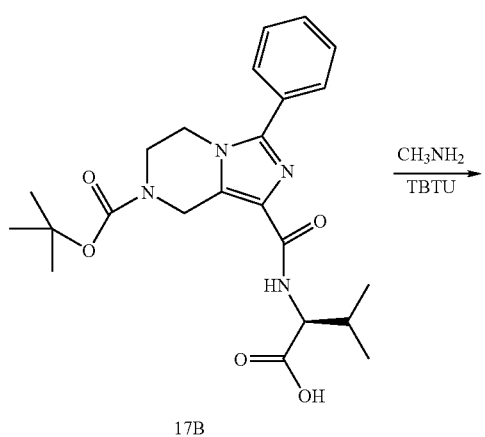

Compound 203 (20 mg, 52 μmol) was dissolved in DMF (1 mL) in a microwave vial. To this solution was added Ph₃P (14 mg, 52 μmol), phenyl acetylene (5 mg, 52 μmol), CuI (10 mg, 52 μmol), K₂CO₃ (21 mg, 155 μmol) and TBAI (2 mg, 5 mmol). The reaction was capped and subjected to microwave irradiation at 160° C. for 10 minutes. The LC/MS indicated about 50% conversion to product. More phenyl acetylene (2.5 mg, 0.5 eq.) was added and the reaction was irradiated and heated for a further 10 more minutes at 160° C. The reaction was diluted with saturated aqueous NaHCO₃ (1 mL) and extracted EtOAc (2×1 mL). The combined organic layers were dried with anhydrous Na₂SO₄, filtered and evaporated. Flash chromatography on silica using a gradient from 100% EtOAc to 5% MeOH in EtOAc yielded the desired product, Compound 204, as an oil (7.5 mg, 36%). LCMS (+ESI) m/z 408.3 [M+H]⁺.

Compound 205 was prepared as described above for Compound 204 except that 3-ethynylpyridine was used in place of phenyl acetylene.

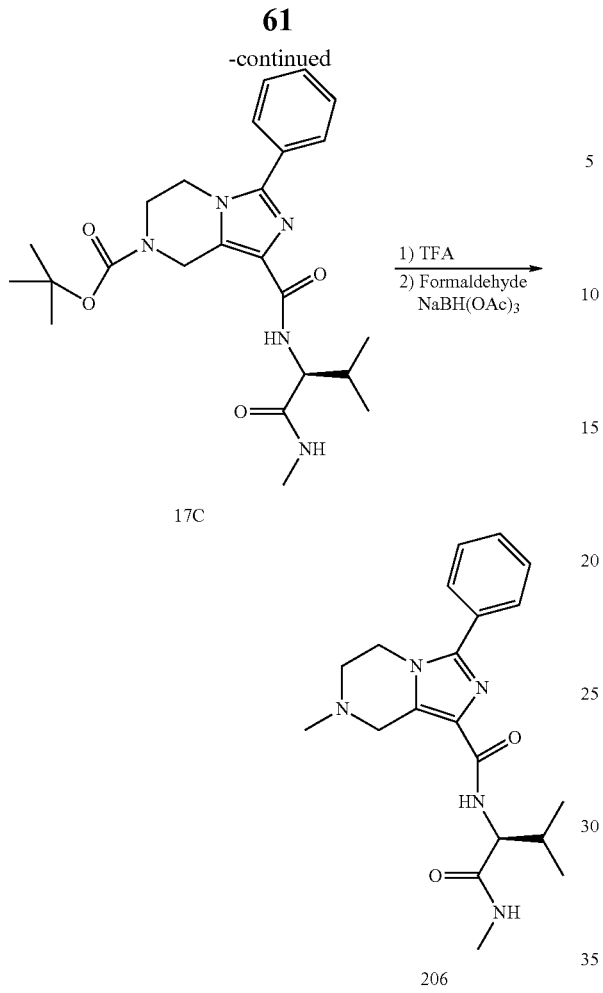

purified by flash chromatography using 0-100% ethyl acetate/hexanes to afford the desired intermediate 17C (0.1 g).

Step 4: Preparation of compound 206. To intermediate 17C (0.1 g, 0.22 mmol) in 1 mL of DCM was added TFA (0.5 mL). After 2 hours, the reaction mixture was concentrated under reduced pressure, dissolved in methanol and purified by ion exchange chromatography using a Strata SCX SPE tube. The desired amine was obtained from the column by eluting with 3N ammonia/methanol. The solvent was evaporated and the crude product was dissolved of THF (2 mL). Acetic acid (10 mg, 0.16 mmol) and 10 eq. aqueous formaldehyde was added to the reaction mixture, followed by sodium triacetoxyborohydride (0.042 g, 0.19 mmol). The reaction mixture stirred for 20 hours. Saturated aqueous NaHCO$_3$ was added and the reaction mixture was extracted with dichloro-methane, dried over anhydrous Na$_2$SO$_4$, filtered and concentrated under reduced pressure. The crude mixture was purified by reverse phase chromatography using and 0-100% acetonitrile/water with 0.1% formic acid to provide the desired compound 206 (14.2 mgs). MS: m/z 370.0 [M+H]$^+$. $^1$H-NMR (400 MHz, CDCl$_3$) δ: 7.58 (m, 2H), 7.40 (m, 3H), 6.29 (s, 1H), 4.27 (m, 1H), 4.07 (m, 1H), 3.98 (m, 1H), 3.13-2.90 (m, 3H), 2.71 (s, 6H), 2.44 (s, 2H), 2.32 (m, 1H), 0.91 (m, 6H).

Compound 207 was synthesized in the same manner as compound 206 except that (S)-methyl 2-amino-2-phenylacetate was used in place of (S)-methyl 2-amino-3-methylbutanoate.

Example 18

Preparation 3-(4-chloro-2-fluorophenyl)-7-methyl-N-(4-sulfamoylphenyl)-5,6,7,8-tetrahydroimidazo[1,5-a]pyrazine-1-carboxamide (Compound 208)

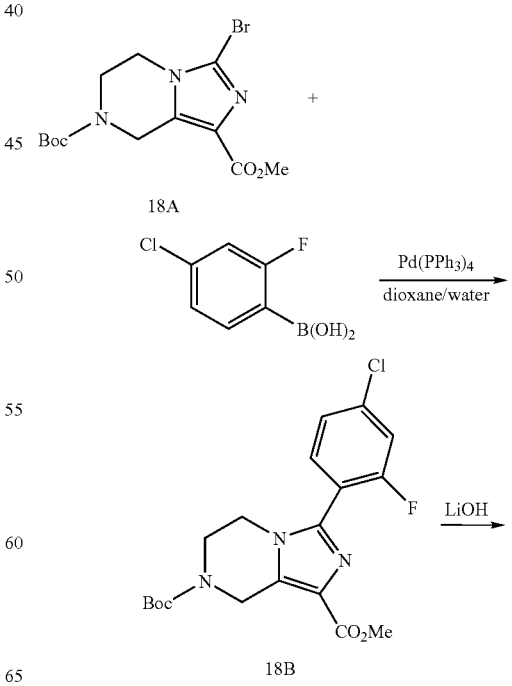

Step 1: Synthesis of intermediate 17A. To intermediate 3B (0.3 g, 0.87 mmol) in DMF was added DIEA (0.3 g, 2.62 mmol), (S)-methyl 2-amino-3-methylbutanoate (0.15 g, 0.87 mmol) and TBTU (0.33 g, 1.05 mmol). The reaction mixture was stirred at ambient temperature for 16 hours. Water was added and the reaction mixture was extracted repeatedly with ethyl acetate. The combined organic extracts were dried with anhydrous Na$_2$SO$_4$, filtered and concentrated. Flash chromatography on silica using 0-100% hexanes/ethyl acetate gradient, provided the desired product, Intermediate 17A (0.32 g), which was used without further purification.

Step 2: Synthesis of Intermediate 17B. To a solution of intermediate 17A (0.32 g, 0.70 mmol) in 3:1 THF/water mixture at 0° C. was added lithium hydroxide (0.84 g, 1.40 mmol). The reaction mixture was stirred at 0° C. for 6 hours. The reaction was acidified (pH<7) by dropwise addition of 1N HCl and repeatedly extracted with ethyl acetate. The combined organic extracts were dried over anhydrous Na$_2$SO$_4$, filtered and concentrated to provide. Intermediate 17B (0.3 g) as a crude product, which was used in the next step without further purification.

Step 3: Preparation of intermediate 17C. To intermediate 17B (0.3 g, 0.67 mmol) in DMF was added 2M methylamine solution THF (1.7 mL, 3.39 mmol) and TBTU (0.26 g, 0.81 mmol). The reaction mixture stirred for 16 hrs at ambient temperature. The reaction mixture was diluted with water and extracted several times with ethyl acetate. The combined organic extracts were dried over anhydrous Na$_2$SO$_4$, filtered and concentrated under reduced pressure. The residue was

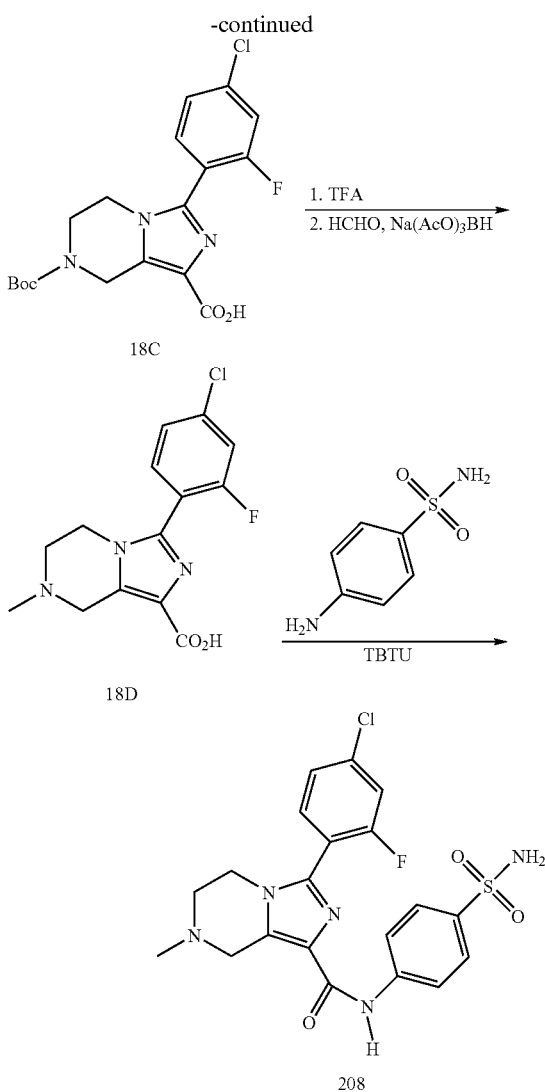

Step 1: Preparation of 7-(tert-butoxycarbonyl)-3-(4-chloro-2-fluorophenyl)-5,6,7,8-tetrahydroimidazo[1,5-a]pyrazine-1-carboxylic acid 18B. A mixture of intermediate 18A (1.50 g, 4.16 mmol), potassium carbonate (1.15 g, 8.33 mmol), 2-fluoro-4-chlorophenylboronic acid (0.91 g, 5.21 mmol) and palladium tetrakis(triphenyl-phosphine) (240 mg, 0.21 mmol) in dioxane (30 mL) and water (10 mL) was heated at 100° C. overnight. LC-MS analysis showed some of the desired methyl ester product 18B was hydrolyzed to carboxylic acid 18C. To the crude reaction mixture was added lithium hydroxide monohydrate (0.80 g, 19.0 mmol) and heated at 70° C. for 1 hour. After evaporation of dioxane, the aqueous phase was acidified to pH 2 and extracted with 10% iPrOH/DCM three times. The combined organic phase was concentrated under reduced pressure and purified by column chromatography with 5% to 20% MeOH/DCM to give intermediate 18C (88% yield). LCMS (+ESI) m/z 396.10, 398.05 [M+H]⁺.

Step 2: Preparation of 3-(4-chloro-2-fluorophenyl)-7-methyl-5,6,7,8-tetrahydroimidazo[1,5-a]pyrazine-1-carboxylic acid 18D. A solution of intermediate 18C (1.45 g, 3.66 mmol) in TFA/DCM (25 mL, 3:2) was stirred at room temperature for 0.5 hour. After evaporation of TFA and DCM, the residue was partitioned between brine (pH=3) and iPrOH/DCM (1:9). The organic phase was retained and the aqueous phase was extracted three times with iPrOH/DCM (1:9). The combined organic extracts were dried and evaporated to give free amine intermediate (0.42 g, 39% yield). To a solution of the amino intermediate (0.42 g, 1.42 mmol) in THF was added AcOH (81 µL, 1.42 mmol) and paraformaldehyde (0.56 mL, 37% aq. 7.11 mmol) followed by sodium triacetoxyborohydride (0.40 g, 1.89 mmol). After stirring at room temperature for 2 hours, THF was evaporated. The residue was extracted between brine (pH=3) and iPrOH/DCM (1:9) twice. The combined organic phase was dried and evaporated to give intermediate 18D (93% yield). LCMS (+ESI) m/z 310.08, 312.03 [M+H]⁺.

Step 3: Preparation of Compound 208. The carboxylic acid intermediate 18D (400 mg) and DIEA (600 µL) were dissolved in DMF (10 mL). An aliquot of this stock solution (400 µL) was dispensed into a vial charged with 4-aminobenzene-sulfonamide (0.10 mmol). TBTU was added (0.50 mmol) to the vial and the mixture was stirred at room temperature for 2 hours. The crude mixture was purified by prep LC-MS using a gradient elution of 5% to 95% MeCN/water in 15 min. The product was taken up with DCM and diluted with hexanes. Evaporation under nitrogen flow gave the desired product, Compound 208 as a solid. LCMS (+ESI) m/z 464 [M+H]⁺

Compounds 209-237 were prepared in the same manner as Compound 208 except that other amines were used in place of 4-aminobenzene-sulfonamide. For example, to synthesize Compound 209, tert-butyl 4-aminopiperidine-1-carboxylate was used in place of 4-aminobenzenesulfonamide. For compounds 229-237, phenyl boronic was used in place of 2-fluoro-4-chlorophenylboronic acid in step 1.

Example 19

Preparation of (S)-3-cyclopentenyl-N-(3,3-dimethyl-1-(methylamino)-1-oxobutan-2-yl)-7-methyl-5,6,7,8-tetrahydroimidazo[1,5-a]pyrazine-1-carboxamide (Compound 238)

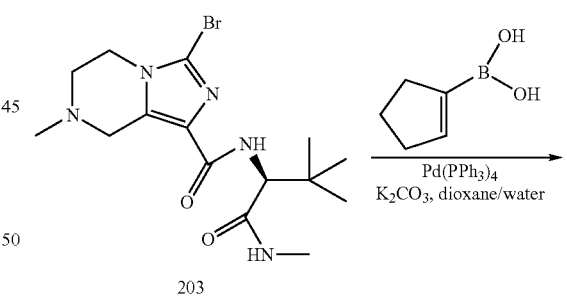

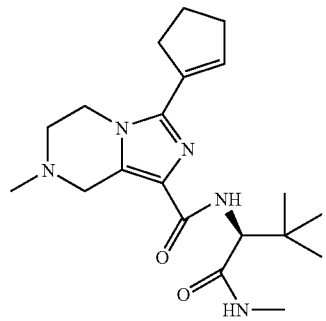

Compound 203 (100 mg, 0.26 mmol) was dissolved in dioxane (2 mL) and cyclopentenylboronic acid (58 mg, 0.52 mmol) was added, followed by potassium carbonate (72 mg, 0.52 mmol) and water (0.40 mL). The resulting solution was degassed with nitrogen gas and Pd(PPh$_3$)$_4$ (18 mg, 0.016 mmol) was added. The mixture was heated at 100° C. for 1 h under nitrogen. The organic layer was separated, solid NaCl was added and the mixture was extracted with ethyl acetate. The combined organic layers were filtered through PL-Thiol MP SPE tube to remove palladium catalyst. The filtrate was concentrated and then purified by prep LC/MS using 5-95% acetonitrile in water with 0.1% formic acid. The formic acid was removed using Strata SCX SPE tube to give a desired product (Compound 238) as a free base (81 mg, 82%). $^1$H-NMR (400 MHz, CDCl$_3$) δ: 1.09 (s, 9H), 1.90-2.05 (m, 2H), 2.51 (s, 3H), 2.55-2.65 (m, 2H), 2.74-2.95 (m, 7H), 3.88-4.14 (m, 4H), 5.95 (s, 1H), 6.09 (m, 1H), 7.66 (d, 1H). LCMS (+ESI) m/z 374.2 [M+H]$^+$.

This transformation is also achieved by heating the reaction mixture in a microwave reactor at 160° C. for 20 minutes. The above compound is also purified by preparative LC/MS using 5-95% gradient acetonitrile in water with 0.1% formic acid.

Compounds 239-273 were synthesized in the same manner as described for Compound 238 using different boronic acids or pinacol esters in place of cyclopentenylboronic acid. For example, Compound 254 was synthesized using 4-cyanophenylboronic acid in place of cyclopentenylboronic acid.

Compound 274 was synthesized in the same manner as compound 238 except that 3,6-dihydro-2H-pyridine-1-tert-butoxycarbonyl-4-boronic acid pinacol ester was used in place of cyclopentenylboronic acid and the Boc group was removed with TFA in DCM using the same procedure as described in Example 2 above.

Example 20

Preparation of (S)-7-methyl-N-(4-methyl-1-(methylamino)-1-oxopentan-2-yl)-3-phenyl-5,6,7,8-tetrahydroimidazo[1,5-a]pyrazine-1-carboxamide (Compound 275)

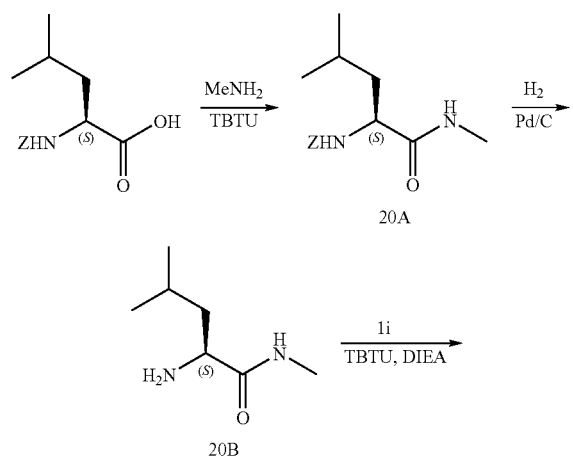

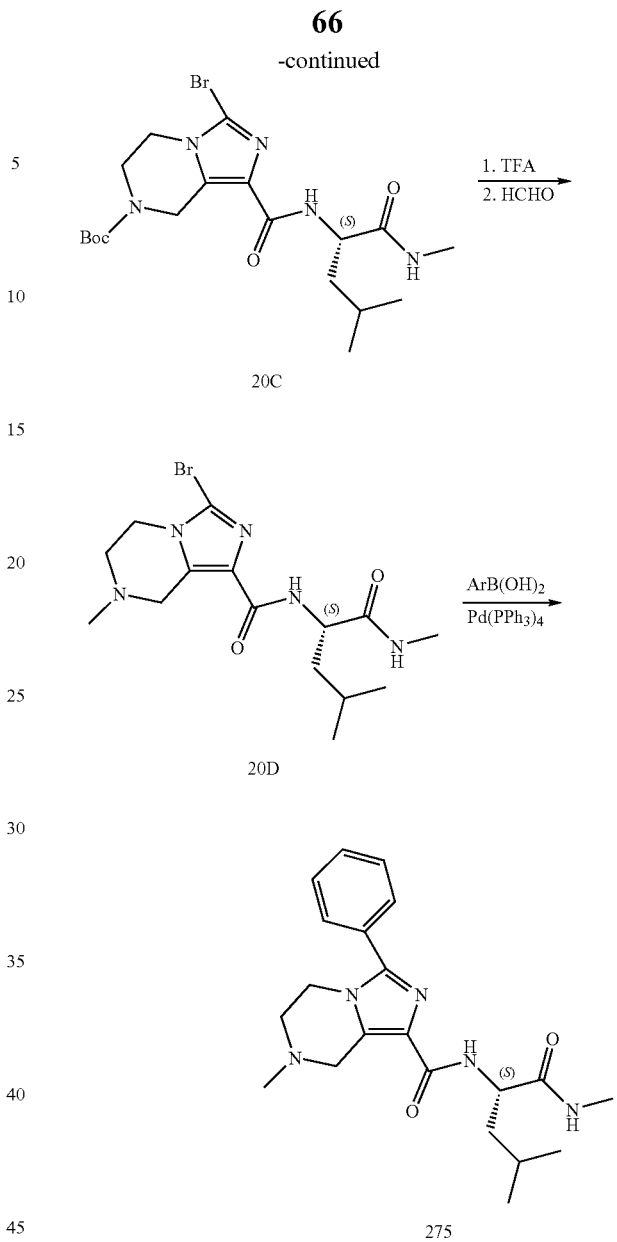

Step 1: Preparation of N-Benzyloxycarbonyl-L-leucine-N-methylamide (20A). To a solution of N-Benzyloxycarbonyl-L-leucine (1.18 g, 4.45 mmol), methylamine hydrochloride (0.60 g, 8.90 mmol) and DIEA (3.0 mL, 17.2 mmol) in DMF (40 mL) was added TBTU (1.43 g, 5.6 mmol) at 0° C. in two batches over 10 minutes. After stirring at room temperature overnight, the reaction was quenched with water (5 mL) and evaporated under vacuum. The residue was partitioned between brine and EtOAc. The organic phase was dried over anhydrous Na$_2$SO$_4$, filtered and evaporated to dryness. The residue was filtered through a short pad of silica gel with EtOAc to give crude product 20A (1.20 g) which was used in the next step without purification. LCMS (+ESI) m/z 301.1 [M+Na]$^+$.

Step 2: Preparation of L-leucine-N-methylamide (20B). A mixture of intermediate 20A (1.20 g, 4.31 mmol) and 10% palladium on carbon (300 mg) in MeOH (30 mL) was hydrogenated with a Parr shaker under 55 psi of hydrogen gas for 3 h. After filtration through celite, the filtrate was evaporated and azeotroped with EtOAc to give the desired intermediate 20B as white solid (quant. yield). LCMS (+ESI) m/z 145.1 [M+H]$^+$.

Step 3: Preparation of (S)-tert-butyl 3-bromo-1-(4-methyl-1-(methylamino)-1-oxopentan-2-ylcarbamoyl)-5,6-dihydroimidazo[1,5-a]pyrazine-7(8H)-carboxylate (20C). To a solution of 3-bromo-7-(tert-butoxycarbonyl)-5,6,7,8-tetrahydroimidazo[1,5-a]pyrazine-1-carboxylic acid (11) (0.53 g, 1.53 mmol), L-leucine-N-methylamide (0.26 g, 1.80 mmol) and DIEA (0.5 mL, 2.9 mmol) in DMF (20 mL) was added TBTU (0.69 g, 2.15 mmol) in two batches over 10 minutes at 0° C. After stirring from 0° C. to room temperature for 2 hours, the reaction was quenched with water and evaporated under vacuum. The residue was extracted between saturated aqueous NaHCO$_3$ and EtOAc. The organic layer was dried over anhydrous Na$_2$SO$_4$ and evaporated to dryness. The crude mixture was purified by column chromatography with 70% to 100% EtOAc/Hexanes to give the desired product 20C as an oil (48% yield). LCMS (+ESI) m/z 474.1, 475.1 [M+H]$^+$.

Step 4: Preparation of (S)-3-bromo-7-methyl-N-(4-methyl-1-(methylamino)-1-oxopentan-2-yl)-5,6,7,8-tetrahydroimidazo[1,5-a]pyrazine-1-carboxamide (20D). A solution of intermediate 20C (0.35 g, 0.74 mmol) in TFA/DCM (20 mL, 1:1) was stirred at room temperature for 0.5 hours. After evaporation of TFA and DCM, the residue was extracted between saturated aqueous NaHCO$_3$ and iPrOH/DCM (1:9) twice. The combined organic phase was dried and evaporated to give free amino intermediate (0.27 g, 98% yield). To a solution of the amino intermediate (0.27 g, 0.73 mmol) in THF was added AcOH (45 µL, 0.79 mmol) and paraformaldehyde (0.50 mL, 37% aq. 6.16 mmol) followed by sodium triacetoxyborohydride (0.20 g, 0.94 mmol). After stirring at room temperature overnight, THF was evaporated. The residue was extracted between saturated aqueous aqueous NaHCO$_3$ and iPrOH/DCM (1:9) twice. The combined organic phase was dried and evaporated to give compound 20D (89% yield). LCMS (+ESI) m/z 386.0, 389.1 [M+H]$^+$.

Step 5: Preparation of (S)-7-methyl-N-(4-methyl-1-(methylamino)-1-oxopentan-2-yl)-3-phenyl-5,6,7,8-tetrahydroimidazo[1,5-a]pyrazine-1-carboxamide (Compound 275). A mixture of intermediate 20D (50 mg, 0.13 mmol), potassium carbonate (32 mg, 0.23 mmol), phenylboronic acid (0.20 mmol) and palladium tetrakis (8 mg) in dioxane (1.0 mL) and water (0.5 mL) was heated at 100° C. in a sealed vial overnight. After cooling down to room temperature, the mixture was passed through a thiol-based palladium scavenger. The residue was concentrated to dryness, to which MeOH (0.5 mL) was added. The solution was filtered to remove insoluble material and purified by preparative LC-MS using a gradient of 5% MeCN/water to 95 MeCN/water (0.1% formic acid) in 15 min. Pure fractions were evaporated with a Savant speedvac. The resulting oil was taken up in DCM (1.0 mL) and diluted with hexane (1.0 mL). Evaporation under air flow with mild heating gave Compound 275 as a white solid product (56% yield). LCMS (+ESI) m/z 384.1 [M+H]$^+$.

Compounds 276-280 were synthesized in the same manner as Compound 275 except that a different boronic acid was used in place of phenyboronic acid. For example, for the synthesis of Compound 277, 3-fluoro-4-chlorophenyl boronic acid was used in place of phenylboronic acid.

Example 21

Preparation of (S)-3,3-dimethyl-2-(7-methyl-3-phenyl-5,6,7,8-tetrahydroimidazo[1,5-a]pyrazine-1-carboxamido)butanoic acid (Compound 281)

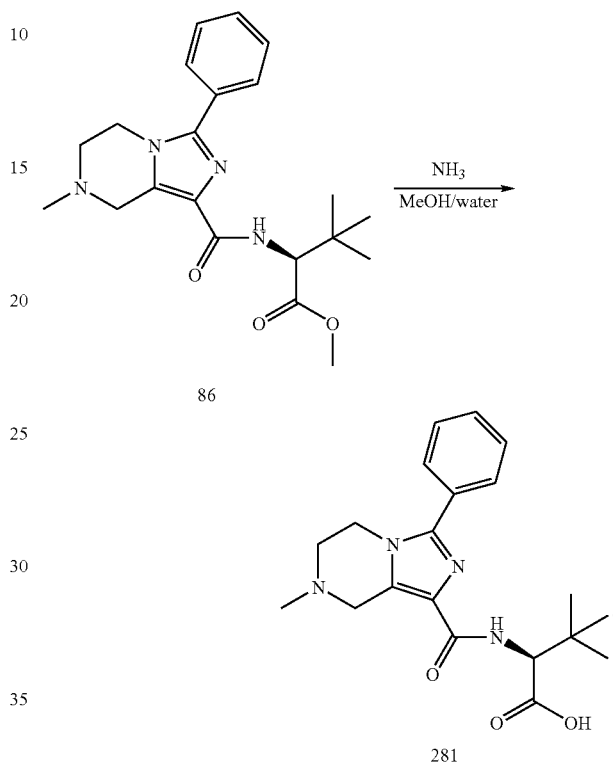

To a solution (S)-methyl 3,3-dimethyl-2-(7-methyl-3-phenyl-5,6,7,8-tetrahydro-imidazo[1,5-a]pyrazine-1-carboxamido)butanoate (Compound 86; 0.05 g, 0.13 mmol) in methanol/water was added 7N methanolic ammonia and the resulting mixture was stirred at 50° C. overnight. The mixture was concentrated, diluted with water and extracted with 10% i-PrOH/DCM. The organic layer was dried over anhydrous Na$_2$SO$_4$, filtered and concentrated to give Compound 281 (0.021 g, 43%). $^1$H-NMR (400 MHz, DMSO-d$_6$) δ: 0.99 (s, 9H), 2.41 (s, 3H), 2.74 (m, 2H), 3.85 (s, 2H), 4.03 (t, 2H), 4.30 (d, 1H), 7.48 (m, 3H), 7.73 (m, 2H), 12.95 (s, 1H); LCMS (+ESI) m/z 371.1 [M+H]$^+$.

Example 22

Preparation of (S)—N-(2,2-dimethyl-1-(3-methyl-1,2,4-oxadiazol-5-yl)propyl)-3-phenyl-5,6,7,8-tetrahydroimidazo[1,5-a]pyrazine-1-carboxamide (Compound 282)

Step 1: Preparation of (S)-tert-butyl 1-(1-methoxy-3,3-dimethyl-1-oxobutan-2-ylcarbamoyl)-3-phenyl-5,6-dihydroimidazo[1,5-a]pyrazine-7(8H)-carboxylate (Intermediate 22A). To a solution of 7-(tert-butoxycarbonyl)-3-phenyl-5,6,7,8-tetrahydroimidazo[1,5-a]pyrazine-1-carboxylic acid (Intermediate 3B) (2.0 g, 5.82 mmol) in DMF was added (S)-methyl 2-amino-3,3-dimethylbutanoate (1.18 g, 8.15 mmol), followed by DIEA (2.26 g, 17.47 mmol). The resulting mixture was stirred for 20 min and TBTU (2.43 g, 7.57 mmol) was added and the mixture was stirred overnight. The reaction mixture was diluted with water and extracted with EtOAc, washed with water, brine, dried over anhydrous $Na_2SO_4$, filtered and concentrated. The residue was purified by flash chromatography eluting with ethyl acetate/hexanes 10-50% gradient to give Intermediate 22A 2.73 g (98%). LCMS (+ESI) m/z 470.0 $[M+H]^+$.

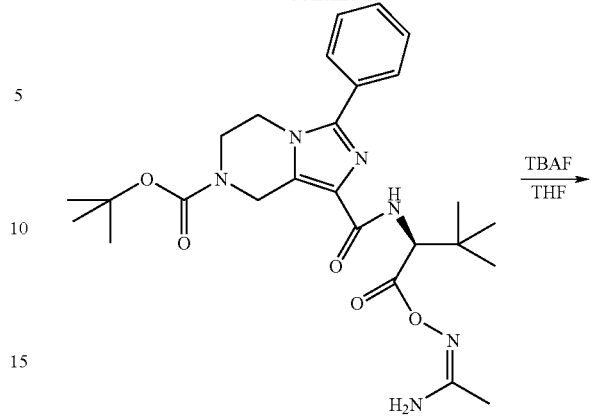

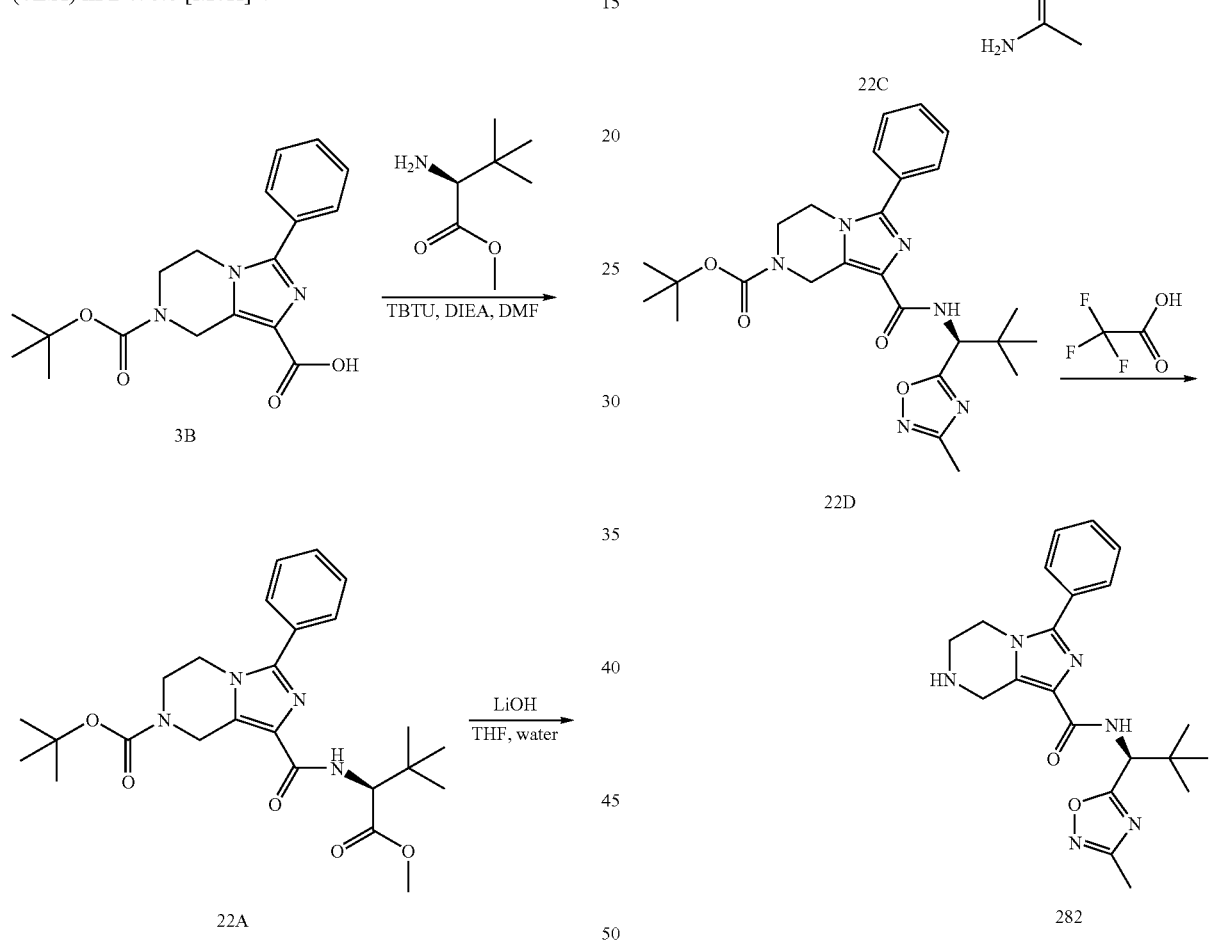

Step 2: Preparation of (S)-2-(7-(tert-butoxycarbonyl)-3-phenyl-5,6,7,8-tetrahydroimidazo[1,5-a]pyrazine-1-carboxamido)-3,3-dimethylbutanoic acid (Intermediate 22B). Intermediate 22A (2.73 g, 5.80 mmol) was dissolved in THF (20 mL) and cooled to 0° C. Lithium hydroxide (0.70 g, 29 mmol) solution in water (4 mL) was added and the mixture was stirred on ice bath for 6 hours. The mixture was concentrated under reduced pressure, cooled in an ice bath and acidified to pH 4 with 1N HCl. The resulting white precipitate was filtered, washed with water and dried in a vacuum oven at 40° C. to provide Intermediate 22B (2.29 g, 86%) as a white solid. $^1$H-NMR (400 MHz, DMSO-$d_6$) δ: 0.97 (s, 9H), 1.44 (s, 9H), 3.67 (m, 2H), 4.14 (t, 2H), 4.48 (d, 1H), 4.84 (s, 2H), 7.49 (m, 3H), 7.72 (m, 2H); LCMS (+ESI) m/z 457.2 $[M+H]^+$.

Step 3: Preparation of (S,Z)-tert-butyl 1-(1-(1-aminoethylideneaminooxy)-3,3-dimethyl-1-oxobutan-2-ylcarbamoyl)-3-phenyl-5,6-dihydroimidazo[1,5-a]pyrazine-7(8H)-carboxylate (Intermediate 22C). Intermediate 22B (0.25 g, 0.55 mmol) was dissolved in DMF and EDCI (0.17 g, 0.87 mmol) was added, followed by HOBt (0.12 g, 0.87 mmol). The resulting mixture was stirred for 30 min and (Z)—N'-hydroxy-acetimidamide (0.06 g, 0.82 mmol) was added and the mixture was stirred overnight. The reaction mixture was diluted with water and extracted with EtOAc. The organic layer was washed successively with water, 2N Na$_2$CO$_3$ solution and brine, dried over anhydrous Na$_2$SO$_4$, filtered, and concentrated under reduced pressure. The residue was used in the next step without purification. LCMS (+ESI) m/z 1025.2 [2M+H]$^+$.

Step 4: Preparation of (S)-tert-butyl 1-(2,2-dimethyl-1-(3-methyl-1,2,4-oxadiazol-5-yl)propylcarbamoyl)-3-phenyl-5,6-dihydroimidazo[1,5-a]pyrazine-7(8H)-carboxylate (Intermediate 22D). Intermediate 22C (0.20 g, 0.39 mmol) was dissolved in a 1N solution of TBAF in THF (0.55 mL). The resulting mixture was stirred overnight, concentrated, diluted with EtOAc and washed successively with water and brine, dried over anhydrous Na$_2$SO$_4$, filtered and concentrated. The residue was purified by preparative flash chromatography on silica, eluting with a 20-70% ethyl acetate/hexanes gradient to provide Intermediate 22D (0.17 g, 88%). $^1$H-NMR (400 MHz, CDCl$_3$-d) δ: 1.09 (s, 9H), 1.51 (s, 9H), 2.40 (s, 3H), 3.78 (m, 2H), 4.11 (m, 2H), 5.01 (m, 2H), 5.37 (d, 1H), 7.35 (m, 3H), 7.64 (m, 2H), 7.78 (d, 1H); LCMS (+ESI) m/z 495.1 [M+H]$^+$.

Step 5 Preparation of (S)—N-(2,2-dimethyl-1-(3-methyl-1,2,4-oxadiazol-5-yl)propyl)-3-phenyl-5,6,7,8-tetrahydroimidazo[1,5-a]pyrazine-1-carboxamide (Compound 282).

Intermediate 22D (170 mg, 0.34 mmol) was dissolved in DCM (2 mL) and TFA (0.5 mL) was added. The resulting mixture was stirred for 2 h. The mixture was concentrated, neutralized with NaHCO$_3$ saturated solution and extracted several times with EtOAc. The combined organic extracts were washed successively with water and brine, dried over anhydrous Na$_2$SO$_4$, filtered and concentrated to give of Compound 282 (125 mg, 87%). $^1$H-NMR (400 MHz, CDCl$_3$-d) δ: 1.09 (s, 9H), 2.40 (s, 3H), 3.78 (m, 2H), 4.11 (m, 2H), 5.01 (m, 2H), 5.37 (d, 1H), 7.35 (m, 3H), 7.64 (m, 2H), 7.78 (d, 1H), LCMS (+ESI) m/z 395.0 [M+H]$^+$.

Compound 283 was synthesized in the same manner as described above for Compound 282 except that N'-hydroxy-2,2-dimethylpropanimidamide was used in place of (Z)—N'-hydroxyacetimidamide in step 3 and the final compound was methylated using the procedure described in Example 5.

Compound 284 was synthesized in the same manner as described above for Compound 282 except that N'-hydroxy-2,2-dimethylpropanimidamide was used in place of (Z)—N'-hydroxyacetimidamide in step 3 and the final compound was reacted with (1-ethoxy-cyclopropoxy)trimethylsilane using the procedure described in Example 13 above.

Example 23

Preparation of (S)—N-(1-amino-3,3-dimethyl-1-oxobutan-2-yl)-7-methyl-3-phenyl-5,6,7,8-tetrahydroimidazo[1,5-a]pyrazine-1-carboxamide (Compound 285)

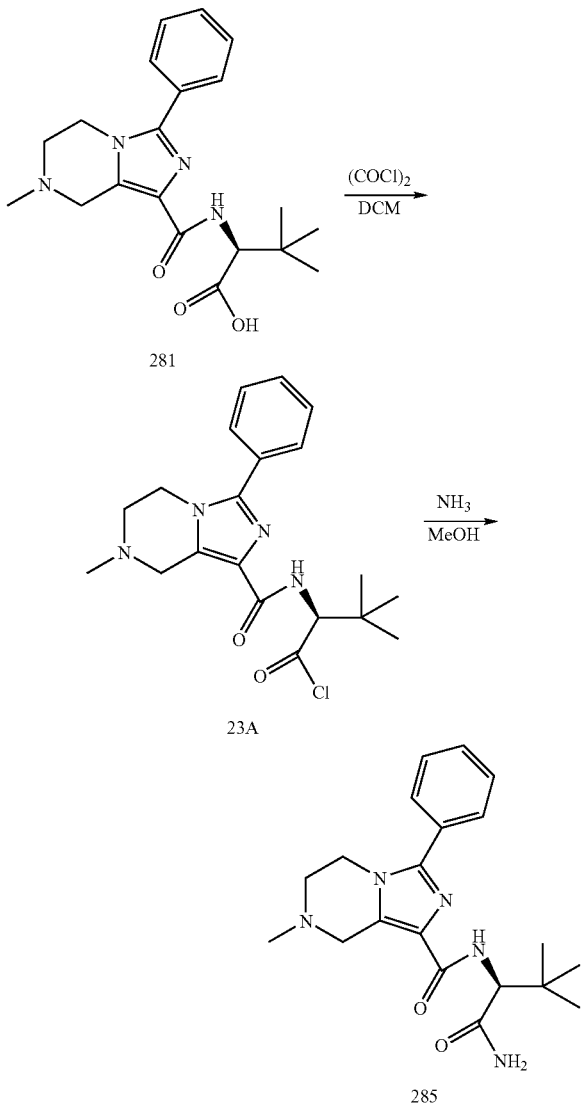

Step 1: Preparation of (S)-3,3-dimethyl-2-(7-methyl-3-phenyl-5,6,7,8-tetrahydroimidazo[1,5-a]pyrazine-1-carboxamido)butanoyl chloride (23A). To a solution (S)-3,3-dimethyl-2-(7-methyl-3-phenyl-5,6,7,8-tetrahydroimidazo[1,5-a]pyrazine-1-carboxamido)butanoic acid (Compound 281) (0.11 g, 0.30 mmol) in DCM was added oxalyl chloride (0.08 g, 0.60 mmol) followed by a catalytic amount of DMF. The resulting mixture was stirred for 2 h and the solvent was evaporated, toluene (2 mL) was added and the mixture was concentrated again. The resulting product (Intermediate 23A) was dried under vacuum and then used in the next step without further purification.

Step 2: Preparation of (S)—N-(1-amino-3,3-dimethyl-1-oxobutan-2-yl)-7-methyl-3-phenyl-5,6,7,8-tetrahydroimidazo[1,5-a]pyrazine-1-carboxamide (Compound 285). Intermediate 23A (0.11 g, 0.3 mmol) was dissolved in THF (2 mL) and 7M ammonia solution in methanol was added. The resulting mixture was stirred for 2 h, the solvent was evaporated and the residue was purified by prep LC/MS using 5-95% gradient acetonitrile/water with 0.1% formic acid to give Compound 285 as a formate salt (20 mg, 15%). ¹H-NMR (400 MHz, CD₃OD) δ: 1.11 (s, 9H), 2.59 (s, 3H), 2.93 (m, 2H), 4.09 (m, 2H), 4.21 (m, 2H), 4.40 (m, 1H), 7.51 (m, 3H), 7.72 (m, 2H), 8.31 (s, 1H); LCMS (+ESI) m/z 370.2 [M+H]⁺.

Example 24

Preparation (S,E)-N-(3,3-dimethyl-1-(methylamino)-1-oxobutan-2-yl)-7-methyl-3-(3-morpholinoprop-1-enyl)-5,6,7,8-tetrahydroimidazo[1,5-a]pyrazine-1-carboxamide (Compound 286)

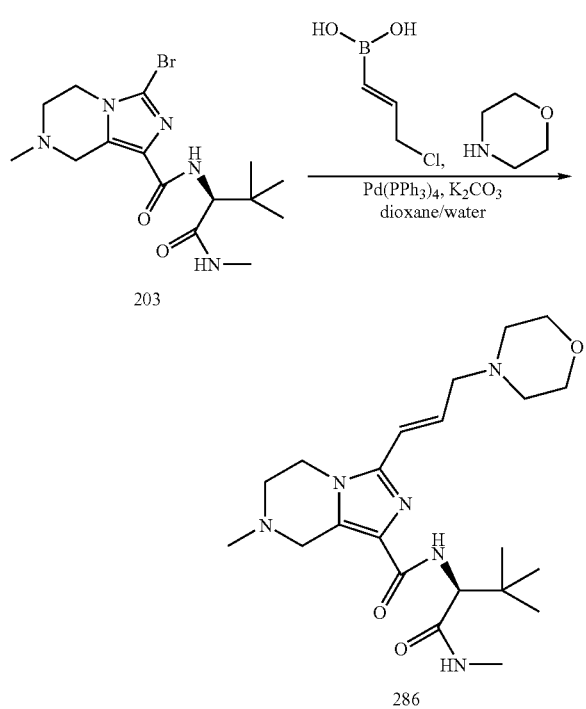

(S)-3-bromo-N-(3,3-dimethyl-1-(methylamino)-1-oxobutan-2-yl)-7-methyl-5,6,7,8-tetrahydroimidazo[1,5-a]pyrazine-1-carboxamide (Compound 203; 0.12 g, 0.31 mmol) was dissolved in dioxane (4 mL) and (E)-3-chloroprop-1-enylboronic acid (0.037 g, 0.31 mmol) was added, followed by K₂CO₃ (0.11 g, 0.82 mmol), morpholine (0.054 g, 0.66 mmol) and water (0.80 mL). The resulting mixture was degassed with nitrogen and Pd(PPh₃)₄ (0.019 g, 0.017 mmol) was added. The mixture was subjected to microwave irradiation at 160° C. for 20 min. The mixture was diluted with EtOAc, and filtered through celite. The organic layer was concentrated, washed with water, dried over anhydrous Na₂SO₄, filtered and concentrated again. The residue was purified by prep LC/MS using 5-95% gradient acetonitrile/water with 0.1% formic acid to provide Compound 286 (0.035 g, 34%) as a yellow solid. ¹H-NMR (400 MHz, CDCl₃) δ: 1.07 (s, 9H), 2.52 (s, 3H), 2.81 (d, 3H), 2.89 (t, 2H), 2.97 (m, 3H), 3.28 (s, 1H), 3.58 (d, 1H), 3.99 (m, 8H), 4.35 (d, 1H), 6.11 (m, 1H), 6.68 (m, 2H), 7.71 (m, 1H); LCMS (+ESI) m/z 433.3 [M+H]⁺.

Compounds 287 and 288 were synthesized in the same manner as Compound 286 except that another amine was used in place of morpholine. For example, Compound 287 was synthesized using piperidine in place of morpholine.

Example 25

Preparation (S)-3-benzoyl-N-(3,3-dimethyl-1-(methylamino)-1-oxobutan-2-yl)-7-methyl-5,6,7,8-tetrahydroimidazo[1,5-a]pyrazine-1-carboxamide (Compound 289)

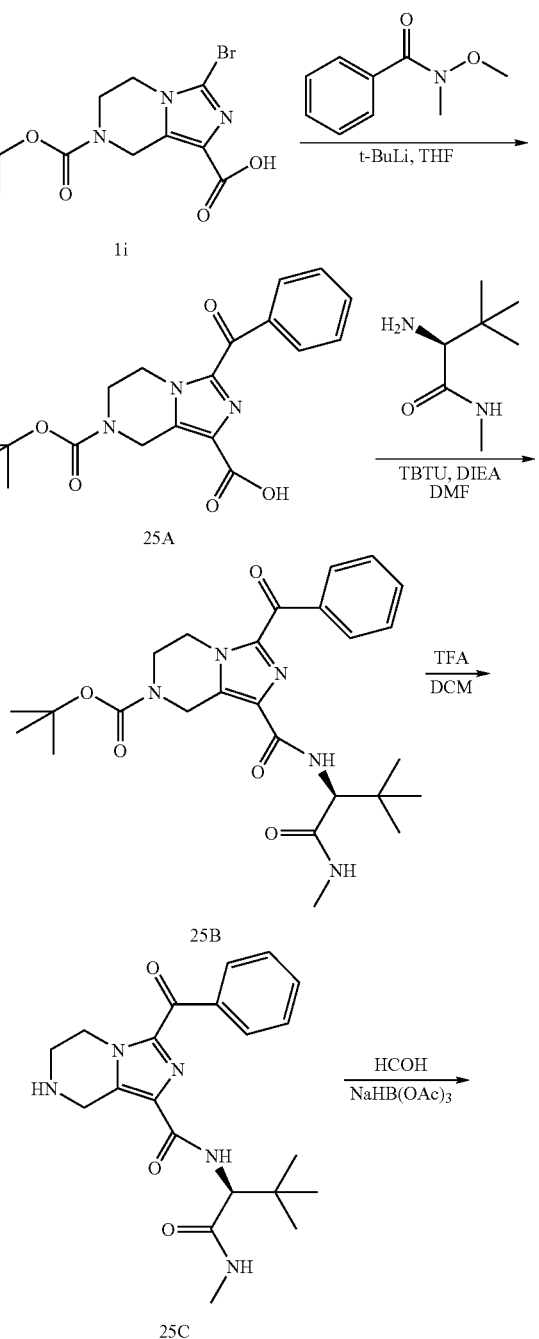

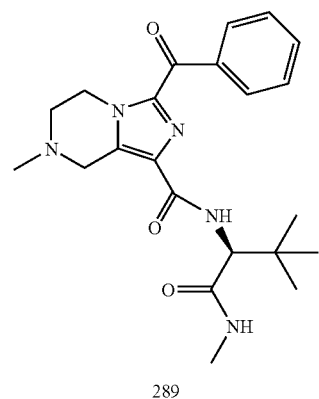

289

Step 1: Preparation of 3-benzoyl-7-(tert-butoxycarbonyl)-5,6,7,8-tetrahydroimidazo[1,5-a]pyrazine-1-carboxylic acid (25A). Under a nitrogen atmosphere Compound 11 (0.15 g, 0.43 mmol) was dissolved in THF (2 mL) and N-methoxy-N-methylbenzamide (0.14 g, 0.86 mmol) was added. The resulting solution was cooled to −78° C. and tert-Butyl lithium (1.7M in THF, 1.02 mL, 1.73 mmol) was added dropwise. The resulting mixture was stirred and cooled for 1 h and quenched with NH$_4$Cl saturated solution. The solid was removed by filtration and the filtrate was concentrated, acidified to pH 6 with 5% TFA and extracted with 20% i-PrOH/DCM. The organic layer was concentrated, diluted with DCM, washed with brine, dried over anhydrous Na$_2$SO$_4$, filtered and concentrated to give product 25A (0.072 g, 45%). LCMS (+ESI) m/z 372.1 [M+H]$^+$.

Step 2: Preparation of (S)-tert-butyl 3-benzoyl-1-(3,3-dimethyl-1-(methylamino)-1-oxobutan-2-ylcarbamoyl)-5,6-dihydroimidazo[1,5-a]pyrazine-7(8H)-carboxylate (25B). Intermediate 25B was synthesized in the same manner as described above for compound 22A in Example 22 except that Intermediate 25A was used in place of 3B and L-tert-Leucine methylamide was used instead of (S)-methyl 2-amino-3,3-dimethylbutanoate. LCMS (+ESI) m/z 498.3 [M+H]$^+$ Step 3: Preparation of (S)-3-benzoyl-N-(3,3-dimethyl-1-(methylamino)-1-oxobutan-2-yl)-5,6,7,8-tetrahydroimidazo[1,5-a]pyrazine-1-carboxamide (25C). Intermediate 25C was synthesized in the same manner as described above for Compound 2 except that Compound 25B was used in place of Compound 1.

Step 4: Preparation of Compound 289. Compound 289 was synthesized in the same manner as described above for Compound 48 in Example 5 except that 25C was used in place of Compound 2. $^1$H-NMR (400 MHz, CD$_3$OD) δ: 1.04 (s, 9H), 2.55 (s, 3H), 2.75 (d, 3H), 2.93 (t, 2H), 4.03 (d, 2H), 4.35 (d, 1H), 4.56 (t, 2H), 7.53 (t, 2H), 7.64 (m 1H), 7.86 (d, 1H), 8.19 (m, 1H), 8.31 (d, 2H); LCMS (+ESI) m/z 412.1 [M+H]$^+$.

Compound 290 was synthesized in the same manner as Compound 289 except that isocyanatobenzene was used instead of N-methoxy-N-methylbenzamide.

Example 26

Preparation 3,3-dimethyl-1-(3-phenyl-5,6,7,8-tetrahydroimidazo[1,5-a]pyrazin-1-yl)butan-1-one 2,2,2-trifluoroacetate (Compound 291)

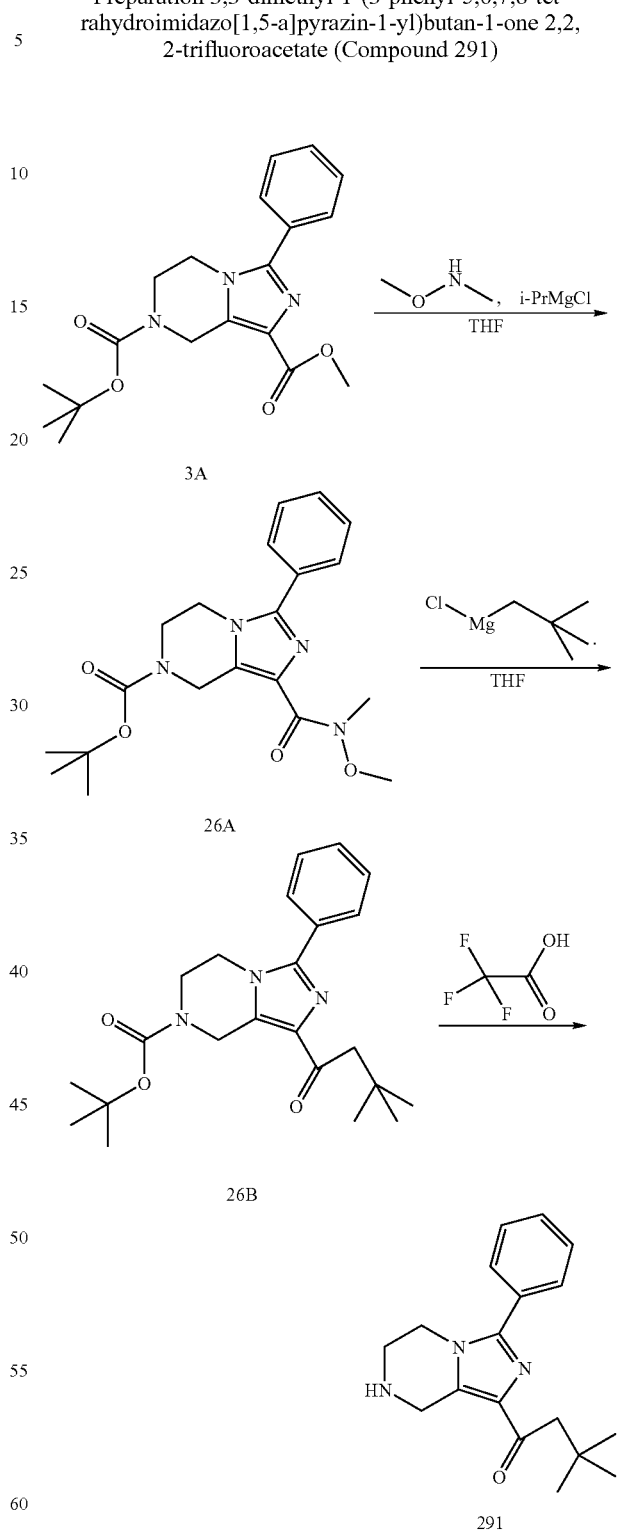

Step 1: Preparation of (tert-butyl 1-(methoxy(methyl)carbamoyl)-3-phenyl-5,6-dihydroimidazo[1,5-a]pyrazine-7

(8H)-carboxylate (Intermediate 26A). Under a nitrogen atmosphere 7-tert-butyl 1-methyl 3-phenyl-5,6-dihydroimidazo[1,5-a]pyrazine-1,7(8H)-dicarboxylate (Intermediate 3A) (1.50 g, 4.20 mmol) was dissolved in THF (6 mL) and N,O-dimethyl-hydroxylamine hydrochloride (1.23 g, 12.59 mmol) was added. The resulting suspension was cooled to −20° C. and a solution of iPrMgCl (2M, 6.3 mL, 12.59 mmol) in THF was added dropwise over 10 min. The mixture was stirred for 20 min at −10° C. and then was quenched with saturated aqueous NH₄Cl. The mixture was extracted with EtOAc, dried over anhydrous Na₂SO₄, filtered and concentrated to provide Intermediate 26A as a white solid (1.35 g, 83%). ¹H-NMR (400 MHz, CDCl₃) δ: 1.52 (s, 9H), 3.63 (s, 3H), 3.80 (m, 2H), 3.90 (s, 3H), 4.12 (t, 2H), 5.02 (s, 2H), 7.46 (m, 3H), 7.65 (m, 2H); LCMS (+ESI) m/z 387.1 [M+H]⁺.

Step 2: Preparation of tert-butyl 1-(3,3-dimethylbutanoyl)-3-phenyl-5,6-dihydro-imidazo[1,5-a]pyrazine-7(8H)-carboxylate (26B). Compound 26A (0.10 g, 0.26 mmol) was dissolved in THF and cooled to 0° C. and neopentylmagnesium chloride (1M in diethyl ether, 0.35 mL) was added and the mixture was stirred for 2 hours. The mixture was quenched with NH₄Cl saturated solution and extracted with EtOAc. The residue was purified by preparative flash chromatography on silica, eluting with 20-80% gradient of ethyl acetate in hexanes to provide intermediate 26B (0.08 g, 77%).

Step 3: Preparation of 3,3-dimethyl-1-(3-phenyl-5,6,7,8-tetrahydroimidazo-[1,5-a]pyrazin-1-yl)butan-1-one 2,2,2-trifluoroacetate (Compound 291). Intermediate 26B (0.08 g, 0.20 mmol) was dissolved in DCM and TFA was added. The resulting mixture was stirred for 2 hours. The mixture was concentrated, diluted with water and acetonitrile and lyophilized to produce the desired product as a TFA salt. The residue was dissolved in methanol and filtered through a SPE SCX tube column, eluting with 2N ammonia in methanol to provide Compound 291 (0.055 g, 90%) as a free base. ¹H-NMR (400 MHz, CD₃OD) δ: 1.05 (s, 9H), 2.87 (s, 2H), 3.15 (t, 2H), 4.07 (t, 2H), 4.35 (s, 2H), 7.52 (m, 3H), 7.67 9 m, 2H); LCMS (+ESI) m/z 298.1 [M+H]⁺.

Compound 292 was synthesized by the same procedure as described above for Compound 48 in Example 5, except that Compound 291 was used in place of Compound 2. Likewise, compound 293 was synthesized in the same manner except that in step 2,2-methyl-1-propenylmagnesium bromide was used in place of neopentyl-magnesium chloride. Similarly, compound 294 was synthesized as described above except that in Step 2,3-phenyl-1-propylmagnesium bromide was used in place of neopentylmagnesium chloride.

Example 27

Preparation N—((S)-3,3-dimethyl-1-(methylamino)-1-oxobutan-2-yl)-3-(hydroxy(phenyl)methyl)-7-methyl-5,6,7,8-tetrahydroimidazo[1,5-a]pyrazine-1-carboxamide (Compound 295)

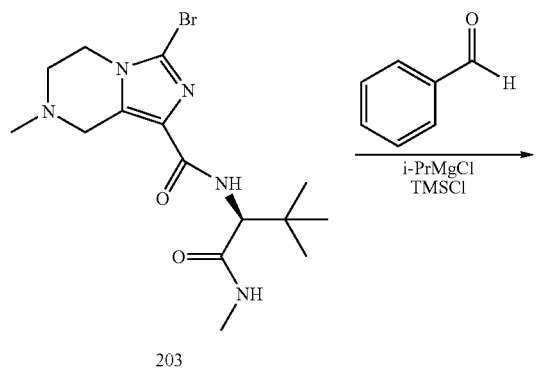

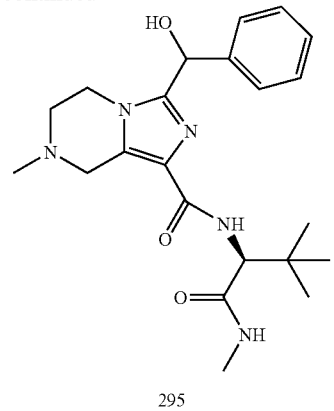

Under a nitrogen atmosphere (S)-3-bromo-N-(3,3-dimethyl-1-(methylamino)-1-oxobutan-2-yl)-7-methyl-5,6,7,8-tetrahydroimidazo[1,5-a]pyrazine-1-carboxamide (Compound 203) (0.050 g, 0.13 mmol) was dissolved in THF and trimethysilylchloride (0.045 g, 0.41 mmol) was added. The resulting solution was stirred for 3 hours. Isopropylmagnesium chloride solution (2M in THF, 0.27 mL, 0.54 mmol) was added dropwise at 0° C. and the mixture was stirred for 15 minutes, then benzaldehyde (0.028 g, 0.26 mmol) was added at 0° C. and the resulting mixture was stirred cold for 40 minutes. The mixture was quenched at 0° C. with NH₄Cl saturated solution, stirred for 10 min and concentrated. The reaction mixture was then extracted repeatedly with 20% i-PrOH/DCM and the combined organic extracts were dried over Na₂SO₄, filtered and concentrated. The residue was purified by prep LC/MS using 5-95% gradient acetonitrile/water with 0.1% formic acid. The resulting material was filtered through Strata SCX SPE tube to give (0.010 g, 18%) of Compound 295 as a free base. ¹H-NMR (400 MHz, CD₃OD) δ: 1.05 (s, 9H), 2.43 (s, 3H), 2.75 (m, 5H), 3.69 (m, 1H), 3.88 (m, 2H), 4.09 (m, 1H), 4.32 (s, 1H), 7.53 (t, 2H), 5.97 (m, 1H), 7.29 (m, 1H), 7.38 (m, 4H); LCMS (+ESI) m/z 414.2 [M+H]⁺.

Compound 296 was synthesized as described above for Compound 295 except that cyclopropanecarboxaldehyde was used in place of benzaldehyde.

Example 28

Preparation of (S)—N-(3,3-dimethyl-1-(methylamino)-1-oxobutan-2-yl)-7-methyl-3-(thiazol-2-yl)-5,6,7,8-tetrahydroimidazo[1,5-a]pyrazine-1-carboxamide (Compound 297)

Compound 203 (20 mg, 52 μmol) was dissolved in 500 μL of THF in a microwave vial. CuI (10 mg, 52 μmol) and Pd[P(Ph)₃]₂Cl₂ (3.6 mg, 5 μmol) were added followed by the 2-thiazolylzinc (II) bromide (104 μL of 0.5M solution, 52 μmol). The vial was capped and the mixture was subjected to microwave irradiation with heating to 160° C. for 5 minutes, after which time the reaction was 50% complete by LC/MS. Addition of further equivalents of zinc reagent followed by irradiation and heating failed to drive the reaction to completion.

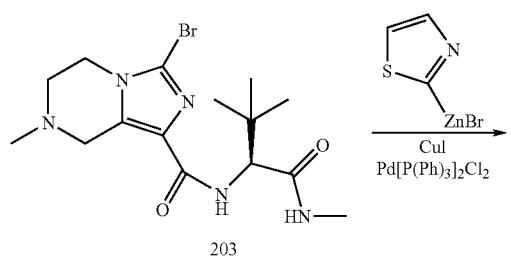
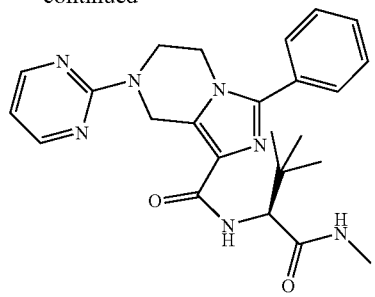

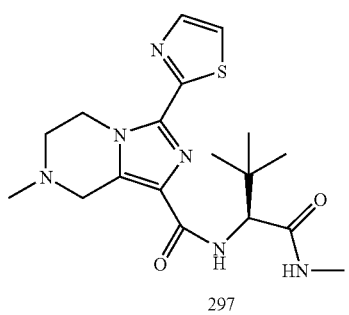

The reaction was quenched by the addition of 2 mL of saturated aqueous NaHCO₃ and extracted with DCM (2×1 mL). The combined organic layers were dried with anhydrous Na₂SO₄, filtered and evaporated. The residue was purified by flash chromatography using a gradient from 100% EtOAc to 5% MeOH in EtOAc to provide the desired product, Compound 297, as a yellow solid (2 mg), LCMS (+ESI) m/z 391.3 [M+H]⁺.

Example 29

Preparation of N-(3,3-dimethyl-1-(methylamino)-1-oxobutan-2-yl)-3-phenyl-7-(pyrimidin-2-yl)-5,6,7,8-tetrahydroimidazo[1,5-a]pyrazine-1-carboxamide (Compound 298)

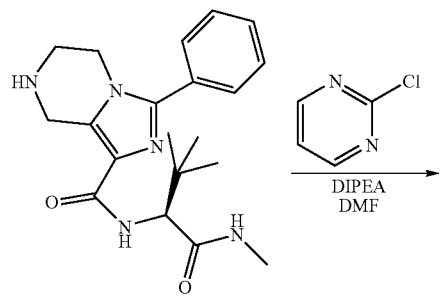

Compound 2 (15 mg, 35 umol) was dissolved in DMF (3 mL). DIPEA was added followed by the 2-chloropyrimidine. The reaction was subjected to microwave irradiation and heated at 160° C. for 15 minutes and then for a further 5 minutes under the same conditions to drive to completion. The reaction was quenched by the addition of 2 mL of saturated aqueous NaHCO₃ and extracted of DCM (2×1 mL). The combined organic layers were dried with anhydrous Na₂SO₄, filtered and evaporated. The residue was purified by preparative LC/MS using a 10 minute gradient from 70% water/acetonitrile to 10% water/acetonitrile with 0.1% formic acid as a modifier. The desired product, Compound 298, was isolated as a clear oil (11 mg, 68% yield). LCMS (+ESI) m/z 448.2 [M+H]⁺.

Compounds 299-301 were synthesized in the same manner as described above for Compound 298 except that different halogenated heterocycles were used in place of the 2-chloropyrimidine. For example, for Compound 301, 2-chloropyrazine was used in place of 2-chloropyrimidine.

Example 30

Preparation of (R)—N-(3,3-dimethyl-1-(methylamino)-1-oxobutan-2-yl)-7-methyl-3-phenyl-5,6,7,8-tetrahydroimidazo[1,5-a]pyrazine-1-carboxamide (Compound 302)

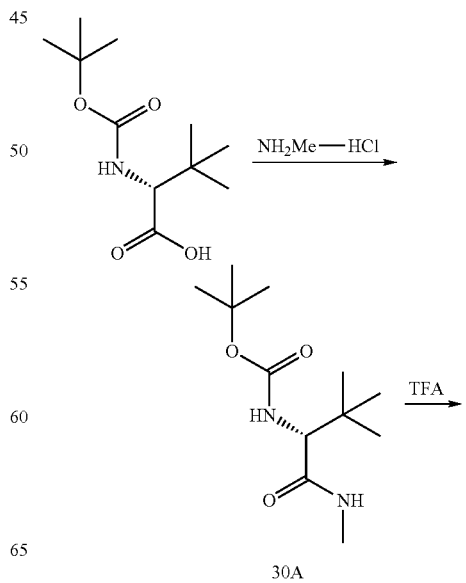

-continued

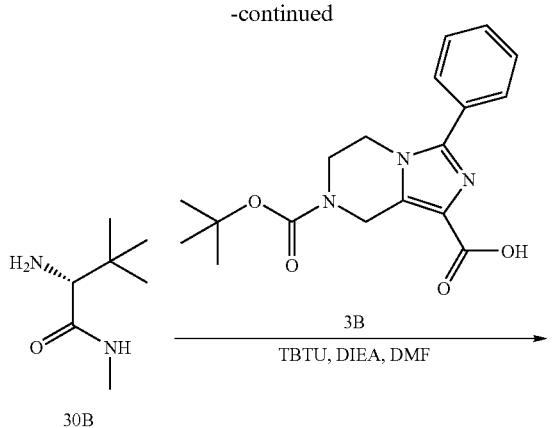

To a cold solution of (R)-2-(tert-butoxycarbonylamino)-3,3-dimethylbutanoic acid (0.50 g, 2.16 mmol) in acetonitrile (8 mL) was added methylamine hydrochloride (0.48 g, 7.13 mmol), followed by DIEA (1.67 g, 12.9 mmol). The resulting mixture was stirred for 20 min and TBTU (0.76 g, 2.37 mmol) was added and the stirring continued overnight. The mixture was concentrated, diluted with EtOAc (30 mL) and washed successively with aqueous 5% KHSO$_4$, saturated NaHCO$_3$ solution and brine, dried over anhydrous Na$_2$SO$_4$, filtered and concentrated to provide Intermediate 30A (0.41 g, 77%).

Step 2: Preparation of (R)-2-amino-N,3,3-trimethylbutanamide. Intermediate 30A (0.40 g, 1.67 mmol) was dissolved in DCM (3 mL) and TFA (1.5 mL) was added. The resulting mixture was stirred for 2 hours. The solvent was evaporated and the residue was diluted with water and lyophilized to give Intermediate 30B (TFA salt) in a quantitative yield.

Step 3 Preparation of (R)-tert-butyl 1-(3,3-dimethyl-1-(methylamino)-1-oxobutan-2-ylcarbamoyl)-3-phenyl-5,6-dihydroimidazo[1,5-a]pyrazine-7(8H)-carboxylate (Intermediate 30C). Intermediate 30B (0.088 g, 0.61 mmol) was dissolved DMF and Compound 3B (0.15 g, 0.44 mmol) was added followed by DIEA (0.34 g, 2.62 mmol). The resulting mixture was stirred for 20 min, TBTU (0.154 g, 0.48 mmol) was added and the resulting solution was stirred overnight. The reaction mixture was diluted with water and extracted with EtOAc, washed successively with water and brine, dried over anhydrous Na$_2$SO$_4$ and concentrated. The residue was purified by preparative flash chromatography, eluting with 10-60% gradient of ethyl acetate/hexane to provide Intermediate 30C (0.18 g, 88%). LCMS (+ESI) m/z 470.0 [M+H]$^+$.

Step 4: Preparation of (R)—N-(3,3-dimethyl-1-(methylamino)-1-oxobutan-2-yl)-3-phenyl-5,6,7,8-tetrahydroimidazo[1,5-a]pyrazine-1-carboxamide (Intermediate 30D). Intermediate 30D was synthesized in the same manner as described above in Example 2 except that Intermediate 30C was used in place of Compound 1. LCMS (+ESI) m/z 370.0 [M+H]$^+$.

Step 5: Preparation of Compound 302. Compound 302 was synthesized in the same manner as described above in Example 5, except that compound Intermediate 30D was used in place of Compound 2. LCMS (+ESI) m/z 384.0 [M+H]$^+$.

Example 31

Preparation of (S)-3-cyclopentyl-N-(3,3-dimethyl-1-(methylamino)-1-oxobutan-2-yl)-7-methyl-5,6,7,8-tetrahydroimidazo[1,5-a]pyrazine-1-carboxamide (Compound 303)

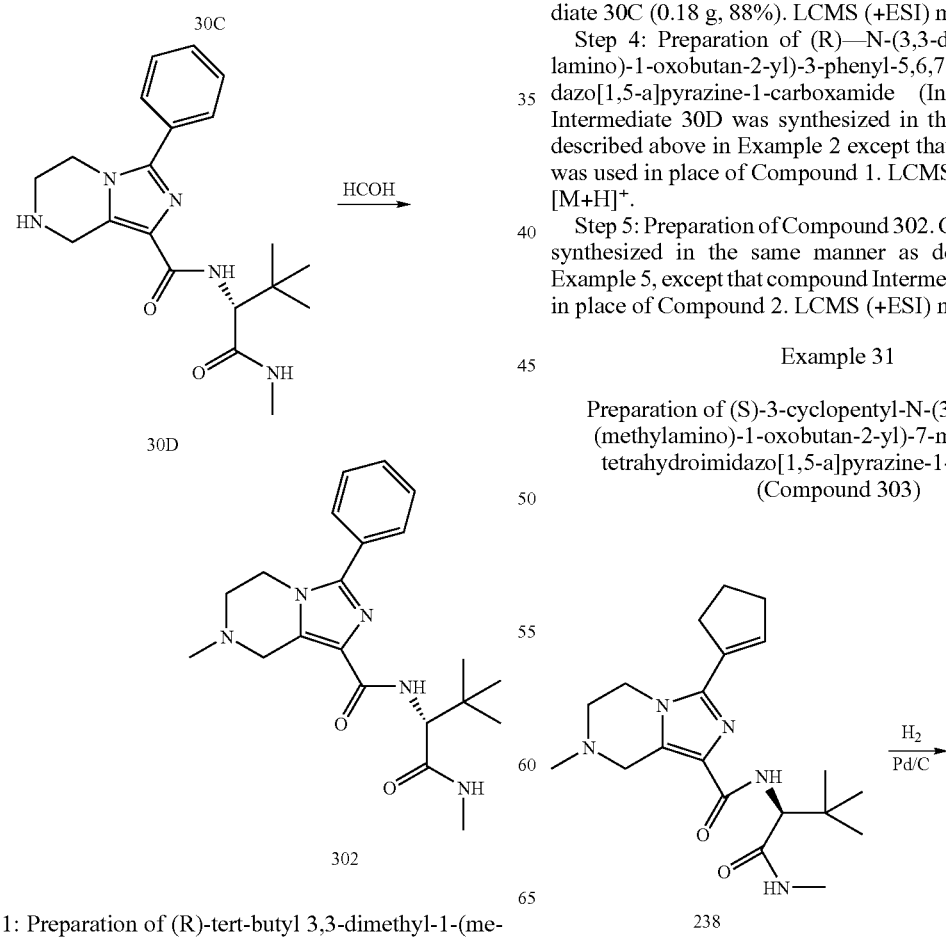

Step 1: Preparation of (R)-tert-butyl 3,3-dimethyl-1-(methylamino)-1-oxobutan-2-ylcarbamate (Intermediate 30A).

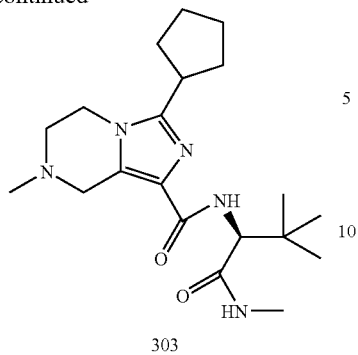

303

Palladium on carbon (wet) (0.014 mg, 0.013 mmol) was suspended in methanol (1 mL) and transferred under nitrogen into a hydrogenation reaction vessel followed by methanol (1 mL). (S)-3-cyclopentenyl-N-(3,3-dimethyl-1-(methylamino)-1-oxobutan-2-yl)-7-methyl-5,6,7,8-tetrahydroimidazo[1,5-a]pyrazine-1-carboxamide (0.062 g, 0.17 mmol) in methanol (3 mL) was added and the mixture was hydrogenated at 60 psi for 2 h. The mixture was filtered through a celite plug and concentrated. The residue was purified ion exchange chromatography, eluting the product with 2N methanolic ammonia to provide Compound 303 (0.05 mg, 78%) as a yellow solid. $^1$H-NMR (400 MHz, CDCl$_3$) δ: 1.01 (s, 9H), 1.55 (m, 2H), 1.76 (m, 2H), 1.87 (m, 2H), 2.39 (s, 3H), 2.69 (m, 5H), 2.90 (s, 1H), 3.84 (m, 4H), 4.28 (s, 1H), 6.40 (m, 1H), 7.59 (d, 1H). LCMS (+ESI) m/z 376.2 [M+H]$^+$.

Compound 304 was synthesized in the same manner as described above for compound 303 except compound 243 was used in place of compound 238. Similarly, compound 305 was synthesized as described except compound 256 was used in place of compound 238. Compound 306 was synthesized in the same manner except compound 257 was used in place of compound 238. Likewise, compound 307 was synthesized in the same manner except compound 287 was used in place of compound 238.

Compound 308 was synthesized in the same manner as described above for compound 303 except compound 288 was used in place of Compound 238. Similarly, compound 309 was synthesized as described above except compound 286 was used in place of compound 238. Compound 310 was synthesized in a like manner except compound 266 was used in place of compound 238.

Example 32

Preparation (S)-1-(3,3-dimethyl-1-(methylamino)-1-oxobutan-2-ylcarbamoyl)-7,7-dimethyl-3-phenyl-5,6,7,8-tetrahydroimidazo[1,5-a]pyrazin-7-ium iodide (Compound 311)

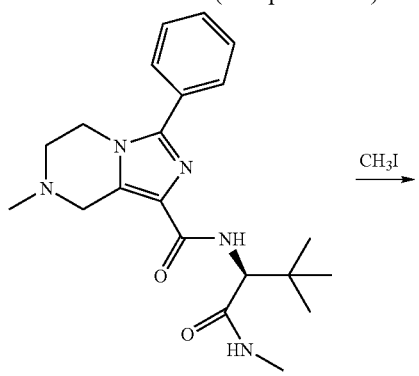

48

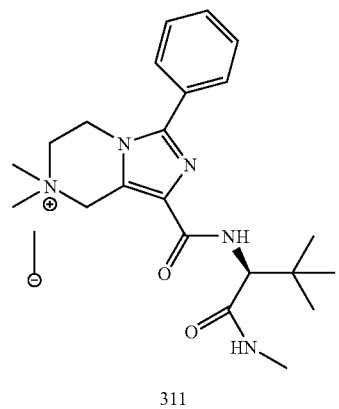

311

(S)—N-(3,3-dimethyl-1-(methylamino)-1-oxobutan-2-yl)-7-methyl-3-phenyl-5,6,7,8-tetrahydroimidazo[1,5-a]pyrazine-1-carboxamide (Compound 48; 0.09 g, 0.24 mmol) was dissolved in acetone (2 mL) and methyl iodide (0.038 g, 0.26 mmol) was added. The reaction mixture was stirred for 18 hours. The mixture was concentrated, ethyl acetate was added and the resulting solid was filtered, washed with cold ethyl acetate and dried under vacuum to provide the desired product, Compound 311 (0.031 g, 24%) as a yellow solid. $^1$H-NMR (400 MHz, DMSO-d$_6$) δ: 0.93 (s, 9H), 2.59 (d, 3H), 3.30 (s, 6H), 3.86 (t, 2H), 4.32 (d, 1H), 4.57 (t, 2H), 5.06 (dd, 2H), 7.54 (m, 4H), 7.82 (m, 2H), 8.17 (m, 1H); LCMS (+ESI) m/z 398.2 [M+H]$^+$.

Example 33

Preparation of (S)-tert-butyl 1-(3,3-dimethyl-1-(methylamino)-1-oxobutan-2-ylcarbamoyl)-3-phenyl-6,7-dihydro-5H-imidazo[1,5-a][1,4]diazepine-8(9H)-carboxylate (Compound 312)

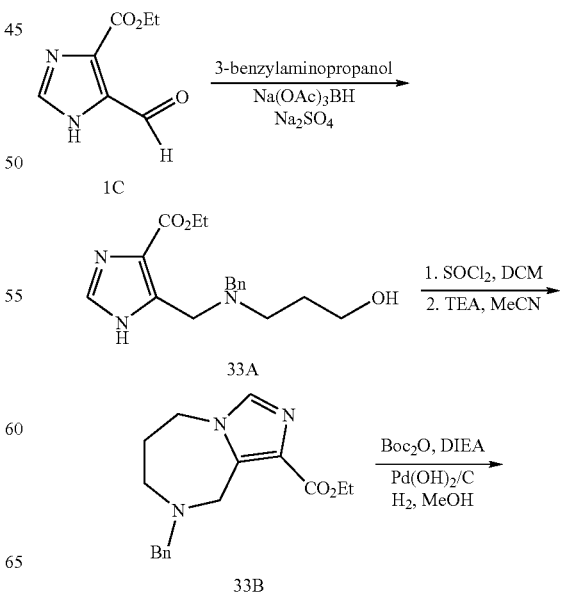

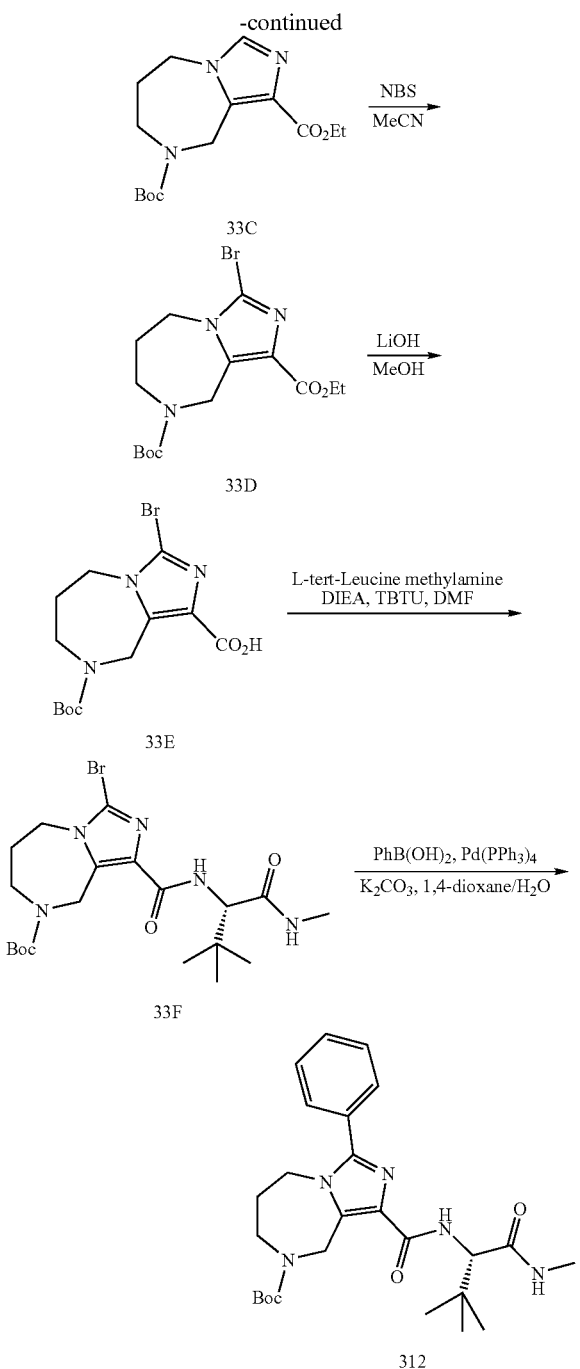

Step 1: Preparation of Intermediate 33A. Compound 1C (5.4 g) was stirred with 3-benzylaminopropanol (1.0 equiv) and anhydrous $Na_2SO_4$ (10 g) in THF for 30 min. Sodium triacetoxyborohydride (2.0 equiv) was added and the mixture was stirred at room temperature over night. The reaction was quenched with brine and extracted with ethyl acetate. The organic phase was dried over anhydrous $Na_2SO_4$ and evaporated to give crude Intermediate 33A (12.05 g) which was used without further purification.

Step 2: Preparation of Intermediate 33B. To a solution of 33A (10.05 g) in DCM (100 mL) was added thionyl chloride (11.0 mL). The mixture was heated at reflux overnight and carefully poured into saturated aqueous $NaHCO_3$. The organic phase was dried over anhydrous $Na_2SO_4$, filtered and evaporated to dryness under reduced pressure. The crude product was passed through a silica gel plug and eluted with ethyl acetate. Evaporation of ethyl acetate gave the corresponding chloro intermediate (6.0 g) which was (immediately) redissolved in MeCN and TEA (7.8 mL) and refluxed overnight. After evaporation of solvent, the residue was partitioned between ethyl acetate and saturated aqueous $NaHCO_3$. The organic phase was dried over anhydrous $Na_2SO_4$, filtered and evaporated to dryness under reduced pressure. The crude product was purified by column chromatography with 4% to 10% MeOH/DCM (with 1% TEA) to give Intermediate 33B (2.71 g). $^1$H NMR ($CDCl_3$) δ 7.41 (s, 1H), 7.24-7.31 (m, 5H), 4.36 (s, 2H), 4.22 (q, J=7 Hz, 2H), 4.11-4.13 (m, 2H), 3.59 (s, 2H), 3.03-3.06 (m, 2H), 1.84-1.87 (m, 2H), 1.28 (t, J=7 Hz, 3H).

Step 3: Preparation of Intermediate 33C. A mixture of Intermediate 33B (2.71 g), di-tert-butyldicarbonate (2.17 g), 10% palladium hydroxide on carbon (1.5 g) and DIEA (2.4 mL) in MeOH (50 mL) was placed under 90 psi hydrogen in a Parr shaker for twenty four hours. After filtration and evaporation of MeOH, the residue was partitioned between EtOAc and saturated aqueous $NaHCO_3$. The organic phase was dried over anhydrous $Na_2SO_4$, filtered and evaporated to give Intermediate 33C (2.35 g).

Step 4: Preparation of Intermediate 33D. To a solution of the Intermediate 33C (2.32 g) in MeCN (40 mL) was added NBS (1.67 g) portionwise. After stirring at room temperature for four hours, more NBS (0.66 g) was added and stirred for additional three hours. MeCN was then evaporated under reduced pressure. The residue was extracted between EtOAc and brine. The organic phase was dried over anhydrous $Na_2SO_4$ and evaporated to give Intermediate 33D (2.72 g). $^1$H NMR ($CDCl_3$) δ 1.37 (m, 12H), 1.95 (br, 2H), 3.73 (br, 2H), 4.21 (m, 2H), 4.23-4.37 (m, 2H), 4.95 (br, 2H).

Step 5: Preparation of Intermediate 33E. A solution of Intermediate 33D (2.72 g) and lithium hydroxide monohydrate (0.67 g) in MeOH was heated at 65° C. for two hours. After evaporation of MeOH, the residue was extracted between EtOAc and water (pH 3). The aqueous phase was saturated with sodium chloride and extracted with EtOAc. The combined organic phase was dried over anhydrous $Na_2SO_4$, filtered and evaporated to give the carboxylic acid Intermediate 33E (2.34 g).

Step 6: Preparation of Intermediate 33F. To a solution of Intermediate 33E (0.68 g), L-tert-Leucine-N methylamide (0.37 g) and DIEA (0.66 mL) in DMF (15 mL) at 0° C. was added TBTU (0.72 g). After stirring for two hours, the DMF was remove by evaporation under reduced pressure. The residue was partitioned between saturated aqueous $NaHCO_3$ and EtOAc. The organic phase was dried over anhydrous $Na_2SO_4$, filtered and evaporated to dryness. The residue was purified by column chromatography with 80% to 100% EtOAc/hexanes to give Intermediate 33F (0.52 g).

Step 7: Preparation of Compound 312. A mixture of Intermediate 33F (0.52 g), palladium tetrakis(triphenylphosphine) (0.1 g), potassium carbonate (0.30 g) and phenylboronic acid (0.20 g) in dioxane (10 mL) and water (5 ml) was heated at 100° C. for two hours. The reaction mixture was diluted with brine and extracted with EtOAc. The organic phase was dried over anhydrous $Na_2SO_4$, filtered and evaporated to dryness. The residue was purified by column chromatography with 60% to 100% EtOAc/hexanes to give Compound 312 (0.48 g).

Compound 313 was prepared in the same manner as Compound 312 except 4-chloro-2-fluorophenyl boronic acid was used in place of phenyl boronic acid.

Example 34

Preparation of (S)—N-(3,3-dimethyl-1-(methylamino)-1-oxobutan-2-yl)-3-phenyl-6,7,8,9-tetrahydro-5H-imidazo[1,5-a][1,4]diazepine-1-carboxamide (Compound 314)

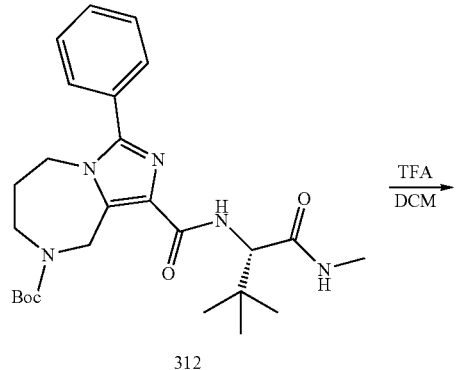

312

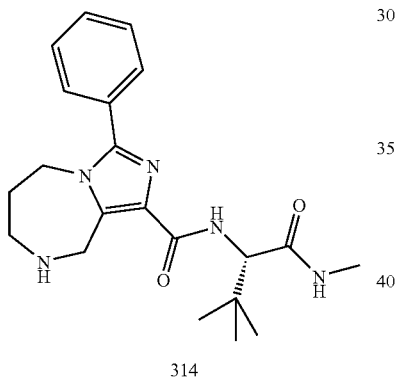

314

A solution of Compound 312 (0.48 g) in DCM (5 mL) and TFA (5 mL) was stirred at room temperature for thirty minutes. The solvents were removed by evaporation under reduced pressure and the residue was extracted between saturated aqueous NaHCO₃ and EtOAc. The aqueous phase was saturated with sodium chloride and extracted with EtOAc. The combined organic extracts were dried over anhydrous Na₂SO₄, filtered and evaporated to dryness under reduced pressure to give Compound 314 (0.38 g).

Compound 315 was synthesized in the same manner as described above for Compound 314 except that 4-chloro-2-fluorophenyl boronic acid was used in place of phenylboronic acid. Similarly, Compound 316 was synthesized as described above for Compound 314 except that 4-methyl-2-fluorophenyl boronic acid was used in place of phenylboronic acid.

Example 35

Preparation of (S)—N-(3,3-dimethyl-1-(methylamino)-1-oxobutan-2-yl)-8-methyl-3-phenyl-6,7,8,9-tetrahydro-5H-imidazo[1,5-a][1,4]diazepine-1-carboxamide (Compound 317)

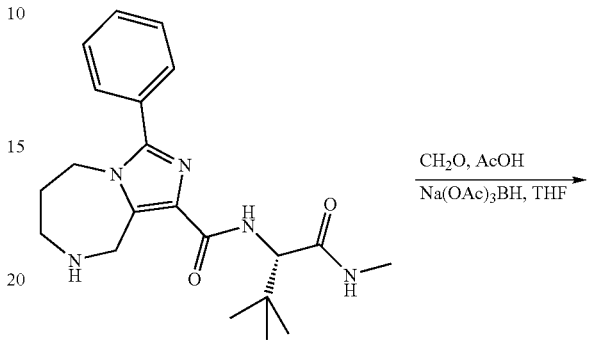

314

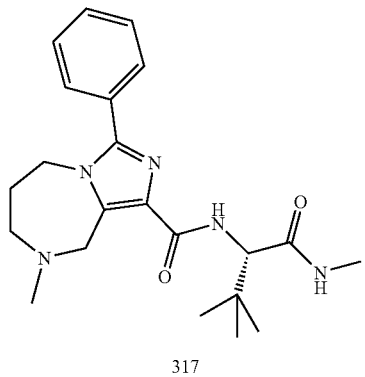

317

To a solution of Compound 314 (0.38 g), 30% aqueous paraformaldehyde (0.8 mL) and acetic acid (60 μL) in THF was added sodium triacetoxyboronhydride (0.42 g). After stirring at room temperature for two hours, the THF was removed by evaporation under reduced pressure. The residue was partitioned between saturated aqueous NaHCO₃ and EtOAc. The organic phase was dried over anhydrous Na₂SO₄, filtered and evaporated to dryness. The residue was purified by column chromatography with 10% to 60% MeOH in DCM. The combined pure fractions were evaporated to give a white solid, which was triturated in EtOAc/DCM (2:1) and filtered. The filtrate was evaporated to dryness under reduced pressure. The resulting residue was extracted between water and DCM. The organic phase was dried over anhydrous Na₂SO₄ and evaporated to give Compound 317 (0.31 g). $^1$H-NMR (400 MHz, CDCl₃) δ: 1.27 (s, 9H), 1.90 (br, 2H), 2.47 (s, 3H), 2.79 (d, J=4.8 Hz, 3H), 3.04 (br, 2H), 4.16 (br, 2H), 4.29 (d, J=9.5 Hz, 1H), 4.32 (br, 2H), 5.95 (br, 1H), 7.20-7.23 (dd, J=2.0, 9.6 Hz, 1H), 7.47-7.53 (m, 5H), 7.82 (d, J=9.5 Hz, 1H). LCMS (+ESI) m/z 398.2 [M+H]⁺.

Compound 318 was prepared following the procedure for the synthesis of Compound 317 except that formaldehyde was replaced with acetaldehyde. Similarly, Compound 319 was prepared following the same procedure but replacing formaldehyde with acetone. In a like manner, Compound 320 was prepared as described for Compound 317, but replacing formaldehyde with isobutyraldehyde.

Compound 321 was prepared following the procedure for the synthesis of compound 317 replacing formaldehyde with cyclopropyl carboxaldehyde. Compound 322 was prepared following the same procedure, but replacing formaldehyde with isobutyraldehyde and replacing Compound 314 with Compound 315. Compound 323 was prepared following the same procedure, but replacing formaldehyde with cyclopropyl carboxaldehyde and replacing Compound 314 with Compound 316.

Example 36

Preparation of (S)-3-bromo-N-(3,3-dimethyl-1-(methylamino)-1-oxobutan-2-yl)-8-methyl-6,7,8,9-tetrahydro-5H-imidazo[1,5-a][1,4]diazepine-1-carboxamide (Compound 324)

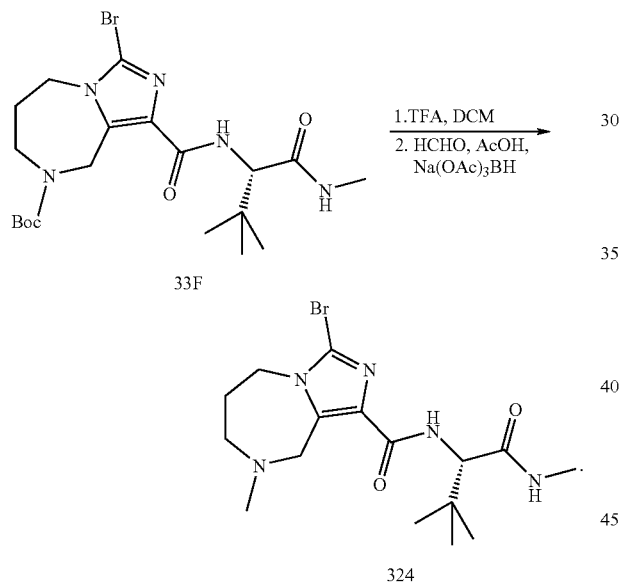

A solution of Intermediate 33F (0.73 g) in DCM (10 mL) and TFA (10 mL) was stirred at room temperature for one hour. After evaporation of DCM and TFA, the residue was partitioned between saturated aqueous NaHCO₃ and DCM. The aqueous phase was saturated with sodium chloride and extracted twice with DCM. The combined organic extracts were dried over anhydrous Na₂SO₄, filtered, and evaporated to dryness under reduced pressure. To a solution of the resulting intermediate (0.55 g), AcOH (82 µL) and 37% aqueous paraformaldehyde (0.5 mL) in THF was added sodium triacetoxyborohydride (0.60 g). After stirring at room temperature overnight, the THF was removed by evaporation under reduced pressure. The residue was partioned between brine and DCM and the aqueous layer was extracted three times with DCM. The combined organic extracts were dried over anhydrous Na₂SO₄, filtered and evaporated to dryness. The residue was purified by column chromatography to give Compound 324 (387 mg).

Example 37

(S)—N-(3,3-dimethyl-1-(methylamino)-1-oxobutan-2-yl)-3-(2-methoxyphenyl)-8-methyl-6,7,8,9-tetrahydro-5H-imidazo[1,5-a][1,4]diazepine-1-carboxamide (Compound 325)

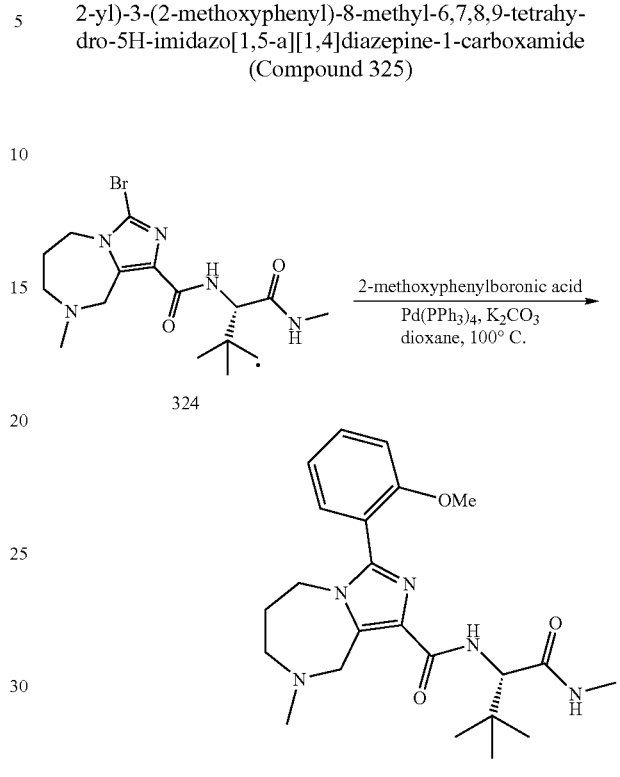

A mixture of Compound 324 (7.7 mg), 2-methoxyphenylboronic acid (0.038 mmol), palladium tetrakis(triphenylphosphine) (2.5 mg) and potassium carbonate (3 mg) in dioxane/water was heated at 100° C. for two hours. The mixture was filtered through a thiol-based palladium scavenger and purified by preparative LC-MS to give Compound 325. LCMS (+ESI) m/z 428.2 [M+H]⁺.

The same reaction was achieved by heating the reaction mixture in a Biotage microwave reactor at 160° C. for 20 minutes.

Compounds 326-460, 599-601 were synthesized in the same manner as compound 325 as described above except other boronic acids or dioxaborolanes were used in place of 2-methoxyphenylboronic acid. For example, compound 329 was synthesized using thiophen-3-ylboronic acid in place of 2-methoxyphenylboronic acid. Compound 366 was synthesized using 4-chloro-2-fluorophenyl boronic acid. Compound 435 was synthesized using 2-cyclopropyl-4,4,5,5-tetramethyl-1,3,2-dioxaborolane. Compound 442 was synthesized using 3,5-dimethyl-4-(4,4,5,5-tetramethyl-1,3,2-dioxaborolane-2-yl)isoxazole. Compound 460 was synthesized using 3,6-dihydro-2H-pyridine-1-tert-butoxycarbonyl-4-boronic acid, pinacol ester and the Boc group was removed with TFA in DCM using the same procedure as described in Example 34.

Example 38

Preparation of (S)—N-(3,3-dimethyl-1-(methylamino)-1-oxobutan-2-yl)-8-(ethylsulfonyl)-3-phenyl-6,7,8,9-tetrahydro-5H-imidazo[1,5-a][1,4]diazepine-1-carboxamide (Compound 461)

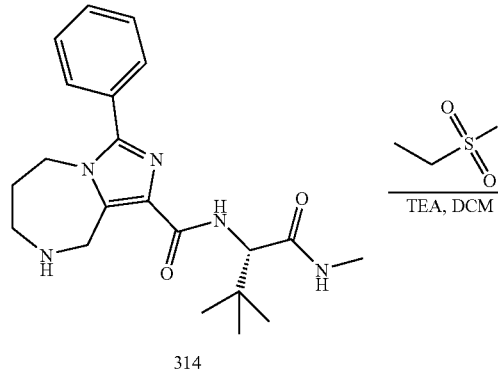

To a solution of Compound 314 (20 mg) and TEA (15 µL) in DCM was added ethanesulfonyl chloride (10 µL). After stirring at room temperature for 1 hour, the reaction was quenched with saturated aqueous NaHCO$_3$. The organic phase was separated and dried over anhydrous Na$_2$SO$_4$. Evaporation under reduced pressure gave Compound 461. LC/MS (+ESI) m/z 476.2 [M+H]$^+$.

Compound 462 was prepared following the procedure for the synthesis of compound 461, but replacing ethanesulfonyl chloride with benzoyl chloride. Similarly, compound 463 was prepared following the procedure but replacing ethanesulfonyl chloride with acetyl chloride. Likewise, compound 464 was prepared by following the procedure for the synthesis of compound 313 except that ethanesulfonyl chloride was replaced with 4-fluorophenylsulfonyl chloride.

Example 39

Preparation of (S)-methyl 3,3-dimethyl-2-(3-phenyl-6,7,8,9-tetrahydro-5H-imidazo[1,5-a][1,4]diazepine-1-carboxamido)butanoate (Compound 465)

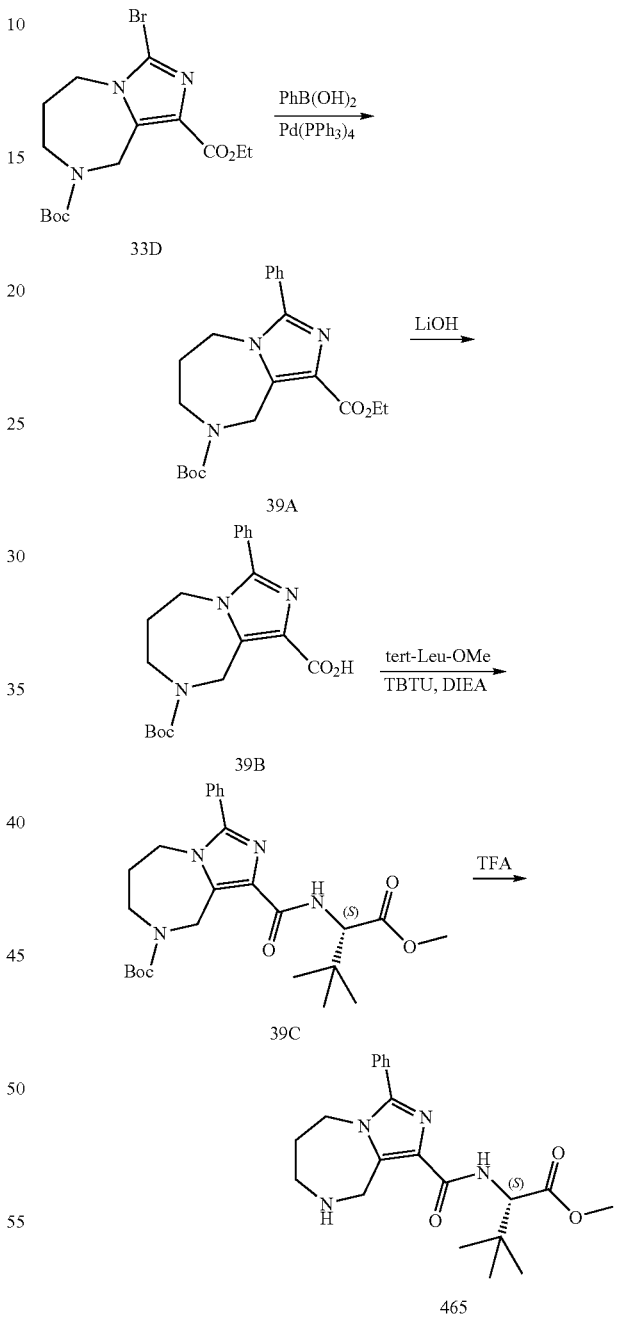

Step 1: Preparation of 8-tert-butyl 1-ethyl 3-phenyl-6,7-dihydro-5H-imidazo[1,5-a][1,4]diazepine-1,8(9H)-dicarboxylate (Intermediate 39A). A solution of intermediate 33D (1.02 g, 2.63 mmol), phenylboronic acid (0.48 g, 3.94 mmol), palladium tetrakis(triphenylphosphine) (182 mg, 0.16 mmol) and potassium carbonate (0.726 g, 5.25 mmol) in 1,4-dioxane (25 mL) and water (5 mL) was refluxed at 100° C. overnight. After evaporation of dioxane, the mixture was partitioned between ethyl acetate and saturated aqueous NaHCO$_3$ solution. The organic phase was dried over anhydrous Na$_2$SO$_4$, filtered and evaporated to dryness. The residue was purified by column chromatography with 50% to 100% EtOAc/Hexanes to give intermediate 39A (0.81 g, 80% yield). $^1$H NMR (CDCl$_3$) δ 1.36 (br, 12H), 1.93 (br, 2H), 3.74 (br, 2H), 4.15 (br, 2H), 4.38 (br, 2H), 5.00 (br, 2H), 7.42-7.49 (m, 5H). LCMS (+ESI) m/z 385.9 [M+H]$^+$.

Step 2: Preparation of 8-(tert-butoxycarbonyl)-3-phenyl-6,7,8,9-tetrahydro-5H-imidazo[1,5-a][1,4]diazepine-1-carboxylic acid (Intermediate 39B). A mixture of Intermediate 39A (0.81 g, 2.10 mmol) and lithium hydroxide monohydrate (706 mg, 16.8 mmol) in methanol (20 mL) was heated at 65° C. for 5 hours. After evaporation of methanol, the residue was dissolved in brine. Concentrated HCl (2.5 mL) was added carefully to acidify and the mixture was extracted twice with DCM. The combined organic extracts were dried and evaporated to give Intermediate 39B as white solid (0.71 g 95% yield). LCMS (+ESI) m/z 357.9 [M+H]$^+$.

Step 3: Preparation of (S)-tert-butyl 1-(1-methoxy-3,3-dimethyl-1-oxobutan-2-ylcarbamoyl)-3-phenyl-6,7-dihydro-5H-imidazo[1,5-a][1,4]diazepine-8(9H)-carboxylate (Intermediate 39C). To a solution of intermediate 39B (0.81 g, 2.27 mmol), L-tert-Leucine methyl ester HCl (378 mg, 2.61 mmol) and DIEA (1.0 mL) in DMF (20 mL) at 0° C. was added TBTU (1.09 g, 3.41 mmol) in two batches over 10 min. The reaction was stirred at 0° C. to room temperature for 1 hour and quenched with saturated aqueous NaHCO$_3$ and evaporated under vacuum. The residue was extracted with EtOAc. The organic phase was dried over anhydrous Na$_2$SO$_4$, filtered and evaporated to dryness. The crude product was purified by column chromatography eluting with 25% to 65% EtOAc/Hexanes to give Intermediate 39C as white solid (0.78 g, 71% yield). $^1$H-NMR (400 MHz, CDCl$_3$) δ: 1.05 (s, 9H), 1.39 (s, 9H), 1.95 (s, 2H), 3.72 (s, 5H), 4.14 (s, 2H), 4.60 (d, 1H), 5.08 (br, 2H), 7.46-7.49 (m, 5H). LCMS (+ESI) m/z 485.0 [M+H]$^+$.

Step 4: Preparation of (S)-methyl 3,3-dimethyl-2-(8-methyl-3-phenyl-6,7,8,9-tetrahydro-5H-imidazo[1,5-a][1,4]diazepine-1-carboxamido)butanoate (Compound 465). A solution of intermediate 39C (0.78 g, 1.61 mmol) in TFA/DCM (30 mL, 1:1) was stirred at room temperature for 0.5 hours. After evaporation of TFA and DCM, the residue was extracted between saturated aqueous NaHCO$_3$ and DCM twice. The combined organic phase was dried and evaporated to give free amino as intermediate (0.61 g, 99% yield).

Compound 466 was prepared in the same manner Compound 465 except 4-methyl-2-fluorophenyl boronic acid was used in place of phenyl boronic acid.

Compound 602 was prepared in the same manner Compound 465 except that (S)—N-methylpyrrolidine-2-carboxamide was used in place of L-tert-Leucine in Step 3.

Example 40

Preparation of (S)-methyl 3,3-dimethyl-2-(8-methyl-3-phenyl-6,7,8,9-tetrahydro-5H-imidazo[1,5-a][1,4]diazepine-1-carboxamido)butanoate (Compound 467)

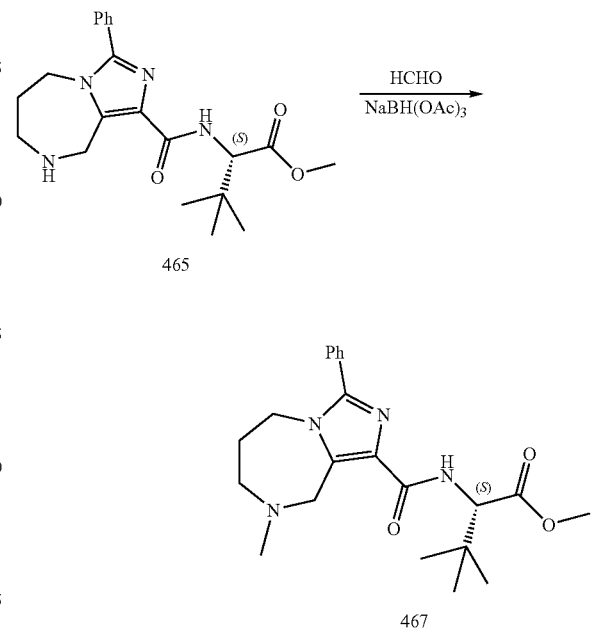

To a solution of Compound 465 (0.61 g, 1.61 mmol) in THF was added AcOH (92 µL, 1.6 mmol) and paraformaldehyde (1.2 mL, 37% aq. 16.0 mmol) followed by sodium triacetoxyborohydride (0.68 g, 3.20 mmol). After stirring at room temperature for 3.5 hours, THF was evaporated. The residue was extracted between saturated aqueous NaHCO$_3$ and DCM twice. The combined organic phase was dried, and evaporated to give Compound 467 (98% yield). $^1$H-NMR (400 MHz, CDCl$_3$) δ: 1.04 (s, 9H), 1.86 (br, 2H), 2.44 (s, 3H), 2.93 (br, 2H), 3.72 (s, 3H), 4.13 (br, 2H), 4.60 (d, 1H), 7.45-7.50 (m, 5H). LCMS (+ESI) m/z 399.0 [M+H]$^+$.

Compound 468 was synthesized in the same manner as described above for Compound 467 except acetone was used in place of paraformaldehyde. Similarly, Compound 469 was synthesized in the same manner as described above for Compound 467 except Compound 466 was used in place of Compound 465. Likewise, compound 470 was synthesized as described above for Compound 467 except cyclopropane carboxaldehyde was used in place of paraformaldehyde and Compound 466 was used in place of Compound 465. Compound 603 was synthesized as described above for Compound 467 except that compound 602 was used in place of compound 465.

Example 41

Preparation of (S)-3,3-dimethyl-2-(8-methyl-3-phenyl-6,7,8,9-tetrahydro-5H-imidazo[1,5-a][1,4]diazepine-1-carboxamido)butanoic acid (Compound 471)

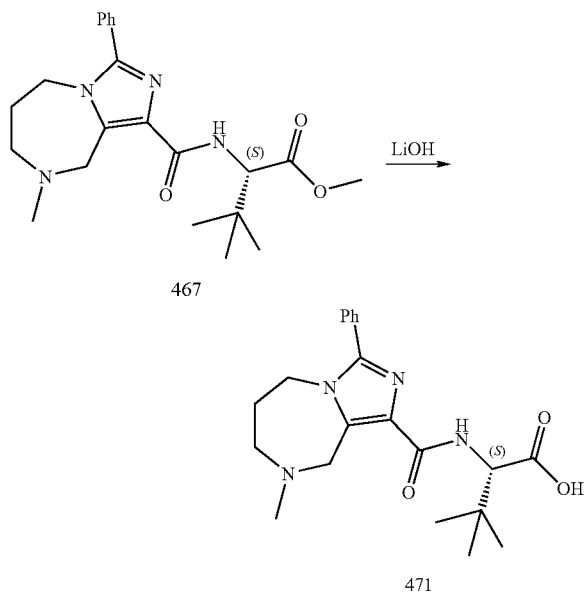

Preparation of (S)-3,3-dimethyl-2-(8-methyl-3-phenyl-6,7,8,9-tetrahydro-5H-imidazo[1,5-a][1,4]diazepine-1-carboxamido)butanoic acid (Compound 471). A solution of Compound 467 (0.63 g, 1.58 mmol) and lithium hydroxide monohydrate (0.33 g, 7.90 mmol) in THF/water (10 mL, 4:1) was stirred from 0° C. to room temperature overnight. After evaporation of THF, the residue was acidified with 1N HCl to pH2 and extracted twice with 20% iPrOH/DCM. The combined organic extracts were evaporated to give Compound 471 (87% yield). LCMS (+ESI) m/z 385.0 [M+H]⁺.

Example 42

Preparation of (S)—N-(1-(isopropylamino)-3,3-dimethyl-1-oxobutan-2-yl)-8-methyl-3-phenyl-6,7,8,9-tetrahydro-5H-imidazo[1,5-a][1,4]diazepine-1-carboxamide (Compounds 472)

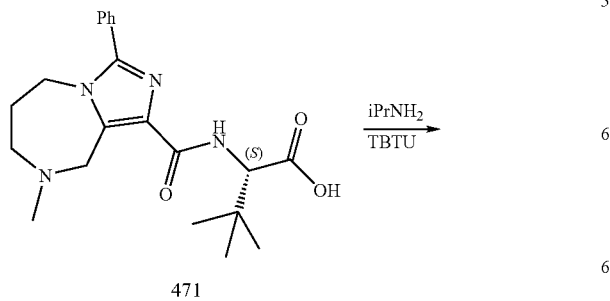

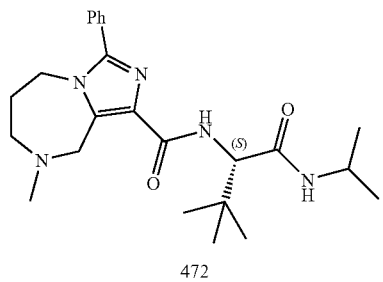

Preparation of (S)—N-(1-(isopropylamino)-3,3-dimethyl-1-oxobutan-2-yl)-8-methyl-3-phenyl-6,7,8,9-tetrahydro-5H-imidazo[1,5-a][1,4]diazepine-1-carboxamide (Compound 472). To a solution of Compound 471 (30 mg, 0.078 mmol) and isopropylamine (33 µL, 0.39 mmol) in DMF was added TBTU (38 mg, 0.15 mmol). After stirring at room temperature overnight, the crude reaction mixture was purified by a prep LC-MS with 5% to 95% MeCN/water in 15 min to give pure Compound 472 at 66% yield. ¹H-NMR (400 MHz, CDCl₃) δ: 1.04 (s, 9H), 1.11-1.28 (m, 6H), 1.95 9 (br, 2H) 2.59 (s, 3H), 3.25 (br, 2H), 4.01-4.16 (m, 1H), 4.23 (d, J=9.3 Hz, 1H), 5.80 (br, 1H), 7.47-7.55 (m, 5H), 7.95 (d, J=9.3 Hz, 1H). LCMS (+ESI) m/z 426.0 [M+H]⁺.

Compounds 473-480 were synthesized in the same manner as described above for Compound 472 except that isopropylamine was replaced with another amine. For example, Compound 473 was synthesized using n-propylamine in place of isopropylamine.

Example 43

Preparation of (S)-1-(3,3-dimethyl-1-(methylamino)-1-oxobutan-2-ylcarbamoyl)-8,8-dimethyl-3-phenyl-6,7,8,9-tetrahydro-5H-imidazo[1,5-a][1,4]diazepin-8-ium (Compound 481)

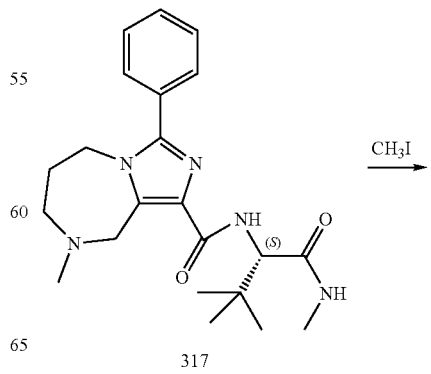

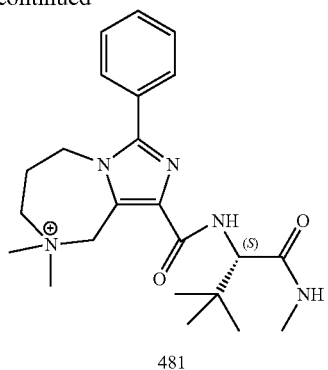

481

To a solution of Compound 317 (51 mg, 0.13 mmol) in acetone (2 mL) was added methyl iodide (8.02 mL, 0.13 mmol). The resulting mixture was stirred under nitrogen for 2 days. The mixture was concentrated under reduced pressure and dried in a 40° C. vacuum oven for 1 hour to give the title Compound 481 as a tan solid in 90% yield. $^1$H-NMR (400 MHz, (CD$_3$)$_2$SO) δ: 0.92 (s, 9H), 2.18 (m, 2H), 2.60 (d, 3H), 3.12 (broad s, 6H), 3.73 (m, 2H), 4.28 (m, 2H), 4.31 (d, 1H), 5.17 (m, 2H), 7.56 (m, 3H), 7.64 (m, 2H), 7.82 (d, 1H), 8.16 (q, 1H). LCMS (+ESI) m/z 412.01 [M]$^+$.

Example 44

Preparation of 3-(4-chloro-2-fluorophenyl)-N-(3,3-dimethyl-1-(methylamino)-1-oxobutan-2-yl)-8-(pyrimidin-2-yl)-6,7,8,9-tetrahydro-5H-imidazo[1,5-a][1,4]diazepine-1-carboxamide (Compound 482)

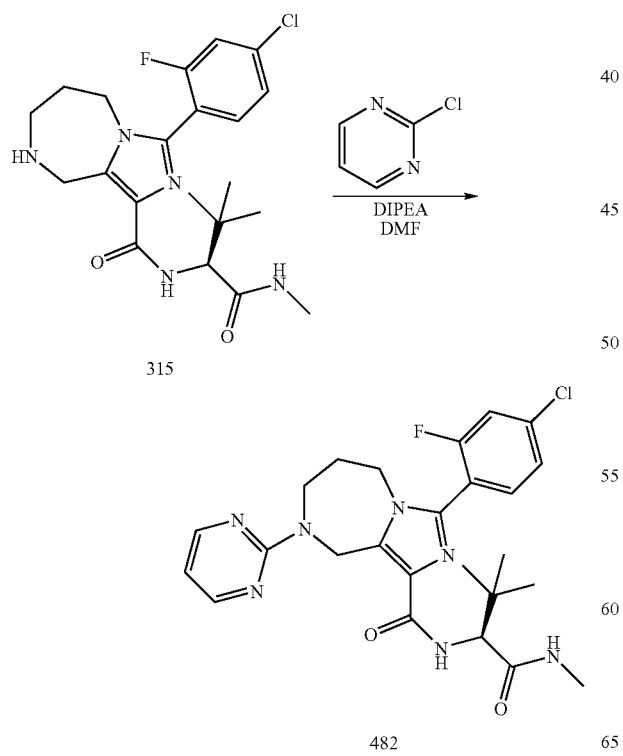

Compound 315 (16 mg, 37 umol) was taken up in 3 mL of DMF. DIPEA was added followed by the 2-chloropyrimidine. The solution was subjected to microwave irradiation and heated for successive 5 minutes periods, with increasing temperatures from 125° C. to 160° C. and addition of more 2-chloropyridine and DIPEA until the reaction was complete. The reaction was quenched by the addition of saturated aqueous NaHCO$_3$ (2 mL) and extracted with DCM (2×1 mL). The combined organic layers were dried with anhydrous Na$_2$SO$_4$, filtered and evaporated. The residue was purified by automated preparative LC/MS using a 10 minute method with a gradient from 70% water/acetonitrile to 10% water/acetonitrile with 0.1% formic acid as a modifier. The desired product Compound 482 was isolated as a white solid (15 mg, 78% yield). LCMS (+ESI) m/z 515.1 [M+H]$^+$.

Compound 483 was synthesized in the same manner as described above for Compound 482 except that Compound 314 was used in place of Compound 315.

Example 45

Preparation of (S)—N-(3,3-dimethyl-1-(methylamino)-1-oxobutan-2-yl)-8-methyl-3-pentyl-6,7,8,9-tetrahydro-5H-imidazo[1,5-a][1,4]diazepine-1-carboxamide (Compound 484)

Compound 434 (42 mg, 0.11 mmol) was dissolved in methanol and was added to a methanolic slurry of 10% palladium on carbon, Degussa type. The mixture was subjected to 65 psi of hydrogen gas for 2 hours, filtered through Celite®, and concentrated under reduced pressure to a yellow oil.

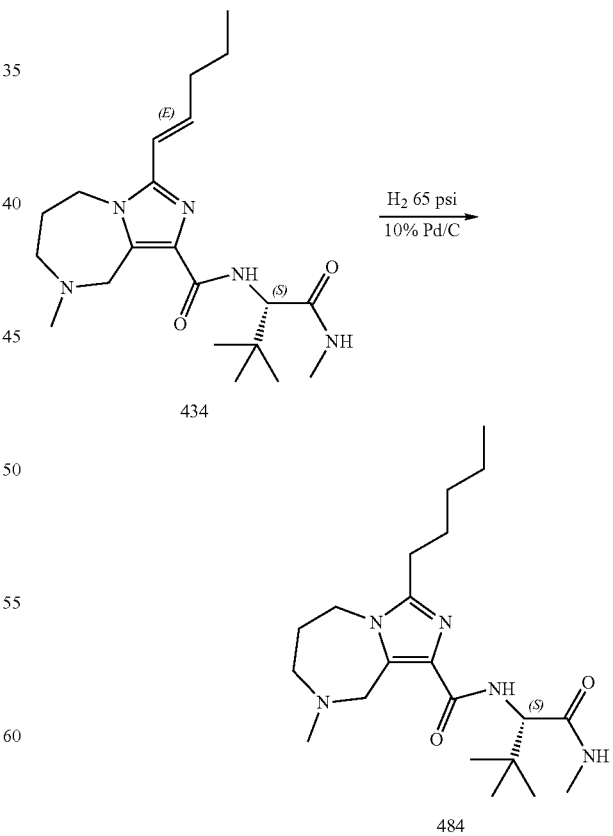

Further drying in a 40° C. vacuum oven overnight provided Compound 484 as a glassy solid (36 mg, 82%). $^1$H-NMR (400

MHz, (CD$_3$)$_2$SO) δ: 0.86 (t, 3H), 0.89 (s, 9H), 1.30 (m, 4H), 1.57 (m, 2H), 1.68 (m, 2H), 2.13 (s, 3H), 2.57 (d, 3H), 2.64 (t, 2H), 2.85 (m, 2H), 4.01 (m, 2H), 4.13 (m, 2H), 4.26 (d, 1H), 7.61 (d, 1H), 8.09 (q, 1H). LCMS (+ESI) m/z 392.2 [M+H]$^+$.

Compound 485 was synthesized in the same manner as described above for compound 484 except compound 376 was used in place of compound 434. Similarly, compound 486 was synthesized as described above for compound 484 except compound 377 was used in place of compound 434. Likewise, compound 487 was synthesized in the same manner as described above for compound 484 except compound 396 was used in place of compound 434.

Compound 488 was synthesized in the same manner as described above for compound 484 except compound 397 was used in place of compound 434. Similarly, compound 489 was synthesized as described above for compound 484 except compound 398 was used in place of compound 434. Likewise, compound 490 was synthesized as described above except compound 436 was used in place of compound 434.

Compound 491 was synthesized in the same manner as described above for compound 484 except compound 400 was used in place of compound 434. Similarly, compound 492 was synthesized as described above for compound 484 except compound 430 was used in place of compound 434. Likewise, compound 493 was synthesized as described above except compound 439 was used in place of compound 434.

Compound 494 was synthesized in the same manner as described above for compound 484 except compound 445 was used in place of compound 434. Similarly, compound 495 was synthesized as described above except compound 446 was used in place of compound 434. Likewise, compound 496 was synthesized in the same manner except compound 441 was used in place of compound 434.

Compound 497 was synthesized in the same manner as described above for compound 484 except compound 456 was used in place of compound 434. Similarly, compound 498 was synthesized as described above for compound 484 except compound 457 was used in place of Compound 434. Likewise, compound 499 was synthesized in the same manner except compound 449 was used in place of compound 434.

Compound 500 was synthesized in the same manner as described above for compound 484 except compound 509 was used in place of compound 434. Similarly, compound 501 was synthesized as described above for compound 484 except compound 510 was used in place of compound 434. In a like manner, compound 502 was synthesized as described above except compound 511 was used in place of compound 434. Likewise, compound 503 was synthesized as described above for compound 484 except that compound 460 was used in place of compound 434.

Compound 504 was synthesized in the same manner as described above for compound 484 except compound 452 was used in place of compound 434. Similarly, compound 505 was synthesized as described above for compound 484 except compound 453 was used in place of compound 434. Likewise, compound 506 was synthesized as described above except that compound 455 was used in place of compound 434.

Compound 507 was synthesized in the same manner as described above for compound 484 except compound 454 was used in place of Compound 434. Compound 508 was similarly synthesized as described above except that compound 514 was used in place of compound 434.

Example 46

Preparation (S,E)-N-(3,3-dimethyl-1-(methylamino)-1-oxobutan-2-yl)-8-methyl-3-(3-morpholinoprop-1-enyl)-6,7,8,9-tetrahydro-5H-imidazo[1,5-a][1,4]diazepine-1-carboxamide (Compound 509)

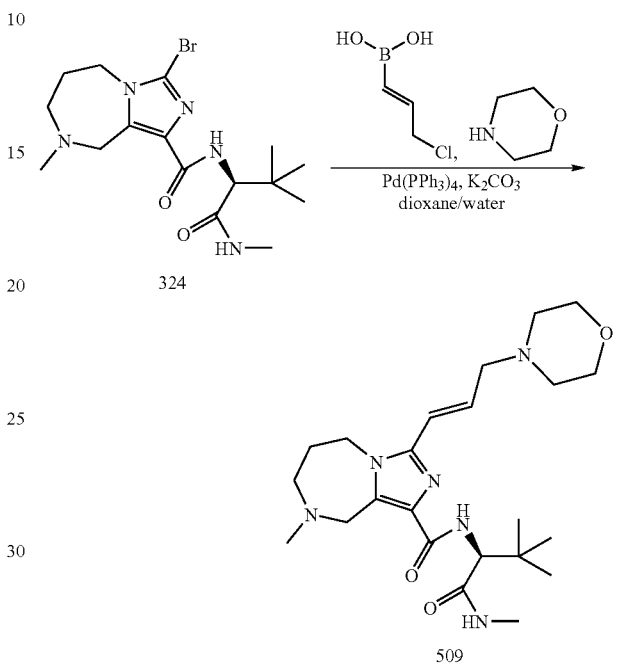

(S)-3-bromo-N-(3,3-dimethyl-1-(methylamino)-1-oxobutan-2-yl)-8-methyl-6,7,8,9-tetrahydro-5H-imidazo[1,5-a][1,4]diazepine-1-carboxamide (Compound 324; 0.10 g, 0.25 mmol) was dissolved in dioxane (4 mL) and (E)-3-chloroprop-1-enylboronic acid (0.040 g, 0.37 mmol) was added, followed by K$_2$CO$_3$ (0.164 g, 1.18 mmol), morpholine (0.052 g, 0.60 mmol) and water (0.80 mL). The resulting mixture was degassed with nitrogen and Pd(PPh3)4 (0.008 g, 0.007 mmol) was added. The mixture was heated in microwave reactor at 160° C. for 20 min. The mixture was diluted with EtOAc, and filtered through celite. The organic layer was concentrated under reduced pressure, washed with water, dried over anhydrous Na$_2$SO$_4$ and concentrated again. The residue was purified by prep LC/MS using 5-95% gradient acetonitrile/water with 0.1% formic acid to provide compound 509 (0.030 g, 39%) as a white solid. $^1$H-NMR (400 MHz, CDCl$_3$) δ: 1.07 (s, 9H), 1.93 (m, 2H), 2.41 (s, 3H), 2.67 (m, 4H), 2.81 (d, 3H), 3.10 (m, 2H), 3.31 (d, 1H), 3.81 (t, 4H), 4.12 (m, 2H), 4.49 (d, 1H), 4.45 (m, 2H), 6.01 (m, 1H), 6.51 (m, 1H), 6.80 (m, 1H), 7.89 (m, 1H); LCMS (+ESI) m/z 447.3 [M+H]$^+$.

Compound 510 was synthesized in the same manner as compound 509 except piperidine was used in place of morpholine. Similarly, compound 511 was synthesized as described for compound 509 except pyrrolidine was used in place of morpholine. Compound 512 was synthesized in the same manner except diethylamine was used in place of morpholine. Compound 513 was synthesized in the same manner except that dimethylamine was used in place of morpholine.

Example 47

Preparation (S,E)-N-(3,3-dimethyl-1-(methylamino)-1-oxobutan-2-yl)-8-methyl-3-(3-morpholinoprop-1-enyl)-6,7,8,9-tetrahydro-5H-imidazo[1,5-a][1,4]diazepine-1-carboxamide (Compound 514)

Step 1: Preparation of (S,E)-3-(4-(tert-butyldimethylsilyloxy)but-1-enyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide (47A). To a solution of compound 324 (0.10 g, 0.25 mmol) in dioxane (2 mL) was (E)-tert-butyldimethyl(4-(4,4,5,5-tetramethyl-1,3,2-dioxaborolan-2-yl)but-3-enyloxy)silane (0.115 g, 0.50 mmol), followed by K$_2$CO$_3$ (0.069 g, 0.50 mmol) and water (0.40 mL). The resulting mixture was degassed with nitrogen and Pd(PPh$_3$)$_4$ (0.023 g, 0.02 mmol) was added. The mixture was heated in microwave reactor at 160° C. for 20 min. The mixture was diluted with EtOAc, and filtered through celite. The organic layer was concentrated, washed with water, dried over anhydrous Na$_2$SO$_4$ and concentrated again. The residue was purified using PL-Thiol MP SPE tube to provide compound 47A (0.126 g, 99%). LCMS (+ESI) m/z 506.4 [M+H]$^+$.

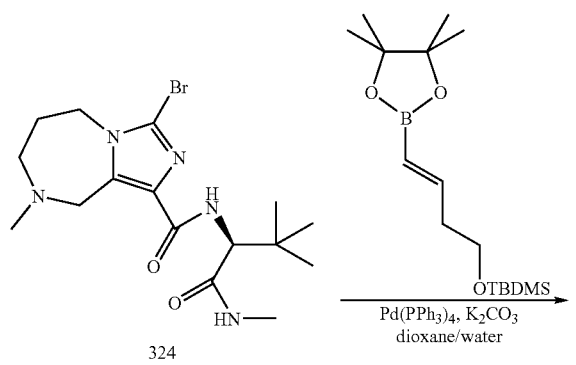

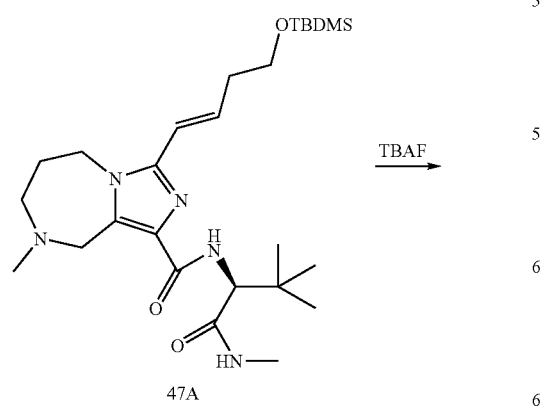

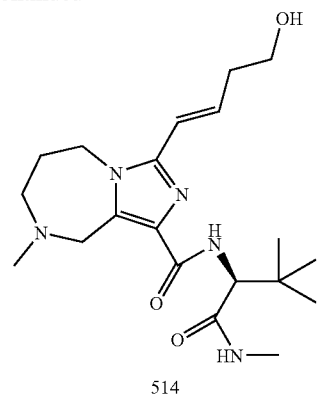

514

Step 2: Preparation of Compound 514. Compound 47A (0.126 g, 0.25 mmol) was dissolved in THF and TBAF (1M in THF, 0.50 mL, 0.50 mmol) solution was added. The resulting mixture was stirred for 18 h. The mixture was concentrated, diluted with NaCl saturated solution and extracted with DCM. The organic layer was dried over anhydrous Na$_2$SO$_4$ and concentrated. The residue was purified by Prep LC/MS using 5-95% gradient of acetonitrile/water with 0.1% formic acid. The resulting material was purified by ion exchange chromatography using a Strata SPE SCX column to remove t-butyl dimethylsilane impurity. Compound 514 (0.070 g, 70%) was isolated as a free base. $^1$H-NMR (400 MHz, CDCl$_3$) δ: 1.07 (s, 9H), 1.85 (m, 3H), 2.37 (s, 3H), 2.53 (m, 2H), 2.80 (d, 3H), 2.95 (m, 2H), 3.82 (t, 2H), 4.06 (m, 2H), 4.29 (m, 3H), 5.93 (m, 1H), 6.34 (d, 1H), 6.73 (m, 1H), 7.86 (m, 1H); LCMS (+ESI) m/z 392.2 [M+H]$^+$.

Example 48

Preparation of (S)-2-(8-(tert-butoxycarbonyl)-3-phenyl-6,7,8,9-tetrahydro-5H-imidazo[1,5-a][1,4]diazepine-1-carboxamido)-3,3-dimethylbutanoic acid (Compound 515)

Preparation of (S)-2-(8-(tert-butoxycarbonyl)-3-phenyl-6,7,8,9-tetrahydro-5H-imidazo[1,5-a][1,4]diazepine-1-carboxamido)-3,3-dimethylbutanoic acid (Compound 515). To a solution of Intermediate 39C (571 mg, 0.77 mmol) in tetrahydrofuran (2 mL) were added a 10M aqueous solution of sodium hydroxide (0.77 mL, 7.7 mmol) and methanol (2 mL). The solution was stirred for 2.5 hours and was then concentrated under reduced pressure. The residue was brought to pH 3 with 1N aqueous hydrochloric acid solution, and a resulting precipitate was collected by filtration and washed with water.

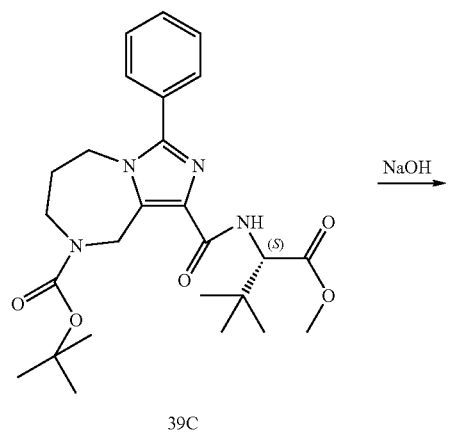

39C

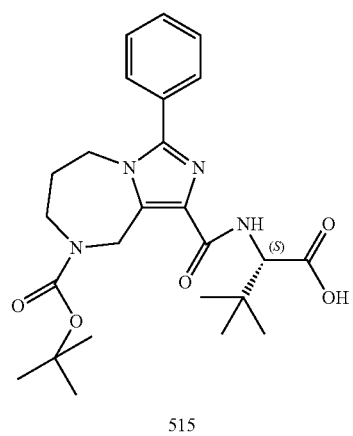

515

The filtrate was extracted twice with diethyl ether. The ether layers were combined, dried over anhydrous MgSO$_4$, concentrated under reduced pressure, and combined with the precipitated solids. The white solids were dried in a 45° C. vacuum oven for 18 hours to provide Compound 515 (326 mg, 90% yield). $^1$H-NMR (400 MHz, (CD$_3$)$_2$SO) δ: 0.98 (s, 9H), 1.27 (s, 9H), 1.85 (m, 2H), 3.63 (m, 2H), 4.18 (t, 2H), 4.30 (d, 1H), 5.02 (m, 2H), 7.52 (m, 5H), 7.56 (d, 1H), 12.88 (broad s, 1H). LCMS (+ESI) m/z 471.2 [M+H]$^+$.

Compound 516 was prepared in the same manner as described above for compound 515 except 4-fluoro-2-methylphenyl boronic acid was used in place of phenyl boronic acid as described in Example 39.

Example 49

Preparation of (S)-tert-butyl 1-(2,2-dimethyl-1-(3-methyl-1,2,4-oxadiazol-5-yl)propylcarbamoyl)-3-phenyl-6,7-dihydro-5H-imidazo[1,5-a][1,4]diazepine-8(9H)-carboxylate (Compound 517)

Step 1: Preparation of (S,Z)-tert-butyl 1-(1-(1-aminoethylideneaminooxy)-3,3-dimethyl-1-oxobutan-2-ylcarbamoyl)-3-phenyl-6,7-dihydro-5H-imidazo[1,5-a][1,4]diazepine-8(9H)-carboxylate (Intermediate 49A). A 2 mL dichloromethane solution of Compound 515 (320 mg, 0.68 mmol) was added to a dichloromethane solution of N-(3-dimethylaminopropyl)-N'-ethylcarbodiimide (209 mg, 1.09 mmol) and 1-hydroxybenzotriazole hydrate (167 mg, 1.09 mmol). The solution was stirred for 15 minutes at ambient temperature. N-hydroxyacetamidine (76 mg, 1.02 mmol) was added in one portion as a solid, and the mixture was stirred overnight. After diluting with additional DCM, the reaction mixture was washed with saturated aqueous NaHCO$_3$ solution and brine, dried over anhydrous Na$_2$SO$_4$, and concentrated to a pale yellow foaming solid (Intermediate 49A). LCMS (+ESI) m/z 527.2 [M+H]$^+$.

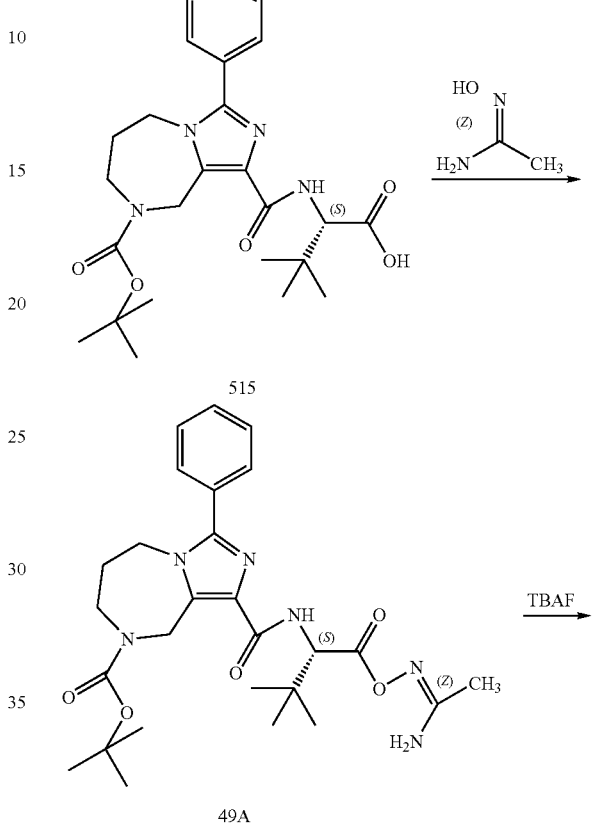

515

49A

517

Step 2: Preparation of (S)-tert-butyl 1-(2,2-dimethyl-1-(3-methyl-1,2,4-oxadiazol-5-yl)propylcarbamoyl)-3-phenyl-6,7-dihydro-5H-imidazo[1,5-a][1,4]diazepine-8(9H)-carboxylate (Compound 517). To a solution of intermediate 49A (358 mg, 0.68 mmol) in tetrahydrofuran (3 mL) was added a 1.0M solution of TBAF in THF (0.68 mL, 0.68.mmol). The mixture was stirred for 24 hours, then concentrated under reduced pressure. The residue was partitioned between ethyl acetate and water. The layers were separated, and the organic layer was washed with brine, dried over anhydrous Na$_2$SO$_4$ and absorbed onto silica gel for purification by flash chromatography. The column was eluted on a gradient from 20%-50% ethyl acetate in hexanes to provide Compound 517 as a yellow solid (223 mg, 64% yield). $^1$H-NMR (400 MHz, (CD$_3$)$_2$SO) δ: 0.99 (s, 9H), 1.18 (s, 9H), 1.84 (m, 2H), 2.32 (s, 3H), 3.63 (m, 2H), 4.19 (t, 2H), 4.96 (m, 2H), 5.15 (d, 1H), 7.53 (m, 5H), 7.82 (d, 1H). LCMS (+ESI) m/z 509.20 [M+H]$^+$.

Compound 518 was prepared in the same manner described above for compound 517 except that compound 516 was used in place of compound 515.

Example 50

Preparation of (S)—N-(2,2-dimethyl-1-(3-methyl-1,2,4-oxadiazol-5-yl)propyl)-3-phenyl-6,7,8,9-tetrahydro-5H-imidazo[1,5-a][1,4]diazepine-1-carboxamide (Compound 519)

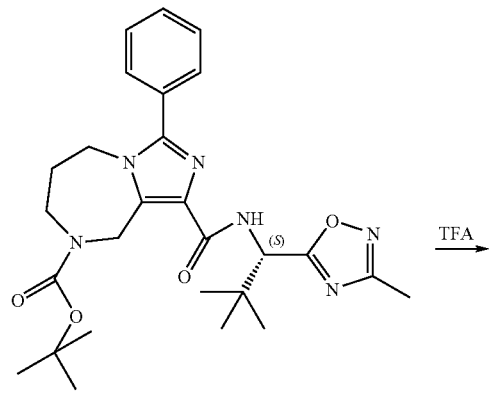

517

TFA →

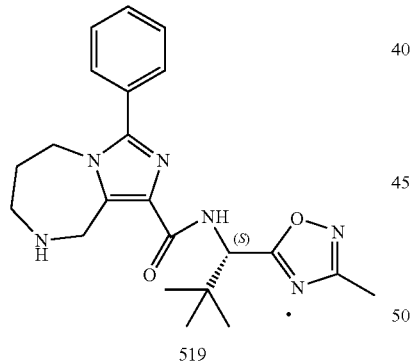

519

Preparation of (S)—N-(2,2-dimethyl-1-(3-methyl-1,2,4-oxadiazol-5-yl)propyl)-3-phenyl-6,7,8,9-tetrahydro-5H-imidazo[1,5-a][1,4]diazepine-1-carboxamide (Compound 519). To Compound 517 (219 mg, 0.43 mmol) in dichloromethane (2 mL) was added trifluoroacetic acid (1.26 mL, 16.36 mmol). After 3 hours of stirring, the solution was concentrated under reduced pressure. The residue was brought to pH 8 with saturated aqueous NaHCO$_3$. The aqueous solution was extracted twice with ethyl acetate. The combined organic layers were dried over anhydrous Na$_2$SO$_4$, filtered, and concentrated under reduced pressure to yield a colorless oil which was dissolved in methanol and loaded onto an ion exchange column (Phenomenex®, SCX). The column was washed with methanol to remove impurities, and the title compound was eluted with a solution of 2N ammonia in methanol. After concentration of the methanol solution, Compound 519 was obtained as a pale yellow solid (148 mg, 84% yield). $^1$H-NMR (400 MHz, (CD$_3$)$_2$SO) δ: 0.99 (s, 9H), 1.72 (m, 2H), 2.34 (s, 3H), 3.00 (m, 2H), 3.29 (s, 1H), 4.14 (t, 2H), 4.27 (m, 2H), 5.15 (d, 1H), 7.53 (m, 5H), 7.85 (d, 1H). LCMS (+ESI) m/z 409.2 [M+H]$^+$.

Compound 520 was prepared in the same manner as described above for Compound 519 except compound 518 was used in place of compound 517.

Example 51

Preparation of (S)—N-(2,2-dimethyl-1-(3-methyl-1,2,4-oxadiazol-5-yl)propyl)-8-methyl-3-phenyl-6,7,8,9-tetrahydro-5H-imidazo[1,5-a][1,4]diazepine-1-carboxamide (Compound 521)

Preparation of (S)—N-(2,2-dimethyl-1-(3-methyl-1,2,4-oxadiazol-5-yl)propyl)-8-methyl-3-phenyl-6,7,8,9-tetrahydro-5H-imidazo[1,5-a][1,4]diazepine-1-carboxamide (Compound 521). To a solution of 519 (45 mg, 0.11 mmol) in tetrahydrofuran (2 mL) was added acetic acid (6.3 mL, 0.11 mmol) and a 37 weight % aqueous solution of formaldehyde (82 mL, 1.10 mmol). After stirring for 5 minutes, sodium triacetoxyborohydride was added as a solid (47 mg, 0.22 mmol).

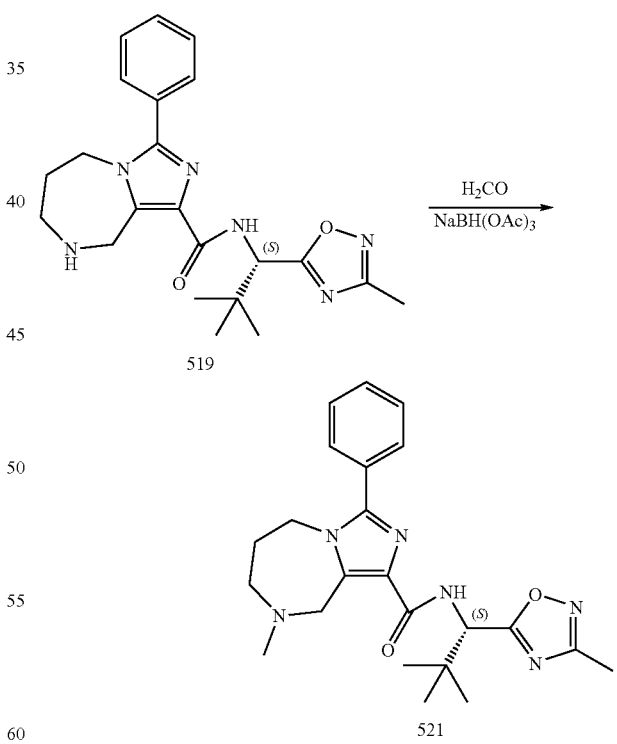

The mixture was stirred for an additional 2 hours then was concentrated under reduced pressure. The residue was dissolved in dichloromethane, was washed with a saturated aqueous NaHCO₃ solution, was dried over anhydrous Na₂SO₄, and was concentrated under reduced pressure to an off-white solid. The solid was dissolved in methanol and loaded onto an ion exchange column (Phenomenex®, SCX). The column was washed with methanol, and the title compound was collected with a solution of 2N ammonia in methanol. After concentration of the methanol solution, a pale yellow solid Compound 521 was obtained (43 mg, 92% yield). ¹H-NMR (400 MHz, (CD₃)₂SO) δ: 0.98 (s, 9H), 1.76 (m, 2H), 2.21 (s, 3H), 2.33 (s, 3H), 2.87 (m, 2H), 4.12 (m, 2H), 4.19 (m, 2H), 5.15 (d, 114), 7.55 (m, 5H), 7.86 (d, 1H). LCMS (+ESI) m/z 423.2 [M+H]⁺.

Compound 522 was prepared in the same manner as described above for compound 521 except that compound 520 was used in place of compound 519. Similarly, compound 523 was prepared in the same manner except that compound 520 was used in place of compound 519 and acetone was used in place of formaldehyde. Likewise, compound 524 was prepared as described above for compound 521 except that acetaldehyde was used in place of formaldehyde. Compound 525 was prepared in the same manner except that acetone was used in place of formaldehyde.

Example 52

Preparation of (S)-3-(4-chloro-2-fluorophenyl)-N-(3,3-dimethyl-1-(methylamino)-1-oxobutan-2-yl)-8-(piperidin-4-yl)-6,7,8,9-tetrahydro-5H-imidazo[1,5-a][1,4]diazepine-1-carboxamide (Compound 526)

To a solution of compound 315 (0.17 g, 0.39 mmol) in THF (10 mL) was added N-Boc-piperidin-4-one (125 mg, 0.63 mmol) and acetic acid (25 µL, 0.44 mmol) followed by sodium triacetoxyborohydride (130 mg, 0.61 mmol). After stirring at room temperature for 3 hours, THF was evaporated. The residue was extracted between saturated aqueous NaHCO₃ and ethyl acetate. The organic phase was dried over anhydrous Na₂SO₄ and evaporated under vacuum.

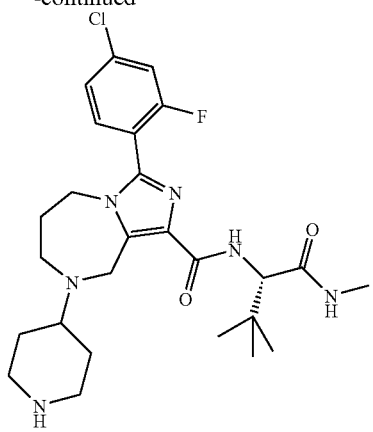

526

The residue purified by column chromatography with 5% to 10% MeOH/DCM to give product at 30% yield. The isolated product (73 mg, 0.12 mmol) was stirred in TFA/DCM (1:1) at room temperature for 30 minutes. After evaporation of TFA/DCM, the residue was extracted between saturated aqueous NaHCO₃ and ethyl acetate. The organic phase was dried over anhydrous Na₂SO₄ and evaporated under vacuum to give 58 mg of compound 526. LCMS (+ESI) m/z 561.2, 520 [M+H]⁺.

Example 53

Preparation of (S)-8-(1-acetylpiperidin-4-yl)-3-(4-chloro-2-fluorophenyl)-N-(3,3-dimethyl-1-(methylamino)-1-oxobutan-2-yl)-6,7,8,9-tetrahydro-5H-imidazo[1,5-a][1,4]diazepine-1-carboxamide (Compound 527)

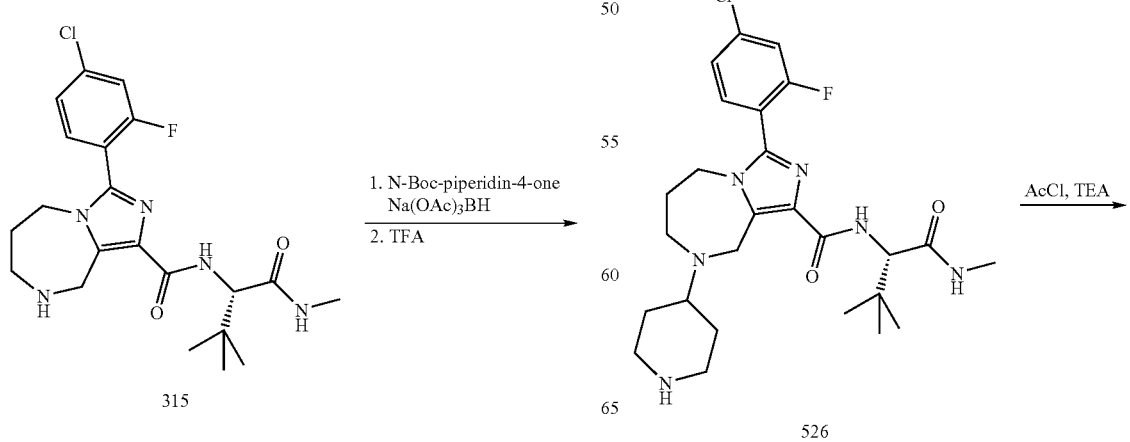

-continued

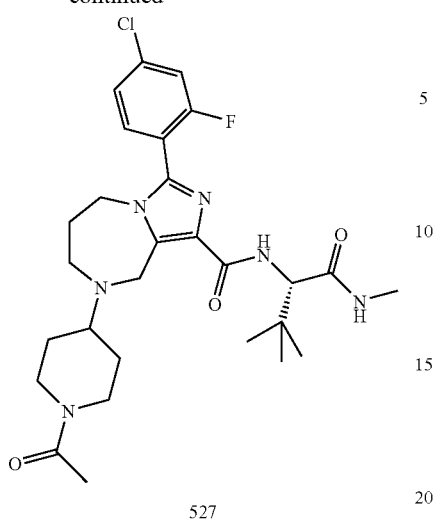

527

To a solution of compound 526 (24 mg, 0.046 mmol) in DCM (0.5 mL) was added TEA (20 µL, 0.14 mmol) and acetyl chloride (10 µL, 0.14 mmol). After stirring at room temperature for 30 min, the reaction mixture was evaporated to dryness. The crude mixture was dissolved in MeOH (0.5 mL) and purified by preparative LC-MS with 5% to 95% MeCN/water (0.5% formic acid) in 15 min. Pure fractions were combined and evaporated with a speedvac to give compound 527 at 68% yield. LCMS (+ESI) m/z 561.2, 563.1 [M+H]$^+$.

Example 54

Preparation of (S)-3-(4,4-difluorocyclohexyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide (Compound 528)

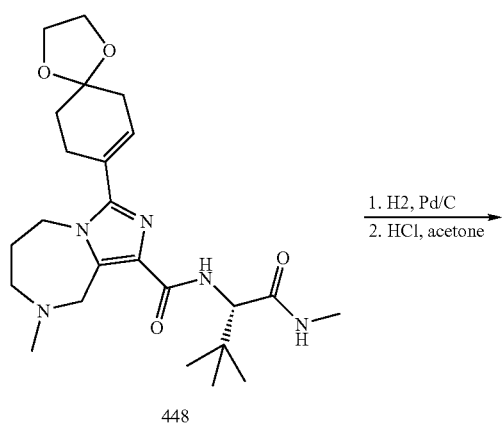

448

-continued

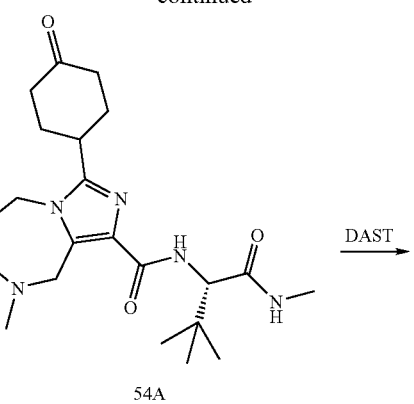

54A

DAST →

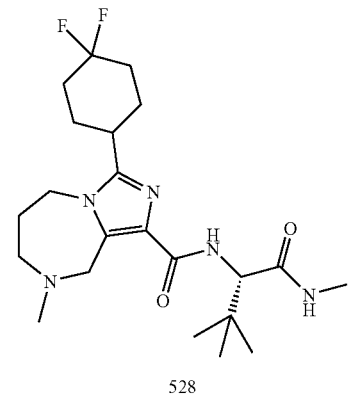

528

Step 1: A mixture of compound 448 (0.65 g, 1.41 mmol) and palladium on carbon (380 mg) in methanol was hydrogenated under 60 psi hydrogen for 2 hours. After filtration of catalyst, the solution was evaporated to dryness. The residue (0.54 g, 1.17 mmol) was stirred with acetone and 2N HCl at room temperature overnight. After evaporation of acetone, the aqueous phase was basified with saturated aqueous NaHCO$_3$ and extracted with 10% iPrOH/DCM twice. The combined organic phase was dried over anhydrous Na$_2$SO$_4$ and evaporated to dryness to give the ketone intermediate 54A at 92% yield. LCMS (+ESI) m/z 418.3, [M+H]$^+$.

Step 2: To a solution of intermediate 54A (0.45 g, 1.08 mmol) in DCE was added DAST (0.40 g, 2.47 mmol) and then heated at 80° C. for 2 hours. The reaction was quenched with aqueous NaHCO$_3$ and extracted with 10% iPrOH/DCM twice. The combined organic phase was dried over anhydrous Na$_2$SO$_4$ and evaporated to dryness. The residue was purified by reverse phase column chromatography with 20% to 60% MeCN/water (0.5 formic acid). Fractions with product were combined and lyophilized to dryness. The obtained solid was dissolved in MeOH and purified by preparative LC-MS with 5% to 95% MeCN/water to give compound 528 at 2% yield. LCMS (+ESI) m/z 440.4, [M+H]$^+$.

Example 55

Preparation of (S)-3-(4-chloro-2-fluorophenyl)-8-methyl-N-(4-methyl-1-(methylamino)-1-oxopentan-2-yl)-6,7,8,9-tetrahydro-5H-imidazo[1,5-a][1,4]diazepine-1-carboxamide (Compound 529)

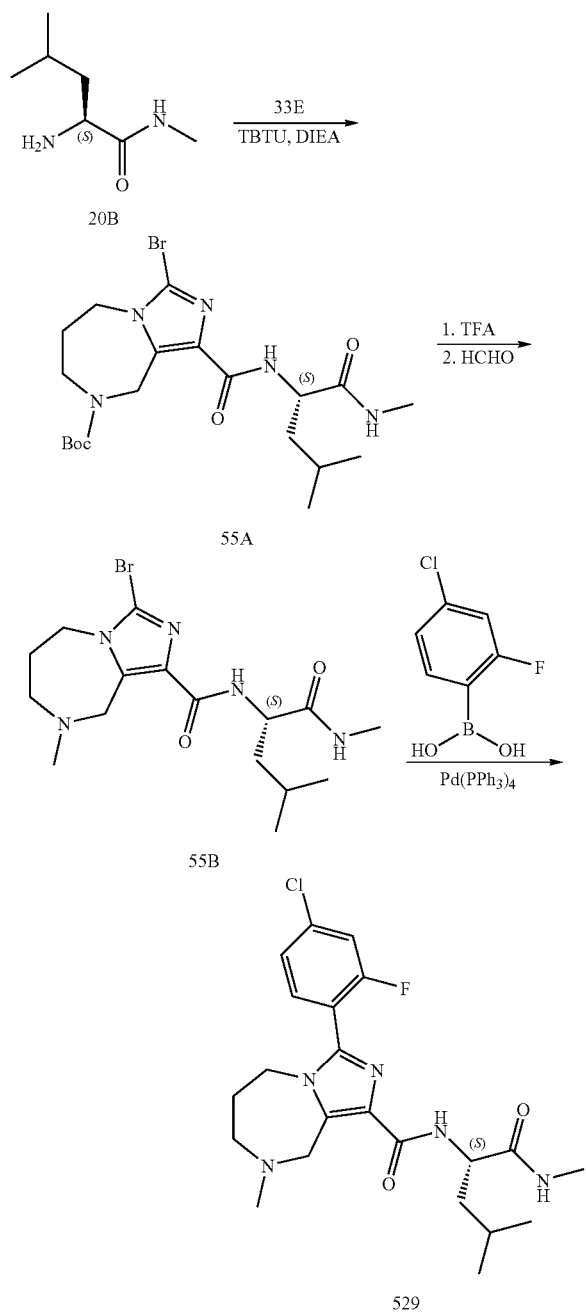

Step 1: Preparation of (S)-tert-butyl 3-bromo-1-(4-methyl-1-(methylamino)-1-oxopentan-2-ylcarbamoyl)-6,7-dihydro-5H-imidazo[1,5-a][1,4]diazepine-8(9H)-carboxylate 55A. To a solution of 3-bromo-8-(tert-butoxycarbonyl)-6,7,8,9-tetrahydro-5H-imidazo[1,5-a][1,4]diazepine-1-carboxylic acid (33E) (1.08 g, 3.0 mmol), H-Leu-NHMe (20B) (0.62 g, 4.30 mmol) and DIEA (0.52 mL, 3.0 mmol) in DMF (25 mL) was added TBTU (1.46 g, 4.55 mmol) in two batches over 10 min at 0° C. After stirring from 0° C. to room temperature overnight, the reaction was quenched with water and evaporated under vacuum. The residue was extracted between saturated aqueous NaHCO$_3$ and EtOAc. The organic layer was dried over anhydrous Na$_2$SO$_4$ and evaporated to dryness. The crude mixture was purified by column chromatography with 60% to 100% EtOAc/Hex to give an oily product 55A at 51% yield. LCMS (+ESI) m/z 486.1, 489.1 [M+H]$^+$.

Step 2: Preparation of (S)-3-bromo-8-methyl-N-(4-methyl-1-(methylamino)-1-oxopentan-2-yl)-6,7,8,9-tetrahydro-5H-imidazo[1,5-a][1,4]diazepine-1-carboxamide 55B. A solution of intermediate 55A (0.74 g, 1.52 mmol) in TFA/DCM (20 mL, 1:1) was stirred at. room temperature for 0.5 hour. After evaporation of TFA and DCM, the residue was extracted between saturated aqueous NaHCO$_3$ and iPrOH/DCM (1:9) twice. The combined organic phase was dried and evaporated to give free amino intermediate (0.52 g, 88% yield). To a solution of the amino intermediate (0.52 g, 1.35 mmol) in THF was added AcOH (100 μL, 1.35 mmol) and paraformaldehyde (0.60 mL, 37% aq. 7.84 mmol) followed by sodium triacetoxyborohydride (0.57 g, 2.69 mmol). After stirring at room temperature overnight, THF was evaporated. The residue was extracted between saturated aqueous NaHCO$_3$ and iPrOH/DCM (1:9) twice. The combined organic phase was dried and evaporated to give compound 55B at 96% yield. LCMS (+ESI) m/z 401.1, 403.1 [M+H]$^+$.

Step 3: Preparation of (S)-3-(4-chloro-2-fluorophenyl)-8-methyl-N-(4-methyl-1-(methylamino)-1-oxopentan-2-yl)-6,7,8,9-tetrahydro-5H-imidazo[1,5-a][1,4]diazepine-1-carboxamide (compound 529). A mixture of intermediate 55B (47 mg, 0.12 mmol), potassium carbonate (40 mg, 0.29 mmol), 2-fluoro-4-chlorophenylboronic acid (0.25 mmol) and palladium tetrakis(triphenylphosphine) (20 mg) in dioxane (1.0 mL) and water (0.5 mL) was heated at 110° C. in a sealed vial for 4 h. After cooling down to room temperature, the mixture was passed through a thiol-based palladium scavenger resin (PolymerLabs). The residue was concentrated to dryness, to which MeOH (0.5 mL) was added. The solution was filtered to remove insoluble material and purified by prep LC-MS with 5% MeCN/water to 95 MeCN/water (0.1% formic acid) in 15 min. Pure fractions were evaporated with a Savant speedvac. The oil residue was taken up in DCM (1.0 mL) and diluted with hexane (1.0 mL). Evaporation under air flow with mild heating give white solid product Compound 529 at 40% yield. $^1$H-NMR (400 MHz, CDCl$_3$) δ: 0.96 (t, J=4.8 Hz, 6H), 1.59-1.72 (m, 2H), 1.81-1.90 (m, 3H), 2.47 (s, 3H), 2.56 (br, 2H), 2.78 (d, J=4.8 Hz, 3H), 2.98 (br, 2H), 3.96 (br, 2H), 4.52-4.58 (m, 1H), 6.48 (br, 1H), 7.21-7.24 (dd, J=2.0, 9.6 Hz, 1H), 7.29-7.31 (dd, J=1.7, 10.0 Hz, 1H), 7.39 (d, J=8.4 Hz, 1H), 7.50 (t, J=8.0 Hz, 1H). LCMS (+ESI) m/z 450.2, 452.2 [M+H]$^+$.

Compounds 530-539 were synthesized in the same manner as described above for compound 529 except that 4-chloro-2-fluorophenyl boronic acid was replaced with another boronic acid or dioxaborolane. For example, compound 530 was synthesized in the same manner as compound 529 except that 4-fluorophenyl boronic acid was used in place of 4-chloro-2-fluorophenyl boronic acid.

Compound 540 was synthesized in the same manner as described above for compound 529 except that 4-chloro-2- fluorophenyl boronic acid was replaced with cyclohexene-1-boronic acid, pinacol ester. The cyclohexenyl intermediate was then reduced using the hydrogenation procedure described in Example 45.

Compounds 541 and 542 were synthesized in the same manner as described above for compound 529 except that (S)-2-amino-2-cyclohexyl-N-methylacetamide (synthesized in the same manner as Intermediate 20B, Example 20) was used in place of 20B and 4-chloro-2-fluorophenyl boronic acid was replaced with 2,4,5-trifluorophenyl boronic acid or 2,4-difluoro-5-chlorophenylboronic acid pinacol ester.

Example 56

Preparation of Synthesis of (S)-8-methyl-N-(2-(methylamino)-2-oxo-1-phenylethyl)-3-phenyl-6,7,8,9-tetrahydro-5H-imidazo[1,5-a][1,4]diazepine-1-carboxamide (Compound 543)

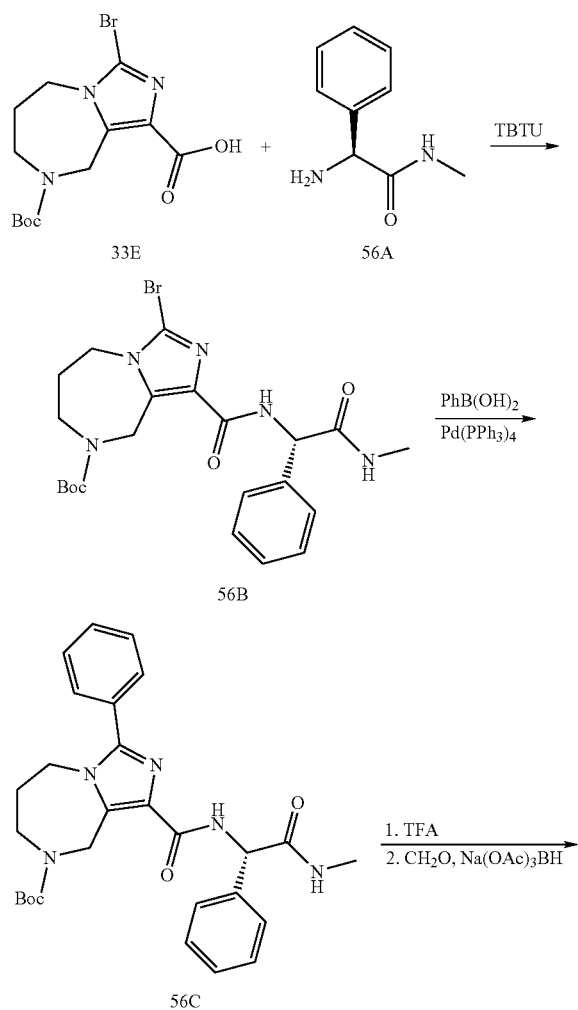

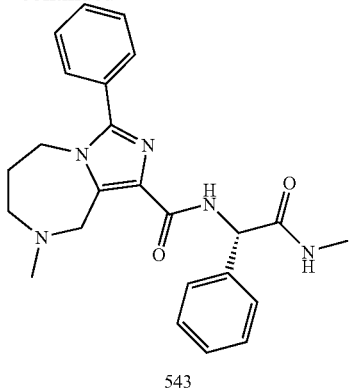

543

Step 1: To a solution of carboxylic acid 33E (100 mg, 0.28 mmol), phenyl glycine methylamide (56A) (86 mg, 0.53 mmol, prepared according to the procedure for the synthesis of leucine-N-methylamide by replacing Z-Leu-OH with Z-Phg-OH in Example 20 and DIEA (100 µL, 0.58 mmol) in DMF was added TBTU (134 mg, 0.53 mmol) at 0° C. After stirring at from 0° C. to room temperature for 4 h, the reaction was quenched with water (5 mL) and evaporated under vacuum. The residue was extracted between brine and EtOAc. The organic phase was dried over anhydrous $Na_2SO_4$ and evaporated to dryness. The residue was purified by column chromatography with 70% to 100% EtOAc/Hex to give Intermediate 56B at 56% yield. LCMS (+ESI) m/z 508.0 [M+Na]$^+$.

Step 2: A mixture of 56B (100 mg, 0.20 mmol), phenylboronic acid (36 mg, 0.30 mmol), potassium carbonate (46 mg, 0.33 mmol) and palladium tetrakis(triphenylphosphine) (10 mg) in dioxane and water (3:1) was heated at 100° C. overnight. The reaction mixture was diluted with brine and extracted with EtOAc. The organic phase was dried and evaporated to dryness and purified by column chromatography with 75% to 100% EtOAc/Hexanes to give Intermediate 56C at 54% yield.

Step 3: A solution of intermediate 56C (54 mg, 0.11 mmol) in TFA/DCM (5 mL, 1:1) was stirred at. room temperature for 0.5 hour. After evaporation of TFA and DCM, the residue was extracted between saturated aqueous $NaHCO_3$ and ethyl acetate twice. The combined organic phase was dried and evaporated to give free amino intermediate (35 mg, 81% yield). To a solution of the amino intermediate (35 mg, 0.087 mmol) in THF (3 mL) was added AcOH (50 µL, 0.087 mmol) and paraformaldehyde (70 µL, 37% aq. 0.94 mmol) followed by sodium triacetoxyborohydride (36 mg, 0.17 mmol). After stirring at room temperature for 2 hours, THF was evaporated. The residue was extracted between saturated aqueous $NaHCO_3$ and ethyl acetate twice. The combined organic phase was dried and purified by preparative LC-MS with 5% to 95% MeCN/water in 15 min to give Compound 543 at 39% yield. LCMS (+ESI) m/z 418.1, [M+H]$^+$.

Example 57

(S)-3-(4-chloro-2-fluorophenyl)-N-(4,4-dimethyl-1-(methylamino)-1-oxopentan-2-yl)-8-methyl-6,7,8,9-tetrahydro-5H-imidazo[1,5-a][1,4]diazepine-1-carboxamide (Compound 544)

Step 1: Preparation of (S)-3-bromo-N-(3,3-dimethyl-1-(methylamino)-1-oxobutan-2-yl)-8-methyl-6,7,8,9-tetrahydro-5H-imidazo[1,5-a][1,4]diazepine-1-carboxamide 57C. This intermediate was prepared following Example 55 of the synthesis of (S)-3-bromo-8-methyl-N-(4-methyl-1-(methylamino)-1-oxopentan-2-yl)-6,7,8,9-tetrahydro-5H-imidazo[1,5-a][1,4]diazepine-1-carboxamide (Intermediate 55B) by replacing Z-Leu-OH with Z-β-tBu-Ala-OH (Chem-Impex). LCMS (+ESI) m/z 416.1, 417.1 [M+H]⁺.

Step 2: Preparation of (S)-3-(4-chloro-2-fluorophenyl)-N-(4,4-dimethyl-1-(methylamino)-1-oxopentan-2-yl)-8-methyl-6,7,8,9-tetrahydro-5H-imidazo[1,5-a][1,4]diazepine-1-carboxamide (Compound 544).

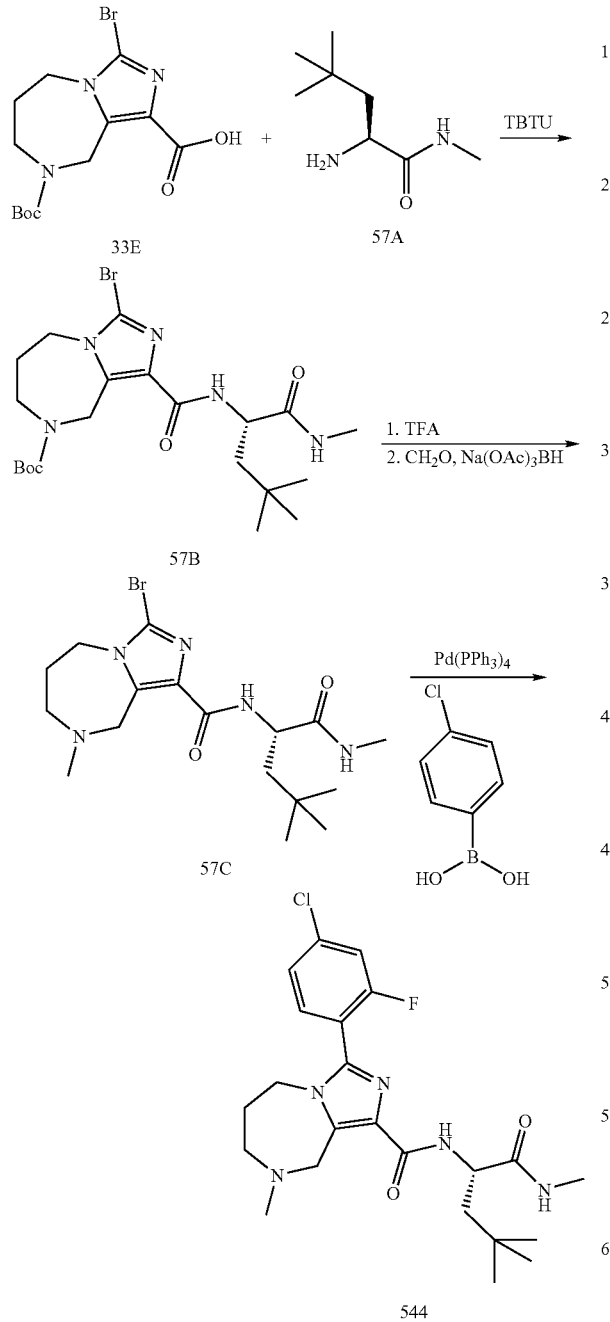

A mixture of Intermediate 57C (80 mg, 0.19 mmol), potassium carbonate (40 mg, 0.29 mmol), 2-fluoro-4-chlorophenylboronic acid (0.30 mmol) and palladium tetrakis(triphenylphosphine) (30 mg) in dioxane (1.0 mL) and water (0.5 mL) was heated at 110° C. in a sealed vial for 4 hours. After cooling down to room temperature, the mixture was passed through a thiol-based palladium scavenger resin (Polymer-Labs). The residue was concentrated to dryness, to which MeOH (0.5 mL) was added. The solution was filtered to remove insoluble material and purified by prep LC-MS with 5% MeCN/water to 95 MeCN/water (0.1% formic acid) in 15 min. LCMS (+ESI) m/z 464.3, 467.3 [M+H]⁺.

Compounds 545-555 were synthesized in the same manner as described above for compound 544 except that 4-chloro-2-fluorophenyl boronic acid was replaced with another boronic acid or dioxaborolane. For example, compound 547 was synthesized in the same manner as compound 544 except that 4-fluorophenyl boronic acid was used in place of 4-chloro-2-fluorophenyl boronic acid.

Example 58

Preparation of (S)-3-(4-chloro-2-fluorophenyl)-N-(1-(dimethylamino)-3,3-dimethyl-1-oxobutan-2-yl)-8-methyl-6,7,8,9-tetrahydro-5H-imidazo[1,5-a][1.4]diazepine-1-carboxamide (Compound 556)

Step 1: Preparation of (S)-3-bromo-N-(1-(dimethylamino)-3,3-dimethyl-1-oxobutan-2-yl)-8-methyl-6,7,8,9-tetrahydro-5H-imidazo[1,5-a][1,4]diazepine-1-carboxamide 58D.

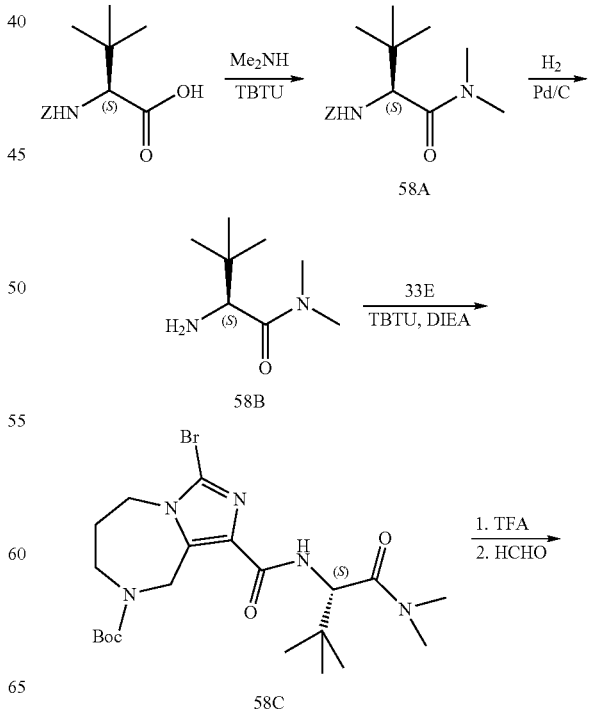

117

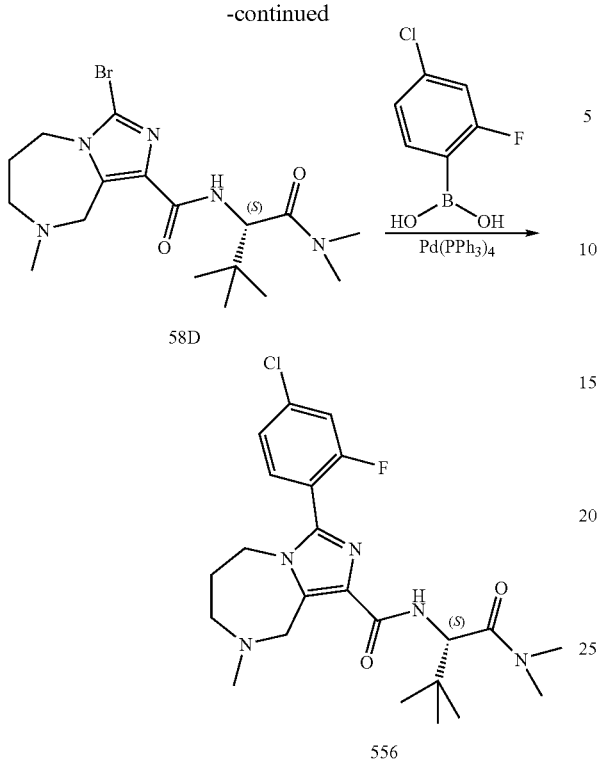

58D

556

This intermediate was prepared following the synthesis of ((S)—N-(1-amino-3,3-dimethyl-1-oxobutan-2-yl)-3-bromo-8-methyl-6,7,8,9-tetrahydro-5H-imidazo[1,5-a][1,4]diazepine-1-carboxamide (Intermediate 55B) by replacing Z-Leu-OH with tert-Leu-OH, and replacing methylamine hydrochloride with dimethylamine solution in THF. LCMS (+ESI) m/z 417.1 [M+H]$^+$.

Step 2: Preparation of (S)-3-(4-chloro-2-fluorophenyl)-N-(1-(dimethylamino)-3,3-dimethyl-1-oxobutan-2-yl)-8-methyl-6,7,8,9-tetrahydro-5H-imidazo[1,5-a][1,4]diazepine-1-carboxamide (Compound 556). A mixture of intermediate 58D (90 mg, 0.22 mmol), potassium carbonate (40 mg, 0.29 mmol), 2-fluoro-4-chloro-phenylboronic acid (0.30 mmol) and palladium tetrakis(triphenylphosphine) (30 mg) in dioxane (1.0 mL) and water (0.5 mL) was heated at 110° C. in a sealed vial for 4 hours. After cooling down to room temperature, the mixture was passed through a thiol-based palladium scavenger resin (PolymerLabs). The residue was concentrated to dryness, to which MeOH (0.5 mL) was added. The solution was filtered to remove insoluble material and purified by prep LC-MS with 5% MeCN/water to 95 MeCN/water (0.1% formic acid) in 15 min. $^1$H-NMR (400 MHz, CDCl$_3$) δ: 1.05 (s, 9H), 1.96 (br, 2H), 2.50 (s, 3H), 2.96 (s, 3H), 3.19-3.23 (m, 4H), 4.00 (br, 2H), 4.62 (br, 2H), 5.04 (d, J=9.8 Hz, 1H), 7.21-7.23 (dd, J=2.0, 9.8 Hz, 1H), 7.29-7.32 (dd, J=1.8, 8.3 Hz, 1H), 7.58 (t, J=8.0 Hz, 1H), 7.90 (d, J=9.8 Hz, 1H), 8.26 (s, 1H). LCMS (+ESI) m/z 464.2, 466.1 [M+H]$^+$.

Compounds 557-563 were synthesized in the same manner as described above for compound 556 except that 4-chloro-2-fluorophenyl boronic acid was replaced with another boronic acid or dioxaborolane. For example, compound 561 was synthesized in the same manner as Compound 556 except that 3,4-difluorophenyl boronic acid was used in place of 4-chloro-2-fluorophenyl boronic acid.

118

Example 59

Preparation of (S)—N-(1-amino-4-methyl-1-oxopentan-2-yl)-3-(4-chloro-2-fluorophenyl)-8-methyl-6,7,8,9-tetrahydro-5H-imidazo[1,5-a][1,4]diazepine-1-carboxamide (Compound 564)

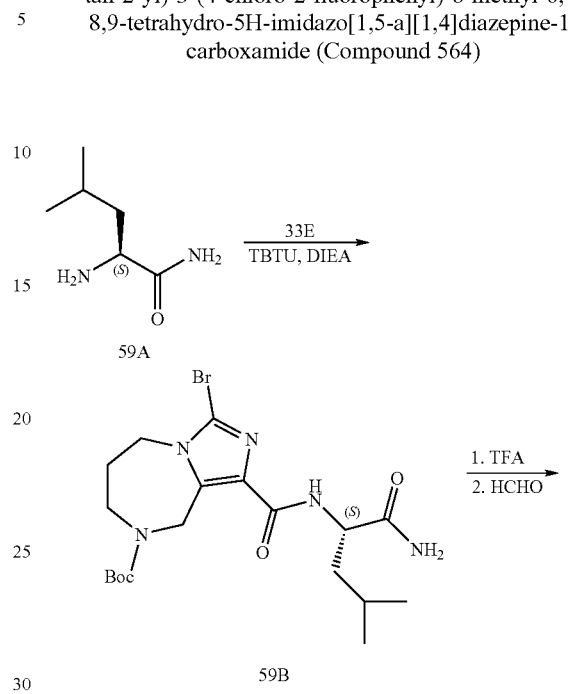

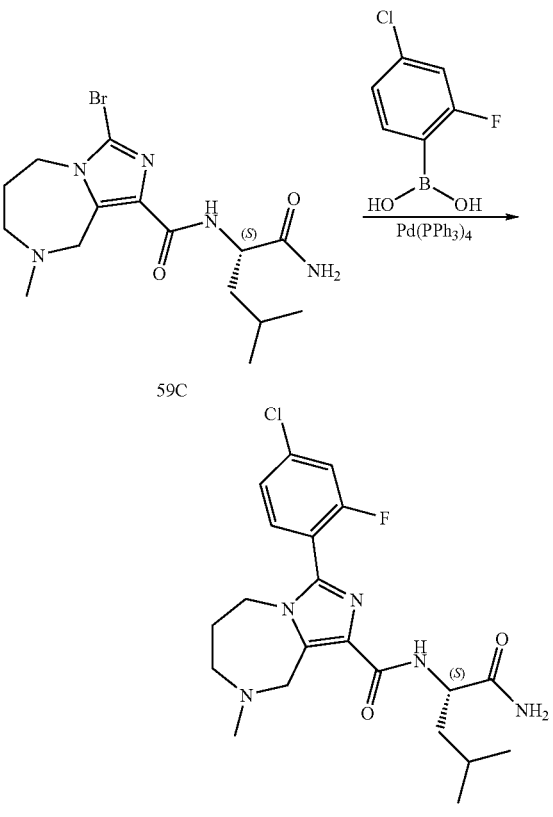

Step 1: Preparation of (S)—N-(1-amino-4-methyl-1-oxopentan-2-yl)-3-bromo-8-methyl-6,7,8,9-tetrahydro-5H-imidazo[1,5-a][1,4]diazepine-1-carboxamide (Intermediate 59C). This intermediate was prepared following the synthesis of (S)-3-bromo-8-methyl-N-(4-methyl-1-(methylamino)-1-oxopentan-2-yl)-6,7,8,9-tetrahydro-5H-imidazo[1,5-a][1,4]diazepine-1-carboxamide (intermediate 55B) by replacing H-Leu-NHMe with Leucine amide 59A (Chem-Impex). LCMS (+ESI) m/z 386.1 [M+H]+.

Step 2: Preparation of (S)—N-(1-amino-4-methyl-1-oxopentan-2-yl)-3-(4-chloro-2-fluorophenyl)-8-methyl-6,7,8,9-tetrahydro-5H-imidazo[1,5-a][1,4]diazepine-1-carboxamide (compound 564). A mixture of intermediate 59C (65 mg, 0.17 mmol), potassium carbonate (40 mg, 0.29 mmol), 2-fluoro-4-chlorophenylboronic acid (0.30 mmol) and palladium tetrakis(triphenylphosphine) (30 mg) in dioxane (1.0 mL) and water (0.5 mL) was heated at 110° C. in a sealed vial for 4 hours. After cooling down to room temperature, the mixture was passed through a thiol-based palladium scavenger resin (PolymerLabs). The residue was concentrated to dryness, to which MeOH (0.5 mL) was added. The solution was filtered to remove insoluble material and purified by prep LC-MS with 5% MeCN/water to 95 MeCN/water (0.1% formic acid) in 15 minutes. $^1$H-NMR (400 MHz, CDCl$_3$) δ: 0.95 (dd, J=5.3, 9.7 Hz, 6H), 1.63-1.85 (m, 3H), 1.98 (br, 2H), 2.52 (s, 3H), 3.16 (br, 2H), 4.01 (br, 2H), 4.52-4.63 (m, 3H), 5.83 (br, 1H), 6.59 (br, 1H), 7.12-7.25 (dd, J=1.9, 9.6 Hz, 1H), 7.30-7.36 (dd, J=6.4, 8.2 Hz, 1H), 7.44 (d, J=8.3 Hz, 1H), 7.54 (t, J=7.9 Hz, 1H), 8.16 (br, 1H). LCMS (+ESI) m/z 436.2, 439.2 [M+H]+.

Compounds 565-572 were synthesized in the same manner as described above for Compound 564 except that 4-chloro-2-fluorophenyl boronic acid was replaced with another boronic acid or dioxaborolane. For example, Compound 565 was synthesized in the same manner as Compound 564 except that 4-difluorophenyl boronic acid was used in place of 4-chloro-2-fluorophenyl boronic acid. Compound 570 was synthesized in the same manner as described above for Compound 564 except that 4-chloro-2-fluorophenyl boronic acid was replaced with cyclohexene-1-boronic acid, pinacol ester. The cyclohexenyl intermediate was then reduced using the hydrogenation procedure described in Example 45.

Example 60

Preparation of (S)—N-(1-amino-3,3-dimethyl-1-oxobutan-2-yl)-3-(4-chloro-2-fluorophenyl)-8-methyl-6,7,8,9-tetrahydro-5H-imidazo[1,5-a][1,4]diazepine-1-carboxamide (Compound 573)

Step 1: To a solution of Z-tert-Leucine dicyclohexylammonium salt (1.78 g, 4.0 mmol) in DCM was added and isobutyl chloroformate (0.80 mL, 6.1 mmol) at 0° C. After stirring at 0° C. for 30 min, ammonia/MeOH (7 M, 6 mL) was added and stirred at 0° C. for 30 min. The suspension was filtered to remove the white precipitate. The filtrate was concentrated and purified by column chromatography with 60% to 100% EtOAc/Hex to give Z-tert-Leu-NH$_2$ at 85% yield. LCMS (+ESI) m/z 287.1 [M+Na]+.

Step 2: Preparation of ((S)—N-(1-amino-3,3-dimethyl-1-oxobutan-2-yl)-3-bromo-8-methyl-6,7,8,9-tetrahydro-5H-imidazo[1,5-a][1,4]diazepine-1-carboxamide 60C. Intermediate 60C was prepared following the synthesis of (S)-3-bromo-8-methyl-N-(4-methyl-1-(methylamino)-1-oxopentan-2-yl)-6,7,8,9-tetrahydro-5H-imidazo[1,5-a]s[1,4]diazepine-1-carboxamide (intermediate 55B). LCMS (+ESI) m/z 388.0, 389.1 [M+H]+.

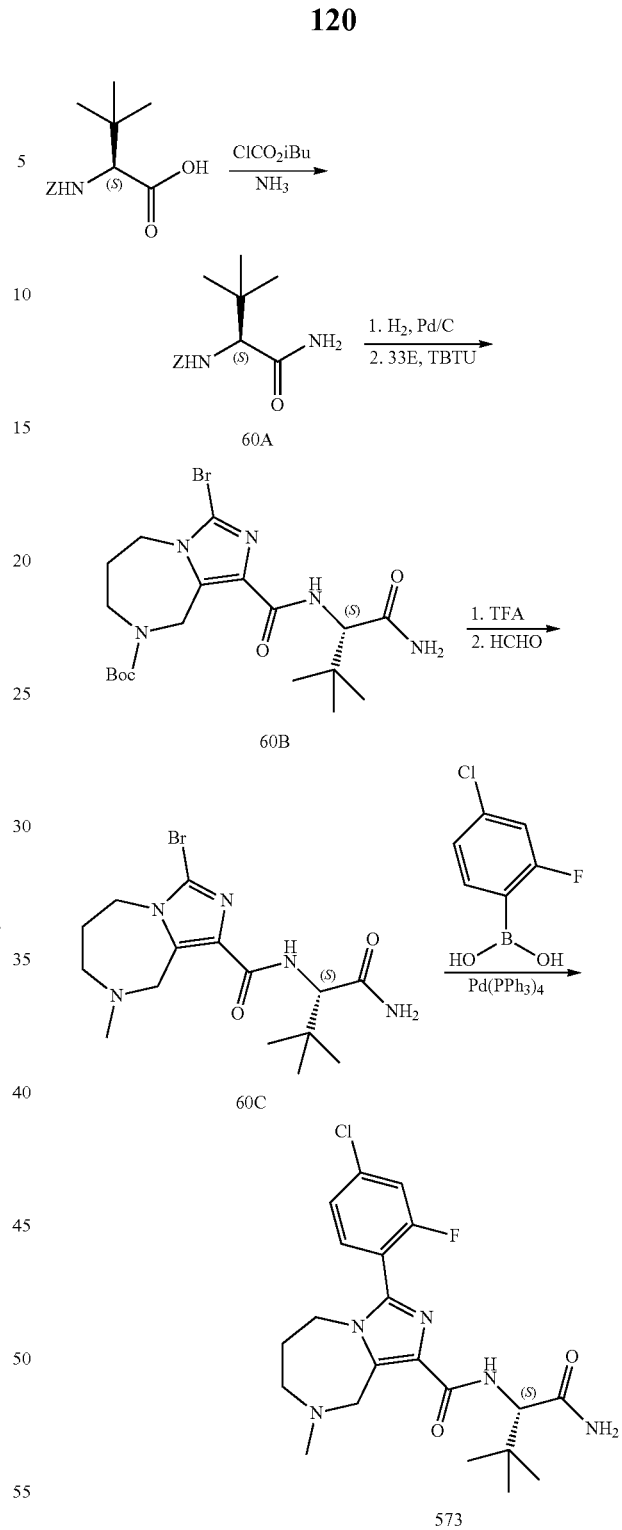

Step 3: Preparation of (S)—N-(1-amino-3,3-dimethyl-1-oxobutan-2-yl)-3-(4-chloro-2-fluorophenyl)-8-methyl-6,7,8,9-tetrahydro-5H-imidazo[1,5-a][1,4]diazepine-1-carboxamide (compound 573). A mixture of intermediate 60C (45 mg, 0.12 mmol), potassium carbonate (20 mg, 0.15 mmol), 2-fluoro-4-chlorophenylboronic acid (0.15 mmol) and palladium tetrakis(triphenylphosphine) (20 mg) in dioxane (1.0 mL) and water (0.5 mL) was heated at 110° C. in a sealed vial for 4 hours. After cooling down to room temperature, the mixture was passed through a thiol-based palladium scavenger resin (PolymerLabs). The residue was concentrated to dryness, to which MeOH (0.5 mL) was added. The solution was filtered to remove insoluble material and purified by preparative LC-MS with 5% MeCN/water to 95 MeCN/water (0.1% formic acid) in 15 min. $^1$H-NMR (400 MHz, CDCl$_3$) δ: 1.07 (s, 9H), 2.02 (br, 2H), 2.56 (s, 3H), 3.31 (br, 2H), 4.06 (br, 2H), 4.41 (d, J=9.3 Hz, 1H), 4.67-4.78 (br, 2H), 6.15 (br, 1H), 6.38 (br, 1H), 7.22-7.27 (dd, J=1.8, 9.8 Hz, 1H), 7.31-7.34 (dd, J=1.7, 8.3 Hz, 1H), 7.58 (t, J=8.0 Hz, 1H), 7.82 (d, J=9.4 Hz, 1H), 8.19 (br, 1H). LCMS (+ESI) m/z 436.2 [M+H]$^+$.

Compounds 574-582 were synthesized in the same manner as described above for compound 573 except that 4-chloro-2-fluorophenyl boronic acid was replaced with another boronic acid or dioxaborolane. For example, Compound 582 was synthesized in the same manner as Compound 573 except that phenyl boronic acid was used in place of 4-chloro-2-fluorophenyl boronic acid.

Example 61

Preparation of (S)—N-(1-amino-4,4-dimethyl-1-oxopentan-2-yl)-3-(2,5-difluorophenyl)-8-methyl-6,7,8,9-tetrahydro-5H-imidazo[1,5-a]11.41 diazepine-1-carboxamide (Compound 583)

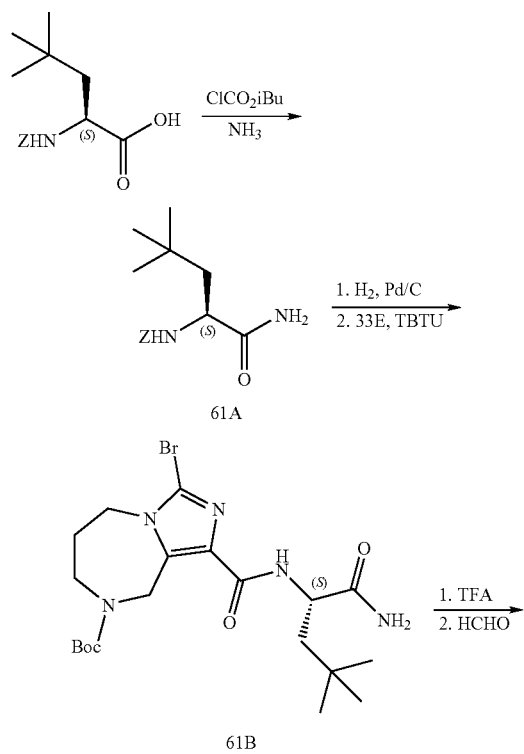

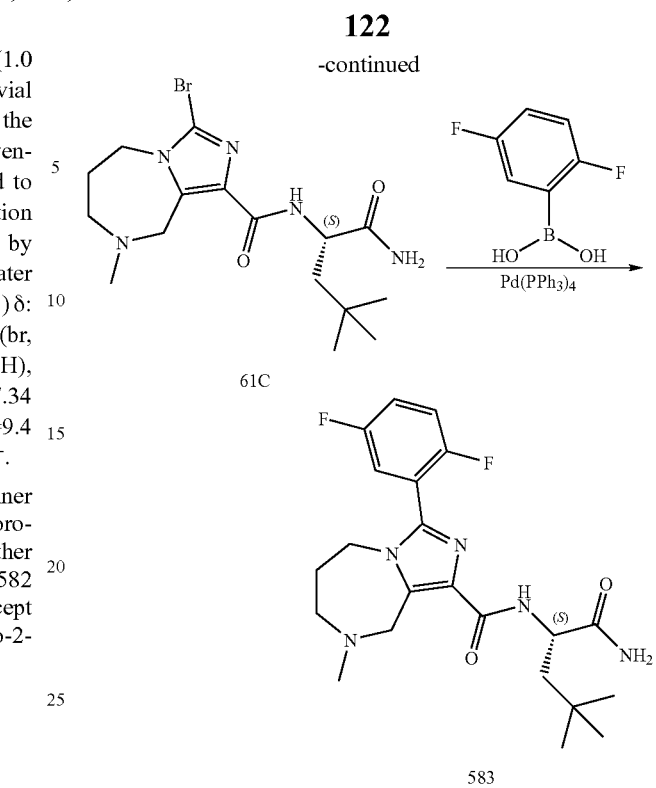

Step 1: Preparation of (S)—N-(1-amino-4,4-dimethyl-1-oxopentan-2-yl)-3-bromo-8-methyl-6,7,8,9-tetrahydro-5H-imidazo[1,5-a][1,4]diazepine-1-carboxamide 61C. This intermediate was prepared following the synthesis of intermediate 60C in Example 60 by replacing Z-tert-Leu-OH with Z-neopentylglycine. LCMS (+ESI) m/z 400.1, 403.1 [M+H]$^+$.

Step 2: Preparation of (S)—N-(1-amino-4,4-dimethyl-1-oxopentan-2-yl)-3-(2,5-difluorophenyl)-8-methyl-6,7,8,9-tetrahydro-5H-imidazo[1,5-a][1,4]diazepine-1-carboxamide (Compound 583). A mixture of intermediate 61C (69 mg), potassium carbonate (40 mg, 0.29 mmol), 2,5-difluorophenylboronic acid (0.20 mmol) and palladium tetrakis(triphenylphosphine) (20 mg) in dioxane (1.0 mL) and water (0.5 mL) was heated at 110° C. in a sealed vial for 4 hours. After cooling down to room temperature, the mixture was passed through a thiol-based palladium scavenger resin (PolymerLabs). The residue was concentrated to dryness, to which MeOH (0.5 mL) was added. The solution was filtered to remove insoluble material and purified by prep LC-MS with 5% MeCN/water to 95% MeCN/water (0.1% formic acid) in 15 min. $^1$H-NMR (400 MHz, CDCl$_3$) δ: 0.98 (s, mix of two rotamers, 9H), 1.56-1.62 (m, 1H), 2.04-2.09 (m, 3H), 2.58 (s, 2H, one rotamer of NMe), 2.68 (s, 1H, the other rotamer of NMe), 3.28-3.40 (m, 2H), 4.07 (br, 2H), 4.52-4.63 (m, 2H), 4.70-4.89 (m, 3H), 6.13 (br, 1H), 6.76 (br, 1H), 7.15-7.24 (m, 2H), 7.28-7.33 (m, 1H), 7.49-7.51 (m, 1H), 8.18 (br, 1H). LCMS (+ESI) m/z 434.2 [M+H]$^+$.

Compounds 584-591 were synthesized in the same manner as described above for Compound 583 except that 2,5-difluorophenyl boronic acid was replaced with another boronic acid or dioxaborolane. For example, compound 584 was synthesized in the same manner as 583 except that 2-fluoro-4-chloro phenyl boronic acid was used in place of 2,5-difluorophenyl boronic acid.

Example 62

Preparation of (S)-8-methyl-N-(1-(methylamino)-1-oxo-3-(thiazol-4-yl)propan-2-yl)-3-(2,4,5-trifluorophenyl)-6,7,8,9-tetrahydro-5H-imidazo[1,5-a][1,4]diazepine-1-carboxamide (Compound 592)

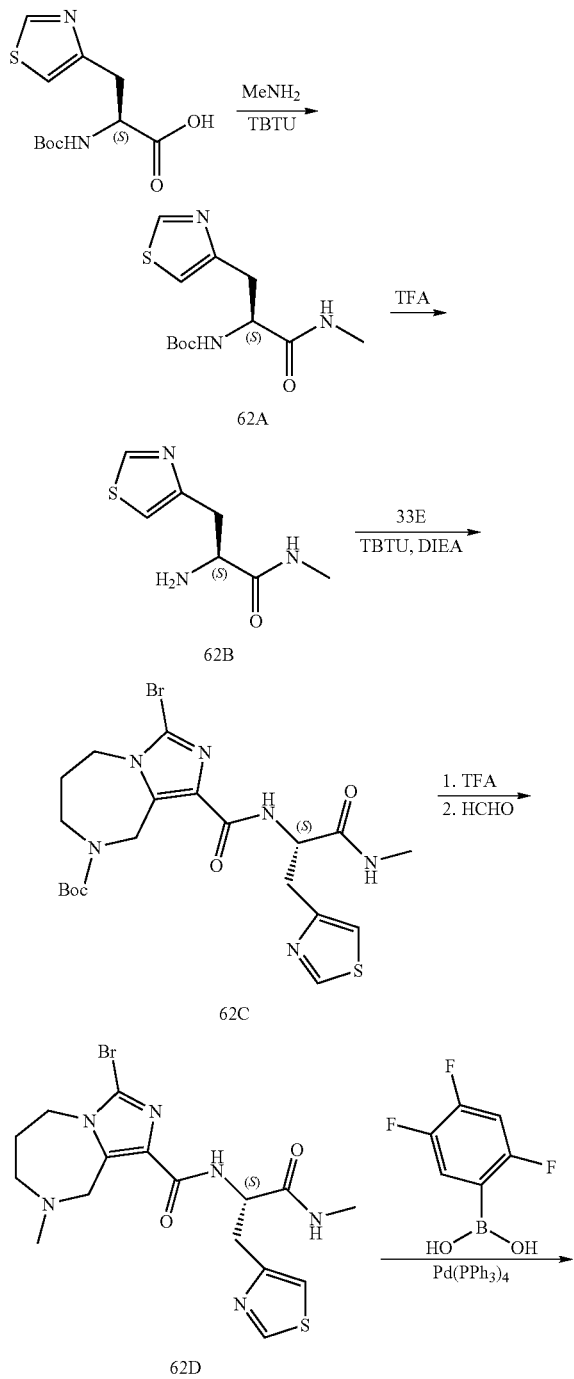

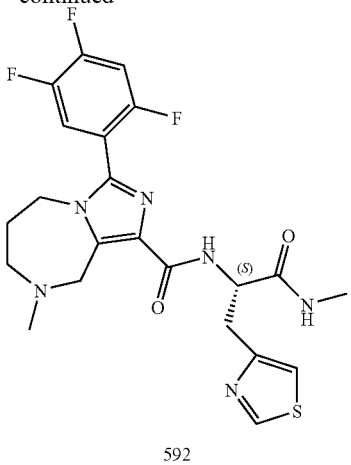

592

Steps 1-2: Preparation of (S)-2-amino-N-methyl-3-(thiazol-4-yl)propanamide (intermediate 62B). To a solution of Boc-Ala(4-thiazoyl)-OH (1.0 g, 3.67 mmol), methylamine hydrochloride (0.89 g, 13.2 mmol) and DIEA (3.0 mL, 17.2 mmol) in DMF (40 mL) was added TBTU (1.80 g, 5.6 mmol) at 0° C. in two batches over 10 min. After stirring at room temperature for 1 hour, the reaction was quenched with water (5 mL) and evaporated under vacuum. The residue was extracted between brine and EtOAc, and washed with aqueous ammonium chloride. The organic phase was dried over anhydrous $Na_2SO_4$ and evaporated to dryness to give Boc-Ala(4-thiazoyl)-NHMe 62A at 73% yield. $^1$H-NMR (400 MHz, $CDCl_3$) δ: 1.42 (s, 9H), 2.73 (d, J=4.8 Hz, 3H), 3.19-3.25 (dd, J=5.6, 14.6 Hz, 1H), 3.34 (br, 1H), 4.51 (br, 1H), 6.03 (br, 1H), 6.57 (br, 1H), 7.12 (s, 1H), 8.75 (s, 1H). LCMS (+ESI) m/z 286.1 $[M+H]^+$.

A solution of intermediate 62A (0.76 g, 2.66 mmol) in TFA/DCM (10 mL, 1:1) was stirred at room temperature for 0.5 hour. After evaporation of TFA and DCM, the residue was extracted between saturated aqueous $NaHCO_3$ and iPrOH/DCM (1:9) twice. The combined organic phase was dried and evaporated to give free amino intermediate 62B (0.20 g, 41% yield).

Steps 3-4: Preparation of (S)-3-bromo-8-methyl-N-(1-(methylamino)-1-oxo-3-(thiazol-4-yl)propan-2-yl)-6,7,8,9-tetrahydro-5H-imidazo[1,5-a][1,4]diazepine-1-carboxamide 62D. This intermediate was prepared following steps 1-2 in Example 55 of the synthesis of (S)-3-bromo-8-methyl-N-(4-methyl-1-(methylamino)-1-oxopentan-2-yl)-6,7,8,9-tetrahydro-5H-imidazo[1,5-a][1,4]diazepine-1-carboxamide (intermediate 55B) by replacing 20B with H-Ala(4-thiazoyl)-NHMe 62B. LCMS (+ESI) m/z 442.06, 443.0 $[M+H]^+$.

Step 5: Preparation of (S)-8-methyl-N-(1-(methylamino)-1-oxo-3-(thiazol-4-yl)propan-2-yl)-3-(2,4,5-trifluorophenyl)-6,7,8,9-tetrahydro-1H-imidazo[1,5-a][1,4]diazepine-1-carboxamide (compound 592). A mixture of intermediate 62D (50 mg, 0.11 mmol), potassium carbonate (23.6 mg, 0.17 mmol), 2,4,5-trifluorophenylboronic acid (29.9 mg, 0.17 mmol) and palladium tetrakis(triphenylphosphine) (25 mg, 0.02 mmol) in dioxane (2.0 mL) and water (0.3 mL) was heated at 110° C. in a sealed vial for 16 h. After cooling down to room temperature, the mixture was passed through a thiol-based palladium scavenger resin (PolymerLabs). The residue was concentrated to dryness, to which MeOH (0.5 mL) was added. The solution was filtered to remove insoluble material and purified by prep LC-MS with 5% MeCN/water to 95 MeCN/water (0.1% formic acid) in 15 min. $^1$H-NMR (400

MHz, CDCl$_3$) δ: 1.25 (s, 1H), 2.1 (br s, 1H), 2.72-2.73 (d, 2H), 3.05-3.14 (m, 2H), 3.32-3.39 (dd, 1H), 3.43-3.49 (dd, 1H), 3.90-4.00 (d, 2H), 4.21-4.52 (br m, 2H), 4.93-4.98 (q, 1H), 6.59 (br, 1H), 7.02-7.10 (m, 1H), 7.15 (d, 1H), 7.43-7.51 (m, 1H), 8.08 (br, 1H), 8.27-8.34 (d, 1H), 8.7 (s, 1H). LCMS (+ESI) m/z 492.16 [M+H]$^+$.

Compound 593 was synthesized in the same manner as described above for compound 592 except that 2,4,5-trifluorophenyl boronic acid was replaced with 2,4-difluoro-5-chlorophenylboronic acid pinacol ester.

Example 63

Preparation of (S)-3-(3,6-dihydro-2H-pyran-4-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide (Compound 594)

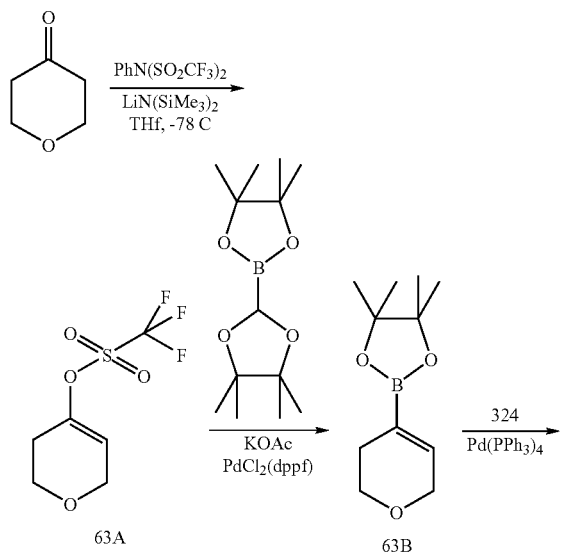

Step 1. Preparation of 3,6-dihydro-2H-pyran-4-yl trifluoromethanesulfonate (Intermediate 63A). Dihydro-2H-pyran-4(3H)-one (0.3 g, 3.30 mmol) was dissolved in THF and 1,1,1-trifluoro-N-phenyl-N-(trifluoromethylsulfonyl)methanesulfonamide (1.18 g, 3.30 mmol) was added. The resulting mixture was cooled to −78° C. and lithium bis(trimethylsilyl)amide (1M in THF, 3.30 mL) was added dropwise and the reaction mixture was stirred at −78° C. for 2 hours. The mixture was then allowed to warm to −5° C. over a period of 15 hours. The reaction mixture was quenched with saturated ammonium chloride solution and extracted with ethyl acetate. The organic extracts were washed with brine, dried over Na$_2$SO$_4$ and concentrated. The residue was purified by regular phase chromatography eluting with 10% ethyl acetate/hexanes. The resulting crude oil 63A (200 mg) was used in the next step without purification.

Step 2. Preparation of 2-(3,6-dihydro-2H-pyran-4-yl)-4,4,5,5-tetramethyl-1,3,2-dioxaborolane (intermediate 63B). Intermediate 63A (0.20 g 0.86 mmol) was dissolved in dioxane and 4,4,4',4',5,5,5',5'-octamethyl-2,2'-bi(1,3,2-dioxaborolane) (0.32 g, 1.29 mmol) was added followed by KOAc (0.25 g, 1.29 mmol). The resulting mixture was degassed with nitrogen and PdCl$_2$(dppf) (0.050 g, 0.069 mmol) was added. The resulting mixture was heated at 80° C. overnight. The mixture was concentrated, and the oily residue was extracted with ethyl acetate. The organic extracts were concentrated and the residue was purified by regular phase chromatography eluting with 10% ethylacetate/hexanes to give a title compound 63B as a clear oil which was used in the next step without purification.

Step 3. Preparation of (S)-3-bromo-N-(3,3-dimethyl-1-(methylamino)-1-oxobutan-2-yl)-8-methyl-6,7,8,9-tetrahydro-5H-imidazo[1,5-a][1,4]diazepine-1-carboxamide (Compound 594). Compound 324 (50 mg, 0.125 mmol) was dissolved in 2 mL dioxane and 2-(3,6-dihydro-2H-pyran-4-yl)-4,4,5,5-tetramethyl-1,3,2-dioxaborolane 63B (52 mg, 0.25 mmol) was added followed by K$_2$CO$_3$ (34 mg, 0.25 mmol) and water (0.40 mL). The resulting suspension was degassed with nitrogen and Pd(PPh$_3$)$_4$ (11 mg, 0.009 mmol) was added. The reaction mixture was heated in a microwave reactor at 160° C. for 20 minutes. The mixture was filtered through celite and concentrated. The residue was purified by prep LCMS using 5-95% acetonitrile/water gradient with 0.1% formic acid to provide 11 mg (19%) of Compound 594. LCMS (+ESI) m/z 404.2 [M+H]$^+$.

Example 64

Preparation of N-(5-tert-butylisoxazol-3-yl)-8-methyl-3-phenyl-6,7,8,9-tetrahydro-5H-imidazo[1,5-a][1,4]diazepine-1-carboxamide (Compound 595)

Step 1. Preparation of ethyl 3-phenyl-6,7,8,9-tetrahydro-5H-imidazo[1,5-a][1,4]diazepine-1-carboxylate (64A). Intermediate 39A (1.22 g, 3.17 mmol) was dissolved in DCM (10 mL) and TFA (5 mL) was added. The resulting mixture was stirred for 2 hours. The mixture was concentrated, toluene was added and the mixture was concentrated again and dried under vacuum to give 1.28 g of intermediate 64A which was used in the next step without purification. LCMS (+ESI) m/z 286.1 [M+H]$^+$ Step 2. Preparation of ethyl 8-methyl-3-phenyl-6,7,8,9-tetrahydro-5H-imidazo[1,5-a][1,4]diazepine-1-carboxylate (64B). To a solution of intermediate 64A (0.91 g, 3.17 mmol) in 20 mL THF was added formaldehyde (37% in water, 2.36 mL) followed by sodium triacetoxyborohydride (1.34 g, 6.34 mmol) and acetic acid (0.27 mL, 4.76 mmol). The resulting mixture was stirred at room temperature overnight and then quenched with NaHCO$_3$ saturated solution and stirred for 10 minutes. The reaction mixture was concentrated under vacuum and extracted with 10% iPrOH/DCM.

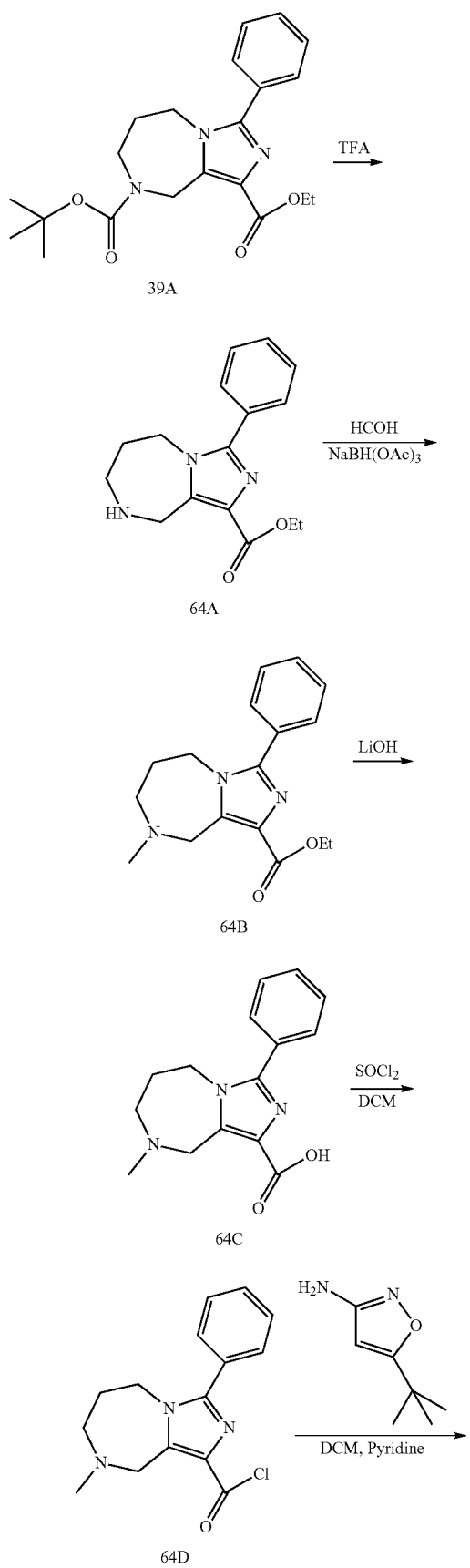

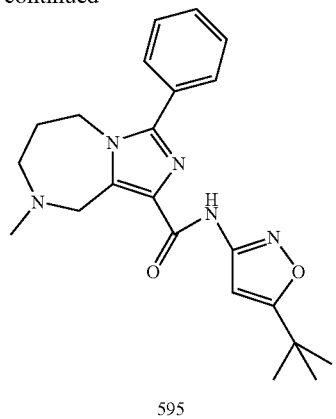

The combined organic layers were washed with brine and dried over Na$_2$SO$_4$, filtered and concentrated to provide intermediate 64B (0.87 g, 92%). LCMS (+ESI) m/z 300.1 [M+H]$^+$ Step 3. Preparation of 8-methyl-3-phenyl-6,7,8,9-tetrahydro-5H-imidazo[1,5-a][1,4]diazepine-1-carboxylic acid (64C). To a solution of intermediate 64B (0.87 g, 2.91 mmol) in 20 mL methanol was added lithium hydroxide (0.139 g, 5.81 mmol) in 5 mL water. The reaction mixture was stirred at 50° C. for 2 hours, filtered, concentrated and neutralized with 1N HCl. The resulting solution was lyophilized to provide intermediate 64C (0.57 g, 72%) as a white solid. LCMS (+ESI) m/z 272.1 [M+H]$^+$ Step 4. Preparation of 8-methyl-3-phenyl-6,7,8,9-tetrahydro-5H-imidazo[1,5-a][1,4]diazepine-1-carbonyl chloride (64D). To a solution of intermediate 64C (0.12 g, 0.44 mmol) in 3 mL DCM was added thionyl chloride (0.16 mL, 2.21 mmol), followed by catalytic amount of DMF. The resulting mixture was stirred at 50° C. for 30 minutes, concentrated and the residual thionyl chloride was azeotroped with toluene. The resulting material 64D was dried under vacuum and used in the next step without purification.

Step 5. Preparation of Compound 595. Intermediate 64D (0.127 g, 0.44 mmol) was dissolved in 3 mL DCM and cooled to 0° C. To the resulting mixture was added 5-tert-butylisoxazol-3-amine (0.093 g, 0.66 mmol), followed by pyridine (0.214 mL, 2.64 mmol). The mixture was stirred at room temperature for 30 minutes, concentrated, dried under vacuum and purified by prep LCMS eluting with 5-95% gradient acetonitrile/water with 0.1% formic acid to provide 60 mg (30%) of compound 595. LCMS (+ESI) m/z 394.1 [M+H]$^+$.

Compound 596 was synthesized in the same manner as compound 595 except that 4-tert-butylthiazol-2-amine was used in place of 5-tert-butylisoxazol-3-amine in Step 5.

Example 65

Preparation of (S)-3-chloro-N-(3,3-dimethyl-1-(methylamino)-1-oxobutan-2-yl)-6,7,8,9-tetrahydro-5H-imidazo[1,5-a][1,4]diazepine-1-carboxamide (Compound 597) and (S)-3-chloro-N-(3,3-dimethyl-1-(methylamino)-1-oxobutan-2-yl)-8-methyl-6,7,8,9-tetrahydro-5H-imidazo[1,5-a][1,4]diazepine-1-carboxamide (Compound 598)

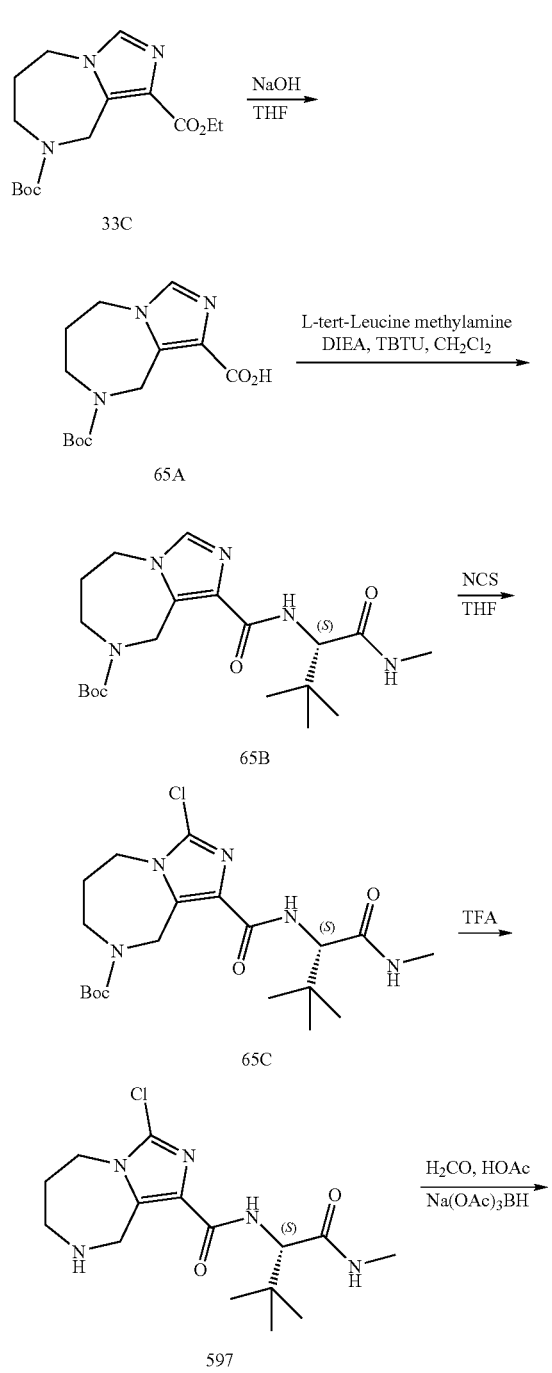

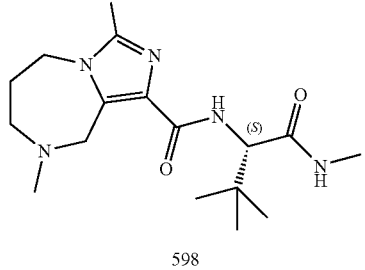

Step 1: Preparation of 8-(tert-butoxycarbonyl)-6,7,8,9-tetrahydro-5H-imidazo[1,5-a][1,4]diazepine-1-carboxylic acid (Intermediate 65A). Intermediate 33C (1.0 g, 3.01 mmol) was dissolved in THF (6 mL) and treated with a 10M aqueous solution of sodium hydroxide (3.0 mL, 30.0 mmol). Methanol was added until a homogeneous solution resulted, and the solution was stirred for 2 hours. The solution was concentrated under reduced pressure, and the residue was brought to pH 3 with 5N aqueous hydrochloric acid solution, and the resulting precipitate was collected by filtration and washed with water. The material was dried in a 40° C. vacuum oven for 18 hours to provide intermediate 65A as a white solid (331 mg, 39% yield). $^1$H-NMR (400 MHz, (CD$_3$)$_2$SO) δ: 1.27 (s, 9H), 1.73 (m, 2H), 3.60 (m, 2H), 4.22 (t, 2H), 4.89 (m, 2H), 7.61 (s, 1H), 12.19 (broad s, 1H). LCMS (+ESI) m/z 282.1 [M+H]$^+$.

Step 2: Preparation of (S)-tert-butyl 1-(3,3-dimethyl-1-(methylamino)-1-oxobutan-2-ylcarbamoyl)-6,7-dihydro-5H-imidazo[1,5-a][1,4]diazepine-8(9H)-carboxylate (Intermediate 65B). Intermediate 65A (290 mg, 1.03 mmol) and (S)-2-amino-N,3,3-trimethylbutanamide (149 mg, 1.03 mmol) were dissolved in dichloromethane (4 mL) and N,N-diisopropylethylamine (0.36 mL, 2.06 mmol). TBTU (497 mg, 1.55 mmol) was added, and the mixture was stirred for 1 hour. The reaction mixture was diluted with additional dichloromethane and was washed with water and saturated aqueous sodium bicarbonate solution. The organic layer was separated, dried over Na$_2$SO$_4$, and absorbed onto silica gel for purification by flash chromatography. The column was eluted with a gradient of 0-5% methanol in dichloromethane over a 10 minute period. The clean fractions were combined, concentrated under reduced pressure, and dried in a 40° C. vacuum oven for 2 hours to provide 65B as a white solid (384 mg, 92% yield). $^1$H NMR (400 MHz, (CD$_3$)$_2$SO) δ: 0.91 (s, 9H), 1.23 (s, 9H), 1.74 (m, 2H), 2.56 (d, 3H), 3.58 (m, 2H), 4.21 (m, 2H), 4.27 (d, 1H), 4.92 (m, 2H), 7.60 (m, 1H), 7.61 (s, 1H), 8.08 (d, 1H). LCMS (+ESI) m/z 408.2 [M+H]$^+$.

Step 3: Preparation of (S)-tert-butyl 3-chloro-1-(3,3-dimethyl-1-(methylamino)-1-oxobutan-2-ylcarbamoyl)-6,7-dihydro-5H-imidazo[1,5-a][1,4]diazepine-8(9H)-carboxylate (Intermediate 65C). Intermediate 65B (200 mg, 0.49 mmol) was dissolved in anhydrous THF (3 mL). Solid N-chlorosuccinimide (NCS) was added (79 mg, 0.59 mmol), and the resulting solution was stirred for 18 hours. The reaction flask was charged with additional NCS (40 mg, 0.30 mmol), and the solution was stirred for another 7 hours. The solution was diluted with excess ethyl acetate. The ethyl acetate solution was washed with saturated aqueous sodium bicarbonate solution, dried over $Na_2SO_4$, and absorbed onto silica gel for purification by flash chromatography. The column was eluted with ethyl acetate, and the clean fractions were combined and concentrated under reduced pressure to provide 65C as a yellow oil (91 mg, 42% yield). $^1$H NMR (400 MHz, $CDCl_3$) δ: 1.04 (s, 9H), 1.34 (s, 9H), 1.91 (m, 2H), 2.75 (d, 3H), 3.68 (m, 2H), 4.14 (m, 2H), 4.23 (d, 1H), 4.94 (m, 2H), 5.95 (m, 1H), 7.58 (d, 1H). LCMS (+ESI) m/z 442.2 $[M+H]^+$.

Step 4: Preparation of (S)-3-chloro-N-(3,3-dimethyl-1-(methylamino)-1-oxobutan-2-yl)-6,7,8,9-tetrahydro-5H-imidazo[1,5-a][1,4]diazepine-1-carboxamide (Compound 597). To intermediate 65C (91 mg, 0.21 mmol) in dichloromethane (2 mL) was added trifluoroacetic acid (0.64 mL, 8.24 mmol). After 1.5 hours of stirring, the solution was concentrated under reduced pressure. The residue was brought to pH 8 with a saturated aqueous solution of sodium bicarbonate. The aqueous solution was extracted with 3:1 chloroform/isopropanol solution. The combined organic layers were dried ($Na_2SO_4$) and concentrated under reduced pressure to an orange solid 597 (62 mg, 89% yield). $^1$H-NMR (400 MHz, $(CD_3)_2SO$) δ: 0.90 (s, 9H), 1.71 (m, 2H), 2.58 (d, 3H), 3.00 (t, 2H), 4.16 (t, 2H), 4.26 (m, 2H), 4.13 (d, 1H), 7.46 (d, 1H), 8.11 (q, 1H). LCMS (+ESI) m/z 342.1 $[M+H]^+$.

Step 5: Preparation of (S)-3-chloro-N-(3,3-dimethyl-1-(methylamino)-1-oxobutan-2-yl)-8-methyl-6,7,8,9-tetrahydro-5H-imidazo[1,5-a][1,4]diazepine-1-carboxamide (Compound 598). To a solution of Compound 597 (53 mg, 0.16 mmol) in tetrahydrofuran (2 mL) was added acetic acid (8.9 mL, 0.16 mmol) and a 37 weight % aqueous solution of formaldehyde (116 μL, 1.6 mmol). After stirring for 5 minutes, sodium triacetoxyborohydride was added as a solid (66 mg, 0.31 mmol). The mixture was stirred for an additional hour then was concentrated under reduced pressure. The residue was dissolved in dichloromethane, was washed with a saturated aqueous sodium bicarbonate solution, was dried ($Na_2SO_4$), and was concentrated under reduced pressure to a yellow solid. The solid was dissolved in methanol and loaded onto an ion exchange column (Phenomenex®, SCX). The column was washed with methanol, and the title compound was collected with a solution of 2N ammonia in methanol. After concentration of the methanol solution, a pale yellow solid of compound 598 was obtained (43 mg, 78% yield). $^1$H-NMR (400 MHz, $(CD_3)_2SO$) δ: 0.90 (s, 9H), 1.74 (m, 2H), 2.16 (s, 3H), 2.58 (d, 3H), 2.89 (t, 2H), 4.13 (m, 2H), 4.20 (m, 2H), 4.26 (d, 1H), 7.46 (d, 1H), 8.11 (q, 1H). LCMS (+ESI) m/z 356.1 $[M+H]^+$.

Example 66

Preparation of N-(3-fluoro-3-methyl-1-(methylamino)-1-oxobutan-2-yl)-3-phenyl-6,7,8,9-tetrahydro-5H-imidazo[1,5-a][1,4]diazepine-1-carboxamide (Compound 604) and 2-amino-3-fluoro-N,3-dimethylbutanamide hydrochloride (Compound 605)

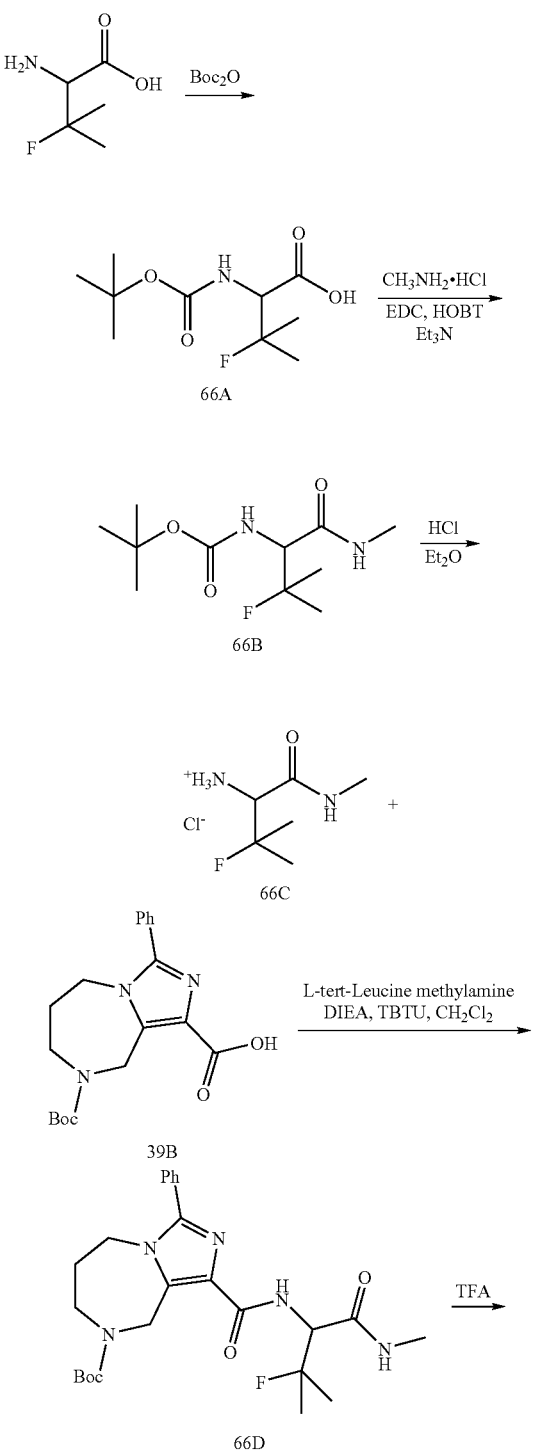

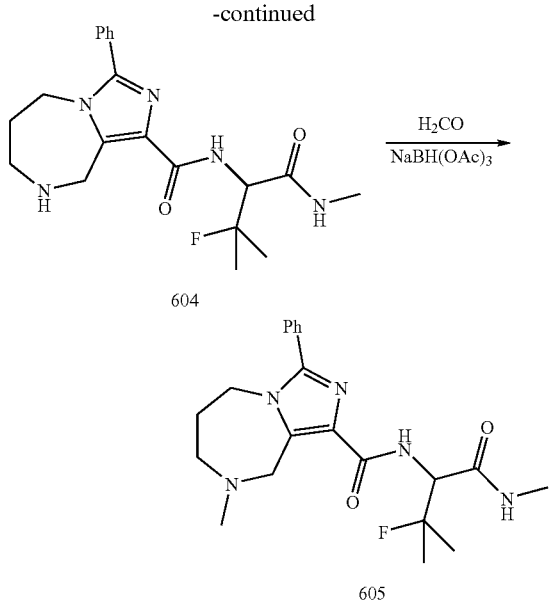

Step 1: Preparation of 2-(tert-butoxycarbonylamino)-3-fluoro-3-methylbutanoic acid (66A). 2-Amino-3-fluoro-3-methylbutanoic acid (211 mg, 1.56 mmol) was suspended in methanol (5 mL) and treated with triethylamine (0.48 mL, 3.44 mmol) and di-tert-butyl dicarbonate (0.44 mL, 1.87 mmol). The reaction mixture was stirred for 18 hours then was concentrated under reduced pressure. The residue was dissolved in water, and the aqueous solution was brought to pH 2-3 with 1N aqueous hydrochloric acid solution and was extracted with 3:1 chloroform/isopropanol. The organic layers were combined, dried (Na$_2$SO$_4$), and concentrated under reduced pressure to a colorless oil. The oil was dried in a 40° C. vacuum oven overnight and crystallized into a white solid 66A (290 mg, 79%). $^1$H-NMR (400 MHz, (CD$_3$)$_2$SO) δ: 1.34 (d, 3H), 1.38 (s, 9H), 1.40 (d, 3H), 4.14 (dd, 1H), 7.09 (d, 1H), 12.80 (broad s, 1H).

Step 2: Preparation of tert-butyl 3-fluoro-3-methyl-1-(methylamino)-1-oxobutan-2-ylcarbamate (66B). Intermediate 66A (290 mg, 1.23 mmol) and methylamine hydrochloride (100 mg, 1.48 mmol) were dissolved in dichloromethane (5 mL) and N,N-diisopropylethylamine (0.65 mL, 3.70 mmol). 1-Hydroxybenzotriazole hydrate (283 mg, 1.85 mmol) and N-(3-dimethylaminopropyl)-N'-ethylcarbodiimide (354 mg, 1.85 mmol) were added, and the solution was stirred for 18 hours. The mixture was diluted additional dichloromethane and washed with saturated aqueous ammonium chloride solution and brine. The organic layer was separated, dried (Na$_2$SO$_4$), and concentrated under reduced pressure to provide intermediate 66B as an off-white solid in quantitative yield. $^1$H-NMR (400 MHz, (CD$_3$)$_2$SO) δ: 1.27 (d, 3H), 1.32 (d, 3H), 1.37 (s, 9H), 2.59 (d, 3H), 4.14 (dd, 1H), 6.72 (d, 1H), 7.93 (q, 1H).

Step 3: Preparation of 2-amino-3-fluoro-N,3-dimethylbutanamide hydrochloride (66C). Intermediate 66B (306 mg, 1.23 mmol) was dissolved in dichloromethane (5 mL) and was treated with 2M hydrochloric acid solution in diethyl ether (6.18 mL, 12.4 mmol). The resulting mixture was stirred for 2 hour then was concentrated under reduced pressure. The oily residue was dried overnight in a 40° C. vacuum oven to provide intermediate 66C as an off-white solid in quantitative yield. $^1$H-NMR (400 MHz, (CD$_3$)$_2$SO) δ: 1.38 (d, 3H), 1.43 (d, 3H), 2.67 (d, 3H), 3.97 (d, 1H), 8.51 (broad s, 3H), 8.76 (q, 1H).

Step 4: Preparation of tert-butyl 1-(3-fluoro-3-methyl-1-(methylamino)-1-oxobutan-2-ylcarbamoyl)-3-phenyl-6,7-dihydro-5H-imidazo[1,5-a][1,4]diazepine-8(9H)-carboxylate (66D). Intermediates 66C (88 mg, 0.43 mmol) and 39B (154 mg, 0.43 mmol) were dissolved in dichloromethane (4 mL) and N,N-diisopropylethylamine (0.15 mL, 0.86 mmol). To the solution was added TBTU (208 mg, 0.65 mmol), and the resulting mixture was stirred for 1 hour at ambient temperature. The reaction mixture was diluted with additional dichloromethane and was washed with saturated aqueous sodium bicarbonate solution, dried over Na$_2$SO$_4$, and absorbed onto silica gel for purification by flash chromatography. The column was eluted from 0-5% methanol in dichloromethane. Clean fractions were collected, concentrated under reduced pressure, and dried in a 40° C. vacuum oven overnight to provide 66D as a yellow solid (180 mg, 86%). $^1$H-NMR (400 MHz, (CD$_3$)$_2$SO) δ: 1.25 (d, 3H), 1.27 (s, 9H), 1.38 (d, 3H), 1.85 (m, 2H), 2.61 (d, 3H), 3.63 (dm, 2H), 4.17 (m, 2H), 4.65 (dd, 1H), 5.02 (m, 2H), 7.53 (m, 5H), 7.78 (d, 1H), 8.24 (m, 1H). LCMS (+ESI) m/z 488.1 [M+H]$^+$.

Step 5: Preparation of N-(3-fluoro-3-methyl-1-(methylamino)-1-oxobutan-2-yl)-3-phenyl-6,7,8,9-tetrahydro-5H-imidazo[1,5-a][1,4]diazepine-1-carboxamide (Compound 604). To 66D (178 mg, 0.37 mmol) in dichloromethane (2 mL) was added trifluoroacetic acid (1.12 mL, 14.60 mmol). After 1 hour of stirring, the solution was concentrated under reduced pressure. The residue was brought to pH 8 with a saturated aqueous solution of sodium bicarbonate. The aqueous solution was extracted with dichloromethane. The combined organic layers were dried over Na$_2$SO$_4$ and concentrated under reduced pressure to yield Compound 604 as a white solid (117 mg, 83%). $^1$H-NMR (400 MHz, (CD$_3$)$_2$SO) δ: 1.31 (d, 3H), 1.37 (d, 3H), 1.71 (m, 2H), 2.61 (d, 3H), 3.00 (m, 2H), 4.13 (m, 2H), 4.28 (m, 2H), 4.64 (dd, 1H), 7.52 (m, 5H), 7.81 (d, 1H), 8.24 (q, 1H). LCMS (+ESI) m/z 388.1 [M+H]$^+$.

Step 6: Preparation of N-(3-fluoro-3-methyl-1-(methylamino)-1-oxobutan-2-yl)-8-methyl-3-phenyl-6,7,8,9-tetrahydro-5H-imidazo[1,5-a][1,4]diazepine-1-carboxamide (Compound 605). To a solution of Compound 604 (80 mg, 0.21 mmol) in tetrahydrofuran (2 mL) was added acetic acid (12 µL, 0.21 mmol) and a 37 weight % aqueous solution of formaldehyde (154 uL, 2.1 mmol). After stirring for 5 minutes, sodium triacetoxyborohydride (88 mg, 0.41 mmol) was added as a solid. The mixture was stirred for an additional hour then was concentrated under reduced pressure. The residue was dissolved in dichloromethane, washed with a saturated aqueous sodium bicarbonate solution, dried over Na$_2$SO$_4$, and was concentrated under reduced pressure. The resulting solid was dissolved in methanol and loaded onto an ion exchange column (Phenomenex®, SCX). The column was washed with methanol, and the title compound was collected with a solution of 2N ammonia in methanol. After concentration of the methanol solution, Compound 605 was collected as a white solid (76 mg, 92%). $^1$H-NMR (400 MHz, (CD$_3$)$_2$SO) δ: 1.31 (d, 3H), 1.36 (d, 3H), 1.77 (m, 2H), 2.25 (s, 3H), 2.61 (d, 3H), 2.91 (m, 2H), 4.13 (m, 2H), 4.27 (m, 2H), 4.64 (dd, 1H), 7.53 (m, 5H), 7.83 (d, 1H), 8.24 (q, 1H). LCMS (+ESI) m/z 402.1 [M+H]$^+$.

Compounds 606 and 607 were prepared in the same manner as described above for 604 and 605 using (S)-2-(tert-butoxycarbonylamino)-3-hydroxy-3-methylbutanoic acid in place of 66A.

TABLE I, below shows the structures of compounds 1-607.

TABLE I

| Cmpd No. | Structure | Chemical Name | m/z | Example No. |
|---|---|---|---|---|
| 1 | 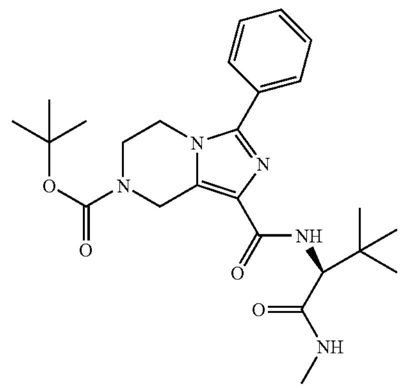 [SMILES: CNC(=O)[C@@H](NC(=O)c1nc(-c2ccccc2)n2c1CN(C(=O)OC(C)(C)C)CC2)C(C)(C)C] | (S)-tert-butyl 1-(3,3-dimethyl-1-(methylamino)-1-oxobutan-2-ylcarbamoyl)-3-phenyl-5,6-dihydroimidazo[1,5-a]pyrazine-7(8H)-carboxylate | 470.5 | 1 |
| 2 | 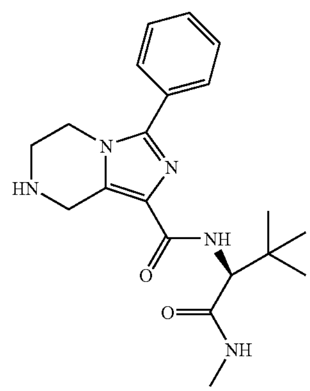 [SMILES: CNC(=O)[C@@H](NC(=O)c1nc(-c2ccccc2)n2c1CNCC2)C(C)(C)C] | (S)-N-(3,3-dimethyl-1-(methylamino)-1-oxobutan-2-yl)-3-phenyl-5,6,7,8-tetrahydroimidazo[1,5-a]pyrazine-1-carboxamide | 370.3 | 2 |
| 3 | 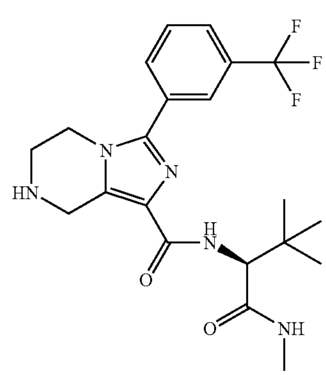 [SMILES: CNC(=O)[C@@H](NC(=O)c1nc(-c2cccc(C(F)(F)F)c2)n2c1CNCC2)C(C)(C)C] | (S)-N-(3,3-dimethyl-1-(methylamino)-1-oxobutan-2-yl)-3-(3-(trifluoromethyl)phenyl)-5,6,7,8-tetrahydroimidazo[1,5-a]pyrazin-1-carboxamide | 438.2 | 2 |
| 4 | 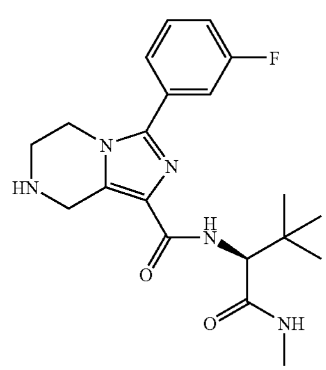 [SMILES: CNC(=O)[C@@H](NC(=O)c1nc(-c2cccc(F)c2)n2c1CNCC2)C(C)(C)C] | (S)-N-(3,3-dimethyl-1-(methylamino)-1-oxobutan-2-yl)-3-(3-fluorophenyl)-5,6,7,8-tetrahydroimidazo[1,5-a]pyrazin-1-carboxamide | 388.2 | 2 |

TABLE I-continued

| Cmpd No. | Structure | Chemical Name | m/z | Example No. |
|---|---|---|---|---|
| 5 | 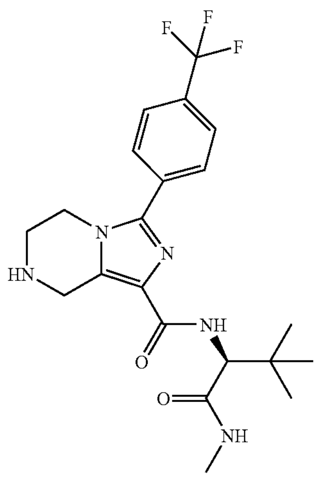 [SMILES: CNC(=O)[C@@H](NC(=O)c1nc(-c2ccc(C(F)(F)F)cc2)n2c1CNCC2)C(C)(C)C] | (S)-N-(3,3-dimethyl-1-(methylamino)-1-oxobutan-2-yl)-3-(4-(trifluoromethyl)phenyl)-5,6,7,8-tetrahydroimidazo[1,5-a]pyrazin-1-carboxamide | 438.3 | 2 |
| 6 | 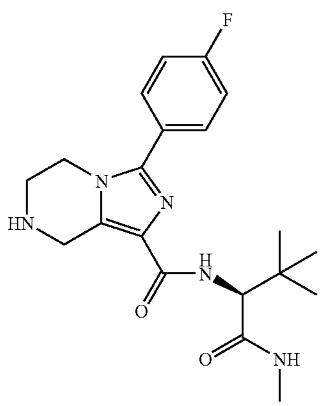 [SMILES: CNC(=O)[C@@H](NC(=O)c1nc(-c2ccc(F)cc2)n2c1CNCC2)C(C)(C)C] | (S)-N-(3,3-dimethyl-1-(methylamino)-1-oxobutan-2-yl)-3-(4-fluorophenyl)-5,6,7,8-tetrahydroimidazo[1,5-a]pyrazine-1-carboxamide | 388.2 | 2 |
| 7 | 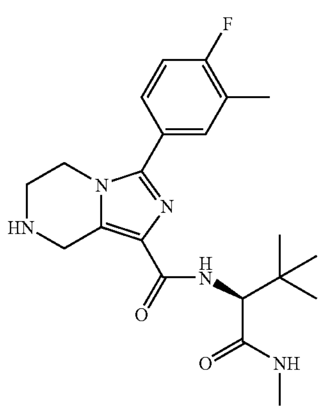 [SMILES: CNC(=O)[C@@H](NC(=O)c1nc(-c2ccc(F)c(C)c2)n2c1CNCC2)C(C)(C)C] | (S)-N-(3,3-dimethyl-1-(methylamino)-1-oxobutan-2-yl)-3-(4-fluoro-3-methylphenyl)-5,6,7,8-tetrahydroimidazo[1,5-a]pyrazin-1-carboxamide | 402.2 | 2 |

TABLE I-continued

| Cmpd No. | Structure | Chemical Name | m/z | Example No. |
|---|---|---|---|---|
| 8 | 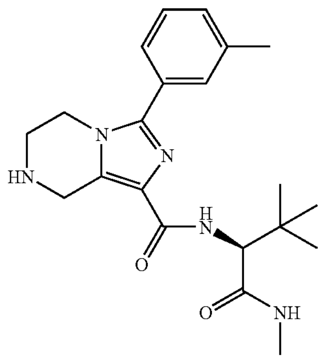 [SMILES: CNC(=O)[C@@H](NC(=O)c1nc(-c2cccc(C)c2)n2c1CNCC2)C(C)(C)C] | (S)-N-(3,3-dimethyl-1-(methylamino)-1-oxobutan-2-yl)-3-m-tolyl-5,6,7,8-tetrahydroimidazo[1,5-a]pyrazine-1-carboxamide | 384.3 | 2 |
| 9 | 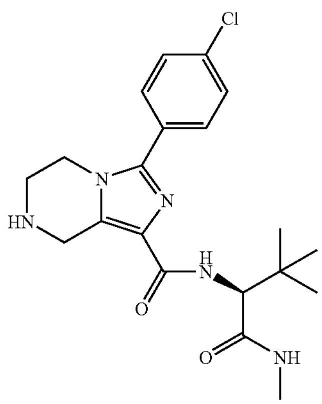 | (S)-3-(4-chlorophenyl)-N-(3,3-dimethyl-1-(methylamino)-1-oxobutan-2-yl)-5,6,7,8-tetrahydroimidazo[1,5-a]pyrazin-1-carboxamide | 404.2 | 2 |
| 10 | 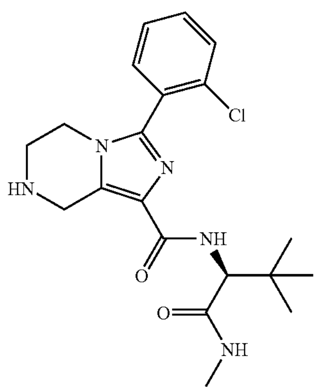 [SMILES: CNC(=O)[C@@H](NC(=O)c1nc(-c2ccccc2Cl)n2c1CNCC2)C(C)(C)C] | (S)-3-(2-chlorophenyl)-N-(3,3-dimethyl-1-(methylamino)-1-oxobutan-2-yl)-5,6,7,8-tetrahydroimidazo[1,5-a]pyrazine-1-carboxamide | 404.2 | 2 |
| 11 | 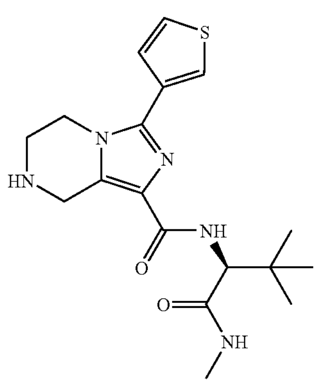 [SMILES: CNC(=O)[C@@H](NC(=O)c1nc(-c2ccsc2)n2c1CNCC2)C(C)(C)C] | (S)-N-(3,3-dimethyl-1-(methylamino)-1-oxobutan-2-yl)-3-(thiophen-3-yl)-5,6,7,8-tetrahydroimidazo[1,5-a]pyrazine-1-carboxamide | 376.2 | 2 |

TABLE I-continued

| Cmpd No. | Structure | Chemical Name | m/z | Example No. |
|---|---|---|---|---|
| 12 | 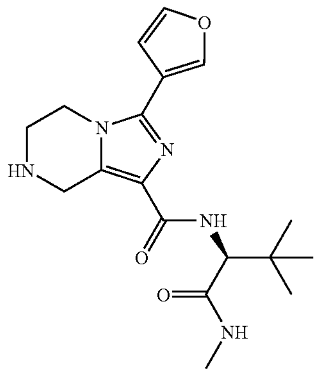 [SMILES: CNC(=O)[C@@H](NC(=O)c1nc(-c2ccoc2)n2c1CNCC2)C(C)(C)C] | (S)-N-(3,3-dimethyl-1-(methylamino)-1-oxobutan-2-yl)-3-(furan-3-yl)-5,6,7,8-tetrahydroimidazo[1,5-a]pyrazine-1-carboxamide | 360.2 | 2 |
| 13 | 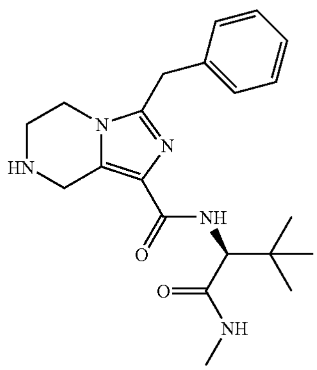 [SMILES: CNC(=O)[C@@H](NC(=O)c1nc(Cc2ccccc2)n2c1CNCC2)C(C)(C)C] | (S)-3-benzyl-N-(3,3-dimethyl-1-(methylamino)-1-oxobutan-2-yl)-5,6,7,8-tetrahydroimidazo[1,5-a]pyrazine-1-carboxamide | 384.2 | 2 |
| 14 | 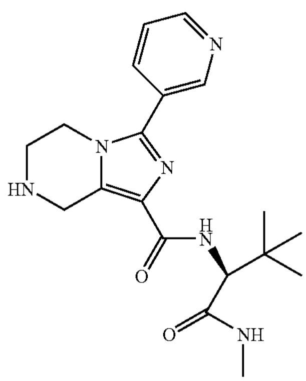 [SMILES: CNC(=O)[C@@H](NC(=O)c1nc(-c2cccnc2)n2c1CNCC2)C(C)(C)C] | (S)-N-(3,3-dimethyl-1-(methylamino)-1-oxobutan-2-yl)-3-(pyridin-3-yl)-5,6,7,8-tetrahydroimidazo[1,5-a]pyrazine-1-carboxamide | 371.2 | 2 |
| 15 | 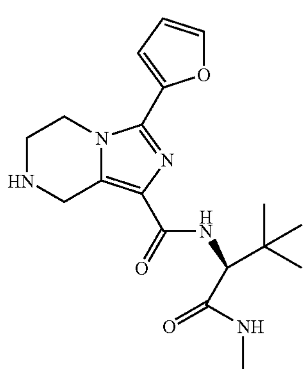 | (S)-N-(3,3-dimethyl-1-(methylamino)-1-oxobutan-2-yl)-3-(furan-2-yl)-5,6,7,8-tetrahydroimidazo[1,5-a]pyrazine-1-carboxamide | 360.3 | 2 |

TABLE I-continued

| Cmpd No. | Structure | Chemical Name | m/z | Example No. |
|---|---|---|---|---|
| 16 | 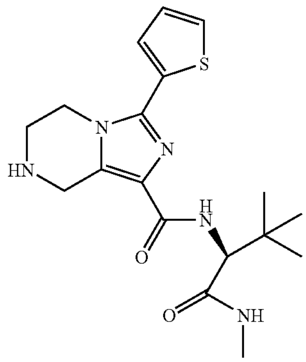 [SMILES: CNC(=O)[C@@H](NC(=O)c1nc(-c2cccs2)n2c1CNCC2)C(C)(C)C] | (S)-N-(3,3-dimethyl-1-(methylamino)-1-oxobutan-2-yl)-3-(thiophen-2-yl)-5,6,7,8-tetrahydroimidazo[1,5-a]pyrazine-1-carboxamide | 376.2 | 2 |
| 17 | 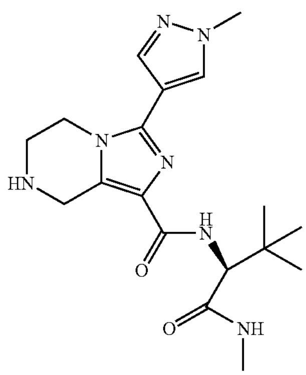 [SMILES: CNC(=O)[C@@H](NC(=O)c1nc(-c2cnn(C)c2)n2c1CNCC2)C(C)(C)C] | (S)-N-(3,3-dimethyl-1-(methylamino)-1-oxobutan-2-yl)-3-(1-methyl-1H-pyrazol-4-yl)-5,6,7,8-tetrahydroimidazo[1,5-a]pyrazine-1-carboxamide | 374.3 | 2 |
| 18 | 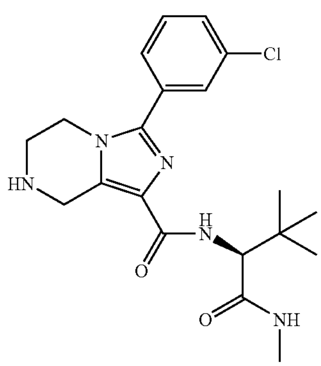 | (S)-3-(3-chlorophenyl)-N-(3,3-dimethyl-1-(methylamino)-1-oxobutan-2-yl)-5,6,7,8-tetrahydroimidazo[1,5-a]pyrazine-1-carboxamide | 404.2 | 2 |
| 19 | 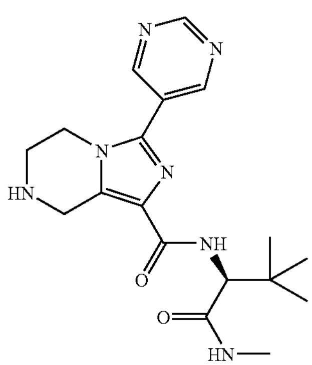 [SMILES: CNC(=O)[C@@H](NC(=O)c1nc(-c2cncnc2)n2c1CNCC2)C(C)(C)C] | (S)-N-(3,3-dimethyl-1-(methylamino)-1-oxobutan-2-yl)-3-(pyrimidin-5-yl)-5,6,7,8-tetrahydroimidazo[1,5-a]pyrazine-1-carboxamide | 372.1 | 2 |

TABLE I-continued

| Cmpd No. | Structure | Chemical Name | m/z | Example No. |
|---|---|---|---|---|
| 20 | 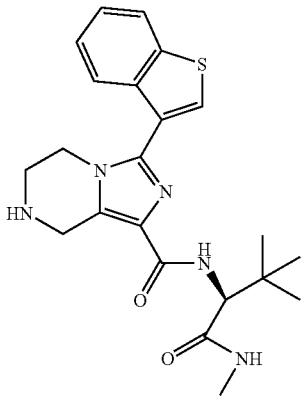 [SMILES: CNC(=O)[C@@H](NC(=O)c1nc(-c2csc3ccccc23)n2c1CNCC2)C(C)(C)C] | (S)-3-(benzo[b]thiophen-3-yl)-N-(3,3-dimethyl-1-(methylamino)-1-oxobutan-2-yl)-5,6,7,8-tetrahydroimidazo[1,5-a]pyrazine-1-carboxamide | 427.1 | 2 |
| 21 | 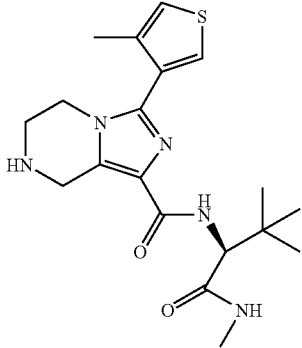 [SMILES: CNC(=O)[C@@H](NC(=O)c1nc(-c2cscc2C)n2c1CNCC2)C(C)(C)C] | (S)-N-(3,3-dimethyl-1-(methylamino)-1-oxobutan-2-yl)-3-(4-methylthiophen-3-yl)-5,6,7,8-tetrahydroimidazo[1,5-a]pyrazine-1-carboxamide | 390.1 | 2 |
| 22 | 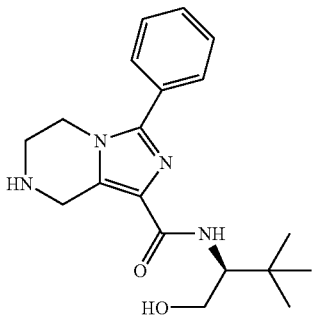 [SMILES: CC(C)(C)[C@@H](CO)NC(=O)c1nc(-c2ccccc2)n2c1CNCC2] | (S)-N-(1-hydroxy-3,3-dimethylbutan-2-yl)-3-phenyl-5,6,7,8-tetrahydroimidazo[1,5-a]pyrazine-1-carboxamide | 343.3 | 2 |
| 23 | 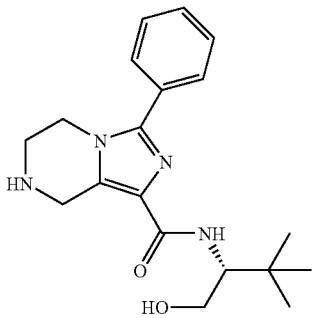 [SMILES: CC(C)(C)[C@H](CO)NC(=O)c1nc(-c2ccccc2)n2c1CNCC2] | (R)-N-(1-hydroxy-3,3-dimethylbutan-2-yl)-3-phenyl-5,6,7,8-tetrahydroimidazo[1,5-a]pyrazine-1-carboxamide | 343.3 | 2 |

TABLE I-continued

| Cmpd No. | Structure | Chemical Name | m/z | Example No. |
|---|---|---|---|---|
| 24 | 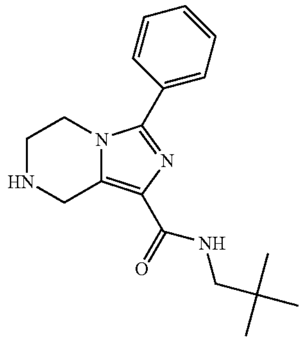 [SMILES: CC(C)(C)CNC(=O)c1nc(-c2ccccc2)n2c1CNCC2] | N-neopentyl-3-phenyl-5,6,7,8-tetrahydroimidazo[1,5-a]pyrazine-1-carboxamide | 313.2 | 2 |
| 25 | 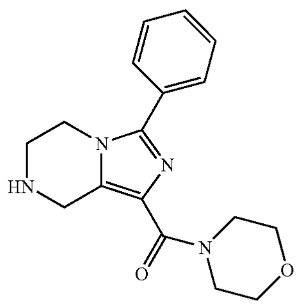 [SMILES: O=C(c1nc(-c2ccccc2)n2c1CNCC2)N1CCOCC1] | morpholino(3-phenyl-5,6,7,8-tetrahydroimidazo[1,5-a]pyrazin-1-yl)methanone | 313.2 | 2 |
| 26 | 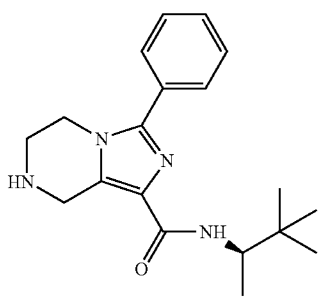 [SMILES: C[C@@H](NC(=O)c1nc(-c2ccccc2)n2c1CNCC2)C(C)(C)C] | (R)-N-(3,3-dimethylbutan-2-yl)-3-phenyl-5,6,7,8-tetrahydroimidazo[1,5-a]pyrazine-1-carboxamide | 327.3 | 2 |
| 27 | 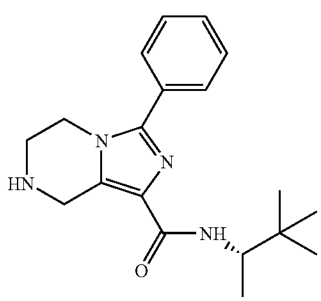 [SMILES: C[C@H](NC(=O)c1nc(-c2ccccc2)n2c1CNCC2)C(C)(C)C] | (S)-N-(3,3-dimethylbutan-2-yl)-3-phenyl-5,6,7,8-tetrahydroimidazo[1,5-a]pyrazine-1-carboxamide | 327.3 | 2 |

TABLE I-continued

| Cmpd No. | Structure | Chemical Name | m/z | Example No. |
|---|---|---|---|---|
| 28 | 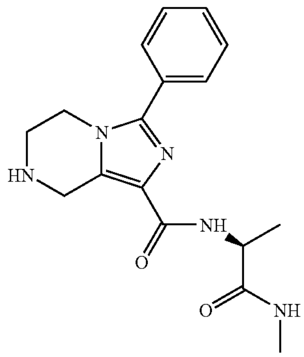 [SMILES: CNC(=O)[C@H](C)NC(=O)c1nc(-c2ccccc2)n2c1CNCC2] | (S)-N-(1-(methylamino)-1-oxopropan-2-yl)-3-phenyl-5,6,7,8-tetrahydroimidazo[1,5-a]pyrazine-1-carboxamide | 328.2 | 2 |
| 29 | 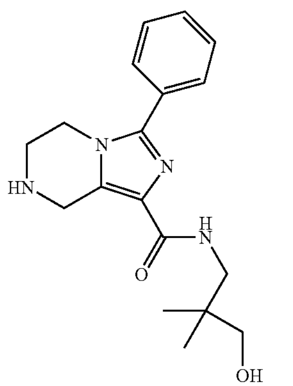 [SMILES: CC(C)(CO)CNC(=O)c1nc(-c2ccccc2)n2c1CNCC2] | N-(3-hydroxy-2,2-dimethylpropyl)-3-phenyl-5,6,7,8-tetrahydroimidazo[1,5-a]pyrazine-1-carboxamide | 329.2 | 2 |
| 30 | 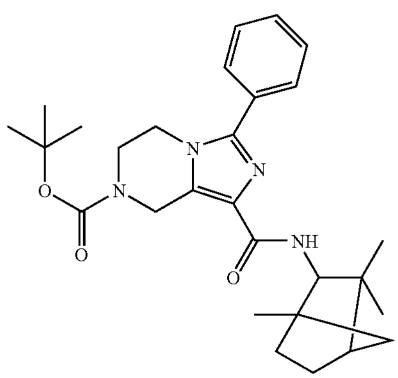 [SMILES: CC(C)(C)OC(=O)N1CCn2c(-c3ccccc3)nc(C(=O)NC3C4(C)CCC(C4)C3(C)C)c2C1] | tert-butyl 3-phenyl-1-(1,3,3-trimethylbicyclo[2.2.1]heptan-2-ylcarbamoyl)-5,6-dihydroimidazo[1,5-a]pyrazine-7(8H)-carboxylate | 479.5 | 3 |
| 31 | 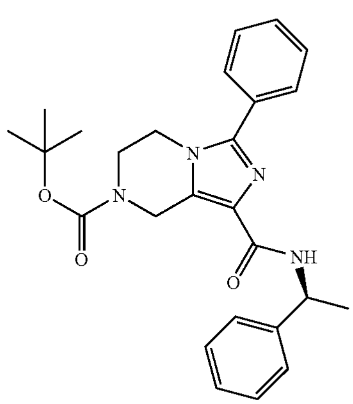 [SMILES: C[C@H](NC(=O)c1nc(-c2ccccc2)n2c1CN(C(=O)OC(C)(C)C)CC2)c1ccccc1] | (S)-tert-butyl 3-phenyl-1-(1-phenylethylcarbamoyl)-5,6-dihydroimidazo[1,5-a]pyrazine-7(8H)-carboxylate | 447.4 | 3 |

TABLE I-continued

| Cmpd No. | Structure | Chemical Name | m/z | Example No. |
|---|---|---|---|---|
| 32 | 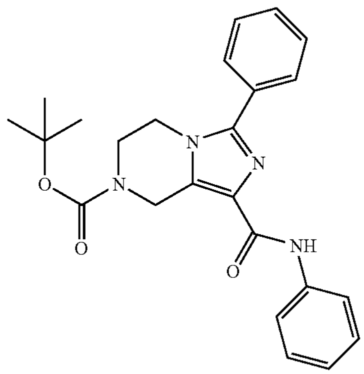 [SMILES: CC(C)(C)OC(=O)N1CCn2c(-c3ccccc3)nc(C(=O)Nc3ccccc3)c2C1] | tert-butyl 3-phenyl-1-(phenylcarbamoyl)-5,6-dihydroimidazo[1,5-a]pyrazine-7(8H)-carboxylate | 419.3 | 3 |
| 33 | 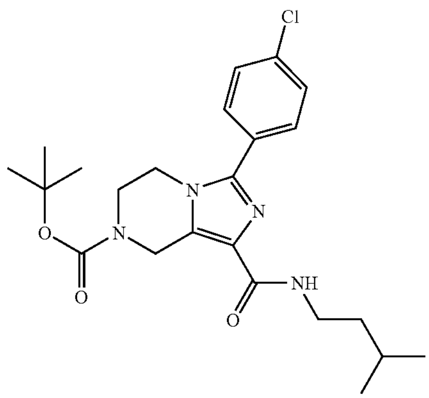 [SMILES: CC(C)CCNC(=O)c1nc(-c2ccc(Cl)cc2)n2c1CN(C(=O)OC(C)(C)C)CC2] | tert-butyl 3-(4-chlorophenyl)-1-(isopentylcarbamoyl)-5,6-dihydroimidazo[1,5-a]pyrazine-7(8H)-carboxylate | 447.4 | 3 |
| 34 | 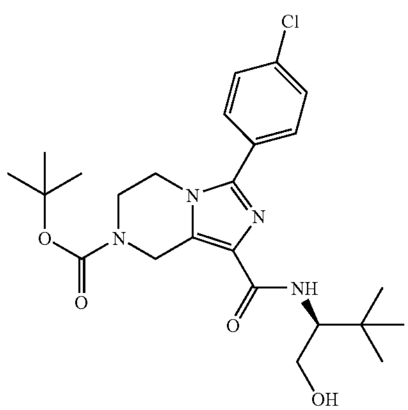 [SMILES: CC(C)(C)OC(=O)N1CCn2c(-c3ccc(Cl)cc3)nc(C(=O)N[C@H](CO)C(C)(C)C)c2C1] | tert-butyl 3-(4-chlorophenyl)-1-(1-hydroxy-3,3-dimethylbutan-2-ylcarbamoyl)-5,6-dihydroimidazo[1,5-a]pyrazine-7(8H)-carboxylate | 477.4 | 3 |
| 35 | 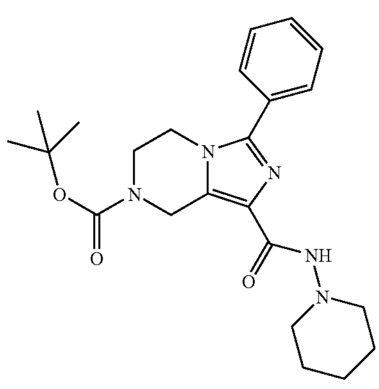 [SMILES: CC(C)(C)OC(=O)N1CCn2c(-c3ccccc3)nc(C(=O)NN3CCCCC3)c2C1] | tert-butyl 3-phenyl-1-(piperidin-1-ylcarbamoyl)-5,6-dihydroimidazo[1,5-a]pyrazine-7(8H)-carboxylate | 426.4 | 3 |

TABLE I-continued

| Cmpd No. | Structure | Chemical Name | m/z | Example No. |
|---|---|---|---|---|
| 36 | 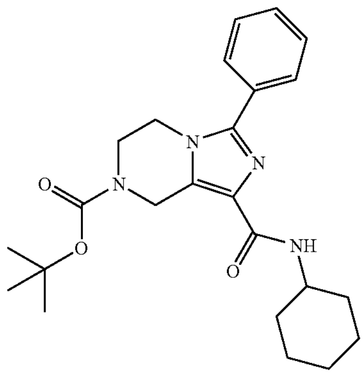 [SMILES: CC(C)(C)OC(=O)N1CCn2c(-c3ccccc3)nc(C(=O)NC3CCCCC3)c2C1] | tert-butyl 1-(cyclohexylcarbamoyl)-3-phenyl-5,6-dihydroimidazo[1,5-a]pyrazine-7(8H)-carboxylate | 425.4 | 3 |
| 37 | 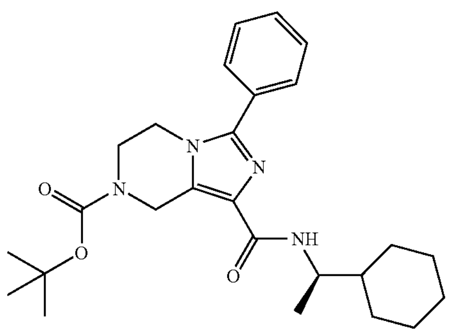 [SMILES: C[C@@H](NC(=O)c1nc(-c2ccccc2)n2c1CN(C(=O)OC(C)(C)C)CC2)C1CCCCC1] | (R)-tert-butyl 1-(1-cyclohexylethylcarbamoyl)-3-phenyl-5,6-dihydroimidazo[1,5-a]pyrazine-7(8H)-carboxylate | 453.4 | 3 |
| 38 | 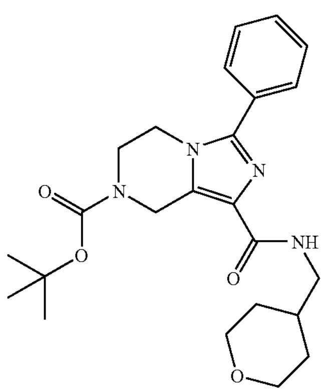 [SMILES: CC(C)(C)OC(=O)N1CCn2c(-c3ccccc3)nc(C(=O)NCC3CCOCC3)c2C1] | tert-butyl 3-phenyl-1-((tetrahydro-2H-pyran-4-yl)methylcarbamoyl)-5,6-dihydroimidazo[1,5-a]pyrazine-7(8H)-carboxylate | 441.3 | 3 |
| 39 | 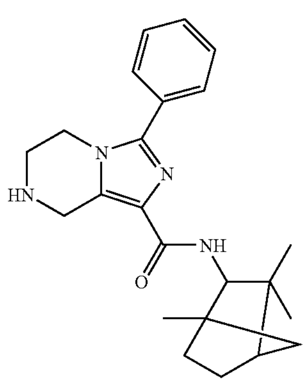 [SMILES: CC12CCC(C1)C(C)(C)C2NC(=O)c1nc(-c2ccccc2)n2c1CNCC2] | 3-phenyl-N-(1,3,3-trimethylbicyclo[2.2.1]heptan-2-yl)-5,6,7,8-tetrahydroimidazo[1,5-a]pyrazine-1-carboxamide | 379.4 | 4 |

TABLE I-continued

| Cmpd No. | Structure | Chemical Name | m/z | Example No. |
|---|---|---|---|---|
| 40 | 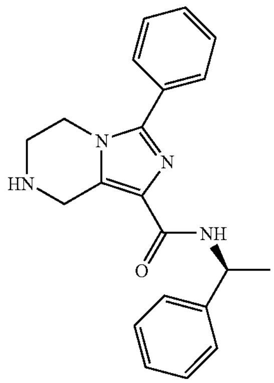 [SMILES: C[C@H](NC(=O)c1nc(-c2ccccc2)n2c1CNCC2)c1ccccc1] | (S)-3-phenyl-N-(1-phenylethyl)-5,6,7,8-tetrahydroimidazo[1,5-a]pyrazine-1-carboxamide | 347.3 | 4 |
| 41 | 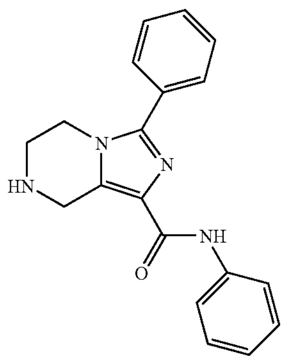 [SMILES: O=C(Nc1ccccc1)c1nc(-c2ccccc2)n2c1CNCC2] | N,3-diphenyl-5,6,7,8-tetrahydroimidazo[1,5-a]pyrazine-1-carboxamide | 319.3 | 4 |
| 42 | 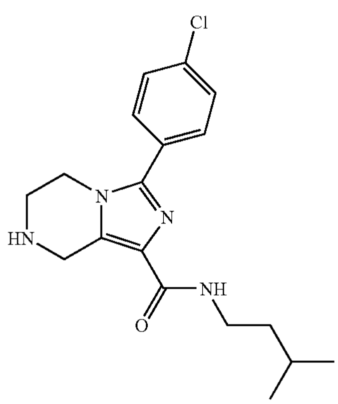 [SMILES: CC(C)CCNC(=O)c1nc(-c2ccc(Cl)cc2)n2c1CNCC2] | 3-(4-chlorophenyl)-N-isopentyl-5,6,7,8-tetrahydroimidazo[1,5-a]pyrazine-1-carboxamide | 347.3 | 4 |
| 43 | 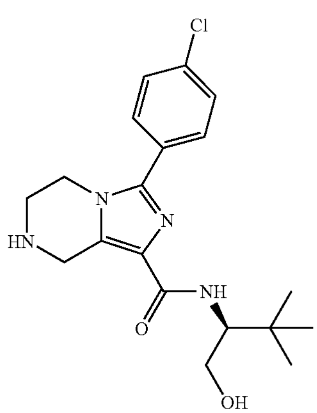 [SMILES: CC(C)(C)[C@@H](CO)NC(=O)c1nc(-c2ccc(Cl)cc2)n2c1CNCC2] | (S)-3-(4-chlorophenyl)-N-(1-hydroxy-3,3-dimethylbutan-2-yl)-5,6,7,8-tetrahydroimidazo[1,5-a]pyrazine-1-carboxamide | 377.3 | 4 |

TABLE I-continued

| Cmpd No. | Structure | Chemical Name | m/z | Example No. |
|---|---|---|---|---|
| 44 | 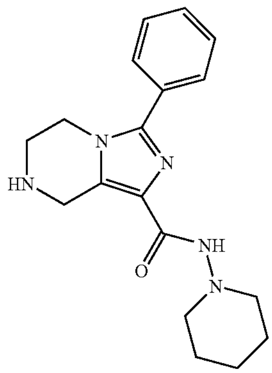 [SMILES: O=C(NN1CCCCC1)c1nc(-c2ccccc2)n2c1CNCC2] | 3-phenyl-N-(piperidin-1-yl)-5,6,7,8-tetrahydroimidazo[1,5-a]pyrazine-1-carboxamide | 326.3 | 4 |
| 45 | 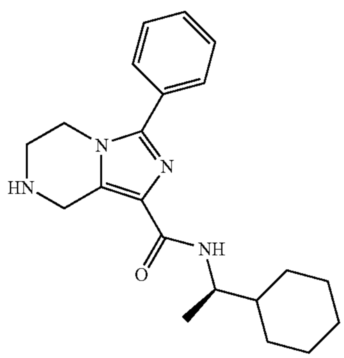 [SMILES: C[C@@H](NC(=O)c1nc(-c2ccccc2)n2c1CNCC2)C1CCCCC1] | (R)-N-(1-cxyclohexylethyl)-3-phenyl-5,6,7,8-tetrahydroimidazo[1,5-a]pyrazine-1-carboxamide | 353.3 | 4 |
| 46 | 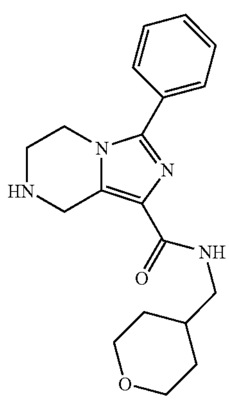 [SMILES: O=C(NCC1CCOCC1)c1nc(-c2ccccc2)n2c1CNCC2] | 3-phenyl-N-((tetrahydro-2H-pyran-4-yl)methyl)-5,6,7,8-tetrahydroimidazo[1,5-a]pyrazine-1-carboxamide | 341.3 | 4 |
| 47 | 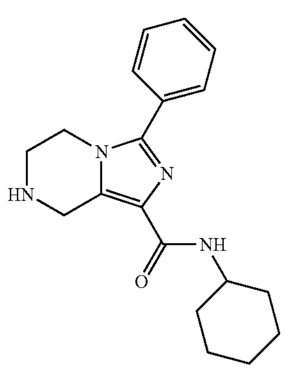 [SMILES: O=C(NC1CCCCC1)c1nc(-c2ccccc2)n2c1CNCC2] | N-cyclohexyl-3-phenyl-5,6,7,8-tetrahydroimidazo[1,5-a]pyrazine-1-carboxamide | 325.3 | 4 |

TABLE I-continued

| Cmpd No. | Structure | Chemical Name | m/z | Example No. |
|---|---|---|---|---|
| 48 | 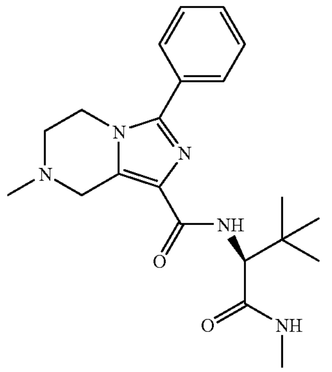 [SMILES: CNC(=O)[C@@H](NC(=O)c1nc(-c2ccccc2)n2c1CN(C)CC2)C(C)(C)C] | (S)-N-(3,3-dimethyl-1-(methylamino)-1-oxobutan-2-yl)-7-methyl-3-phenyl-5,6,7,8-tetrahydroimidazo[1,5-a]pyrazine-1-carboxamide | 384.2 | 5 |
| 49 | 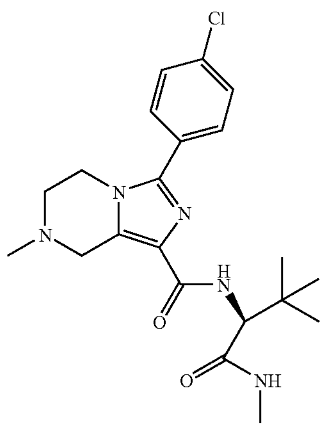 [SMILES: CNC(=O)[C@@H](NC(=O)c1nc(-c2ccc(Cl)cc2)n2c1CN(C)CC2)C(C)(C)C] | (S)-3-(4-chlorophenyl)-N-(3,3-dimethyl-1-(methylamino)-1-oxobutan-2-yl)-7-methyl-5,6,7,8-tetrahydroimidazo[1,5-a]pyrazine-1-carboxamide | 418.3 | 5 |
| 50 | 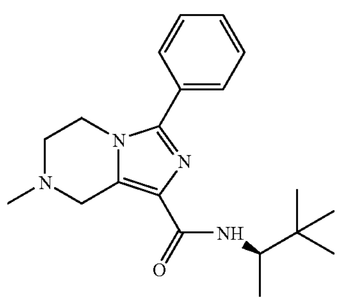 [SMILES: C[C@@H](NC(=O)c1nc(-c2ccccc2)n2c1CN(C)CC2)C(C)(C)C] | (R)-N-(3,3-dimethylbutan-2-yl)-7-methyl-3-phenyl-5,6,7,8-tetrahydroimidazo[1,5-a]pyrazine-1-carboxamide | 341.3 | 5 |
| 51 | 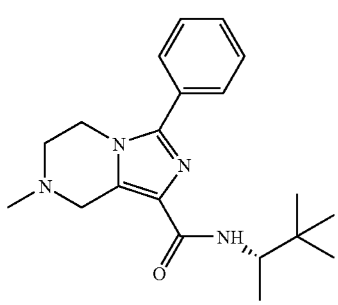 [SMILES: C[C@H](NC(=O)c1nc(-c2ccccc2)n2c1CN(C)CC2)C(C)(C)C] | (S)-N-(3,3-dimethylbutan-2-yl)-7-methyl-3-phenyl-5,6,7,8-tetrahydroimidazo[1,5-a]pyrazine-1-carboxamide | 341.3 | 5 |

TABLE I-continued

| Cmpd No. | Structure | Chemical Name | m/z | Example No. |
|---|---|---|---|---|
| 52 | 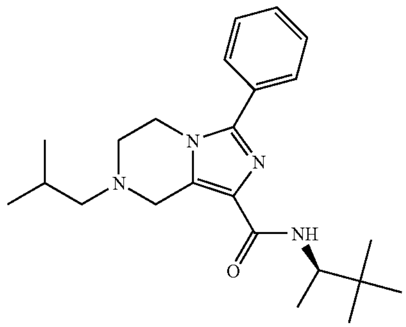 [SMILES: CC(C)CN1CCn2c(-c3ccccc3)nc(C(=O)N[C@H](C)C(C)(C)C)c2C1] | (R)-N-(3,3-dimethylbutan-2-yl)-7-isobutyl-3-phenyl-5,6,7,8-tetrahydrimidazo[1,5-a]pyrazine-1-carboxamide | 383.3 | 5 |
| 53 | 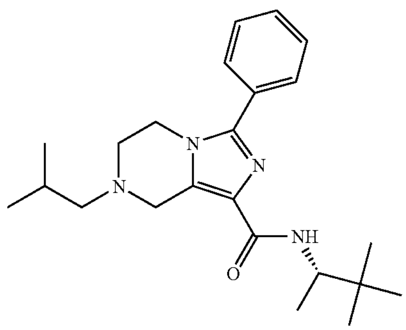 [SMILES: CC(C)CN1CCn2c(-c3ccccc3)nc(C(=O)N[C@@H](C)C(C)(C)C)c2C1] | (S)-N-(3,3-dimethylbutan-2-yl)-7-isobutyl-3-phenyl-5,6,7,8-tetrahydroimidazo[1,5-a]pyrazine-1-carboxamide | 383.3 | 5 |
| 54 | 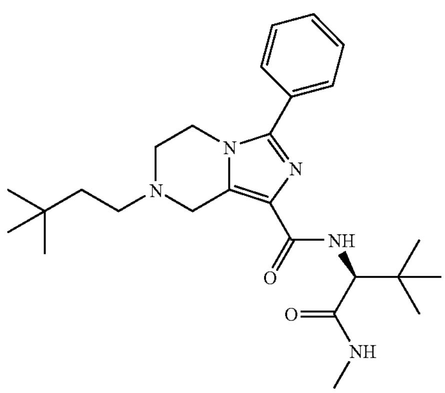 [SMILES: CNC(=O)[C@@H](NC(=O)c1nc(-c2ccccc2)n2c1CN(CCC(C)(C)C)CC2)C(C)(C)C] | (S)-N-(3,3-dimethyl-1-(methylamino)-1-oxobutan-2-yl)-7-(3,3-dimethylbutyl)-3-phenyl-5,6,7,8-tetrahydroimidazo[1,5-a]pyrazine-1-carboxamide | 454.0 | 5 |
| 55 | 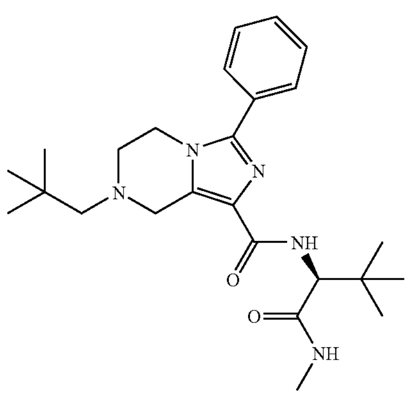 [SMILES: CNC(=O)[C@@H](NC(=O)c1nc(-c2ccccc2)n2c1CN(CC(C)(C)C)CC2)C(C)(C)C] | (S)-N-(3,3-dimethyl-1-(methylamino)-1-oxobutan-2-yl)-7-neopentyl-3-phenyl-5,6,7,8-tetrahydrimidazo[1,5-a]pyrazine-1-carboxamide | 440.5 | 5 |

TABLE I-continued

| Cmpd No. | Structure | Chemical Name | m/z | Example No. |
|---|---|---|---|---|
| 56 | 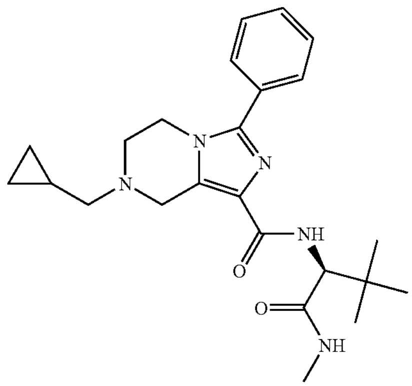 [SMILES: CNC(=O)[C@@H](NC(=O)c1nc(-c2ccccc2)n2c1CN(CC1CC1)CC2)C(C)(C)C] | (S)-7-(cyclopropylmethyl)-N-(3,3-dimethyl-1-(methylamino)-1-oxobutan-2-yl)-3-phenyl-5,6,7,8-tetrahydroimidazo[1,5-a]pyrazine-1-carboxamide | 424.3 | 5 |
| 57 | 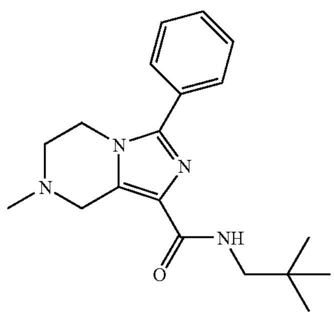 [SMILES: CN1CCn2c(-c3ccccc3)nc(C(=O)NCC(C)(C)C)c2C1] | 7-methyl-N-neopentyl-3-phenyl-5,6,7,8-tetrahydroimidazo[1,5-a]pyrazine-1-carboxamide | 327.3 | 5 |
| 58 | 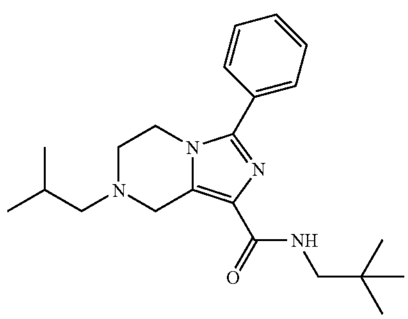 [SMILES: CC(C)CN1CCn2c(-c3ccccc3)nc(C(=O)NCC(C)(C)C)c2C1] | 7-isobutyl-N-neopentyl-3-phenyl-5,6,7,8-tetrahydroimidazo[1,5-a]pyrazine-1-carboxamide | 369.4 | 5 |
| 59 | 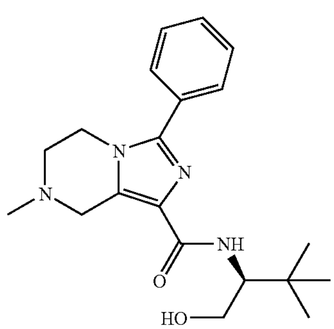 [SMILES: CN1CCn2c(-c3ccccc3)nc(C(=O)N[C@H](CO)C(C)(C)C)c2C1] | (S)-N-(1-hydroxy-3,3-dimethylbutan-2-yl)-7-methyl-3-phenyl-5,6,7,8-tetrahydroimidazo[1,5-a]pyrazine-1-carboxamide | 357.3 | 5 |

TABLE I-continued

| Cmpd No. | Structure | Chemical Name | m/z | Example No. |
|---|---|---|---|---|
| 60 | 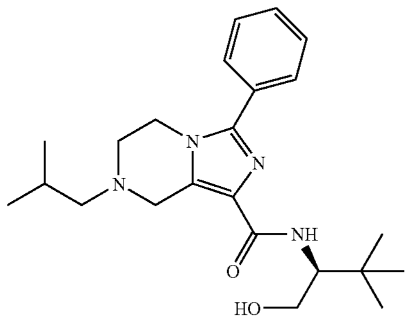 [SMILES: CC(C)CN1CCn2c(-c3ccccc3)nc(C(=O)N[C@H](CO)C(C)(C)C)c2C1] | (S)-N-(1-hydroxy-3,3-dimethylbutan-2-yl)-7-isobutyl-3-phenyl-5,6,7,8-tetrahydroimidazo[1,5-a]pyrazine-1-carboxamide | 399.3 | 5 |
| 61 | 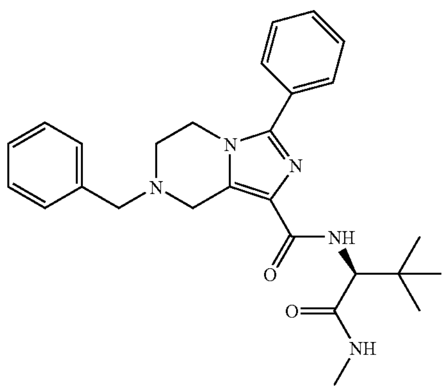 [SMILES: CNC(=O)[C@@H](NC(=O)c1nc(-c2ccccc2)n2c1CN(Cc1ccccc1)CC2)C(C)(C)C] | (S)-7-benzyl-N-(3,3-dimethyl-1-(methylamino)-1-oxobutan-2-yl)-3-phenyl-5,6,7,8-tetrahydroimidazo[1,5-a]pyrazine-1-carboxamide | 460.3 | 5 |
| 62 | 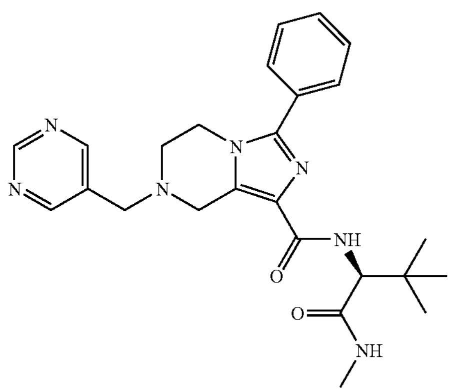 [SMILES: CNC(=O)[C@@H](NC(=O)c1nc(-c2ccccc2)n2c1CN(Cc1cncnc1)CC2)C(C)(C)C] | (S)-N-(3,3-dimethyl-1-(methylamino)-1-oxobutan-2-yl)-3-phenyl-7-(pyrimidin-5-ylmethyl)-5,6,7,8-tetrahydroimidazo[1,5-a]pyrazine-1-carboxamide | 462.3 | 5 |
| 63 | 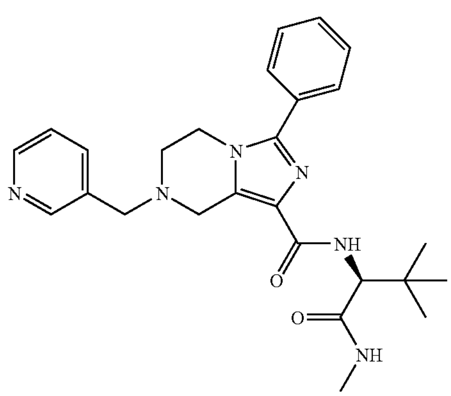 | (S)-N-(3,3-dimethyl-1-(methylamino)-1-oxobutan-2-yl)-3-phenyl-7-(pyridin-3-ylmethyl)-5,6,7,8-tetrahydroimidazo[1,5-a]pyrazine-1-carboxamide | 461.3 | 5 |

TABLE I-continued

| Cmpd No. | Structure | Chemical Name | m/z | Example No. |
|---|---|---|---|---|
| 64 | 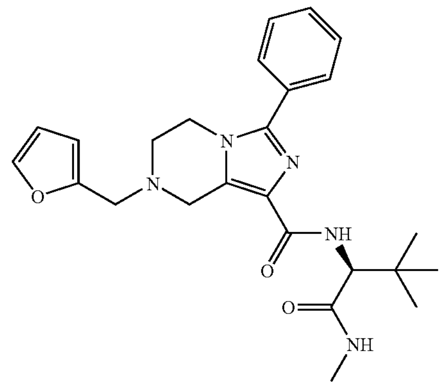 [SMILES: CNC(=O)[C@@H](NC(=O)c1nc(-c2ccccc2)n2c1CN(Cc1ccco1)CC2)C(C)(C)C] | (S)-N-(3,3-dimethyl-1-(methylamino)-1-oxobutan-2-yl)-7-(furan-2-ylmethyl)-3-phenyl-5,6,7,8-tetrahydroimidazo[1,5-a]pyrazine-1-carboxamide | 450.2 | 5 |
| 65 | 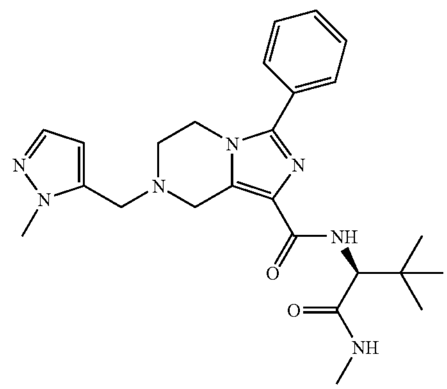 [SMILES: CNC(=O)[C@@H](NC(=O)c1nc(-c2ccccc2)n2c1CN(Cc1ccnn1C)CC2)C(C)(C)C] | (S)-N-(3,3-dimethyl-1-(methylamino)-1-oxobutan-2-yl)-7-((1-methyl-1H-pyrazol-5-yl)methyl)-3-phenyl-5,6,7,8-tetrahydroimidazo[1,5-a]pyrazine-1-carboxamide | 463.3 | 5 |
| 66 | 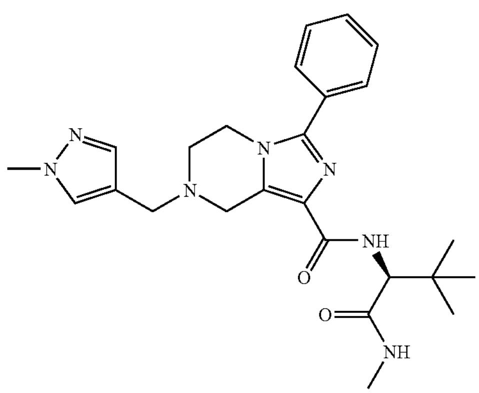 [SMILES: CNC(=O)[C@@H](NC(=O)c1nc(-c2ccccc2)n2c1CN(Cc1cnn(C)c1)CC2)C(C)(C)C] | (S)-N-(3,3-dimethyl-1-(methylamino)-1-oxobutan-2-yl)-7-((1-methyl-1H-pyrazol-4-yl)methyl)-3-phenyl-5,6,7,8-tetrahydroimidazo[1,5-a]pyrazine-1-carboxamide | 464.3 | 5 |
| 67 | 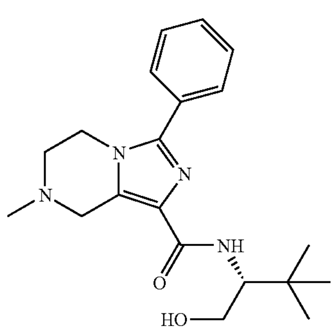 [SMILES: CN1CCn2c(-c3ccccc3)nc(C(=O)N[C@@H](CO)C(C)(C)C)c2C1] | (R)-N-(1-hydroxy-3,3-dimethylbutan-2-yl)-7-methyl-3-phenyl-5,6,7,8-tetrahydroimidazo[1,5-a]pyrazine-1-carboxamide | 357.2 | 5 |

TABLE I-continued

| Cmpd No. | Structure | Chemical Name | m/z | Example No. |
|---|---|---|---|---|
| 68 | 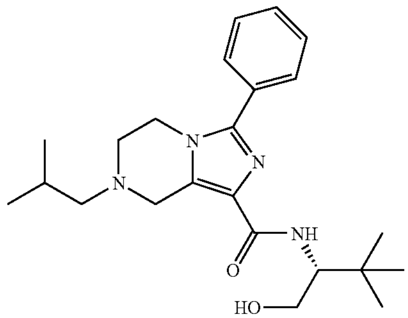 [SMILES: CC(C)CN1CCn2c(-c3ccccc3)nc(C(=O)N[C@@H](CO)C(C)(C)C)c2C1] | (R)-N-(1-hydroxy-3,3-dimethylbutan-2-yl)-7-isobutyl-3-phenyl-5,6,7,8-tetrahydroimidazo[1,5-a]pyrazine-1-carboxamide | 399.2 | 5 |
| 69 | 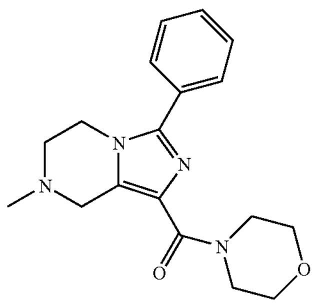 [SMILES: CN1CCn2c(-c3ccccc3)nc(C(=O)N3CCOCC3)c2C1] | (7-methyl-3-phenyl-5,6,7,8-tetrahydroimidazo[1,5-a]pyrazin-1-yl)(morpholino)methanone | 327.2 | 5 |
| 70 | 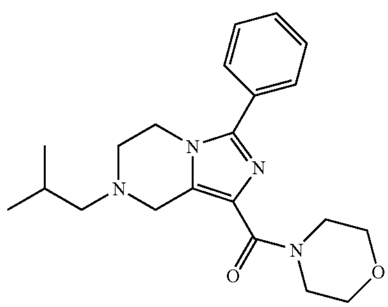 [SMILES: CC(C)CN1CCn2c(-c3ccccc3)nc(C(=O)N3CCOCC3)c2C1] | (7-isobutyl-3-phenyl-5,6,7,8-tetrahydroimidazo[1,5-a]pyrazin-1-yl)(morpholino)methanone | 369.2 | 5 |
| 71 | 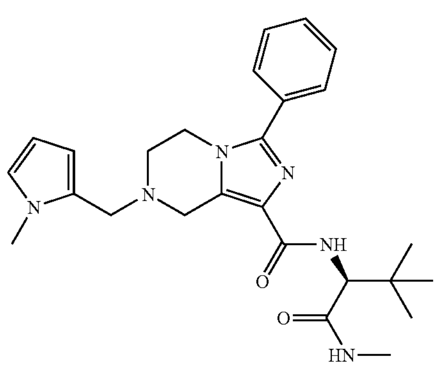 [SMILES: CNC(=O)[C@@H](NC(=O)c1nc(-c2ccccc2)n2c1CN(Cc1cccn1C)CC2)C(C)(C)C] | (S)-N-(3,3-dimethyl-1-(methylamino)-1-oxobutan-2-yl)-7-((1-methyl-1H-pyrrol-2-yl)methyl)-3-phenyl-5,6,7,8-tetrahydroimidazo[1,5-a]pyrazine-1-carboxamide | 463.3 | 5 |

TABLE I-continued

| Cmpd No. | Structure | Chemical Name | m/z | Example No. |
|---|---|---|---|---|
| 72 | 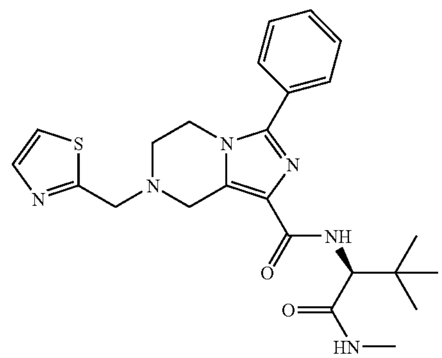 [SMILES: CNC(=O)[C@@H](NC(=O)c1nc(-c2ccccc2)n2c1CN(Cc1nccs1)CC2)C(C)(C)C] | (S)-N-(3,3-dimethyl-1-(methylamino)-1-oxobutan-2-yl)-3-phenyl-7-(thiazol-2-ylmethyl)-5,6,7,8-tetrahydroimidazo[1,5-a]pyrazine-1-carboxamide | 467.2 | 5 |
| 73 | 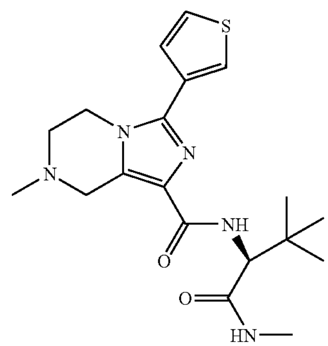 [SMILES: CNC(=O)[C@@H](NC(=O)c1nc(-c2ccsc2)n2c1CN(C)CC2)C(C)(C)C] | (S)-N-(3,3-dimethyl-1-(methylamino)-1-oxobutan-2-yl)-7-methyl-3-(thiophen-3-yl)-5,6,7,8-tetrahydroimidazo[1,5-a]pyrazine-1-carboxamide | 391.1 | 5 |
| 74 | 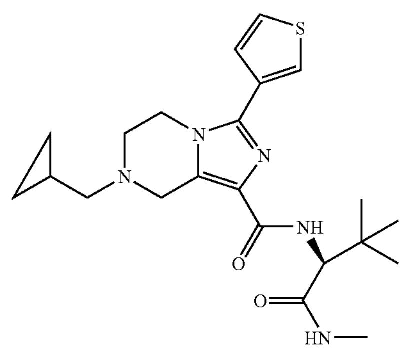 [SMILES: CNC(=O)[C@@H](NC(=O)c1nc(-c2ccsc2)n2c1CN(CC1CC1)CC2)C(C)(C)C] | (S)-7-(cyclopropylmethyl)-N-(3,3-dimethyl-1-(methylamino)-1-oxobutan-2-yl)-3-(thiophen-3-yl)-5,6,7,8-tetrahydroimidazo[1,5-a]pyrazine-1-carboxamide | 431.1 | 5 |
| 75 | 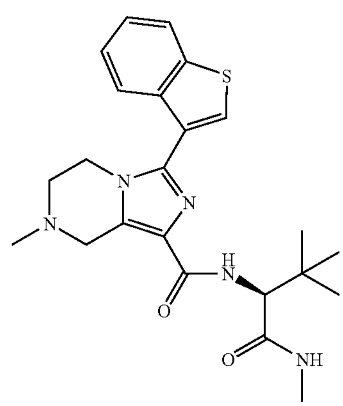 [SMILES: CNC(=O)[C@@H](NC(=O)c1nc(-c2csc3ccccc23)n2c1CN(C)CC2)C(C)(C)C] | (S)-3-(benzo[b]thiophen-3-yl)-N-(3,3-dimethyl-1-(methylamino)-1-oxobutan-2-yl)-7-methyl-5,6,7,8-tetrahydroimidazo[1,5-a]pyrazine-1-carboxamide | 440.0 | 5 |

TABLE I-continued

| Cmpd No. | Structure | Chemical Name | m/z | Example No. |
|---|---|---|---|---|
| 76 | 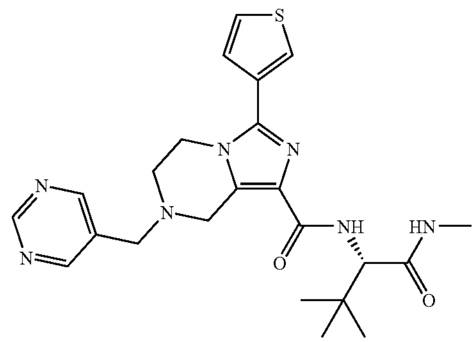 [SMILES: CNC(=O)[C@@H](NC(=O)c1nc(-c2ccsc2)n2c1CN(Cc1cncnc1)CC2)C(C)(C)C] | (S)-N-(3,3-dimethyl-1-(methylamino)-1-oxobutan-2-yl)-7-(pyrimidin-5-ylmethyl)-3-(thiophen-3-yl)-5,6,7,8-tetrahydroimidazo[1,5-a]pyrazine-1-carboxamide | 468.0 | 5 |
| 77 | 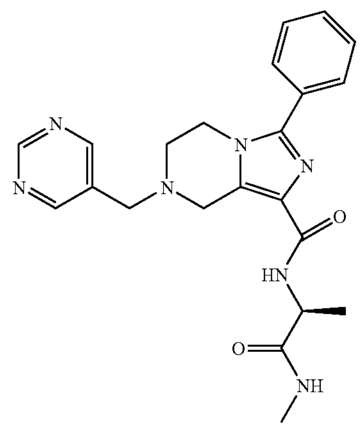 [SMILES: CNC(=O)[C@H](C)NC(=O)c1nc(-c2ccccc2)n2c1CN(Cc1cncnc1)CC2] | (S)-N-(1-(methylamino)-1-oxopropan-2-yl)-3-phenyl-7-(pyrimidin-5-ylmethyl)-5,6,7,8-tetrahydroimidazo[1,5-a]pyrazine-1-carboxamide | 419.0 | 5 |
| 78 | 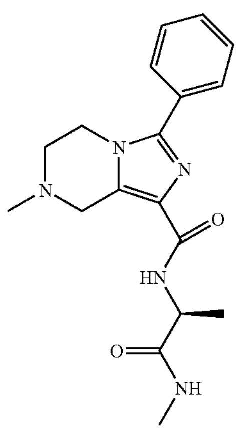 [SMILES: CNC(=O)[C@H](C)NC(=O)c1nc(-c2ccccc2)n2c1CN(C)CC2] | (S)-7-methyl-N-(1-(methylamino)-1-oxopropan-2-yl)-3-phenyl-5,6,7,8-tetrahydroimidazo[1,5-a]pyrazine-1-carboxamide | 341.0 | 5 |
| 79 | 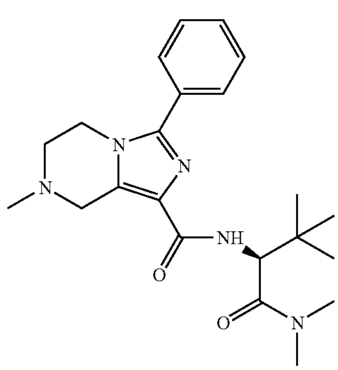 | (S)-N-(1-(dimethylamino)-3,3-dimethyl-1-oxobutan-2-yl)-7-methyl-3-phenyl-5,6,7,8-tetrahydroimidazo[1,5-a]pyrazine-1-carboxamide | 398.3 | 5 |

TABLE I-continued

| Cmpd No. | Structure | Chemical Name | m/z | Example No. |
|---|---|---|---|---|
| 80 | 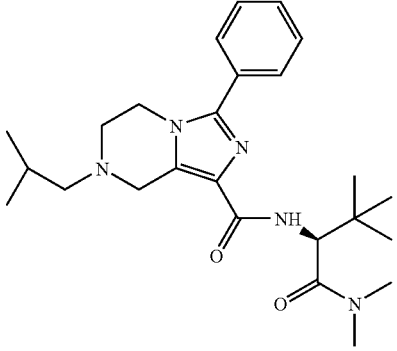 [SMILES: CC(C)CN1CCn2c(-c3ccccc3)nc(C(=O)N[C@H](C(=O)N(C)C)C(C)(C)C)c2C1] | (S)-N-(1-(dimethylamino)-3,3-dimethyl-1-oxobutan-2-yl)-7-isobutyl-3-phenyl-5,6,7,8-tetrahydroimidazo[1,5-a]pyrazine-1-carboxamide | 440.3 | 5 |
| 81 | 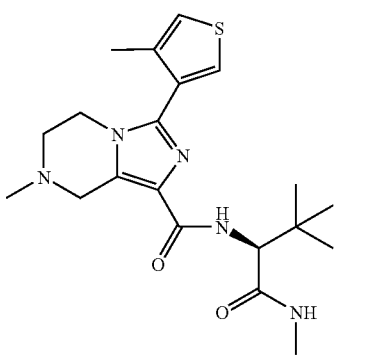 [SMILES: CNC(=O)[C@@H](NC(=O)c1nc(-c2cscc2C)n2c1CN(C)CC2)C(C)(C)C] | (S)-N-(3,3-dimethyl-1-(methylamino)-1-oxobutan-2-yl)-7-methyl-3-(4-methylthiophen-3-yl)-5,6,7,8-tetrahydroimidazo[1,5-a]pyrazine-1-carboxamide | 404.9 | 5 |
| 82 | 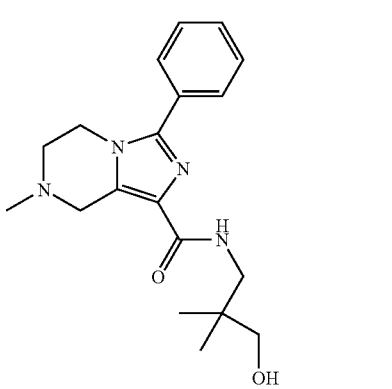 [SMILES: CN1CCn2c(-c3ccccc3)nc(C(=O)NCC(C)(C)CO)c2C1] | N-(3-hydroxy-2,2-dimethylpropyl)-7-methyl-3-phenyl-5,6,7,8-tetrahydroimidazo[1,5-a]pyrazine-1-carboxamide | 343.9 | 5 |
| 83 | 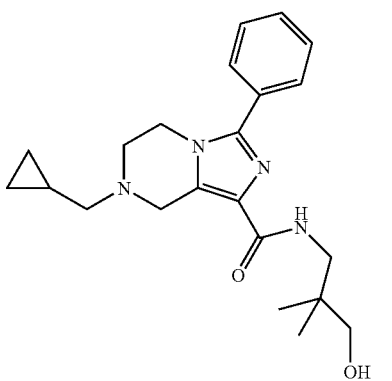 [SMILES: CC(C)(CO)CNC(=O)c1nc(-c2ccccc2)n2c1CN(CC1CC1)CC2] | 7-(cyclopropylmethyl)-N-(3-hydroxy-2,2-dimethylpropyl)-3-phenyl-5,6,7,8-tetrahydroimidazo[1,5-a]pyrazine-1-carboxamide | 382.2 | 5 |

TABLE I-continued

| Cmpd No. | Structure | Chemical Name | m/z | Example No. |
|---|---|---|---|---|
| 84 | 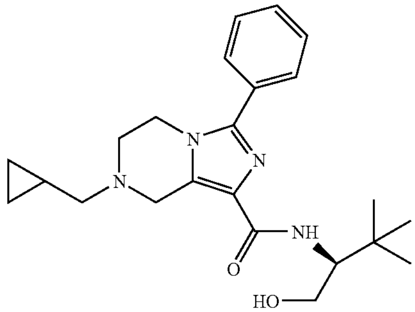 [SMILES: CC(C)(C)[C@@H](CO)NC(=O)c1nc(-c2ccccc2)n2c1CN(CC1CC1)CC2] | (S)-7-(cyclopropylmethyl)-N-(1-hydroxy-3,3-dimethylbutan-2-yl)-3-phenyl-5,6,7,8-tetrahydroimidazo[1,5-a]pyrazine-1-carboxamide | 396.2 | 5 |
| 85 | 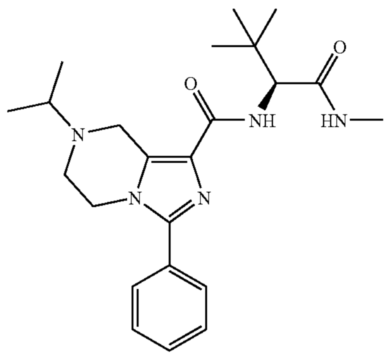 [SMILES: CNC(=O)[C@@H](NC(=O)c1nc(-c2ccccc2)n2c1CN(C(C)C)CC2)C(C)(C)C] | (S)-N-(3,3-dimethyl-1-(methylamino)-1-oxobutan-2-yl)-7-isopropyl-3-phenyl-5,6,7,8-tetrahydroimidazo[1,5-a]pyrazine-1-carboxamide | 412.0 | 5 |
| 86 | 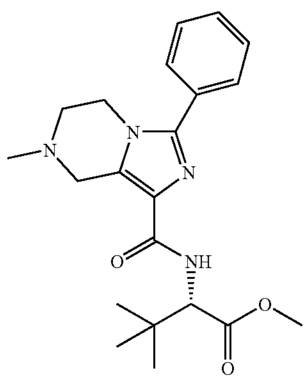 | (S)-methyl 3,3-dimethyl-2-(7-methyl-3-phenyl-5,6,7,8-tetrahydroimidazo[1,5-a]pyrazine-1-carboxamide)butanone | 385.1 | 5 |
| 87 | 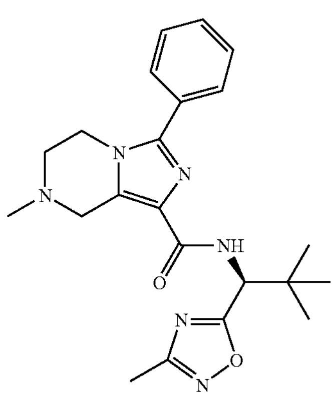 [SMILES: Cc1noc([C@@H](NC(=O)c2nc(-c3ccccc3)n3c2CN(C)CC3)C(C)(C)C)n1] | (S)-N-(2,2-dimethyl-1-(3-methyl-1,2,4-oxadiazol-5-yl)propyl)-7-methyl-3-phenyl-5,6,7,8-tetrahydroimidazo[1,5-a]pyrazine-1-carboxamide | 409.0 | 5 |

TABLE I-continued

| Cmpd No. | Structure | Chemical Name | m/z | Example No. |
|---|---|---|---|---|
| 88 | 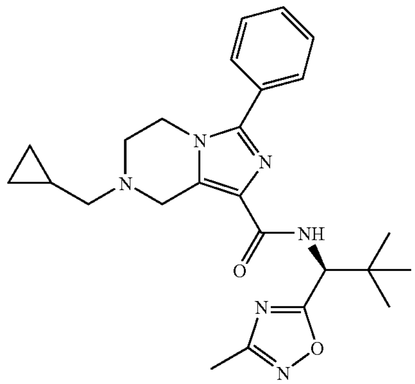 [SMILES: Cc1noc([C@@H](NC(=O)c2nc(-c3ccccc3)n3c2CN(CC2CC2)CC3)C(C)(C)C)n1] | (S)-7-(cyclopropylmethyl)-N-(2,2-dimethyl-1-(3-methyl-1,2,4-oxadiazol-5-yl)propyl)-3-phenyl-5,6,7,8-tetrahydroimidazo[1,5-a]pyrazine-1-carboxamide | 449.0 | 5 |
| 89 | 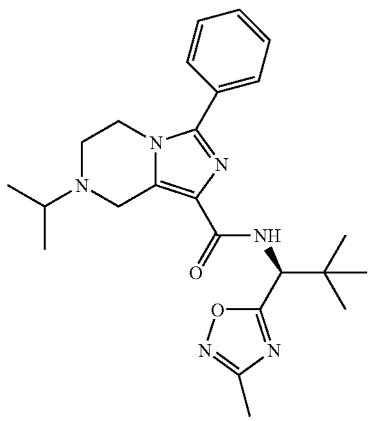 [SMILES: Cc1noc([C@@H](NC(=O)c2nc(-c3ccccc3)n3c2CN(C(C)C)CC3)C(C)(C)C)n1] | (S)-N-(2,2-dimethyl-1-(3-methyl-1,2,4-oxadiazol-5-yl)propyl)-7-isopropyl-3-phenyl-5,6,7,8-tetrahydrimidazo[1,5-a]pyrazine-1-carboxamide | 437.0 | 5 |
| 90 | 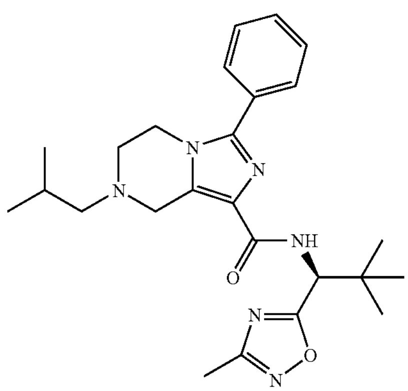 [SMILES: Cc1noc([C@@H](NC(=O)c2nc(-c3ccccc3)n3c2CN(CC(C)C)CC3)C(C)(C)C)n1] | (S)-N-(2,2-dimethyl-1-(3-methyl-1,2,4-oxadiazol-5-yl)propyl)-7-isobutyl-3-phenyl-5,6,7,8-tetrahydroimidazo[1,5-a]pyrazine-1-carboxamide | 451.0 | 5 |
| 91 | 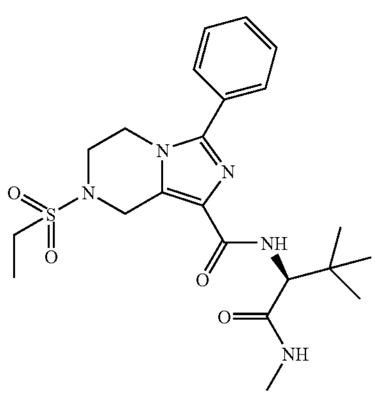 [SMILES: CCS(=O)(=O)N1CCn2c(-c3ccccc3)nc(C(=O)N[C@H](C(=O)NC)C(C)(C)C)c2C1] | (S)-N-(3,3-dimethyl-1-(methylamino)-1-oxobutan-2-yl)-7-(ethylsulfonyl)-3-phenyl-5,6,7,8-tetrahydroimidazo[1,5-a]pyrazine-1-carboxamide | 462.3 | 6 |

TABLE I-continued

| Cmpd No. | Structure | Chemical Name | m/z | Example No. |
|---|---|---|---|---|
| 92 | 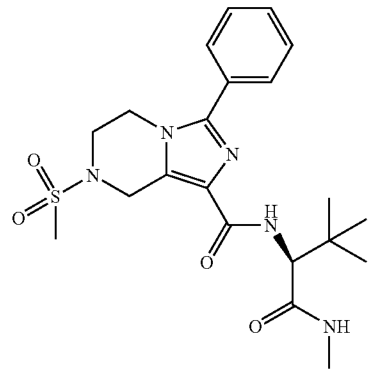 [SMILES: CNC(=O)[C@@H](NC(=O)c1nc(-c2ccccc2)n2c1CN(S(C)(=O)=O)CC2)C(C)(C)C] | (S)-N-(3,3-dimethyl-1-(methylamino)-1-oxobutan-2-yl)-7-(methylsulfonyl)-3-phenyl-5,6,7,8-tetrahydroimidazo[1,5-a]pyrazine-1-carboxamide | 448.3 | 6 |
| 93 | 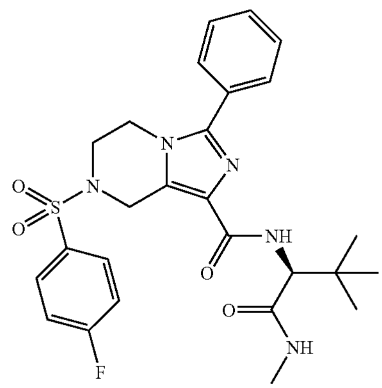 [SMILES: CNC(=O)[C@@H](NC(=O)c1nc(-c2ccccc2)n2c1CN(S(=O)(=O)c1ccc(F)cc1)CC2)C(C)(C)C] | (S)-N-(3,3-dimthyl-1-(methylamino)-1-oxobutan-2-yl)-7-(4-fluorophenylsulfonyl)-3-phenyl-5,6,7,8-tetrahydroimidazo[1,5-a]pyrazine-1-carboxamide | 528.4 | 6 |
| 94 | 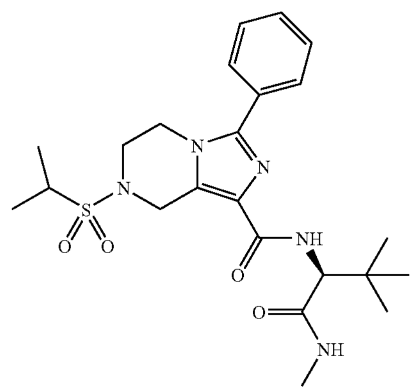 [SMILES: CNC(=O)[C@@H](NC(=O)c1nc(-c2ccccc2)n2c1CN(S(=O)(=O)C(C)C)CC2)C(C)(C)C] | (S)-N-(3,3-dimethyl-1-(methylamino)-1-oxobutan-2-yl)-7-(isopropylsulfonyl)-3-phenyl-5,6,7,8-tetrahydrimidazo[1,5-a]pyrazine-1-carboxamide | 476.4 | 6 |
| 95 | 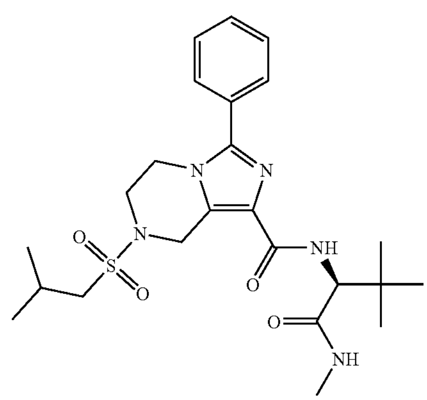 [SMILES: CNC(=O)[C@@H](NC(=O)c1nc(-c2ccccc2)n2c1CN(S(=O)(=O)CC(C)C)CC2)C(C)(C)C] | (S)-N-(3,3-dimethyl-1-(methylamino)-1-oxobutan-2-yl)-7-(isobutylsulfonyl)-3-phenyl-5,6,7,8-tetrahydroimidazo[1,5-a]pyrazine-1-carboxamide | 490.3 | 6 |

TABLE I-continued

| Cmpd No. | Structure | Chemical Name | m/z | Example No. |
|---|---|---|---|---|
| 96 | 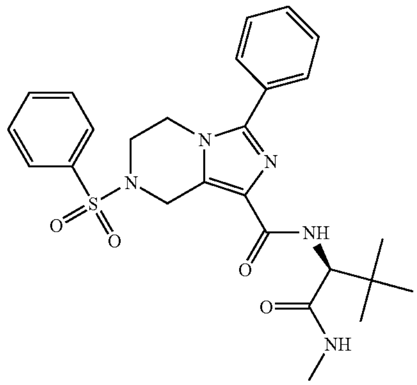 [SMILES: CNC(=O)[C@@H](NC(=O)c1nc(-c2ccccc2)n2c1CN(S(=O)(=O)c1ccccc1)CC2)C(C)(C)C] | (S)-N-(3,3-dimethyl-1-(methylamino)-1-oxobutan-2-yl)-3-phenyl-7-(phenylsulfonyl)-5,6,7,8-tetrahydroimidazo[1,5-a]pyrazine-1-carboxamide | 510.2 | 6 |
| 97 | 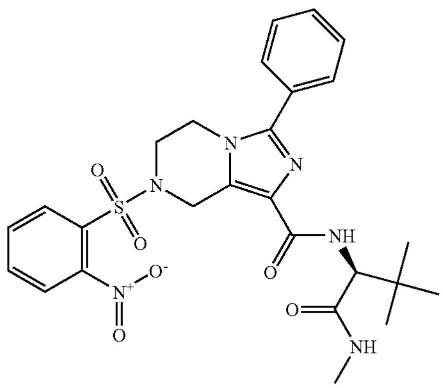 [SMILES: CNC(=O)[C@@H](NC(=O)c1nc(-c2ccccc2)n2c1CN(S(=O)(=O)c1ccccc1[N+](=O)[O-])CC2)C(C)(C)C] | (S)-N-(3,3-dimethyl-1-(methylamino)-1-oxobutan-2-yl)-7-(2-nitrophenylsulfonyl)-3-phenyl-5,6,7,8-tetrahydroimidazo[1,5-a]pyrazine-1-carboxamide | 555.2 | 6 |
| 98 | 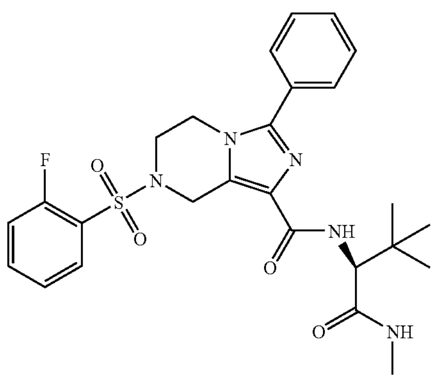 [SMILES: CNC(=O)[C@@H](NC(=O)c1nc(-c2ccccc2)n2c1CN(S(=O)(=O)c1ccccc1F)CC2)C(C)(C)C] | (S)-N-(3,3-dimethyl-1-(methylamino)-1-oxobutan-2-yl)-7-(2-fluorophenylsulfonyl)-3-phenyl-5,6,7,8-tetrahydroimidazo[1,5-a]pyrqazine-1-carboxamide | 528.3 | 6 |
| 99 | 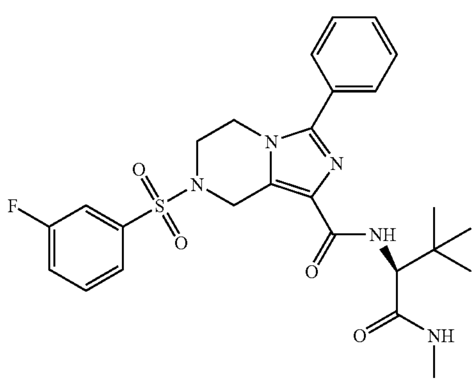 [SMILES: CNC(=O)[C@@H](NC(=O)c1nc(-c2ccccc2)n2c1CN(S(=O)(=O)c1cccc(F)c1)CC2)C(C)(C)C] | (S)-N-(3,3-dimethyl-1-(methylamino)-1-oxobutan-2-yl)-7-(3-fluorophenylsulfonyl)-3-phenyl-5,6,7,8-tetrahydroimidazo[1,5-a]pyrazine-1-carboxamide | 528.3 | 6 |

TABLE I-continued

| Cmpd No. | Structure | Chemical Name | m/z | Example No. |
|---|---|---|---|---|
| 100 | 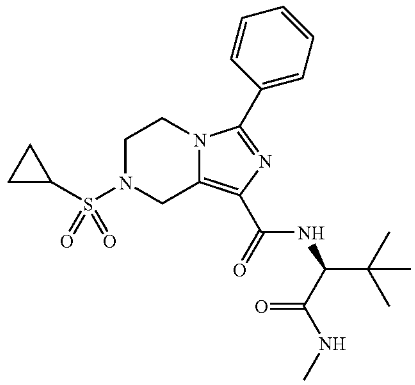 [SMILES: CNC(=O)[C@@H](NC(=O)c1nc(-c2ccccc2)n2c1CN(S(=O)(=O)C1CC1)CC2)C(C)(C)C] | (S)-7-(cyclopropylsulfonyl)-N-(3,3-dimethyl-1-(methylamino)-1-oxobutan-2-yl)-3-phenyl-5,6,7,8-tetrahydroimidazo[1,5-a]pyrazine-1-carboxamide | 474.2 | 6 |
| 101 | 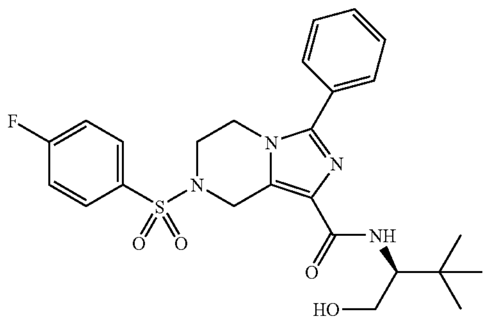 [SMILES: CC(C)(C)[C@@H](CO)NC(=O)c1nc(-c2ccccc2)n2c1CN(S(=O)(=O)c1ccc(F)cc1)CC2] | (S)-7-(4-fluorophenylsulfonyl)-N-(1-hydroxy-3,3-dimethylbutan-2-yl)-3-phenyl-5,6,7,8-tetrahydroimidazo[1,5-a]pyrazine-1-carboxamide | 501.3 | 6 |
| 102 | 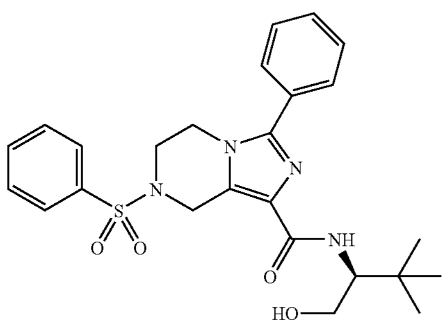 [SMILES: CC(C)(C)[C@@H](CO)NC(=O)c1nc(-c2ccccc2)n2c1CN(S(=O)(=O)c1ccccc1)CC2] | (S)-N-(1-hydroxy-3,3-dimethylbutan-2-yl)-3-(phenyl-7-(phenylsulfonyl)-5,6,7,8-tetrahydroimidazo[1,5-a]pyrazine-1-carboxamide | 483.3 | 6 |
| 103 | 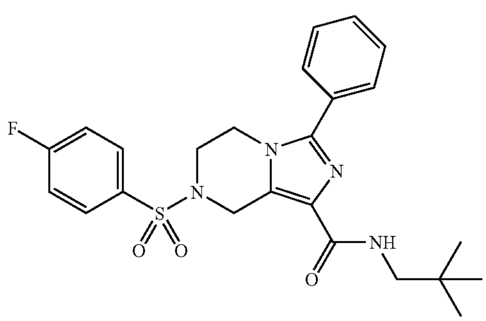 [SMILES: CC(C)(C)CNC(=O)c1nc(-c2ccccc2)n2c1CN(S(=O)(=O)c1ccc(F)cc1)CC2] | 7-(4-fluorophenylsulfonyl)-N-neopentyl-3-phenyl-5,6,7,8-tetrahydroimidazo[1,5-a]pyrazine-1-carboxamide | 471.3 | 6 |

TABLE I-continued

| Cmpd No. | Structure | Chemical Name | m/z | Example No. |
|---|---|---|---|---|
| 104 | 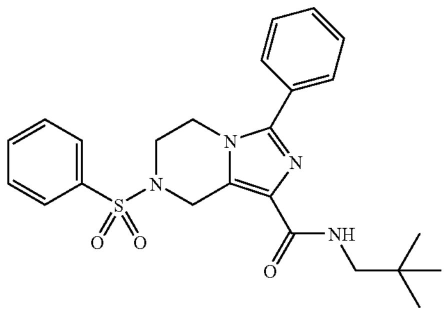 [SMILES: CC(C)(C)CNC(=O)c1nc(-c2ccccc2)n2c1CN(S(=O)(=O)c1ccccc1)CC2] | N-neopentyl-3-phenyl-7-(phenylsulfonyl)-5,6,7,8-tetrahydroimidazo[1,5-a]pyrazine-1-carboxamide | 453.3 | 6 |
| 105 | 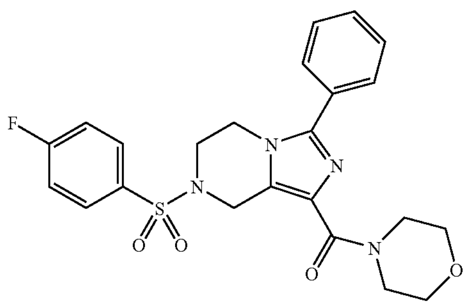 [SMILES: O=C(c1nc(-c2ccccc2)n2c1CN(S(=O)(=O)c1ccc(F)cc1)CC2)N1CCOCC1] | (7-(4-fluorophenylsulfonyl)-3-phenyl-5,6,7,8-tetrahydroimidazo[1,5-a]pyrazin-1-yl)(morpholino)methanone | 471.1 | 6 |
| 106 | 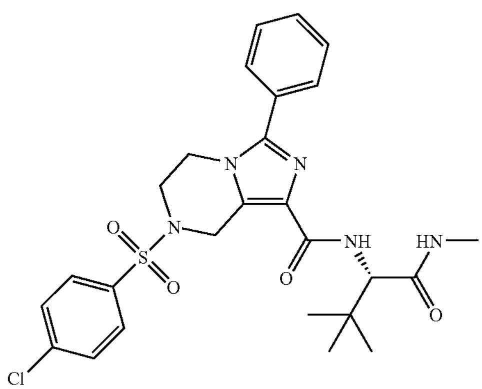 [SMILES: CNC(=O)[C@@H](NC(=O)c1nc(-c2ccccc2)n2c1CN(S(=O)(=O)c1ccc(Cl)cc1)CC2)C(C)(C)C] | (S)-7-(4-chlorophenylsulfonyl)-N-(3,3-dimethyl-1-(methylamino)-1-oxobutan-2-yl)-3-phenyl-5,6,7,8-tetrahydroimidazo[1,5-a]pyrazine-1-carboxamide | 546.0 | 6 |
| 107 | 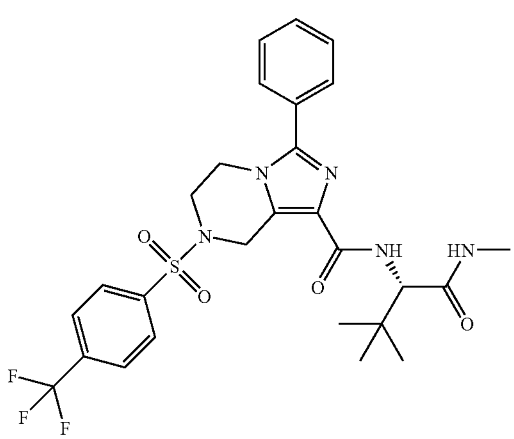 [SMILES: CNC(=O)[C@@H](NC(=O)c1nc(-c2ccccc2)n2c1CN(S(=O)(=O)c1ccc(C(F)(F)F)cc1)CC2)C(C)(C)C] | (S)-N-(3,3-dimethyl-1-(methylamino)-1-oxobutan-2-yl)-3-phenyl-7-(4-(trifluoromethyl)phenylsulfonyl)-5,6,7,8-tetrahydroimidazo[1,5-a]pyrazine-1-carboxamide | 579.0 | 6 |

TABLE I-continued

| Cmpd No. | Structure | Chemical Name | m/z | Example No. |
|---|---|---|---|---|
| 108 | 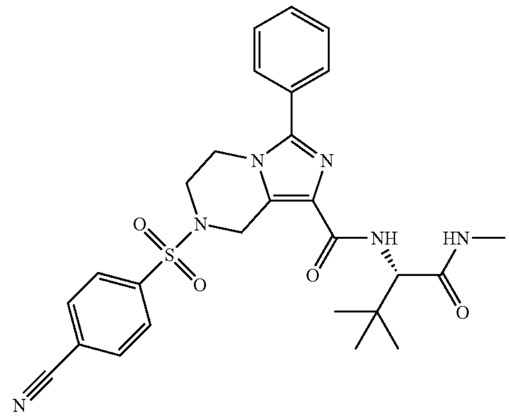 [SMILES: CNC(=O)[C@@H](NC(=O)c1nc(-c2ccccc2)n2c1CN(S(=O)(=O)c1ccc(C#N)cc1)CC2)C(C)(C)C] | (S)-7-(4-cyanophenylsulfonyl)-N-(3,3-dimethyl-1-(methylamino)-1-oxobutan-2-yl)-3-phenyl-5,6,7,8-tetrahydroimidazo[1,5-a]pyrazine-1-carboxamide | 536.1 | 6 |
| 109 | 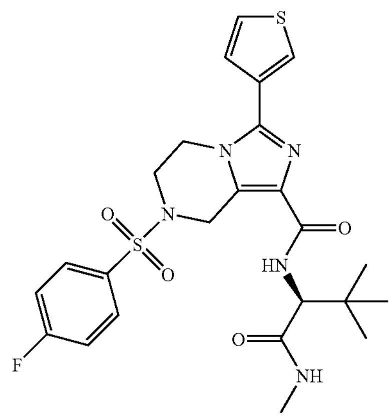 [SMILES: CNC(=O)[C@@H](NC(=O)c1nc(-c2ccsc2)n2c1CN(S(=O)(=O)c1ccc(F)cc1)CC2)C(C)(C)C] | (S)-N-(3,3-dimethyl-1-(methylamino)-1-oxobutan-2-yl)-7-(4-fluorophenylsulfonyl)-3-(thiophen-3-yl)-5,6,7,8-tetrahydroimidazo[1,5-a]pyrazine-1-carboxamide | 535.1 | 6 |
| 110 | 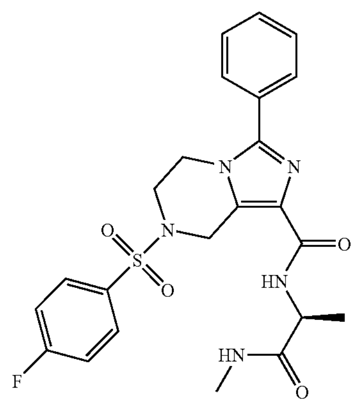 [SMILES: CNC(=O)[C@H](C)NC(=O)c1nc(-c2ccccc2)n2c1CN(S(=O)(=O)c1ccc(F)cc1)CC2] | (S)-7-(4-fluorophenylsulfonyl)-N-(1-(methylamino)-1-oxopropan-2-yl)-3-phenyl-5,6,7,8-tetrahydroimidazo[1,5-a]pyrazine-1-carboxamide | 486.2 | 6 |
| 111 | 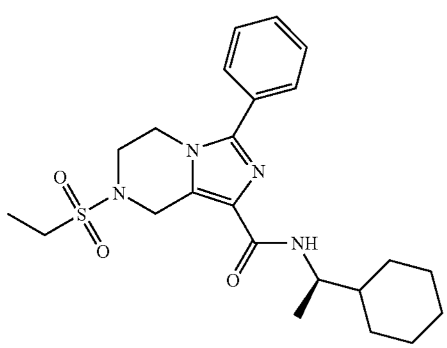 [SMILES: CCS(=O)(=O)N1CCn2c(-c3ccccc3)nc(C(=O)N[C@H](C)C3CCCCC3)c2C1] | (R)-N-(1-cyclohexylethyl)-7-(ethylsulfonyl)-3-phenyl-5,6,7,8-tetrahydroimidazo[1,5-a]pyrazine-1-carboxamide | 445.2 | 7 |

TABLE I-continued

| Cmpd No. | Structure | Chemical Name | m/z | Example No. |
|---|---|---|---|---|
| 112 | 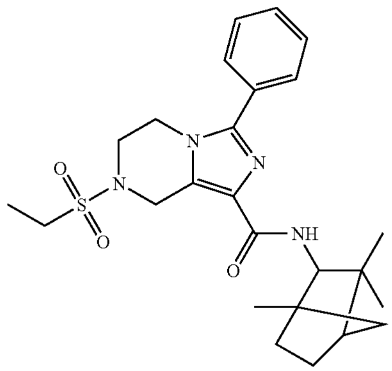 [SMILES: CCS(=O)(=O)N1CCn2c(-c3ccccc3)nc(C(=O)NC3C4(C)CCC(C4)C3(C)C)c2C1] | 7-(ethylsulfonyl)-3-phenyl-N-(1,3,3-trimethylbicyclo[2.2.1]heptan-2-yl)-5,6,7,8-tetrahydroimidazo[1,5-a]pyrazine-1-carboxamide | 471.3 | 7 |
| 113 | 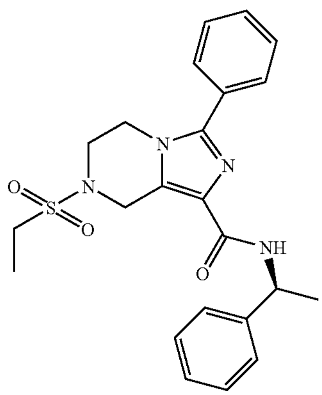 [SMILES: CCS(=O)(=O)N1CCn2c(-c3ccccc3)nc(C(=O)N[C@@H](C)c3ccccc3)c2C1] | (S)-7-(ethylsulfonyl)-3-phenyl-N-(1-phenylethyl)-5,6,7,8-tetrahydroimidazo[1,5-a]pyrazine-1-carboxamide | 439.3 | 7 |
| 114 | 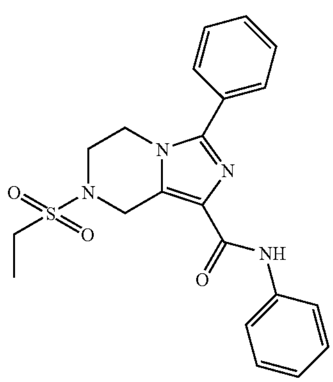 [SMILES: CCS(=O)(=O)N1CCn2c(-c3ccccc3)nc(C(=O)Nc3ccccc3)c2C1] | 7-(ethylsulfonyl)-N,3-diphenyl-5,6,7,8-tetrahydroimidazo[1,5-a]pyrazine-1-carboxamide | 411.3 | 7 |
| 115 | 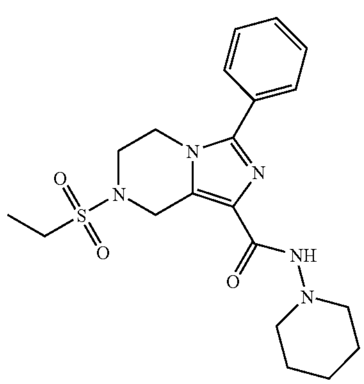 | 7-(ethylsulfonyl)-3-phenyl-N-(piperidin-1-yl)-5,6,7,8-tetrahydroimidazo[1,5-a]pyrazine-1-carboxamide | 418.3 | 7 |

| Cmpd No. | Structure | Chemical Name | m/z | Example No. |
|---|---|---|---|---|
| 116 | 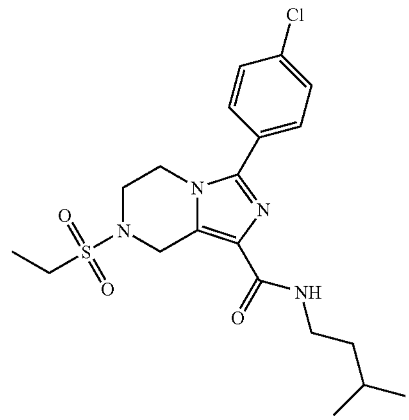 [SMILES: CCS(=O)(=O)N1CCn2c(-c3ccc(Cl)cc3)nc(C(=O)NCCC(C)C)c2C1] | 3-(4-chlorophenyl)-7-(ethylsulfonyl)-N-isopentyl-5,6,7,8-tetrahydroimidazo[1,5-a]pyrazine-1-carboxamide | 439.2 | 7 |
| 117 | 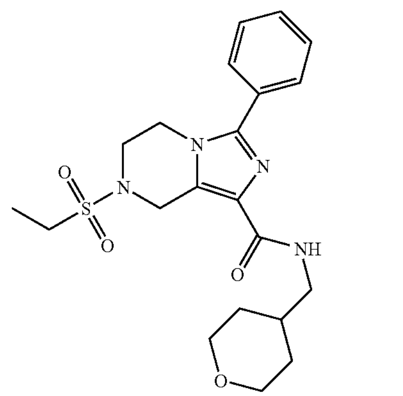 [SMILES: CCS(=O)(=O)N1CCn2c(-c3ccccc3)nc(C(=O)NCC3CCOCC3)c2C1] | 7-(ethylsulfonyl)-3-phenyl-N-((tetrahydro-2H-pyran-4-yl)methyl)-5,6,7,8-tetrahydroimidazo[1,5-a]pyrazine-1-carboxamide | 433.1 | 7 |
| 118 | 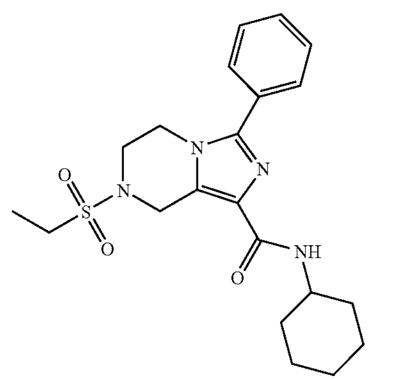 [SMILES: CCS(=O)(=O)N1CCn2c(-c3ccccc3)nc(C(=O)NC3CCCCC3)c2C1] | N-cyclohexyl-7-(ethylsulfonyl)-3-phenyl-5,6,7,8-tetrahydroimidazo[1,5-a]pyrazine-1-carboxamide | 417.3 | 7 |
| 119 | 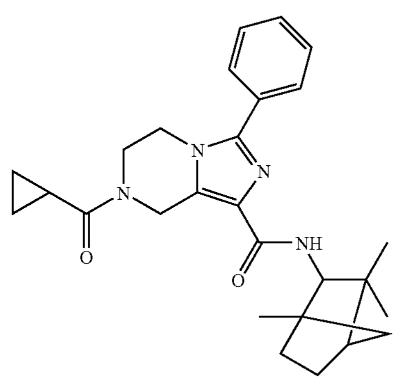 [SMILES: CC12CCC(C1)C(C)(C)C2NC(=O)c1nc(-c2ccccc2)n2c1CN(C(=O)C1CC1)CC2] | 7-(cyclopropanecarbonyl)-3-phenyl-N-(1,3,3-trimethylbicyclo[2.2.1]heptan-2-yl)-5,6,7,8-tetrahydroimidazo[1,5-a]pyrazine-1-carboxamide | 447.4 | 8 |

TABLE I-continued

| Cmpd No. | Structure | Chemical Name | m/z | Example No. |
|---|---|---|---|---|
| 120 | 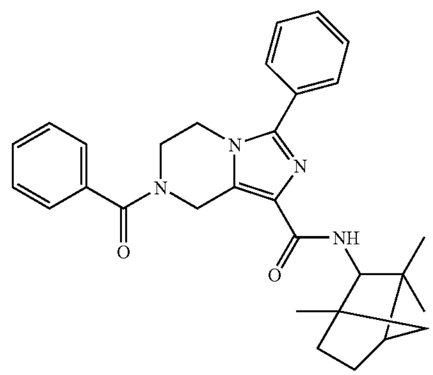 [SMILES: CC12CCC(C1)C(C)(C)C2NC(=O)c1nc(-c2ccccc2)n2c1CN(C(=O)c1ccccc1)CC2] | 7-benzoyl-3-phenyl-N-(1,3,3-trimethylbicyclo[2.2.1]heptan-2-yl)-5,6,7,8-tetrahydroimidazo[1,5-a]pyrazine-1-carboxamide | 483.4 | 8 |
| 121 | 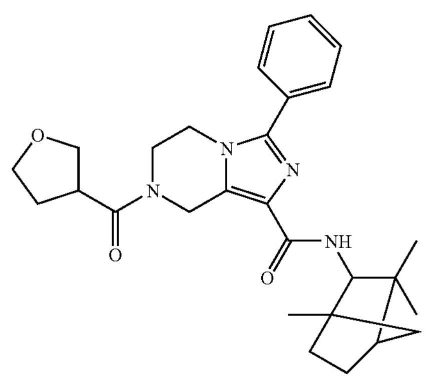 [SMILES: CC12CCC(C1)C(C)(C)C2NC(=O)c1nc(-c2ccccc2)n2c1CN(C(=O)C1CCOC1)CC2] | 3-phenyl-7-(tetrahydrfuran-3-carbonyl)-N-(1,3,3-trimethylbicyclo[2.2.1]heptan-2-yl)-5,6,7,8-tetrahydroimidazo[1,5-a]pyrazine-1-carboxamide | 477.3 | 8 |
| 122 | 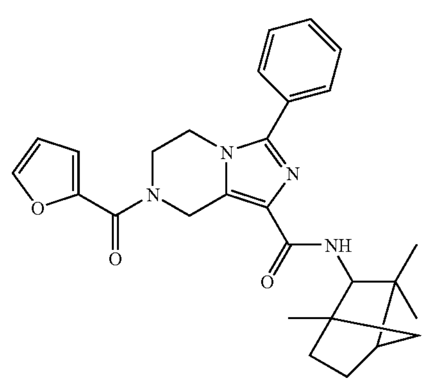 [SMILES: CC12CCC(C1)C(C)(C)C2NC(=O)c1nc(-c2ccccc2)n2c1CN(C(=O)c1ccco1)CC2] | 7-(furan-2-carbonyl)-3-phenyl-N-(1,3,3-trimethylbicyclo[2.2.1]heptan-2-yl)-5,6,7,8-tetrahydroimidazo[1,5-a]pyrazine-1-carboxamide | 473.4 | 8 |
| 123 | 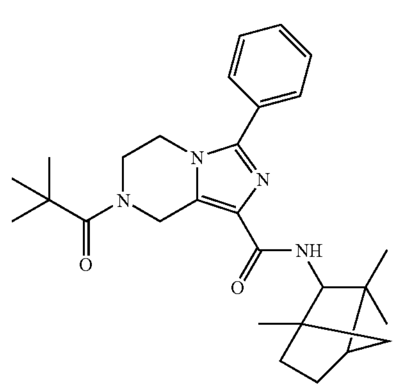 [SMILES: CC(C)(C)C(=O)N1CCn2c(-c3ccccc3)nc(C(=O)NC3C4(C)CCC(C4)C3(C)C)c2C1] | 3-phenyl-7-pivaolyl-N-(1,3,3-trimethylbicyclo[2.2.1]heptan-2-yl)-5,6,7,8-tetrahydroimidazo[1,5-a]pyrazine-1-carboxamide | 463.4 | 8 |

TABLE I-continued

| Cmpd No. | Structure | Chemical Name | m/z | Example No. |
|---|---|---|---|---|
| 124 | 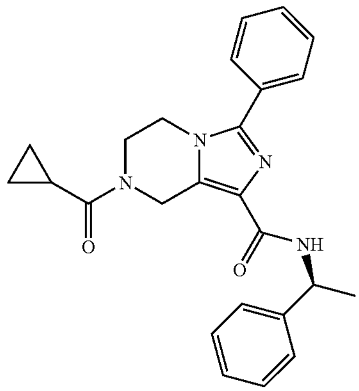 [SMILES: C[C@H](NC(=O)c1nc(-c2ccccc2)n2c1CN(C(=O)C1CC1)CC2)c1ccccc1] | (S)-7-(cyclopropylcarbonyl)-3-phenyl-N-(1-phenylethyl)-5,6,7,8-tetrahydroimidazo[1,5-a]pyrazine-1-carboxamide | 415.3 | 8 |
| 125 | 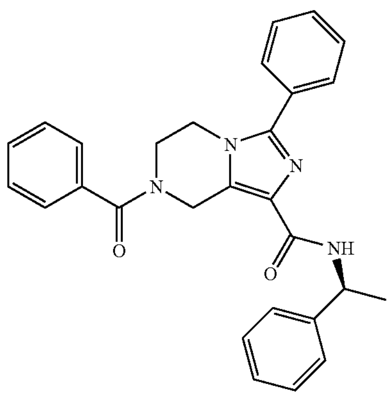 [SMILES: C[C@H](NC(=O)c1nc(-c2ccccc2)n2c1CN(C(=O)c1ccccc1)CC2)c1ccccc1] | (S)-7-benzoyl-3-phenyl-N-(1-phenylethyl)-5,6,7,8-tetrahydroimidazo[1,5-a]pyrazine-1-carboxamide | 451.3 | 8 |
| 126 | 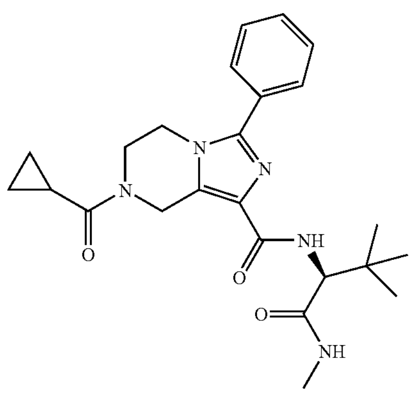 [SMILES: CNC(=O)[C@@H](NC(=O)c1nc(-c2ccccc2)n2c1CN(C(=O)C1CC1)CC2)C(C)(C)C] | (S)-7-(cyclopropanecarbonyl)-N-(3,3-dimethyl-1-(methylamino)-1-oxobutan-2-yl)-3-phenyl-5,6,7,8-tetrahydroimidazo[1,5-a]pyrazine-1-carboxamide | 438.4 | 8 |
| 127 | 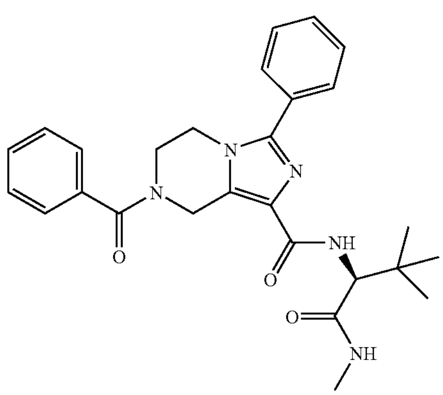 [SMILES: CNC(=O)[C@@H](NC(=O)c1nc(-c2ccccc2)n2c1CN(C(=O)c1ccccc1)CC2)C(C)(C)C] | (S)-7-benzoyl-N-(3,3-dimethyl-1-(mehtylamino)-1-oxobutan-2-yl)-3-phenyl-5,6,7,8-tetrahydroimidazo[1,5-a]pyrazine-1-carboxamide | 474.4 | 8 |

TABLE I-continued

| Cmpd No. | Structure | Chemical Name | m/z | Example No. |
|---|---|---|---|---|
| 128 | 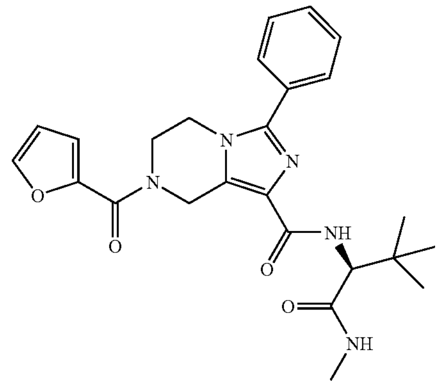 [SMILES: CNC(=O)[C@@H](NC(=O)c1nc(-c2ccccc2)n2c1CN(C(=O)c1ccco1)CC2)C(C)(C)C] | (S)-N-(3,3-dimethyl-1-(methylamino)-1-oxobutan-2-yl)-7-(furan-2-carbonyl)-3-phenyl-5,6,7,8-tetrahydroimidazo[1,5-a]pyrazine-1-carboxamide | 464.4 | 8 |
| 129 | 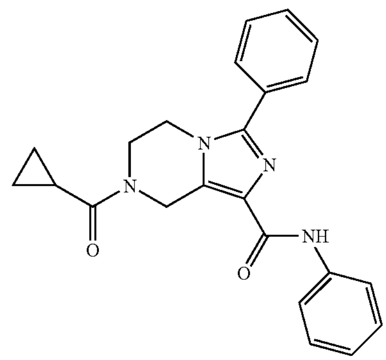 [SMILES: O=C(Nc1ccccc1)c1nc(-c2ccccc2)n2c1CN(C(=O)C1CC1)CC2] | 7-(cyclopropanecarbonyl)-N,3-diphenyl-5,6,7,8-tetrahydroimidazo[1,5-a]pyrazine-1-carboxamide | 387.3 | 8 |
| 130 | 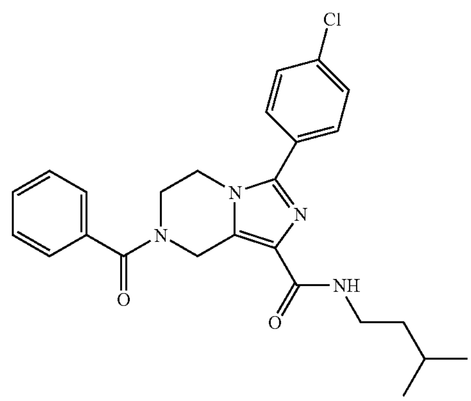 [SMILES: CC(C)CCNC(=O)c1nc(-c2ccc(Cl)cc2)n2c1CN(C(=O)c1ccccc1)CC2] | 7-benzoyl-3-(4-chlorophenyl)-N-isopentyl-5,6,7,8-tetrahydroimidazo[1,5-a]pyrazine-1-carboxamide | 451.3 | 8 |
| 131 | 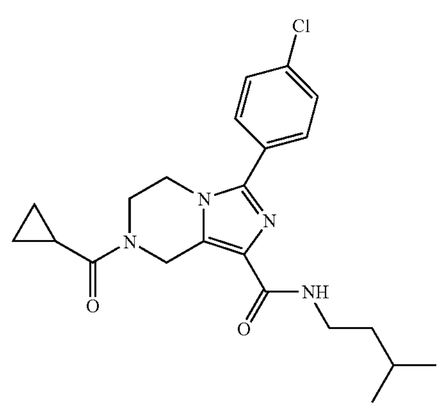 [SMILES: CC(C)CCNC(=O)c1nc(-c2ccc(Cl)cc2)n2c1CN(C(=O)C1CC1)CC2] | 3-(4-chlorophenyl)-7-(cyclopropanecarbonyl)-N-isopentyl-5,6,7,8-tetrahydroimidazo[1,5-a]pyrazine-1-carboxamide | 415.3 | 8 |

TABLE I-continued

| Cmpd No. | Structure | Chemical Name | m/z | Example No. |
|---|---|---|---|---|
| 132 | 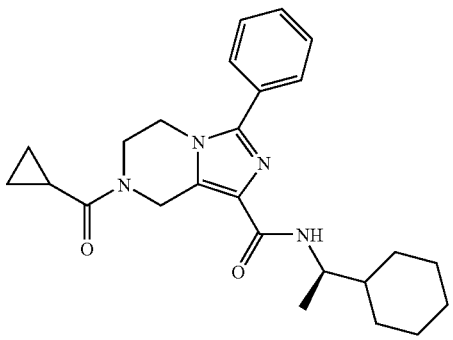 [SMILES: C[C@@H](NC(=O)c1nc(-c2ccccc2)n2c1CN(C(=O)C1CC1)CC2)C1CCCCC1] | (R)-N-(1-cyclohexylethyl)-7-(cyclopropanecarbonyl)-3-phenyl-5,6,7,8-tetrahydroimidazo[1,5-a]pyrazine-1-carboxamide | 421.3 | 8 |
| 133 | 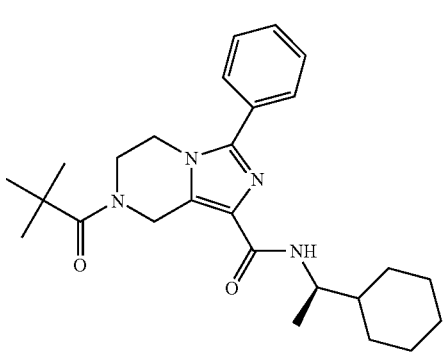 [SMILES: C[C@@H](NC(=O)c1nc(-c2ccccc2)n2c1CN(C(=O)C(C)(C)C)CC2)C1CCCCC1] | (R)-N-(1-cyclohexylethyl)-3-phenyl-7-pivaloyl-5,6,7,8-tetrahydroimidazo[1,5-a]pyrazine-1-carboxamide | 437.2 | 8 |
| 134 | 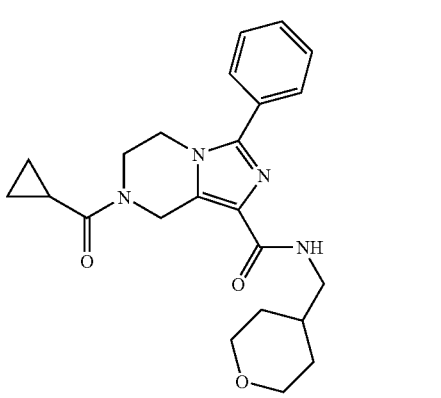 [SMILES: O=C(NCC1CCOCC1)c1nc(-c2ccccc2)n2c1CN(C(=O)C1CC1)CC2] | 7-(cyclopropanecarbonyl)-3-phenyl-N-((tetrahydro-2H-pyran-4-yl)methyl)-5,6,7,8-tetrahydroimidazo[1,5-a]pyrazine-1-carboxamide | 409.1 | 8 |
| 135 | 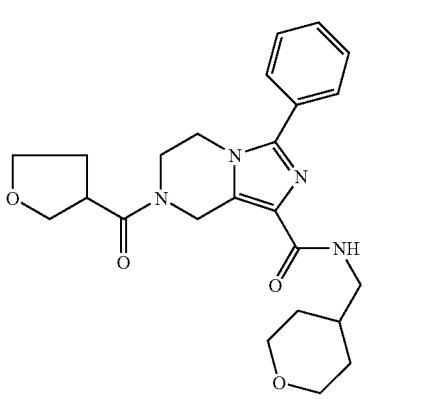 [SMILES: O=C(NCC1CCOCC1)c1nc(-c2ccccc2)n2c1CN(C(=O)C1CCOC1)CC2] | 3-phenyl-N-((tetrahydro-2H-pyran-4-yl)methyl)-7-(tetrahydrofuran-3-carbonyl)-5,6,7,8-tetrahydroimidazo[1,5-a]pyrazine-1-carboxamide | 439.3 | 8 |

TABLE I-continued

| Cmpd No. | Structure | Chemical Name | m/z | Example No. |
|---|---|---|---|---|
| 136 | 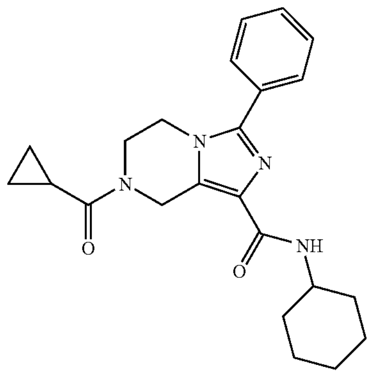 [SMILES: O=C(NC1CCCCC1)c1nc(-c2ccccc2)n2c1CN(C(=O)C1CC1)CC2] | N-cyclohexyl-7-(cyclopropanecarbonyl)-3-phenyl-5,6,7,8-tetrahydroimidazo[1,5-a]pyrazine-1-carboxamide | 393.2 | 8 |
| 137 | 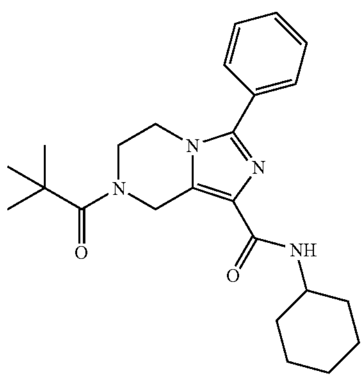 [SMILES: CC(C)(C)C(=O)N1CCn2c(-c3ccccc3)nc(C(=O)NC3CCCCC3)c2C1] | N-cyclohexyl-3-phenyl-7-pivaloyl-5,6,7,8-tetrahydroimidazo[1,5-a]pyrazine-1-carboxamide | 409.2 | 8 |
| 138 | 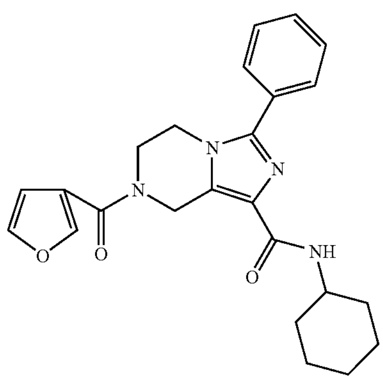 [SMILES: O=C(NC1CCCCC1)c1nc(-c2ccccc2)n2c1CN(C(=O)c1ccoc1)CC2] | N-cyclohexyl-7-(furan-3-carbonyl)-3-phenyl-5,6,7,8-tetrahydroimidazo[1,5-a]pyrazine-1-carboxamide | 419.1 | 8 |
| 139 | 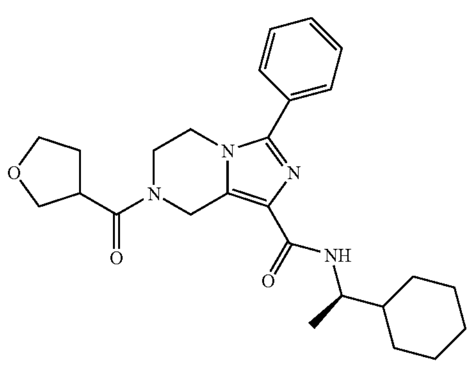 [SMILES: C[C@@H](NC(=O)c1nc(-c2ccccc2)n2c1CN(C(=O)C1CCOC1)CC2)C1CCCCC1] | N-((R)-1-cyclohexylethyl)-3-phenyl-7-(tetrahydrofuran-3-carbonyl)-5,6,7,8-tetrahydroimidazo[1,5-a]pyrazine-1-carboxamide | 451.4 | 8 |

TABLE I-continued

| Cmpd No. | Structure | Chemical Name | m/z | Example No. |
|---|---|---|---|---|
| 140 | 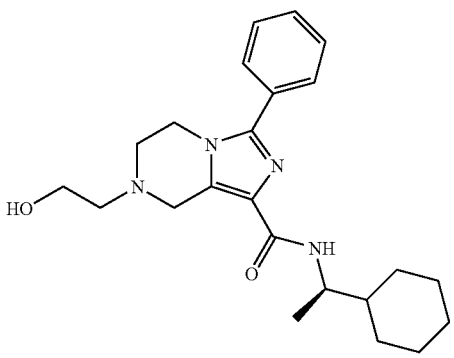 [SMILES: C[C@@H](NC(=O)c1nc(-c2ccccc2)n2c1CN(CCO)CC2)C1CCCCC1] | (R)-N-(1-cyclohexylethyl)-7-(2-hydroxyethyl)-3-phenyl-5,6,7,8-tetrahydroimidazo[1,5-a]pyrazine-1-carboxamide | 397.2 | 9 |
| 141 | 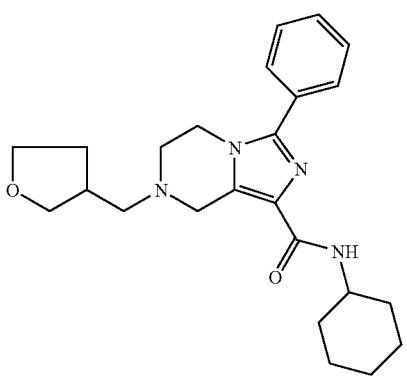 [SMILES: O=C(NC1CCCCC1)c1nc(-c2ccccc2)n2c1CN(CC1CCOC1)CC2] | N-cyclohexyl-3-phenyl-7-((tetrahydrofuran-3-yl)methyl)-5,6,7,8-tetrahydroimidazo[1,5-a]pyrazine-1-carboxamide | 409.2 | 9 |
| 142 | 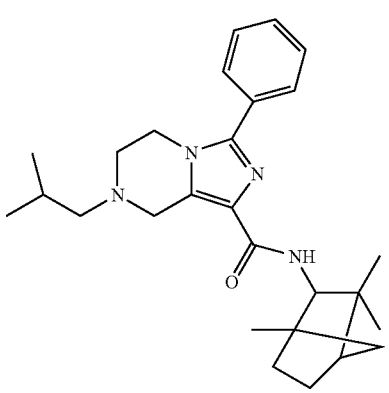 [SMILES: CC(C)CN1CCn2c(-c3ccccc3)nc(C(=O)NC3C4(C)CCC(C4)C3(C)C)c2C1] | 7-isobutyl-3-phenyl-N-(1,3,3-trimethylbicyclo[2.2.1]heptan-2-yl)-5,6,7,8-tetrahydroimidazo[1,5-a]pyrazine-1-carboxamide | 435.4 | 9 |
| 143 | 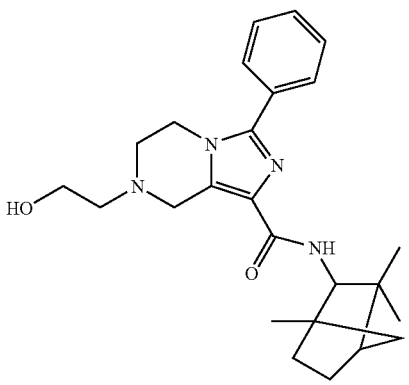 [SMILES: CC12CCC(C1)C(C)(C)C2NC(=O)c1nc(-c2ccccc2)n2c1CN(CCO)CC2] | 7-(2-hydroxyethyl)-3-phenyl-N-(1,3,3-trimethylbicyclo[2.2.1]heptan-2-yl)-5,6,7,8-tetrahydroimidazo[1,5-a]pyrazine-1-carboxamide | 423.4 | 9 |

| Cmpd No. | Structure | Chemical Name | m/z | Example No. |
|---|---|---|---|---|
| 144 | 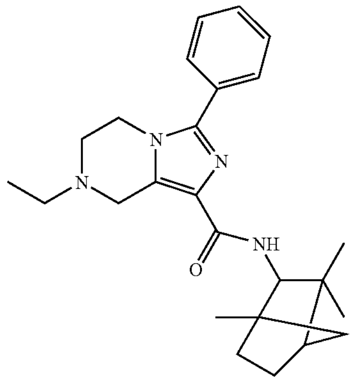 [SMILES: CCN1CCn2c(-c3ccccc3)nc(C(=O)NC3C4(C)CCC(C4)C3(C)C)c2C1] | 7-ethyl-3-phenyl-N-(1,3,3-trimethylbicyclo[2.2.1]heptan-2-yl)-5,6,7,8-tetrahydroimidazo[1,5-a]pyrazine-1-carboxamide | 407.4 | 9 |
| 145 | 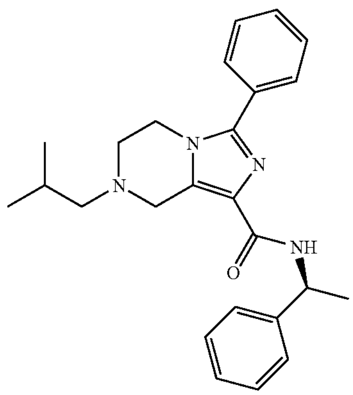 [SMILES: CC(C)CN1CCn2c(-c3ccccc3)nc(C(=O)N[C@@H](C)c3ccccc3)c2C1] | (S)-7-isobutyl-3-phenyl-N-(1-phenylethyl)-5,6,7,8-tetrahydroimidazo[1,5-a]pyrazine-1-carboxamide | 403.4 | 9 |
| 146 | 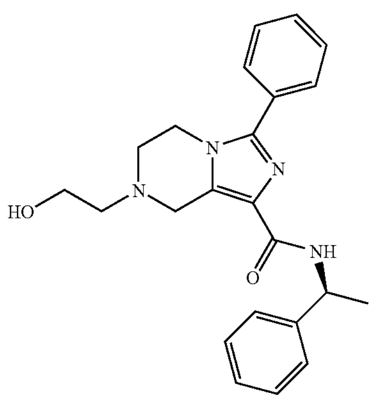 [SMILES: C[C@H](NC(=O)c1nc(-c2ccccc2)n2c1CN(CCO)CC2)c1ccccc1] | (S)-7-(2-hydroxyethyl)-3-phenyl-N-(1-phenylethyl)-5,6,7,8-tetrahydroimidazo[1,5-a]pyrazine-1-carboxamide | 391.3 | 9 |
| 147 | 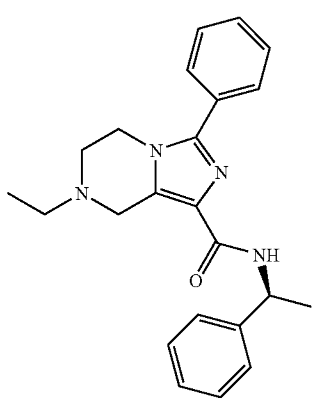 [SMILES: CCN1CCn2c(-c3ccccc3)nc(C(=O)N[C@@H](C)c3ccccc3)c2C1] | (S)-7-ethyl-3-phenyl-N-(1-phenylethyl)-5,6,7,8-tetrahydroimidazo[1,5-a]pyrazine-1-carboxamide | 375.3 | 9 |

TABLE I-continued

| Cmpd No. | Chemical Name | m/z | Example No. |
|---|---|---|---|
| 148 | (S)-N-(3,3-dimethyl-1-(methylamino)-1-oxobutan-2-yl)-7-isobutyl-3-phenyl-5,6,7,8-tetrahydroimidazo[1,5-a]pyrazine-1-carboxamide | 426.4 | 9 |
| 149 | (S)-N-(3,3-dimethyl-1-(methylamino)-1-oxobutan-2-yl)-7-ethyl-3-phenyl-5,6,7,8-tetrahydroimidazo[1,5-a]pyrazine-1-carboxamide | 398.4 | 9 |
| 150 | 7-isobutyl-N,3-diphenyl-5,6,7,8-tetrahydroimidazo[1,5-a]pyrazine-1-carboxamide | 375.3 | 9 |
| 151 | 7-(2-hydroxyethyl)-N,3-diphenyl-5,6,7,8-tetrahydroimidazo[1,5-a]pyrazine-1-carboxamide | 363.3 | 9 |

TABLE I-continued

| Cmpd No. | Structure | Chemical Name | m/z | Example No. |
|---|---|---|---|---|
| 152 | 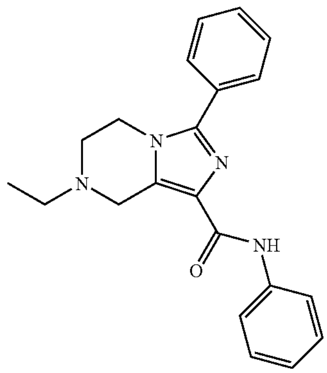 [SMILES: CCN1CCn2c(-c3ccccc3)nc(C(=O)Nc3ccccc3)c2C1] | 7-ethyl-N,3-diphenyl-5,6,7,8-tetrahydroimidazo[1,5-a]pyrazine-1-carboxamide | 347.3 | 9 |
| 153 | 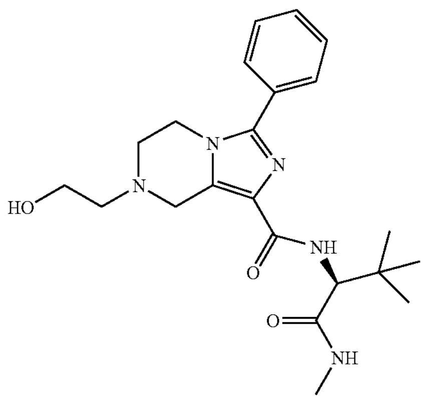 [SMILES: CNC(=O)[C@@H](NC(=O)c1nc(-c2ccccc2)n2c1CN(CCO)CC2)C(C)(C)C] | (S)-N-(3,3-dimethyl-1-(methylamino)-1-oxobutan-2-yl)-7-(2-hydroxyethyl)-3-phenyl-5,6,7,8-tetrahydroimidazo[1,5-a]pyrazine-1-carboxamide | 414.2 | 9 |
| 154 | 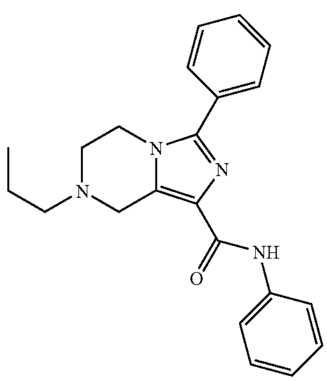 [SMILES: CCCN1CCn2c(-c3ccccc3)nc(C(=O)Nc3ccccc3)c2C1] | N,3-diphenyl-7-propyl-5,6,7,8-tetrahydroimidazo[1,5-a]pyrazine-1-carboxamide | 361.3 | 9 |
| 155 | 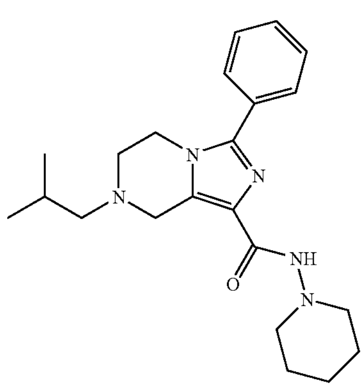 [SMILES: CC(C)CN1CCn2c(-c3ccccc3)nc(C(=O)NN3CCCCC3)c2C1] | 7-isobutyl-3-phenyl-N-(piperidin-1-yl)-5,6,7,8-tetrahydroimidazo[1,5-a]pyrazine-1-carboxamide | 382.3 | 9 |

TABLE I-continued

| Cmpd No. | Structure | Chemical Name | m/z | Example No. |
|---|---|---|---|---|
| 156 | 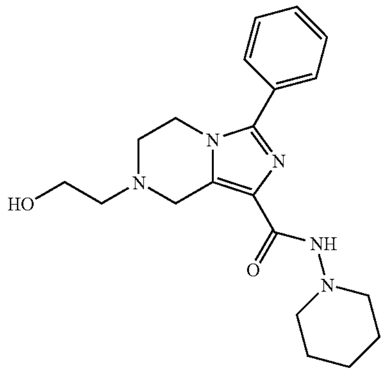 [SMILES: O=C(NN1CCCCC1)c1nc(-c2ccccc2)n2c1CN(CCO)CC2] | 7-(2-hydroxyethyl)-3-phenyl-N-(piperidin-1-yl)-5,6,7,8-tetrahydroimidazo[1,5-a]pyrazine-1-carboxamide | 370.3 | 9 |
| 157 | 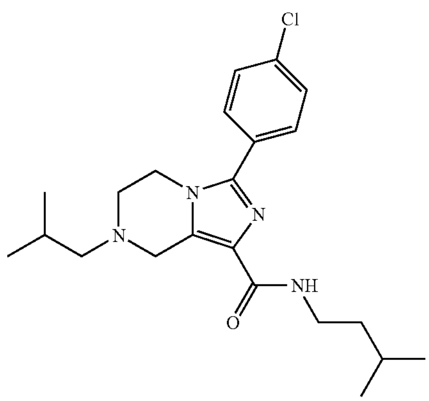 [SMILES: CC(C)CCNC(=O)c1nc(-c2ccc(Cl)cc2)n2c1CN(CC(C)C)CC2] | 3-(4-chlorophenyl)-7-isobutyl-N-isopentyl-5,6,7,8-tetrahydroimidazo[1,5-a]pyrazine-1-carboxamide | 403.3 | 9 |
| 158 | 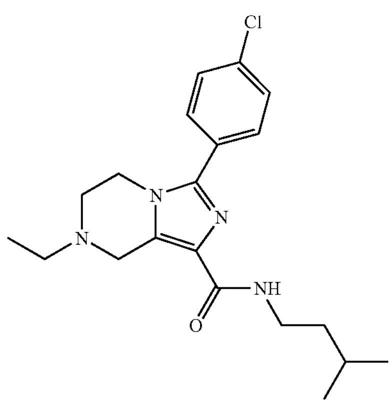 [SMILES: CCN1CCn2c(-c3ccc(Cl)cc3)nc(C(=O)NCCC(C)C)c2C1] | 3-(4-chlorophenyl)-7-ethyl-N-isopentyl-5,6,7,8-tetrahydroimidazo[1,5-a]pyrazine-1-carboxamide | 375.3 | 9 |
| 159 | 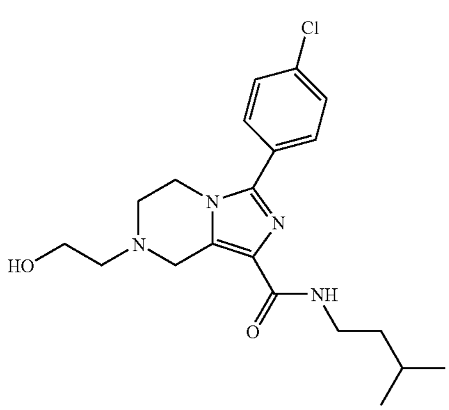 [SMILES: CC(C)CCNC(=O)c1nc(-c2ccc(Cl)cc2)n2c1CN(CCO)CC2] | 3-(4-chlorophenyl)-7-(2-hydroxyethyl)-N-isopentyl-5,6,7,8-tetrahydroimidazo[1,5-a]pyrazine-1-carboxamide | 391.2 | 9 |

TABLE I-continued

| Cmpd No. | Structure | Chemical Name | m/z | Example No. |
|---|---|---|---|---|
| 160 | 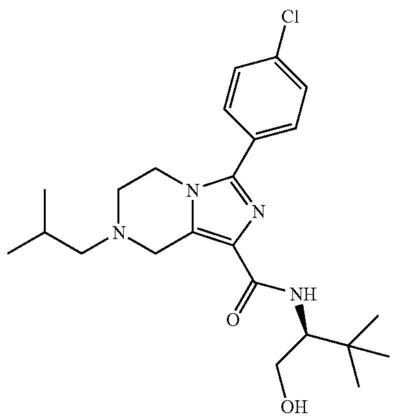 [SMILES: CC(C)CN1CCn2c(-c3ccc(Cl)cc3)nc(C(=O)N[C@H](CO)C(C)(C)C)c2C1] | (S)-3-(4-chlorophenyl)-N-(1-hydroxy-3,3-dimethylbutan-2-yl)-7-isobutyl-5,6,7,8-tetrahydroimidazo[1,5-a]pyrazine-1-carboxamide | 433.3 | 9 |
| 161 | 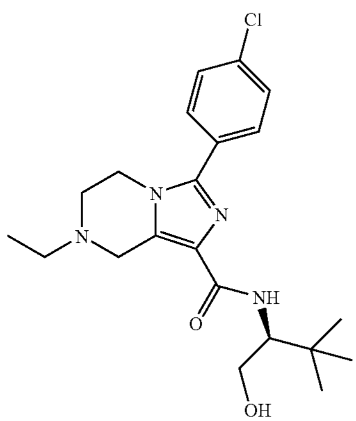 [SMILES: CCN1CCn2c(-c3ccc(Cl)cc3)nc(C(=O)N[C@H](CO)C(C)(C)C)c2C1] | (S)-3-(4-chlorophenyl)-7-ethyl-N-(1-hydroxy-3,3-dimethylbutan-2-yl)-5,6,7,8-tetrahydroimidazo[1,5-a]pyrazine-1-carboxamide | 405.3 | 9 |
| 162 | 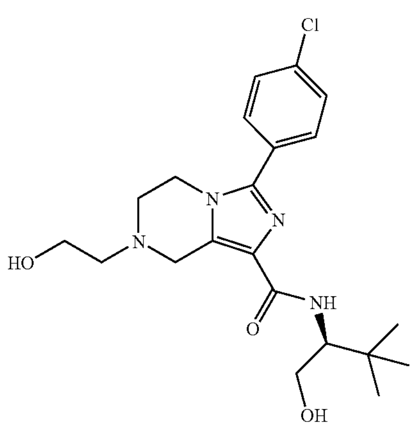 [SMILES: CC(C)(C)[C@@H](CO)NC(=O)c1nc(-c2ccc(Cl)cc2)n2c1CN(CCO)CC2] | (S)-3-(4-chlorophenyl)-N-(1-hydroxy-3,3-dimethylbutan-2-yl)-7-(2-hydroxyethyl)-5,6,7,8-tetrahydroimidazo[1,5-a]pyrazine-1-carboxamide | 421.3 | 9 |

TABLE I-continued

| Cmpd No. | Structure | Chemical Name | m/z | Example No. |
|---|---|---|---|---|
| 163 | 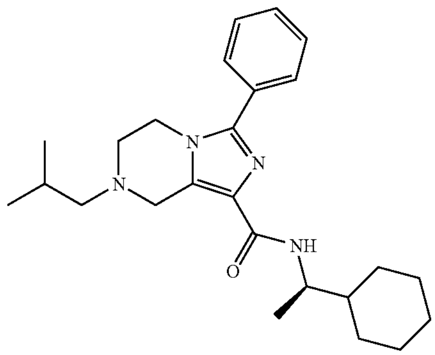 [SMILES: CC(C)CN1CCn2c(-c3ccccc3)nc(C(=O)N[C@H](C)C3CCCCC3)c2C1] | (R)-N-(1-cyclohexylethyl)-7-isobutyl-3-phenyl-5,6,7,8-tetrahydroimidazo[1,5-a]pyrazine-1-carboxamide | 409.2 | 9 |
| 164 | 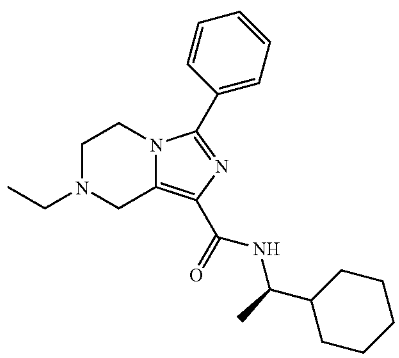 [SMILES: CCN1CCn2c(-c3ccccc3)nc(C(=O)N[C@H](C)C3CCCCC3)c2C1] | (R)-N-(1-cyclohexylethyl)-7-ethyl-3-phenyl-5,6,7,8-tetrahydroimidazo[1,5-a]pyrazine-1-carboxamide | 381.2 | 9 |
| 165 | 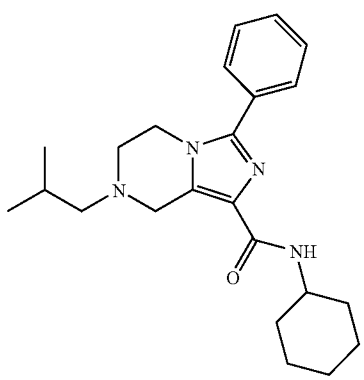 [SMILES: CC(C)CN1CCn2c(-c3ccccc3)nc(C(=O)NC3CCCCC3)c2C1] | N-cyclohexyl-7-isobutyl-3-phenyl-5,6,7,8-tetrahydroimidazo[1,5-a]pyrazine-1-carboxamide | 381.2 | 9 |
| 166 | 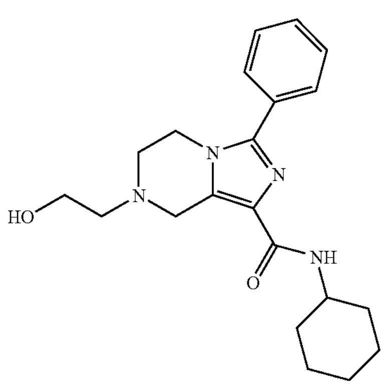 [SMILES: O=C(NC1CCCCC1)c1nc(-c2ccccc2)n2c1CN(CCO)CC2] | N-cyclohexyl-7-(2-hydroxyethyl)-3-phenyl-5,6,7,8-tetrahydroimidazo[1,5-a]pyrazine-1-carboxamide | 369.3 | 9 |

TABLE I-continued

| Cmpd No. | Structure | Chemical Name | m/z | Example No. |
|---|---|---|---|---|
| 167 | 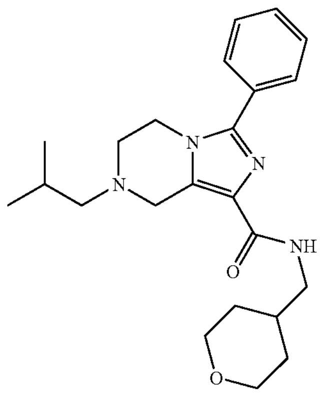 [SMILES: CC(C)CN1CCn2c(-c3ccccc3)nc(C(=O)NCC3CCOCC3)c2C1] | 7-isobutyl-3-phenyl-N-((tetrahydro-2H-pyran-4-yl)methyl)-5,6,7,8-tetrahydroimidazo[1,5-a]pyrazine-1-carboxamide | 397.2 | 9 |
| 168 | 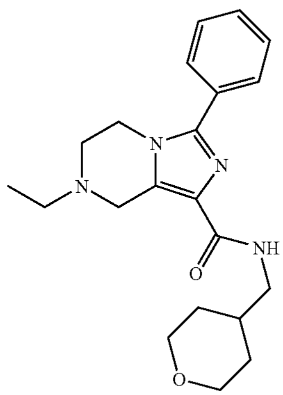 [SMILES: CCN1CCn2c(-c3ccccc3)nc(C(=O)NCC3CCOCC3)c2C1] | 7-ethyl-3-phenyl-N-((tetrahydro-2H-pyran-4-yl)methyl)-5,6,7,8-tetrahydroimidazo[1,5-a]pyrazine-1-carboxamide | 369.2 | 9 |
| 169 | 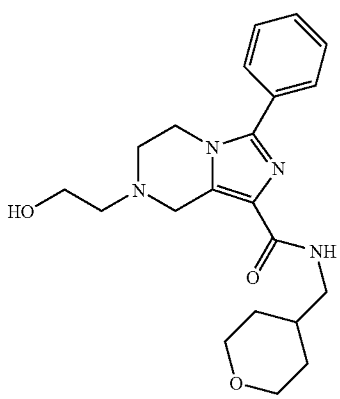 [SMILES: O=C(NCC1CCOCC1)c1nc(-c2ccccc2)n2c1CN(CCO)CC2] | 7-(2-hydrodxyethyl)-3-phenyl-N-((tetrahydro-2H-pyran-4-yl)methyl)-5,6,7,8-tetrahydroimidazo[1,5-a]pyrazine-1-carboxamide | 385.3 | 9 |
| 170 | 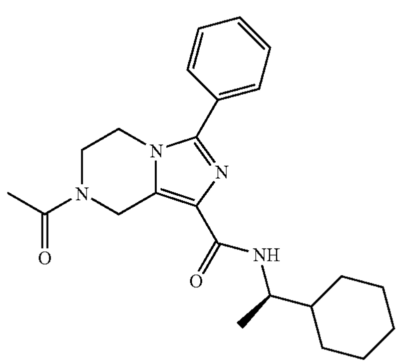 [SMILES: CC(=O)N1CCn2c(-c3ccccc3)nc(C(=O)N[C@H](C)C3CCCCC3)c2C1] | (R)-7-acetyl-N-(1-cyclohexylethyl)-3-phenyl-5,6,7,8-tetrahydroimidazo[1,5-a]pyrazine-1-carboxamide | 395.2 | 10 |

| Cmpd No. | Structure | Chemical Name | m/z | Example No. |
|---|---|---|---|---|
| 171 | 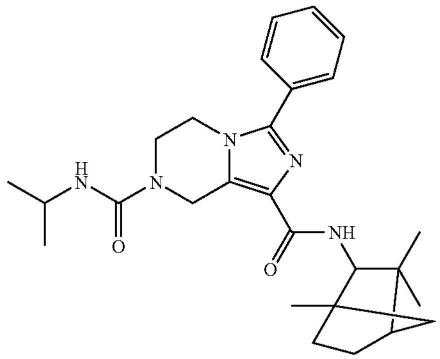 [SMILES: CC(C)NC(=O)N1CCn2c(-c3ccccc3)nc(C(=O)NC3C4(C)CCC(C4)C3(C)C)c2C1] | N7-isopropyl-3-phenyl-N1-(1,3,3-trimethylbicyclo[2.2.1]heptan-2-yl)-5,6-dihydroimidazo[1,5-a]pyrazine-1,7(8H)-dicarboxamide | 464.4 | 10 |
| 172 | 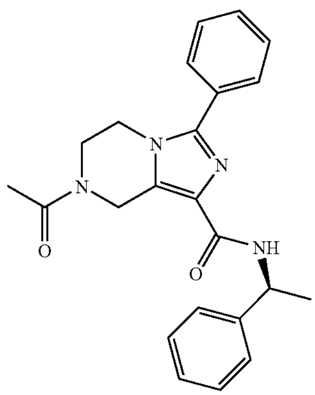 [SMILES: CC(=O)N1CCn2c(-c3ccccc3)nc(C(=O)N[C@@H](C)c3ccccc3)c2C1] | (S)-7-acetyl-3-phenyl-N-(1-phenylethyl)-5,6,7,8-tetrahydroimidazo[1,5-a]pyrazine-1-carboxamide | 389.3 | 10 |
| 173 | 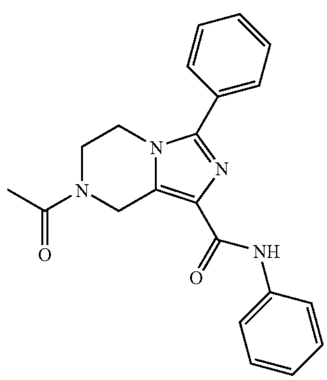 [SMILES: CC(=O)N1CCn2c(-c3ccccc3)nc(C(=O)Nc3ccccc3)c2C1] | 7-acetyl-N,3-diphenyl-5,6,7,8-tetrahydroimidazo[1,5-a]pyrazine-1-carboxamide | 361.3 | 10 |
| 174 | 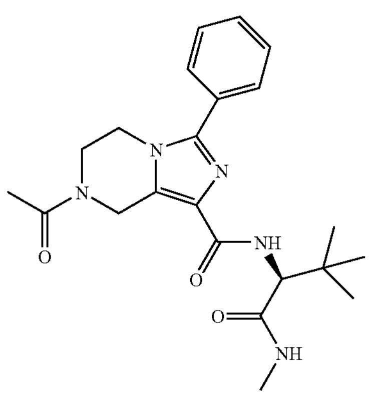 [SMILES: CNC(=O)[C@@H](NC(=O)c1nc(-c2ccccc2)n2c1CN(C(C)=O)CC2)C(C)(C)C] | (S)-7-acetyl-N-(3,3-dimethyl-1-(methylamino)-1-oxobutan-2-yl)-3-phenyl-5,6,7,8-tetrahydroimidazo[1,5-a]pyrazine-1-carboxamide | 412.3 | 10 |

TABLE I-continued

| Cmpd No. | Structure | Chemical Name | m/z | Example No. |
|---|---|---|---|---|
| 175 | 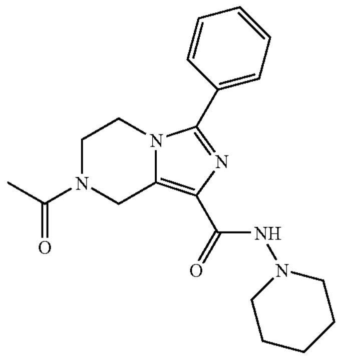 [SMILES: CC(=O)N1CCn2c(-c3ccccc3)nc(C(=O)NN3CCCCC3)c2C1] | 7-acetyl-3-phenyl-N-(piperidin-1-yl)-5,6,7,8-tetrahydroimidazo-[1,5-a]pyrazine-1-carboxamide | 368.3 | 10 |
| 176 | 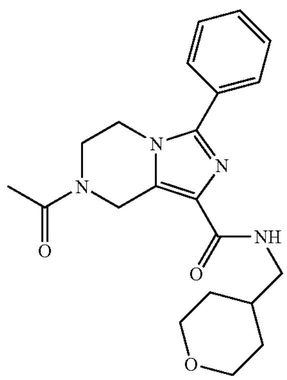 [SMILES: CC(=O)N1CCn2c(-c3ccccc3)nc(C(=O)NCC3CCOCC3)c2C1] | 7-acetyl-3-phenyl-N-((tetrahydro-2H-pyran-4-yl)methyl)-5,6,7,8-tetrahydroimidazo[1,5-a]pyrazine-1-carboxamide | 383.1 | 10 |
| 177 | 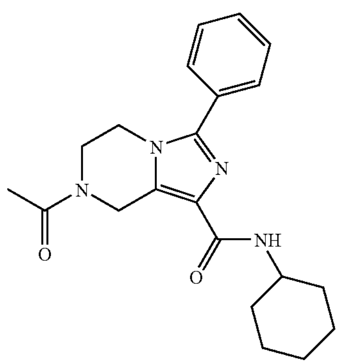 [SMILES: CC(=O)N1CCn2c(-c3ccccc3)nc(C(=O)NC3CCCCC3)c2C1] | 7-acetyl-N-cyclohexyl-3-phenyl-5,6,7,8-tetrahydroimidazo[1,5-a]pyrazine-1-carboxamide | 367.2 | 10 |
| 178 | 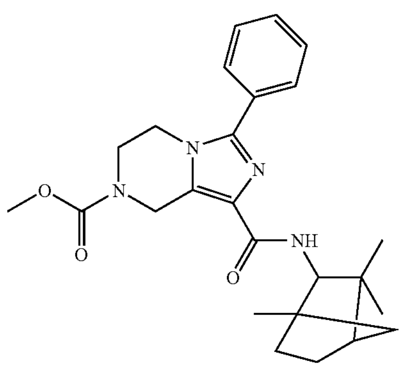 [SMILES: COC(=O)N1CCn2c(-c3ccccc3)nc(C(=O)NC3C4(C)CCC(C4)C3(C)C)c2C1] | methyl 3-phenyl-1-(1,3,3-trimethylbicyclo[2.2.1]heptan-2-ylcarbamoyl)-5,6-dihydroimidazo[1,5-a]pyrazine-7(8H)-carboxylate | 437.3 | 10 |

TABLE I-continued

| Cmpd No. | Structure | Chemical Name | m/z | Example No. |
|---|---|---|---|---|
| 179 | 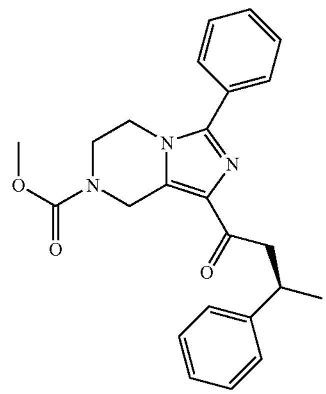 [SMILES: COC(=O)N1CCn2c(-c3ccccc3)nc(C(=O)C[C@@H](C)c3ccccc3)c2C1] | (S)-methyl 3-phenyl-1-(1-phenylethylcarbamoyl)-5,6-dihydroimidazo[1,5-a]pyrazine-7(8H)-carboxylate | 405.3 | 10 |
| 180 | 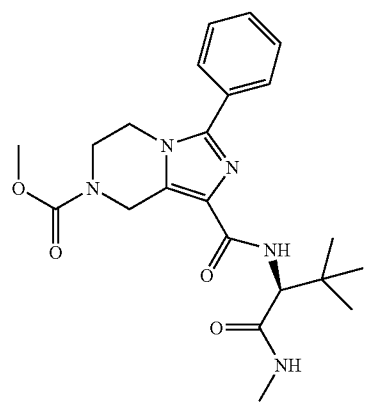 [SMILES: CNC(=O)[C@@H](NC(=O)c1nc(-c2ccccc2)n2c1CN(C(=O)OC)CC2)C(C)(C)C] | (S)-methyl 1-(3,3-dimethyl-1-(methylamino)-1-oxobutan-2-ylcarbamoyl)-3-phenyl-5,6-dihydroimidazo[1,5-a]pyrazine-7(8H)-carboxylate | 428.4 | 10 |
| 181 | 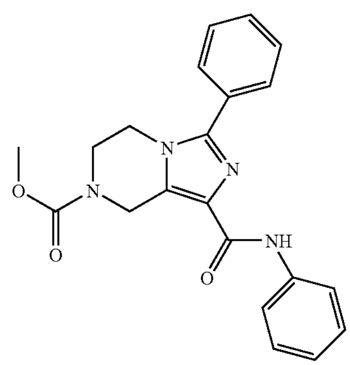 [SMILES: COC(=O)N1CCn2c(-c3ccccc3)nc(C(=O)Nc3ccccc3)c2C1] | methyl 3-phenyl-1-(phenylcarbamoyl)-5,6-dihydroimidazo[1,5-a]pyrazine-7(8H)-carboxylate | 377.1 | 10 |
| 182 | 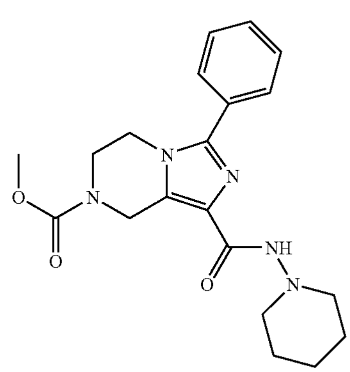 [SMILES: COC(=O)N1CCn2c(-c3ccccc3)nc(C(=O)NN3CCCCC3)c2C1] | methyl 3-phenyl-1-(piperidin-1-ylcarbamoyl)-5,6-dihydroimidazo[1,5-a]pyrazine-7(8H)-carboxylate | 384.3 | 10 |

TABLE I-continued

| Cmpd No. | Structure | Chemical Name | m/z | Example No. |
|---|---|---|---|---|
| 183 | 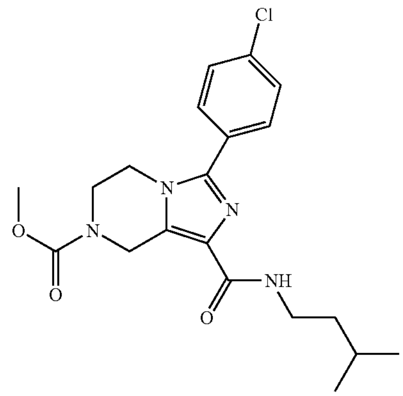 [SMILES: COC(=O)N1CCn2c(-c3ccc(Cl)cc3)nc(C(=O)NCCC(C)C)c2C1] | methyl 3-(4-chlorophenyl)-1-(isopentylcarbamoyl)-5,6-dihydroimidazol[1,5-a]pyrazine-7(8H)-carboxylate | 405.2 | 10 |
| 184 | 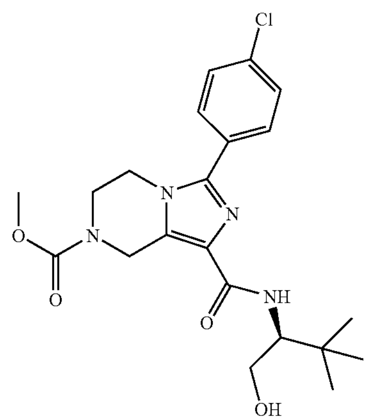 [SMILES: COC(=O)N1CCn2c(-c3ccc(Cl)cc3)nc(C(=O)N[C@H](CO)C(C)(C)C)c2C1] | (S)-methyl 3-(4-chlorophenyl)-1-(1-hydroxy-3,3-dimethylbutan-2-ylcarbamoyl)-5,6-dihydroimidazo[1,5-a]pyrazine-7(8H)-carboxylate | 435.3 | 10 |
| 185 | 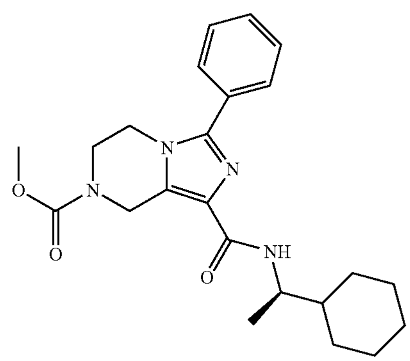 [SMILES: COC(=O)N1CCn2c(-c3ccccc3)nc(C(=O)N[C@H](C)C3CCCCC3)c2C1] | (R)-methyl 1-(1-cyclohexylethylcarbamoyl)-3-phenyl-5,6-dihydroimidazo[1,5-a]pyrazine-7(8H)-carboxylate | 411.1 | 10 |
| 186 | 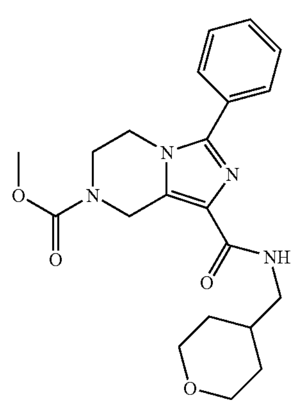 [SMILES: COC(=O)N1CCn2c(-c3ccccc3)nc(C(=O)NCC3CCOCC3)c2C1] | methyl 3-phenyl-1-((tetrahydro-2H-pyran-4-yl)methylcarbamoyl)-5,6-dihydroimidazo[1,5-a]pyrazin-7(8H)-carboxylate | 399.1 | 10 |

TABLE I-continued

| Cmpd No. | Structure | Chemical Name | m/z | Example No. |
|---|---|---|---|---|
| 187 | 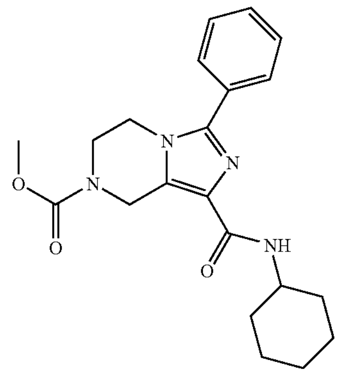 [SMILES: COC(=O)N1CCn2c(-c3ccccc3)nc(C(=O)NC3CCCCC3)c2C1] | methyl 1-(cyclohexylcarbamoyl)-3-phenyl-5,6-dihydroimidazo[1,5-a]pyrazine-7(8H)-carboxylate | 383.1 | 10 |
| 188 | 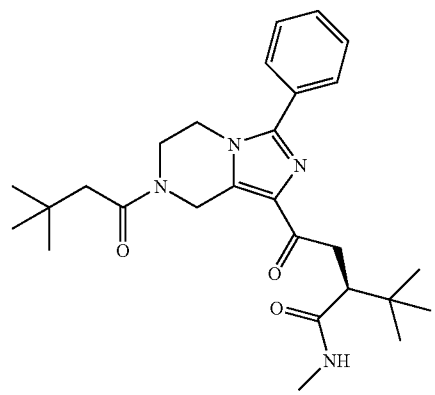 [SMILES: CNC(=O)[C@@H](CC(=O)c1nc(-c2ccccc2)n2c1CN(C(=O)CC(C)(C)C)CC2)C(C)(C)C] | (S)-N-(3,3-dimethyl-1-(methylamino)-1-oxobutan-2-yl)-7-(3,3-dimethylbutanoyl)-3-phenyl-5,6,7,8-tetrahydroimidazo[1,5-a]pyrazine-1-carboxamide | 468.0 | 10 |
| 189 | 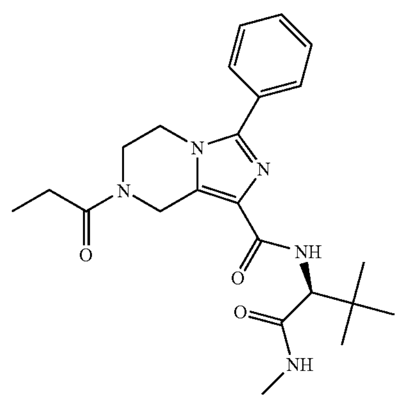 [SMILES: CCC(=O)N1CCn2c(-c3ccccc3)nc(C(=O)N[C@H](C(=O)NC)C(C)(C)C)c2C1] | (S)-N-(3,3-dimethyl-1-(methylamino)-1-oxobutan-2-yl)-3-phenyl-7-propionyl-5,6,7,8-tetrahydroimidazo[1,5-a]pyrazine-1-carboxamide | 426.2 | 10 |
| 190 | 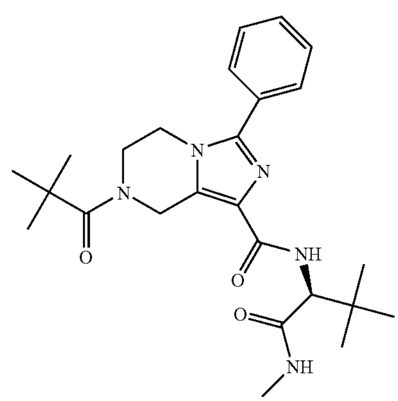 [SMILES: CNC(=O)[C@@H](NC(=O)c1nc(-c2ccccc2)n2c1CN(C(=O)C(C)(C)C)CC2)C(C)(C)C] | (S)-N-(3,3-dimethyl-1-(methylamino)-1-oxobutan-2-yl)-3-phenyl-7-pivaloyl-5,6,7,8-tetrahydroimidazo[1,5-a]pyrazine-1-carboxamide | 454.3 | 10 |

| Cmpd No. | Structure | Chemical Name | m/z | Example No. |
|---|---|---|---|---|
| 191 | 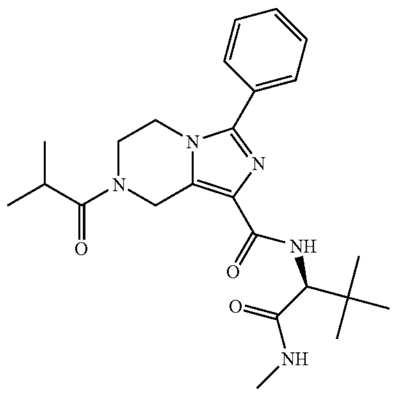 [SMILES: CNC(=O)[C@@H](NC(=O)c1nc(-c2ccccc2)n2c1CN(C(=O)C(C)C)CC2)C(C)(C)C] | (S)-N-(3,3-dimethyl-1-(methylamino)-1-oxobutan-2-yl)-7-isobutyryl-3-phenyl-5,6,7,8-tetrahydroimidazo[1,5-a]pyrazine-1-carboxamide | 440.3 | 10 |
| 192 | 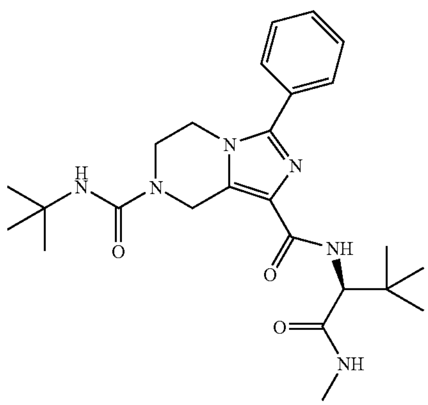 [SMILES: CNC(=O)[C@@H](NC(=O)c1nc(-c2ccccc2)n2c1CN(C(=O)NC(C)(C)C)CC2)C(C)(C)C] | (S)-N7-tert-butyl-N1-(3,3-dimethyl-1-(methylamino)-1-oxobutan-2-yl)-3-phenyl-5,6-dihydroimidazo[1,5-a]pyrazine-1,7(8H)-dicarboxamide | 469.5 | 10 |
| 193 | 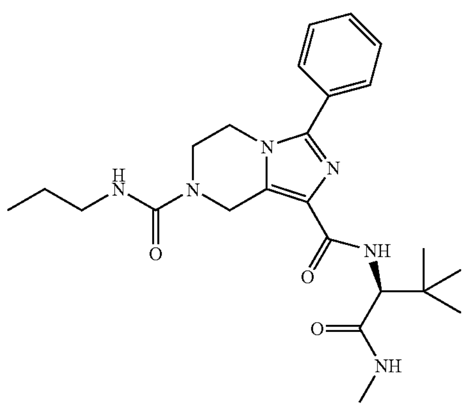 [SMILES: CCCNC(=O)N1CCn2c(-c3ccccc3)nc(C(=O)N[C@H](C(=O)NC)C(C)(C)C)c2C1] | (S)-N1-(3,3-dimethyl-1-(methylamino)-1-oxobutan-2-yl)-3-phenyl-N7-propyl-5,6-dihydroimidazo[1,5-a]pyrazine-1,7-(8H)-dicarboxamide | 455.4 | 10 |
| 194 | 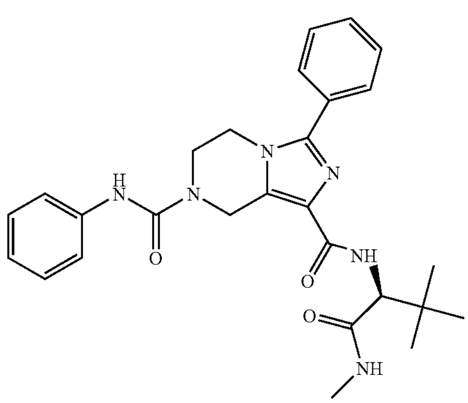 [SMILES: CNC(=O)[C@@H](NC(=O)c1nc(-c2ccccc2)n2c1CN(C(=O)Nc1ccccc1)CC2)C(C)(C)C] | (S)-N1-(3,3-dimethyl-1-(methylamino)-1-oxobutan-2-yl)-N7,3-diphenyl-5,6-dihydroimidazo[1,5-a]pyrazine-1,7(8H)-dicarboxamide | 489.2 | 10 |

TABLE I-continued

| Cmpd No. | Structure | Chemical Name | m/z | Example No. |
|---|---|---|---|---|
| 195 | 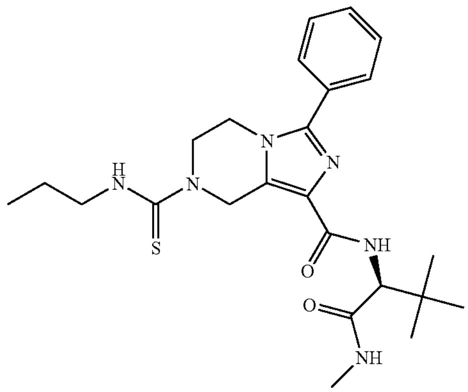 [SMILES: CCCNC(=S)N1CCn2c(-c3ccccc3)nc(C(=O)N[C@H](C(=O)NC)C(C)(C)C)c2C1] | (S)-N-(3,3-dimethyl-1-(methylamino)-1-oxobutan-2-yl)-3-phenyl-7-(propylcarbamothioyl)-5,6,7,8-tetrahydroimidazo[1,5-a]pyrazine-1-carboxamide | 471.4 | 11 |
| 196 | 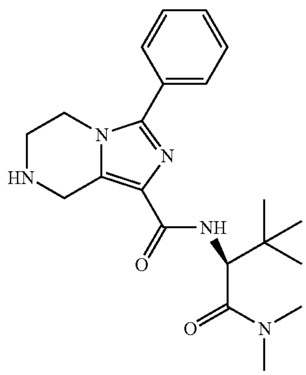 [SMILES: CN(C)C(=O)[C@@H](NC(=O)c1nc(-c2ccccc2)n2c1CNCC2)C(C)(C)C] | (S)-N-(1-(dimethylamino)-3-dimethyl-1-oxobutan-2-yl)-3-phenyl-5,6,7,8-tetrahydroimidazo[1,5-a]pyrazine-1-carboxamide | 384.3 | 12 |
| 197 | 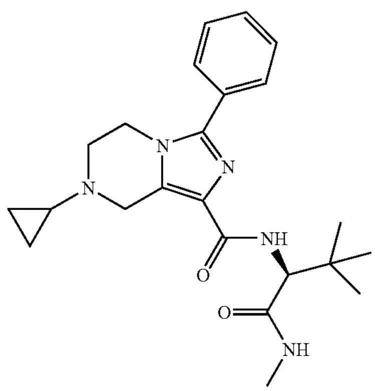 [SMILES: CNC(=O)[C@@H](NC(=O)c1nc(-c2ccccc2)n2c1CN(C1CC1)CC2)C(C)(C)C] | (S)-7-cyclopropyl-N-(3,3-dimethyl-1-(methylamino)-1-oxobutan-2-yl)-3-phenyl-5,6,7,8-tetrahydroimidazo[1,5-a]pyrazine-1-carboxamide | 410.2 | 13 |
| 198 | 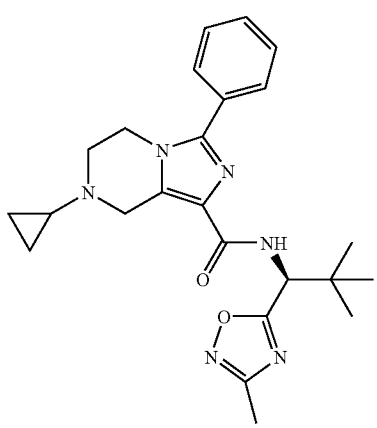 [SMILES: Cc1noc([C@@H](NC(=O)c2nc(-c3ccccc3)n3c2CN(C2CC2)CC3)C(C)(C)C)n1] | (S)-7-cyclopropyl-N-(2,2-dimethyl-1-(3-methyl-1,2,4-oxadiazol-5-yl)propyl)-3-phenyl-5,6,7,8-tetrahydroimidazo[1,5-a]pyrazine-1-carboxamide | 435.0 | 13 |

TABLE I-continued

| Cmpd No. | Structure | Chemical Name | m/z | Example No. |
|---|---|---|---|---|
| 199 | 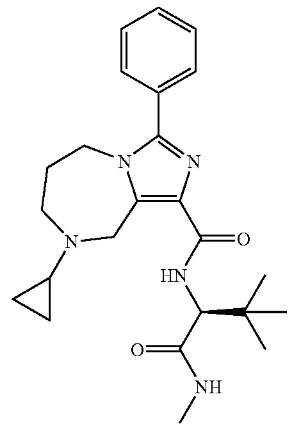 [SMILES: CNC(=O)[C@@H](NC(=O)c1nc(-c2ccccc2)n2c1CN(C1CC1)CCC2)C(C)(C)C] | (S)-8-cyclopropyl-N-(3,3-dimethyl-1-(methylamino)-1-oxobutan-2-yl)-3-phenyl-6,7,8,9-tetrahydro-5H-imidazo[1,5-a][1,4]diazepine-1-carboxamide | 424.0 | 13 |
| 200 | 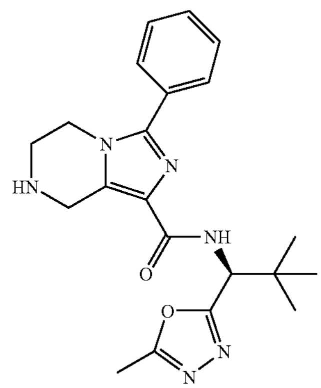 [SMILES: Cc1nnc([C@@H](NC(=O)c2nc(-c3ccccc3)n3c2CNCC3)C(C)(C)C)o1] | (S)-N-(2,2-dimethyl-1-(5-methyl-1,3,4-oxadiazol-2-yl)propyl)-3-phenyl-5,6,7,8-tetrahydroimidazo[1,5-a]pyrazine-1-carboxamide | 395.0 | 14 |
| 201 | 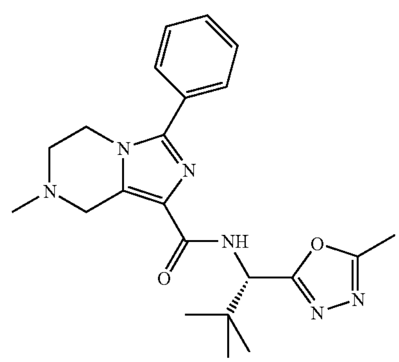 | (S)-N-(2,2-dimethyl-1-(5-methyl-1,3,4-oxadiazol-2-yl)propyl)-7-methyl-3-phenyl-5,6,7,8-tetrahydroimidazo[1,5-a]pyrazine-1-carboxamide | 409.0 | 14 |
| 202 | 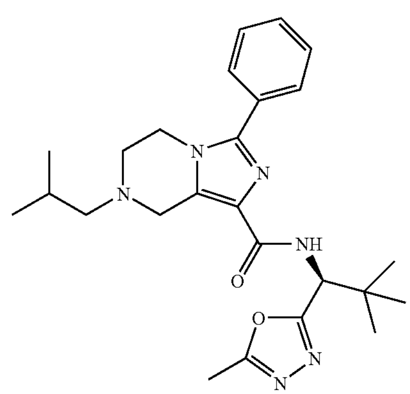 [SMILES: Cc1nnc([C@@H](NC(=O)c2nc(-c3ccccc3)n3c2CN(CC(C)C)CC3)C(C)(C)C)o1] | (S)-N-(2,2-dimethyl-1-(5-methyl-1,3,4-oxadiazol-2-yl)propyl)-7-isobutyl-3-phenyl-5,6,7,8-tetrahydroimidazo[1,5-a]pyrazine-1-carboxamide | 451.0 | 14 |

TABLE I-continued

| Cmpd No. | Structure | Chemical Name | m/z | Example No. |
|---|---|---|---|---|
| 203 | 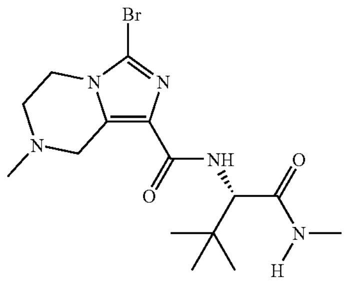 | (S)-3-bromo-N-(3,3-dimethyl-1-(methylamino)-1-oxobutan-2-yl)-7-methyl-5,6,7,8-tetrahydroimidazo[1,5-a]pyrazine-1-carboxamide | 388.9 | 15 |
| 204 | 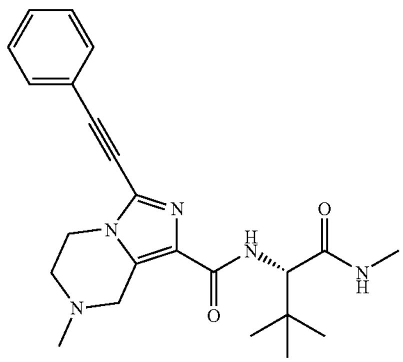 [SMILES: CNC(=O)[C@@H](NC(=O)c1nc(C#Cc2ccccc2)n2c1CN(C)CC2)C(C)(C)C] | (S)-N-(3,3-dimethyl-1-(methylamino)-1-oxobutan-2-yl)-7-methyl-3-(phenylethynyl)-5,6,7,8-tetrahydroimidazo[1,5-a]pyrazine-1-carboxamide | 408.0 | 16 |
| 205 | 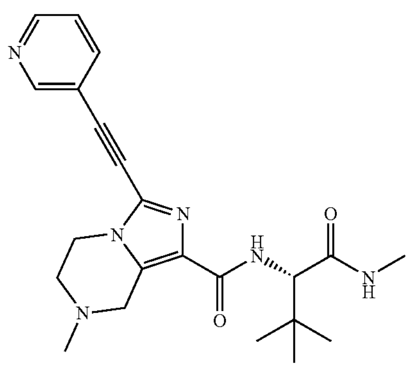 [SMILES: CNC(=O)[C@@H](NC(=O)c1nc(C#Cc2cccnc2)n2c1CN(C)CC2)C(C)(C)C] | (S)-N-(3,3-dimethyl-1-(methylamino)-1-oxobutan-2-yl)-7-methyl-3-(pyridin-3-ylethynyl)-5,6,7,8-tetrahydroimidazo[1,5-a]pyrazine-1-carboxamide | 409.0 | 15 |
| 206 | 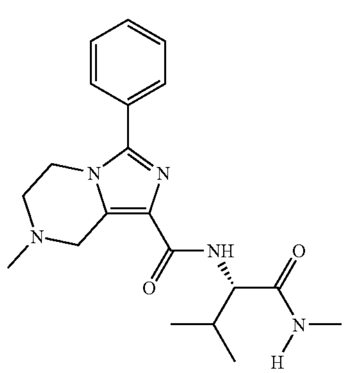 | (S)-7-methyl-N-(3-methyl-1-(methylamino)-1-oxobutan-2-yl)-3-phenyl-5,6,7,8-tetrahydroimidazo[1,5-a]pyrazine-1-carboxamide | 369.1 | 17 |

TABLE I-continued
| Cmpd No. | Structure | Chemical Name | m/z | Example No. |
|---|---|---|---|---|
| 207 | 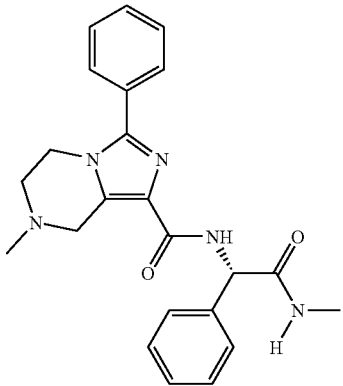 | (S)-7-methyl-N-(2-(methylamino)-2-oxo-1-phenylethyl)-3-phenyl-5,6,7,8-tetrahydroimidazo[1,5-a]pyrazine-1-carboxamide | 404.0 | 17 |
| 208 | 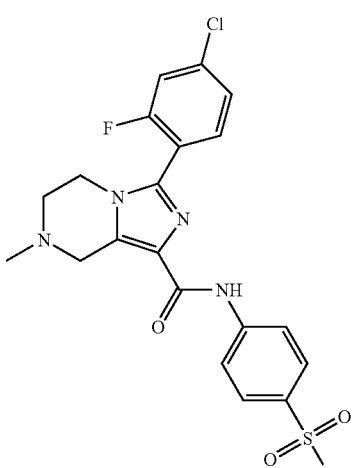 | 3-(4-chloro-2-fluorophenyl)-7-methyl-N-(4-sulfamoylphenyl)-5,6,7,8-tetrahydroimidazo[1,5-a]pyrazine-1-carboxamide | 464.0 | 18 |
| 209 | 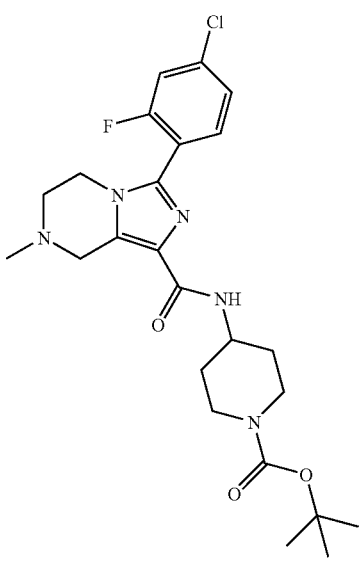 [SMILES: CN1CCn2c(-c3ccc(Cl)cc3F)nc(C(=O)NC3CCN(C(=O)OC(C)(C)C)CC3)c2C1] | tert-butyl 4-(3-(4-chloro-2-fluorophenyl)-7-methyl-5,6,7,8-tetrahydroimidazo[1,5-a]pyrazine-1-carboxamide)piperidine-1-carboxylate | 492.0 | 18 |

TABLE I-continued

| Cmpd No. | Structure | Chemical Name | m/z | Example No. |
|---|---|---|---|---|
| 210 | 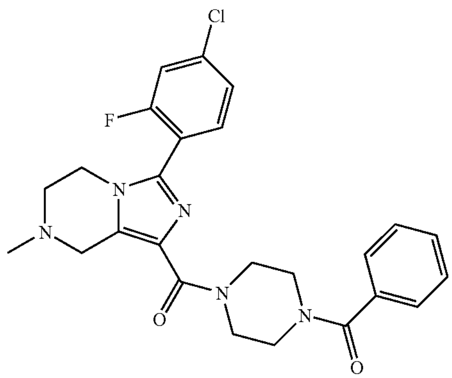 [SMILES: CN1CCn2c(-c3ccc(Cl)cc3F)nc(C(=O)N3CCN(C(=O)c4ccccc4)CC3)c2C1] | (4-benzoylpiperazin-1-yl)(3-(4-chloro-2-fluorophenyl)-7-methyl-5,6,7,8-tetrahydroimidazo[1,5-a]pyrazin-1-yl)methanone | 482.0 | 18 |
| 211 | 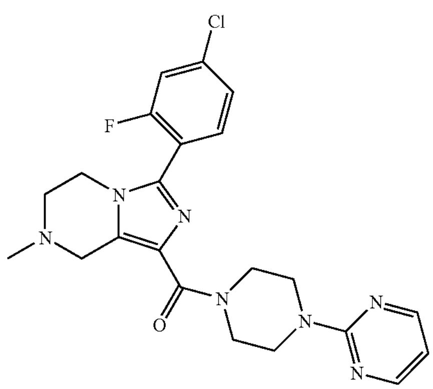 [SMILES: CN1CCn2c(-c3ccc(Cl)cc3F)nc(C(=O)N3CCN(c4ncccn4)CC3)c2C1] | (3-(4-chloro-2-fluorophenyl)-7-methyl-5,6,7,8-tetrahydroimidazo[1,5-a]pyrazin-1-yl)(4-(pyrimidin-2-yl)piperazin)-1-yl)methanone | 456.0 | 18 |
| 212 | 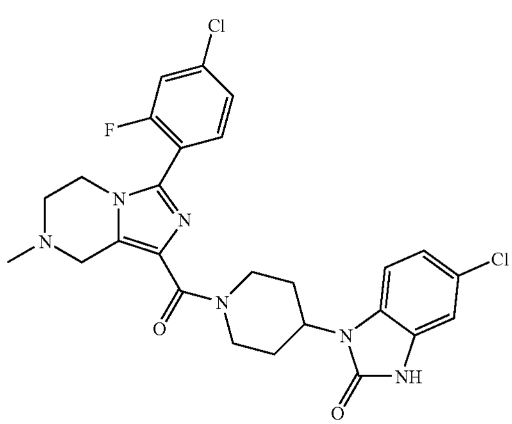 [SMILES: CN1CCn2c(-c3ccc(Cl)cc3F)nc(C(=O)N3CCC(n4c(=O)[nH]c5cc(Cl)ccc54)CC3)c2C1] | 5-chloro-1-(1-(3-(4-chloro-2-fluorophenyl)-7-methyl-5,6,7,8-tetrahydroimidazo[1,5-a]pyrazine-1-carbonyl)piperidin-4-yl)-1H-benzo[d]imidazol-2(3H)-one | 543.0 | 18 |

TABLE I-continued

| Cmpd No. | Structure | Chemical Name | m/z | Example No. |
|---|---|---|---|---|
| 213 | 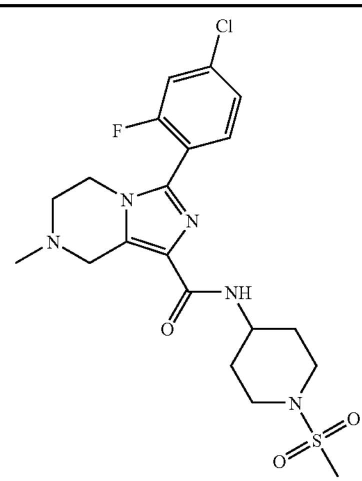 | 3-(4-chloro-2-fluorophenyl)-7-methyl-N-(1-(methylsulfonyl)piperidin-4-yl)-5,6,7,8-tetrahydroimidazo[1,5-a]pyrazine-1-carboxamide | 470.0 | 18 |
| 214 | 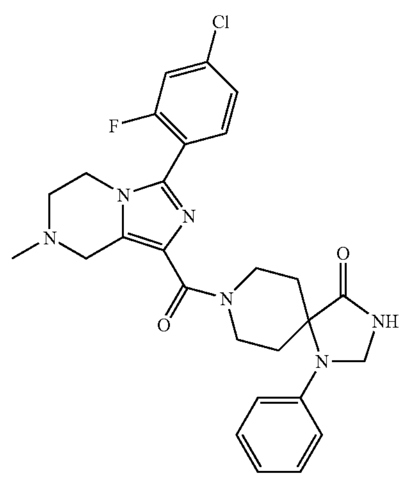 [SMILES: CN1CCn2c(-c3ccc(Cl)cc3F)nc(C(=O)N3CCC4(CC3)C(=O)NCN4c3ccccc3)c2C1] | 8-(3-(4-chloro-2-fluorophenyl)-7-methyl-5,6,7,8-tetrahydroimidazo[1,5-a]pyrazine-1-carbonyl)-1-phenyl-1,3,8-triazaspiro[4.5]decan-4-one | 523.0 | 18 |
| 215 | 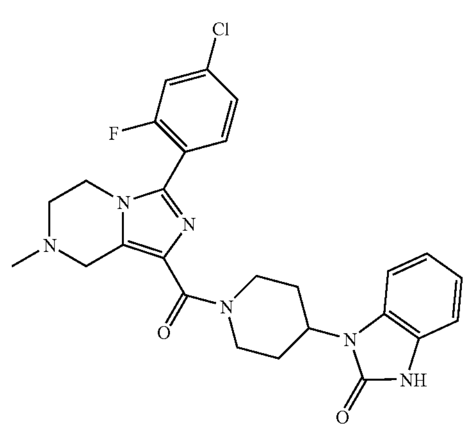 [SMILES: CN1CCn2c(-c3ccc(Cl)cc3F)nc(C(=O)N3CCC(n4c(=O)[nH]c5ccccc54)CC3)c2C1] | 1-(1-(3-(4-chloro-2-fluorophenyl)-7-methyl-5,6,7,8-tetrahydroimidazo[1,5-a]pyrazine-1-carbonyl)piperidin-4-yl)-1H-benzo[d]imidazol-2(3H)-one | 509.0 | 18 |

TABLE I-continued

| Cmpd No. | Structure | Chemical Name | m/z | Example No. |
|---|---|---|---|---|
| 216 | 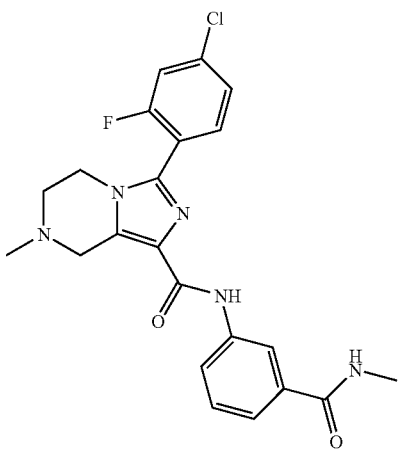 | 3-(4-chloro-2-fluorophenyl)-7-methyl-N-(3-(methylcarbamoyl)phenyl)-5,6,7,8-tetrahydroimidazo[1,5-a]pyrazine-1-carboxamide | 442.0 | 18 |
| 217 | 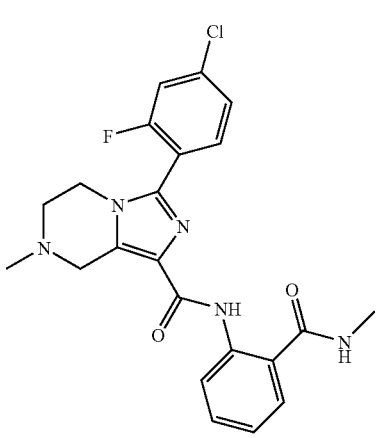 | 3-(4-chloro-2-fluorophenyl)-7-methyl-N-(2-(methylcarbamoyl)phenyl)-5,6,7,8-tetrahydroimidazo[1,5-a]pyrazine-1-carboxamide | 442.0 | 18 |
| 218 | 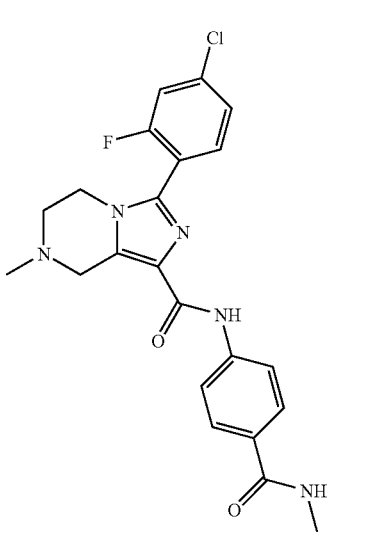 | 3-(4-chloro-2-fluorophenyl)-7-methyl-N-(4-(methylcarbamoyl)phenyl)-5,6,7,8-tetrahydroimidazo[1,5-a]pyrazine-1-carboxamide | 442.0 | 18 |

| Cmpd No. | Structure | Chemical Name | m/z | Example No. |
|---|---|---|---|---|
| 219 | 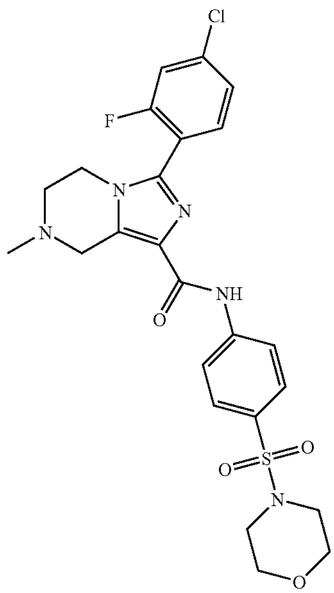 [SMILES: CN1CCn2c(-c3ccc(Cl)cc3F)nc(C(=O)Nc3ccc(S(=O)(=O)N4CCOCC4)cc3)c2C1] | 3-(4-chloro-2-fluorophenyl)-7-methyl-N-(4-morpholinosulfonyl)phenyl)-5,6,7,8-tetrahydroimidazo[1,5-a]pyrazine-1-carboxamide | 534.0 | 18 |
| 220 | 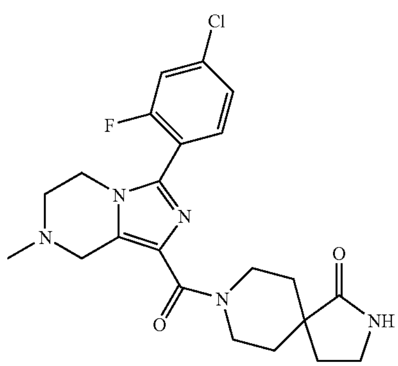 [SMILES: CN1CCn2c(-c3ccc(Cl)cc3F)nc(C(=O)N3CCC4(CCNC4=O)CC3)c2C1] | 8-(3-(4-chloro-2-fluorophenyl)-7-methyl-5,6,7,8-tetrahydroimidazo[1,5-a]pyrazine-1-carbonyl)-2,8-diazaspiro[4.5]decan-1-one | 446.0 | 18 |
| 221 | 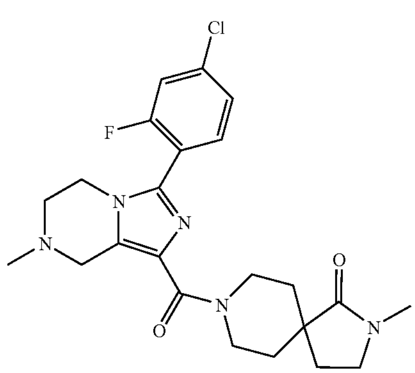 | 8-(3-(4-chloro-2-fluorophenyl)-7-methyl-5,6,7,8-tetrahydroimidazo[1,5-a]pyrazine-1-carbonyl)-2-methyl-2,8-diazaspiro[4.5]decan-1-one | 460.0 | 18 |

TABLE I-continued

| Cmpd No. | Structure | Chemical Name | m/z | Example No. |
|---|---|---|---|---|
| 222 | 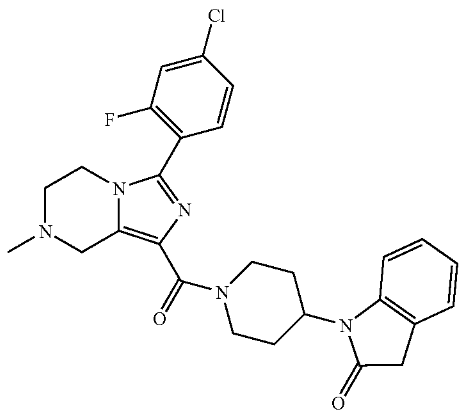 [SMILES: CN1CCn2c(-c3ccc(Cl)cc3F)nc(C(=O)N3CCC(N4C(=O)Cc5ccccc54)CC3)c2C1] | 1-(1-(3-(4-chloro-2-fluorophenyl)-7-methyl-5,6,7,8-tetrahydroimidazo[1,5-a]pyrazine-1-carbonyl)piperidin-4-yl)indolin-2-one | 508.0 | 18 |
| 223 | 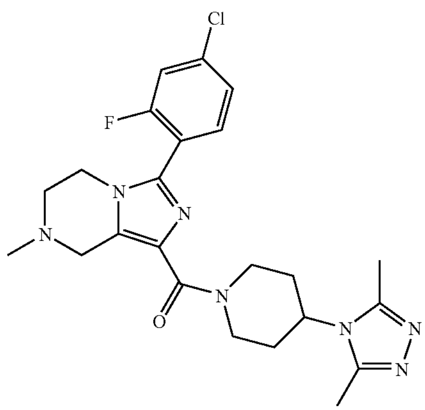 [SMILES: Cc1nnc(C)n1C1CCN(C(=O)c2nc(-c3ccc(Cl)cc3F)n3c2CN(C)CC3)CC1] | (3-(4-chloro-2-fluorophenyl)-7-methyl-5,6,7,8-tetrahydroimidazo[1,5-a]pyrazin-1-yl)(4-(3,5-dimethyl-4H-1,2,4-triazol-4-yl)piperidin-1-yl)methanone | 472.0 | 18 |
| 224 | 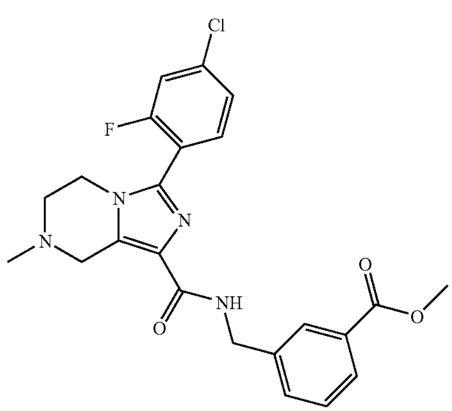 | methyl 3-((3-(4-chloro-2-fluorophenyl)-7-methyl-5,6,7,8-tetrahydroimidazo[1,5-a]pyrazine-1-carboxamido)methyl)benzoate | 457.0 | 18 |

TABLE I-continued

| Cmpd No. | Structure | Chemical Name | m/z | Example No. |
|---|---|---|---|---|
| 225 | 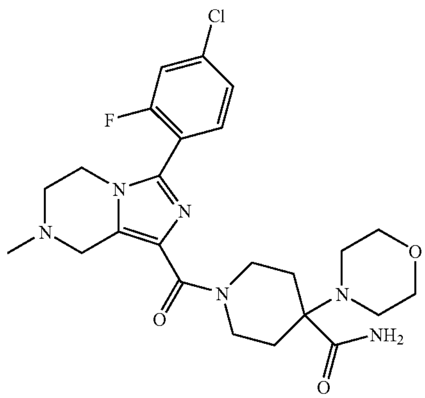 [SMILES: CN1CCn2c(-c3ccc(Cl)cc3F)nc(C(=O)N3CCC(C(N)=O)(N4CCOCC4)CC3)c2C1] | 1-(3-(4-chloro-2-fluorophenyl)-7-methyl-5,6,7,8-tetrahydroimidazo[1,5-a]pyrazine-1-carbonyl)-4-morpholinopiperidine-4-carboxamide | 505.0 | 18 |
| 226 | 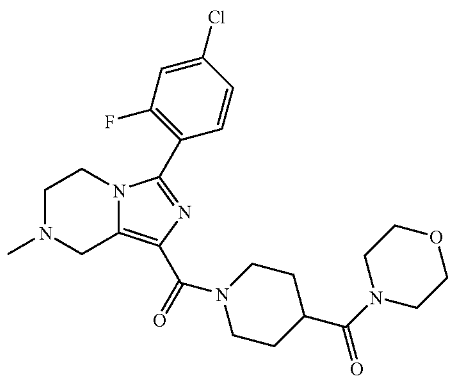 [SMILES: CN1CCn2c(-c3ccc(Cl)cc3F)nc(C(=O)N3CCC(C(=O)N4CCOCC4)CC3)c2C1] | (3-(4-chloro-2-fluorophenyl)-7-methyl-5,6,7,8-tetrahydroimidazo[1,5-a]pyrazin-1-yl)(4-(morpholine-4-carbonyl)piperidin-1-yl)methanone | 490.0 | 18 |
| 227 | 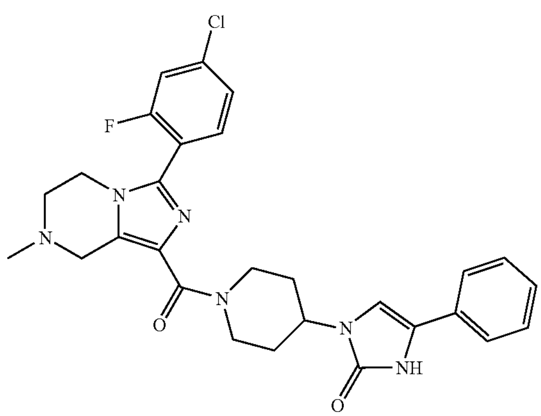 [SMILES: CN1CCn2c(-c3ccc(Cl)cc3F)nc(C(=O)N3CCC(n4cc(-c5ccccc5)[nH]c4=O)CC3)c2C1] | 1-(1-(3-(4-chloro-2-fluorophenyl)-7-methyl-5,6,7,8-tetrahydroimidazo[1,5-a]pyrazine-1-carbonyl)piperidin-4-yl)-4-phenyl-1H-imidazol-2(3H)-one | 535.0 | 18 |
| 228 | 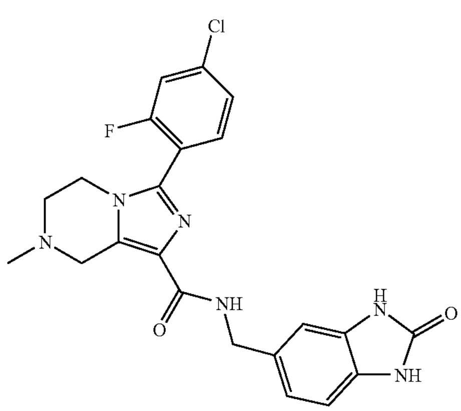 [SMILES: CN1CCn2c(-c3ccc(Cl)cc3F)nc(C(=O)NCc3ccc4[nH]c(=O)[nH]c4c3)c2C1] | 3-(4-chloro-2-fluorophenyl)-7-methyl-N-((2-oxo-2,3-dihydro-1H-benzo[d]imidazol-5-yl)methyl)-5,6,7,8-tetrahydroimidazo[1,5-a]pyrazine-1-carboxamide | 455.0 | 18 |

TABLE I-continued

| Cmpd No. | Chemical Name | m/z | Example No. |
|---|---|---|---|
| 229 | N-(3-hydroxypropyl)-7-methyl-3-phenyl-5,6,7,8-tetrahydroimidazo[1,5-a]pyrazine-1-carboxamide | 315.0 | 18 |
| 230 | N-(1-hydroxy-2-methylpropan-2-yl)-7-methyl-3-phenyl-5,6,7,8-tetrahydroimidazo[1,5-a]pyrazine-1-carboxamide | 329.0 | 18 |
| 231 | N-(1-hydroxypropan-2-yl)-7-methyl-3-phenyl-5,6,7,8-tetrahydroimidazo[1,5-a]pyrazine-1-carboxamide | 315.0 | 18 |
| 232 | N-(1-hydroxybutan-2-yl)-7-methyl-3-phenyl-5,6,7,8-tetrahydroimidazo[1,5-a]pyrazine-1-carboxamide | 329.0 | 18 |

TABLE I-continued

| Cmpd No. | Structure | Chemical Name | m/z | Example No. |
|---|---|---|---|---|
| 233 | 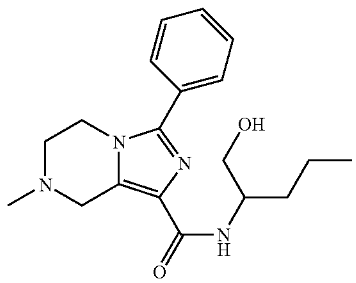 [SMILES: CCCC(CO)NC(=O)c1nc(-c2ccccc2)n2c1CN(C)CC2] | N-(1-hydroxypentan-2-yl)-7-methyl-3-phenyl-5,6,7,8-tetrahydroimidazo[1,5-a]pyrazine-1-carboxamide | 343.0 | 18 |
| 234 | 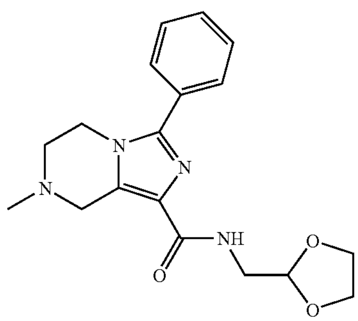 [SMILES: CN1CCn2c(-c3ccccc3)nc(C(=O)NCC3OCCO3)c2C1] | N-((1,3-dioxolan-2-yl)methyl)-7-methyl-3-phenyl-5,6,7,8-tetrahydroimidazo[1,5-a]pyrazine-1-carboxamide | 343.2 | 18 |
| 235 | 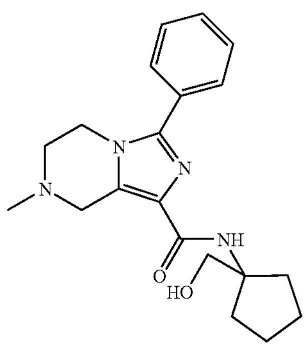 [SMILES: CN1CCn2c(-c3ccccc3)nc(C(=O)NC3(CO)CCCC3)c2C1] | N-(1-(hydroxymethyl)cyclopentyl)-7-methyl-3-phenyl-5,6,7,8-tetrahydroimidazo[1,5-a]pyrazine-1-carboxamide | 355.3 | 18 |
| 236 | 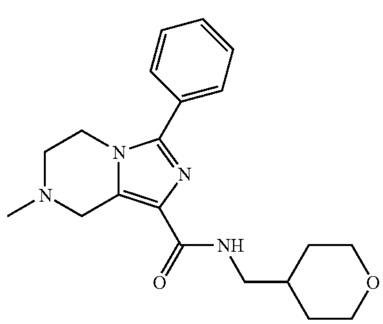 [SMILES: CN1CCn2c(-c3ccccc3)nc(C(=O)NCC3CCOCC3)c2C1] | 7-methyl-3-phenyl-N-((tetrahydro-2H-pyran-4-yl)methyl)-5,6,7,8-tetrahydroimidazo[1,5-a]pyrazine-1-carboxamide | 355.3 | 18 |

TABLE I-continued

| Cmpd No. | Structure | Chemical Name | m/z | Example No. |
|---|---|---|---|---|
| 237 | 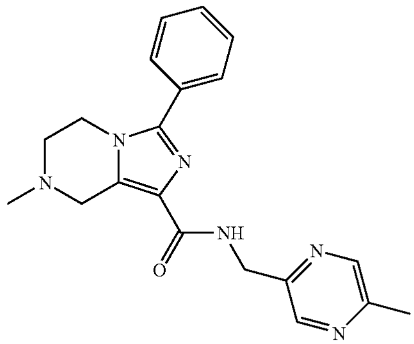 | 7-methyl-N-((5-methylpyrazin-2-yl)methyl)-3-phenyl-5,6,7,8-tetrahydroimidazo[1,5-a]pyrazine-1-carboxamide | 363.3 | 18 |
| 238 | 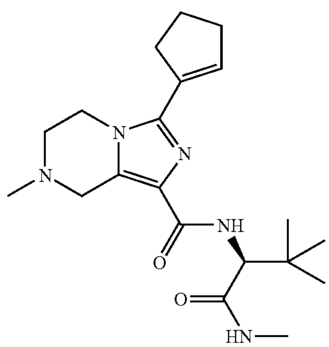 [SMILES: CNC(=O)[C@@H](NC(=O)c1nc(C2=CCCC2)n2c1CN(C)CC2)C(C)(C)C] | (S)-3-cyclopentyl-N-(3,3-dimethyl-1-(methylamino)-1-oxobutan-2-yl)-7-methyl-5,6,7,8-tetrahydroimidazo[1,5-a]pyrazine-1-carboxamide | 374.2 | 19 |
| 239 | 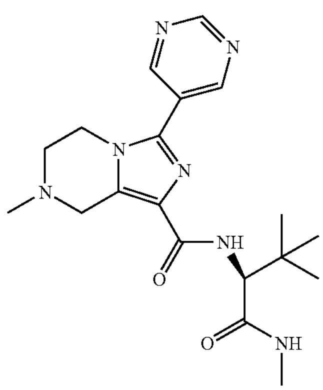 [SMILES: CNC(=O)[C@@H](NC(=O)c1nc(-c2cncnc2)n2c1CN(C)CC2)C(C)(C)C] | (S)-N-(3,3-dimethyl-1-(methylamino)-1-oxobutan-2-yl)-7-methyl-3-(pyrimidin-5-yl)-5,6,7,8-tetrahydroimidazo[1,5-a]pyrazine-1-carboxamide | 386.1 | 19 |
| 240 | 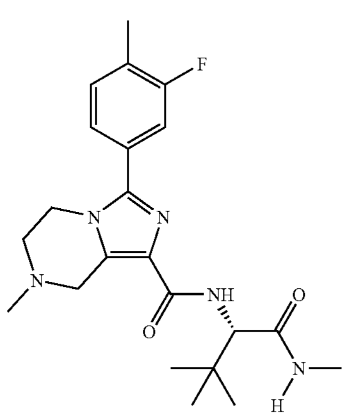 | (S)-N-(3,3-dimethyl-1-(methylamino)-1-oxobutan-2-yl)-3-(3-fluoro-4-methylphenyl)-7-methyl-5,6,7,8-tetrahydroimidazo[1,5-a]pyrazine-1-carboxamide | 416.0 | 19 |

TABLE I-continued

| Cmpd No. | Structure | Chemical Name | m/z | Example No. |
|---|---|---|---|---|
| 241 | 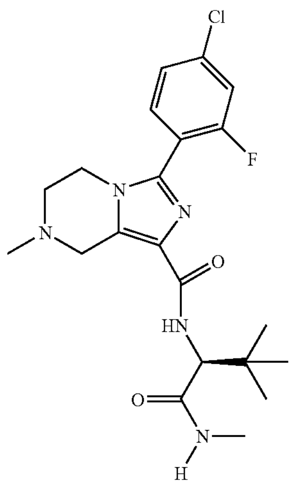 [SMILES: CNC(=O)[C@@H](NC(=O)c1nc(-c2ccc(Cl)cc2F)n2c1CN(C)CC2)C(C)(C)C] | (S)-3-(4-chloro-2-fluorophenyl)-N-(3,3-dimethyl-1-(methylamino)-1-oxobutan-2-yl)-7-methyl-5,6,7,8-tetrahydroimidazo[1,5-a]pyrazine-1-carboxamide | 435.9 | 19 |
| 242 | 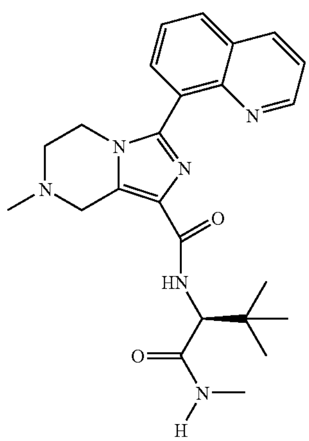 [SMILES: CNC(=O)[C@@H](NC(=O)c1nc(-c2cccc3cccnc23)n2c1CN(C)CC2)C(C)(C)C] | (S)-N-(3,3-dimethyl-1-(methylamino)-1-oxobutan-2-yl)-7-methyl-3-(quinolin-8-yl)-5,6,7,8-tetrahydroimidazo[1,5-a]pyrazine-1-carboxamide | 435.0 | 19 |
| 243 | 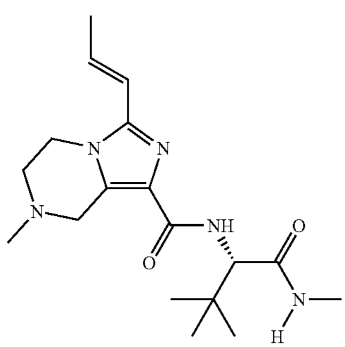 | (S,E)-N-(3,3-dimethyl-1-(methylamino)-1-oxobutan-2-yl)-7-methyl-3-(prop-1-enyl)-5,6,7,8-tetrahydroimidazo[1,5-a]pyrazine-1-carboxamide | 348.0 | 19 |
| 244 | 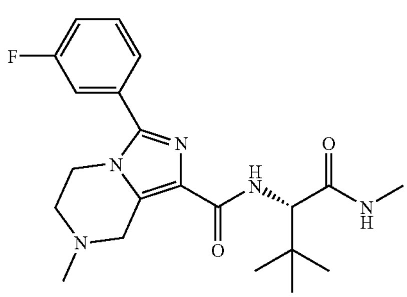 [SMILES: CNC(=O)[C@@H](NC(=O)c1nc(-c2cccc(F)c2)n2c1CN(C)CC2)C(C)(C)C] | (S)-N-(3,3-dimethyl-1-(methylamino)-1-oxobutan-2-yl)-3-(3-fluorophenyl)-7-methyl-5,6,7,8-tetrahydroimidazo[1,5-a]pyrazine-1-carboxamide | 402.0 | 19 |

TABLE I-continued

| Cmpd No. | Structure | Chemical Name | m/z | Example No. |
|---|---|---|---|---|
| 245 | 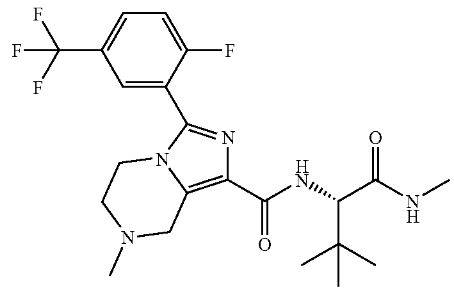 [SMILES: CNC(=O)[C@@H](NC(=O)c1nc(-c2cc(C(F)(F)F)ccc2F)n2c1CN(C)CC2)C(C)(C)C] | (S)-N-(3,3-dimethyl-1-(methylamino)-1-oxobutan-2-yl)-3-(2-fluoro-5-(trifluoromethyl)phenyl)-7-methyl-5,6,7,8-tetrahydroimidazo[1,5-a]pyrazine-1-carboxamide | 470.0 | 19 |
| 246 | 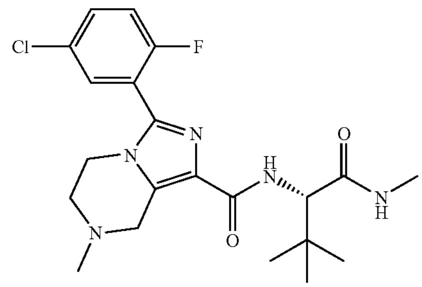 [SMILES: CNC(=O)[C@@H](NC(=O)c1nc(-c2cc(Cl)ccc2F)n2c1CN(C)CC2)C(C)(C)C] | (S)-3-(5-chloro-2-fluorophenyl)-N-(3,3-dimethyl-1-(methylamino)-1-oxobutan-2-yl)-7-methyl-5,6,7,8-tetrahydroimidazo[1,5-a]pyrazine-1-carboxamide | 436.0 | 19 |
| 247 | 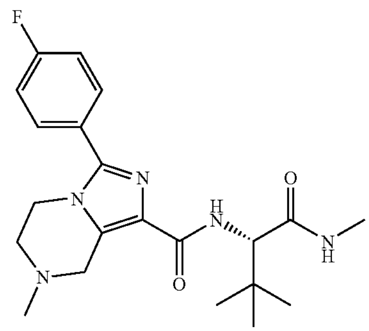 [SMILES: CNC(=O)[C@@H](NC(=O)c1nc(-c2ccc(F)cc2)n2c1CN(C)CC2)C(C)(C)C] | (S)-N-(3,3-dimethyl-1-(methylamino)-1-oxobutan-2-yl)-3-(4-fluorophenyl)-7-methyl-5,6,7,8-tetrahydroimidazo[1,5-a]pyrazine-1-carboxamide | 402.0 | 19 |
| 248 | 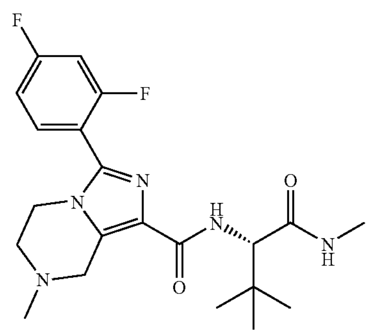 [SMILES: CNC(=O)[C@@H](NC(=O)c1nc(-c2ccc(F)cc2F)n2c1CN(C)CC2)C(C)(C)C] | (S)-3-(2,4-difluorophenyl)-N-(3,3-dimethyl-1-(methylamino)-1-oxobutan-2-yl)-7-methyl-5,6,7,8-tetrahydroimidazo[1,5-a]pyrazine-1-carboxamide | 420.0 | 19 |
| 249 | 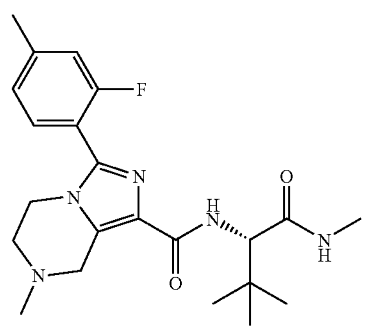 [SMILES: CNC(=O)[C@@H](NC(=O)c1nc(-c2ccc(C)cc2F)n2c1CN(C)CC2)C(C)(C)C] | (S)-N-(3,3-dimethyl-1-(methylamino)-1-oxobutan-2-yl)-3-(2-fluoro-4-methylphenyl)-7-methyl-5,6,7,8-tetrahydroimidazo[1,5-a]pyrazine-1-carboxamide | 416.0 | 19 |

TABLE I-continued

| Cmpd No. | Structure | Chemical Name | m/z | Example No. |
|---|---|---|---|---|
| 250 | 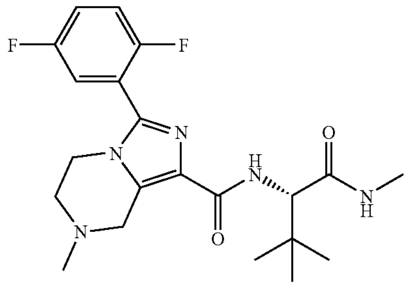 [SMILES: CNC(=O)[C@@H](NC(=O)c1nc(-c2cc(F)ccc2F)n2c1CN(C)CC2)C(C)(C)C] | (S)-3-(2,5-difluorophenyl)-N-(3,3-dimethyl-1-(methylamino)-1-oxobutan-2-yl)-7-methyl-5,6,7,8-tetrahydroimidazo[1,5-a]pyrazine-1-carboxamide | 420.0 | 19 |
| 251 | 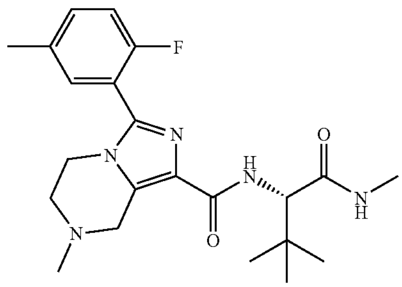 | (S)-N-(3,3-dimethyl-1-(methylamino)-1-oxobutan-2-yl)-3-(2-fluoro-5-methylphenyl)-7-methyl-5,6,7,8-tetrahydroimidazo[1,5-a]pyrazine-1-carboxamide | 416.0 | 19 |
| 252 | 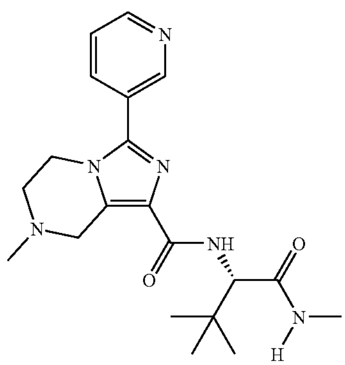 | (S)-N-(3,3-dimethyl-1-(methylamino)-1-oxobutan-2-yl)-7-methyl-3-(pyridin-3-yl)-5,6,7,8-tetrahydroimidazo[1,5-a]pyrazine-1-carboxamide | 385.2 | 19 |
| 253 | 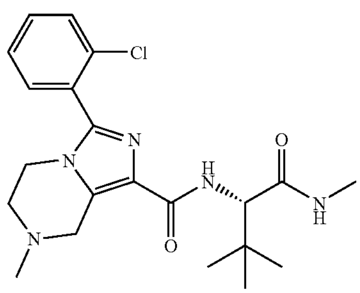 [SMILES: CNC(=O)[C@@H](NC(=O)c1nc(-c2ccccc2Cl)n2c1CN(C)CC2)C(C)(C)C] | (S)-3-(2-chlorophenyl)-N-(3,3-dimethyl-1-(methylamino)-1-oxobutan-2-yl)-7-methyl-5,6,7,8-tetrahydroimidazo[1,5-a]pyrazine-1-carboxamide | 418.0 | 19 |
| 254 | 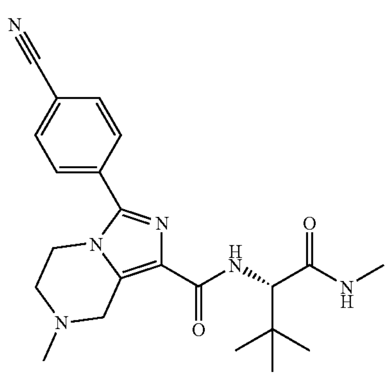 [SMILES: CNC(=O)[C@@H](NC(=O)c1nc(-c2ccc(C#N)cc2)n2c1CN(C)CC2)C(C)(C)C] | (S)-3-(4-cyanophenyl)-N-(3,3-dimethyl-1-(methylamino)-1-oxobutan-2-yl)-7-methyl-5,6,7,8-tetrahydroimidazo[1,5-a]pyrazine-1-carboxamide | 409.0 | 19 |

TABLE I-continued

| Cmpd No. | Structure | Chemical Name | m/z | Example No. |
|---|---|---|---|---|
| 255 | 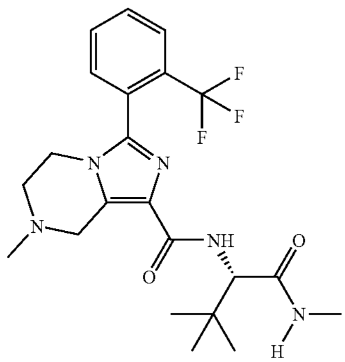 | (S)-N-(3,3-dimethyl-1-(methylamino)-1-oxobutan-2-yl)-7-methyl-3-(2-(trifluoromethyl)phenyl)-5,6,7,8-tetrahydroimidazo[1,5-a]pyrazine-1-carboxamide | 452.1 | 19 |
| 256 | 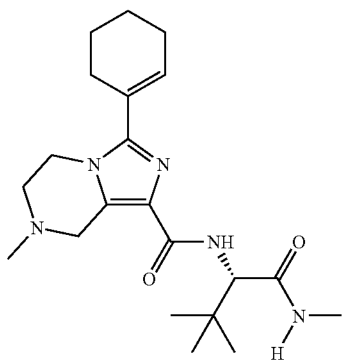 | (S)-3-cyclohexyl-N-(3,3-dimethyl-1-(methylamino)-1-oxobutan-2-yl)-7-methyl-5,6,7,8-tetrahydroimidazo[1,5-a]pyrazine-1-carboxamide | 388.2 | 19 |
| 257 | 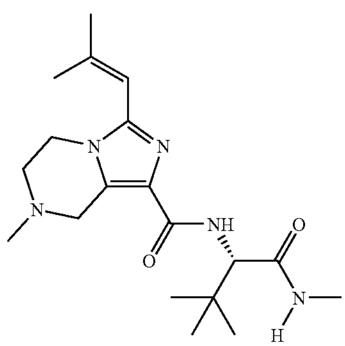 | (S)-N-(3,3-dimethyl-1-(methylamino)-1-oxobutan-2-yl)-7-methyl-3-(2-methylprop-1-enyl)-5,6,7,8-tetrahydroimidazo[1,5-a]pyrazine-1-carboxamide | 362.2 | 19 |
| 258 | 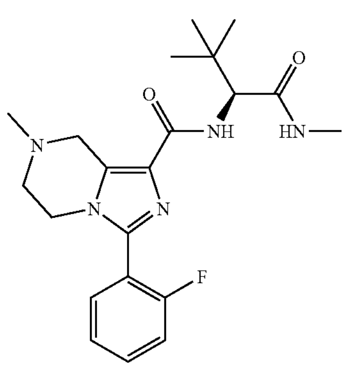 | (S)-N-(3,3-dimethyl-1-(methylamino)-1-oxobutan-2-yl)-3-(2-fluorophenyl)-7-methyl-5,6,7,8-tetrahydroimidazo[1,5-a]pyrazine-1-carboxamide | 402.4 | 19 |

TABLE I-continued

| Cmpd No. | Structure | Chemical Name | m/z | Example No. |
|---|---|---|---|---|
| 259 | 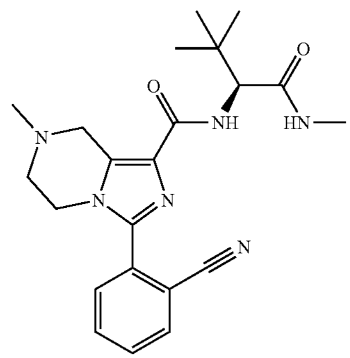 | (S)-3-(2-cyanophenyl)-N-(3,3-dimethyl-1-(methylamino)-1-oxobutan-2-yl)-7-methyl-5,6,7,8-tetrahydroimidazo[1,5-a]pyrazine-1-carboxamide | 408.3 | 19 |
| 260 | 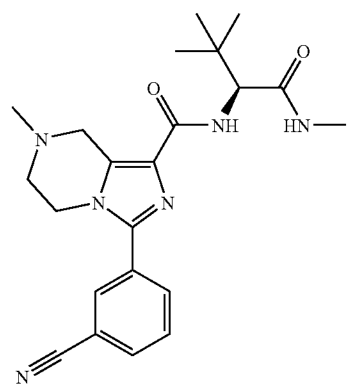 | (S)-3-(3-cyanophenyl)-N-(3,3-dimethyl-1-(methylamino)-1-oxobutan-2-yl)-7-methyl-5,6,7,8-tetrahydroimidazo[1,5-a]pyrazine-1-carboxamide | 409.4 | 19 |
| 261 | 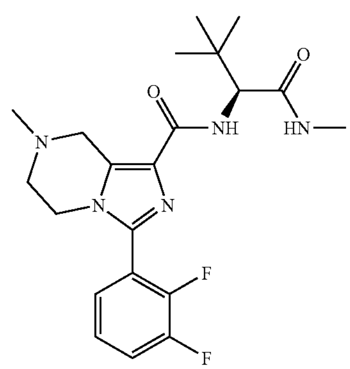 | (S)-3-(2,3-difluorophenyl)-N-(3,3-dimethyl-1-(methylamino)-1-oxobutan-2-yl)-7-methyl-5,6,7,8-tetrahydroimidazo[1,5-a]pyrazine-1-carboxamide | 420.4 | 19 |
| 262 | 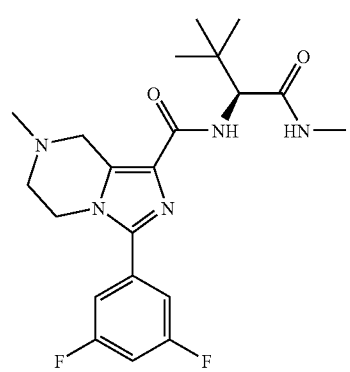 | (S)-3-(3,5-difluorophenyl)-N-(3,3-dimethyl-1-(methylamino)-1-oxobutan-2-yl)-7-methyl-5,6,7,8-tetrahydroimidazo[1,5-a]pyrazine-1-carboxamide | 420.4 | 19 |

TABLE I-continued

| Cmpd No. | Structure | Chemical Name | m/z | Example No. |
|---|---|---|---|---|
| 263 | 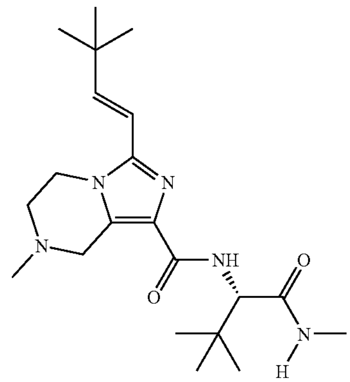 | (S,E)-N-(3,3-dimethyl-1-(methylamino)-1-oxobutan-2-yl)-3-(3,3-dimethylbut-1-enyl)-7-methyl-5,6,7,8-tetrahydroimidazo[1,5-a]pyrazine-1-carboxamide | 390.2 | 19 |
| 264 | 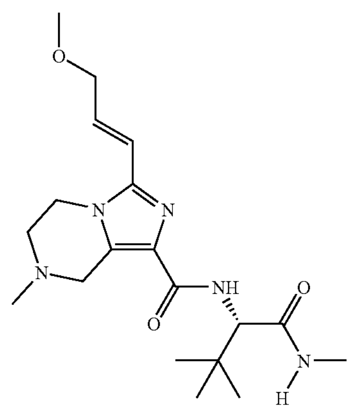 | (S,E)-N-(3,3-dimethyl-1-(methylamino)-1-oxobutan-2-yl)-3-(3-methoxyprop-1-enyl)-7-methyl-5,6,7,8-tetrahydroimidazo[1,5-a]pyrazine-1-carboxamide | 378.2 | 19 |
| 265 | 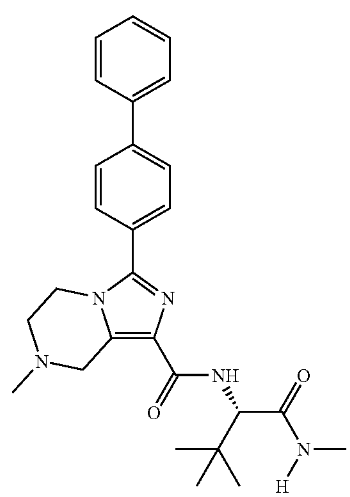 | (S)-3-(biphenyl-4-yl)-N-(3,3-dimethyl-1-(methylamino)-1-oxobutan-2-yl)-7-methyl-5,6,7,8-tetrahydroimidazo[1,5-a]pyrazine-1-carboxamide | 460.2 | 19 |
| 266 | 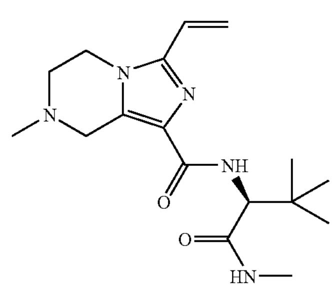 [SMILES: C=Cc1nc(C(=O)N[C@H](C(=O)NC)C(C)(C)C)c2n1CCN(C)C2] | (S)-N-(3,3-dimethyl-1-(methylamino)-1-oxobutan-2-yl)-7-methyl-2-vinyl-5,6,7,8-tetrahydroimidazo[1,5-a]pyrazine-1-carboxamide | 334.2 | 19 |

TABLE I-continued

| Cmpd No. | Structure | Chemical Name | m/z | Example No. |
|---|---|---|---|---|
| 267 | 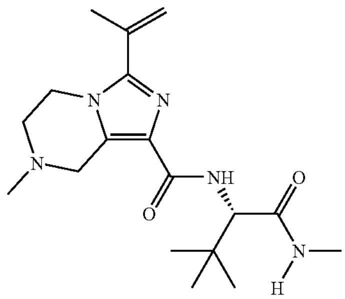 | (S)-N-(3,3-dimethyl-1-(methylamino)-1-oxobutan-2-yl)-7-methyl-3-(prop-1-en-2-yl)-5,6,7,8-tetrahydroimidazo[1,5-a]pyrazine-1-carboxamide | 348.2 | 19 |
| 268 | 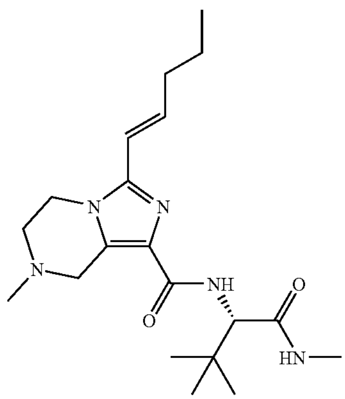 | (S,E)-N-(3,3-dimethyl-1-(methylamino)-1-oxobutan-2-yl)-7-methyl-3-(pent-1-enyl)-5,6,7,8-tetrahydroimidazo[1,5-a]pyrazine-1-carboxamide | 376.0 | 19 |
| 269 | 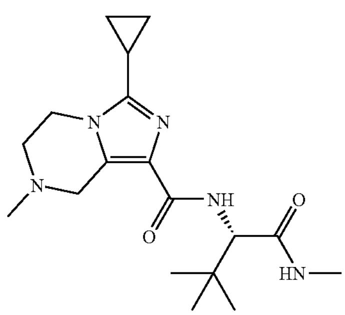 | (S)-3-cyclopropyl-N-(3,3-dimethyl-1-(methylamino)-1-oxobutan-2-yl)-7-methyl-5,6,7,8-tetrahydroimidazo[1,5-a]pyrazine-1-carboxamide | 348.0 | 19 |
| 270 | 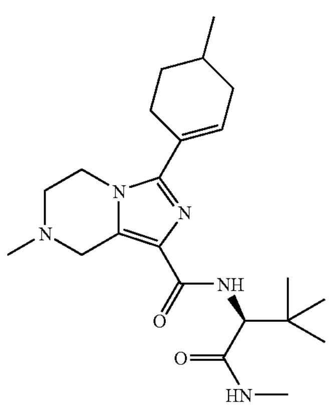 [SMILES: CNC(=O)[C@@H](NC(=O)c1nc(C2=CCC(C)CC2)n2c1CN(C)CC2)C(C)(C)C] | N-((S)-3,3-dimethyl-1-(methylamino)-1-oxobutan-2-yl)-7-methyl-3-(4-methylcyclohex-1-enyl)-5,6,7,8-tetrahydroimidazo[1,5-a]pyrazine-1-carboxamide | 402.3 | 19 |

TABLE I-continued

| Cmpd No. | Structure | Chemical Name | m/z | Example No. |
|---|---|---|---|---|
| 271 | 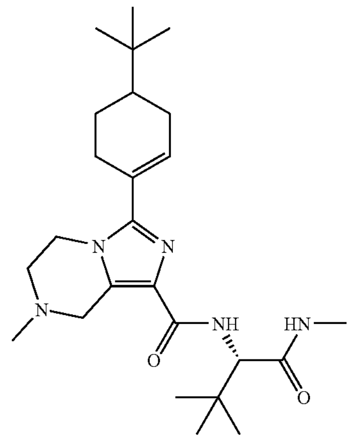 | 3-(4-tert-butylcyclohex-1-enyl)-N-((S)-3,3-dimethyl-1-(methylamino)-1-oxobutan-2-yl)-7-methyl-5,6,7,8-tetrahydroimidazo[1,5-a]pyrazine-1-carboxamide | 444.3 | 19 |
| 272 | 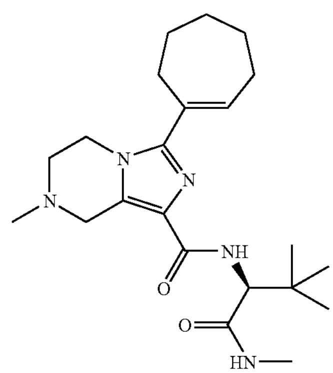 [SMILES: CNC(=O)[C@@H](NC(=O)c1nc(C2=CCCCCC2)n2c1CN(C)CC2)C(C)(C)C] | (S,E)-3-cycloheptenyl-N-(3,3-dimethyl-1-(methylamino)-1-oxobutan-2-yl)-7-methyl-5,6,7,8-tetrahydroimidazo[1,5-a]pyrazine-1-carboxamide | 402.3 | 19 |
| 273 | 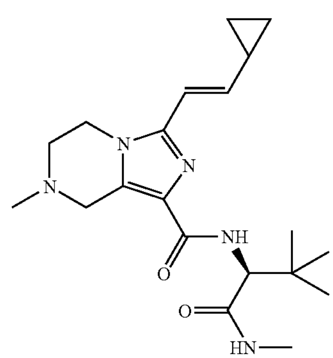 [SMILES: CNC(=O)[C@@H](NC(=O)c1nc(/C=C/C2CC2)n2c1CN(C)CC2)C(C)(C)C] | (S,E)-3-(2-cyclopropylvinyl)-N-(3,3-dimethyl-1-(methylamino)-1-oxobutan-2-yl)-7-methyl-5,6,7,8-tetrahydroimidazo[1,5-a]pyrazine-1-carboxamide | 374.3 | 19 |

TABLE I-continued

| Cmpd No. | Structure | Chemical Name | m/z | Example No. |
|---|---|---|---|---|
| 274 | 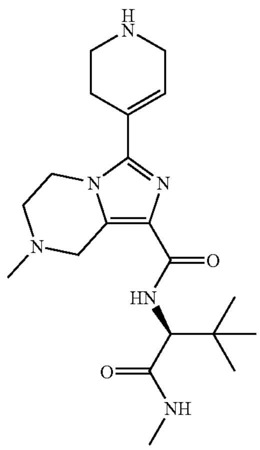 [SMILES: CNC(=O)[C@@H](NC(=O)c1nc(C2=CCNCC2)n2c1CN(C)CC2)C(C)(C)C] | (S)-N-(3,3-dimethyl-1-(methylamino)-1-oxobutan-2-yl)-7-methyl-3-(1,2,3,6-tetrahydropyridin-4-yl)-5,6,7,8-tetrahydroimidazo[1,5-a]pyrazine-1-carboxamide | 389.3 | 19 |
| 275 | 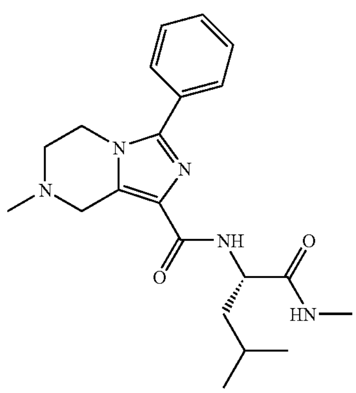 | (S)-7-methyl-N-(4-methyl-1-(methylamino)-1-oxopentan-2-yl)-3-phenyl-5,6,7,8-tetrahydroimidazo[1,5-a]pyrazine-1-carboxamide | 384.0 | 20 |
| 276 | 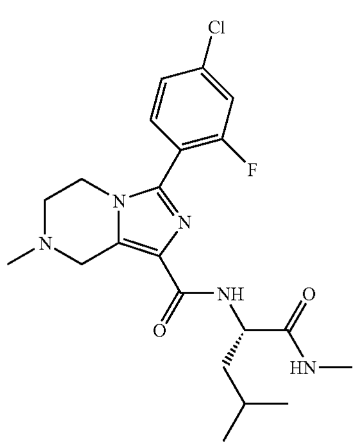 | (S)-3-(4-chloro-2-fluorophenyl)-7-methyl-N-(4-methyl-1-(methylamino)-1-oxopentan-2-yl)-5,6,7,8-tetrahydroimidazo[1,5-a]pyrazine-1-carboxamide | 436.0 | 20 |

TABLE I-continued

| Cmpd No. | Structure | Chemical Name | m/z | Example No. |
|---|---|---|---|---|
| 277 | 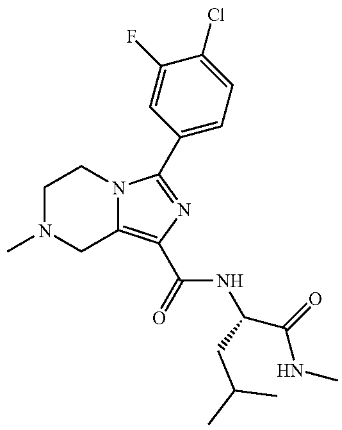 | (S)-3-(4-chloro-3-fluorophenyl)-7-methyl-N-(4-methyl-1-(methylamino)-1-oxopentan-2-yl)-5,6,7,8-tetrahydroimidazo[1,5-a]pyrazine-1-carboxamide | 436.0 | 20 |
| 278 | 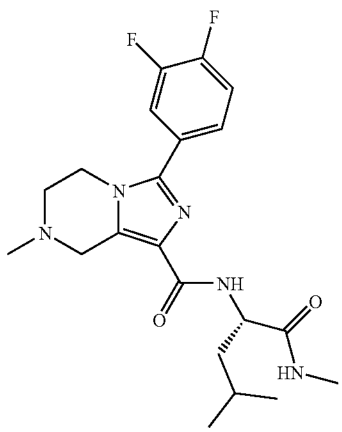 | (S)-3-(3,4-difluorophenyl)-7-methyl-N-(4-methyl-1-(methylamino)-1-oxopentan-2-yl)-5,6,7,8-tetrahydroimidazo[1,5-a]pyrazine-1-carboxamide | 420.0 | 20 |
| 279 | 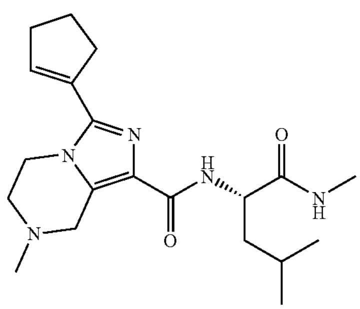 [SMILES: CNC(=O)[C@H](CC(C)C)NC(=O)c1nc(C2=CCCC2)n2c1CN(C)CC2] | (S)-3-cyclopentyl-7-methyl-N-(4-methyl-1-(methylamino)-1-oxopentan-2-yl)-5,6,7,8-tetrahydroimidazo[1,5-a]pyrazine-1-carboxamide | 374.3 | 20 |
| 280 | 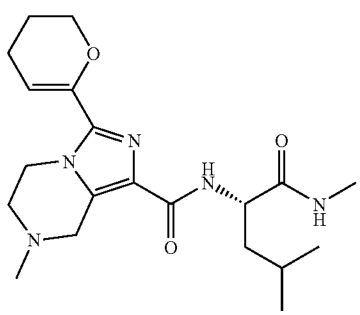 [SMILES: CNC(=O)[C@H](CC(C)C)NC(=O)c1nc(C2=CCCCO2)n2c1CN(C)CC2] | (S)-3-(3,4-dihydro-2H-pyran-6-yl)-7-methyl-N-(4-methyl-1-(methylamino)-1-oxopentan-2-yl)-5,6,7,8-tetrahydroimidazo[1,5-a]pyrazine-1-carboxamide | 390.3 | 20 |

TABLE I-continued

| Cmpd No. | Structure | Chemical Name | m/z | Example No. |
|---|---|---|---|---|
| 281 | 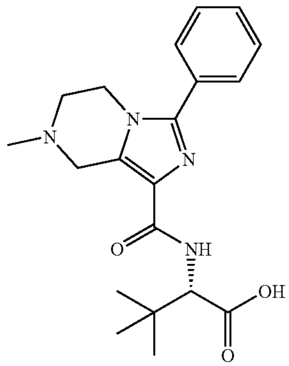 [SMILES: CN1CCn2c(-c3ccccc3)nc(C(=O)N[C@H](C(=O)O)C(C)(C)C)c2C1] | (S)-3,3-dimethyl-2-(7-methyl-3-phenyl-5,6,7,8-tetrahydroimidazo[1,5-a]pyrazine-1-carboxamido)butanoic acid | 371.1 | 21 |
| 282 | 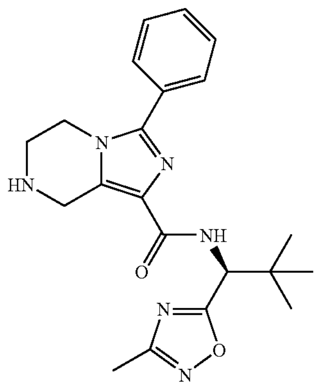 [SMILES: Cc1noc([C@@H](NC(=O)c2nc(-c3ccccc3)n3c2CNCC3)C(C)(C)C)n1] | (S)-N-(2,2-dimethyl-1-(3-methyl-1,2,4-oxadiazol-5-yl)propyl)-3-phenyl-5,6,7,8-tetrahydroimidazo[1,5-a]pyrazine-1-carboxamide | 395.0 | 22 |
| 283 | 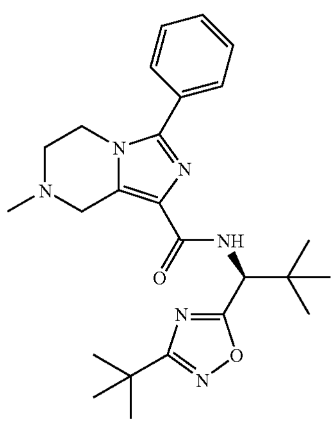 [SMILES: CN1CCn2c(-c3ccccc3)nc(C(=O)N[C@H](c3nc(C(C)(C)C)no3)C(C)(C)C)c2C1] | (S)-N-(1-(3-tert-butyl-1,2,4-oxadiazol-5-yl)-2,2-dimethylpropyl)-7-methyl-3-phenyl-5,6,7,8-tetrahydroimidazo[1,5-a]pyrazine-1-carboxamide | 451.0 | 22 |
| 284 | 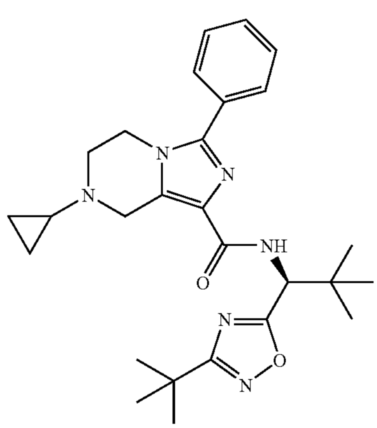 [SMILES: CC(C)(C)c1noc([C@@H](NC(=O)c2nc(-c3ccccc3)n3c2CN(C2CC2)CC3)C(C)(C)C)n1] | (S)-N-(1-(3-tert-butyl-1,2,4-oxadiazol-5-yl)-2,2-dimethylpropyl)-7-cyclopropyl-3-phenyl-5,6,7,8-tetrahydroimidazo[1,5-a]pyrazine-1-carboxamide | 477.0 | 22 |

| Cmpd No. | Structure | Chemical Name | m/z | Example No. |
|---|---|---|---|---|
| 285 | 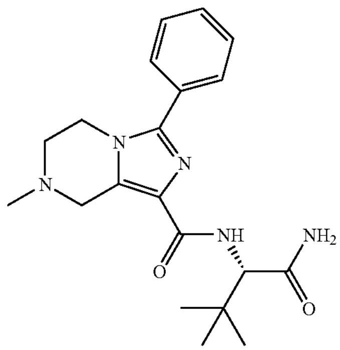 [SMILES: CN1CCn2c(-c3ccccc3)nc(C(=O)N[C@H](C(N)=O)C(C)(C)C)c2C1] | (S)-N-(1-amino-3,3-dimethyl-1-oxobutan-2-yl)-7-methyl-3-phenyl-5,6,7,8-tetrahydroimidazo[1,5-a]pyrazine-1-carboxamide | 370.2 | 23 |
| 286 | 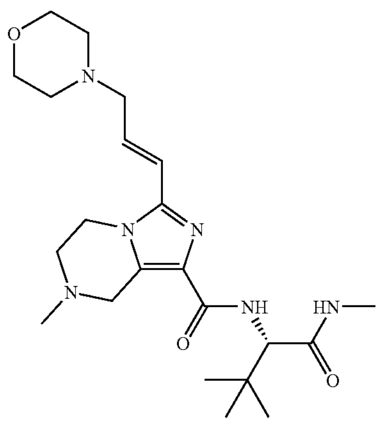 [SMILES: CNC(=O)[C@@H](NC(=O)c1nc(/C=C/CN2CCOCC2)n2c1CN(C)CC2)C(C)(C)C] | (S,E)-N-(3,3-dimethyl-1-(methylamino)-1-oxobutan-2-yl)-7-methyl-3-(3-morpholinoprop-1-enyl)-5,6,7,8-tetrahydroimidazo[1,5-a]pyrazine-1-carboxamide | 433.3 | 24 |
| 287 | 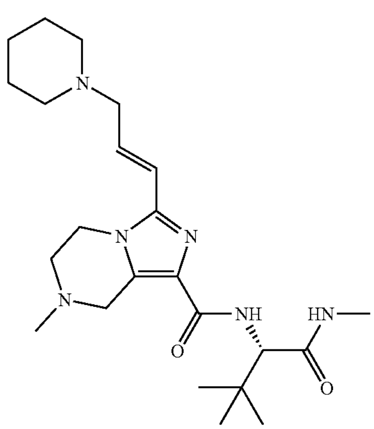 [SMILES: CNC(=O)[C@@H](NC(=O)c1nc(/C=C/CN2CCCCC2)n2c1CN(C)CC2)C(C)(C)C] | (S,E)-N-(3,3-dimethyl-1-(methylamino)-1-oxobutan-2-yl)-7-methyl-3-(3-(piperidin-1-yl)prop-1-enyl)-5,6,7,8-tetrahydroimidazo[1,5-a]pyrazine-1-carboxamide | 431.2 | 24 |

TABLE I-continued

| Cmpd No. | Structure | Chemical Name | m/z | Example No. |
|---|---|---|---|---|
| 288 | 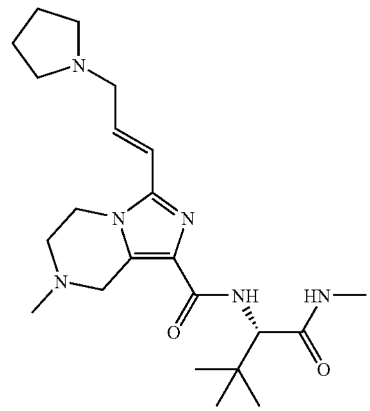 [SMILES: CNC(=O)[C@@H](NC(=O)c1nc(/C=C/CN2CCCC2)n2c1CN(C)CC2)C(C)(C)C] | (S,E)-N-(3,3-dimethyl-1-(methylamino)-1-oxobutan-2-yl)-7-methyl-3-(3-(pyrrolidin-1-yl)prop-1-enyl)-5,6,7,8-tetrahydroimidazo[1,5-a]pyrazine-1-carboxamide | 417.2 | 24 |
| 289 | 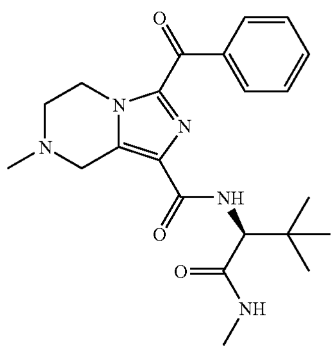 [SMILES: CNC(=O)[C@@H](NC(=O)c1nc(C(=O)c2ccccc2)n2c1CN(C)CC2)C(C)(C)C] | (S)-3-benzoyl-N-(3,3-dimethyl-1-(methylamino)-1-oxobutan-2-yl)-7-methyl-5,6,7,8-tetrahydroimidazo[1,5-a]pyrazine-1-carboxamide | 412.1 | 25 |
| 290 | 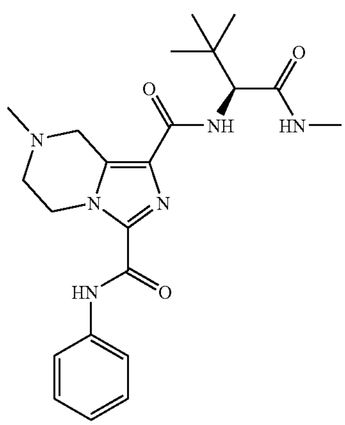 | (S)-N1-(3,3-dimethyl-1-(methylamino)-1-oxobutan-2-yl)-7-methyl-N3-phenyl-5,6,7,8-tetrahydroimidazo[1,5-a]pyrazine-1,3-dicarboxamide | 427.2 | 25 |
| 291 | 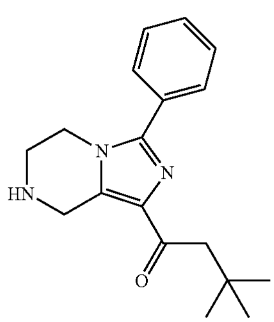 [SMILES: CC(C)(C)CC(=O)c1nc(-c2ccccc2)n2c1CNCC2] | 3,3-dimethyl-1-(3-phenyl-5,6,7,8-tetrahydroimidazo[1,5-a]pyrazin-1-yl)butan-1-one | 298.1 | 26 |

TABLE I-continued

| Cmpd No. | Structure | Chemical Name | m/z | Example No. |
|---|---|---|---|---|
| 292 | 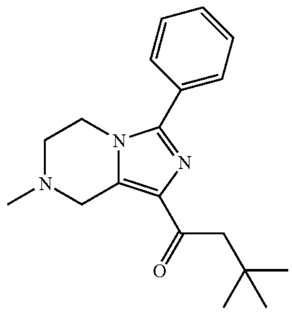 [SMILES: CN1CCn2c(-c3ccccc3)nc(C(=O)CC(C)(C)C)c2C1] | 3,3-dimethyl-1-(7-methyl-3-phenyl-5,6,7,8-tetrahydroimidazo[1,5-a]pyrazin-1-yl)butan-1-one | 312.1 | 26 |
| 293 | 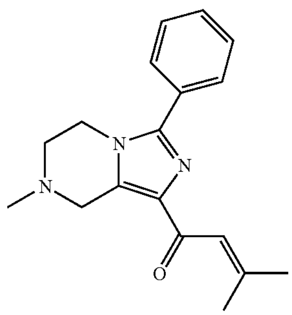 [SMILES: CC(C)=CC(=O)c1nc(-c2ccccc2)n2c1CN(C)CC2] | 3-methyl-1-(7-methyl-3-phenyl-5,6,7,8-tetrahydroimidazo[1,5-a]pyrazin-1-yl)but-2-en-1-one | 296.1 | 26 |
| 294 | 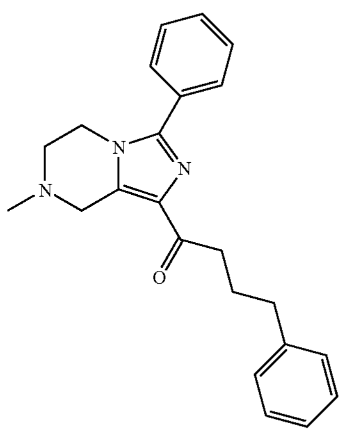 [SMILES: CN1CCn2c(-c3ccccc3)nc(C(=O)CCCc3ccccc3)c2C1] | 1-(7-methyl-3-phenyl-5,6,7,8-tetrahydroimidazo[1,5-a]pyrazin-1-yl)-4-phenylbutan-1-one | 360.1 | 26 |
| 295 | 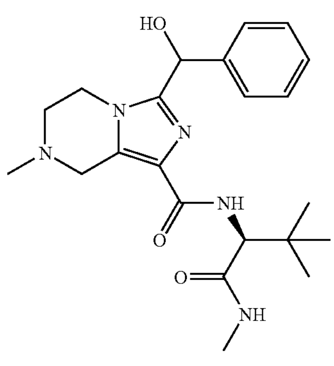 [SMILES: CNC(=O)[C@@H](NC(=O)c1nc(C(O)c2ccccc2)n2c1CN(C)CC2)C(C)(C)C] | N-((S)-3,3-dimethyl-1-(methylamino)-1-oxobutan-2-yl)-3-(hydroxy(phenyl)methyl)-7-methyl-5,6,7,8-tetrahydroimidazo[1,5-a]pyrazine-1-carboxamide | 414.2 | 27 |

TABLE I-continued

| Cmpd No. | Structure | Chemical Name | m/z | Example No. |
|---|---|---|---|---|
| 296 | 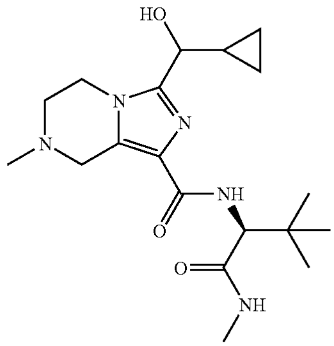 [SMILES: CNC(=O)[C@@H](NC(=O)c1nc(C(O)C2CC2)n2c1CN(C)CC2)C(C)(C)C] | 3-(cyclopropyl(hydroxy)methyl)-N-((S)-3,3-dimethyl-1-(methylamino)-1-oxobutan-2-yl)-7-methyl-5,6,7,8-tetrahydroimidazo[1,5-a]pyrazine-1-carboxamide | 378.2 | 27 |
| 297 | 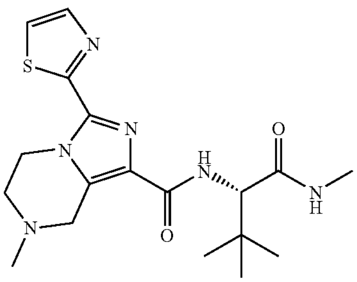 [SMILES: CNC(=O)[C@@H](NC(=O)c1nc(-c2nccs2)n2c1CN(C)CC2)C(C)(C)C] | (S)-N-(3,3-dimethyl-1-(methylamino)-1-oxobutan-2-yl)-7-methyl-3-(thiazol-2-yl)-5,6,7,8-tetrahydroimidazo[1,5-a]pyrazine-1-carboxamide | 391.0 | 28 |
| 298 | 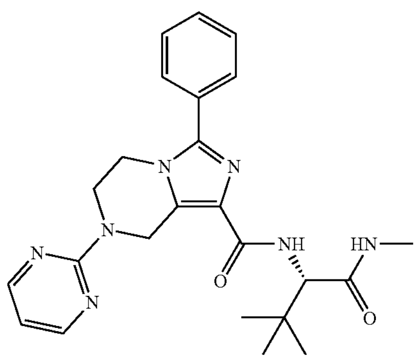 [SMILES: CNC(=O)[C@@H](NC(=O)c1nc(-c2ccccc2)n2c1CN(c1ncccn1)CC2)C(C)(C)C] | (S)-N-(3,3-dimethyl-1-(methylamino)-1-oxobutan-2-yl)-3-phenyl-7-(pyrimidin-2-yl)-5,6,7,8-tetrahydroimidazo[1,5-a]pyrazine-1-carboxamide | 448.2 | 29 |
| 299 | 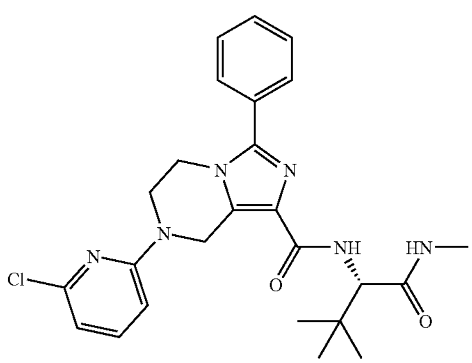 [SMILES: CNC(=O)[C@@H](NC(=O)c1nc(-c2ccccc2)n2c1CN(c1cccc(Cl)n1)CC2)C(C)(C)C] | (S)-7-(6-chloropyridin-2-yl)-N-(3,3-dimethyl-1-(methylamino)-1-oxobutan-2-yl)-3-phenyl-5,6,7,8-tetrahydroimidazo[1,5-a]pyrazine-1-carboxamide | 481.2 | 29 |

TABLE I-continued

| Cmpd No. | Structure | Chemical Name | m/z | Example No. |
|---|---|---|---|---|
| 300 | 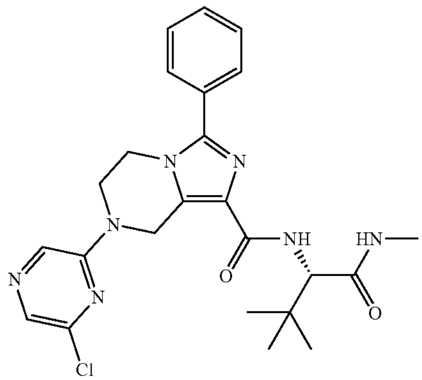 [SMILES: CNC(=O)[C@@H](NC(=O)c1nc(-c2ccccc2)n2c1CN(c1cncc(Cl)n1)CC2)C(C)(C)C] | (S)-7-(6-chloropyrazin-2-yl)-N-(3,3-dimethyl-1-(methylamino)-1-oxobutan-2-yl)-3-phenyl-5,6,7,8-tetrahydroimidazo[1,5-a]pyrazine-1-carboxamide | 482.2 | 29 |
| 301 | 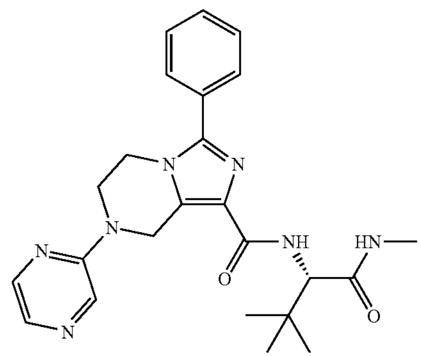 [SMILES: CNC(=O)[C@@H](NC(=O)c1nc(-c2ccccc2)n2c1CN(c1cnccn1)CC2)C(C)(C)C] | (S)-N-(3,3-dimethyl-1-(methylamino)-1-oxobutan-2-yl)-3-phenyl-7-(pyrazin-2-yl)-5,6,7,8-tetrahydroimidazo[1,5-a]pyrazine-1-carboxamide | 448.2 | 29 |
| 302 | 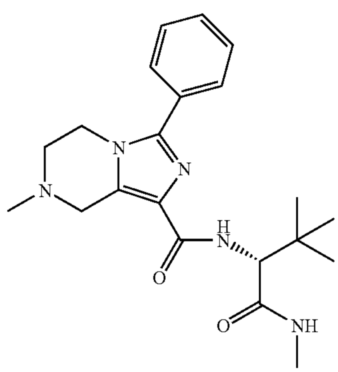 [SMILES: CNC(=O)[C@H](NC(=O)c1nc(-c2ccccc2)n2c1CN(C)CC2)C(C)(C)C] | (R)-N-(3,3-dimethyl-1-(methylamino)-1-oxobutan-2-yl)-7-methyl-3-phenyl-5,6,7,8-tetrahydroimidazo[1,5-a]pyrazine-1-carboxamide | 384.0 | 30 |
| 303 | 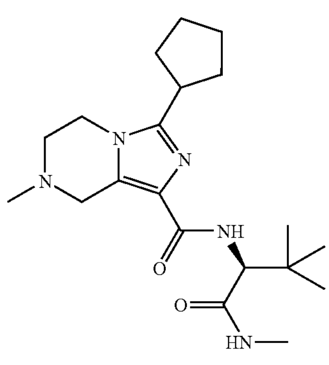 [SMILES: CNC(=O)[C@@H](NC(=O)c1nc(C2CCCC2)n2c1CN(C)CC2)C(C)(C)C] | (S)-3-cyclopentyl-N-(3,3-dimethyl-1-(methylamino)-1-oxobutan-2-yl)-7-methyl-5,6,7,8-tetrahydroimidazo[1,5-a]pyrazine-1-carboxamide | 376.2 | 31 |

TABLE I-continued

| Cmpd No. | Structure | Chemical Name | m/z | Example No. |
|---|---|---|---|---|
| 304 | 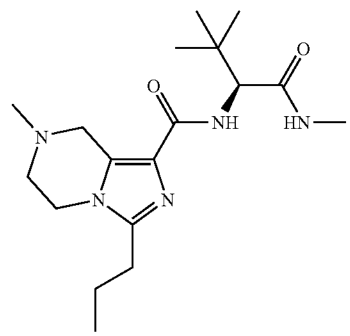 | (S)-N-(3,3-dimethyl-1-(methylamino)-1-oxobutan-2-yl)-7-methyl-3-propyl-5,6,7,8-tetrahydroimidazo[1,5-a]pyrazine-1-carboxamide | 350.4 | 31 |
| 305 | 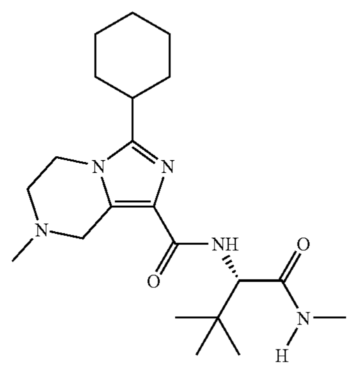 | (S)-3-cyclohexyl-N-(3,3-dimethyl-1-(methylamino)-1-oxobutan-2-yl)-7-methyl-5,6,7,8-tetrahydroimidazo[1,5-a]pyrazine-1-carboxamide | 390.2 | 31 |
| 306 | 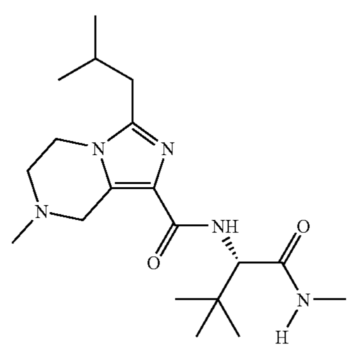 | (S)-N-(3,3-dimethyl-1-(methylamino)-1-oxobutan-2-yl)-3-isobutyl-7-methyl-5,6,7,8-tetrahydroimidazo[1,5-a]pyrazine-1-carboxamide | 364.2 | 31 |
| 307 | 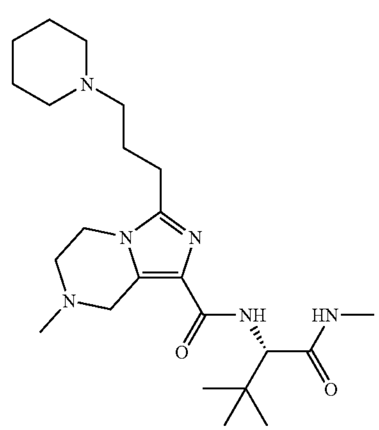 [SMILES: CNC(=O)[C@@H](NC(=O)c1nc(CCCN2CCCCC2)n2c1CN(C)CC2)C(C)(C)C] | (S)-N-(3,3-dimethyl-1-(methylamino)-1-oxobutan-2-yl)-7-methyl-3-(3-(piperidin-1-yl)propyl-5,6,7,8-tetrahydroimidazo[1,5-a]pyrazine-1-carboxamide | 433.3 | 31 |

TABLE I-continued

| Cmpd No. | Structure | Chemical Name | m/z | Example No. |
|---|---|---|---|---|
| 308 | 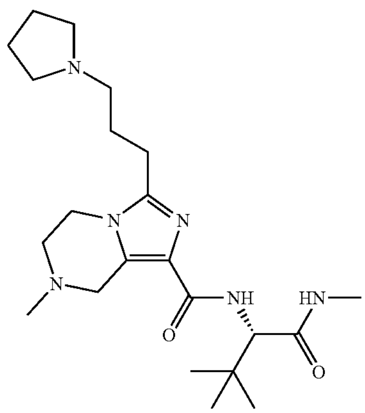 [SMILES: CNC(=O)[C@@H](NC(=O)c1nc(CCCN2CCCC2)n2c1CN(C)CC2)C(C)(C)C] | (S)-N-(3,3-dimethyl-1-(methylamino)-1-oxobutan-2-yl)-7-methyl-3-(3-(pyrrolidin-1-yl)propyl)-5,6,7,8-tetrahydroimidazo[1,5-a]pyrazine-1-carboxamide | 419.2 | 31 |
| 309 | 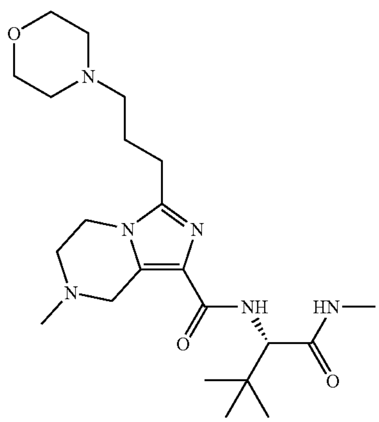 [SMILES: CNC(=O)[C@@H](NC(=O)c1nc(CCCN2CCOCC2)n2c1CN(C)CC2)C(C)(C)C] | (S)-N-(3,3-dimethyl-1-(methylamino)-1-oxobutan-2-yl)-7-methyl-3-(3-morpholinopropyl)-5,6,7,8-tetrahydroimidazo[1,5-a]pyrazine-1-carboxamide | 435.2 | 31 |
| 310 | 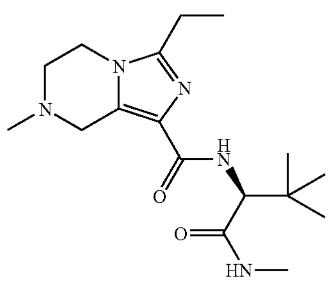 [SMILES: CCc1nc(C(=O)N[C@H](C(=O)NC)C(C)(C)C)c2n1CCN(C)C2] | (S)-N-(3,3-dimethyl-1-(methylamino)-1-oxobutan-2-yl)-3-ethyl-7-methyl-5,6,7,8-tetrahydroimidazo[1,5-a]pyrazine-1-carboxamide | 336.2 | 31 |
| 311 | 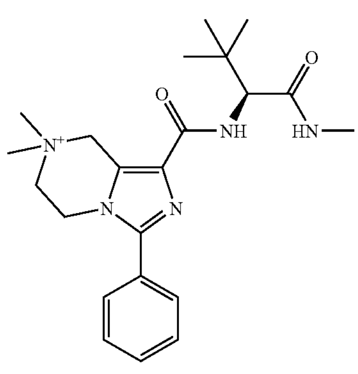 | (S)-1-(3,3-dimethyl-1-(methylamino)-1-oxobutan-2-ylcarbamoyl)-7,7-dimethyl-3-phenyl-5,6,7,8-tetrahydroimidazo[1,5-a]pyrazin-7-ium | 398.0 | 32 |

TABLE I-continued

| Cmpd No. | Structure | Chemical Name | m/z | Example No. |
|---|---|---|---|---|
| 312 | 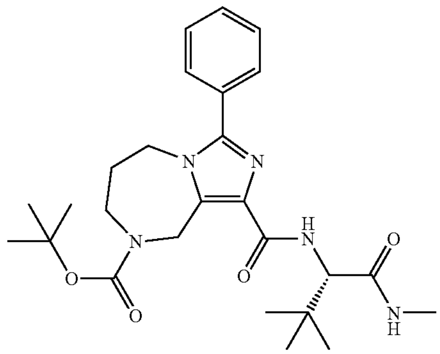 [SMILES: CNC(=O)[C@@H](NC(=O)c1nc(-c2ccccc2)n2c1CN(C(=O)OC(C)(C)C)CCC2)C(C)(C)C] | (S)-tert-butyl 1-(3,3-dimethyl-1-(methylamino)-1-oxobutan-2-ylcarbamoyl)-3-phenyl-6,7-dihydro-5H-imidazo[1,5-a][1,4]diazepine-8(9H)-carboxylate | 484.3 | 33 |
| 313 | 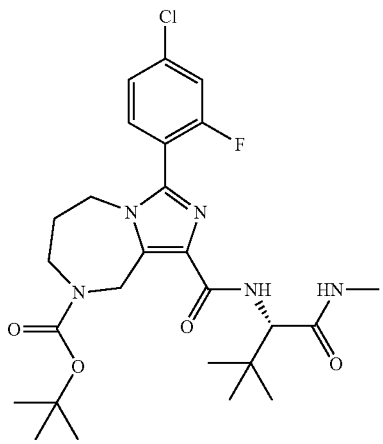 [SMILES: CNC(=O)[C@@H](NC(=O)c1nc(-c2ccc(Cl)cc2F)n2c1CN(C(=O)OC(C)(C)C)CCC2)C(C)(C)C] | (S)-tert-butyl 3-(4-chloro-2-fluorophenyl)-1-(3,3-dimethyl-1-(methylamino)-1-oxobutan-2-ylcarbamoyl)-6,7-dihydro-5H-imidazo[1,5-a][1,4]diazepine-8(9H)-carboxylate | 537.0 | 33 |
| 314 | 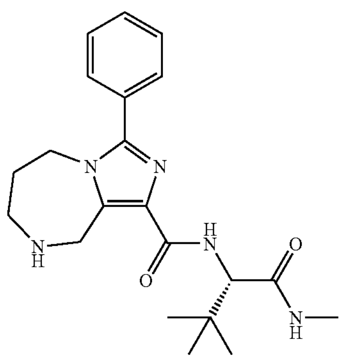 [SMILES: CNC(=O)[C@@H](NC(=O)c1nc(-c2ccccc2)n2c1CNCCC2)C(C)(C)C] | (S)-N-(3,3-dimethyl-1-(methylamino)-1-oxobutan-2-yl)-3-phenyl-6,7,8,9-tetrahydro-5H-imidazo[1,5-a][1,4]diazepine-1-carboxamide | 384.1 | 34 |
| 315 | 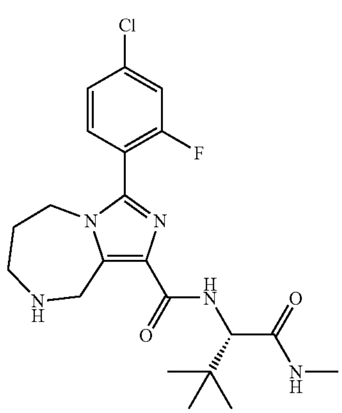 [SMILES: CNC(=O)[C@@H](NC(=O)c1nc(-c2ccc(Cl)cc2F)n2c1CNCCC2)C(C)(C)C] | (S)-3-(4-chloro-2-fluorophenyl)-N-(3,3-dimethyl-1-(methylamino)-1-oxobutan-2-yl)-6,7,8,9-tetrahydro-5H-imidazo[1,5-a][1,4]diazepine-1-carboxamide | 437.0 | 34 |

TABLE I-continued

| Cmpd No. | Structure | Chemical Name | m/z | Example No. |
|---|---|---|---|---|
| 316 | 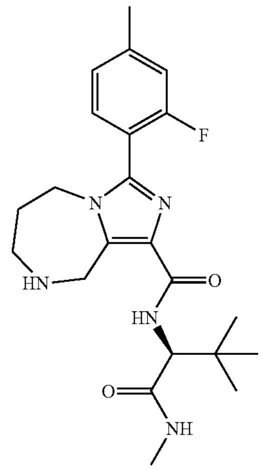 [SMILES: CNC(=O)[C@@H](NC(=O)c1nc(-c2ccc(C)cc2F)n2c1CNCCC2)C(C)(C)C] | (S)-N-(3,3-dimethyl-1-(methylamino)-1-oxobutan-2-yl)-3-(2-fluoro-4-methylphenyl)-6,7,8,9-tetrahydro-5H-imidazo[1,5-a][1,4]diazepine-1-carboxamide | 416.2 | 34 |
| 317 | 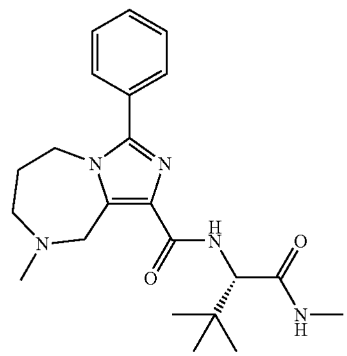 [SMILES: CNC(=O)[C@@H](NC(=O)c1nc(-c2ccccc2)n2c1CN(C)CCC2)C(C)(C)C] | (S)-N-(3,3-dimethyl-1-(methylamino)-1-oxobutan-2-yl)-8-methyl-3-phenyl-6,7,8,9-tetrahydro-5H-imidazo[1,5-a][1,4]diazepine-1-carboxamide | 398.0 | 35 |
| 318 | 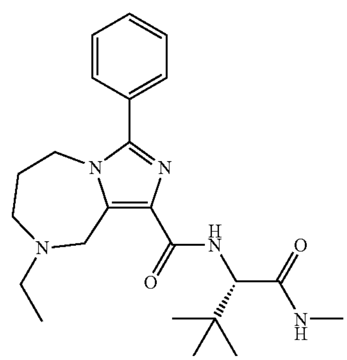 [SMILES: CCN1CCCn2c(-c3ccccc3)nc(C(=O)N[C@H](C(=O)NC)C(C)(C)C)c2C1] | (S)-N-(3,3-dimethyl-1-(methylamino)-1-oxobutan-2-yl)-8-ethyl-3-phenyl-6,7,8,9-tetrahydro-5H-imidazo[1,5-a][1,4]diazepine-1-carboxamide | 412.0 | 35 |
| 319 | 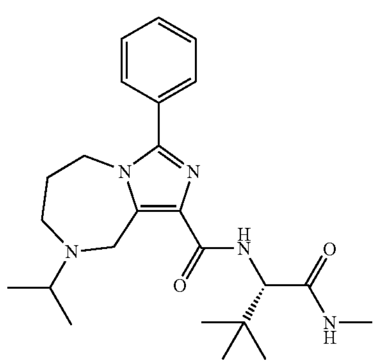 [SMILES: CNC(=O)[C@@H](NC(=O)c1nc(-c2ccccc2)n2c1CN(C(C)C)CCC2)C(C)(C)C] | (S)-N-(3,3-dimethyl-1-(methylamino)-1-oxobutan-2-yl)-8-isopropyl-3-phenyl-6,7,8,9-tetrahydro-5H-imidazo[1,5-a][1,4]diazepine-1-carboxamide | 426.0 | 35 |

TABLE I-continued

| Cmpd No. | Structure | Chemical Name | m/z | Example No. |
|---|---|---|---|---|
| 320 | 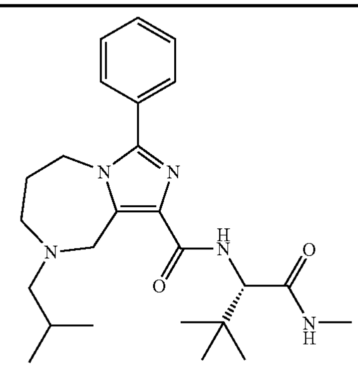 | (S)-N-(3,3-dimethyl-1-(methylamino)-1-oxobutan-2-yl)-8-isobutyl-3-phenyl-6,7,8,9-tetrahydro-5H-imidazo[1,5-a][1,4]diazepine-1-carboxamide | 440.3 | 35 |
| 321 | 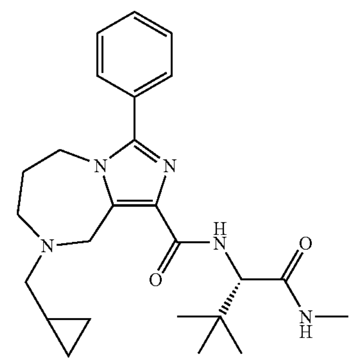 [SMILES: CNC(=O)[C@@H](NC(=O)c1nc(-c2ccccc2)n2c1CN(CC1CC1)CCC2)C(C)(C)C] | (S)-8-(cyclopropylmethyl)-N-(3,3-dimethyl-1-(methylamino)-1-oxobutan-2-yl)-3-phenyl-6,7,8,9-tetrahydro-5H-imidazo[1,5-a][1,4]diazepine-1-carboxamide | 438.3 | 35 |
| 322 | 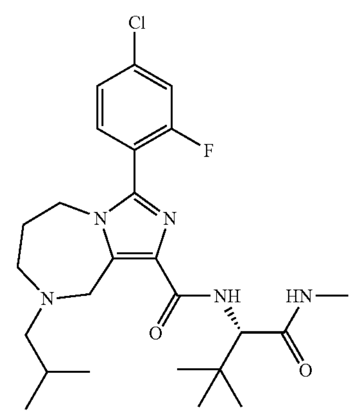 [SMILES: CNC(=O)[C@@H](NC(=O)c1nc(-c2ccc(Cl)cc2F)n2c1CN(CC(C)C)CCC2)C(C)(C)C] | (S)-3-(4-chloro-2-fluorophenyl)-N-(3,3-dimethyl-1-(methylamino)-1-oxobutan-2-yl)-8-isobutyl-6,7,8,9-tetrahydro-5H-imidazo[1,5-a][1,4]diazepine-1-carboxamide | 494.0 | 35 |
| 323 | 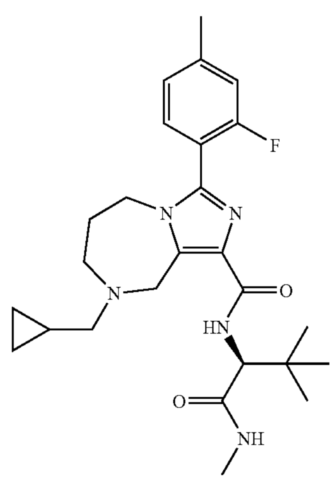 [SMILES: CNC(=O)[C@@H](NC(=O)c1nc(-c2ccc(C)cc2F)n2c1CN(CC1CC1)CCC2)C(C)(C)C] | (S)-8-(cyclopropylmethyl)-N-(3,3-dimethyl-1-(methylamino)-1-oxobutan-2-yl)-3-(2-fluoro-4-methylphenyl)-6,7,8,9-tetrahydro-5H-imidazo[1,5-a][1,4]diazepine-1-carboxamide | 470.2 | 35 |

TABLE I-continued

| Cmpd No. | Structure | Chemical Name | m/z | Example No. |
|---|---|---|---|---|
| 324 | 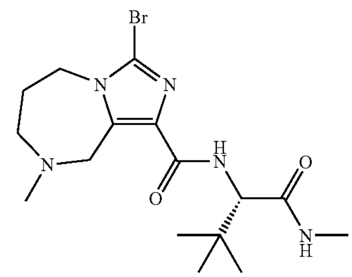 [SMILES: CNC(=O)[C@@H](NC(=O)c1nc(Br)n2c1CN(C)CCC2)C(C)(C)C] | (S)-3-bromo-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 402.9 | 36 |
| 325 | 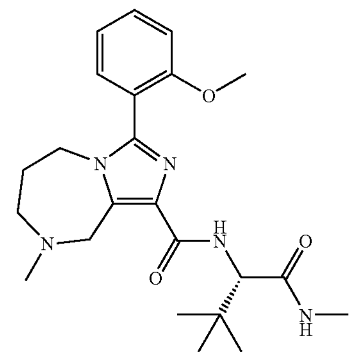 [SMILES: CNC(=O)[C@@H](NC(=O)c1nc(-c2ccccc2OC)n2c1CN(C)CCC2)C(C)(C)C] | (S)-N-(3,3-dimethyl-1-(methylamino)-1-oxobutan-2-yl)-3-(2-methoxyphenyl)-8-methyl-6,7,8,9-tetrahydro-5H-imidazo[1,5-a][1,4]diazepine-1-carboxamide | 428.2 | 37 |
| 326 | 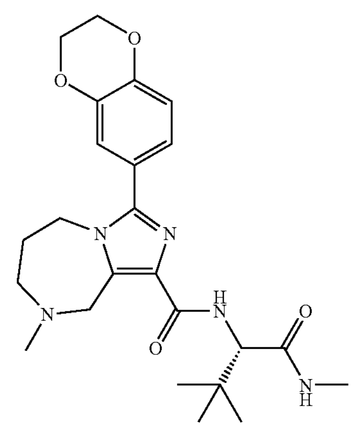 [SMILES: CNC(=O)[C@@H](NC(=O)c1nc(-c2ccc3c(c2)OCCO3)n2c1CN(C)CCC2)C(C)(C)C] | (S)-3-(2,3-dihydrobenzo[b][1,4]dioxin-6-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 456.1 | 37 |
| 327 | 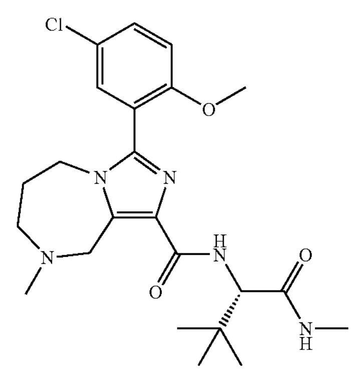 [SMILES: CNC(=O)[C@@H](NC(=O)c1nc(-c2cc(Cl)ccc2OC)n2c1CN(C)CCC2)C(C)(C)C] | (S)-3-(5-chloro-2-methoxyphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 462.1 | 37 |

TABLE I-continued

| Cmpd No. | Structure | Chemical Name | m/z | Example No. |
|---|---|---|---|---|
| 328 | 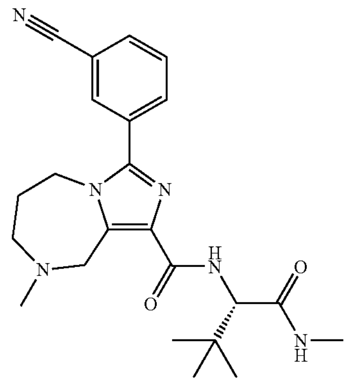 [SMILES: CNC(=O)[C@@H](NC(=O)c1nc(-c2cccc(C#N)c2)n2c1CN(C)CCC2)C(C)(C)C] | (S)-3-(3-cyanophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 423.1 | 37 |
| 329 | 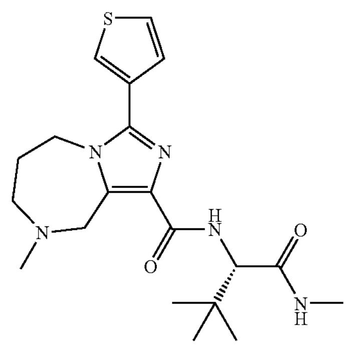 [SMILES: CNC(=O)[C@@H](NC(=O)c1nc(-c2ccsc2)n2c1CN(C)CCC2)C(C)(C)C] | (S)-N-(3,3-dimethyl-1-(methylamino)-1-oxobutan-2-yl)-8-methyl-3-(thiophen-3-yl)-6,7,8,9-tetrahydro-5H-imidazo[1,5-a][1,4]diazepine-1-carboxamide | 404.0 | 37 |
| 330 | 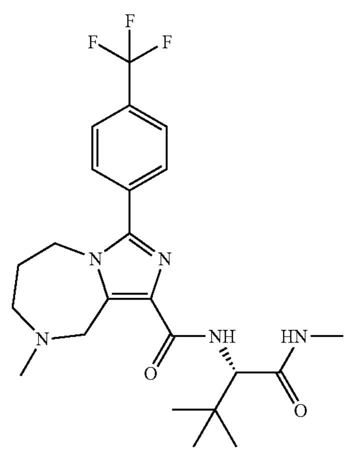 [SMILES: CNC(=O)[C@@H](NC(=O)c1nc(-c2ccc(C(F)(F)F)cc2)n2c1CN(C)CCC2)C(C)(C)C] | (S)-N-(3,3-dimethyl-1-(methylamino)-1-oxobutan-2-yl)-8-methyl-3-(4-(trifluoromethyl)phenyl)-6,7,8,9-tetrahydro-5H-imidazo[1,5-a][1,4]diazepine-1-carboxamide | 466.1 | 37 |
| 331 | 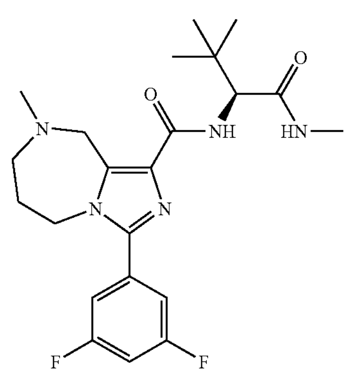 [SMILES: CNC(=O)[C@@H](NC(=O)c1nc(-c2cc(F)cc(F)c2)n2c1CN(C)CCC2)C(C)(C)C] | (S)-3-(3,5-difluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 434.1 | 37 |

| Cmpd No. | Structure | Chemical Name | m/z | Example No. |
|---|---|---|---|---|
| 332 | 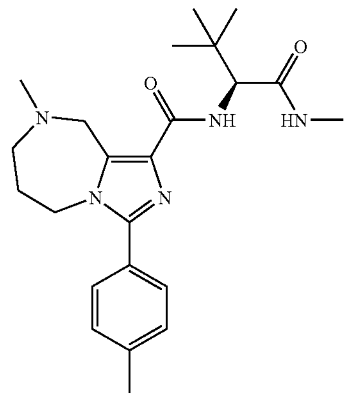 [SMILES: CNC(=O)[C@@H](NC(=O)c1nc(-c2ccc(C)cc2)n2c1CN(C)CCC2)C(C)(C)C] | (S)-N-(3,3-dimethyl-1-(methylamino)-1-oxobutan-2-yl)-8-methyl-3-p-tolyl-6,7,8,9-tetrahydro-5H-imidazo[1,5-a][1,4]diazepine-1-carboxamide | 412.2 | 37 |
| 333 | 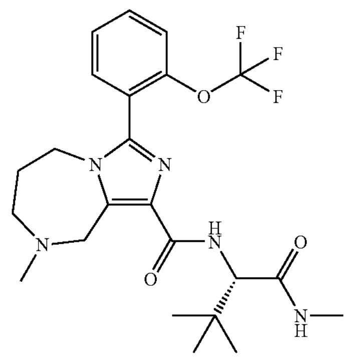 [SMILES: CNC(=O)[C@@H](NC(=O)c1nc(-c2ccccc2OC(F)(F)F)n2c1CN(C)CCC2)C(C)(C)C] | (S)-N-(3,3-dimethyl-1-(methylamino)-1-oxobutan-2-yl)-8-methyl-3-(2-(trifluoromethoxy)phenyl)-6,7,8,9-tetrahydro-5H-imidazo[1,5-a][1,4]diazepine-1-carboxamide | 482.1 | 37 |
| 334 | 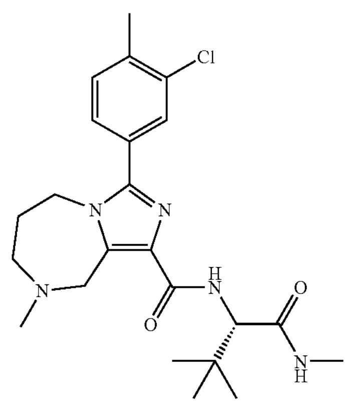 [SMILES: CNC(=O)[C@@H](NC(=O)c1nc(-c2ccc(C)c(Cl)c2)n2c1CN(C)CCC2)C(C)(C)C] | (S)-3-(3-chloro-4-methylphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 446.1 | 37 |
| 335 | 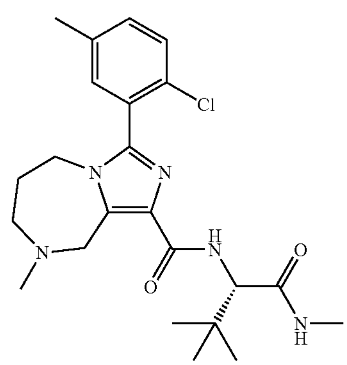 [SMILES: CNC(=O)[C@@H](NC(=O)c1nc(-c2cc(C)ccc2Cl)n2c1CN(C)CCC2)C(C)(C)C] | (S)-3-(2-chloro-5-methylphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 446.1 | 37 |

TABLE I-continued

| Cmpd No. | Structure | Chemical Name | m/z | Example No. |
|---|---|---|---|---|
| 336 | 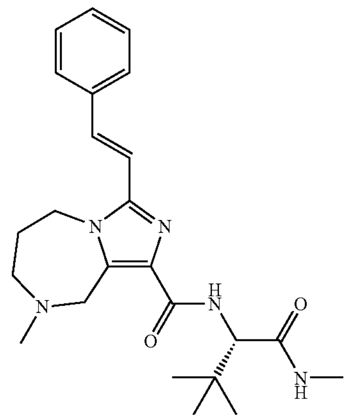 [SMILES: CNC(=O)[C@@H](NC(=O)c1nc(/C=C/c2ccccc2)n2c1CN(C)CCC2)C(C)(C)C] | (S,E)-N-(3,3-dimethyl-1-(methylamino)-1-oxobutan-2-yl)-8-methyl-3-styryl-6,7,8,9-tetrahydro-5H-imidazo[1,5-a][1,4]diazepine-1-carboxamide | 424.2 | 37 |
| 337 | 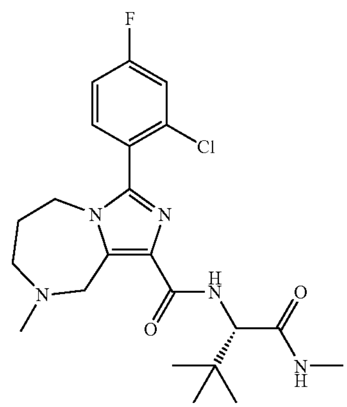 [SMILES: CNC(=O)[C@@H](NC(=O)c1nc(-c2ccc(F)cc2Cl)n2c1CN(C)CCC2)C(C)(C)C] | (S)-3-(2-chloro-4-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 450.2 | 37 |
| 338 | 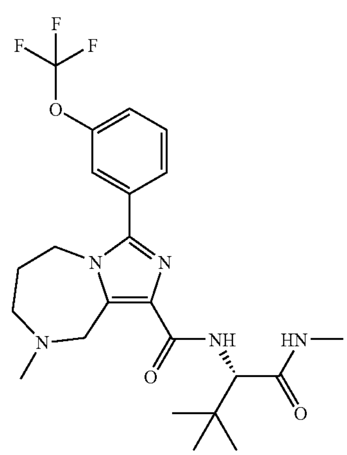 [SMILES: CNC(=O)[C@@H](NC(=O)c1nc(-c2cccc(OC(F)(F)F)c2)n2c1CN(C)CCC2)C(C)(C)C] | (S)-N-(3,3-dimethyl-1-(methylamino)-1-oxobutan-2-yl)-8-methyl-3-(3-(trifluoromethoxy)phenyl)-6,7,8,9-tetrahydro-5H-imidazo[1,5-a][1,4]diazepine-1-carboxamide | 482.1 | 37 |

TABLE I-continued

| Cmpd No. | Structure | Chemical Name | m/z | Example No. |
|---|---|---|---|---|
| 339 | 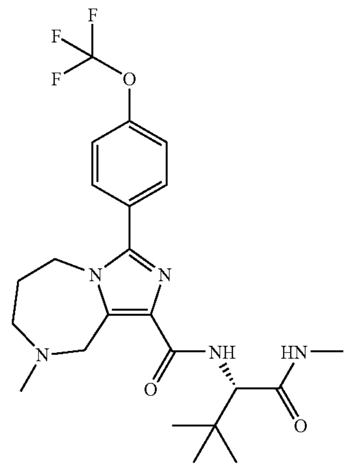 [SMILES: CNC(=O)[C@@H](NC(=O)c1nc(-c2ccc(OC(F)(F)F)cc2)n2c1CN(C)CCC2)C(C)(C)C] | (S)-N-(3,3-dimethyl-1-(methylamino)-1-oxobutan-2-yl)-8-methyl-3-(4-(trifluoromethoxy)phenyl)-6,7,8,9-tetrahydro-5H-imidazo[1,5-a][1,4]diazepine-1-carboxamide | 482.1 | 37 |
| 340 | 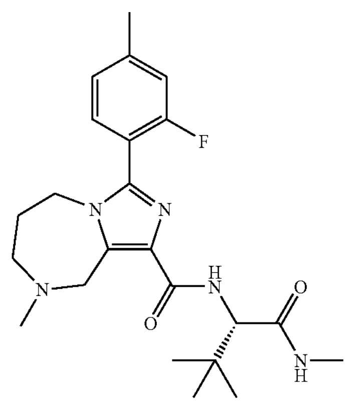 [SMILES: CNC(=O)[C@@H](NC(=O)c1nc(-c2ccc(C)cc2F)n2c1CN(C)CCC2)C(C)(C)C] | (S)-N-(3,3-dimethyl-1-(methylamino)-1-oxobutan-2-yl)-3-(2-fluoro-4-methylphenyl)-8-methyl-6,7,8,9-tetrahydro-5H-imidazo[1,5-a][1,4]diazepine-1-carboxamide | 430.0 | 37 |
| 341 | 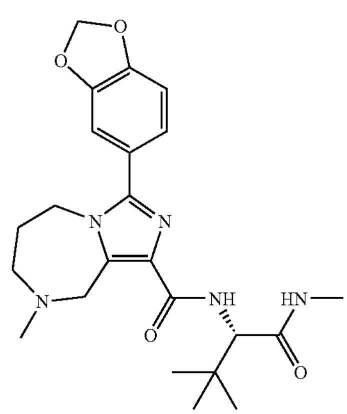 [SMILES: CNC(=O)[C@@H](NC(=O)c1nc(-c2ccc3c(c2)OCO3)n2c1CN(C)CCC2)C(C)(C)C] | (S)-3-(benzo[d][1,3]dioxol-5-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 442.1 | 37 |

TABLE I-continued

| Cmpd No. | Structure | Chemical Name | m/z | Example No. |
|---|---|---|---|---|
| 342 | 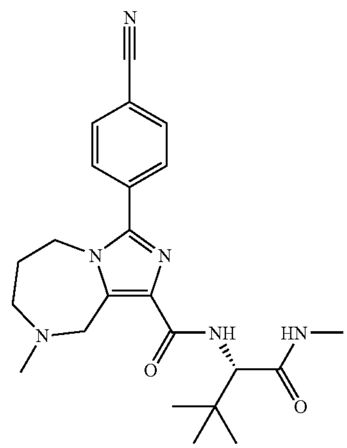 [SMILES: CNC(=O)[C@@H](NC(=O)c1nc(-c2ccc(C#N)cc2)n2c1CN(C)CCC2)C(C)(C)C] | (S)-3-(4-cyanophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 423.1 | 37 |
| 343 | 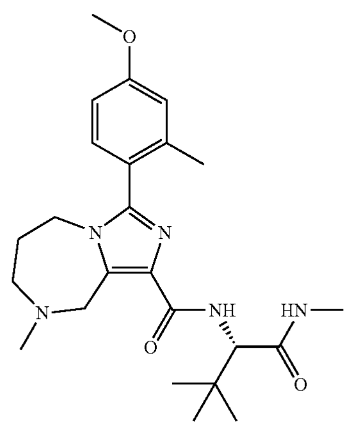 [SMILES: CNC(=O)[C@@H](NC(=O)c1nc(-c2ccc(OC)cc2C)n2c1CN(C)CCC2)C(C)(C)C] | (S)-N-(3,3-dimethyl-1-(methylamino)-1-oxobutan-2-yl)-3-(4-methoxy-2-methylphenyl)-8-methyl-6,7,8,9-tetrahydro-5H-imidazo[1,5-a][1,4]diazepine-1-carboxamide | 442.2 | 37 |
| 344 | 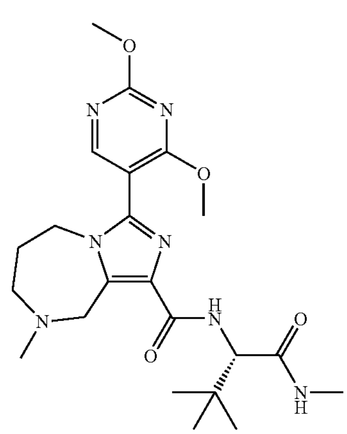 [SMILES: CNC(=O)[C@@H](NC(=O)c1nc(-c2cnc(OC)nc2OC)n2c1CN(C)CCC2)C(C)(C)C] | (S)-3-(2,4-dimethoxypyrimidin-5-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 460.1 | 37 |

TABLE I-continued

| Cmpd No. | Structure | Chemical Name | m/z | Example No. |
|---|---|---|---|---|
| 345 | 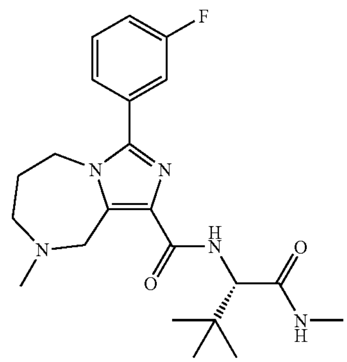 [SMILES: CNC(=O)[C@@H](NC(=O)c1nc(-c2cccc(F)c2)n2c1CN(C)CCC2)C(C)(C)C] | (S)-N-(3,3-dimethyl-1-(methylamino)-1-oxobutan-2-yl)-3-(3-fluorophenyl)-8-methyl-6,7,8,9-tetrahydro-5H-imidazo[1,5-a][1,4]diazepine-1-carboxamide | 416.0 | 37 |
| 346 | 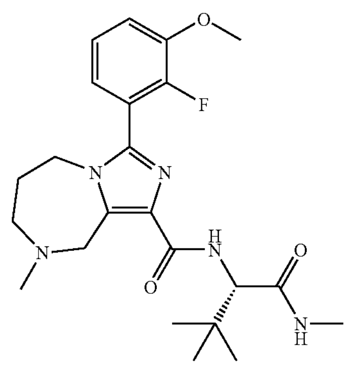 [SMILES: CNC(=O)[C@@H](NC(=O)c1nc(-c2cccc(OC)c2F)n2c1CN(C)CCC2)C(C)(C)C] | (S)-N-(3,3-dimethyl-1-(methylamino)-1-oxobutan-2-yl)-3-(2-fluoro-3-methoxyphenyl)-8-methyl-6,7,8,9-tetrahydro-5H-imidazo[1,5-a][1,4]diazepine-1-carboxamide | 446.1 | 37 |
| 347 | 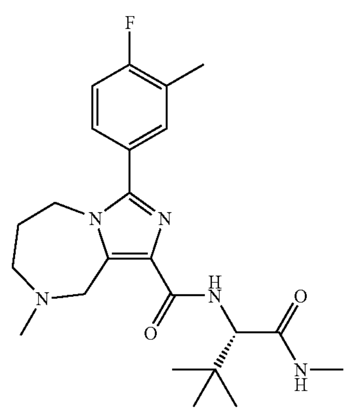 [SMILES: CNC(=O)[C@@H](NC(=O)c1nc(-c2ccc(F)c(C)c2)n2c1CN(C)CCC2)C(C)(C)C] | (S)-N-(3,3-dimethyl-1-(methylamino)-1-oxobutan-2-yl)-3-(4-fluoro-3-methylphenyl)-8-methyl-6,7,8,9-tetrahydro-5H-imidazo[1,5-a][1,4]diazepine-1-carboxamide | 430.1 | 37 |
| 348 | 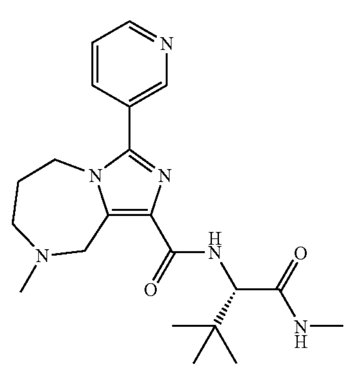 [SMILES: CNC(=O)[C@@H](NC(=O)c1nc(-c2cccnc2)n2c1CN(C)CCC2)C(C)(C)C] | (S)-N-(3,3-dimethyl-1-(methylamino)-1-oxobutan-2-yl)-8-methyl-3-(pyridin-3-yl)-6,7,8,9-tetrahydro-5H-imidazo[1,5-a][1,4]diazepine-1-carboxamide | 399.1 | 37 |

TABLE I-continued

| Cmpd No. | Structure | Chemical Name | m/z | Example No. |
|---|---|---|---|---|
| 349 | 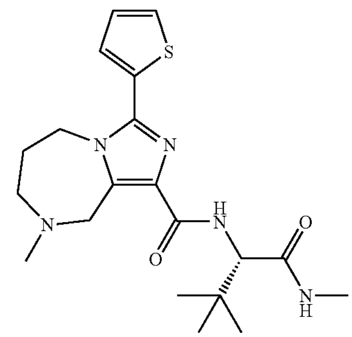 [SMILES: CNC(=O)[C@@H](NC(=O)c1nc(-c2cccs2)n2c1CN(C)CCC2)C(C)(C)C] | (S)-N-(3,3-dimethyl-1-(methylamino)-1-oxobutan-2-yl)-8-methyl-3-(thiophen-2-yl)-6,7,8,9-tetrahydro-5H-imidazo[1,5-a][1,4]diazepine-1-carboxamide | 404.0 | 37 |
| 350 | 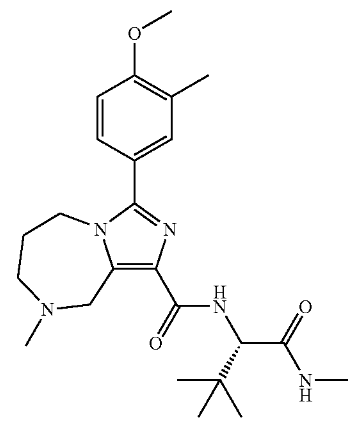 [SMILES: CNC(=O)[C@@H](NC(=O)c1nc(-c2ccc(OC)c(C)c2)n2c1CN(C)CCC2)C(C)(C)C] | (S)-N-(3,3-dimethyl-1-(methylamino)-1-oxobutan-2-yl)-3-(4-methoxy-3-methylphenyl)-8-methyl-6,7,8,9-tetrahydro-5H-imidazo[1,5-a][1,4]diazepine-1-carboxamide | 442.0 | 37 |
| 351 | 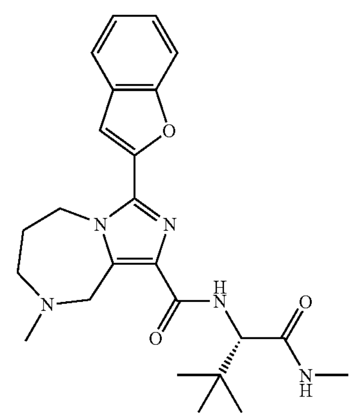 [SMILES: CNC(=O)[C@@H](NC(=O)c1nc(-c2cc3ccccc3o2)n2c1CN(C)CCC2)C(C)(C)C] | (S)-3-(benzofuran-2-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 438.0 | 37 |
| 352 | 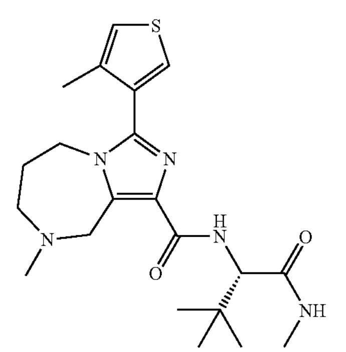 [SMILES: CNC(=O)[C@@H](NC(=O)c1nc(-c2cscc2C)n2c1CN(C)CCC2)C(C)(C)C] | (S)-N-(3,3-dimethyl-1-(methylamino)-1-oxobutan-2-yl)-8-methyl-3-(4-methylthiophen-3-yl)-6,7,8,9-tetrahydro-5H-imidazo[1,5-a][1,4]diazepine-1-carboxamide | 418.0 | 37 |

TABLE I-continued

| Cmpd No. | Structure | Chemical Name | m/z | Example No. |
|---|---|---|---|---|
| 353 | 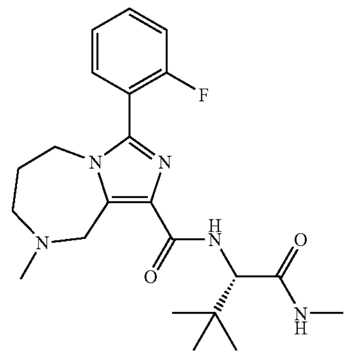 [SMILES: CNC(=O)[C@@H](NC(=O)c1nc(-c2ccccc2F)n2c1CN(C)CCC2)C(C)(C)C] | (S)-N-(3,3-dimethyl-1-(methylamino)-1-oxobutan-2-yl)-3-(2-fluorophenyl)-8-methyl-6,7,8,9-tetrahydro-5H-imidazo[1,5-a][1,4]diazepine-1-carboxamide | 416.0 | 37 |
| 354 | 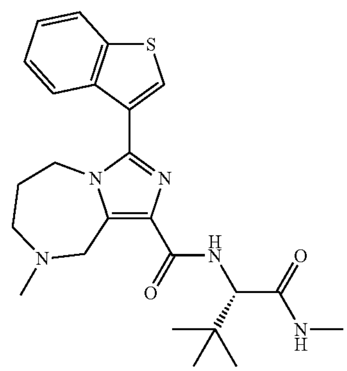 [SMILES: CNC(=O)[C@@H](NC(=O)c1nc(-c2csc3ccccc23)n2c1CN(C)CCC2)C(C)(C)C] | (S)-3-(benzo[b]thiophen-3-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 454.0 | 37 |
| 355 | 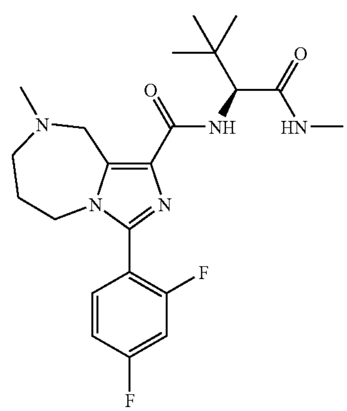 [SMILES: CNC(=O)[C@@H](NC(=O)c1nc(-c2ccc(F)cc2F)n2c1CN(C)CCC2)C(C)(C)C] | (S)-3-(2,4-difluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 434.0 | 37 |
| 356 | 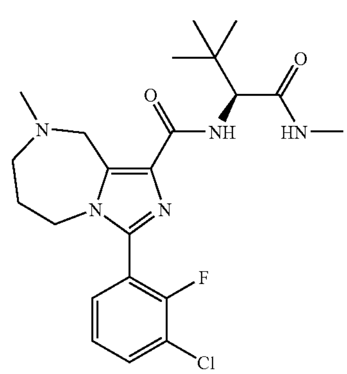 | (S)-3-(3-chloro-2-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 450.1 | 37 |

| Cmpd No. | Structure | Chemical Name | m/z | Example No. |
|---|---|---|---|---|
| 357 | 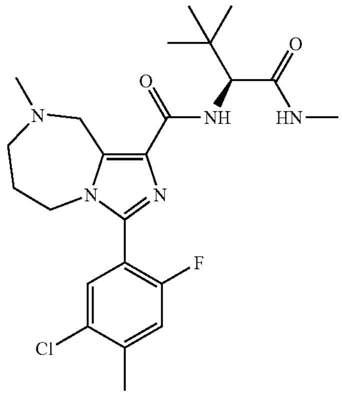 [SMILES: CNC(=O)[C@@H](NC(=O)c1nc(-c2cc(Cl)c(C)cc2F)n2c1CN(C)CCC2)C(C)(C)C] | (S)-3-(5-chloro-2-fluoro-4-methylphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 464.0 | 37 |
| 358 | 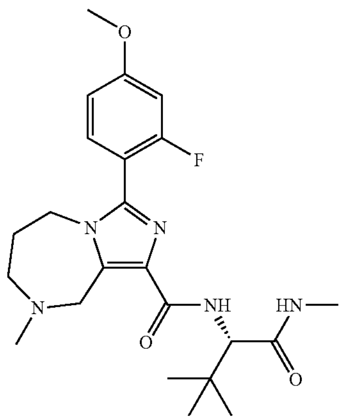 [SMILES: CNC(=O)[C@@H](NC(=O)c1nc(-c2ccc(OC)cc2F)n2c1CN(C)CCC2)C(C)(C)C] | (S)-N-(3,3-dimethyl-1-(methylamino)-1-oxobutan-2-yl)-3-(2-fluoro-4-methoxyphenyl)-8-methyl-6,7,8,9-tetrahydro-5H-imidazo[1,5-a][1,4]diazepine-1-carboxamide | 446.0 | 37 |
| 359 | 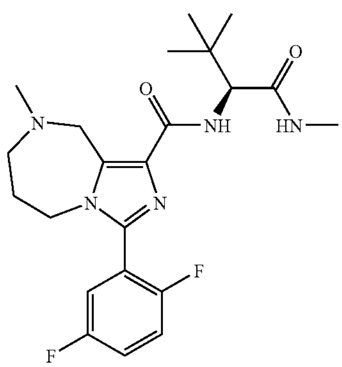 [SMILES: CNC(=O)[C@@H](NC(=O)c1nc(-c2cc(F)ccc2F)n2c1CN(C)CCC2)C(C)(C)C] | (S)-3-(2,5-difluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 434.0 | 37 |
| 360 | 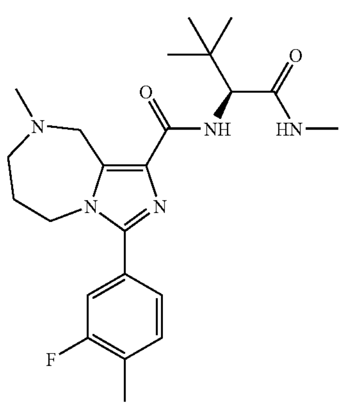 [SMILES: CNC(=O)[C@@H](NC(=O)c1nc(-c2ccc(C)c(F)c2)n2c1CN(C)CCC2)C(C)(C)C] | (S)-N-(3,3-dimethyl-1-(methylamino)-1-oxobutan-2-yl)-3-(3-fluoro-4-methylphenyl)-8-methyl-6,7,8,9-tetrahydro-5H-imidazo[1,5-a][1,4]diazepine-1-carboxamide | 430.0 | 37 |

TABLE I-continued

| Cmpd No. | Structure | Chemical Name | m/z | Example No. |
|---|---|---|---|---|
| 361 | 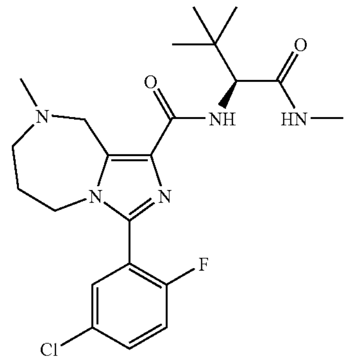 [SMILES: CNC(=O)[C@@H](NC(=O)c1nc(-c2cc(Cl)ccc2F)n2c1CN(C)CCC2)C(C)(C)C] | (S)-3-(5-chloro-2-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 450.0 | 37 |
| 362 | 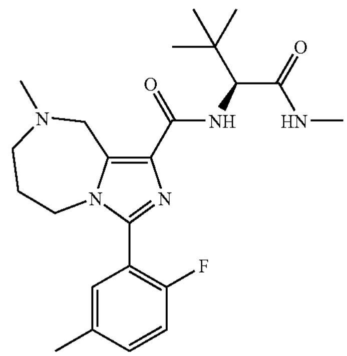 [SMILES: CNC(=O)[C@@H](NC(=O)c1nc(-c2cc(C)ccc2F)n2c1CN(C)CCC2)C(C)(C)C] | (S)-N-(3,3-dimethyl-1-(methylamino)-1-oxobutan-2-yl)-3-(2-fluoro-5-methylphenyl)-8-methyl-6,7,8,9-tetrahydro-5H-imidazo[1,5-a][1,4]diazepine-1-carboxamide | 430.0 | 37 |
| 363 | 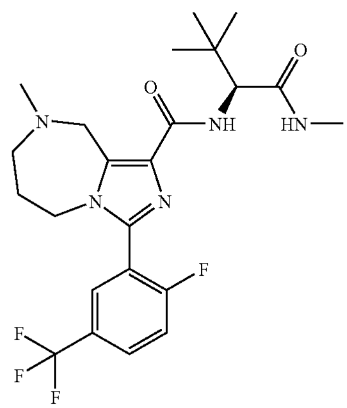 [SMILES: CNC(=O)[C@@H](NC(=O)c1nc(-c2cc(C(F)(F)F)ccc2F)n2c1CN(C)CCC2)C(C)(C)C] | (S)-N-(3,3-dimethyl-1-(methylamino)-1-oxobutan-2-yl)-3-(2-fluoro-5-(trifluoromethyl)phenyl)-8-methyl-6,7,8,9-tetrahydro-5H-imidazo[1,5-a][1,4]diazepine-1-carboxamide | 484.0 | 37 |
| 364 | 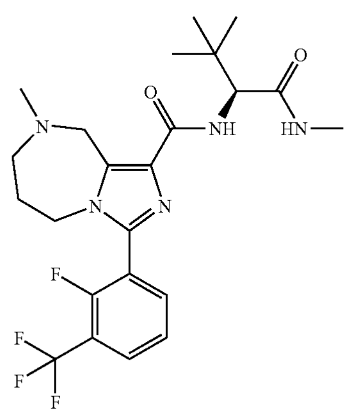 [SMILES: CNC(=O)[C@@H](NC(=O)c1nc(-c2cccc(C(F)(F)F)c2F)n2c1CN(C)CCC2)C(C)(C)C] | (S)-N-(3,3-dimethyl-1-(methylamino)-1-oxobutan-2-yl)-3-(2-fluoro-3-(trifluoromethyl)phenyl)-8-methyl-6,7,8,9-tetrahydro-5H-imidazo[1,5-a][1,4]diazepine-1-carboxamide | 484.0 | 37 |

TABLE I-continued

| Cmpd No. | Structure | Chemical Name | m/z | Example No. |
|---|---|---|---|---|
| 365 | 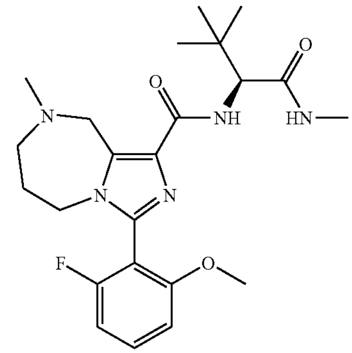 [SMILES: CNC(=O)[C@@H](NC(=O)c1nc(-c2c(F)cccc2OC)n2c1CN(C)CCC2)C(C)(C)C] | N-((S)-3,3-dimethyl-1-(methylamino)-1-oxobutan-2-yl)-3-(2-fluoro-6-methoxyphenyl)-8-methyl-6,7,8,9-tetrahydro-5H-imidazo[1,5-a][1,4]diazepine-1-carboxamide | 446.0 | 37 |
| 366 | 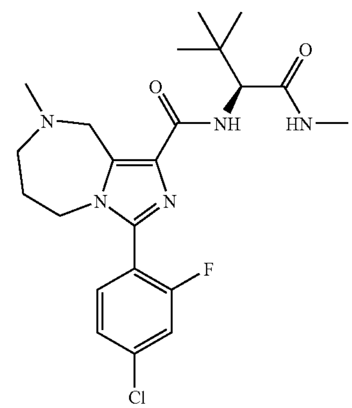 [SMILES: CNC(=O)[C@@H](NC(=O)c1nc(-c2ccc(Cl)cc2F)n2c1CN(C)CCC2)C(C)(C)C] | (S)-3-(4-chloro-2-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 450.0 | 37 |
| 367 | 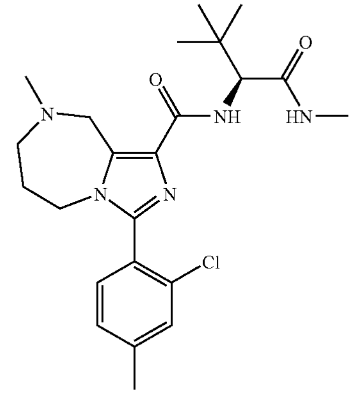 [SMILES: CNC(=O)[C@@H](NC(=O)c1nc(-c2ccc(C)cc2Cl)n2c1CN(C)CCC2)C(C)(C)C] | (S)-3-(2-chloro-4-methylphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 446.0 | 37 |

TABLE I-continued

| Cmpd No. | Structure | Chemical Name | m/z | Example No. |
|---|---|---|---|---|
| 368 | 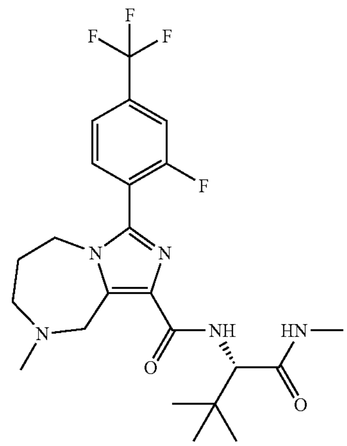 [SMILES: CNC(=O)[C@@H](NC(=O)c1nc(-c2ccc(C(F)(F)F)cc2F)n2c1CN(C)CCC2)C(C)(C)C] | (S)-N-(3,3-dimethyl-1-(methylamino)-1-oxobutan-2-yl)-3-(2-fluoro-4-(trifluoromethyl)phenyl)-8-methyl-6,7,8,9-tetrahydro-5H-imidazo[1,5-a][1,4]diazepine-1-carboxamide | 484.0 | 37 |
| 369 | 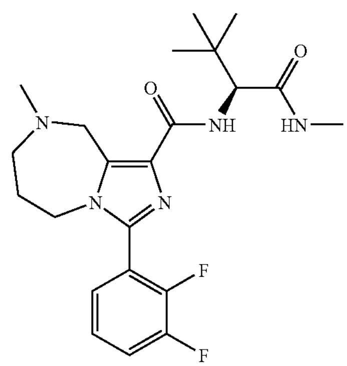 [SMILES: CNC(=O)[C@@H](NC(=O)c1nc(-c2cccc(F)c2F)n2c1CN(C)CCC2)C(C)(C)C] | (S)-3-(2,3-difluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 434.0 | 37 |
| 370 | 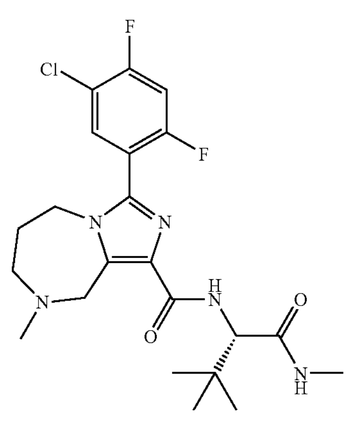 [SMILES: CNC(=O)[C@@H](NC(=O)c1nc(-c2cc(Cl)c(F)cc2F)n2c1CN(C)CCC2)C(C)(C)C] | (S)-3-(5-chloro-2,4-difluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 468.0 | 37 |

TABLE I-continued

| Cmpd No. | Structure | Chemical Name | m/z | Example No. |
|---|---|---|---|---|
| 371 | 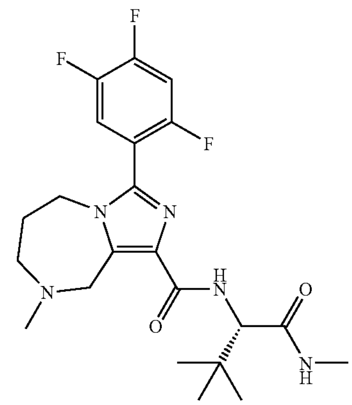 [SMILES: CNC(=O)[C@@H](NC(=O)c1nc(-c2cc(F)c(F)cc2F)n2c1CN(C)CCC2)C(C)(C)C] | (S)-N-(3,3-dimethyl-1-(methylamino)-1-oxobutan-2-yl)-8-methyl-3-(2,4,5-trifluorophenyl)-6,7,8,9-tetrahydro-5H-imidazo[1,5-a][1,4]diazepine-1-carboxamide | 452.2 | 37 |
| 372 | 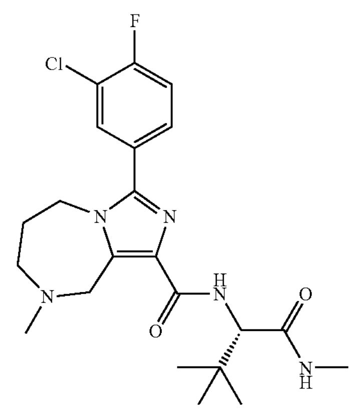 [SMILES: CNC(=O)[C@@H](NC(=O)c1nc(-c2ccc(F)c(Cl)c2)n2c1CN(C)CCC2)C(C)(C)C] | (S)-3-(3-chloro-4-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 450.0 | 37 |
| 373 | 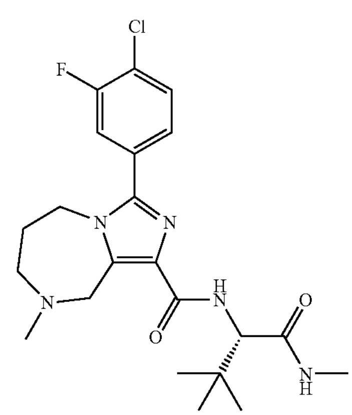 [SMILES: CNC(=O)[C@@H](NC(=O)c1nc(-c2ccc(Cl)c(F)c2)n2c1CN(C)CCC2)C(C)(C)C] | (S)-3-(4-chloro-3-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 450.0 | 37 |

TABLE I-continued

| Cmpd No. | Structure | Chemical Name | m/z | Example No. |
|---|---|---|---|---|
| 374 | 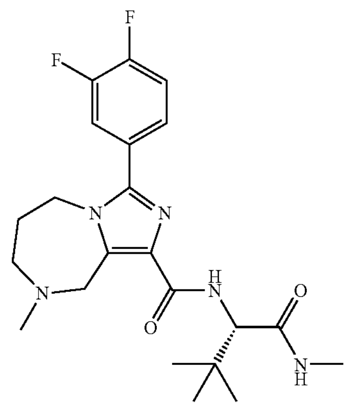 [SMILES: CNC(=O)[C@@H](NC(=O)c1nc(-c2ccc(F)c(F)c2)n2c1CN(C)CCC2)C(C)(C)C] | (S)-3-(3,4-difluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 434.0 | 37 |
| 375 | 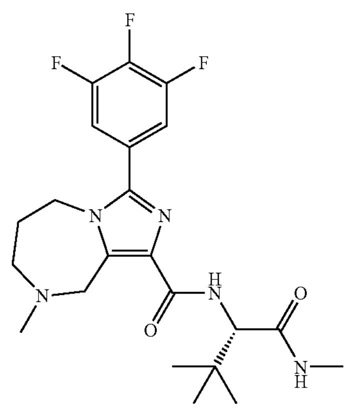 [SMILES: CNC(=O)[C@@H](NC(=O)c1nc(-c2cc(F)c(F)c(F)c2)n2c1CN(C)CCC2)C(C)(C)C] | (S)-N-(3,3-dimethyl-1-(methylamino)-1-oxobutan-2-yl)-8-methyl-3-(3,4,5-trifluorophenyl)-6,7,8,9-tetrahydro-5H-imidazo[1,5-a][1,4]diazepine-1-carboxamide | 452.0 | 37 |
| 376 | 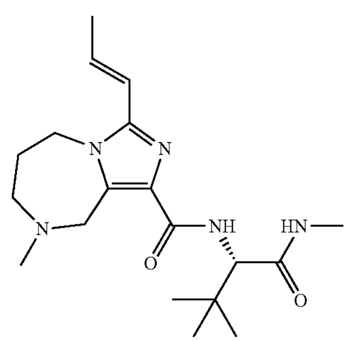 [SMILES: C/C=C/c1nc(C(=O)N[C@H](C(=O)NC)C(C)(C)C)c2n1CCCN(C)C2] | (S,E)-N-(3,3-dimethyl-1-(methylamino)-1-oxobutan-2-yl)-8-methyl-3-(prop-1-enyl)-6,7,8,9-tetrahydro-5H-imidazo[1,5-a][1,4]diazepine-1-carboxamide | 362.0 | 37 |
| 377 | 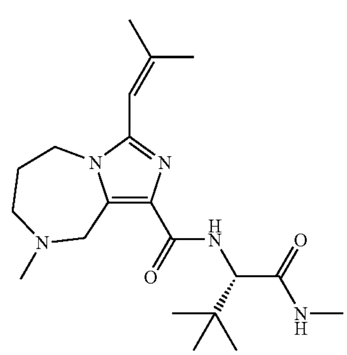 [SMILES: CNC(=O)[C@@H](NC(=O)c1nc(C=C(C)C)n2c1CN(C)CCC2)C(C)(C)C] | (S)-N-(3,3-dimethyl-1-(methylamino)-1-oxobutan-2-yl)-8-methyl-3-(2-methylprop-1-enyl)-6,7,8,9-tetrahydro-5H-imidazo[1,5-a][1,4]diazepine-1-carboxamide | 376.0 | 37 |

TABLE I-continued

| Cmpd No. | Structure | Chemical Name | m/z | Example No. |
|---|---|---|---|---|
| 378 | 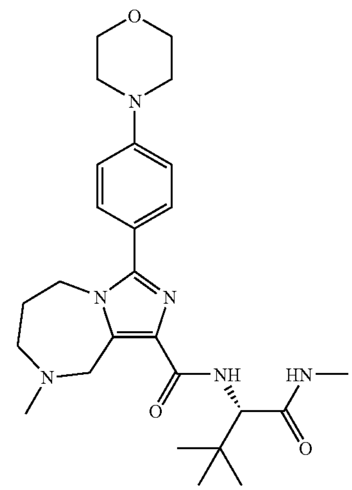 [SMILES: CNC(=O)[C@@H](NC(=O)c1nc(-c2ccc(N3CCOCC3)cc2)n2c1CN(C)CCC2)C(C)(C)C] | (S)-N-(3,3-dimethyl-1-(methylamino)-1-oxobutan-2-yl)-8-methyl-3-(4-morpholinophenyl)-6,7,8,9-tetrahydro-5H-imidazo[1,5-a][1,4]diazepine-1-carboxamide | 483.0 | 37 |
| 379 | 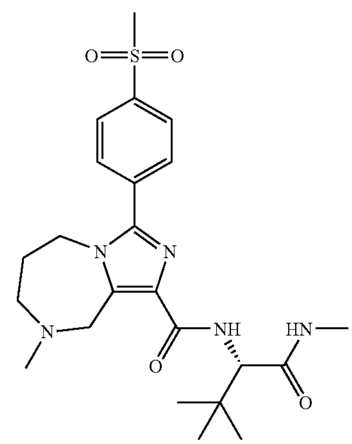 [SMILES: CNC(=O)[C@@H](NC(=O)c1nc(-c2ccc(S(C)(=O)=O)cc2)n2c1CN(C)CCC2)C(C)(C)C] | (S)-N-(3,3-dimethyl-1-(methylamino)-1-oxobutan-2-yl)-8-methyl-3-(4-(methylsulfonyl)phenyl)-6,7,8,9-tetrahydro-5H-imidazo[1,4-a][1,5]diazpeine-1-carboxamide | 476.0 | 37 |
| 380 | 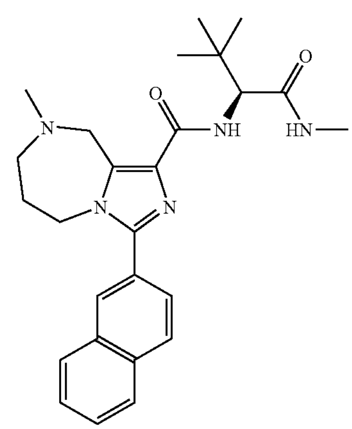 [SMILES: CNC(=O)[C@@H](NC(=O)c1nc(-c2ccc3ccccc3c2)n2c1CN(C)CCC2)C(C)(C)C] | (S)-N-(3,3-dimethyl-1-(methylamino)-1-oxobutan-2-yl)-8-methyl-3-(naphthalen-2-yl)-6,7,8,9-tetrahydro-5H-imidazo[1,5-a][1,4]diazepine-1-carboxamide | 448.0 | 37 |

TABLE I-continued

| Cmpd No. | Structure | Chemical Name | m/z | Example No. |
|---|---|---|---|---|
| 381 | 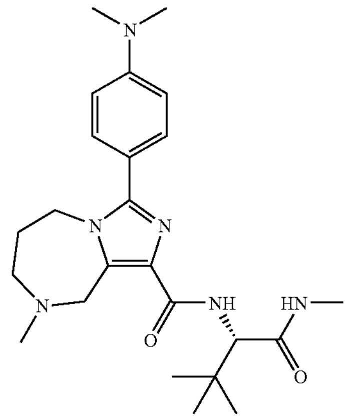 [SMILES: CNC(=O)[C@@H](NC(=O)c1nc(-c2ccc(N(C)C)cc2)n2c1CN(C)CCC2)C(C)(C)C] | (S)-N-(3,3-dimethyl-1-(methylamino)-1-oxobutan-2-yl)-3-(4-(dimethylamino)phenyl)-8-methyl-6,7,8,9-tetrahydro-5H-imidazo[1,5-a][1,4]diazepine-1-carboxamide | 441.0 | 37 |
| 382 | 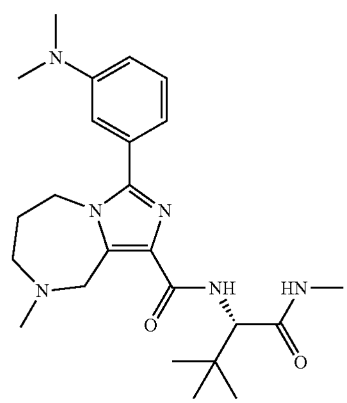 [SMILES: CNC(=O)[C@@H](NC(=O)c1nc(-c2cccc(N(C)C)c2)n2c1CN(C)CCC2)C(C)(C)C] | (S)-N-(3,3-dimethyl-1-(methylamino)-1-oxobutan-2-yl)-3-(3-(dimethylamino)phenyl)-8-methyl-6,7,8,9-tetrahydro-5H-imidazo[1,5-a][1,4]diazepine-1-carboxamide | 441.0 | 37 |
| 383 | 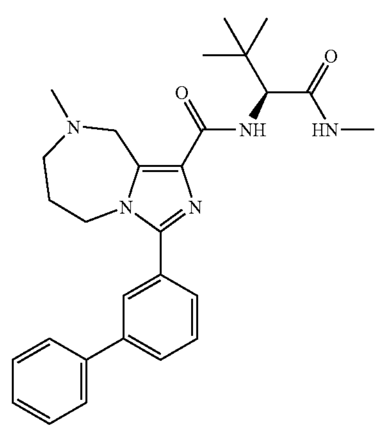 [SMILES: CNC(=O)[C@@H](NC(=O)c1nc(-c2cccc(-c3ccccc3)c2)n2c1CN(C)CCC2)C(C)(C)C] | (S)-3-(biphenyl-3-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 474.0 | 37 |

TABLE I-continued

| Cmpd No. | Structure | Chemical Name | m/z | Example No. |
|---|---|---|---|---|
| 384 | 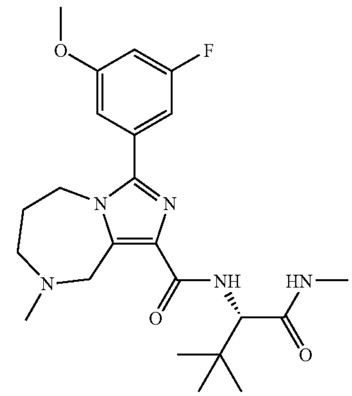 [SMILES: CNC(=O)[C@@H](NC(=O)c1nc(-c2cc(F)cc(OC)c2)n2c1CN(C)CCC2)C(C)(C)C] | (S)-N-(3,3-dimethyl-1-(methylamino)-1-oxobutan-2-yl)-3-(3-fluoro-5-methoxyphenyl)-8-methyl-6,7,8,9-tetrahydro-5H-imidazo[1,5-a][1,4]diazpeine-1-carboxamide | 446.0 | 37 |
| 385 | 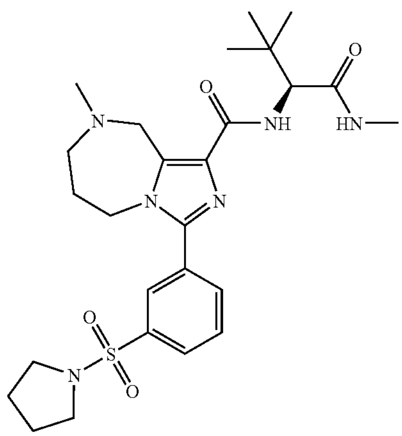 [SMILES: CNC(=O)[C@@H](NC(=O)c1nc(-c2cccc(S(=O)(=O)N3CCCC3)c2)n2c1CN(C)CCC2)C(C)(C)C] | (S)-N-(3,3-dimethyl-1-(methylamino)-1-oxobutan-2-yl)-8-methyl-3-(3-(pyrrolidin-1-ylsulfonyl)phenyl)-6,7,8,9-tetrahydro-5H-imidazo[1,5-a][1,4]diazepine-1-carboxamide | 531.0 | 37 |
| 386 | 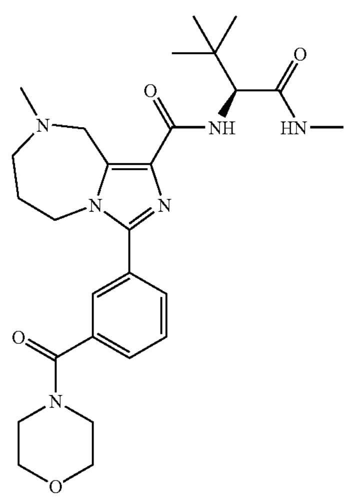 [SMILES: CNC(=O)[C@@H](NC(=O)c1nc(-c2cccc(C(=O)N3CCOCC3)c2)n2c1CN(C)CCC2)C(C)(C)C] | (S)-N-(3,3-dimethyl-1-(methylamino)-1-oxobutan-2-yl)-8-methyl-3-(3-(morpholine-4-carbonyl)phenyl)-6,7,8,9-tetrahydro-5H-imidazo[1,5-a][1,4]diazepine-1-carboxamide | 511.0 | 37 |

TABLE I-continued

| Cmpd No. | Structure | Chemical Name | m/z | Example No. |
|---|---|---|---|---|
| 387 | 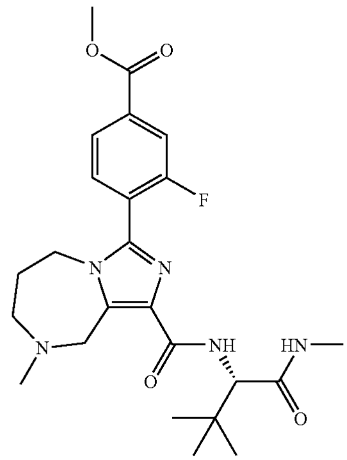 [SMILES: CNC(=O)[C@@H](NC(=O)c1nc(-c2ccc(C(=O)OC)cc2F)n2c1CN(C)CCC2)C(C)(C)C] | (S)-methyl-4-(1-(3,3-dimethyl-1-(methylamino)-1-oxobutan-2-ylcarbamoyl)-8-methyl-6,7,8,9-tetrahydro-5H-imidazo[1,5-a][1,4]diazepine-3-yl)-3-fluorobenzoate | 474.0 | 37 |
| 388 | 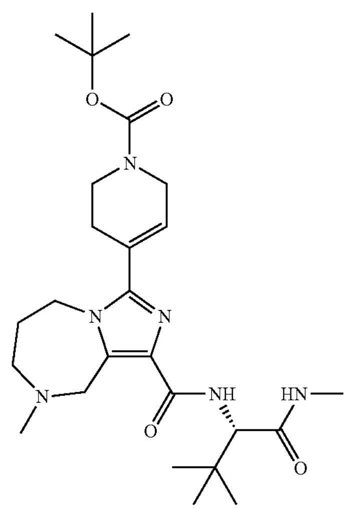 [SMILES: CNC(=O)[C@@H](NC(=O)c1nc(C2=CCN(C(=O)OC(C)(C)C)CC2)n2c1CN(C)CCC2)C(C)(C)C] | (S)-tert-butyl 4-(1-(3,3-dimethyl-1-(methylamino)-1-oxobutan-2-ylcarbamoyl)-8-methyl-6,7,8,9-tetrahydro-5H-imidazo[1,5-a][1,4]diazepine-3-yl)-5,6-dihydropyridine-1(2H)-carboxylate | 503.0 | 37 |
| 389 | 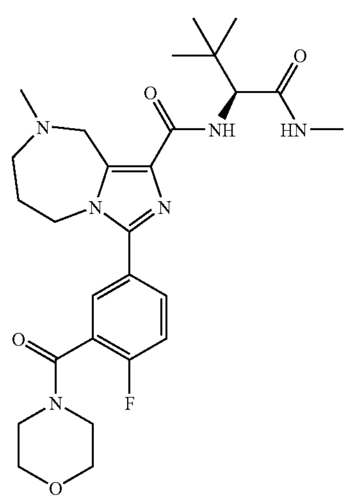 [SMILES: CNC(=O)[C@@H](NC(=O)c1nc(-c2ccc(F)c(C(=O)N3CCOCC3)c2)n2c1CN(C)CCC2)C(C)(C)C] | (S)-N-(3,3-dimethyl-1-(methylamino)-1-oxobutan-2-yl)-3-(4-fluoro-3-(morpholine-4-carbonyl)phenyl)-8-methyl-6,7,8,9-tetrahydro-5H-imidazo[1,5-a][1,4]diazepine-1-carboxamide | 529.0 | 37 |

TABLE I-continued

| Cmpd No. | Structure | Chemical Name | m/z | Example No. |
|---|---|---|---|---|
| 390 | 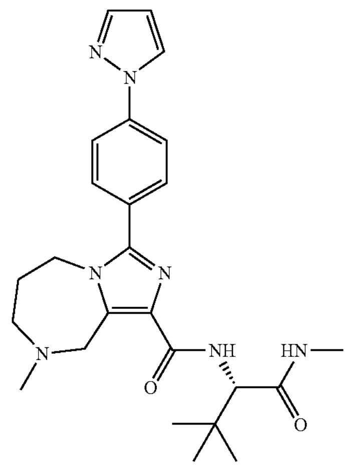 [SMILES: CNC(=O)[C@@H](NC(=O)c1nc(-c2ccc(-n3cccn3)cc2)n2c1CN(C)CCC2)C(C)(C)C] | (S)-3-(4-(1H-pyrazol-1-yl)phenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 464.0 | 37 |
| 391 | 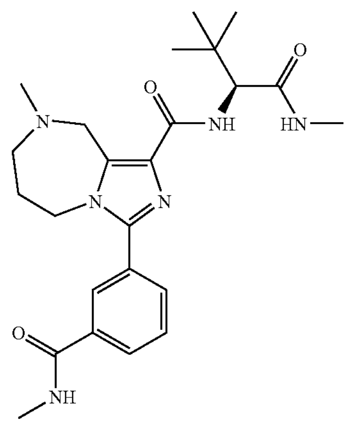 [SMILES: CNC(=O)c1cccc(-c2nc(C(=O)N[C@H](C(=O)NC)C(C)(C)C)c3n2CCCN(C)C3)c1] | (S)-N-(3,3-dimethyl-1-(methylamino)-1-oxobutan-2-yl)-8-methyl-3-(3-(methylcarbamoyl)phenyl)-6,7,8,9-tetrahydro-5H-imiedazo[1,5-a][1,4]diazepine-1-carboxamide | 455.0 | 37 |
| 392 | 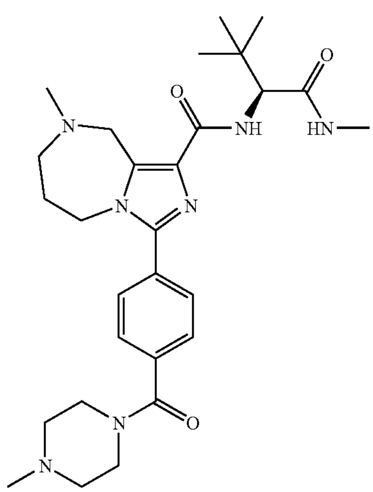 | (S)-N-(3,3-dimethyl-1-(methylamino)-1-oxobutan-2-yl)-8-methyl-3-(4-(4-methylpiperazine-1-carbonyl)phenyl)-6,7,8,9-tetrahydro-5H-imidazo[1,5-a][1,4]diazepine-1-carboxamide | 524.0 | 37 |

TABLE I-continued

| Cmpd No. | Structure | Chemical Name | m/z | Example No. |
|---|---|---|---|---|
| 393 | 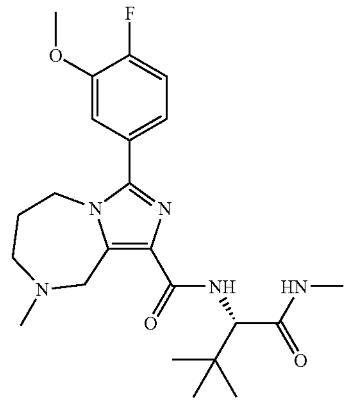 [SMILES: CNC(=O)[C@@H](NC(=O)c1nc(-c2ccc(F)c(OC)c2)n2c1CN(C)CCC2)C(C)(C)C] | (S)-N-(3,3-dimethyl-1-(methylamino)-1-oxobutan-2-yl)-3-(4-fluoro-3-methoxyphenyl)-8-methyl-6,7,8,9-tetrahydro-5H-imidazo[1,5-a][1,4-]diazepine-1-carboxamide | 446.0 | 37 |
| 394 | 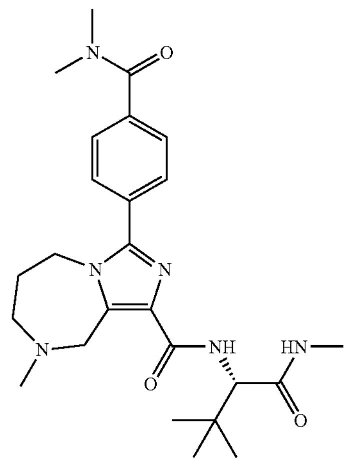 [SMILES: CNC(=O)[C@@H](NC(=O)c1nc(-c2ccc(C(=O)N(C)C)cc2)n2c1CN(C)CCC2)C(C)(C)C] | (S)-N-(3,3-dimethyl-1-(methylamino)-1-oxobutan-2-yl)-3-(4-(dimethylcarbamoyl)phenyl)-8-methyl-6,7,8,9-tetrahydro-5H-imidazo[1,5-a][1,4]diazepine-1-carboxamide | 469.0 | 37 |
| 395 | 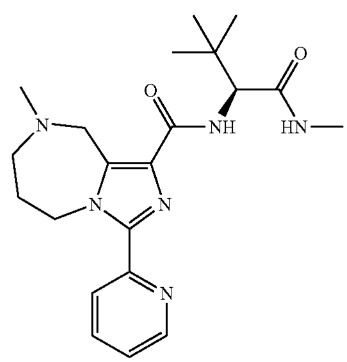 [SMILES: CNC(=O)[C@@H](NC(=O)c1nc(-c2ccccn2)n2c1CN(C)CCC2)C(C)(C)C] | (S)-N-(3,3-dimethyl-1-(methylamino)-1-oxobutan-2-yl)-8-methyl-3-(pyridin-2-yl)-6,7,8,9-tetrahydro-5H-imidazo[1,5-a][1,4]diazepine-1-carboxamide | 399.0 | 37 |
| 396 | 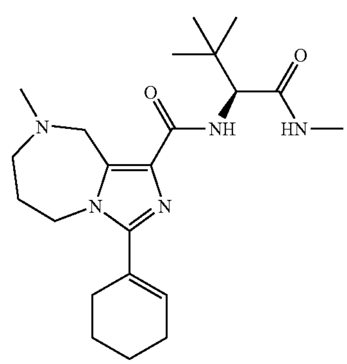 [SMILES: CNC(=O)[C@@H](NC(=O)c1nc(C2=CCCCC2)n2c1CN(C)CCC2)C(C)(C)C] | (S)-3-cyclohexyl-N-(3,3-dimethyl-1-(methylamino)-1-oxobutan-2-yl)-8-methyl-6,7,8,9-tetrahydro-5H-imidazo[1,5-a][1,4]diazerpine-1-carboxamide | 402.0 | 37 |

TABLE I-continued

| Cmpd No. | Structure | Chemical Name | m/z | Example No. |
|---|---|---|---|---|
| 397 | 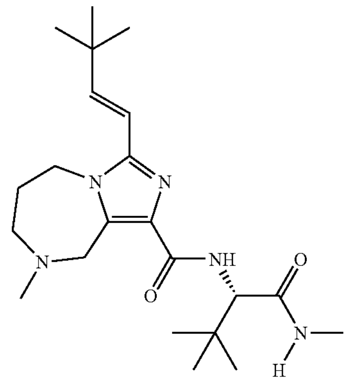 [SMILES: CNC(=O)[C@@H](NC(=O)c1nc(/C=C/C(C)(C)C)n2c1CN(C)CCC2)C(C)(C)C] | (S,E)-N-(3,3-dimethyl-1-(methylamino)-1-oxobutan-2-yl)-3-(3,3-dimethylbut-1-enyl)-8-methyl-6,7,8,9-tetrahydro-5H-imidazol[1,5-a][1,4]diazepine-1-carboxamide | 404.3 | 37 |
| 398 | 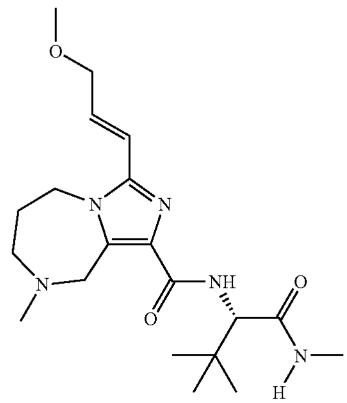 [SMILES: CNC(=O)[C@@H](NC(=O)c1nc(/C=C/COC)n2c1CN(C)CCC2)C(C)(C)C] | (S,E)-N-(3,3-dimethyl-1-(methylamino)-1-oxobutan-2-yl)-3-(3-methoxyprop-1-enyl)-8-methyl-6,7,8,9-tetrahydro-5H-imidazo[1,5-a][1,4]diazepine-1-carboxamide | 392.2 | 37 |
| 399 | 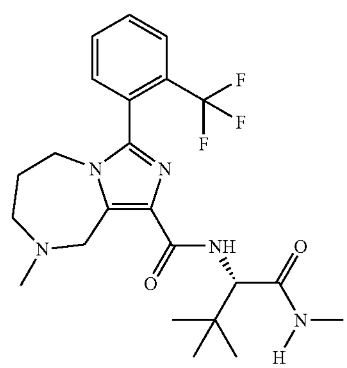 [SMILES: CNC(=O)[C@@H](NC(=O)c1nc(-c2ccccc2C(F)(F)F)n2c1CN(C)CCC2)C(C)(C)C] | (S)-N-(3,3-dimethyl-1-(methylamino)-1-oxobutan-2-yl)-8-methyl-3-(2-(trifluoromethyl)phenyl)-6,7,8,9-tetrahydro-5H-imidazo[1,5-a][1,4]diazepine-1-carboxamide | 466.2 | 37 |
| 400 | 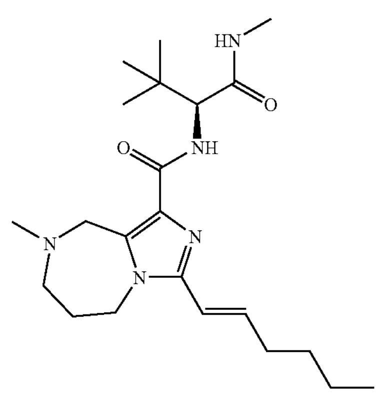 [SMILES: CCCC/C=C/c1nc(C(=O)N[C@H](C(=O)NC)C(C)(C)C)c2n1CCCN(C)C2] | (S,E)-N-(3,3-dimethyl-1-(methylamino)-1-oxobutan-2-yl)-3-(hex-1-enyl)-8-methyl-6,7,8,9-tetrahydro-5H-imidazo[1,5-a][1,4]diazepine-1-carboxamide | 404.3 | 37 |

TABLE I-continued

| Cmpd No. | Structure | Chemical Name | m/z | Example No. |
|---|---|---|---|---|
| 401 | 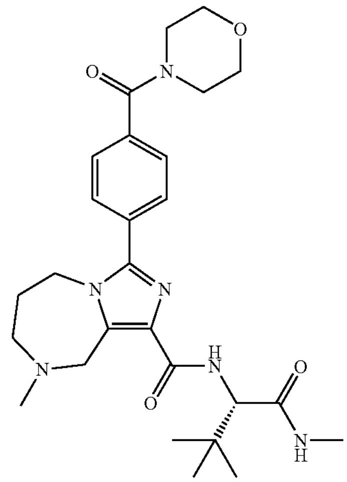 [SMILES: CNC(=O)[C@@H](NC(=O)c1nc(-c2ccc(C(=O)N3CCOCC3)cc2)n2c1CN(C)CCC2)C(C)(C)C] | (S)-N-(3,3-dimethyl-1-(methylamino)-1-oxobutan-2-yl)-8-methyl-3-(4-(morpholine-4-carbonyl)phenyl)-6,7,8,9-tetrahydro-5H-imidazo[1,5-a][1,4]diazapine-1-carboxamide | 511.0 | 37 |
| 402 | 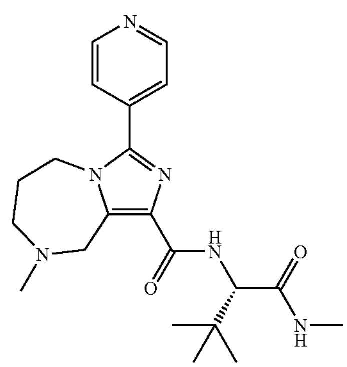 [SMILES: CNC(=O)[C@@H](NC(=O)c1nc(-c2ccncc2)n2c1CN(C)CCC2)C(C)(C)C] | (S)-N-(3,3-dimethyl-1-(methylamino)-1-oxobutan-2-yl)-8-methyl-3-(pyridin-4-yl)-6,7,8,9-tetrahydro-5H-imidazo[1,5-a][1,4]diazepine-1-carboxamide | 399.0 | 37 |
| 403 | 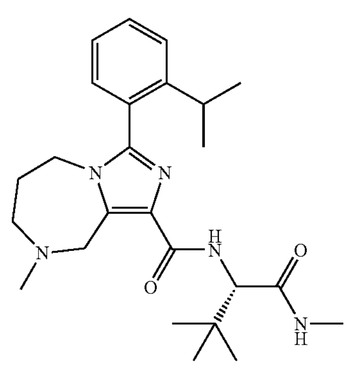 [SMILES: CNC(=O)[C@@H](NC(=O)c1nc(-c2ccccc2C(C)C)n2c1CN(C)CCC2)C(C)(C)C] | (S)-N-(3,3-dimethyl-1-(methylamino)-1-oxobutan-2-yl)-3-(2-isopropylphenyl)-8-methyl-6,7,8,9-tetrahydro-5H-imidazo[1,5-a][1,4]diazepine-1-carboxamide | 440.0 | 37 |

TABLE I-continued

| Cmpd No. | Structure | Chemical Name | m/z | Example No. |
|---|---|---|---|---|
| 404 | 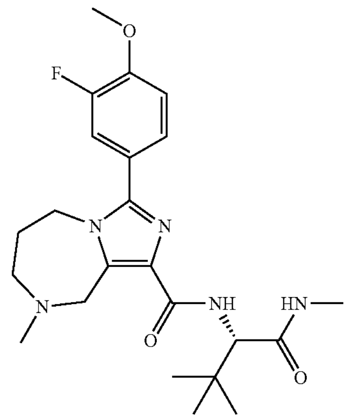 [SMILES: CNC(=O)[C@@H](NC(=O)c1nc(-c2ccc(OC)c(F)c2)n2c1CN(C)CCC2)C(C)(C)C] | (S)-N-(3,3-dimethyl-1-(methylamino)-1-oxobutan-2-yl)-3-(3-fluoro-4-methoxyphenyl)-8-methyl-6,7,8,9-tetrahydro-5H-imidazo[1,5-a][1,4]diazepine-1-carboxamide | 446.0 | 37 |
| 405 | 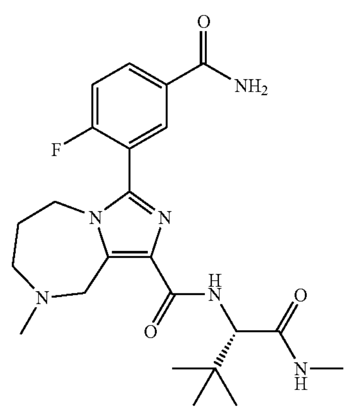 [SMILES: CNC(=O)[C@@H](NC(=O)c1nc(-c2cc(C(N)=O)ccc2F)n2c1CN(C)CCC2)C(C)(C)C] | (S)-3-(5-carbamoyl-2-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 459.0 | 37 |
| 406 | 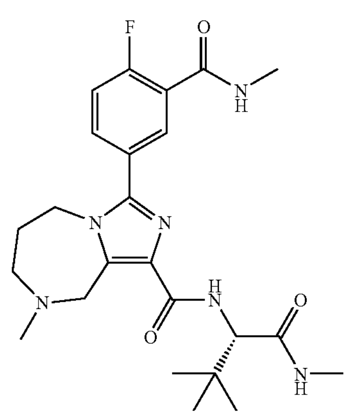 [SMILES: CNC(=O)c1cc(-c2nc(C(=O)N[C@H](C(=O)NC)C(C)(C)C)c3n2CCCN(C)C3)ccc1F] | (S)-N-(3,3-dimethyl-1-(methylamino)-1-oxobutan-2-yl)-3-(4-fluoro-3-(methylcarbamoyl)phenyl)-8-methyl-6,7,8,9-tetrahydro-5H-imidazo[1,5-a][1,4]diazepine-1-carboxamide | 473.0 | 37 |

TABLE I-continued

| Cmpd No. | Structure | Chemical Name | m/z | Example No. |
|---|---|---|---|---|
| 407 | 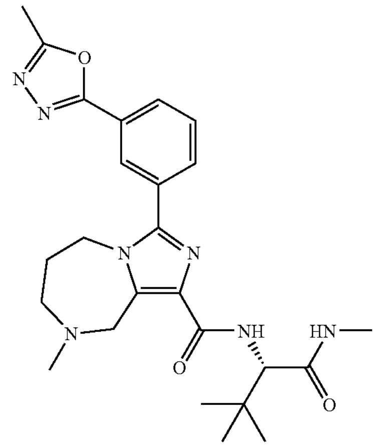 [SMILES: CNC(=O)[C@@H](NC(=O)c1nc(-c2cccc(-c3nnc(C)o3)c2)n2c1CN(C)CCC2)C(C)(C)C] | (S)-N-(3,3-dimethyl-1-(methylamino)-1-oxobutan-2-yl)-8-methyl-3-(3-(5-methyl-1,3,4-oxadiazol-2-yl)phenyl)-6,7,8,9-tetrahydro-5H-imidazo[1,5-a][1,4]diazepine-1-carboxamide | 480.0 | 37 |
| 408 | 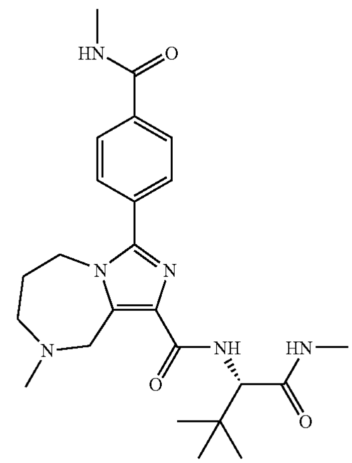 [SMILES: CNC(=O)c1ccc(-c2nc(C(=O)N[C@H](C(=O)NC)C(C)(C)C)c3n2CCCN(C)C3)cc1] | (S)-N-(3,3-dimethyl-1-(methylamino)-1-oxobutan-2-yl)-8-methyl-3-(4-(methylcarbamoyl)phenyl)-6,7,8,9-tetrahydro-5H-imidazo[1,5-a][1,4]diazepine-1-carboxamide | 455.0 | 37 |
| 409 | 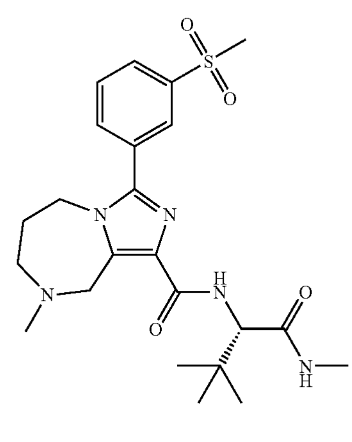 [SMILES: CNC(=O)[C@@H](NC(=O)c1nc(-c2cccc(S(C)(=O)=O)c2)n2c1CN(C)CCC2)C(C)(C)C] | (S)-N-(3,3-dimethyl-1-(methylamino)-1-oxobutan-2-yl)-8-methyl-3-(3-(methylsulfonyl)phenyl)-6,7,8,9-tetrahydro-5H-imidazo[1,5-a][1,4]diazepine-1-carboxamide | 476.0 | 37 |

TABLE I-continued

| Cmpd No. | Structure | Chemical Name | m/z | Example No. |
|---|---|---|---|---|
| 410 | 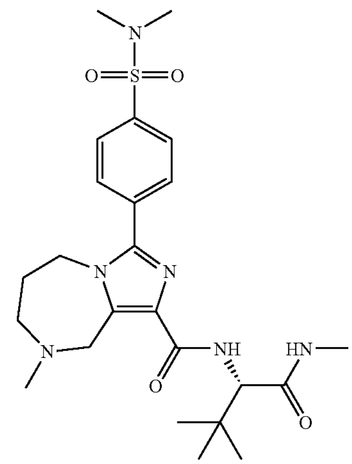 [SMILES: CNC(=O)[C@@H](NC(=O)c1nc(-c2ccc(S(=O)(=O)N(C)C)cc2)n2c1CN(C)CCC2)C(C)(C)C] | (S)-N-(3,3-dimethyl-1-(methylamino)-1-oxobutan-2-yl)-3-(4-(N,N-dimethylsulfamoyl)phenyl)-8-methyl-6,7,8,9-tetrahydro-5H-imidazol[1,5-a][1,4]diazepine-1-carboxamide | 505.0 | 37 |
| 411 | 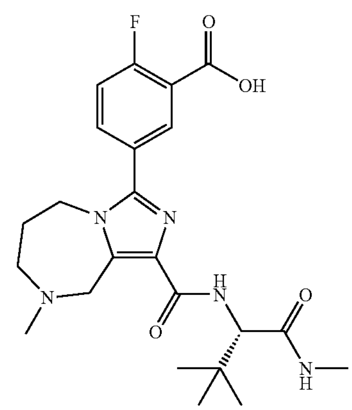 | (S)-5-(1-(3,3-dimethyl-1-(methylamino)-1-oxobutan-2-ylcarbamoyl)-8-methyl-6,7,8,9-tetrahydro-5H-imidazo[1,5-a][1,4]diazepin-3-yl)-2-fluorobenzoic acid | 460.0 | 37 |
| 412 | 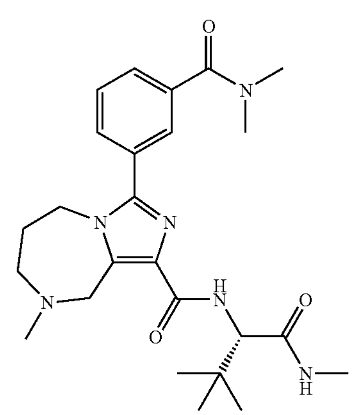 [SMILES: CNC(=O)[C@@H](NC(=O)c1nc(-c2cccc(C(=O)N(C)C)c2)n2c1CN(C)CCC2)C(C)(C)C] | (S)-N-(3,3-dimethyl-1-(methylamino)-1-oxobutan-2-yl)-3-(3-(dimethylcarbamoyl)phenyl)-8-methyl-6,7,8,9-tetrahydro-5H-imidazo[1,5-a][1,4]diazepine-1-carboxamide | 469.0 | 37 |

TABLE I-continued

| Cmpd No. | Structure | Chemical Name | m/z | Example No. |
|---|---|---|---|---|
| 413 | 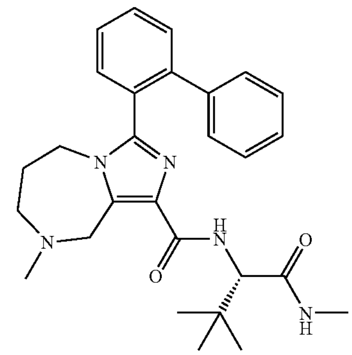 [SMILES: CNC(=O)[C@@H](NC(=O)c1nc(-c2ccccc2-c2ccccc2)n2c1CN(C)CCC2)C(C)(C)C] | (S)-3-(biphenyl-2-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 474.0 | 37 |
| 414 | 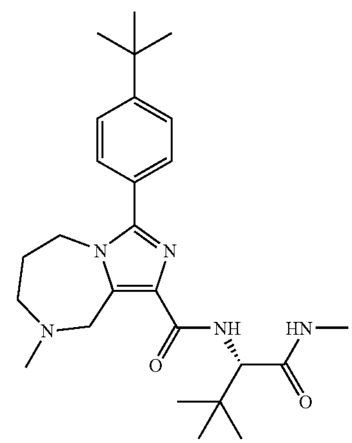 [SMILES: CNC(=O)[C@@H](NC(=O)c1nc(-c2ccc(C(C)(C)C)cc2)n2c1CN(C)CCC2)C(C)(C)C] | (S)-3-(4-tert-butylphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 454.0 | 37 |
| 415 | 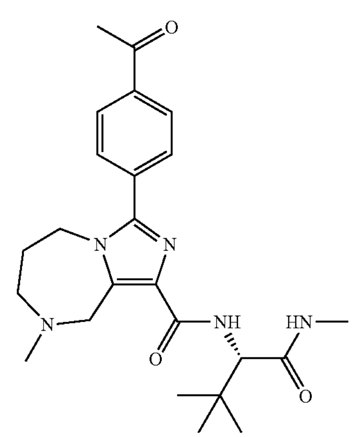 [SMILES: CNC(=O)[C@@H](NC(=O)c1nc(-c2ccc(C(C)=O)cc2)n2c1CN(C)CCC2)C(C)(C)C] | (S)-3-(4-acetylphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 440.0 | 37 |

TABLE I-continued

| Cmpd No. | Structure | Chemical Name | m/z | Example No. |
|---|---|---|---|---|
| 416 | 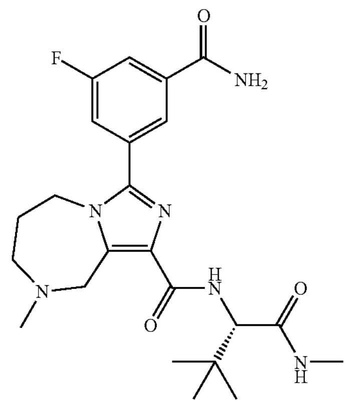 [SMILES: CNC(=O)[C@@H](NC(=O)c1nc(-c2cc(F)cc(C(N)=O)c2)n2c1CN(C)CCC2)C(C)(C)C] | (S)-3-(3-carbamoyl-5-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 459.0 | 37 |
| 417 | 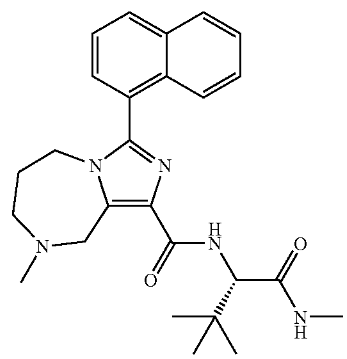 [SMILES: CNC(=O)[C@@H](NC(=O)c1nc(-c2cccc3ccccc23)n2c1CN(C)CCC2)C(C)(C)C] | (S)-N-(3,3-dimethyl-1-(methylamino)-1-oxobutan-2-yl)-8-methyl-3-(naphthalen-1-yl)-6,7,8,9-tetrahydro-5H-imidazo[1,5-a][1,4]diazepine-1-carboxamide | 448.0 | 37 |
| 418 | 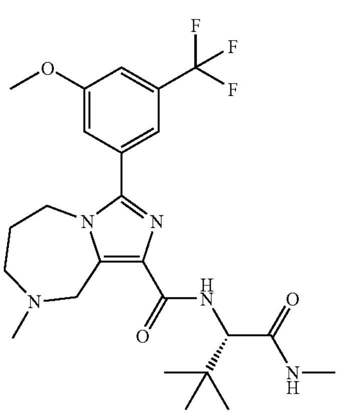 [SMILES: CNC(=O)[C@@H](NC(=O)c1nc(-c2cc(OC)cc(C(F)(F)F)c2)n2c1CN(C)CCC2)C(C)(C)C] | (S)-N-(3,3-dimethyl-1-(methylamino)-1-oxobutan-2-yl)-3-(3-methoxy-5-(trifluoromethyl)phenyl)-8-methyl-6,7,8,9-tetrahydro-5H-imidazo[1,5-a][1,4]diazepine-1-carboxamide | 496.0 | 37 |

TABLE I-continued

| Cmpd No. | Structure | Chemical Name | m/z | Example No. |
|---|---|---|---|---|
| 419 | 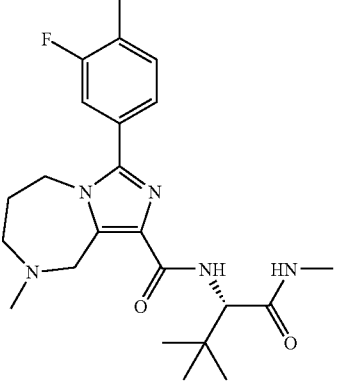 | (S)-N-(3,3-dimethyl-1-(methylamino)-1-oxobutan-2-yl)-3-(2-fluorobiphenyl-4-yl)-8-methyl-6,7,8,9-tetrahydro-5H-imidazo[1,5-a][1,4]diazepine-1-carboxamide | 492.0 | 37 |
| 420 | 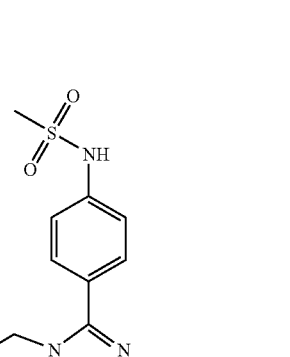 | (S)-N-(3,3-dimethyl-1-(methylamino)-1-oxobutan-2-yl)-8-methyl-3-(4-(methylsulfonamido)phenyl)-6,7,8,9-tetrahydro-5H-imidazo[1,5-a][1,4]diazepine-1-carboxamide | 491.0 | 37 |
| 421 | 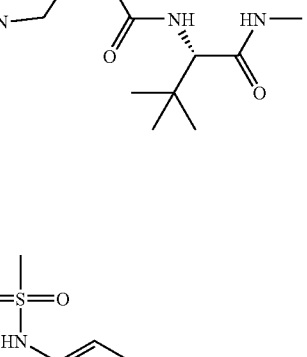 | (S)-N-(3,3-dimethyl-1-(methylamino)-1-oxobutan-2-yl)-8-methyl-3-(3-(methylsulfonamido)phenyl)-6,7,8,9-tetrahydro-5H-imidazo[1,5-a][1,4]diazepine-1-carboxamide | 491.0 | 37 |

TABLE I-continued

| Cmpd No. | Structure | Chemical Name | m/z | Example No. |
|---|---|---|---|---|
| 422 | 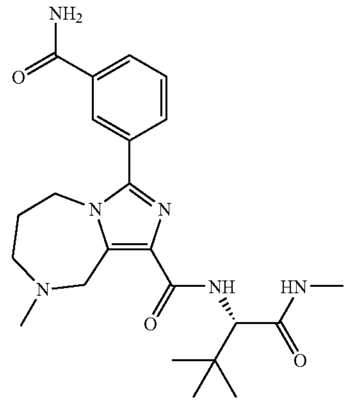 [SMILES: CNC(=O)[C@@H](NC(=O)c1nc(-c2cccc(C(N)=O)c2)n2c1CN(C)CCC2)C(C)(C)C] | (S)-3-(3-carbamoylphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 441.0 | 37 |
| 423 | 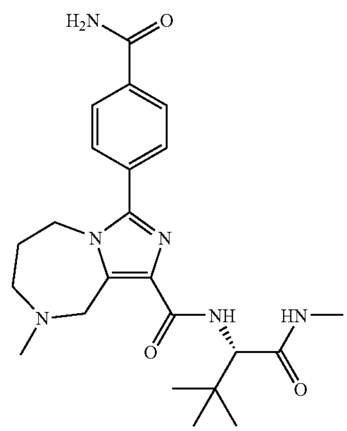 [SMILES: CNC(=O)[C@@H](NC(=O)c1nc(-c2ccc(C(N)=O)cc2)n2c1CN(C)CCC2)C(C)(C)C] | (S)-3-(4-carbamoylphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 441.0 | 37 |
| 424 | 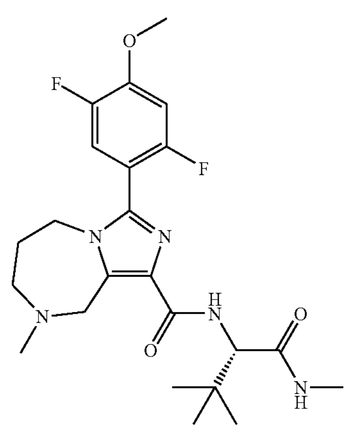 [SMILES: CNC(=O)[C@@H](NC(=O)c1nc(-c2cc(F)c(OC)cc2F)n2c1CN(C)CCC2)C(C)(C)C] | (S)-3-(2,5-difluoro-4-methoxyphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 464.0 | 37 |

TABLE I-continued

| Cmpd No. | Structure | Chemical Name | m/z | Example No. |
|---|---|---|---|---|
| 425 | 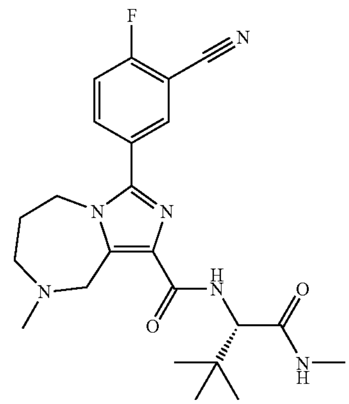 [SMILES: CNC(=O)[C@@H](NC(=O)c1nc(-c2ccc(F)c(C#N)c2)n2c1CN(C)CCC2)C(C)(C)C] | (S)-3-(3-cyano-4-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 441.0 | 37 |
| 426 | 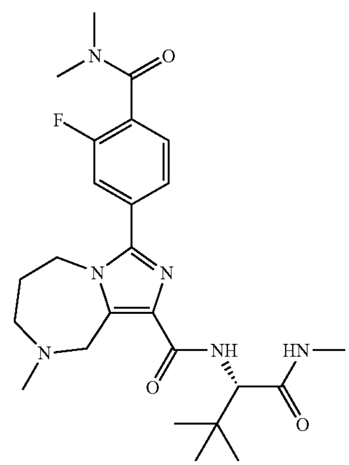 [SMILES: CNC(=O)[C@@H](NC(=O)c1nc(-c2ccc(C(=O)N(C)C)c(F)c2)n2c1CN(C)CCC2)C(C)(C)C] | (S)-N-(3,3-dimethyl-1-(methylamino)-1-oxobutan-2-yl)-3-(4-(dimethylcarbamoyl)-3-fluorophenyl)-8-methyl-6,7,8,9-tetrahydro-5H-imidazo[1,5-a][1,4]diazepine-1-carboxamide | 487.0 | 37 |
| 427 | 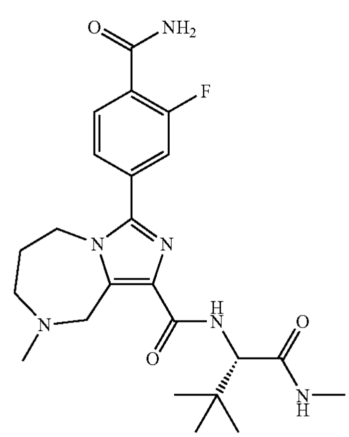 [SMILES: CNC(=O)[C@@H](NC(=O)c1nc(-c2ccc(C(N)=O)c(F)c2)n2c1CN(C)CCC2)C(C)(C)C] | (S)-3-(4-carbamoyl-3-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 459.0 | 37 |

TABLE I-continued

| Cmpd No. | Structure | Chemical Name | m/z | Example No. |
|---|---|---|---|---|
| 428 | 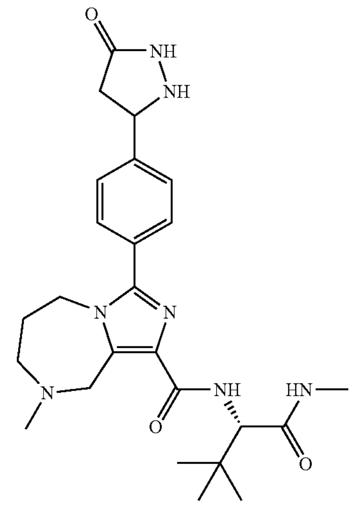 [SMILES: CNC(=O)[C@@H](NC(=O)c1nc(-c2ccc(C3CC(=O)NN3)cc2)n2c1CN(C)CCC2)C(C)(C)C] | N-((S)-3,3-dimethyl-1-(methylamino)-1-oxobutan-2-yl)-8-methyl-3-(4-(5-oxopyrazolidin-3-yl)phenyl)-6,7,8,9-tetrahydro-5H-imidazo[1,5-a][1,4]diazepine-1-carboxamide | 482.0 | 37 |
| 429 | 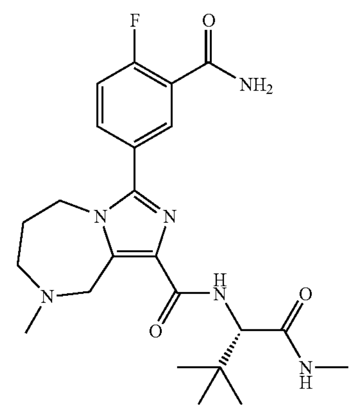 [SMILES: CNC(=O)[C@@H](NC(=O)c1nc(-c2ccc(F)c(C(N)=O)c2)n2c1CN(C)CCC2)C(C)(C)C] | (S)-3-(3-carbamoyl-4-fluorophenyl)-N-(3,3-dimethyl-1-(methylamino)-1-oxobutan-2-yl)-8-methyl-6,7,8,9-tetrahydro-5H-imidazo[1,5-a][1,4]diazpeine-1-carboxamide | 459.0 | 37 |
| 430 | 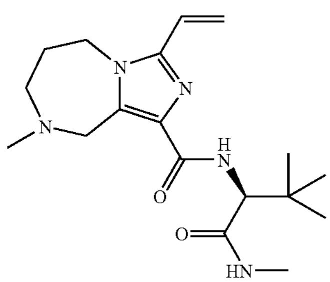 [SMILES: C=Cc1nc(C(=O)N[C@H](C(=O)NC)C(C)(C)C)c2n1CCCN(C)C2] | (S)-N-(3,3-dimethyl-1-(methylamino)-1-oxobutan-2-yl)-8-methyl-3-vinyl-6,7,8,9-tetrahydro-5H-imidazo[1,5-a][1,4]diazepine-1-carboxamide | 348.2 | 37 |
| 431 | 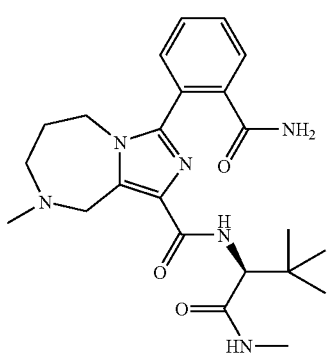 [SMILES: CNC(=O)[C@@H](NC(=O)c1nc(-c2ccccc2C(N)=O)n2c1CN(C)CCC2)C(C)(C)C] | (S)-3-(2-carbamoylphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 441.2 | 37 |

TABLE I-continued

| Cmpd No. | Structure | Chemical Name | m/z | Example No. |
|---|---|---|---|---|
| 432 | 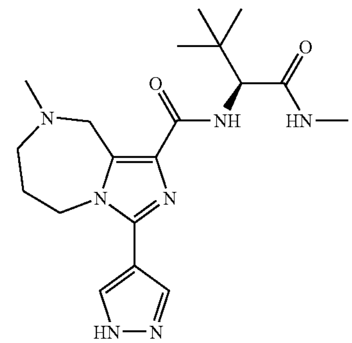 [SMILES: CNC(=O)[C@@H](NC(=O)c1nc(-c2cn[nH]c2)n2c1CN(C)CCC2)C(C)(C)C] | (S)-N-(3,3-dimethyl-1-(methylamino)-1-oxobutan-2-yl)-8-methyl-3-(1H-pyrazol-4-yl)-6,7,8,9-tetrahydro-5H-imidazo[1,5-a][1,4]diazepine-1-carboxamide | 388.2 | 37 |
| 433 | 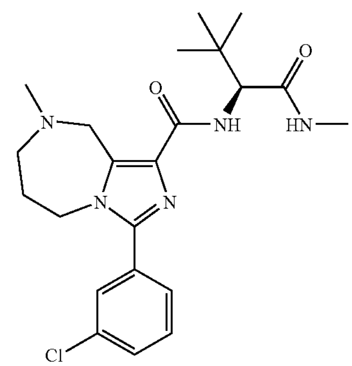 [SMILES: CNC(=O)[C@@H](NC(=O)c1nc(-c2cccc(Cl)c2)n2c1CN(C)CCC2)C(C)(C)C] | (S)-3-(3-chlorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 432.1 | 37 |
| 434 | 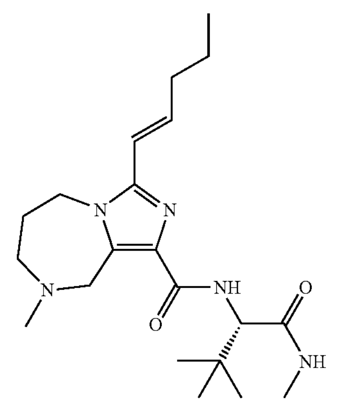 [SMILES: CCC/C=C/c1nc(C(=O)N[C@H](C(=O)NC)C(C)(C)C)c2n1CCCN(C)C2] | (S,E)-N-(3,3-dimethyl-1-(methylamino)-1-oxobutan-2-yl)-8-methyl-3-(pent-1-enyl)-6,7,8,9-tetrahydro-5H-imidazo[1,5-a][1,4]diazepine-1-carboxamide | 390.2 | 37 |
| 435 | 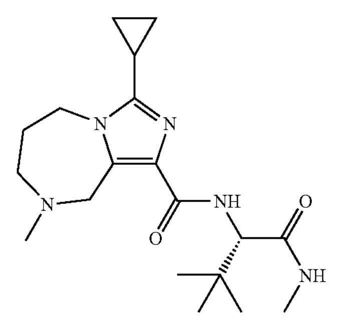 [SMILES: CNC(=O)[C@@H](NC(=O)c1nc(C2CC2)n2c1CN(C)CCC2)C(C)(C)C] | (S)-3-cyclopropyl-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 362.2 | 37 |

TABLE I-continued

| Cmpd No. | Structure | Chemical Name | m/z | Example No. |
|---|---|---|---|---|
| 436 | 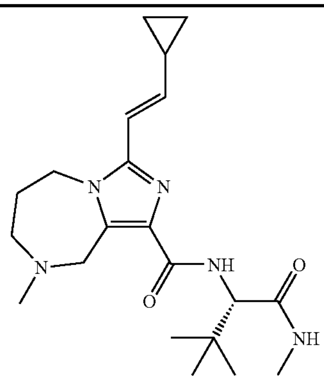 | (S,E)-3-(2-cyclopropylvinyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 388.2 | 37 |
| 437 | 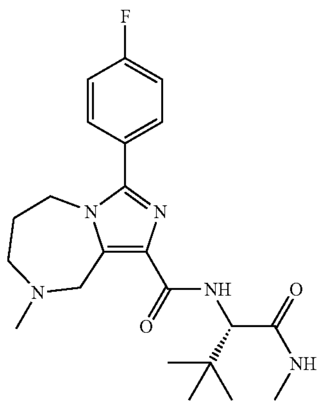 [SMILES: CNC(=O)[C@@H](NC(=O)c1nc(-c2ccc(F)cc2)n2c1CN(C)CCC2)C(C)(C)C] | (S)-N-(3,3-dimethyl-1-(methylamino)-1-oxobutan-2-yl)-3-(4-fluorophenyl)-8-methyl-6,7,8,9-tetrahydro-5H-imidazo[1,5-a][1,4]diazepine-1-carboxamide | 416.2 | 37 |
| 438 | 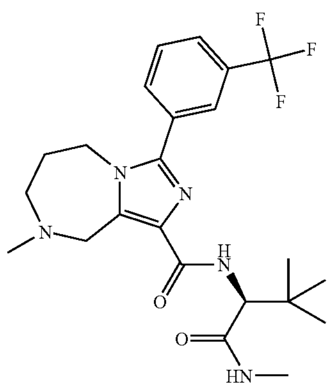 [SMILES: CNC(=O)[C@@H](NC(=O)c1nc(-c2cccc(C(F)(F)F)c2)n2c1CN(C)CCC2)C(C)(C)C] | (S)-N-(3,3-dimethyl-1-(methylamino)-1-oxobutan-2-yl)-8-methyl-3-(3-(trifluoromethyl)phenyl)-6,7,8,9-tetrahydro-5H-imidazo[1,5-a][1,4]diazepine-1-carboxamide | 466.2 | 37 |
| 439 | 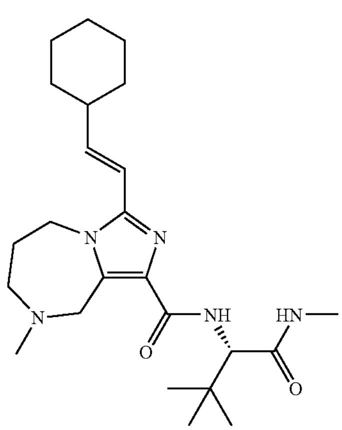 [SMILES: CNC(=O)[C@@H](NC(=O)c1nc(/C=C/C2CCCCC2)n2c1CN(C)CCC2)C(C)(C)C] | (S,E)-3-(2-cyclohexylvinyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 430.2 | 37 |

TABLE I-continued

| Cmpd No. | Structure | Chemical Name | m/z | Example No. |
|---|---|---|---|---|
| 440 | 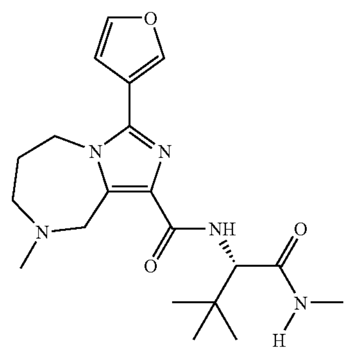 [SMILES: CNC(=O)[C@@H](NC(=O)c1nc(-c2ccoc2)n2c1CN(C)CCC2)C(C)(C)C] | (S)-N-(3,3-dimethyl-1-(methylamino)-1-oxobutan-2-yl)-3-(furan-3-yl)-8-methyl-6,7,8,9-tetrahydro-5H-imidazo[1,5-a][1,4]diazepine-1-carboxamide | 388.1 | 37 |
| 441 | 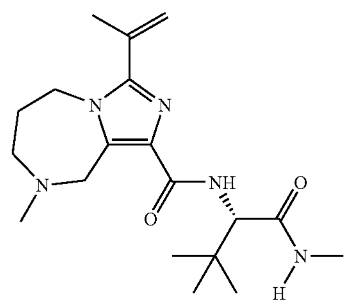 [SMILES: C=C(C)c1nc(C(=O)N[C@H](C(=O)NC)C(C)(C)C)c2n1CCCN(C)C2] | (S)-N-(3,3-dimethyl-1-(methylamino)-1-oxobutan-2-yl)-8-methyl-3-(prop-1-en-2-yl)-6,7,8,9-tetrahydro-5H-imidazo[1,5-a][1,4]diazepine-1-carboxamide | 362.2 | 37 |
| 442 | 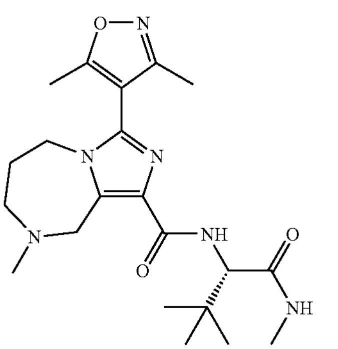 [SMILES: CNC(=O)[C@@H](NC(=O)c1nc(-c2c(C)noc2C)n2c1CN(C)CCC2)C(C)(C)C] | N-((S)-3,3-dimethyl-1-(methylamino)-1-oxobutan-2-yl)-3-(3,5-dimethylisoxazol-4-yl)-8-methyl-6,7,8,9-tetrahydro-5H-imidazo[1,5-a][1,4]diazepine-1-carboxamide | 417.2 | 37 |
| 443 | 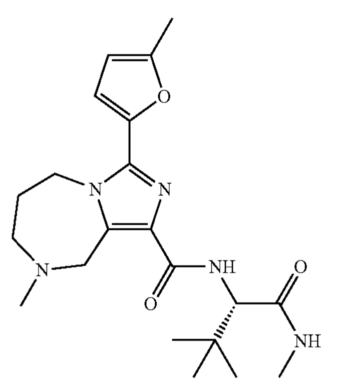 [SMILES: CNC(=O)[C@@H](NC(=O)c1nc(-c2ccc(C)o2)n2c1CN(C)CCC2)C(C)(C)C] | (S)-N-(3,3-dimethyl-1-(methylamino)-1-oxobutan-2-yl)-8-methyl-3-(5-methylfuran-2-yl)-6,7,8,9-tetrahydro-5H-imidazo[1,5-a][1,4]diazepine-1-carboxamide | 402.2 | 37 |

TABLE I-continued

| Cmpd No. | Structure | Chemical Name | m/z | Example No. |
|---|---|---|---|---|
| 444 | 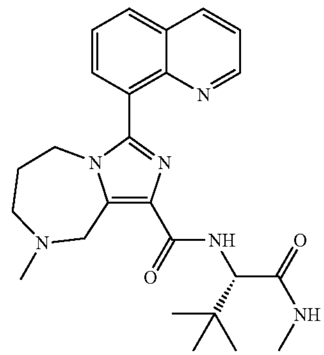 [SMILES: CNC(=O)[C@@H](NC(=O)c1nc(-c2cccc3cccnc23)n2c1CN(C)CCC2)C(C)(C)C] | (S)-N-(3,3-dimethyl-1-(methylamino)-1-oxobutan-2-yl)-8-methyl-3-(quinolin-8-yl)-6,7,8,9-tetrahydro-5H-imidazo[1,5-a][1,4]diazepine-1-carboxamide | 449.2 | 37 |
| 445 | 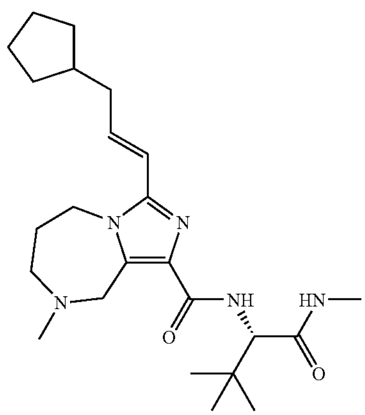 | (S,E)-3-(3-cyclopentylprop-1-enyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 430.2 | 37 |
| 446 | 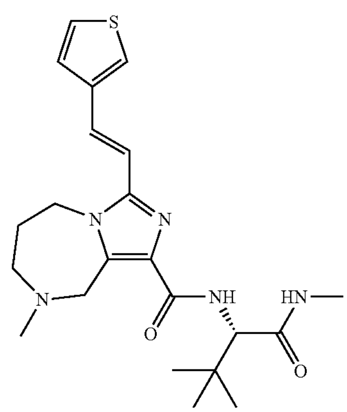 [SMILES: CNC(=O)[C@@H](NC(=O)c1nc(/C=C/c2ccsc2)n2c1CN(C)CCC2)C(C)(C)C] | (S,E)-N-(3,3-dimethyl-1-(methylamino)-1-oxobutan-2-yl)-8-methyl-3-(2-(thiophen-3-yl)vinyl)-6,7,8,9-tetrahydro-5H-imidazo[1,5-a][1,4]diazepine-1-carboxamide | 430.1 | 37 |
| 447 | 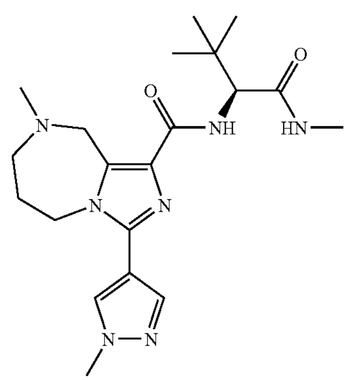 [SMILES: CNC(=O)[C@@H](NC(=O)c1nc(-c2cnn(C)c2)n2c1CN(C)CCC2)C(C)(C)C] | (S)-N-(3,3-dimethyl-1-(methylamino)-1-oxobutan-2-yl)-8-methyl-3-(1-methyl-1H-pyrazol-4-yl)-6,7,8,9-tetrahydro-5H-imidazo[1,5-a][1,4]diazepine-1-carboxamide | 402.2 | 37 |

TABLE I-continued

| Cmpd No. | Structure | Chemical Name | m/z | Example No. |
|---|---|---|---|---|
| 448 | 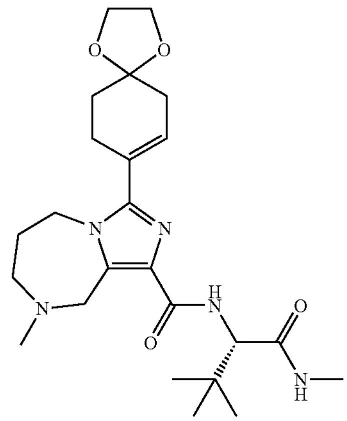 [SMILES: CNC(=O)[C@@H](NC(=O)c1nc(C2=CCC3(CC2)OCCO3)n2c1CN(C)CCC2)C(C)(C)C] | (S)-N-(3,3-dimethyl-1-(methylamino)-1-oxobutan-2-yl)-8-methyl-3-(1,4-dioxaspiro[4.5]dec-7-en-8-yl)-6,7,8,9-tetrahydro-5H-imidazo[1,5-a][1,4]diazepine-1-carboxamide | 460.0 | 37 |
| 449 | 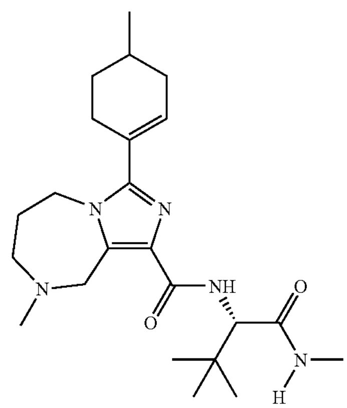 [SMILES: CNC(=O)[C@@H](NC(=O)c1nc(C2=CCC(C)CC2)n2c1CN(C)CCC2)C(C)(C)C] | N-((S)-3,3-dimethyl-1-(methylamino)-1-oxobutan-2-yl)-8-methyl-3-(4-methylcyclohex-1-enyl)-6,7,8,9-tetrahydro-5H-imidazo[1,5-a][1,4]diazepine-1-carboxamide | 416.2 | 37 |
| 450 | 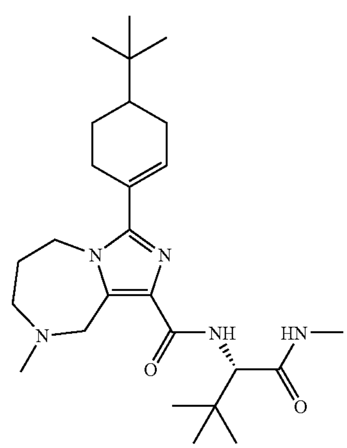 [SMILES: CNC(=O)[C@@H](NC(=O)c1nc(C2=CCC(C(C)(C)C)CC2)n2c1CN(C)CCC2)C(C)(C)C] | 3-(4-tert-butylcyclohex-1-enyl)-N-((S)-3,3-dimethyl-1-(methylamino)-1-oxobutan-2-yl)-8-methyl-6,7,8,9-tetrahydro-5H-imidazo[1,5-a][1,4]diazepine-1-carboxamide | 358.4 | 37 |

TABLE I-continued

| Cmpd No. | Structure | Chemical Name | m/z | Example No. |
|---|---|---|---|---|
| 451 | 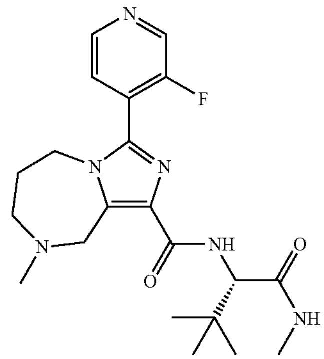 [SMILES: CNC(=O)[C@@H](NC(=O)c1nc(-c2ccncc2F)n2c1CN(C)CCC2)C(C)(C)C] | (S)-N-(3,3-dimethyl-1-(methylamino)-1-oxobutan-2-yl)-3-(3-fluoropyridin-4-yl)-8-methyl-6,7,8,9-tetrahydro-5H-imidazo[1,5-a][1,4]diazepine-1-carboxamide | 417.2 | 37 |
| 452 | 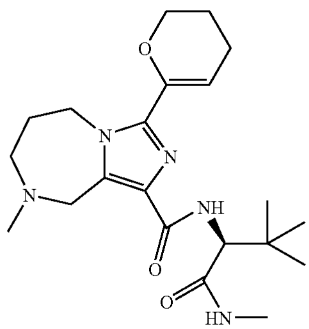 [SMILES: CNC(=O)[C@@H](NC(=O)c1nc(C2=CCCCO2)n2c1CN(C)CCC2)C(C)(C)C] | (S)-3-(3,4-dihydro-2H-pyran-6-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 404.3 | 37 |
| 453 | 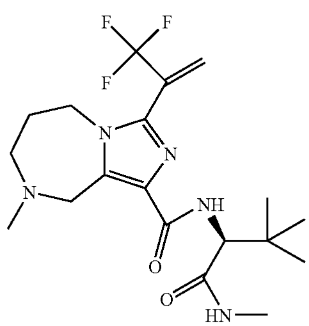 [SMILES: C=C(c1nc(C(=O)N[C@H](C(=O)NC)C(C)(C)C)c2n1CCCN(C)C2)C(F)(F)F] | (S)-N-(3,3-dimethyl-1-(methylamino)-1-oxobutan-2-yl)-8-methyl-3-(3,3,3-trifluoroprop-1-en-2-yl)-6,7,8,9-tetrahydro-5H-imidazo[1,5-a][1,4]diazepine-1-carboxamide | 416.1 | 37 |
| 454 | 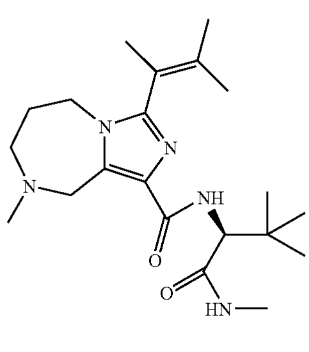 [SMILES: CNC(=O)[C@@H](NC(=O)c1nc(C(C)=C(C)C)n2c1CN(C)CCC2)C(C)(C)C] | (S)-N-(3,3-dimethyl-1-(methylamino)-1-oxobutan-2-yl)-8-methyl-3-(3-methylbut-2-en-2-yl)-6,7,8,9-tetrahydro-5H-imidazo[1,5-a][1,4]diazepine-1-carboxamide | 390.2 | 37 |

TABLE I-continued

| Cmpd No. | Structure | Chemical Name | m/z | Example No. |
|---|---|---|---|---|
| 455 | 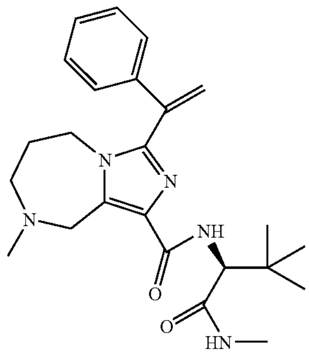 [SMILES: C=C(c1ccccc1)c1nc(C(=O)N[C@H](C(=O)NC)C(C)(C)C)c2n1CCCN(C)C2] | (S)-N-(3,3-dimethyl-1-(methylamino)-1-oxobutan-2-yl)-8-methyl-3-(1-phenylvinyl)-6,7,8,9-tetrahydro-5H-imidazo[1,5-a][1,4]diazepine-1-carboxamide | 424.2 | 37 |
| 456 | 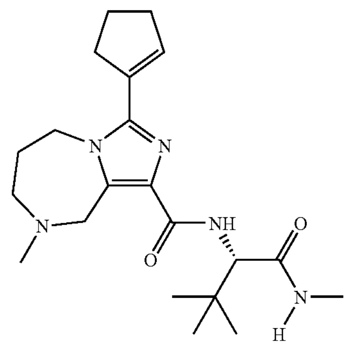 [SMILES: CNC(=O)[C@@H](NC(=O)c1nc(C2=CCCC2)n2c1CN(C)CCC2)C(C)(C)C] | (S)-3-cyclopentenyl-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 388.2 | 37 |
| 457 | 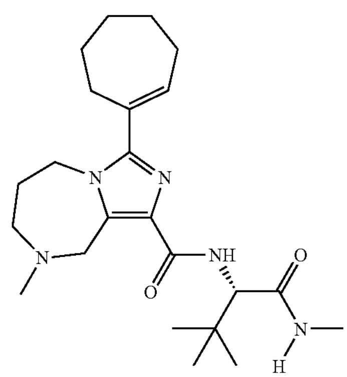 [SMILES: CNC(=O)[C@@H](NC(=O)c1nc(C2=CCCCCC2)n2c1CN(C)CCC2)C(C)(C)C] | (S,E)-3-cycloheptenyl-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 416.3 | 37 |
| 458 | 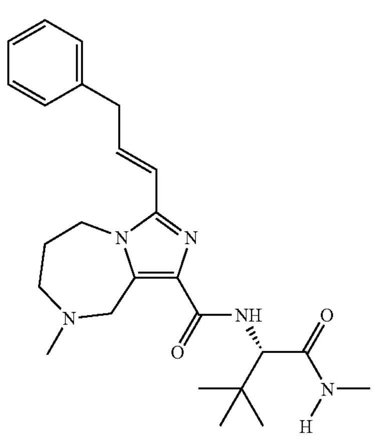 [SMILES: CNC(=O)[C@@H](NC(=O)c1nc(/C=C/Cc2ccccc2)n2c1CN(C)CCC2)C(C)(C)C] | (S,E)-N-(3,3-dimethyl-1-(methylamino)-1-oxobutan-2-yl)-8-methyl-3-(3-phenylprop-1-enyl)-6,7,8,9-tetrahydro-5H-imidazo[1,5-a][1,4]diazepine-1-carboxamide | 438.2 | 37 |

TABLE I-continued

| Cmpd No. | Structure | Chemical Name | m/z | Example No. |
|---|---|---|---|---|
| 459 | 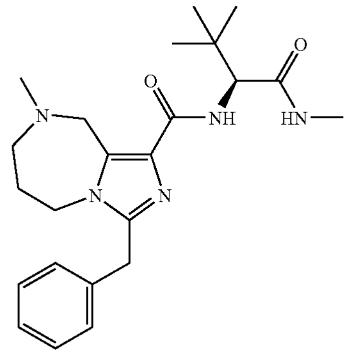 [SMILES: CNC(=O)[C@@H](NC(=O)c1nc(Cc2ccccc2)n2c1CN(C)CCC2)C(C)(C)C] | (S)-3-benzyl-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 412.2 | 37 |
| 460 | 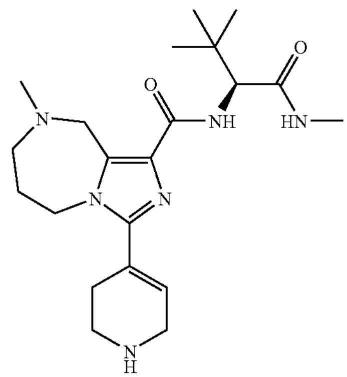 [SMILES: CNC(=O)[C@@H](NC(=O)c1nc(C2=CCNCC2)n2c1CN(C)CCC2)C(C)(C)C] | (S)-N-(3,3-dimethyl-1-(methylamino)-1-oxobutan-2-yl)-8-methyl-3-(1,2,3,6-tetrahydropyridin-4-yl)-6,7,8,9-tetrahydro-5H-imidazo[1,5-a][1,4]diazepine-1-carboxamide | 403.2 | 37 |
| 461 | 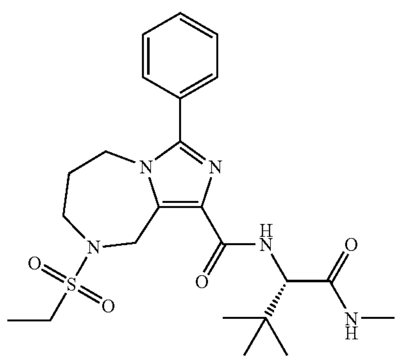 [SMILES: CCS(=O)(=O)N1CCCn2c(-c3ccccc3)nc(C(=O)N[C@H](C(=O)NC)C(C)(C)C)c2C1] | (S)-N-(3,3-dimethyl-1-(methylamino)-1-oxobutan-2-yl)-8-(ethylsulfonyl)-3-phenyl-6,7,8,9-tetrahydro-5H-imidazo[1,5-a][1,4]diazepine-1-carboxamide | 476.3 | 38 |
| 462 | 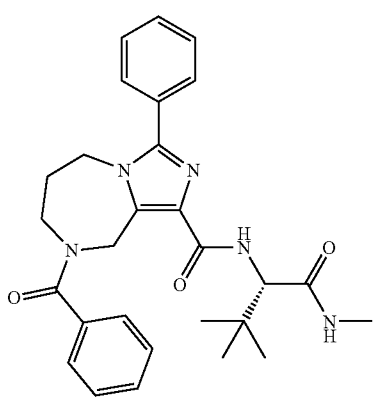 [SMILES: CNC(=O)[C@@H](NC(=O)c1nc(-c2ccccc2)n2c1CN(C(=O)c1ccccc1)CCC2)C(C)(C)C] | (S)-8-benzoyl-N-(3,3-dimethyl-1-(methylamino)-1-oxobutan-2-yl)-3-phenyl-6,7,8,9-tetrahydro-5H-imidazo[1,5-a][1,4]diazepine-1-carboxamide | 488.3 | 38 |

TABLE I-continued

| Cmpd No. | Structure | Chemical Name | m/z | Example No. |
|---|---|---|---|---|
| 463 | 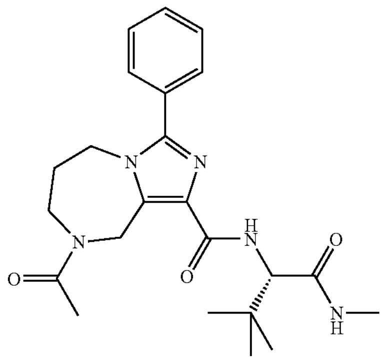 [SMILES: CNC(=O)[C@@H](NC(=O)c1nc(-c2ccccc2)n2c1CN(C(C)=O)CCC2)C(C)(C)C] | (S)-8-acetyl-N-(3,3-dimethyl-1-(methylamino)-1-oxobutan-2-yl)-3-phenyl-6,7,8,9-tetrahydro-5H-imidazo[1,5-a][1,4]diazepine-1-carboxamide | 426.3 | 38 |
| 464 | 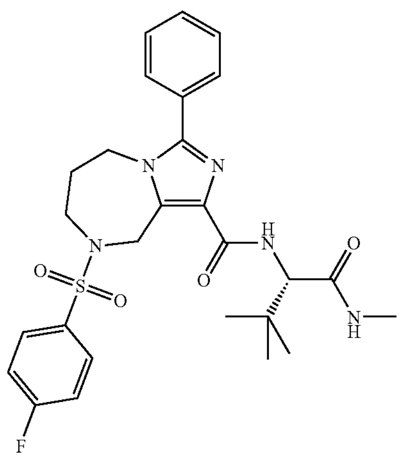 [SMILES: CNC(=O)[C@@H](NC(=O)c1nc(-c2ccccc2)n2c1CN(S(=O)(=O)c1ccc(F)cc1)CCC2)C(C)(C)C] | (S)-N-(3,3-dimethyl-1-(methylamino)-1-oxobutan-2-yl)-8-(4-fluorophenylsulfonyl)-3-phenyl-6,7,8,9-tetrahydro-5H-imidazo[1,5-a][1,4]diazepine-1-carboxamide | 542.3 | 38 |
| 465 | 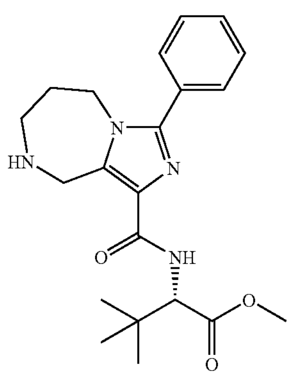 [SMILES: COC(=O)[C@@H](NC(=O)c1nc(-c2ccccc2)n2c1CNCCC2)C(C)(C)C] | (S)-methyl 3,3-dimethyl-2-(3-phenyl-6,7,8,9-tetrahydro-5H-imidazo[1,5-a][1,4]diazepine-1-carboxamido)butanoate | 385.1 | 39 |
| 466 | 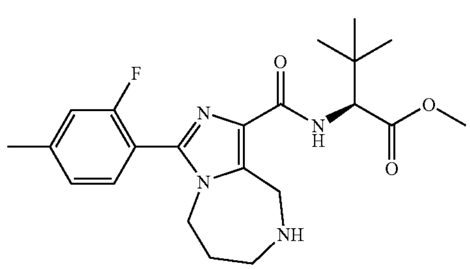 | (S)-methyl-2-(3-(2-fluoro-4-methylphenyl)-6,7,8,9-tetrahydro-5H-imidazo[1,5-a][1,4]diazepine-1-carboxamido)-3,3-dimethylbutanoate | 417.2 | 39 |

TABLE I-continued

| Cmpd No. | Structure | Chemical Name | m/z | Example No. |
|---|---|---|---|---|
| 467 | 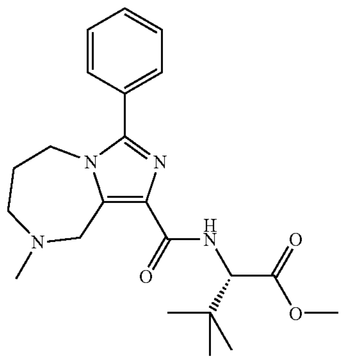 [SMILES: COC(=O)[C@@H](NC(=O)c1nc(-c2ccccc2)n2c1CN(C)CCC2)C(C)(C)C] | (S)-methyl 3,3-dimethyl-2-(8-methyl-3-phenyl-6,7,8,9-tetrahydro-5H-imidazo[1,5-a][1,4]diazepine-1-carboxamido)butanoate | 399.0 | 39 |
| 468 | 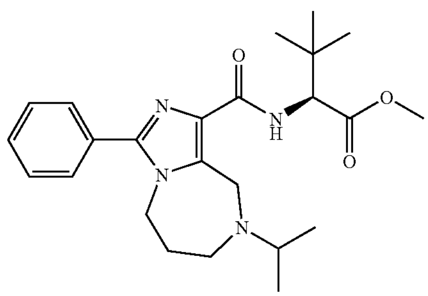 [SMILES: COC(=O)[C@@H](NC(=O)c1nc(-c2ccccc2)n2c1CN(C(C)C)CCC2)C(C)(C)C] | (S)-methyl 2-(8-isopropyl-3-phenyl-6,7,8,9-tetrahydro-5H-imidazo[1,5-a][1,4]diazepine-1-carboxamido)-3,3-dimethylbutanoate | 427.2 | 40 |
| 469 | 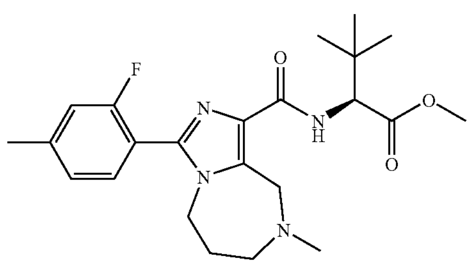 | (S)-methyl 2-(3-(2-fluoro-4-methylphenyl)-8-methyl-6,7,8,9-tetrahydro-5H-imidazo[1,5-a][1,4]diazepine-1-carboxamido)-3,3-dimethylbutanoate | 431.2 | 40 |
| 470 | 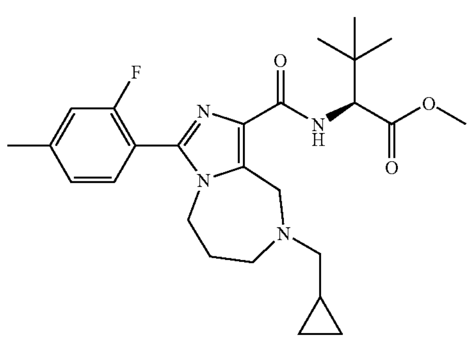 | (S)-methyl 2-(8-(cyclopropylmethyl)-3-(2-fluoro-4-methylphenyl)-6,7,8,9-tetrahydro-5H-imidazo[1,5-a][1,4]diazepine-1-carboxamido)-3,3-dimethylbutanoate | 471.2 | 40 |

| Cmpd No. | Structure | Chemical Name | m/z | Example No. |
|---|---|---|---|---|
| 471 | 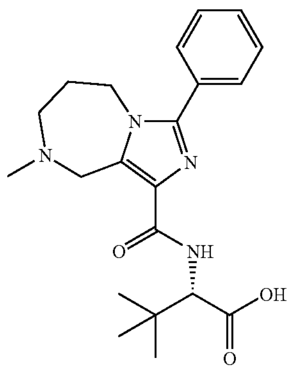 [SMILES: CN1CCCn2c(-c3ccccc3)nc(C(=O)N[C@H](C(=O)O)C(C)(C)C)c2C1] | (S)-3,3-dimethyl-2-(8-methyl-3-phenyl-6,7,8,9-tetrahydro-5H-imidazo[1,5-a][1,4]diazepine-1-carboxamido)butanoic acid | 385.0 | 41 |
| 472 | 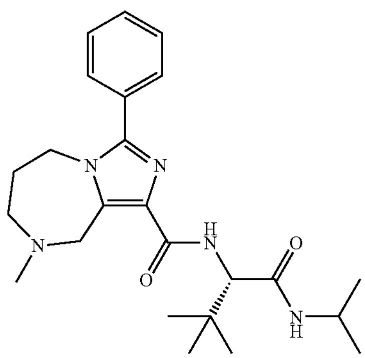 [SMILES: CC(C)NC(=O)[C@@H](NC(=O)c1nc(-c2ccccc2)n2c1CN(C)CCC2)C(C)(C)C] | (S)-N-(1-(isopropylamino)-3,3-dimethyl-1-oxobutan-2-yl)-8-methyl-3-phenyl-6,7,8,9-tetrahydro-5H-imidazo[1,5-a][1,4]diazepine-1-carboxamide | 426.0 | 42 |
| 473 | 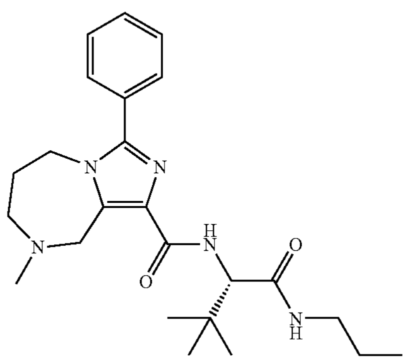 [SMILES: CCCNC(=O)[C@@H](NC(=O)c1nc(-c2ccccc2)n2c1CN(C)CCC2)C(C)(C)C] | (S)-N-(3,3-dimethyl-1-oxo-1-(propylamino)butan-2-yl)-8-methyl-3-phenyl-6,7,8,9-tetrahydro-5H-imidazo[1,5-a][1,4]diazepine-1-carboxamide | 426.0 | 42 |
| 474 | 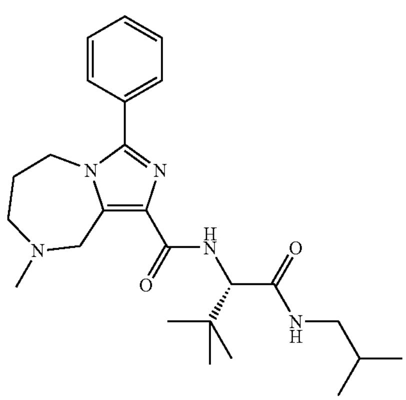 [SMILES: CC(C)CNC(=O)[C@@H](NC(=O)c1nc(-c2ccccc2)n2c1CN(C)CCC2)C(C)(C)C] | (S)-N-(1-(isobutylamino)-3,3-dimethyl-1-oxobutan-2-yl)-8-methyl-3-phenyl-6,7,8,9-tetrahydro-5H-imidazo[1,5-a][1,4]diazepine-1-carboxamide | 440.0 | 42 |

TABLE I-continued

| Cmpd No. | Structure | Chemical Name | m/z | Example No. |
|---|---|---|---|---|
| 475 | 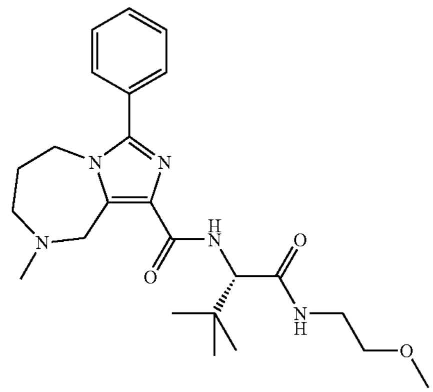 [SMILES: COCCNC(=O)[C@@H](NC(=O)c1nc(-c2ccccc2)n2c1CN(C)CCC2)C(C)(C)C] | (S)-N-(1-(2-methoxyethylamino)-3,3-dimethyl-1-oxobutan-2-yl)-8-methyl-3-phenyl-6,7,8,9-tetrahydro-5H-imidazo[1,5-a][1,4]diazepine-1-carboxamide | 442.0 | 42 |
| 476 | 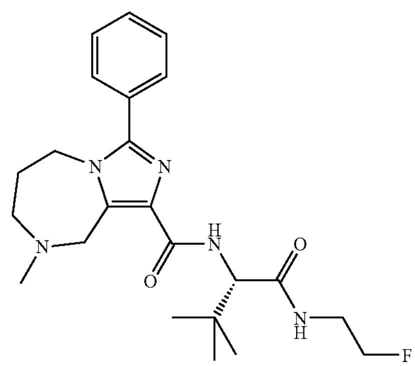 [SMILES: CN1CCCn2c(-c3ccccc3)nc(C(=O)N[C@H](C(=O)NCCF)C(C)(C)C)c2C1] | (S)-N-(1-(2-fluoroethylamino)-3,3-dimethyl-1-oxobutan-2-yl)-8-methyl-3-phenyl-6,7,8,9-tetrahydro-5H-imidazo[1,5-a][1,4]diazepine-1-carboxamide | 430.0 | 42 |
| 477 | 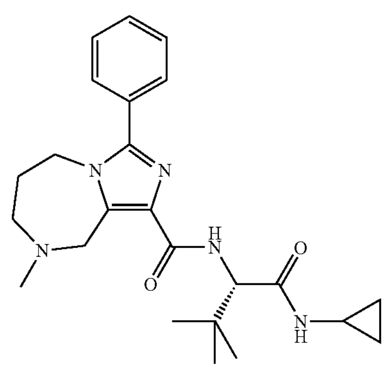 [SMILES: CN1CCCn2c(-c3ccccc3)nc(C(=O)N[C@H](C(=O)NC3CC3)C(C)(C)C)c2C1] | (S)-N-(1-(cyclopropylamino)-3,3-dimethyl-1-oxobutan-2-yl)-8-methyl-3-phenyl-6,7,8,9-tetrahydro-5H-imidazo[1,5-a][1,4]diazepine-1-carboxamide | 424.0 | 42 |
| 478 | 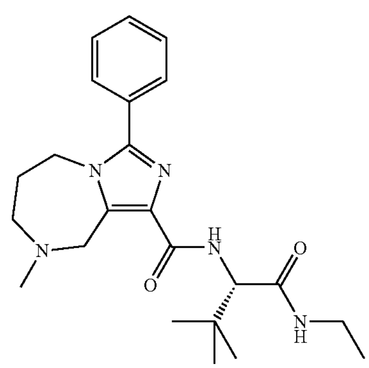 [SMILES: CCNC(=O)[C@@H](NC(=O)c1nc(-c2ccccc2)n2c1CN(C)CCC2)C(C)(C)C] | (S)-N-(1-(ethylamino)-3,3-dimethyl-1-oxobutan-2-yl)-8-methyl-3-phenyl-6,7,8,9-tetrahydro-5H-imidazo[1,5-a][1,4]diazepine-1-carboxamide | 412.0 | 42 |

TABLE I-continued

| Cmpd No. | Structure | Chemical Name | m/z | Example No. |
|---|---|---|---|---|
| 479 | 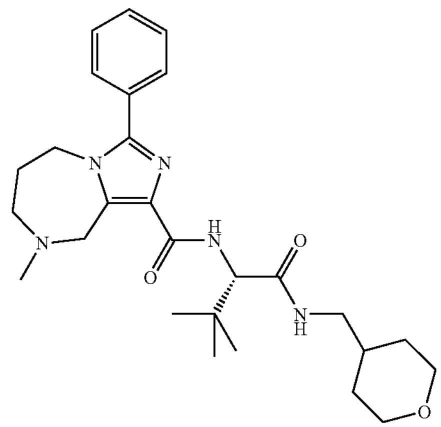 [SMILES: CN1CCCn2c(-c3ccccc3)nc(C(=O)N[C@H](C(=O)NCC3CCOCC3)C(C)(C)C)c2C1] | (S)-N-(3,3-dimethyl-1-oxo-1-((tetrahydro-2H-pyran-4-yl)methylamino)butan-2-yl)-8-methyl-3-phenyl-6,7,8,9-tetrahydro-5H-imidazo[1,5-a][1,4]diazepine-1-carboxamide | 482.0 | 42 |
| 480 | 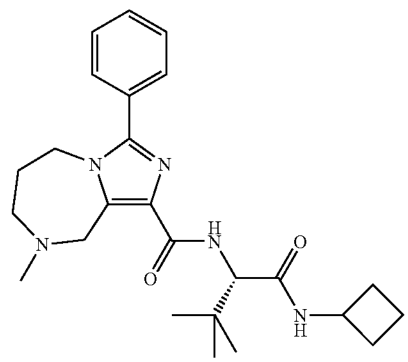 [SMILES: CN1CCCn2c(-c3ccccc3)nc(C(=O)N[C@H](C(=O)NC3CCC3)C(C)(C)C)c2C1] | (S)-N-(1-(cyclobutylamino)-3,3-dimethyl-1-oxobutan-2-yl)-8-methyl-3-phenyl-6,7,8,9-tetrahydro-5H-imidazo[1,5-a][1,4]diazepine-1-carboxamide | 438.0 | 42 |
| 481 | 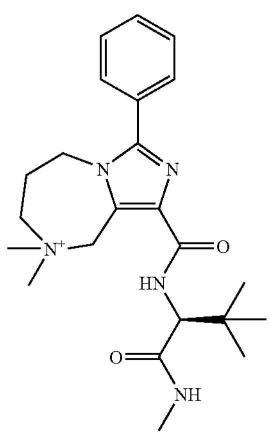 [SMILES: CNC(=O)[C@@H](NC(=O)c1nc(-c2ccccc2)n2c1C[N+](C)(C)CCC2)C(C)(C)C] | (S)-1-(3,3-dimethyl-1-(methylamino)-1-oxobutan-2-ylcarbamoyl)-8,8-dimethyl-3-phenyl-6,7,8,9-tetrahydro-5H-imidazo[1,5-a][1,4]diazepin-8-ium | 412.0 | 43 |
| 482 | 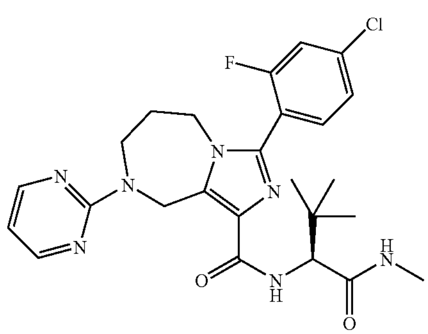 [SMILES: CNC(=O)[C@@H](NC(=O)c1nc(-c2ccc(Cl)cc2F)n2c1CN(c1ncccn1)CCC2)C(C)(C)C] | (S)-3-(4-chloro-2-fluorophenyl)-N-(3,3-dimethyl-1-(methylamino)-1-oxobutan-2-yl)-8-(pyrimidin-2-yl)-6,7,8,9-tetrahydro-5H-imidazo[1,5-a][1,4]diazepine-1-carboxamide | 514.2 | 44 |

TABLE I-continued

| Cmpd No. | Structure | Chemical Name | m/z | Example No. |
|---|---|---|---|---|
| 483 | 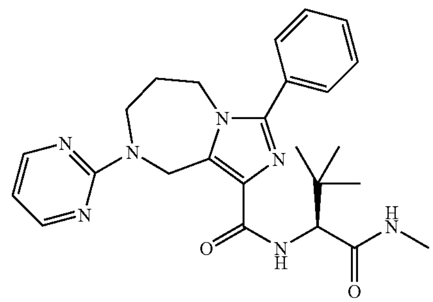 [SMILES: CNC(=O)[C@@H](NC(=O)c1nc(-c2ccccc2)n2c1CN(c1ncccn1)CCC2)C(C)(C)C] | (S)-N-(3,3-dimethyl-1-(methylamino)-1-oxobutan-2-yl)-3-phenyl-8-(pyrimidin-2-yl)-6,7,8,9-tetrahydro-5H-imidazo[1,5-a][1,4]diazepine-1-carboxamide | 462.2 | 44 |
| 484 | 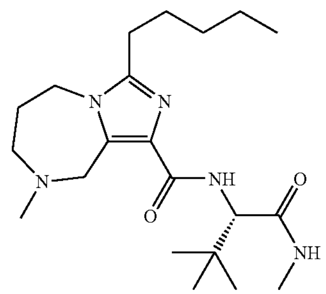 [SMILES: CCCCCc1nc(C(=O)N[C@H](C(=O)NC)C(C)(C)C)c2n1CCCN(C)C2] | (S)-N-(3,3-dimethyl-1-(methylamino)-1-oxobutan-2-yl)-8-methyl-3-pentyl-6,7,8,9-tetrahydro-5H-imidazo[1,5-a][1,4]diazepine-1-carboxamide | 392.2 | 45 |
| 485 | 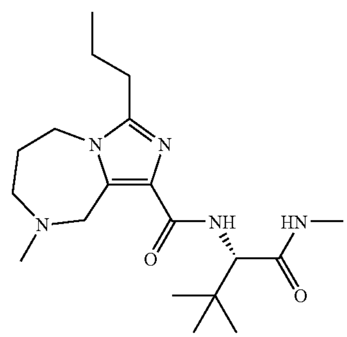 | (S)-N-(3,3-dimethyl-1-(methylamino)-1-oxobutan-2-yl)-8-methyl-3-propyl-6,7,8,9-tetrahydro-5H-imidazo[1,5-a][1,4]diazepine-1-carboxamide | 364.0 | 45 |
| 486 | 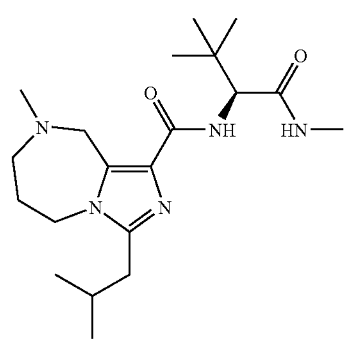 [SMILES: CNC(=O)[C@@H](NC(=O)c1nc(CC(C)C)n2c1CN(C)CCC2)C(C)(C)C] | (S)-N-(3,3-dimethyl-1-(methylamino)-1-oxobutan-2-yl)-3-isobutyl-8-methyl-6,7,8,9-tetrahydro-5H-imidazo[1,5-a][1,4]diazepine-1-carboxamide | 378.0 | 45 |

TABLE I-continued

| Cmpd No. | Structure | Chemical Name | m/z | Example No. |
|---|---|---|---|---|
| 487 | 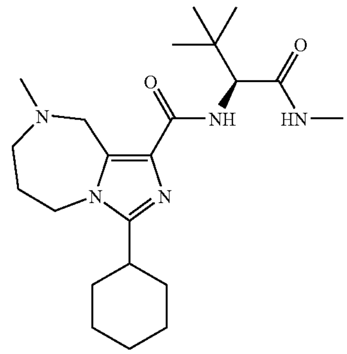 [SMILES: CNC(=O)[C@@H](NC(=O)c1nc(C2CCCCC2)n2c1CN(C)CCC2)C(C)(C)C] | (S)-3-cyclohexyl-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 404.0 | 45 |
| 488 | 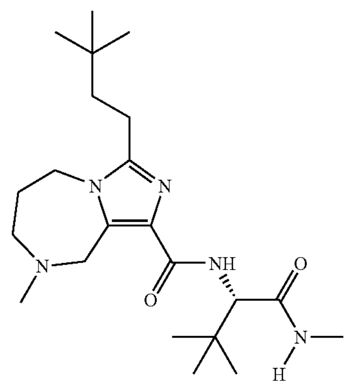 [SMILES: CNC(=O)[C@@H](NC(=O)c1nc(CCC(C)(C)C)n2c1CN(C)CCC2)C(C)(C)C] | (S)-N-(3,3-dimethyl-1-(methylamino)-1-oxobutan-2-yl)-3-(3,3-dimethylbutyl)-8-methyl-6,7,8,9-tetrahydro-5H-imidazo[1,5-a][1,4]diazepine-1-carboxamide | 406.3 | 45 |
| 489 | 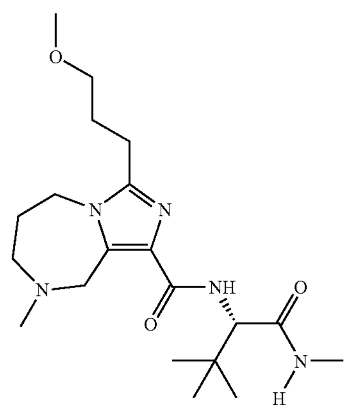 [SMILES: CNC(=O)[C@@H](NC(=O)c1nc(CCCOC)n2c1CN(C)CCC2)C(C)(C)C] | (S)-N-(3,3-dimethyl-1-(methylamino)-1-oxobutan-2-yl)-3-(3-methoxypropyl)-8-methyl-6,7,8,9-tetrahydro-5H-imidazo[1,5-a][1,4]diazepine-1-carboxamide | 394.2 | 45 |
| 490 | 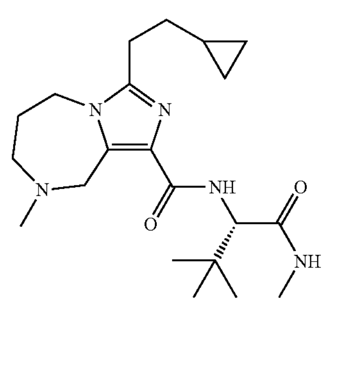 [SMILES: CNC(=O)[C@@H](NC(=O)c1nc(CCC2CC2)n2c1CN(C)CCC2)C(C)(C)C] | (S)-3-(2-cyclopropylethyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 390.2 | 45 |

TABLE I-continued

| Cmpd No. | Structure | Chemical Name | m/z | Example No. |
|---|---|---|---|---|
| 491 | 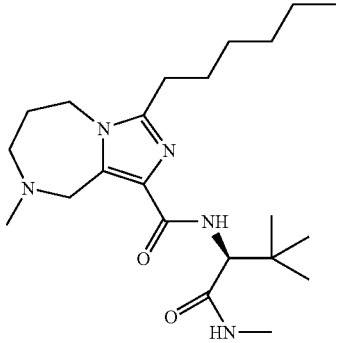 [SMILES: CCCCCCc1nc(C(=O)N[C@H](C(=O)NC)C(C)(C)C)c2n1CCCN(C)C2] | (S)-N-(3,3-dimethyl-1-(methylamino)-1-oxobutan-2-yl)-3-hexyl-8-methyl-6,7,8,9-tetrahydro-5H-imidazo[1,5-a][1,4]diazepine-1-carboxamide | 406.3 | 45 |
| 492 | 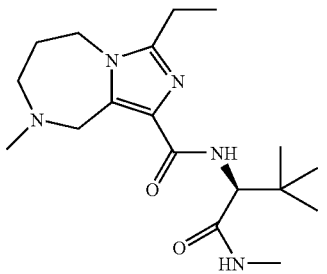 [SMILES: CCc1nc(C(=O)N[C@H](C(=O)NC)C(C)(C)C)c2n1CCCN(C)C2] | (S)-N-(3,3-dimethyl-1-(methylamino)-1-oxobutan-2-yl)-3-ethyl-8-methyl-6,7,8,9-tetrahydro-5H-imidazo[1,5-a][1,4]diazepine-1-carboxamide | 350.2 | 45 |
| 493 | 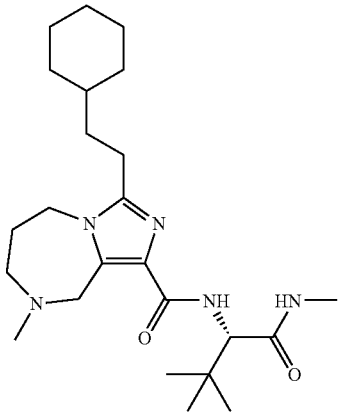 [SMILES: CNC(=O)[C@@H](NC(=O)c1nc(CCC2CCCCC2)n2c1CN(C)CCC2)C(C)(C)C] | (S)-3-(2-cyclohexylethyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 432.3 | 45 |
| 494 | 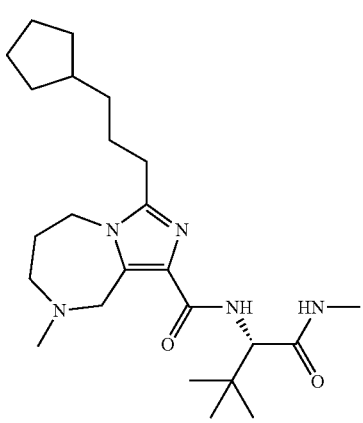 | (S)-3-(3-cyclopentylpropyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 432.3 | 45 |

TABLE I-continued

| Cmpd No. | Structure | Chemical Name | m/z | Example No. |
|---|---|---|---|---|
| 495 | 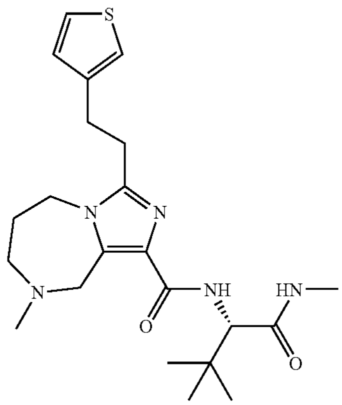 [SMILES: CNC(=O)[C@@H](NC(=O)c1nc(CCc2ccsc2)n2c1CN(C)CCC2)C(C)(C)C] | (S)-N-(3,3-dimethyl-1-(methylamino)-1-oxobutan-2-yl)-8-methyl-3-(2-(thiophen-3-yl)ethyl)-6,7,8,9-tetrahydro-5H-imidazo[1,5-a][1,4]diazepine-1-carboxamide | 432.2 | 45 |
| 496 | 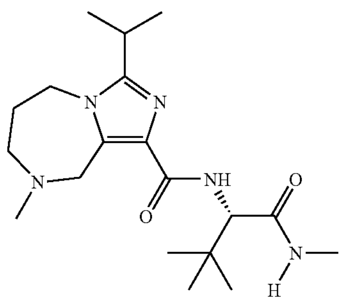 [SMILES: CNC(=O)[C@@H](NC(=O)c1nc(C(C)C)n2c1CN(C)CCC2)C(C)(C)C] | (S)-N-(3,3-dimethyl-1-(methylamino)-1-oxobutan-2-yl)-3-isopropyl-8-methyl-6,7,8,9-tetrahydro-5H-imidazo[1,5-a][1,4]diazepine-1-carboxamide | 364.3 | 45 |
| 497 | 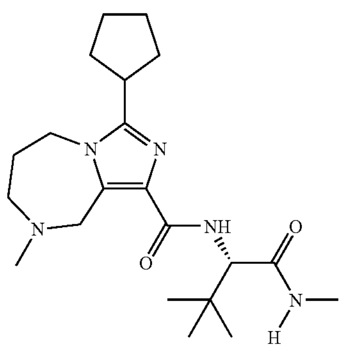 [SMILES: CNC(=O)[C@@H](NC(=O)c1nc(C2CCCC2)n2c1CN(C)CCC2)C(C)(C)C] | (S)-3-cyclopentyl-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 390.2 | 45 |
| 498 | 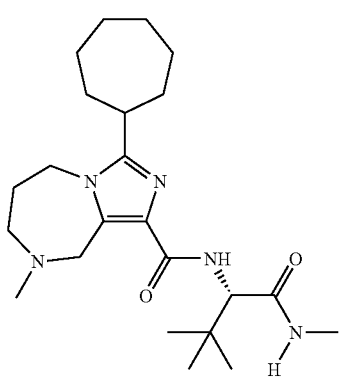 [SMILES: CNC(=O)[C@@H](NC(=O)c1nc(C2CCCCCC2)n2c1CN(C)CCC2)C(C)(C)C] | (S)-3-cycloheptyl-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 418.3 | 45 |

TABLE I-continued

| Cmpd No. | Structure | Chemical Name | m/z | Example No. |
|---|---|---|---|---|
| 499 | 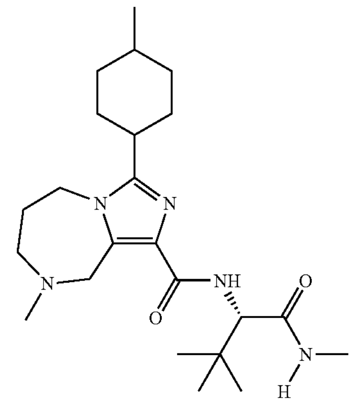 [SMILES: CNC(=O)[C@@H](NC(=O)c1nc(C2CCC(C)CC2)n2c1CN(C)CCC2)C(C)(C)C] | (S)-N-(3,3-dimethyl-1-(methylamino)-1-oxobutan-2-yl)-8-methyl-3-(4-methylcyclohexyl)-6,7,8,9-tetrahydro-5H-imidazo[1,5-a][1,4]diazepine-1-carboxamide | 418.3 | 45 |
| 500 | 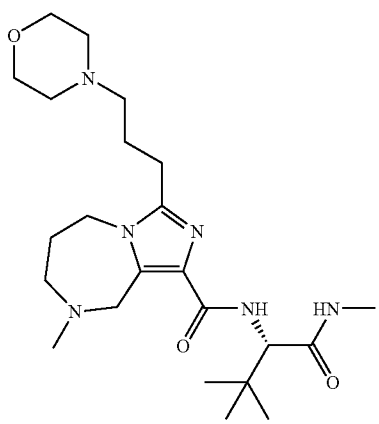 [SMILES: CNC(=O)[C@@H](NC(=O)c1nc(CCCN2CCOCC2)n2c1CN(C)CCC2)C(C)(C)C] | (S)-N-(3,3-dimethyl-1-(methylamino)-1-oxobutan-2-yl)-8-methyl-3-(3-morpholinopropyl)-6,7,8,9-tetrahydro-5H-imidazo[1,5-a][1,4]diazepine-1-carboxamide | 449.2 | 45 |
| 501 | 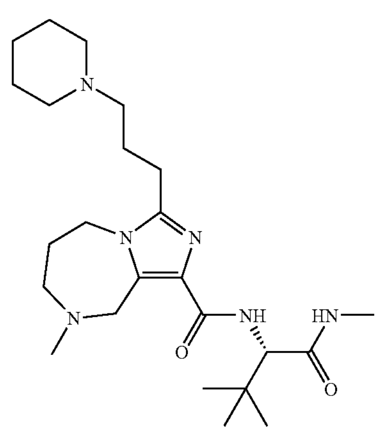 [SMILES: CNC(=O)[C@@H](NC(=O)c1nc(CCCN2CCCCC2)n2c1CN(C)CCC2)C(C)(C)C] | (S)-N-(3,3-dimethyl-1-(methylamino)-1-oxobutan-2-yl)-8-methyl-3-(3-(piperidin-1-yl)propyl)-6,7,8,9-tetrahydro-5H-imidazo[1,5-a][1,4]diazepine-1-carboxamide | 447.3 | 45 |

TABLE I-continued

| Cmpd No. | Structure | Chemical Name | m/z | Example No. |
|---|---|---|---|---|
| 502 | 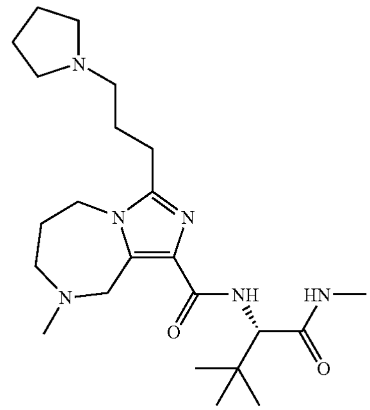 [SMILES: CNC(=O)[C@@H](NC(=O)c1nc(CCCN2CCCC2)n2c1CN(C)CCC2)C(C)(C)C] | (S)-N-(3,3-dimethyl-1-(methylamino)-1-oxobutan-2-yl)-8-methyl-3-(3-(pyrrolidin-1-yl)propyl)-6,7,8,9-tetrahydro-5H-imidazo[1,5-a][1,4]diazepine-1-carboxamide | 433.3 | 45 |
| 503 | 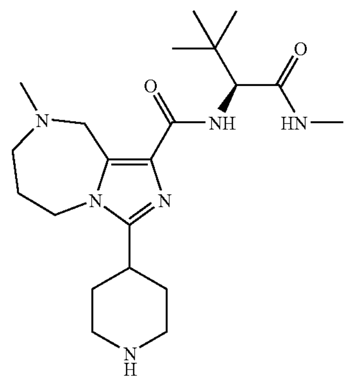 [SMILES: CNC(=O)[C@@H](NC(=O)c1nc(C2CCNCC2)n2c1CN(C)CCC2)C(C)(C)C] | (S)-N-(3,3-dimethyl-1-(methylamino)-1-oxobutan-2-yl)-8-methyl-3-(piperidin-4-yl)-6,7,8,9-tetrahydro-5H-imidazo[1,5-a][1,4]diazepine-1-carboxamide | 405.3 | 45 |
| 504 | 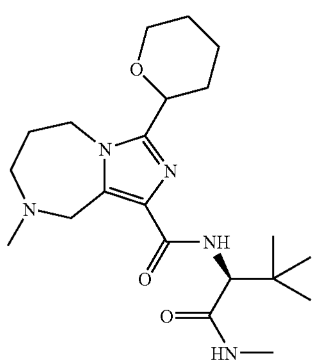 [SMILES: CNC(=O)[C@@H](NC(=O)c1nc(C2CCCCO2)n2c1CN(C)CCC2)C(C)(C)C] | N-((S)-3,3-dimethyl-1-(methylamino)-1-oxobutan-2-yl)-8-methyl-3-(tetrahydro-2H-pyran-2-yl)-6,7,8,9-tetrahydro-5H-imidazo[1,5-a][1,4]diazepine-1-carboxamide | 406.3 | 45 |
| 505 | 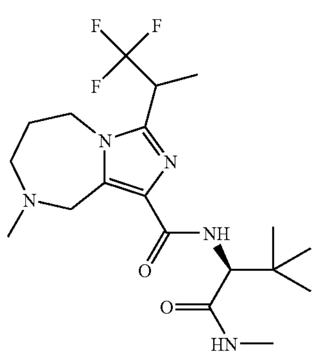 [SMILES: CNC(=O)[C@@H](NC(=O)c1nc(C(C)C(F)(F)F)n2c1CN(C)CCC2)C(C)(C)C] | N-((S)-3,3-dimethyl-1-(methylamino)-1-oxobutan-2-yl)-8-methyl-3-(1,1,1-trifluoropropan-2-yl)-6,7,8,9-tetrahydro-5H-imidazo[1,5-a][1,4]diazepine-1-carboxamide | 418.1 | 45 |

TABLE I-continued

| Cmpd No. | Structure | Chemical Name | m/z | Example No. |
|---|---|---|---|---|
| 506 | 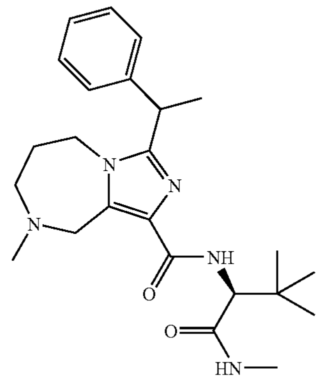 [SMILES: CNC(=O)[C@@H](NC(=O)c1nc(C(C)c2ccccc2)n2c1CN(C)CCC2)C(C)(C)C] | N-((S)-3,3-dimethyl-1-(methylamino)-1-oxobutan-2-yl)-8-methyl-3-(1-phenylethyl)-6,7,8,9-tetrahydro-5H-imidazo[1,5-a][1,4]diazepine-1-carboxamide | 426.3 | 45 |
| 507 | 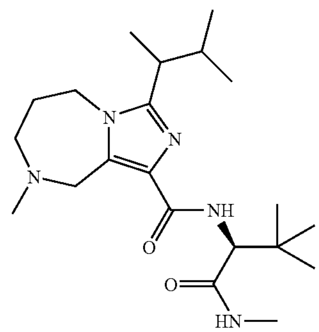 [SMILES: CNC(=O)[C@@H](NC(=O)c1nc(C(C)C(C)C)n2c1CN(C)CCC2)C(C)(C)C] | N-((S)-3,3-dimethyl-1-(methylamino)-1-oxobutan-2-yl)-8-methyl-3-(3-methylbutan-2-yl)-6,7,8,9-tetrahydro-5H-imidazo[1,5-a][1,4]diazepine-1-carboxamide | 392.3 | 45 |
| 508 | 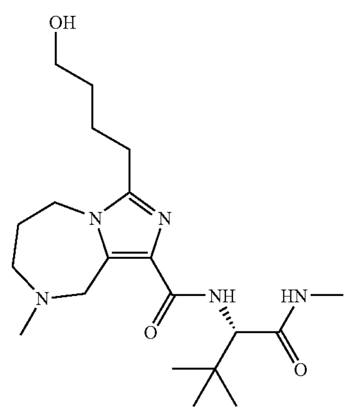 [SMILES: CNC(=O)[C@@H](NC(=O)c1nc(CCCCO)n2c1CN(C)CCC2)C(C)(C)C] | (S)-N-(3,3-dimethyl-1-(methylamino)-1-oxobutan-2-yl)-3-(4-hydroxybutyl)-8-methyl-6,7,8,9-tetrahydro-5H-imidazo[1,5-a][1,4]diazepine-1-carboxamide | 394.2 | 45 |
| 509 | 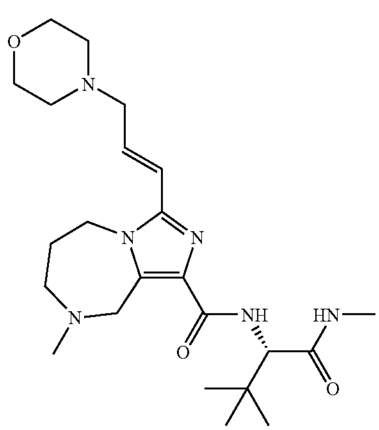 [SMILES: CNC(=O)[C@@H](NC(=O)c1nc(/C=C/CN2CCOCC2)n2c1CN(C)CCC2)C(C)(C)C] | (S,E)-N-(3,3-dimethyl-1-(methylamino)-1-oxobutan-2-yl)-8-methyl-3-(3-morpholinoprop-1-enyl)-6,7,8,9-tetrahydro-5H-imidazo[1,5-a][1,4]diazepine-1-carboxamide | 447.3 | 46 |

TABLE I-continued

| Cmpd No. | Structure | Chemical Name | m/z | Example No. |
|---|---|---|---|---|
| 510 | 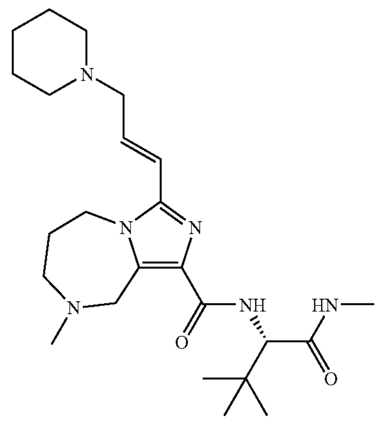 [SMILES: CNC(=O)[C@@H](NC(=O)c1nc(/C=C/CN2CCCCC2)n2c1CN(C)CCC2)C(C)(C)C] | (S,E)-N-(3,3-dimethyl-1-(methylamino)-1-oxobutan-2-yl)-8-methyl-3-(3-(piperidin-1-yl)prop-1-enyl)-6,7,8,9-tetrahydro-5H-imidazo[1,5-a][1,4]diazepine-1-carboxamide | 445.2 | 46 |
| 511 | 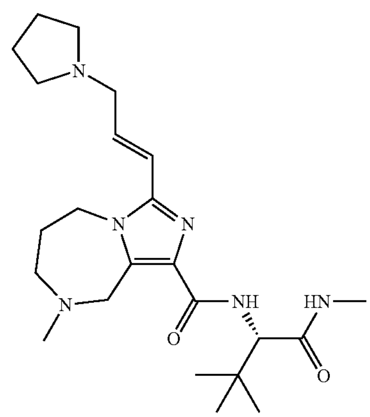 | (S,E)-N-(3,3-dimethyl-1-(methylamino)-1-oxobutan-2-yl)-8-methyl-3-(3-(pyrrolidin-1-yl)prop-1-enyl)-6,7,8,9-tetrahydro-5H-imidazo[1,5-a][1,4]diazepine-1-carboxamide | 431.2 | 46 |
| 512 | 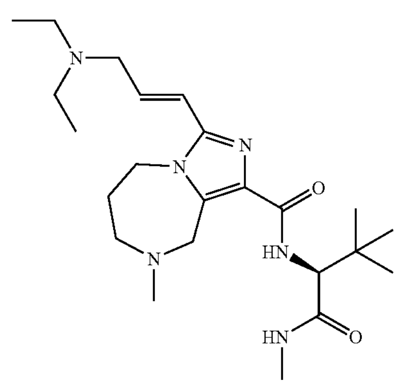 [SMILES: CCN(CC)C/C=C/c1nc(C(=O)N[C@H](C(=O)NC)C(C)(C)C)c2n1CCCN(C)C2] | (S,E)-3-(3-(diethylamino)prop-1-enyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 433.3 | 46 |

TABLE I-continued

| Cmpd No. | Structure | Chemical Name | m/z | Example No. |
|---|---|---|---|---|
| 513 | 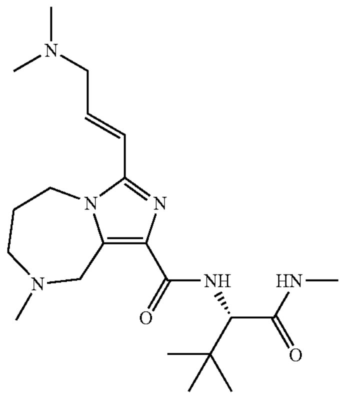 [SMILES: CNC(=O)[C@@H](NC(=O)c1nc(/C=C/CN(C)C)n2c1CN(C)CCC2)C(C)(C)C] | (S,E)-N-(3,3-dimethyl-1-(methylamino)-1-oxobutan-2-yl)-3-(3-(dimethylamino)prop-1-enyl)-8-methyl-6,7,8,9-tetrahydro-5H-imidazo[1,5-a][1,4]diazepine-1-carboxamide | 405.2 | 46 |
| 514 | 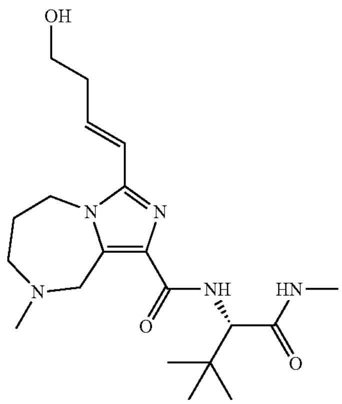 [SMILES: CNC(=O)[C@@H](NC(=O)c1nc(/C=C/CCO)n2c1CN(C)CCC2)C(C)(C)C] | (S,E)-N-(3,3-dimethyl-1-(methylamino)-1-oxobutan-2-yl)-3-(4-hydroxybut-1-enyl)-8-methyl-6,7,8,9-tetrahydro-5H-imidazo[1,5-a][1,4]diazepine-1-carboxamide | 392.2 | 47 |
| 515 | 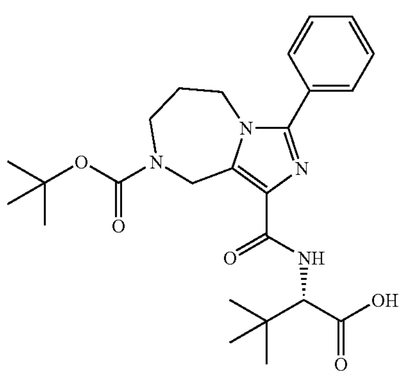 [SMILES: CC(C)(C)OC(=O)N1CCCn2c(-c3ccccc3)nc(C(=O)N[C@H](C(=O)O)C(C)(C)C)c2C1] | (S)-2-(8-tert-butoxycarbonyl)-3-phenyl-6,7,8,9-tetrahydro-5H-imidazo[1,5-a][1,4]diazepine-1-carboxamido)-3,3-dimethylbutanoic acid | 471.2 | 48 |
| 516 | 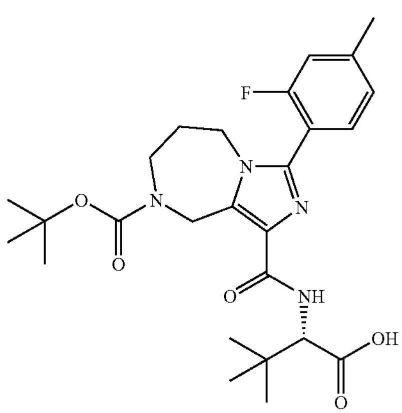 [SMILES: Cc1ccc(-c2nc(C(=O)N[C@H](C(=O)O)C(C)(C)C)c3n2CCCN(C(=O)OC(C)(C)C)C3)c(F)c1] | (S)-2-(8-(tert-butoxycarbonyl)-3-(2-fluoro-4-methylphenyl)-6,7,8,9-tetrahydro-5H-imidazo[1,5-a][1,4]diazepine-1-carboxamido)-3,3-dimethylbutanoic acid | 503.3 | 48 |

TABLE I-continued

| Cmpd No. | Structure | Chemical Name | m/z | Example No. |
|---|---|---|---|---|
| 517 | 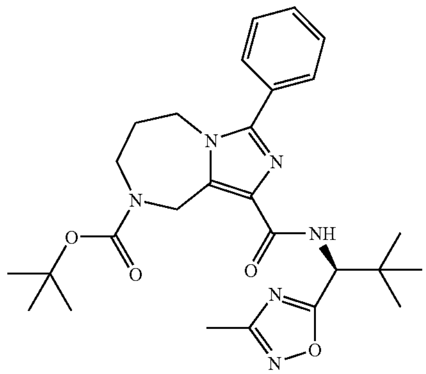 [SMILES: Cc1noc([C@@H](NC(=O)c2nc(-c3ccccc3)n3c2CN(C(=O)OC(C)(C)C)CCC3)C(C)(C)C)n1] | (S)-tert-butyl 1-(2,2-dimethyl-1-(3-methyl-1,2,4-oxadiazol-5-yl)propylcarbamoyl)-3-phenyl-6,7-dihydro-5H-imidazo[1,5-a][1,4]diazepine-8(9H)-carboxylate | 509.2 | 49 |
| 518 | 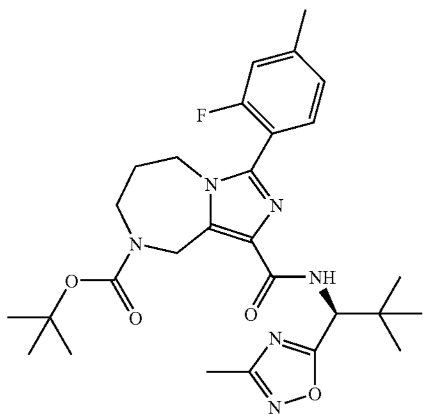 [SMILES: Cc1ccc(-c2nc(C(=O)N[C@H](c3nc(C)no3)C(C)(C)C)c3n2CCCN(C(=O)OC(C)(C)C)C3)c(F)c1] | (S)-tert-butyl 1-(2,2-dimethyl-1-(3-methyl-1,2,4-oxadiazol-5-yl)propylcarbamoyl)-3-(2-fluoro-4-methylphenyl)-6,7-dihydro-5H-imidazo[1,5-a][1,4]diazepine-8(9H)-carboxylate | 541.2 | 49 |
| 519 | 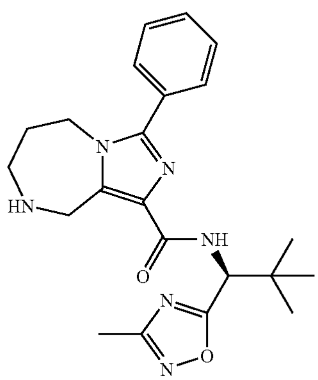 [SMILES: Cc1noc([C@@H](NC(=O)c2nc(-c3ccccc3)n3c2CNCCC3)C(C)(C)C)n1] | (S)-N-(2,2-dimethyl-1-(3-methyl-1,2,4-oxadiazol-5-yl)propyl)-3-phenyl-6,7,8,9-tetrahydro-5H-imidazo[1,5-a][1,4]diazepine-1-carboxamide | 409.2 | 50 |
| 520 | 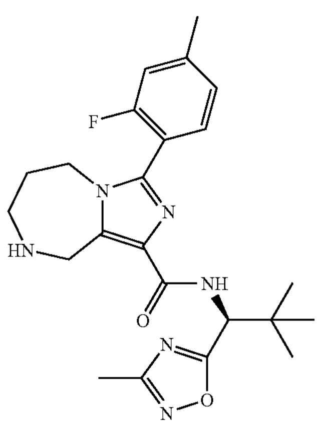 [SMILES: Cc1ccc(-c2nc(C(=O)N[C@H](c3nc(C)no3)C(C)(C)C)c3n2CCCNC3)c(F)c1] | (S)-N-(2,2-dimethyl-1-(3-methyl-1,2,4-oxadiazol-5-yl)propyl)-3-(2-fluoro-4-methylphenyl)-6,7,8,9-tetrahydro-5H-imidazo[1,5-a][1,4]diazepine-1-carboxamide | 441.2 | 50 |

TABLE I-continued

| Cmpd No. | Structure | Chemical Name | m/z | Example No. |
|---|---|---|---|---|
| 521 | 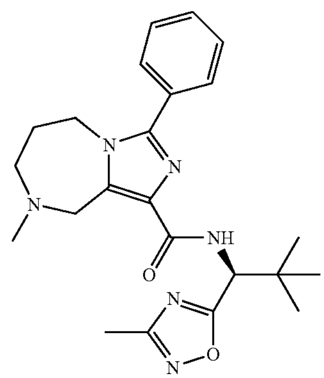 [SMILES: Cc1noc([C@@H](NC(=O)c2nc(-c3ccccc3)n3c2CN(C)CCC3)C(C)(C)C)n1] | (S)-N-(2,2-dimethyl-1-(3-methyl-1,2,4-oxadiazol-5-yl)propyl)-8-methyl-3-phenyl-6,7,8,9-tetrahydro-5H-imidazo[1,5-a][1,4]diazepine-1-carboxamide | 423.2 | 51 |
| 522 | 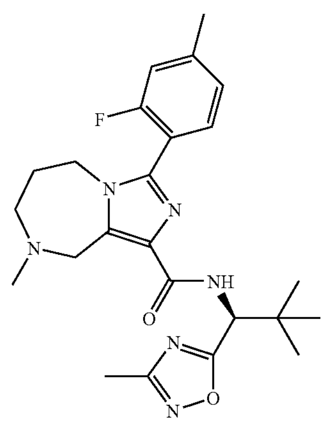 [SMILES: Cc1ccc(-c2nc(C(=O)N[C@H](c3nc(C)no3)C(C)(C)C)c3n2CCCN(C)C3)c(F)c1] | (S)-N-(2,2-dimethyl-1-(3-methyl-1,2,4-oxadiazol-5-yl)propyl)-3-(2-fluoro-4-methylphenyl)-8-methyl-6,7,8,9-tetrahydro-5H-imidazo[1,5-a][1,4]diazepine-1-carboxamide | 455.2 | 51 |
| 523 | 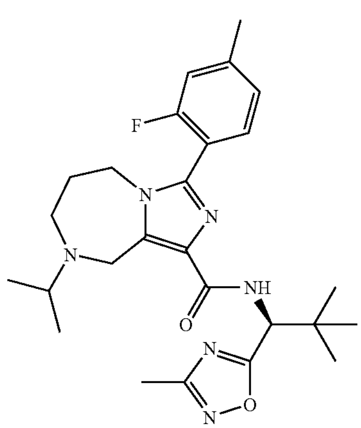 [SMILES: Cc1ccc(-c2nc(C(=O)N[C@H](c3nc(C)no3)C(C)(C)C)c3n2CCCN(C(C)C)C3)c(F)c1] | (S)-N-(2,2-dimethyl-1-(3-methyl-1,2,4-oxadiazol-5-yl)propyl)-3-(2-fluoro-4-methylphenyl)-8-isopropyl-6,7,8,9-tetrahydro-5H-imidazo[1,5-a][1,4]diazepine-1-carboxamide | 483.3 | 51 |

TABLE I-continued

| Cmpd No. | Structure | Chemical Name | m/z | Example No. |
|---|---|---|---|---|
| 524 | 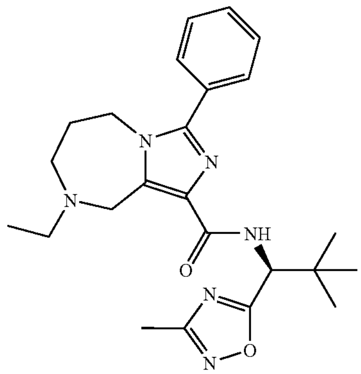 [SMILES: CCN1CCCn2c(-c3ccccc3)nc(C(=O)N[C@H](c3nc(C)no3)C(C)(C)C)c2C1] | (S)-N-(2,2-dimethyl-1-(3-methyl-1,2,4-oxadiazol-5-yl)propyl)-8-ethyl-3-phenyl-6,7,8,9-tetrahydro-5H-imidazo[1,5-a][1,4]diazepine-1-carboxamide | 437.2 | 51 |
| 525 | 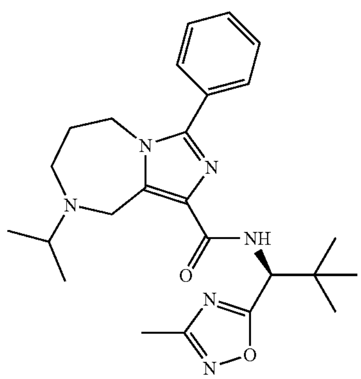 [SMILES: Cc1noc([C@@H](NC(=O)c2nc(-c3ccccc3)n3c2CN(C(C)C)CCC3)C(C)(C)C)n1] | (S)-N-(2,2-dimethyl-1-(3-methyl-1,2,4-oxadiazol-5-yl)propyl)-8-isopropyl-3-phenyl-6,7,8,9-tetrahydro-5H-imidazo[1,5-a][1,4]diazepine-1-carboxamide | 451.2 | 51 |
| 526 | 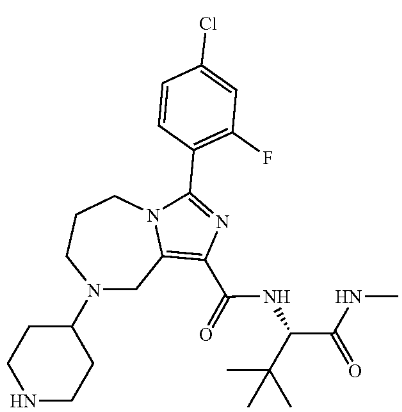 [SMILES: CNC(=O)[C@@H](NC(=O)c1nc(-c2ccc(Cl)cc2F)n2c1CN(C1CCNCC1)CCC2)C(C)(C)C] | (S)-3-(4-chloro-2-fluorophenyl)-N-(3,3-dimethyl-1-(methylamino)-1-oxobutan-2-yl)-8-(piperidin-4-yl)-6,7,8,9-tetrahydro-5H-imidazo[1,5-a][1,4]diazepine-1-carboxamide | 520.0 | 52 |

| Cmpd No. | Structure | Chemical Name | m/z | Example No. |
|---|---|---|---|---|
| 527 | 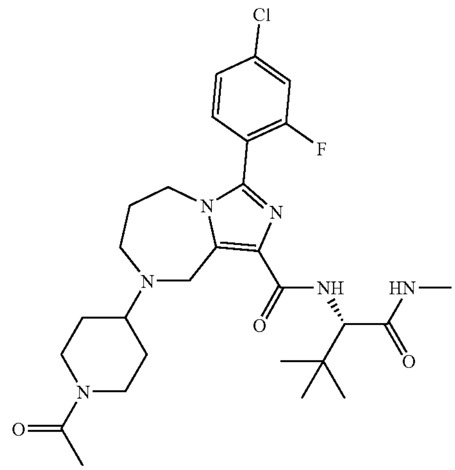 [SMILES: CNC(=O)[C@@H](NC(=O)c1nc(-c2ccc(Cl)cc2F)n2c1CN(C1CCN(C(C)=O)CC1)CCC2)C(C)(C)C] | (S)-8-(1-acetylpiperidin-4-yl)-3-(4-chloro-2-fluorophenyl)-N-(3,3-dimethyl-1-(methylamino)-1-oxobutan-2-yl)-6,7,8,9-tetrahydro-5H-imidazo[1,5-a][1,4]diazepine-1-carboxamide | 562.0 | 53 |
| 528 | 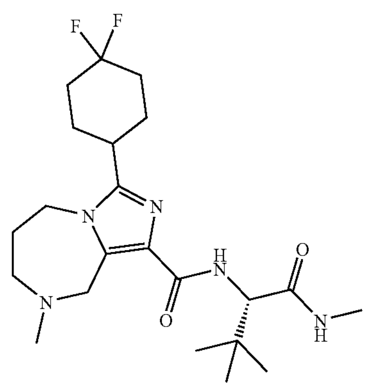 [SMILES: CNC(=O)[C@@H](NC(=O)c1nc(C2CCC(F)(F)CC2)n2c1CN(C)CCC2)C(C)(C)C] | (S)-3-(4,4-difluorocyclohexyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 440.0 | 54 |
| 529 | 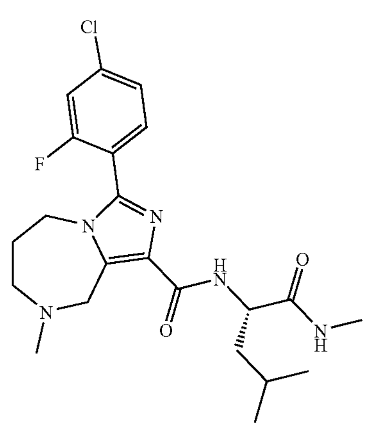 [SMILES: CNC(=O)[C@H](CC(C)C)NC(=O)c1nc(-c2ccc(Cl)cc2F)n2c1CN(C)CCC2] | (S)-3-(4-chloro-2-fluorophenyl)-8-methyl-N-(4-methyl-1-(methylamino)-1-oxopentan-2-yl)-6,7,8,9-tetrahydro-5H-imidazo[1,5-a][1,4]diazepine-1-carboxamide | 450.0 | 55 |

TABLE I-continued

| Cmpd No. | Structure | Chemical Name | m/z | Example No. |
|---|---|---|---|---|
| 530 | 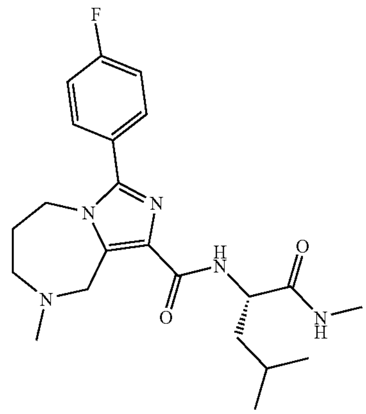 [SMILES: CNC(=O)[C@H](CC(C)C)NC(=O)c1nc(-c2ccc(F)cc2)n2c1CN(C)CCC2] | (S)-3-(4-fluorophenyl)-8-methyl-N-(4-methyl-1-(methylamino)-1-oxopentan-2-yl)-6,7,8,9-tetrahydro-5H-imidazo[1,5-a][1,4]diazepine-1-carboxamide | 416.0 | 55 |
| 531 | 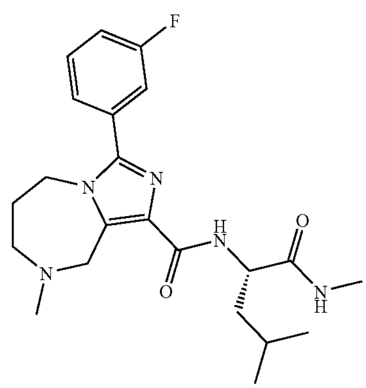 [SMILES: CNC(=O)[C@H](CC(C)C)NC(=O)c1nc(-c2cccc(F)c2)n2c1CN(C)CCC2] | (S)-3-(3-fluorophenyl)-8-methyl-N-(4-methyl-1-(methylamino)-1-oxopentan-2-yl)-6,7,8,9-tetrahydro-5H-imidazo[1,5-a][1,4]diazepine-1-carboxamide | 416.0 | 55 |
| 532 | 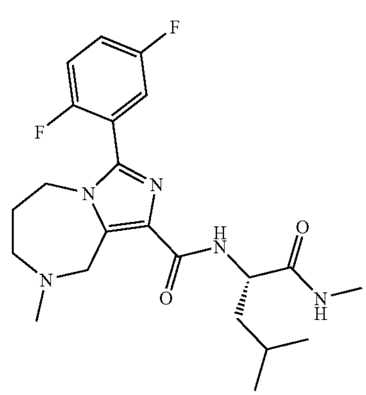 [SMILES: CNC(=O)[C@H](CC(C)C)NC(=O)c1nc(-c2cc(F)ccc2F)n2c1CN(C)CCC2] | (S)-3-(2,5-difluorophenyl)-8-methyl-N-(4-methyl-1-(methylamino)-1-oxopentan-2-yl)-6,7,8,9-tetrahydro-5H-imidazo[1,5-a][1,4]diazepine-1-carboxamide | 434.0 | 55 |

TABLE I-continued

| Cmpd No. | Structure | Chemical Name | m/z | Example No. |
|---|---|---|---|---|
| 533 | 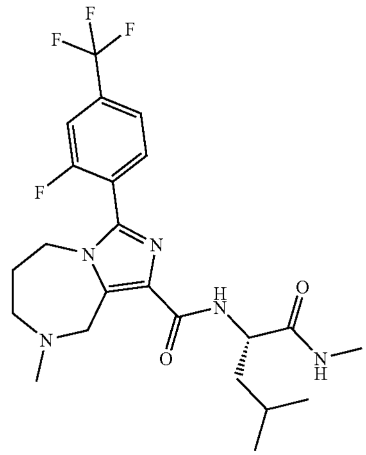 [SMILES: CNC(=O)[C@H](CC(C)C)NC(=O)c1nc(-c2ccc(C(F)(F)F)cc2F)n2c1CN(C)CCC2] | (S)-3-(2-fluoro-4-(trifluoromethyl)phenyl)-8-methyl-N-(4-methyl-1-(methylamino)-1-oxopentan-2-yl)-6,7,8,9-tetrahydro-5H-imidazo[1,5-a][1,4]diazepine-1-carboxamide | 484.0 | 55 |
| 534 | 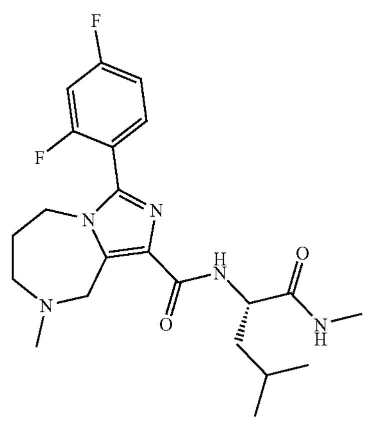 [SMILES: CNC(=O)[C@H](CC(C)C)NC(=O)c1nc(-c2ccc(F)cc2F)n2c1CN(C)CCC2] | (S)-3-(2,4-difluorophenyl)-8-methyl-N-(4-methyl-1-(methylamino)-1-oxopentan-2-yl)-6,7,8,9-tetrahydro-5H-imidazo[1,5-a][1,4]diazepine-1-carboxamide | 434.0 | 55 |
| 535 | 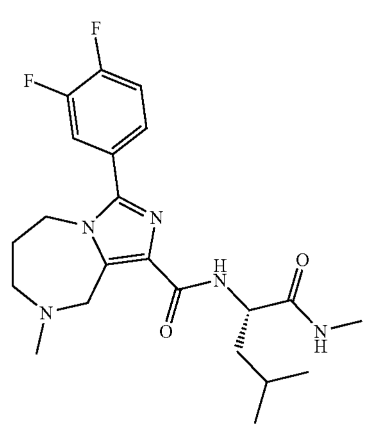 [SMILES: CNC(=O)[C@H](CC(C)C)NC(=O)c1nc(-c2ccc(F)c(F)c2)n2c1CN(C)CCC2] | (S)-3-(3,4-difluorophenyl)-8-methyl-N-(4-methyl-1-(methylamino)-1-oxopentan-2-yl)-6,7,8,9-tetrahydro-5H-imidazo[1,5-a][1,4]diazepine-1-carboxamide | 434.0 | 55 |

TABLE I-continued

| Cmpd No. | Structure | Chemical Name | m/z | Example No. |
|---|---|---|---|---|
| 536 | 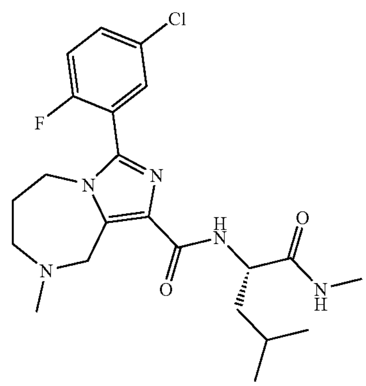 | (S)-3-(5-chloro-2-fluorophenyl)-8-methyl-N-(4-methyl-1-(methylamino)-1-oxopentan-2-yl)-6,7,8,9-tetrahydro-5H-imidazo[1,5-a][1,4]diazepine-1-carboxamide | 450.0 | 55 |
| 537 | 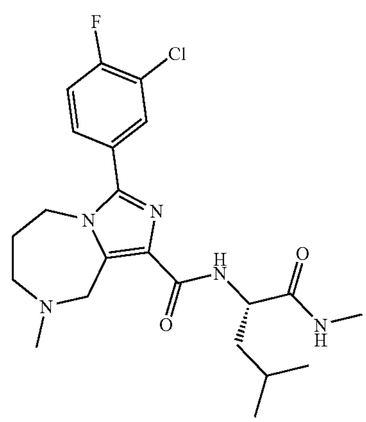 [SMILES: CNC(=O)[C@H](CC(C)C)NC(=O)c1nc(-c2ccc(F)c(Cl)c2)n2c1CN(C)CCC2] | (S)-3-(3-chloro-4-fluorophenyl)-8-methyl-N-(4-methyl-1-(methylamino)-1-oxopentan-2-yl)-6,7,8,9-tetrahydro-5H-imidazo[1,5-a][1,4]diazepine-1-carboxamide | 450.0 | 55 |
| 538 | 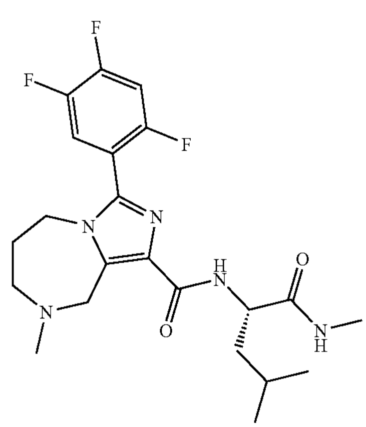 [SMILES: CNC(=O)[C@H](CC(C)C)NC(=O)c1nc(-c2cc(F)c(F)cc2F)n2c1CN(C)CCC2] | (S)-8-methyl-N-(4-methyl-1-(methylamino)-1-oxopentan-2-yl)-3-(2,4,5-trifluorophenyl)-6,7,8,9-tetrahydro-5H-imidazo[1,5-a][1,4]diazepine-1-carboxamide | 452.2 | 55 |

TABLE I-continued

| Cmpd No. | Structure | Chemical Name | m/z | Example No. |
|---|---|---|---|---|
| 539 | 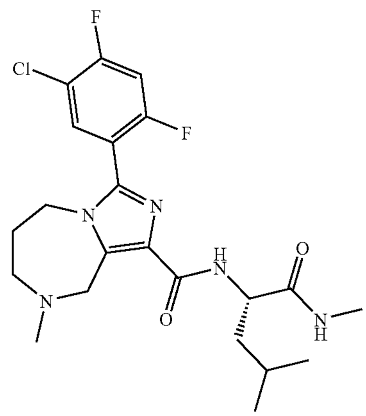 [SMILES: CNC(=O)[C@H](CC(C)C)NC(=O)c1nc(-c2cc(Cl)c(F)cc2F)n2c1CN(C)CCC2] | (S)-3-(5-chloro-2,4-difluorophenyl)-8-methyl-N-(4-methyl-1-(methylamino)-1-oxopentan-2-yl)-6,7,8,9-tetrahydro-5H-imidazo[1,5-a][1,4]diazepine-1-carboxamide | 468.2 | 55 |
| 540 | 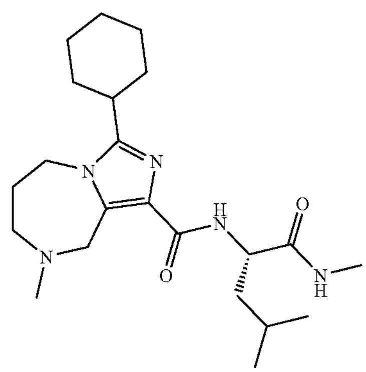 [SMILES: CNC(=O)[C@H](CC(C)C)NC(=O)c1nc(C2CCCCC2)n2c1CN(C)CCC2] | (S)-3-cyclohexyl-8-methyl-N-(4-methyl-1-(methylamino)-1-oxopentan-2-yl)-6,7,8,9-tetrahydro-5H-imidazo[1,5-a][1,4]diazepine-1-carboxamide | 404.0 | 55 |
| 541 | 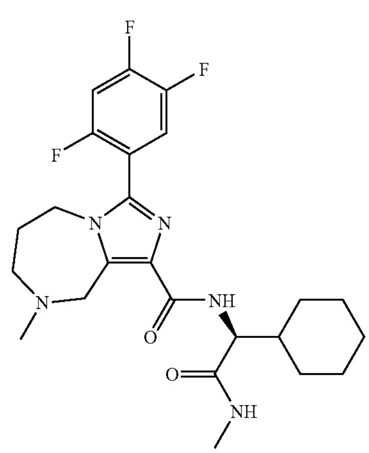 | (S)-N-(1-cyclohexyl-2-(methylamino)-2-oxoethyl)-8-methyl-3-(2,4,5-trifluorophenyl)-6,7,8,9-tetrahydro-5H-imidazo[1,5-a][1,4]diazepine-1-carboxamide | 478.1 | 55 |

TABLE I-continued

| Cmpd No. | Structure | Chemical Name | m/z | Example No. |
|---|---|---|---|---|
| 542 | 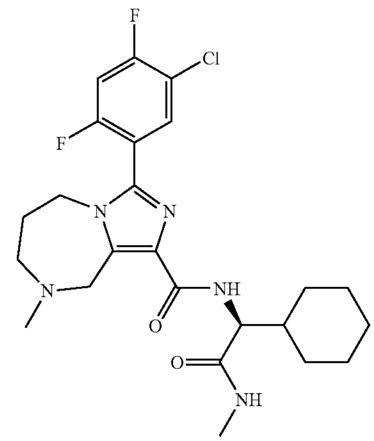 [SMILES: CNC(=O)[C@@H](NC(=O)c1nc(-c2cc(Cl)c(F)cc2F)n2c1CN(C)CCC2)C1CCCCC1] | (S)-3-(5-chloro-2,4-difluorophenyl)-N-(1-cyclohexyl-2-(methylamino)-2-oxoethyl)-8-methyl-6,7,8,9-tetrahydro-5H-imidazo[1,5-a][1,4]diazepine-1-carboxamide | 494.0 | 55 |
| 543 | 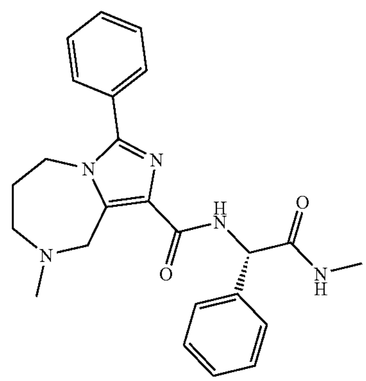 [SMILES: CNC(=O)[C@@H](NC(=O)c1nc(-c2ccccc2)n2c1CN(C)CCC2)c1ccccc1] | (S)-8-methyl-N-(2-(methylamino)-2-oxo-1-phenylethyl)-3-phenyl-6,7,8,9-tetrahydro-5H-imidazo[1,5-a][1,4]diazepine-1-carboxamide | 418.0 | 56 |
| 544 | 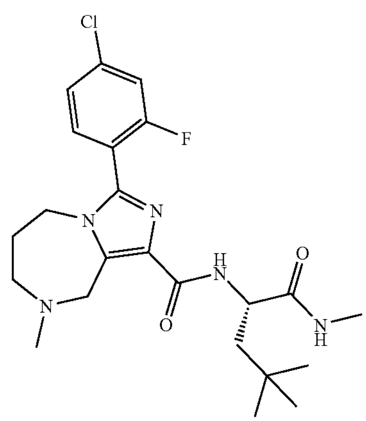 [SMILES: CNC(=O)[C@H](CC(C)(C)C)NC(=O)c1nc(-c2ccc(Cl)cc2F)n2c1CN(C)CCC2] | (S)-3-(4-chloro-2-fluorophenyl)-N-(4,4-dimethyl-1-(methylamino)-1-oxopentan-2-yl)-8-methyl-6,7,8,9-tetrahydro-5H-imidazo[1,5-a][1,4]diazepine-1-carboxamide | 464.0 | 57 |
| 545 | 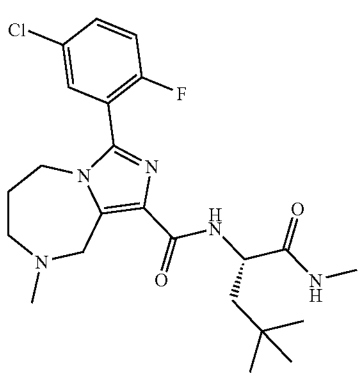 [SMILES: CNC(=O)[C@H](CC(C)(C)C)NC(=O)c1nc(-c2cc(Cl)ccc2F)n2c1CN(C)CCC2] | (S)-3-(5-chloro-2-fluorophenyl)-N-(4,4-dimethyl-1-(methylamino)-1-oxopentan-2-yl)-8-methyl-6,7,8,9-tetrahydro-5H-imidazo[1,5-a][1,4]diazepine-1-carboxamide | 464.0 | 57 |

TABLE I-continued

| Cmpd No. | Structure | Chemical Name | m/z | Example No. |
|---|---|---|---|---|
| 546 | 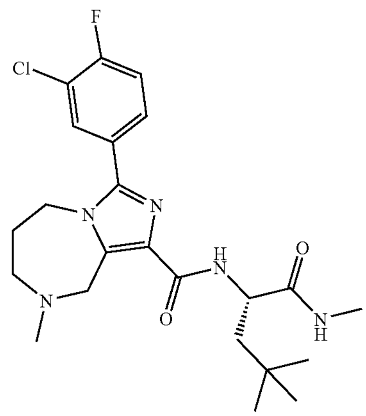 [SMILES: CNC(=O)[C@H](CC(C)(C)C)NC(=O)c1nc(-c2ccc(F)c(Cl)c2)n2c1CN(C)CCC2] | (S)-3-(3-chloro-4-fluorophenyl)-N-(4,4-dimethyl-1-(methylamino)-1-oxopentan-2-yl)-8-methyl-6,7,8,9-tetrahydro-5-imidazo[1,5-a][1,4]diazepine-1-carboxamide | 464.0 | 57 |
| 547 | 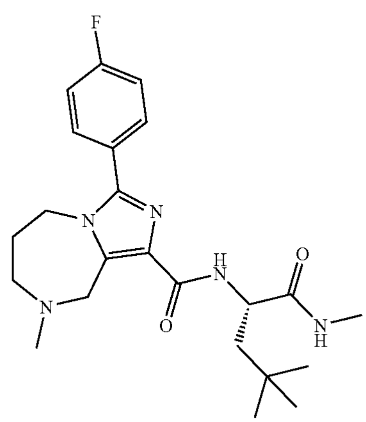 [SMILES: CNC(=O)[C@H](CC(C)(C)C)NC(=O)c1nc(-c2ccc(F)cc2)n2c1CN(C)CCC2] | (S)-N-(4,4-dimethyl-1-(methylamino)-1-oxopentan-2-yl)-3-(4-fluorophenyl)-8-methyl-6,7,8,9-tetrahydro-5H-imidazo[1,5-a][1,4]diazepine-1-carboxamide | 430.0 | 57 |
| 548 | 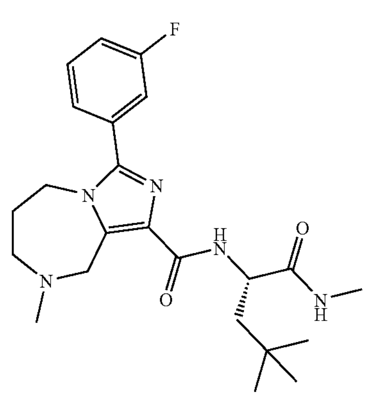 [SMILES: CNC(=O)[C@H](CC(C)(C)C)NC(=O)c1nc(-c2cccc(F)c2)n2c1CN(C)CCC2] | (S)-N-(4,4-dimethyl-1-(methylamino)-1-oxopentan-2-yl)-3-(3-fluorophenyl)-8-methyl-6,7,8,9-tetrahydro-5H-imidazo[1,5-a][1,4]diazepine-1-carboxamide | 430.0 | 57 |

TABLE I-continued

| Cmpd No. | Structure | Chemical Name | m/z | Example No. |
|---|---|---|---|---|
| 549 | 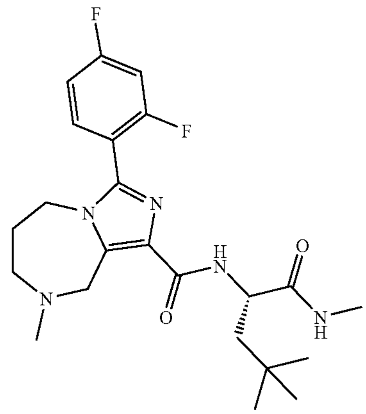 [SMILES: CNC(=O)[C@H](CC(C)(C)C)NC(=O)c1nc(-c2ccc(F)cc2F)n2c1CN(C)CCC2] | (S)-3-(2,4-difluorophenyl)-N-(4,4-dimethyl-1-(methylamino)-1-oxopentan-2-yl)-8-methyl-6,7,8,9-tetrahydro-5H-imidazo[1,5-a][1,4]diazepine-1-carboxamide | 448.0 | 57 |
| 550 | 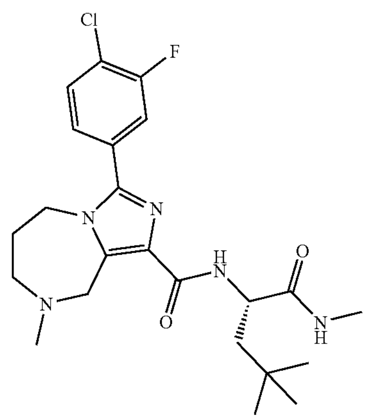 [SMILES: CNC(=O)[C@H](CC(C)(C)C)NC(=O)c1nc(-c2ccc(Cl)c(F)c2)n2c1CN(C)CCC2] | (S)-3-(4-chloro-3-fluorophenyl)-N-(4,4-dimethyl-1-(methylamino)-1-oxopentan-2-yl)-8-methyl-6,7,8,9-tetrahydro-5H-imidazo[1,5-a][1,4]diazepine-1-carboxamide | 464.0 | 57 |
| 551 | 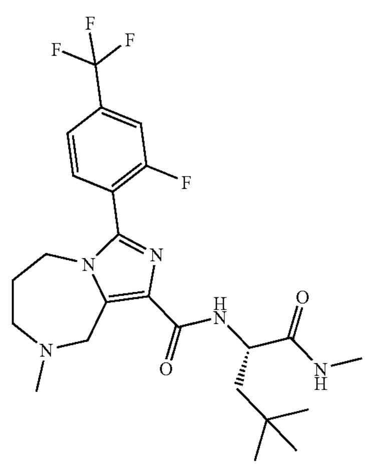 [SMILES: CNC(=O)[C@H](CC(C)(C)C)NC(=O)c1nc(-c2ccc(C(F)(F)F)cc2F)n2c1CN(C)CCC2] | (S)-N-(4,4-dimethyl-1-(methylamino)-1-oxopentan-2-yl)-3-(2-fluoro-4-(trifluoromethyl)phenyl)-8-methyl-6,7,8,9-tetrahydro-5H-imidazo[1,5-a][1,4]diazepine-1-carboxamide | 498.0 | 57 |

TABLE I-continued

| Cmpd No. | Structure | Chemical Name | m/z | Example No. |
|---|---|---|---|---|
| 552 | 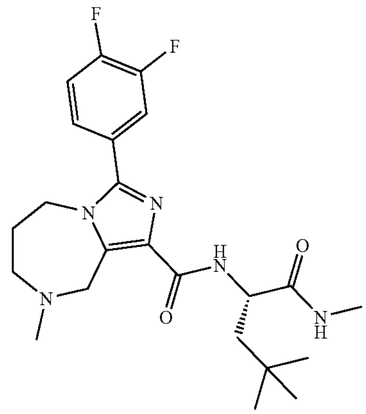 [SMILES: CNC(=O)[C@H](CC(C)(C)C)NC(=O)c1nc(-c2ccc(F)c(F)c2)n2c1CN(C)CCC2] | (S)-3-(3,4-difluorophenyl)-N-(4,4-dimethyl-1-(methylamino)-1-oxopentan-2-yl)-8-methyl-6,7,8,9-tetrahydro-5H-imidazo[1,5-a][1,4]diazepine-1-carboxamide | 448.0 | 57 |
| 553 | 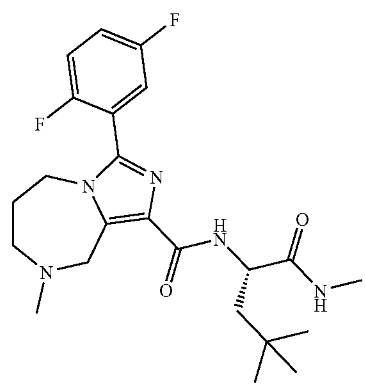 [SMILES: CNC(=O)[C@H](CC(C)(C)C)NC(=O)c1nc(-c2cc(F)ccc2F)n2c1CN(C)CCC2] | (S)-3-(2,5-difluorophenyl)-N-(4,4-dimethyl-1-(methylamino)-1-oxopentan-2-yl)-8-methyl-6,7,8,9-tetrahydro-5H-imidazo[1,5-a][1,4]diazepine-1-carboxamide | 448.0 | 57 |
| 554 | 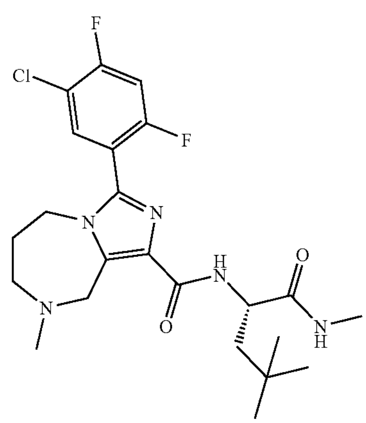 [SMILES: CNC(=O)[C@H](CC(C)(C)C)NC(=O)c1nc(-c2cc(Cl)c(F)cc2F)n2c1CN(C)CCC2] | (S)-3-(5-chloro-2,4-difluorophenyl)-N-(4,4-dimethyl-1-(methylamino)-1-oxopentan-2-yl)-8-methyl-6,7,8,9-tetrahydro-5H-imidazo[1,5-a][1,4]diazepine-1-carboxamide | 482.2 | 57 |

TABLE I-continued

| Cmpd No. | Structure | Chemical Name | m/z | Example No. |
|---|---|---|---|---|
| 555 | 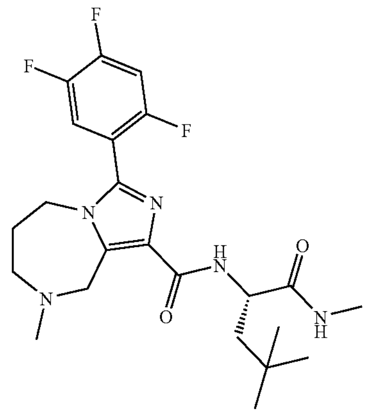 [SMILES: CNC(=O)[C@H](CC(C)(C)C)NC(=O)c1nc(-c2cc(F)c(F)cc2F)n2c1CN(C)CCC2] | (S)-N-(4,4-dimethyl-1-(methylamino)-1-oxopentan-2-yl)-8-methyl-3-(2,4,5-trifluorophenyl)-6,7,8,9-tetrahydro-5H-imidazo[1,5-a][1,4]diazepine-1-carboxamide | 466.2 | 57 |
| 556 | 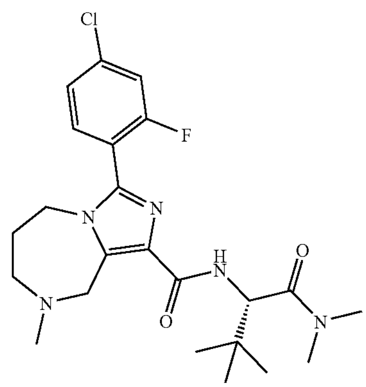 [SMILES: CN1CCCn2c(-c3ccc(Cl)cc3F)nc(C(=O)N[C@H](C(=O)N(C)C)C(C)(C)C)c2C1] | (S)-3-(4-chloro-2-fluorophenyl)-N-(1-(dimethylamino)-3,3-dimethyl-1-oxobutan-2-yl)-8-methyl-6,7,8,9-tetrahydro-5H-imidazo[1,5-a][1,4]diazepine-1-carboxamide | 464.0 | 58 |
| 557 | 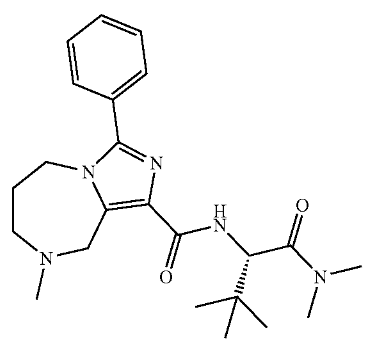 [SMILES: CN1CCCn2c(-c3ccccc3)nc(C(=O)N[C@H](C(=O)N(C)C)C(C)(C)C)c2C1] | (S)-N-(1-(dimethylamino)-3,3-dimethyl-1-oxobutan-2-yl)-8-methyl-3-phenyl-6,7,8,9-tetrahydro-5H-imidazo[1,5-a][1,4]diazepine-1-carboxamide | 412.0 | 58 |
| 558 | 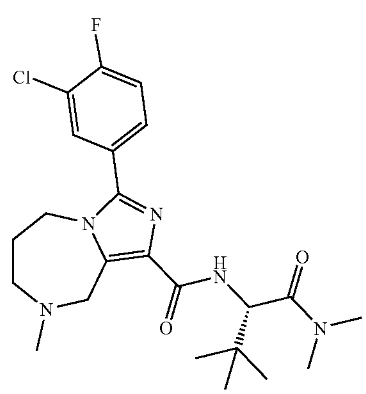 [SMILES: CN1CCCn2c(-c3ccc(F)c(Cl)c3)nc(C(=O)N[C@H](C(=O)N(C)C)C(C)(C)C)c2C1] | (S)-3-(3-chloro-4-fluorophenyl)-N-(1-(dimethylamino)-3,3-dimethyl-1-oxobutan-2-yl)-8-methyl-6,7,8,9-tetrahydro-5H-imidazo[1,5-a][1,4]diazepine-1-carboxamide | 464.0 | 58 |

| Cmpd No. | Structure | Chemical Name | m/z | Example No. |
|---|---|---|---|---|
| 559 | 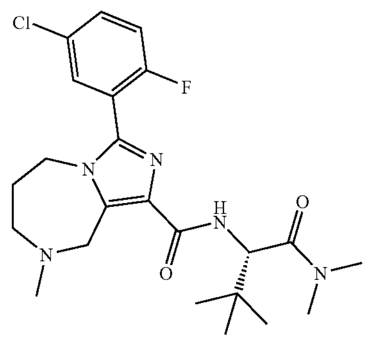 [SMILES: CN1CCCn2c(-c3cc(Cl)ccc3F)nc(C(=O)N[C@H](C(=O)N(C)C)C(C)(C)C)c2C1] | (S)-3-(5-chloro-2-fluorophenyl)-N-(1-(dimethylamino)-3,3-dimethyl-1-oxobutan-2-yl)-8-methyl-6,7,8,9-tetrahydro-5H-imidazo[1,5-a][1,4]diazepine-1-carboxamide | 464.0 | 58 |
| 560 | 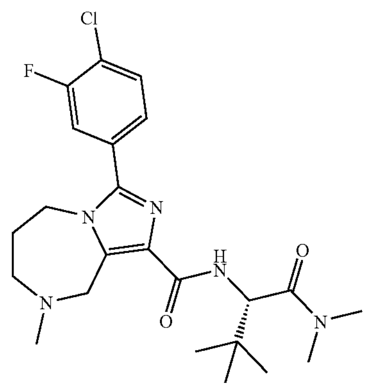 [SMILES: CN1CCCn2c(-c3ccc(Cl)c(F)c3)nc(C(=O)N[C@H](C(=O)N(C)C)C(C)(C)C)c2C1] | (S)-3-(4-chloro-3-fluorophenyl)-N-(1-(dimethylamino)-3,3-dimethyl-1-oxobutan-2-yl)-8-methyl-6,7,8,9-tetrahydro-5H-imidazo[1,5-a][1,4]diazepine-1-carboxamide | 464.0 | 58 |
| 561 | 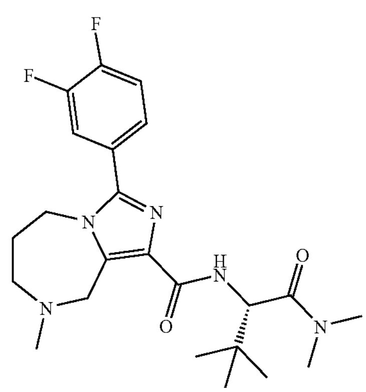 [SMILES: CN1CCCn2c(-c3ccc(F)c(F)c3)nc(C(=O)N[C@H](C(=O)N(C)C)C(C)(C)C)c2C1] | (S)-3-(3,4-difluorophenyl)-N-(1-(dimethylamino)-3,3-dimethyl-1-oxobutan-2-yl)-8-methyl-6,7,8,9-tetrahydro-5H-imidazo[1,5-a][1,4]diazepine-1-carboxamide | 448.0 | 58 |
| 562 | 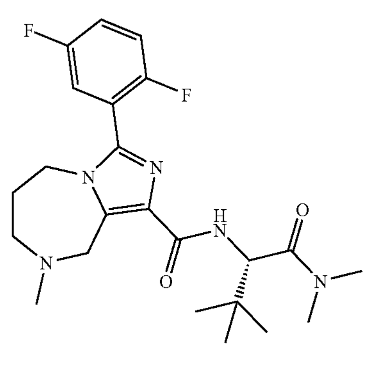 [SMILES: CN1CCCn2c(-c3cc(F)ccc3F)nc(C(=O)N[C@H](C(=O)N(C)C)C(C)(C)C)c2C1] | (S)-3-(2,5-difluorophenyl)-N-(1-(dimethylamino)-3,3-dimethyl-1-oxobutan-2-yl)-8-methyl-6,7,8,9-tetrahydro-5H-imidazo[1,5-a][1,4]diazepine-1-carboxamide | 448.0 | 58 |

TABLE I-continued

| Cmpd No. | Structure | Chemical Name | m/z | Example No. |
|---|---|---|---|---|
| 563 | 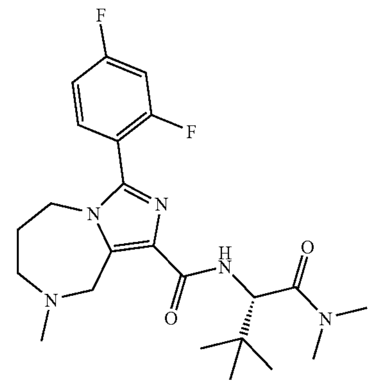 | (S)-3-(2,4-difluorophenyl)-N-(1-(dimethylamino)-3,3-dimethyl-1-oxobutan-2-yl)-8-methyl-6,7,8,9-tetrahydro-5H-imidazo[1,5-a][1,4]diazepine-1-carboxamide | 448.0 | 58 |
| 564 | 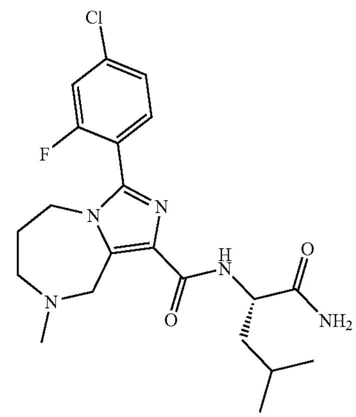 [SMILES: CC(C)C[C@H](NC(=O)c1nc(-c2ccc(Cl)cc2F)n2c1CN(C)CCC2)C(N)=O] | (S)-N-(1-amino-4-methyl-1-oxopentan-2-yl)-3-(4-chloro-2-fluorophenyl)-8-methyl-6,7,8,9-tetrahydro-5H-imidazo[1,5-a][1,4]diazepine-1-carboxamide | 436.0 | 59 |
| 565 | 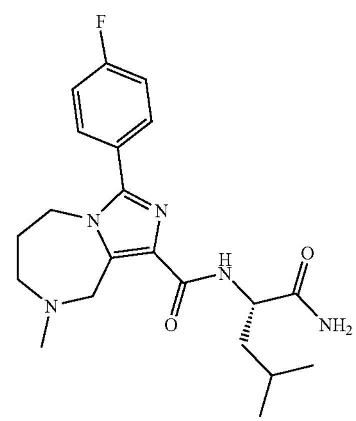 [SMILES: CC(C)C[C@H](NC(=O)c1nc(-c2ccc(F)cc2)n2c1CN(C)CCC2)C(N)=O] | (S)-N-(1-amino-4-methyl-1-oxopentan-2-yl)-3-(4-fluorophenyl)-8-methyl-6,7,8,9-tetrahydro-5H-imidazo[1,5-a][1,4]diazepine-1-carboxamide | 402.0 | 59 |
| 566 | 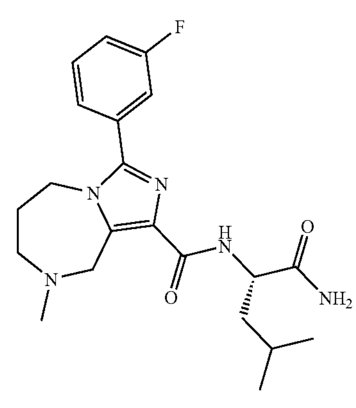 [SMILES: CC(C)C[C@H](NC(=O)c1nc(-c2cccc(F)c2)n2c1CN(C)CCC2)C(N)=O] | (S)-N-(1-amino-4-methyl-1-oxopentan-2-yl)-3-(3-fluorophenyl)-8-methyl-6,7,8,9-tetrahydro-5H-imidazo[1,5-a][1,4]diazepine-1-carboxamide | 402.0 | 59 |

| Cmpd No. | Structure | Chemical Name | m/z | Example No. |
|---|---|---|---|---|
| 567 | 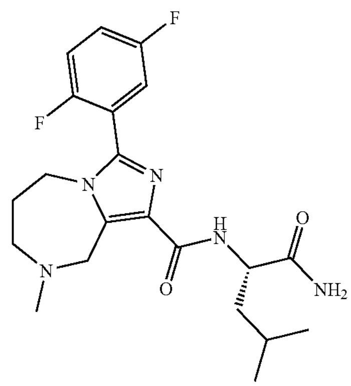 [SMILES: CC(C)C[C@H](NC(=O)c1nc(-c2cc(F)ccc2F)n2c1CN(C)CCC2)C(N)=O] | (S)-N-(1-amino-4-methyl-1-oxopentan-2-yl)-3-(2,5-difluorophenyl)-8-methyl-6,7,8,9-tetrahydro-5H-imidazo[1,5-a][1,4]diazepine-1-carboxamide | 420.0 | 59 |
| 568 | 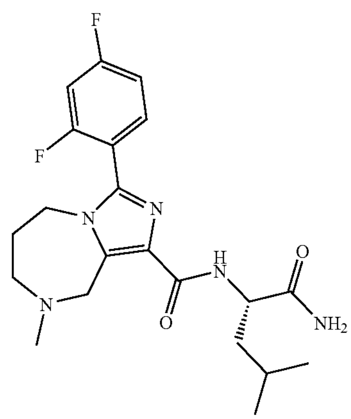 [SMILES: CC(C)C[C@H](NC(=O)c1nc(-c2ccc(F)cc2F)n2c1CN(C)CCC2)C(N)=O] | (S)-N-(1-amino-4-methyl-1-oxopentan-2-yl)-3-(2,4-difluorophenyl)-8-methyl-6,7,8,9-tetrahydro-5H-imidazo[1,5-a][1,4]diazepine-1-carboxamide | 420.0 | 59 |
| 569 | 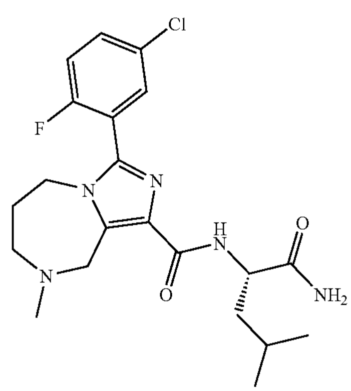 | (S)-N-(1-amino-4-methyl-1-oxopentan-2-yl)-3-(5-chloro-2-fluorophenyl)-8-methyl-6,7,8,9-tetrahydro-5H-imidazo[1,5-a][1,4]diazepine-1-carboxamide | 436.0 | 59 |

TABLE I-continued

| Cmpd No. | Structure | Chemical Name | m/z | Example No. |
|---|---|---|---|---|
| 570 | 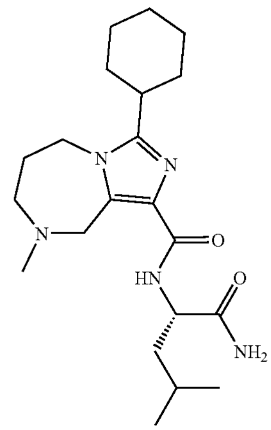 [SMILES: CC(C)C[C@H](NC(=O)c1nc(C2CCCCC2)n2c1CN(C)CCC2)C(N)=O] | (S)-N-(1-amino-4-methyl-1-oxopentan-2-yl)-3-cyclohexyl-8-methyl-6,7,8,9-tetrahydro-5H-imidazo[1,5-a][1,4]diazepine-1-carboxamide | 390.0 | 59 |
| 571 | 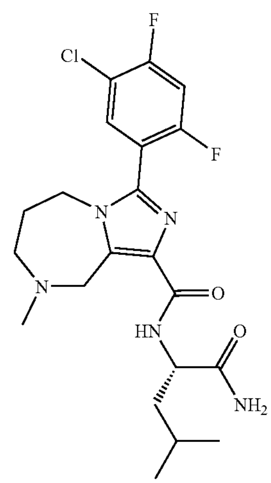 [SMILES: CC(C)C[C@H](NC(=O)c1nc(-c2cc(Cl)c(F)cc2F)n2c1CN(C)CCC2)C(N)=O] | (S)-N-(1-amino-4-methyl-1-oxopentan-2-yl)-3-(5-chloro-2,4-difluorophenyl)-8-methyl-6,7,8,9-tetrahydro-5H-imidazo[1,5-a][1,4]diazepine-1-carboxamide | 454.1 | 59 |
| 572 | 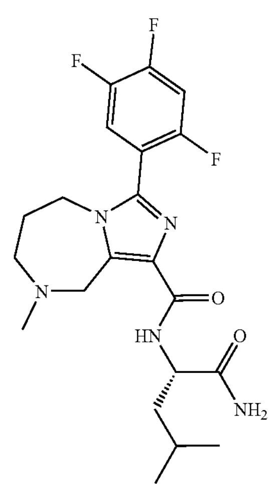 [SMILES: CC(C)C[C@H](NC(=O)c1nc(-c2cc(F)c(F)cc2F)n2c1CN(C)CCC2)C(N)=O] | (S)-N-(1-amino-4-methyl-1-oxopentan-2-yl)-8-methyl-3-(2,4,5-trifluorophenyl)-6,7,8,9-tetrahydro-5H-imidazo[1,5-a][1,4]diazepine-1-carboxamide | 438.2 | 59 |

TABLE I-continued

| Cmpd No. | Structure | Chemical Name | m/z | Example No. |
|---|---|---|---|---|
| 573 | 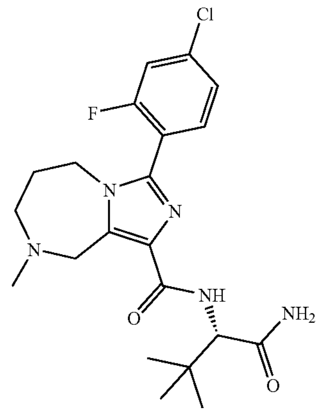 [SMILES: CN1CCCn2c(-c3ccc(Cl)cc3F)nc(C(=O)N[C@H](C(N)=O)C(C)(C)C)c2C1] | (S)-N-(1-amino-3,3-dimethyl-1-oxobutan-2-yl)-3-(4-chloro-2-fluorophenyl)-8-methyl-6,7,8,9-tetrahydro-5H-imidazo[1,5-a][1,4]diazepine-1-carboxamide | 436.0 | 60 |
| 574 | 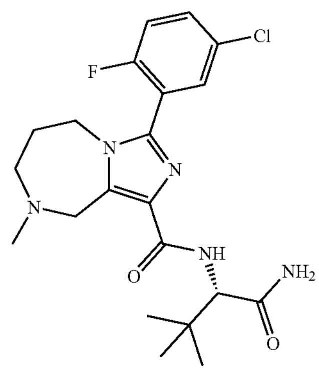 [SMILES: CN1CCCn2c(-c3cc(Cl)ccc3F)nc(C(=O)N[C@H](C(N)=O)C(C)(C)C)c2C1] | (S)-N-(1-amino-3,3-dimethyl-1-oxobutan-2-yl)-3-(5-chloro-2-fluorophenyl)-8-methyl-6,7,8,9-tetrahydro-5H-imidazo[1,5-a][1,4]diazepine-1-carboxamide | 436.0 | 60 |
| 575 | 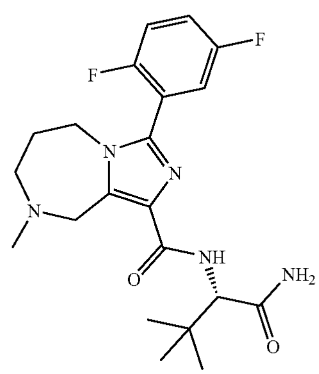 [SMILES: CN1CCCn2c(-c3cc(F)ccc3F)nc(C(=O)N[C@H](C(N)=O)C(C)(C)C)c2C1] | (S)-N-(1-amino-3,3-dimethyl-1-oxobutan-2-yl)-3-(2,5-difluorophenyl)-8-methyl-6,7,8,9-tetrahydro-5H-imidazo[1,5-a][1,4]diazepine-1-carboxamide | 420.0 | 60 |
| 576 | 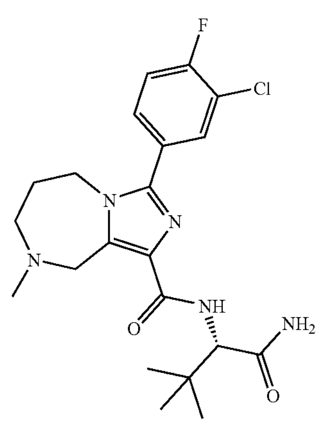 [SMILES: CN1CCCn2c(-c3ccc(F)c(Cl)c3)nc(C(=O)N[C@H](C(N)=O)C(C)(C)C)c2C1] | (S)-N-(1-amino-3,3-dimethyl-1-oxobutan-2-yl)-3-(3-chloro-4-fluorophenyl)-8-methyl-6,7,8,9-tetrahydro-5H-imidazo[1,5-a][1,4]diazepine-1-carboxamide | 436.0 | 60 |

TABLE I-continued

| Cmpd No. | Structure | Chemical Name | m/z | Example No. |
|---|---|---|---|---|
| 577 | 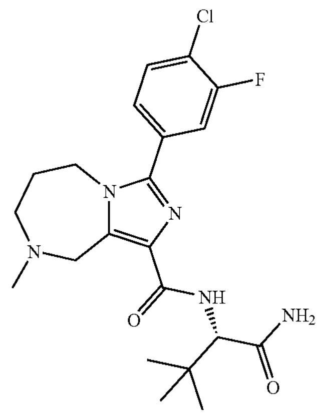 [SMILES: CN1CCCn2c(-c3ccc(Cl)c(F)c3)nc(C(=O)N[C@H](C(N)=O)C(C)(C)C)c2C1] | (S)-N-(1-amino-3,3-dimethyl-1-oxobutan-2-yl)-3-(4-chloro-3-fluorophenyl)-8-methyl-6,7,8,9-tetrahydro-5H-imidazo[1,5-a][1,4]diazepine-1-carboxamide | 436.0 | 60 |
| 578 | 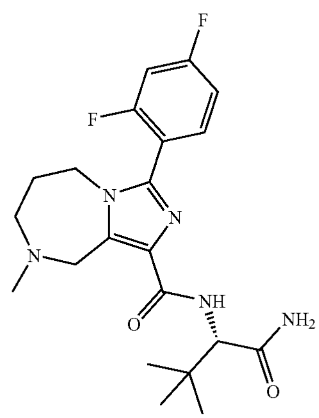 [SMILES: CN1CCCn2c(-c3ccc(F)cc3F)nc(C(=O)N[C@H](C(N)=O)C(C)(C)C)c2C1] | (S)-N-(1-amino-3,3-dimethyl-1-oxobutan-2-yl)-3-(2,4-difluorophenyl)-8-methyl-6,7,8,9-tetrahydro-5H-imidazo[1,5-a][1,4]diazepine-1-carboxamide | 420.0 | 60 |
| 579 | 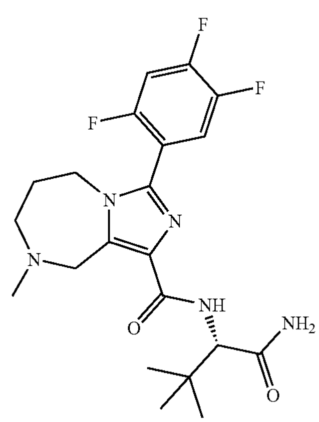 [SMILES: CN1CCCn2c(-c3cc(F)c(F)cc3F)nc(C(=O)N[C@H](C(N)=O)C(C)(C)C)c2C1] | (S)-N-(1-amino-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide | 438.0 | 60 |

| Cmpd No. | Structure | Chemical Name | m/z | Example No. |
|---|---|---|---|---|
| 580 | 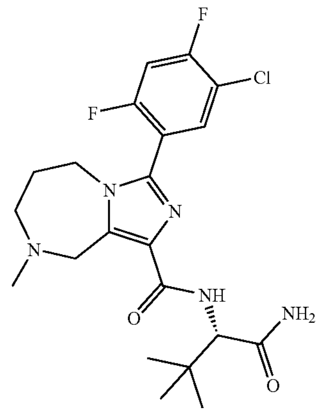 [SMILES: CN1CCCn2c(-c3cc(Cl)c(F)cc3F)nc(C(=O)N[C@H](C(N)=O)C(C)(C)C)c2C1] | (S)-N-(1-amino-3,3-dimethyl-1-oxobutan-2-yl)-3-(5-chloro-2,4-difluorophenyl)-8-methyl-6,7,8,9-tetrahydro-5H-imidazo[1,5-a][1,4]diazepine-1-carboxamide | 454.0 | 60 |
| 581 | 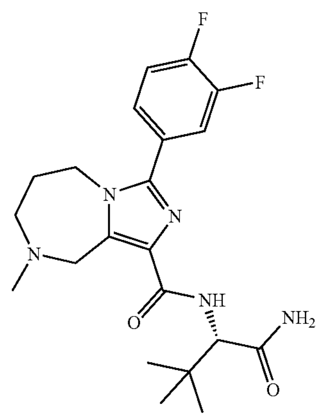 [SMILES: CN1CCCn2c(-c3ccc(F)c(F)c3)nc(C(=O)N[C@H](C(N)=O)C(C)(C)C)c2C1] | (S)-N-(1-amino-3,3-dimethyl-1-oxobutan-2-yl)-3-(3,4-difluorophenyl)-8-methyl-6,7,8,9-tetrahydro-5H-imidazo[1,5-a][1,4]diazepine-1-carboxamide | 420.0 | 60 |
| 582 | 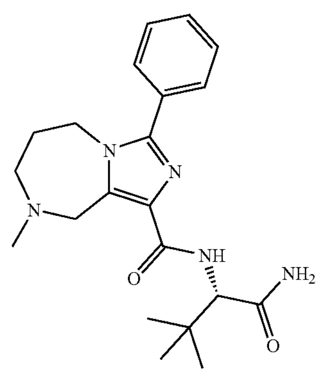 [SMILES: CN1CCCn2c(-c3ccccc3)nc(C(=O)N[C@H](C(N)=O)C(C)(C)C)c2C1] | (S)-N-(1-amino-3,3-dimethyl-1-oxobutan-2-yl)-8-methyl-3-phenyl-6,7,8,9-tetrahydro-5H-imidazo[1,5-a][1,4]diazepine-1-carboxamide | 384.0 | 60 |
| 583 | 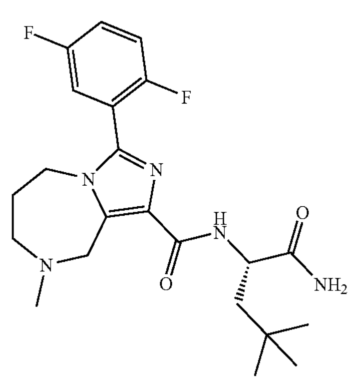 [SMILES: CN1CCCn2c(-c3cc(F)ccc3F)nc(C(=O)N[C@@H](CC(C)(C)C)C(N)=O)c2C1] | (S)-N-(1-amino-4,4-dimethyl-1-oxopentan-2-yl)-3-(2,5-difluorophenyl)-8-methyl-6,7,8,9-tetrahydro-5H-imidazo[1,5-a][1,4]diazepine-1-carboxamide | 434.0 | 61 |

TABLE I-continued

| Cmpd No. | Structure | Chemical Name | m/z | Example No. |
|---|---|---|---|---|
| 584 | 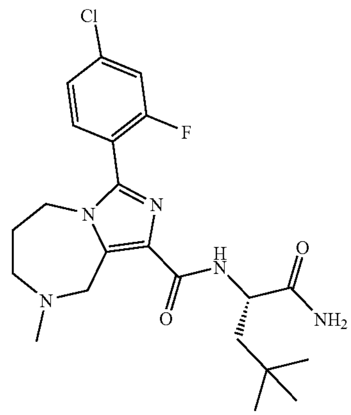 [SMILES: CN1CCCn2c(-c3ccc(Cl)cc3F)nc(C(=O)N[C@@H](CC(C)(C)C)C(N)=O)c2C1] | (S)-N-(1-amino-4,4-dimethyl-1-oxopentan-2-yl)-3-(4-chloro-2-fluorophenyl)-8-methyl-6,7,8,9-tetrahydro-5H-imidazo[1,5-a][1,4]diazepine-1-carboxamide | 450.0 | 61 |
| 585 | 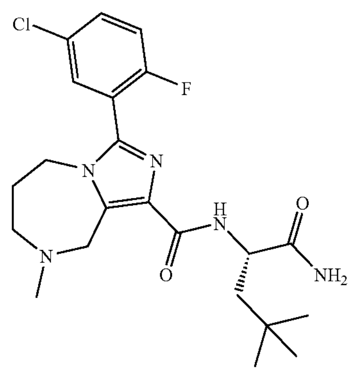 [SMILES: CN1CCCn2c(-c3cc(Cl)ccc3F)nc(C(=O)N[C@@H](CC(C)(C)C)C(N)=O)c2C1] | (S)-N-(1-amino-4,4-dimethyl-1-oxopentan-2-yl)-3-(5-chloro-2-fluorophenyl)-8-methyl-6,7,8,9-tetrahydro-5H-imidazo[1,5-a][1,4]diazepine-1-carboxamide | 450.0 | 61 |
| 586 | 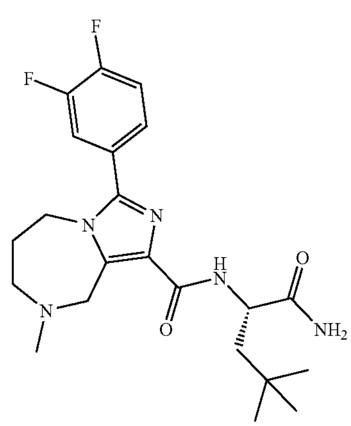 [SMILES: CN1CCCn2c(-c3ccc(F)c(F)c3)nc(C(=O)N[C@@H](CC(C)(C)C)C(N)=O)c2C1] | (S)-N-(1-amino-4,4-dimethyl-1-oxopentan-2-yl)-3-(3,4-difluorophenyl)-8-methyl-6,7,8,9-tetrahydro-5H-imidazo[1,5-a][1,4]diazepine-1-carboxamide | 434.0 | 61 |

| Cmpd No. | Structure | Chemical Name | m/z | Example No. |
|---|---|---|---|---|
| 587 | 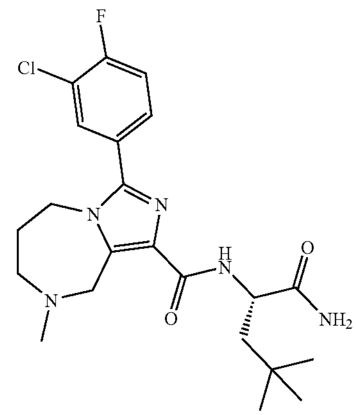 [SMILES: CN1CCCn2c(-c3ccc(F)c(Cl)c3)nc(C(=O)N[C@@H](CC(C)(C)C)C(N)=O)c2C1] | (S)-N-(1-amino-4,4-dimethyl-1-oxopentan-2-yl)-3-(3-chloro-4-fluorophenyl)-8-methyl-6,7,8,9-tetrahydro-5H-imidazo[1,5-a][1,4]diazepine-1-carboxamide | 450.0 | 61 |
| 588 | 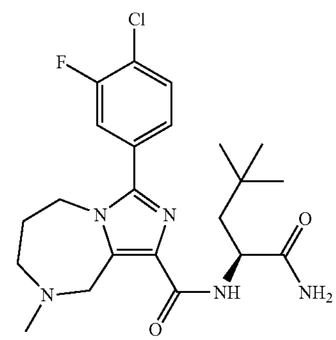 [SMILES: CN1CCCn2c(-c3ccc(Cl)c(F)c3)nc(C(=O)N[C@@H](CC(C)(C)C)C(N)=O)c2C1] | (S)-N-(1-amino-4,4-dimethyl-1-oxopentan-2-yl)-3-(4-chloro-3-fluorophenyl)-8-methyl-6,7,8,9-tetrahydro-5H-imidazo[1,5-a][1,4]diazepine-1-carboxamide | 450.0 | 61 |
| 589 | 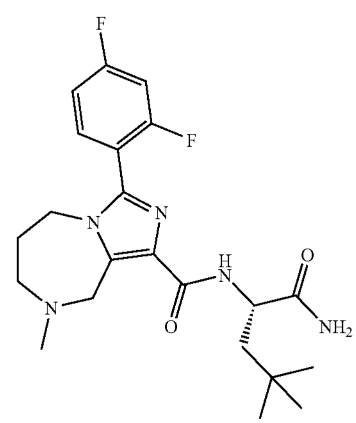 [SMILES: CN1CCCn2c(-c3ccc(F)cc3F)nc(C(=O)N[C@@H](CC(C)(C)C)C(N)=O)c2C1] | (S)-N-(1-amino-4,4-dimethyl-1-oxopentan-2-yl)-3-(2,4-difluorophenyl)-8-methyl-6,7,8,9-tetrahydro-5H-imidazo[1,5-a][1,4]diazepine-1-carboxamide | 434.0 | 61 |
| 590 | 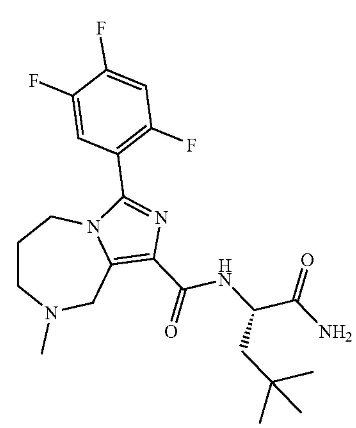 [SMILES: CN1CCCn2c(-c3cc(F)c(F)cc3F)nc(C(=O)N[C@@H](CC(C)(C)C)C(N)=O)c2C1] | (S)-N-(1-amino-4,4-dimethyl-1-oxopentan-2-yl)-8-methyl-3-(2,4,5-trifluorophenyl)-6,7,8,9-tetrahydro-5H-imidazo[1,5-a][1,4]diazepine-1-carboxamide | 452.0 | 61 |

TABLE I-continued

| Cmpd No. | Structure | Chemical Name | m/z | Example No. |
|---|---|---|---|---|
| 591 | 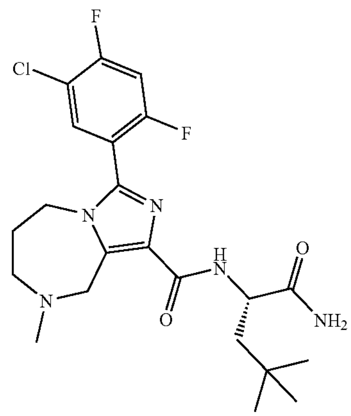 [SMILES: CN1CCCn2c(-c3cc(Cl)c(F)cc3F)nc(C(=O)N[C@@H](CC(C)(C)C)C(N)=O)c2C1] | (S)-N-(1-amino-4,4-dimethyl-1-oxopentan-2-yl)-3-(5-chloro-2,4-difluorophenyl)-8-methyl-6,7,8,9-tetrahydro-5H-imidazo[1,5-a][1,4]diazepine-1-carboxamide | 468.0 | 61 |
| 592 | 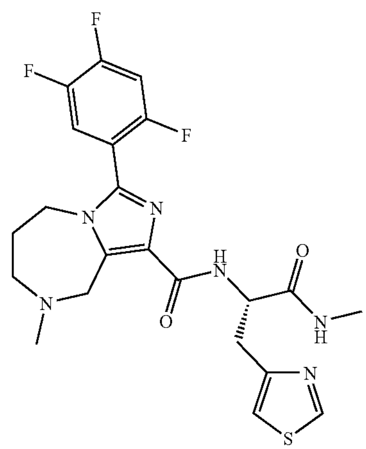 [SMILES: CNC(=O)[C@H](Cc1cscn1)NC(=O)c1nc(-c2cc(F)c(F)cc2F)n2c1CN(C)CCC2] | (S)-8-methyl-N-(1-(methylamino)-1-oxo-3-(thiazol-4-yl)propan-2-yl)-3-(2,4,5-trifluorophenyl)-6,7,8,9-tetrahydro-5H-imidazo[1,5-a][1,4]diazepine-1-carboxamide | 493.1 | 62 |
| 593 | 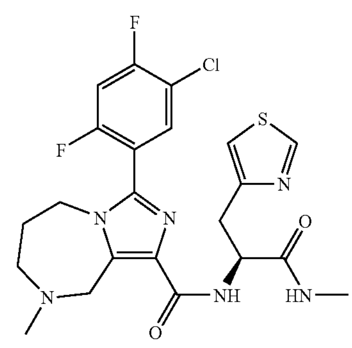 [SMILES: CNC(=O)[C@H](Cc1cscn1)NC(=O)c1nc(-c2cc(Cl)c(F)cc2F)n2c1CN(C)CCC2] | (S)-3-(5-chloro-2,4-difluorophenyl)-8-methyl-N-(1-(methylamino)-1-oxo-3-(thiazol-4-yl)propan-2-yl)-6,7,8,9-tetrahydro-5H-imidazo[1,5-a][1,4]diazepine-1-carboxamide | 509.1 | 62 |
| 594 | 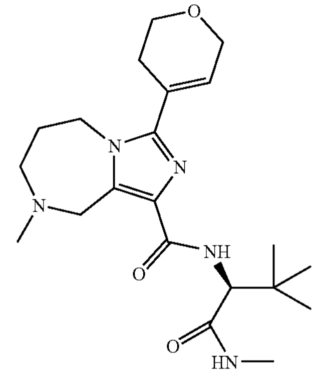 [SMILES: CNC(=O)[C@@H](NC(=O)c1nc(C2=CCOCC2)n2c1CN(C)CCC2)C(C)(C)C] | (S)-3-(3,6-dihydro-2H-pyran-4-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 404.2 | 63 |

TABLE I-continued

| Cmpd No. | Structure | Chemical Name | m/z | Example No. |
|---|---|---|---|---|
| 595 | 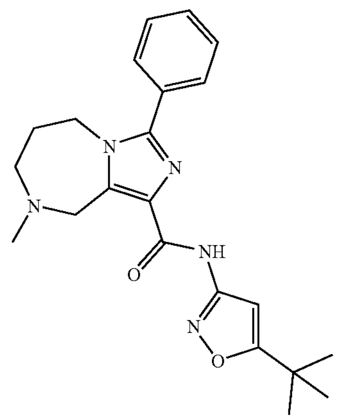 [SMILES: CN1CCCn2c(-c3ccccc3)nc(C(=O)Nc3cc(C(C)(C)C)on3)c2C1] | N-(5-tert-butylisoxazol-3-yl)-8-methyl-3-phenyl-6,7,8,9-tetrahydro-5H-imidazo[1,5-a][1,4]diazepine-1-carboxamide | 394.1 | 64 |
| 596 | 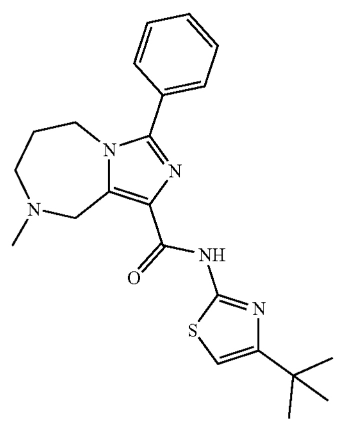 [SMILES: CN1CCCn2c(-c3ccccc3)nc(C(=O)Nc3nc(C(C)(C)C)cs3)c2C1] | N-(4-tert-butylthiazol-2-yl)-8-methyl-3-phenyl-6,7,8,9-tetrahydro-5H-imidazo[1,5-a][1,4]diazepine-1-carboxamide | 410.1 | 64 |
| 597 | 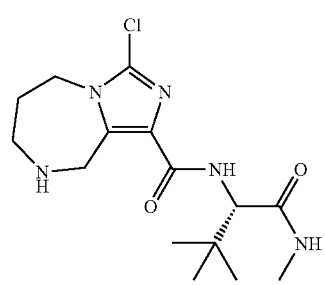 [SMILES: CNC(=O)[C@@H](NC(=O)c1nc(Cl)n2c1CNCCC2)C(C)(C)C] | (S)-3-chloro-N-(3,3-dimethyl-1-(methylamino)-1-oxobutan-2-yl)-6,7,8,9-tetrahydro-5H-imidazo[1,5-a][1,4]diazepine-1-carboxamide | 342.1 | 65 |
| 598 | 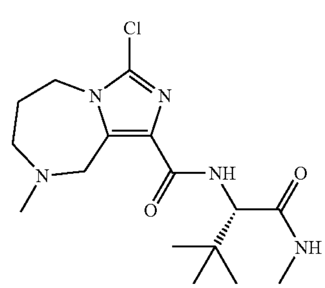 [SMILES: CNC(=O)[C@@H](NC(=O)c1nc(Cl)n2c1CN(C)CCC2)C(C)(C)C] | (S)-3-chloro-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 356.1 | 65 |

TABLE I-continued

| Cmpd No. | Structure | Chemical Name | m/z | Example No. |
|---|---|---|---|---|
| 599 | 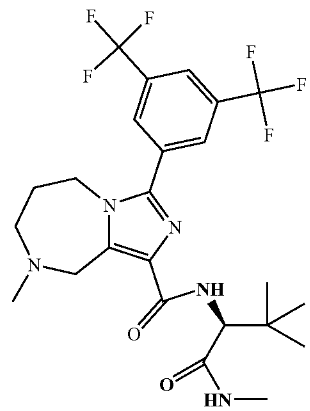 [SMILES: CNC(=O)[C@@H](NC(=O)c1nc(-c2cc(C(F)(F)F)cc(C(F)(F)F)c2)n2c1CN(C)CCC2)C(C)(C)C] | (S)-3-(3,5-bis(trifluoromethyl)phenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 534.1 | 37 |
| 600 | 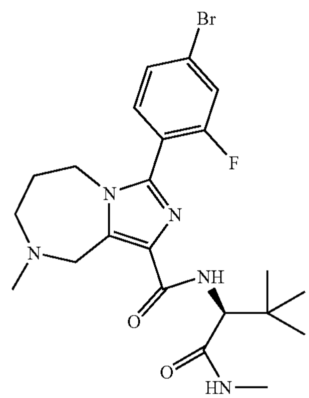 [SMILES: CNC(=O)[C@@H](NC(=O)c1nc(-c2ccc(Br)cc2F)n2c1CN(C)CCC2)C(C)(C)C] | (S)-3-(4-bromo-2-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 494.1 | 37 |
| 601 | 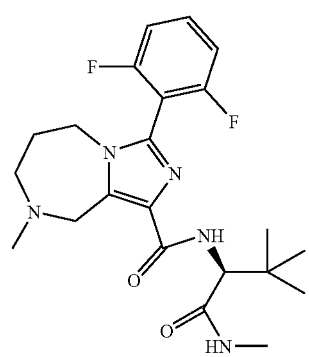 [SMILES: CNC(=O)[C@@H](NC(=O)c1nc(-c2c(F)cccc2F)n2c1CN(C)CCC2)C(C)(C)C] | (S)-3-(2,6-difluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 434.2 | 37 |
| 602 | 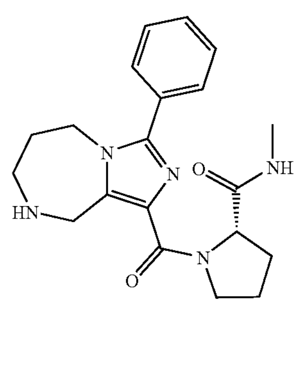 [SMILES: CNC(=O)[C@@H]1CCCN1C(=O)c1nc(-c2ccccc2)n2c1CNCCC2] | (S)-N-methyl-1-(3-phenyl-6,7,8,9-tetrahydro-5H-imidazo[1,5-a][1,4]diazepine-1-carbonyl)pyrrolidine-2-carboxamide | 368.1 | 39 |

TABLE I-continued

| Cmpd No. | Structure | Chemical Name | m/z | Example No. |
|---|---|---|---|---|
| 603 | 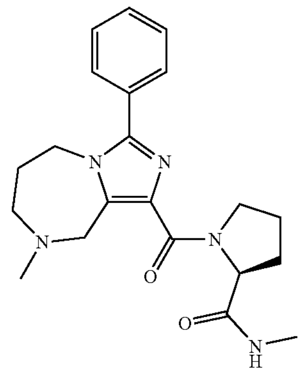 [SMILES: CNC(=O)[C@@H]1CCCN1C(=O)c1nc(-c2ccccc2)n2c1CN(C)CCC2] | (S)-N-methyl-1-(8-methyl-3-phenyl-6,7,8,9-tetrahydro-5H-imidazo[1,5-a][1,4]diazepine-1-carbonyl)pyrrolidine-2-carboxamide | 382.1 | 40 |
| 604 | 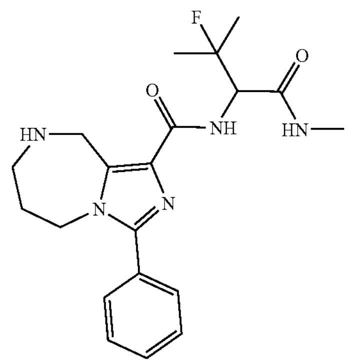 [SMILES: CNC(=O)C(NC(=O)c1nc(-c2ccccc2)n2c1CNCCC2)C(C)(C)F] | N-(3-fluoro-3-methyl-1-(methylamino)-1-oxobutan-2-yl)-3-phenyl-6,7,8,9-tetrahydro-5H-imidazo[1,5-a][1,4]diazepine-1-carboxamide | 388.1 | 66 |
| 605 | 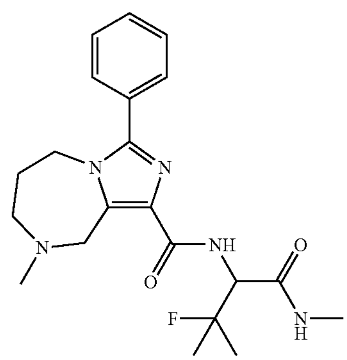 [SMILES: CNC(=O)C(NC(=O)c1nc(-c2ccccc2)n2c1CN(C)CCC2)C(C)(C)F] | N-(3-fluoro-3-methyl-1-(methylamino)-1-oxobutan-2-yl)-8-methyl-3-phenyl-6,7,8,9-tetrahydro-5H-imidazo[1,5-a][1,4]diazepine-1-carboxamide | 402.1 | 66 |
| 606 | 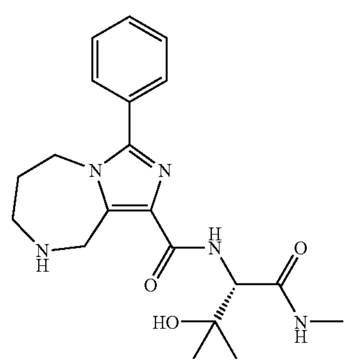 [SMILES: CNC(=O)[C@@H](NC(=O)c1nc(-c2ccccc2)n2c1CNCCC2)C(C)(C)O] | (S)-N-(3-hydroxy-3-methyl-1-(methylamino)-1-oxobutan-2-yl)-3-phenyl-6,7,8,9-tetrahydro-5H-imidazo[1,5-a][1,4]diazepine-1-carboxamide | 386.1 | 66 |

TABLE I-continued

| Cmpd No. | Structure | Chemical Name | m/z | Example No. |
|---|---|---|---|---|
| 607 | 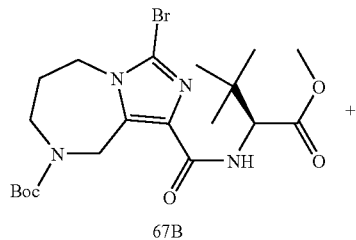 | (S)-N-(3-hydroxy-3-methyl-1-(methylamino)-1-oxobutan-2-yl)-8-methyl-3-phenyl-6,7,8,9-tetrahydro-5H-imidazo[1,5-a][1,4]diazepine-1-carboxamide | 400.1 | 66 |

Example 67

Preparation of N—((S)-3,3-dimethyl-1-morpholino-1-oxobutan-2-yl)-8-methyl-3-(2,4,55-trifluorophenyl)-6,7,8,9-tetrahydro-5H-imidazo[1,5-a][1,4]diazepine-1-carboxamide (Compound 668)

Step 1: Preparation of (S)-tert-butyl 3-bromo-1-(1-methoxy-3,3-dimethyl-1-oxobutan-2-ylcarbamoyl)-6,7-dihydro-5H-imidazo[1,5-a][1,4]diazepine-8(9H)-carboxylate (Intermediate 67B). To 33E (0.901 g, 2.50 mmol) in DCM (8 mL) was added triethylamine (1.40 mL, 10.01 mmol), (S)-methyl 2-amino-3,3-dimethylbutanoate hydrochloride (0.5 g, 2.75 mmol) and dimethylimidazolidinium chloride (DMC) (0.51 g, 3.00 mmol). The reaction mixture was stirred at room temperature for 2 hours. Aqueous NaOH was added and the organic phase was separated, dried with sodium sulfate, filtered and concentrated under reduced pressure. The residue was purified by chromatography on silica-gel eluting with 10-100% hexanes/ethyl acetate gradient and 1.18 g of 67B was obtained. LCMS (+ESI) m/z 487.1 [M+H]$^+$.

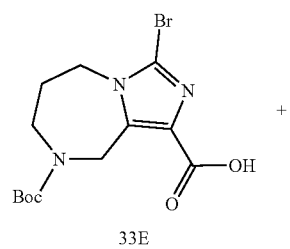

33E

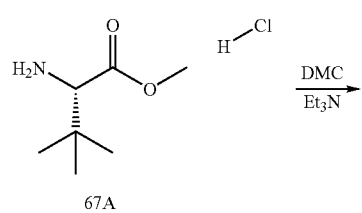

67A

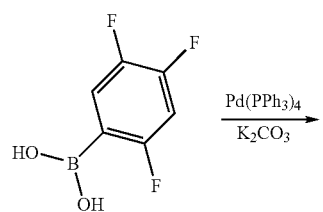

67B

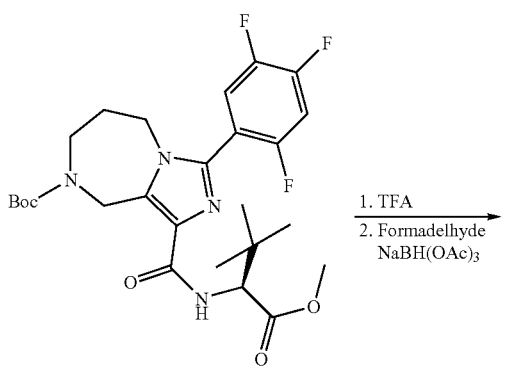

67C

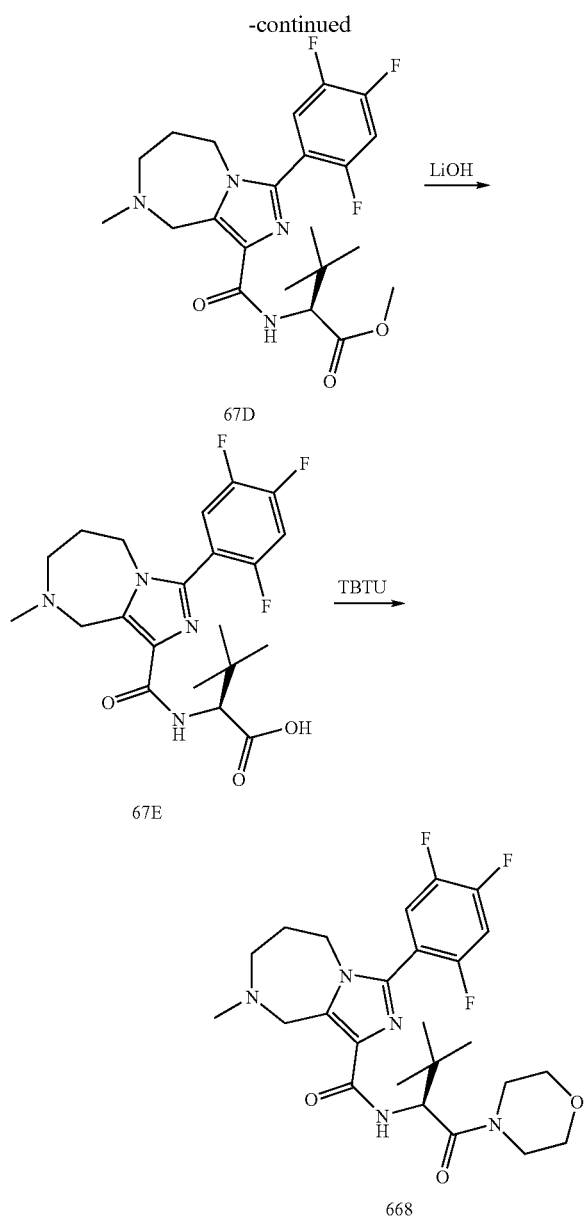

dazo[1,5-a][1,4]diazepine-1-carboxamido)butanoate (Intermediate 67D). To 67C (1.14 g, 2.1 mmol) in DCM (20 mL) was added TFA (10 mL). After 2 hours, the reaction mixture was concentrated and azeotroped with toluene. The crude was dissolved in 10 mL of dichloroethane. Acetic acid (97 mg, 2.1 mmol) and formaldehyde (0.85 g, 10.5 mmol) were added to the reaction mixture followed by sodium triacetoxyborohydride (0.67 g, 3.15 mmol). The reaction mixture stirred for 6 hours. Saturated sodium bicarbonate was added and the reaction mixture was extracted with dichloromethane, dried over sodium sulfate, filtered and concentrated under reduced pressure. The crude mixture was purified by chromatography on silica-gel eluting with 30-100% ethyl acetate/hexanes followed by elution with 10% MeOH/ethyl acetate to provide 0.73 g (1.61 mmol) of 67D. LCMS (+ESI) m/z 453.1 [M+H]$^+$.

Step 4: Preparation of (2S)-3,3-dimethyl-2-(8-methyl-3-(2,4,5-trifluorophenyl)-6,7,8,9-tetrahydro-5H-imidazo[1,5-a][1,4]diazepine-1-carboxamido)butanoic acid (Intermediate 67E). To a solution of 67D in THF (10 mL) at 0° C. was added a solution of lithium hydroxide monohydrate (0.12 g, 4.84 mmol) in water (10 mL). The reaction was allowed to warm slowly to room temperature and allowed to stir for 12 hours. The reaction was cooled to 0° C. and acidified to pH 2 with conc. HCl, and extracted with 10% iPrOH/DCM three times. The combined organic extracts were concentrated under vacuum to give 0.41 g of intermediate 67E. LCMS (+ESI) m/z 439.1 [M+H]$^+$.

Step 5: Preparation of N—((S)-3,3-dimethyl-1-morpholino-1-oxobutan-2-yl)-8-methyl-3-(2,4,5-trifluorophenyl)-6,7,8,9-tetrahydro-5H-imidazo[1,5-a][1,4]diazepine-1-carboxamide (Compound 668). To 67E (25 mg, 0.057 mmol) in DCM (1 mL) was added morpholine (14.9 mg, 0.171 mmol), DIPEA (28.8 mg, 0.285 mmol) and TBTU (11.3 mg, 0.086 mmol). The reactions were heated at 50° C. for 12 hours. The reaction was cooled to room temperature and saturated sodium bicarbonate was added. The organic layer was separated, filtered and purified by preparative LC/MS using 5-95% gradient acetonitrile in water with 0.1% formic acid to provide compound 668. LCMS (+ESI) m/z 508.1 [M+H]$^+$. $^1$H-NMR (400 MHz, CDCl$_3$) δ: 8.21 (s, 1H), 7.94 (d, 1H), 7.47-7.55 (m, 1H), 7.06-7.11 (m, 1H), 5.0 (d, 1H), 4.07 (m, 2H), 3.55-3.76 (m, 8H), 3.38-3.58 (m, 2H), 2.60 (s, 3H), 2.04-2.05 (br, 2H), 1.05 (s, 9H).

Compounds 669-673, 675-678, 721-724, 729-730, 735-757, 772-774, 778, 779, 832-853, 860-863, 867, 870, 874, 882-888, 895-897, 899-901, 909 were synthesized in the same manner as 668 except that different amines were used in place of morpholine. For example, compound 670 was synthesized using pyrrolidine instead of morpholine.

Example 68

Preparation of (S)-3-(2,4-difluorobenzyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide (Compound 685)

Compound 685 was synthesized in the same manner as compound 325 in example 37 except that 2-(2,4-difluorobenzyl)-4,4,5,5-tetramethyl-1,3,2-dioxaborolane (intermediate 68B) was used in place of 2-methoxyphenyl boronic acid. The synthesis of 68B is shown below.

Step 2: Preparation of tert-butyl 1-((S)-1-methoxy-3,3-dimethyl-1-oxobutan-2-ylcarbamoyl)-3-(2,4,5-trifluorophenyl)-6,7-dihydro-5H-imidazo[1,5-a][1,4]diazepine-8(9H)-carboxylate (Intermediate 67C). To 67B (1.18 g, 2.42 mmol) in 1,4-dioxane (20 mL) was added 2,4,5-trifluorophenylboronic acid (0.85 g, 4.84 mmol), potassium carbonate (1.00 g, 7.26 mmol) dissolved in water (10 mL), palladium tetrakistriphenylphosphine (0.42 g, 0.36 mmol). The reaction mixture was heated at 110° C. for 16 hours. The reaction was cooled to room temperature and washed with a saturated sodium bicarbonate solution. The mixture was extracted with ethyl acetate multiple times. The combined organic extracts were dried over sodium sulfate, filtered and concentrated under reduced pressure. The residue was purified by chromatography on silica-gel eluting with 20-100% ethyl acetate/hexanes gradient and 1.14 g of 67C was obtained. LCMS (+ESI) m/z 539.2 [M+H]$^+$.

Step 3: Preparation of (2S)-methyl 3,3-dimethyl-2-(8-methyl-3-(2,4,5-trifluorophenyl)-6,7,8,9-tetrahydro-5H-imi-

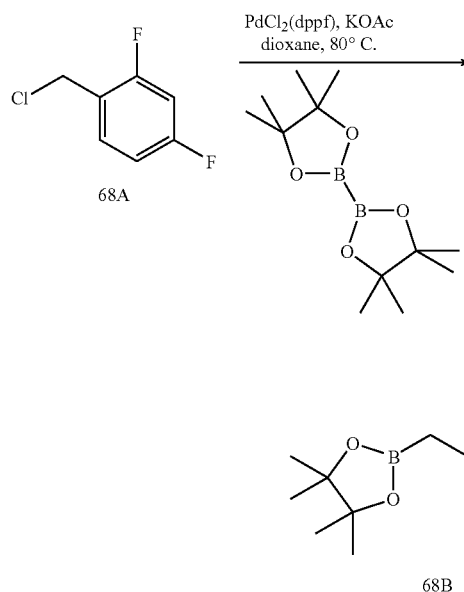

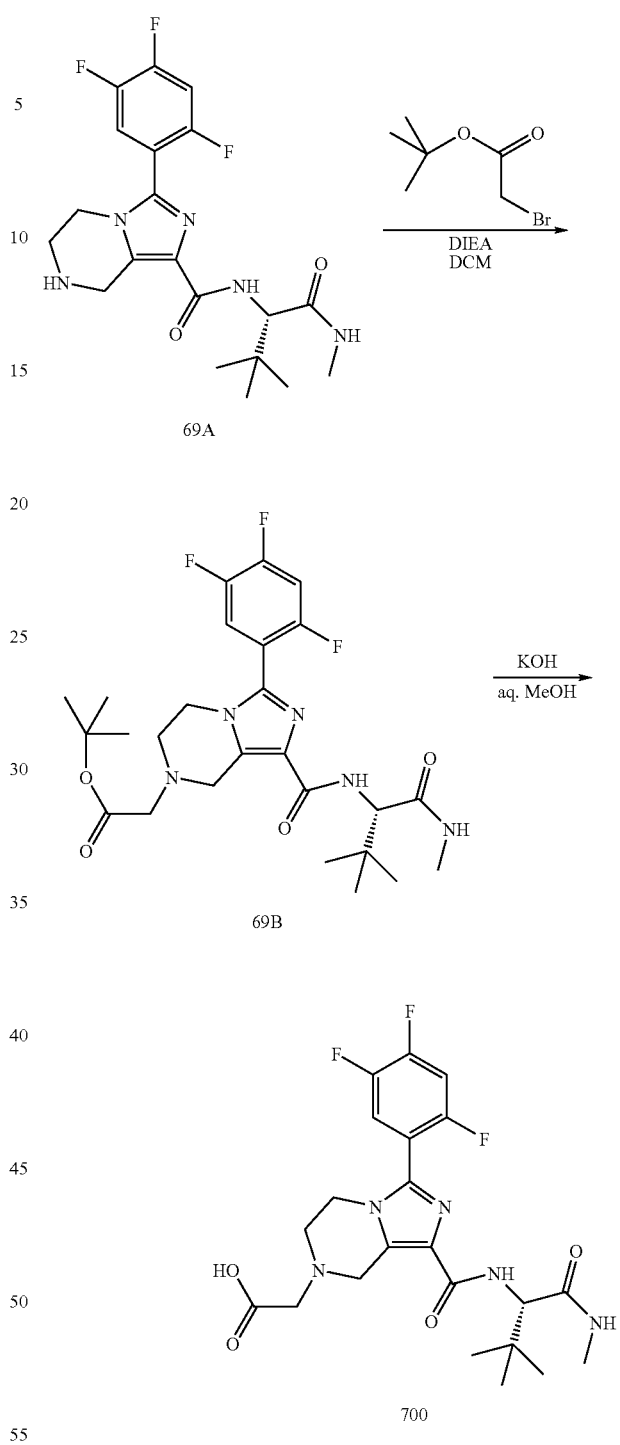

1-(Chloromethyl)-2,4-difluorobenzene (1.00 g, 6.15 mmol) was dissolved in dioxane and 4,4,4',4',5,5,5',5'-octamethyl-2,2'-bis(1,3,2-dioxaborolane) (1.72 g, 6.77 mmol) was added followed by potassium acetate (2.42 g, 24.61 mol). The resulting mixture was degassed, placed under nitrogen and PdCl$_2$(dppf) (0.36 g, 0.49 mmol) was added. The mixture was heated at 80° C. overnight, concentrated, and the oily residue was extracted with EtOAc. The organic extracts were concentrated and purified by chromatography on silica-gel eluting with 10% ethyl acetate/hexane to provide 0.60 g (38% yield) of 68B. $^1$H-NMR (400 MHz, CDCl$_3$) δ: 1.16 (s, 12H), 2.13 (s, 2H), 6.66 (m, 2H), 7.06 (m, 1H); LCMS (+ESI) m/z 255.1 [M+H]$^+$.

Example 69

Preparation of (S)-2-(1-(3,3-dimethyl-1-(methylamino)-1-oxobutan-2-ylcarbamoyl)-3-(2,4,5-trifluorophenyl)-5,6-dihydroimidazo[1,5-a]pyrazin-7(8H)-yl)acetic acid (Compound 700)

Step 1 Preparation of (S)-tert-butyl 2-(1-(3,3-dimethyl-1-(methylamino)-1-oxobutan-2-ylcarbamoyl)-3-(2,4,5-trifluorophenyl)-5,6-dihydroimidazo[1,5-a]pyrazin-7(8H)-yl)acetate (Intermediate 69B) To compound 69A (25 mg, 0.059 mmol) (prepared in a similar manner to compound 2 except that 2,4,5 trifluorophenyl boronic acid was used in place of phenyl boronic acid) in DCM (1 mL) was added DIEA (23 mg, 0.177 mmol) and tert-butyl-2-bromoacetate (35 mg, 0.177 mmol). The reaction mixture stirred for 30 minutes at room temperature. The reaction mixture was diluted with saturated sodium bicarbonate solution and extracted with DCM. The organic layer was dried, filtered and evaporated to provide 28 mg (88% yield) of 69B as a yellow oil that was used in the next step without further purification.

Step 2 Preparation of (S)-2-(1-(3,3-dimethyl-1-(methylamino)-1-oxobutan-2-ylcarbamoyl)-3-(2,4,5-trifluorophenyl)-5,6-dihydroimidazo[1,5-a]pyrazin-7(8H)-yl)acetic acid (Compound 700). To compound 69B (20 mg, 0.037 mmol) in 1 mL of a 3:1 mixture of MeOH/water was added KOH (6.3 mg, 0.112 mmol). The reaction vessel was capped and heated in the microwave at 100° C. for 10 minutes. The reaction mixture was quenched with 1N HCl and evaporated to dryness. The residue was purified by automated preparative LC/MS to provide 2.5 mg (13% yield) of a white solid. LCMS (+ESI) m/z 482.6 [M+H]$^+$.

Example 70

Preparation of (S)-3-(1-benzoylpiperidin-4-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide (Compound 726)

To compound 503 (100 mg, 0.247 mmol) in THF (2 mL) was added triethylamine (0.069 mL, 0.494 mmol) and benzoyl chloride (0.032 mL, 0.272 mmol). The reaction mixture stirred for 1 hour at room temperature and was then concentrated under reduced pressure, dissolved in methanol and loaded on an ion exchange column (Phenomenex, SCX). The column was washed with methanol, and the desired compound was eluted from the column using 2N ammonia in methanol. Solvents were removed by rotary evaporation, and compound 726 was obtained as tan colored solid (78.8 mg, 62% yield). LCMS (+ESI) m/z 509.4 [M+H]$^+$.

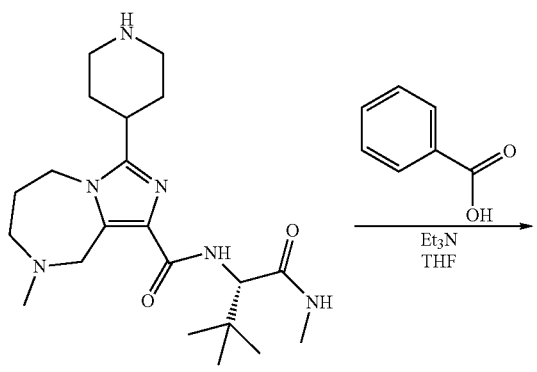

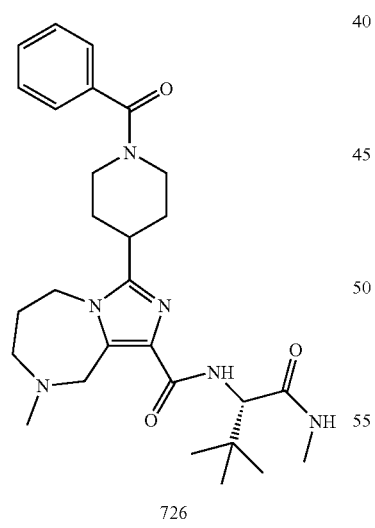

Compounds 727, 728 and 775 were synthesized in the same manner as described for 726 except that benzene sulfonyl chloride, isobutyryl chloride and propane-2-sulfonyl chloride were used in place of benzoyl chloride.

Example 71

Preparation of (S)—N-(1-(2-fluoroethylamino)-3,3-dimethyl-1-oxobutan-2-yl)-7-methyl-3-phenyl-5,6,7,8-tetrahydroimidazo[1,5-a]pyrazine-1-carboxamide (Compound 732)

Step 1: Preparation of (S)-tert-butyl 1-(1-(2-fluoroethylamino)-3,3-dimethyl-1-oxobutan-2-ylcarbamoyl)-3-phenyl-5,6-dihydroimidazo[1,5-a]pyrazine-7(8H)-carboxylate (Intermediate 71A). Intermediate 17B (0.10 g, 0.22 mmol) was dissolved in DMF (2 mL) and 2-fluoroethanamine (0.055 g, 0.88 mmol) was added was followed by TBTU (0.113 g, 0.35 mmol) and DIEA (0.113 g, 0.88 mmol). The resulting mixture was stirred overnight, diluted with water and extracted with EtOAc. The organic layer was washed with water, saturated NaHCO$_3$ solution, and brine, dried over Na$_2$SO$_4$ and concentrated to give 71A which was used without further purification. (0.08 g, 73% yield). LCMS (+ESI) m/z 502.3 [M+H]$^+$.

Step 2: Preparation of (S)—N-(1-(2-fluoroethylamino)-3,3-dimethyl-1-oxobutan-2-yl)-3-phenyl-5,6,7,8-tetrahydroimidazo[1,5-a]pyrazine-1-carboxamide (Compound 731). Intermediate 71A (0.08 g, 0.16 mmol) was dissolved in DCM (1 mL) and TFA (0.5 mL) was added. The resulting mixture was stirred at room temperature for 1 hour. The mixture was concentrated, and azeotroped repeatedly with toluene to remove traces of TFA. The residue was dissolved in MeOH and purified using Strata SCX SPE tube to give compound 731 (0.06 g, 92%). LCMS (+ESI) m/z 402.3 [M+H]$^+$. $^1$H-NMR (400 MHz, CDCl$_3$) δ: 1.09 (s, 9H), 3.19 (m, 2H), 3.58 (m, 2H), 4.08 (m, 2H), 4.46 (m, 4H), 6.51 (m, 1H), 7.45 (m, 3H), 7.66 (d, 2H), 7.74 (d, 1H).

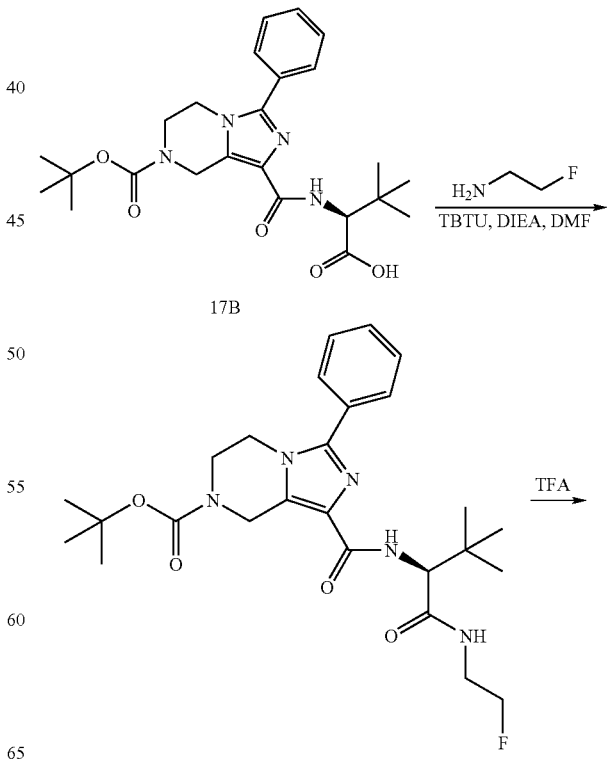

-continued

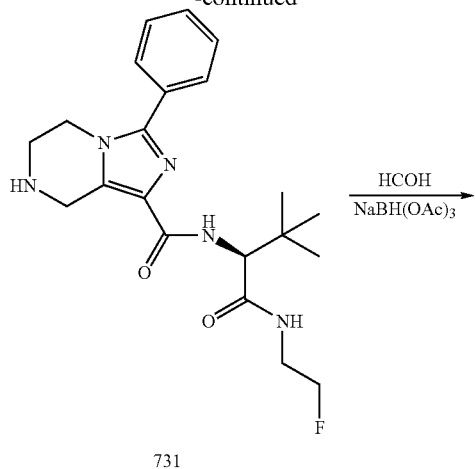

731

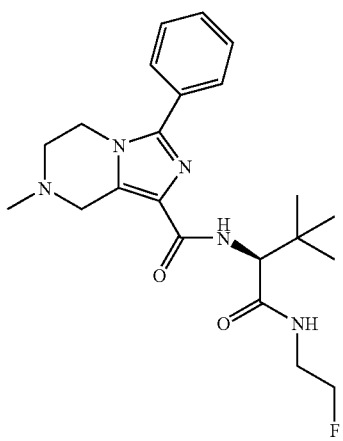

732

Step 3 Preparation of (S)—N-(1-(2-fluoroethylamino)-3,3-dimethyl-1-oxobutan-2-yl)-7-methyl-3-phenyl-5,6,7,8-tetrahydroimidazo[1,5-a]pyrazine-1-carboxamide (Compound 732). Compound 731 (0.06 g) was dissolved in THF and formaldehyde (37% in water) was added followed by NaBH(OAc)₃ and acetic acid. The resulting mixture was stirred at room temperature overnight, quenched with saturated NaHCO₃ solution, concentrated under reduced pressure and extracted with 20% iPrOH/DCM. The combined organic layers were washed with brine and dried over Na₂SO₄, filtered, concentrated and purified using Strata SCX SPE tube to provide the title compound 732 (0.035 g, 53%). LCMS (+ESI) m/z 416.3 [M+H]⁺. ¹H-NMR (400 MHz, CDCl₃) δ: 1.09 (s, 9H), 2.58 9 s, 3H), 2.76 (m, 2H), 3.58 (m, 2H), 4.08 (m, 3H), 4.46 (m, 3H), 6.74 (m, 1H), 7.45 (m, 3H), 7.66 (d, 2H), 7.74 (m, 1H).

Compounds 733 and 734 were synthesized in the same manner as 731 and 732 except that morpholine was used in place of 2-fluoroethanamine.

Example 72

Preparation of (3R)—N-methyl-1-(8-methyl-3-(2,4,5-trifluorophenyl)-6,7,8,9-tetrahydro-5H-imidazo[1,5-a][1,4]diazepine-1-carbonyl)pyrrolidine-3-carboxamide (Compound 758)

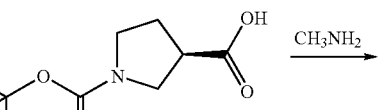

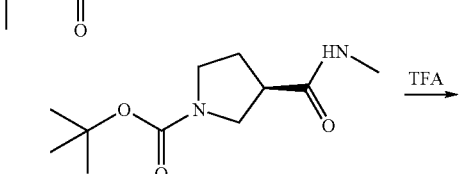

72A

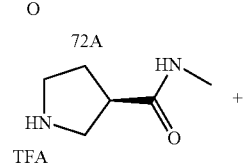

72B

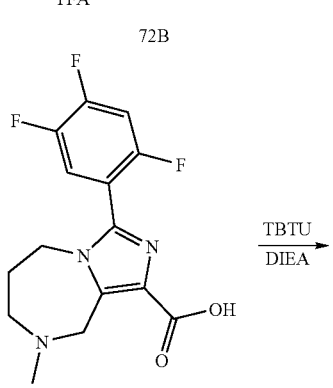

72C

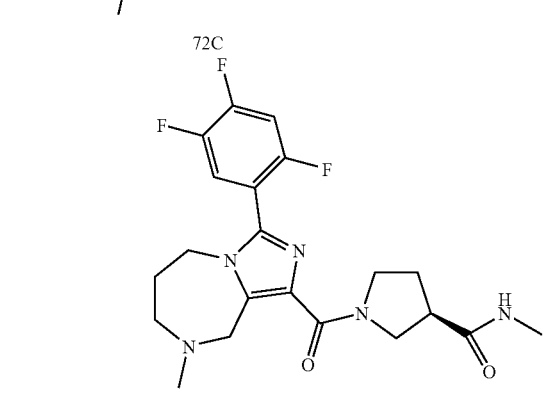

758

Step 1: Preparation of (R)-tert-butyl-3-(methylcarbamoyl)pyrrolidine-1-carboxylic acid (Intermediate 72A) To a solution of (R)-1-(tert-butoxycarbonyl)pyrrolidine-3-carboxylic acid (215 mg, 1.0 mmol) in DCM (5 mL) was added 4-methylmorpholine (0.11 mL, 1.00 mmol) and the mixture was then cooled in an ice water bath. Isobutyl chloroformate (0.013 mL, 1.00 mmol) was added and reaction was stirred 2 hours. Methyl amine (0.35 mL of a 40% aqueous solution) was added drop wise and the mixture was stirred for 2 hours at ice bath temperature. Water (5 mL) was added and the two layers were separated. The aqueous phase was extracted with 5 mL of DCM and the combined organic phases were extracted with 10 mL of 1M aqueous H₃PO₄, dried over anhydrous Na₂SO₄, filtered and concentrated in vacuo. The residue was dried in a vacuum oven (~40° C.) to provide the title compound (212 mg, 0.93 mmol, 93% yield) as a foam that was used without further purification. LCMS (+ESI) m/z=173.0 [(M-56)+H]⁺; ¹H-NMR (DMSO d₆) δ 7.75 (bs, 1H), 3.23-3.18 (m, 2H), 3.16-3.01 (m, 2H), 2.74 (m, 1H), 2.46 (d, 3H), 1.90-1.69 (m, 2H), 1.27 (s, 9H).

Step 2: Preparation of (R)—N-methylpyrrolidine-3-carboxamide, (2,2,2-trifluoroacetate) (Intermediate 72B) Intermediate 72A (200 mg, 0.88 mmol) was dissolved in DCM (3 mL) and the stirred solution was treated drop wise with TFA (3 mL). After stirring for 1 hour, the mixture was concentrated in vacuo. The residue was azeotroped with toluene to remove the excess TFA and then dried in a vacuum oven (40° C.) overnight. The thick, syrupy residue obtained (278 mg, 0.78 mmol, 89%) was used directly. ¹H-NMR (DMSO d₆) δ 8.86 (bs, 2H), 8.10 (bs, 1H), 3.56-3.08 (m, 4H), 3.00 (pentet, 1H), 2.56 (d, 3H), 2.11 (ddd, 1H), 1.92 (ddd, 1H).

Step 3: Preparation of (3R)—N-methyl-1-(8-methyl-3-(2,4,5-trifluorophenyl)-6,7,8,9-tetrahydro-5H-imidazo[1,5-a][1,4]diazepine-1-carbonyl)pyrrolidine-3-carboxamide (Compound 758). To intermediate 72C (prepared in the same manner as compound 18D using 33D in place of 18A using the appropriate boronic acid) (33 mg, 0.101 mmol) in DMF (1 mL) was added TBTU (45.6 mg, 0.142 mmol). After 10 minutes, 72B (47 mg, 0.132 mmol) and DIEA (52 mg, 0.406 mmol) were added. The reaction mixture stirred at room temperature for 3 hours. The reaction mixture was diluted with saturated sodium bicarbonate and extracted with ethyl acetate. The organic layer was dried over sodium sulfate, filtered and concentrated. The residue was dissolved in methanol and loaded on an ion exchange column (Phenomenex, SCX). The column was washed with methanol, and the desired compound was removed from the column using 2N ammonia in methanol. The solvent was removed in vacuo to obtain compound 758 (44 mg, 34%). LCMS (+ESI) m/z=436.2 [M+H]⁺; ¹H-NMR (DMSO d₆) δ 7.86 (m, 1H), 7.77-7.52 (m, 2H), 4.20-3.92 (m, 2H), 3.91-3.84 (m, 3H), 3.71 (m, 1H), 3.56 (m, 1H), 3.39 (m, 1H), 2.90-2.72 (m, 3H), 2.51 (dd, 3H), 2.16 (s, 3H), 2.02-1.77 (m, 2H), 1.71-1.60 (m, 2H).

Compounds 759-766, 777, 787-789, 807-809, 820-826, 828, 830, 854-859, 875-881, 910 were synthesized in the same manner as 758 except that 72B was replaced with other amines and/or 72C was replaced with other acids. For example, compound 761 was synthesized in the same manner except that (S)-2-amino-3,3-dimethylbutan-1-ol was used in place of 72B.

Example 73

Preparation of (S)—N-(1-amino-3,3-dimethylbutan-2-yl)-3-(5-chloro-2-fluorophenyl)-8-methyl-6,7,8,9-tetrahydro-5H-imidazo[1,5-a][1,4]diazepine-1-carboxamide (Compound 768)

Step 1: Preparation of (S)-tert-butyl 3-(5-chloro-2-fluorophenyl)-1-(1-(1,3-dioxoisoindolin-2-yl)-3,3-dimethylbutan-2-ylcarbamoyl)-6,7-dihydro-5H-imidazo[1,5-a][1,4]diazepine-8(9H)-carboxylate (Intermediate 73C). To a solution of 8-(tert-butoxycarbonyl)-3-(5-chloro-2-fluorophenyl)-6,7,8,9-tetrahydro-5H-imidazo[1,5-a][1,4]diazepine-1-carboxylic acid (409 mg, 1.0 mmol) (prepared in the same manner as 39B except that 2-fluoro-5-chlorophenyl boronic acid was used in place of phenyl boronic acid), (S)-2-(2-amino-3,3-dimethylbutyl)isoindoline-1,3-dione (250 mg, 1.0 mmol) and DIEA (0.4 mL) in DMF was added TBTU (450 mg, 1.4 mmol). After stirring at room temperature for 60 hours, DMF was removed by evaporation under reduced pressure. The residue was dissolved in EtOAc and extracted twice with aqueous sodium bicarbonate. The organic phase was dried over sodium sulfate and evaporated to dryness. The crude mixture was purified by column chromatography with 30% to 60% EtOAc/hexanes to give intermediate 73C (0.53 g, 83%). LCMS (+ESI) m/z 639 [M+H]⁺.

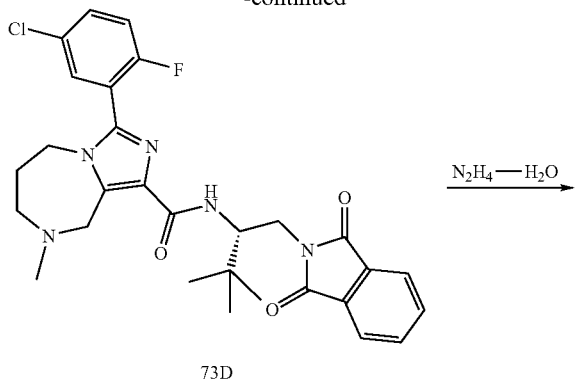

73D

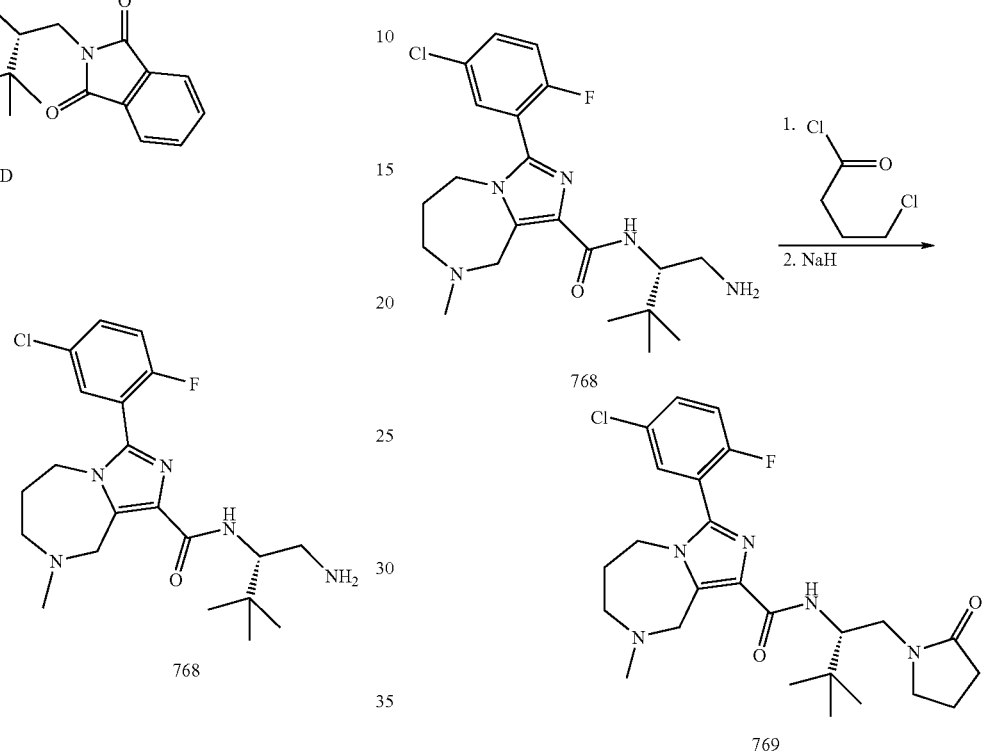

768

769

Step 2: Preparation of (S)-3-(5-chloro-2-fluorophenyl)-N-(1-(1,3-dioxo-isoindolin-2-yl)-3,3-dimethylbutan-2-yl)-8-methyl-6,7,8,9-tetrahydro-5H-imidazo[1,5-a][1,4]diazepine-1-carboxamide (Intermediate 73D). Intermediate 73C (0.53 g, 0.83 mmol) was stirred in DCM (5 mL) and TFA (10 mL) at room temperature for 1 hour. The reaction mixture was evaporated to dryness and azeotroped with toluene twice. The residue was dissolved in THF (5 mL) and paraformaldehyde (310 µL, 37% in water) was added followed by sodium triacetoxyborohydride (275 mg) and the reaction mixture stirred at room temperature for 2 hours. The THF was removed by evaporation under reduced pressure and the residue was extracted between brine and 10% iPrOH/DCM. The organic phase was dried over sodium sulfate and evaporated to dryness to give 73D (0.45 g, 98%) which was used without further purification.

Step 3: Preparation of (S)—N-(1-amino-3,3-dimethylbutan-2-yl)-3-(5-chloro-2-fluorophenyl)-8-methyl-6,7,8,9-tetrahydro-5H-imidazo[1,5-a][1,4]diazepine-1-carboxamide (Compound 768) To a solution of intermediate 73D (0.45 g, 0.82 mmol) in EtOH was added hydrazine monohydrate (0.45 mL) and the reaction mixture was stirred at room temperature for 2 hours. After evaporation of solvent, the residue was extracted between 10% iPrOH/DCM and brine. The organic phase was dried over sodium sulfate and evaporated to give a solid product. The solid product was purified by preparative LC-MS to give compound 768 (30.8 mg, 90% yield). LCMS (+ESI) m/z 422 [M+H]$^+$.

Example 74

Preparation of (S)-3-(5-chloro-2-fluorophenyl)-N-(3,3-dimethyl-1-(2-oxopyrrolidin-1-yl)butan-2-yl)-8-methyl-6,7,8,9-tetrahydro-5H-imidazo[1,5-a][1,4]diazepine-1-carboxamide (Compound 769)

To a solution of 768 (60 mg) in DCM and DIEA (70 µL) was added 4-chloro butyrylchloride (33 µL). After stirring at room temperature for 30 minutes, the reaction was quenched with aqueous sodium bicarbonate. The DCM phase was separated, dried over sodium sulfate and concentrated under reduced pressure. The residual oil was dissolved in THF and sodium hydride (60% dispersion, 12 mg) was added and stirred at room temperature for 1 hour. The reaction was quenched with brine and extracted with EtOAc. The organic phase was evaporated under reduced pressure. The crude material was purified by preparative LC-MS and pure fractions were evaporated to give compound 769 (27.5 mg, 40%). LCMS (+ESI) m/z 490.3 [M+H]$^+$.

Example 75

Preparation of (S)—N-(1-acetamido-3,3-dimethylbutan-2-yl)-3-(5-chloro-2-fluorophenyl)-8-methyl-6,7,8,9-tetrahydro-5H-imidazo[1,5-a][1,4]diazepine-1-carboxamide (Compound 770)

To a solution of 768 (50 mg) and DIEA (41 µL) in DCM (2 mL) was added acetyl chloride (25 µL). After stirring at room temperature for 45 minutes, the reaction mixture was concentrated under reduced pressure. The residue was dissolved in MeOH and purified by a preparative LC-MS to give compound 770 (32 mg). LCMS (+ESI) m/z 464.2 [M+H]⁺.

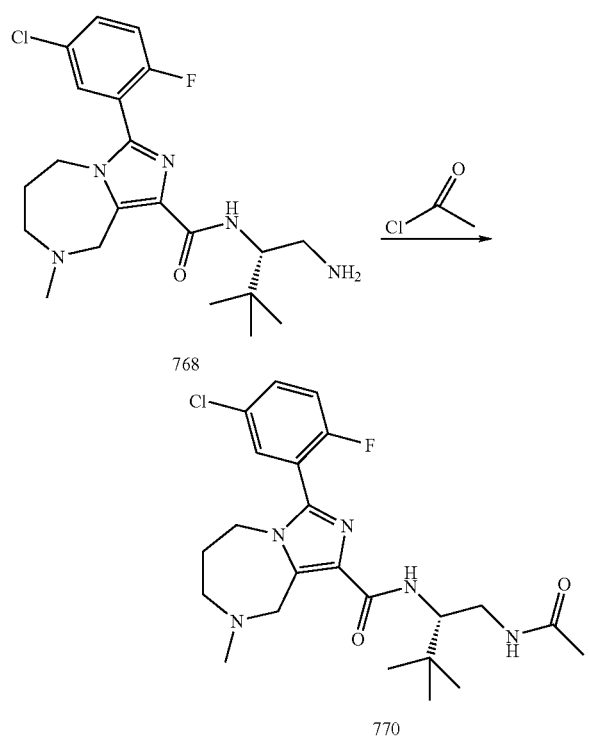

Compound 771 was prepared according to the procedure for 770 by replacing acetyl chloride with methanesulfonyl chloride. LCMS (+ESI) m/z 501 [M+H]⁺.

Example 76

Preparation of (S)—N-(3,3-dimethyl-1-(methylamino)-1-oxobutan-2-yl)-8-methyl-3-(1-(phenylsulfonyl)-1H-pyrazol-4-yl)-6,7,8,9-tetrahydro-5H-imidazo[1,5-a][1,4]diazepine-1-carboxamide (Compound 776)

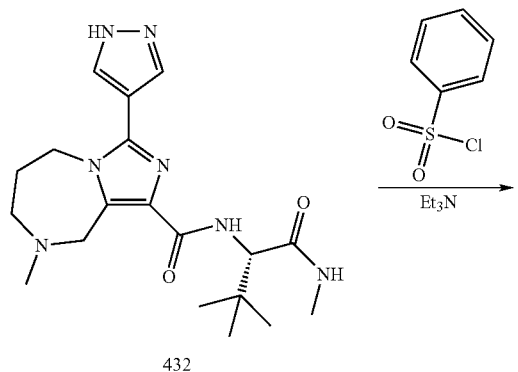

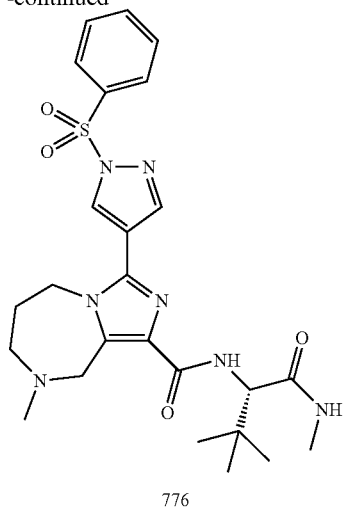

To compound 432 (41 mg, 0.106 mmol) in DCM (2 mL) was added triethylamine (21 mg, 0.212 mmol) and benzene sulfonyl chloride (20 mg, 0.116 mmol). The reaction mixture stirred at room temperature for 4 hours. The volatile solvents were removed by rotary evaporation, and the residue was dissolved in methanol and purified by automated preparative LC/MS. A white solid (compound 776) was obtained. (6.8 mg, 12% yield) LCMS (+ESI) m/z 528.3 [M+H]⁺.

Example 77

Preparation of (S)-3-(3,4-difluorophenyl)-N-(1-(3,3-difluoropyrrolidin-1-yl)-3,3-dimethyl-1-oxobutan-2-yl)-8-methyl-6,7,8,9-tetrahydro-5H-imidazo[1,5-a][1,4]diazepine-1-carboxamide (Compound 780)

Step 1: Preparation of (S)-3-bromo-N-(1-(3,3-difluoropyrrolidin-1-yl)-3,3-dimethyl-1-oxobutan-2-yl)-8-(3,3-dimethylbutanoyl)-6,7,8,9-tetrahydro-5H-imidazo[1,5-a][1,4]diazepine-1-carboxamide (Intermediate 77B). To 33E (0.60 g, 1.66 mmol) in CH₂Cl₂ (10 mL) was added triethylamine (0.70 mL, 4.98 mmol), 77A (0.44 g, 1.99 mmol) and 2-chloro-N,N-dimethylimidazolidinium chloride (DMC) (0.42 g, 2.50 mmol). The reaction mixture was stirred at 50° C. for 3 hours. Aqueous NaOH was added and the organics were separated, dried with sodium sulfate and concentrated. The residue was purified on silica using 20-80% hexanes/ethyl acetate gradient to give intermediate 77B. LCMS (+ESI) m/z 561.1 [M+H]⁺.

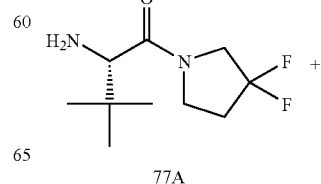

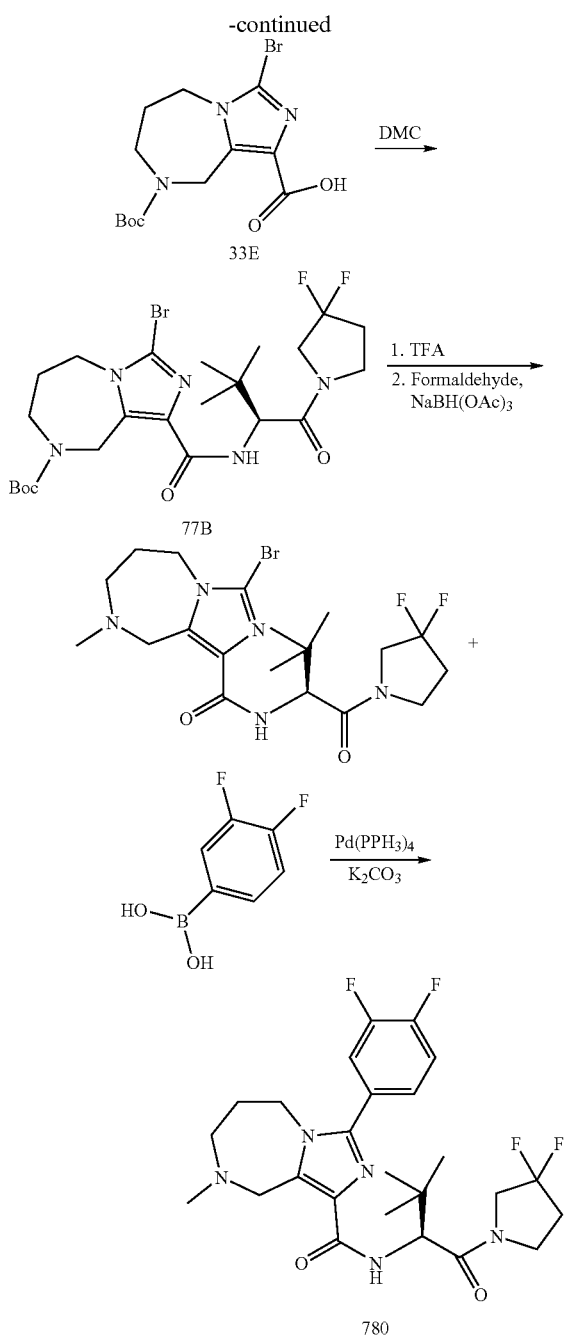

Step 2: Preparation of (S)-3-bromo-N-(1-(3,3-difluoropyrrolidin-1-yl)-3,3-dimethyl-1-oxobutan-2-yl)-8-methyl-6,7,8,9-tetrahydro-5H-imidazo[1,5-a][1,4]diazepine-1-carboxamide (Intermediate 77C). Following the same procedure as described in Example 73, Step 2, intermediate 77C was prepared from intermediate 77B.

Step 3: Preparation of (S)-3-(3,4-difluorophenyl)-N-(1-(3,3-difluoro-pyrrolidin-1-yl)-3,3-dimethyl-1-oxobutan-2-yl)-8-methyl-6,7,8,9-tetrahydro-5H-imidazo[1,5-a][1,4]diazepine-1-carboxamide (Compound 780). A solution of 77C (0.11 mmol), 3,4-difluorophenylboronic acid (0.16 mmol), potassium carbonate (0.21 mmol) and palladium tetrakis (triphenylphosphine) (24 mg) in dioxane/water was heated at 130° C. in a sealed vial over night. The reaction was quenched with 1N NaOH and extracted twice with DCM. The combined organic extracts were passed through a thiol-based resin scavenger to remove palladium. The crude mixture was purified by preparative LC-MS to give compound 780 (5.9 mg) LCMS (+ESI) m/z 510.1 [M+H]+.

Synthesis of intermediate 77A:

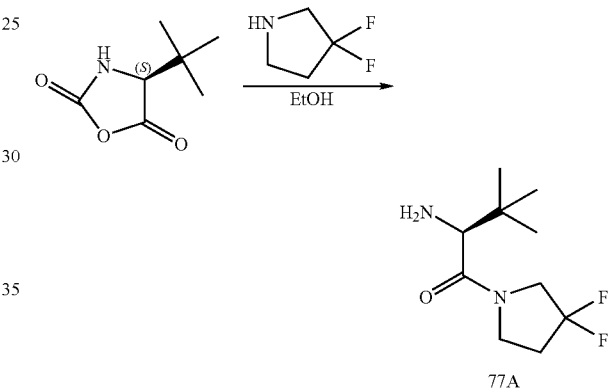

(S)-4-tert-butyloxazolidine-2,5-dione (0.314 g, 2.0 mmol) and 3,3-difluoropyrrolidine hydrochloride (0.25 g, 2.4 mmol) were suspended in EtOH (5 mL) and heated in the microwave at 150° C. for 15 minutes. The reaction was concentrated under reduced pressure and azeotroped with toluene to provide 0.42 g (95% yield) of intermediate 77A. LCMS (+ESI) m/z 221.1 [M+H]+.

Compounds 781-783, 790-802, 810-816, 831, 868, 869, 908 were prepared in the same manner as 780 except that different boronic acids were used in step 3 and/or different amines were used in place of 3,3-difluoropyrrolidine. Compounds 784-786, 803-806 were prepared in the same manner as 780 except that the morpholine intermediate 77D was used in place of 77A.

Step 1: Preparation of (S)-3-bromo-N-(1-(3,3-difluoropyrrolidin-1-yl)-3,3-dimethyl-1-oxobutan-2-yl)-8-(3,3-dimethylbutanoyl)-6,7,8,9-tetrahydro-5H-imidazo[1,5-a][1,4]diazepine-1-carboxamide (Intermediate 77B). To 33E (0.60 g, 1.66 mmol) in CH₂Cl₂ (10 mL) was added triethylamine (0.70 mL, 4.98 mmol), 77A (0.44 g, 1.99 mmol) and 2-chloro-N,N-dimethylimidazolidinium chloride (DMC) (0.42 g, 2.50 mmol). The reaction mixture was stirred at 50° C. for 3 hours. Aqueous NaOH was added and the organics were separated, dried with sodium sulfate and concentrated. The residue was purified on silica using 20-80% hexanes/ethyl acetate gradient to give intermediate 77B. LCMS (+ESI) m/z 561.1 [M+H]+.

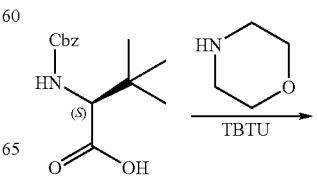

-continued

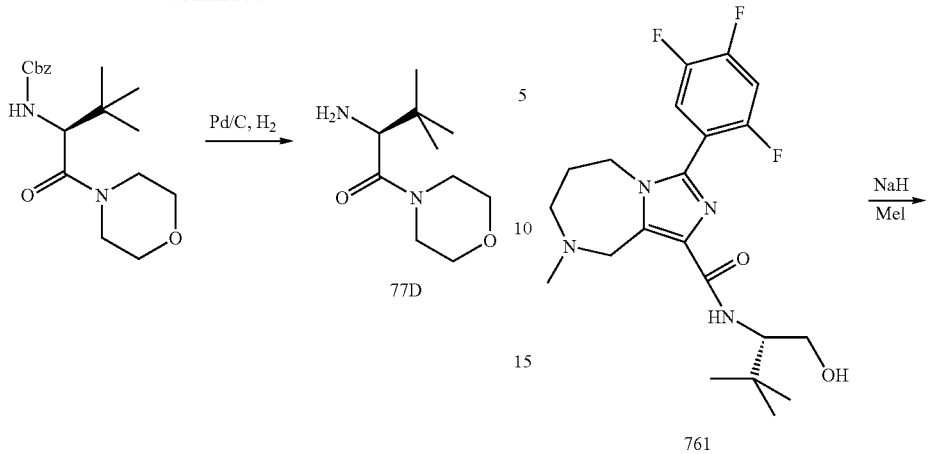

Preparation of (S)-2-amino-3,3-dimethyl-1-morpholinobutan-1-one (intermediate 77D). To a solution of (S)-2-(benzyloxycarbonylamino)-3,3-dimethylbutanoic acid (2.0 g, 7.54 mmol) in DMF (10 mL) were added morpholine (1.31 g, 15.1 mmol) and DIEA (3.95 mL, 22.62 mmol). TBTU (3.63 g, 11.31 mmol) was added in three portions 15 minutes apart. The reaction stirred at room temperature for 2 hours. DMF was removed under vacuum and the residue was partitioned between ethyl acetate and saturated sodium bicarbonate. The organic layer was separated, dried over sodium sulfate, filtered and concentrated under reduced pressure. The resulting crude material (2.11 g, 7.54 mmol) was combined with palladium on carbon, 10% dry basis, (0.29 g, 2.69 mmol) in MeOH (15 mL) and placed on a Parr Shaker under $H_2$ atmosphere, 20 psi, for 3 hours. The reaction was filtered through a celite plug and concentrated under reduced pressure to provide 1.46 g (7.31 mmol) of intermediate 77D. LCMS (+ESI) m/z 201.1 [M+H]$^+$.

Compound 890 was prepared in the same manner as 780 except that acetaldehyde was used in place of formaldehyde in Step 2, ethylamine was used in place of 3,3-difluoropyrrolidine and 2,4-fluoro-5-chlorophenyl boronic acid was used in place of 3,4-difluorophenylboronic acid.

Example 78

Preparation of (S)—N-(1-methoxy-3,3-dimethylbutan-2-yl)-8-methyl-3-(2,4,5-trifluorophenyl)-6,7,8,9-tetrahydro-5H-imidazo[1,5-a][1,4]diazepine-1-carboxamide methiodide (Compound 827)

To compound 761 (0.1 g, 0.236 mmol) in THF (3 mL) was added sodium hydride (6 mg, 0.24 mmol) and iodomethane (33 mg, 0.236 mmol). The reaction mixture was stirred for 5 hrs. Water was added dropwise and the mixture was extracted with ethyl acetate. The organic layer was dried over magnesium sulfate, filtered and concentrated in vacuo. The residue was purified by automated preparative LC/MS.

The desired compound 827 was isolated as a white solid, 13.7 mg (13% yield). LCMS (+ESI) m/z 454.2 [M+H]$^+$.

Example 79

Preparation of (S)-3-(3,4-difluorophenyl)-N-(1-methoxy-3,3-dimethylbutan-2-yl)-8-methyl-6,7,8,9-tetrahydro-5H-imidazo[1,5-a][1,4]diazepine-1-carboxamide (Compound 829)

-continued

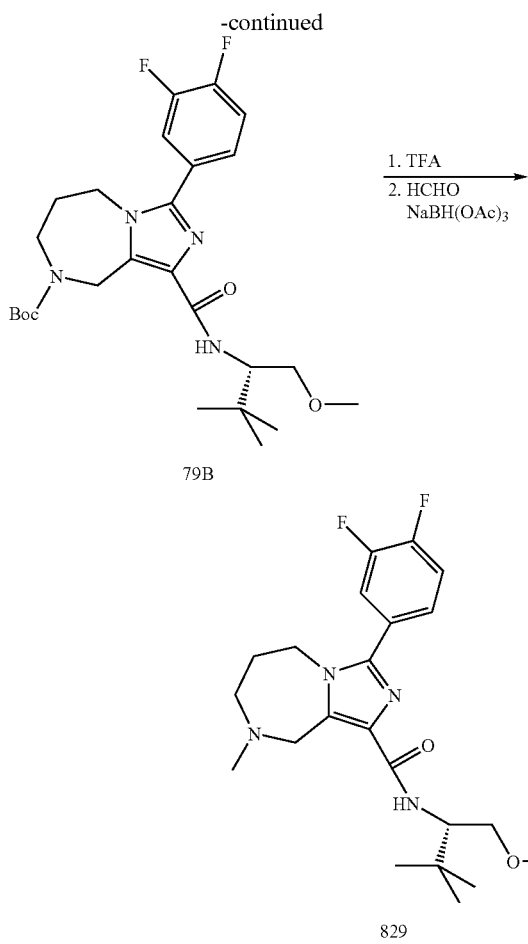

79B

1. TFA
2. HCHO
   NaBH(OAc)₃

829

Step 1: Preparation of (S)-tert-butyl 3-(3,4-difluorophenyl)-1-(1-methoxy-3,3-dimethylbutan-2-ylcarbamoyl)-6,7-dihydro-5H-imidazo[1,5-a][1,4]diazepine-8(9H)-carboxylate (Intermediate 79B). To 79A (120 mg, 0.24 mmol) (prepared in the same manner as 39C except that 3,4 difluorophenylboronic acid was used in place of phenyl boronic acid and (S)-tert-leucinol was used in place of tert-Leu-OMe) in THF (3 mL) was added sodium hydride (15 mg, 0.365 mmol) followed by iodomethane (35 mg, 0.244 mmol). The reaction mixture stirred for 18 hours at room temperature. The reaction mixture was quenched dropwise with water and extracted with ethyl acetate. The organic layer was dried with magnesium sulfate, filtered and concentrated to provide 80 mgs of 79B.

Step 2: Preparation of (S)-3-(3,4-difluorophenyl)-N-(1-methoxy-3,3-dimethylbutan-2-yl)-8-methyl-6,7,8,9-tetrahydro-5H-imidazo[1,5-a][1,4]diazepine-1-carboxamide (Compound 829). To 79B (80 mg, 0.158 mmol) in DCM (3 mL) was added 10 eq. of TFA. The reaction mixture stirred at room temperature for 2 hours. The reaction mixture was concentrated, dissolved in methanol and loaded on an ion exchange column (Phenomenex, SCX). The column was washed with methanol, and the desired compound was eluted from the column using 2N ammonia in methanol. The solvent was removed in vacuo. The residue was dissolved up in 3 mL of THF and 30% formaldehyde solution (0.098 g, 0.984 mmol) was added followed by acetic acid (5.9 mg, 0.098 mmol) and sodium triacetoxyborohydride (42 mg, 0.197 mmol). The reaction mixture stirred at room temperature for 18 hours. The reaction mixture was diluted with saturated sodium bicarbonate and extracted with ethyl acetate and dried over magnesium sulfate, filtered and concentrated in vacuo. The residue was purified by automated preparative LC/MS. The desired compound 829 was isolated as an oil, 7.4 mg (13% yield). LCMS (+ESI) m/z 421.2 [M+H]⁺. ¹H-NMR (400 MHz, CDCl₃) δ: 7.29-7.34 (m, 2H), 7.19-7.26 (m, 1H), 3.99-4.10 (m, 2H), 3.41-3.52 (m, 2H), 3.27 (s, 3H), 2.92-3.06 (m, 2H), 2.42 (s, 3H), 1.80-2.08 (m, 6H), 0.90 (s, 9H).

Example 80

Preparation of (S)—N-(2-hydroxy-2,4,4-trimethylpentan-3-yl)-8-methyl-3-(2,4,5-trifluorophenyl)-6,7,8,9-tetrahydro-5H-imidazo[1,5-a][1,4]diazepine-1-carboxamide (Compound 865)

Step 1 Preparation of 8-tert-butyl 1-ethyl 3-(2,4,5-trifluorophenyl)-6,7-dihydro-5H-imidazo[1,5-a][1,4]diazepine-1,8(9H)-dicarboxylate (Intermediate 80A). Intermediate 33D (2.0 g, 10.30 mmol) was dissolved in dioxane (10 mL) and 2,4,5-trifluorophenylboronic acid (1.81 g, 15.45 mmol) was added, followed by K₂CO₃ (2.13 g, 15.45 mmol) and water (2 mL). The resulting mixture was degassed with nitrogen and Pd(PPh₃)₄ (0.83 g, 0.72 mmol) was added. The mixture was heated in a microwave reactor at 170° C. for 30 minutes. The residue was diluted with methanol filtered through celite and concentrated. The resulting crude material was dissolved in ethyl acetate, washed with brine, dried over Na₂SO₄, filtered, concentrated and purified by normal phase chromatography using 10-60% ethyl acetate/hexanes to provide product 80A (1.1 g, 48% yield). LCMS (+ESI) m/z 440.1 [M+H]⁺.

Step 2 Preparation of 8-(tert-butoxycarbonyl)-3-(2,4,5-trifluorophenyl)-6,7,8,9-tetrahydro-5H-imidazo[1,5-a][1,4]diazepine-1-carboxylic acid (Intermediate 80B). Intermediate 80A (0.60 g, 1.36 mmol) was dissolved in methanol (6 mL) and lithium hydroxide (0.11 g, 2.72 mmol) in water (2 mL) was added. The resulting mixture was stirred at 65° C. for 1 hour, concentrated, acidified to pH3 with 4N HCl and extracted with 10% i-PrOH/DCM mixture. The organic layer was dried over Na₂SO₄, filtered and concentrated to provide product 80B (0.50 g, 89%). LCMS (+ESI) m/z 435.0 [M+Na]⁺.

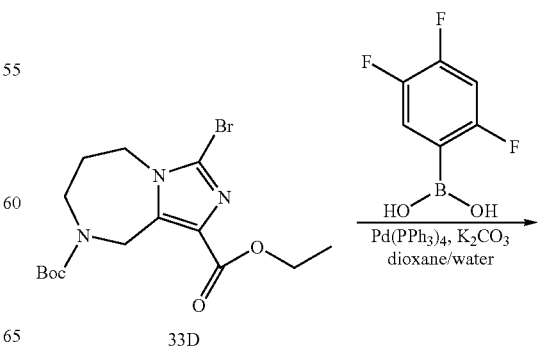

33D

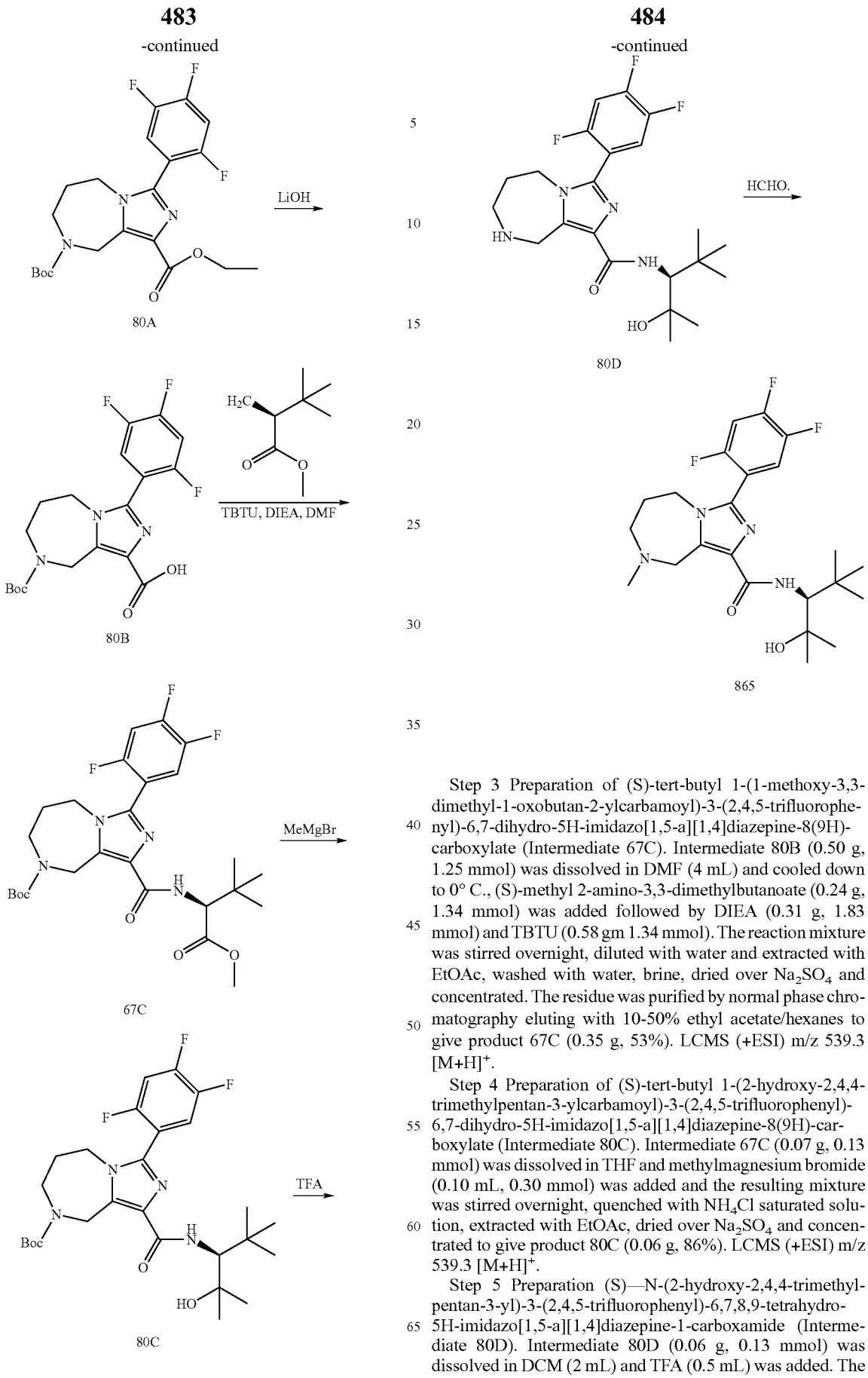

Step 3 Preparation of (S)-tert-butyl 1-(1-methoxy-3,3-dimethyl-1-oxobutan-2-ylcarbamoyl)-3-(2,4,5-trifluorophenyl)-6,7-dihydro-5H-imidazo[1,5-a][1,4]diazepine-8(9H)-carboxylate (Intermediate 67C). Intermediate 80B (0.50 g, 1.25 mmol) was dissolved in DMF (4 mL) and cooled down to 0° C., (S)-methyl 2-amino-3,3-dimethylbutanoate (0.24 g, 1.34 mmol) was added followed by DIEA (0.31 g, 1.83 mmol) and TBTU (0.58 gm 1.34 mmol). The reaction mixture was stirred overnight, diluted with water and extracted with EtOAc, washed with water, brine, dried over Na₂SO₄ and concentrated. The residue was purified by normal phase chromatography eluting with 10-50% ethyl acetate/hexanes to give product 67C (0.35 g, 53%). LCMS (+ESI) m/z 539.3 [M+H]⁺.

Step 4 Preparation of (S)-tert-butyl 1-(2-hydroxy-2,4,4-trimethylpentan-3-ylcarbamoyl)-3-(2,4,5-trifluorophenyl)-6,7-dihydro-5H-imidazo[1,5-a][1,4]diazepine-8(9H)-carboxylate (Intermediate 80C). Intermediate 67C (0.07 g, 0.13 mmol) was dissolved in THF and methylmagnesium bromide (0.10 mL, 0.30 mmol) was added and the resulting mixture was stirred overnight, quenched with NH₄Cl saturated solution, extracted with EtOAc, dried over Na₂SO₄ and concentrated to give product 80C (0.06 g, 86%). LCMS (+ESI) m/z 539.3 [M+H]⁺.

Step 5 Preparation (S)—N-(2-hydroxy-2,4,4-trimethylpentan-3-yl)-3-(2,4,5-trifluorophenyl)-6,7,8,9-tetrahydro-5H-imidazo[1,5-a][1,4]diazepine-1-carboxamide (Intermediate 80D). Intermediate 80C (0.06 g, 0.13 mmol) was dissolved in DCM (2 mL) and TFA (0.5 mL) was added. The resulting mixture was stirred at room temperature for 1 hour, concentrated, and toluene was added and the mixture was evaporated to remove traces of TFA. The resulting product 80D was dried under vacuum used in the next step without purification. LCMS (+ESI) m/z 439.3 [M+H]+.

Step 6 Preparation of (S)—N-(2-hydroxy-2,4,4-trimethyl-pentan-3-yl)-8-methyl-3-(2,4,5-trifluorophenyl)-6,7,8,9-tetrahydro-5H-imidazo[1,5-a][1,4]diazepine-1-carboxamide (Compound 865). Intermediate 80D (0.06 g, 0.11 mmol) was dissolved in THF (2 mL) and formaldehyde (0.04 g, 1.37 mmol) was added followed by NaBH(OAc)₃ (0.06 g, 0.27 mmol). The resulting mixture was stirred at room temperature overnight, quenched with NaHCO₃ saturated solution and concentrated. The residue was dissolved in DCM, washed with brine, dried over Na₂SO₄ and concentrated. The resulting material was purified by preparative LCMS to provide 7 mg (7% yield) of compound 865. ¹H-NMR (400 MHz, CDCl₃) δ: 1.06 (d, 9H), 1.31 (t, 3H), 1.47 (t, 3H), 1.83 (m, 2H), 2.38 (d, 3H), 2.94 (m, 2H), 3.81 (d, 1H), 3.89 (m, 2H), 7.00 (m, 1H), 7.41 (m, 2H), 7.55 (d, 1H). LCMS (+ESI) m/z 453.3 [M+H]+.

Example 81

Preparation of (S)—N-(2,2-dimethyl-1-(3-methyl-1,2,4-oxadiazol-5-yl)propyl)-8-methyl-3-(2,4,5-trifluorophenyl)-6,7,8,9-tetrahydro-5H-imidazo[1,5-a][1,4]diazepine-1-carboxamide (Compound 866)

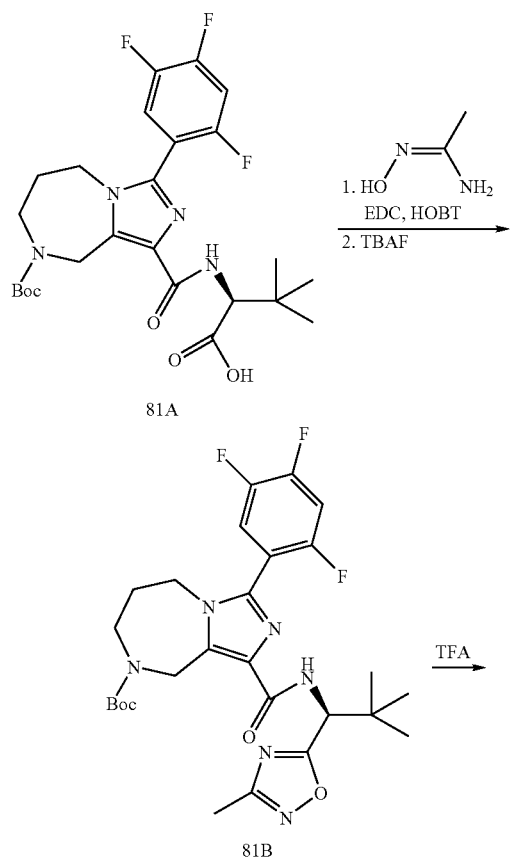

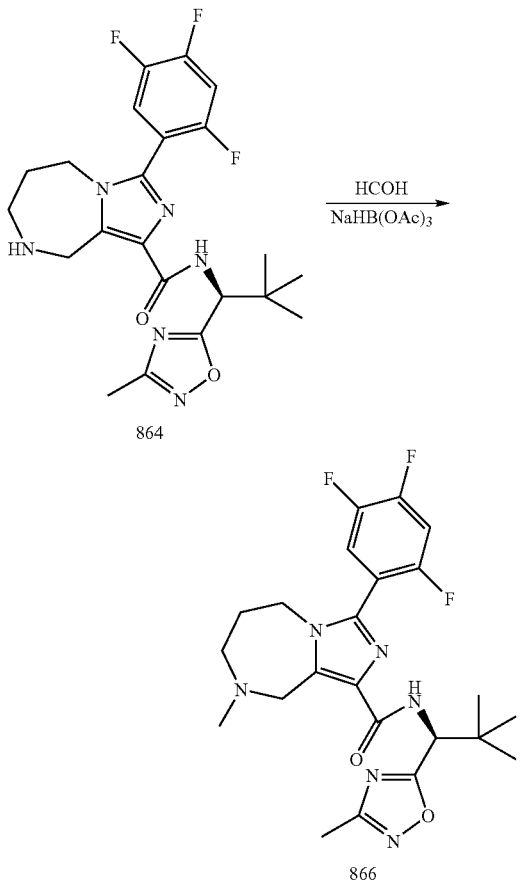

Step 1 Preparation of (S)-tert-butyl 1-(2,2-dimethyl-1-(3-methyl-1,2,4-oxadiazol-5-yl)propylcarbamoyl)-3-(2,4,5-trifluorophenyl)-6,7-dihydro-5H-imidazo[1,5-a][1,4]diazepine-8(9H)-carboxylate (Intermediate 81B). Intermediate 81A (prepared in the same manner as 17B) (0.15 g, 0.29 mmol) was dissolved in DMF (3 mL) and EDCI (0.088 g, 0.46 mmol) was added followed by HOBt (0.062 g, 0.46 mmol). The resulting mixture was stirred for 30 minutes and (Z)—N'-hydroxyacetimidamide (0.03 g, 0.46 mmol) was added and the mixture was stirred overnight. The reaction mixture was diluted with water and extracted with EtOAc. The organic layer was washed with water, 2N Na₂CO₃ solution, and brine, dried over Na₂SO₄ and concentrated. The resulting product (0.16 g, 0.27 mmol) was dissolved in THF and TBAF (2M solution in THF, 0.28 mL) was added. The mixture was stirred overnight, concentrated, diluted with EtOAc and washed with water, brine, dried over Na₂SO₄, filtered and concentrated. The residue was purified by flash chromatography on silica eluting with 20-70% hexane/EtOAc gradient to give product 81B (0.09 g, 58% yield). LCMS (+ESI) m/z 563.3 [M+H]+.

Step 2 Preparation of (S)—N-(2,2-dimethyl-1-(3-methyl-1,2,4-oxadiazol-5-yl)propyl)-3-(2,4,5-trifluorophenyl)-6,7,8,9-tetrahydro-5H-imidazo[1,5-a][1,4]diazepine-1-carboxamates (Compound 864). Intermediate 81B (90 mg, 0.16 mmol) was dissolved in dichloromethane (2 mL) and TFA (0.5 mL) was added. The resulting mixture was stirred for 2 hours. Toluene was added and the mixture was evaporated again to remove traces of TFA. The residue was purified by flash chromatography on silica eluting with 0-20% ethanol/acetonitrile to give 50 mg (68% yield) of 864. ¹H-NMR (400

MHz, CDCl₃-d) δ: 1.09 (s, 9H), 1.83 (m, 2H), 2.40 (s, 3H), 3.20 (m, 2H), 3.98 (m, 2H), 4.96 (s, 2H), 5.33 (d, 1H), 7.07 (m, 1H), 7.46 (m, 1H), 7.84 (d, 1H), LCMS (+ESI) m/z 463.2 [M+H]⁺.

Step 3 Preparation of (S)—N-(2,2-dimethyl-1-(3-methyl-1,2,4-oxadiazol-5-yl)propyl)-8-methyl-3-(2,4,5-trifluorophenyl)-6,7,8,9-tetrahydro-5H-imidazo[1,5-a][1,4]diazepine-1-carboxamide (Compound 866). Compound 864 (0.05 g, 0.11 mmol) was dissolved in THF and formaldehyde (0.08 mL, 1.08 mmol) was added followed by NaBH(OAc)₃ (0.06 g, 0.22 mmol) and acetic acid (0.01 mL, 0.22 mmol). The resulting mixture was stirred at room temperature for 18 hours and quenched with NaHCO₃ and concentrated. The residue was extracted with DCM, washed with brine, dried over Na₂SO₄, filtered and concentrated. The resulting material was purified by preparative LCMS to provide 0.03 g (50% yield) compound 866. ¹H-NMR (400 MHz, CDCl₃-d) δ: 1.09 (s, 9H), 2.03 (m, 2H), 2.40 (s, 3H), 2.55 (s, 3H), 3.27 (m, 2H), 4.04 (m, 2H), 4.64 (s, 2H), 5.33 (d, 1H), 7.07 (m, 1H), 7.46 (m, 1H), 7.84 (d, 1H), LCMS (+ESI) m/z 477.2 [M+H]⁺.

Compounds 911-914 were prepared in a similar manner to 864 and 866 except that 2,5-difluorophenylboronic acid and 3,4-difluorophenylboronic acid were used in place of 2,3,4-trifluorophenylboronic acid.

Example 82

3-(5-chloro-2,4-difluorophenyl)-8-methyl-N-(2-methyl-1-(methylamino)-1-oxopropan-2-yl)-6,7,8,9-tetrahydro-5H-imidazo[1,5-a][1,4]diazepine-1-carboxamide (Compound 872)

Step 1 Preparation of methyl 2-(3-(5-chloro-2,4-difluorophenyl)-8-methyl-6,7,8,9-tetrahydro-5H-imidazo[1,5-a][1,4]diazepine-1-carboxamido)-2-methylpropanoate (Compound 871). To 82A (50 mg, 0.146 mmol) (prepared in the same manner as compound 18D using 33D in place of 18A and the appropriate boronic acid) in DMF (0.5 mL) was added α-aminoisobutyric acid methyl ester hydrochloride (24.7 mg, 0.161 mmol), TBTU (51.7 mg, 0.161 mmol) and DIEA (0.077 mL, 0.439 mmol). The reaction mixture stirred for 1 hour at room temperature. The reaction mixture was diluted with water and extracted with ethyl acetate. The organic layer was dried over sodium sulfate, filtered and concentrated. The residue was purified using a 4 g silica column eluting with 20-100% ethyl acetate/hexanes to provide 35 mg of compound 871. LCMS (+ESI) m/z 441.2 [M+H]⁺.

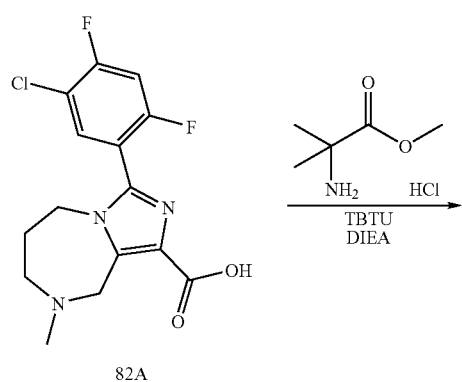

82A

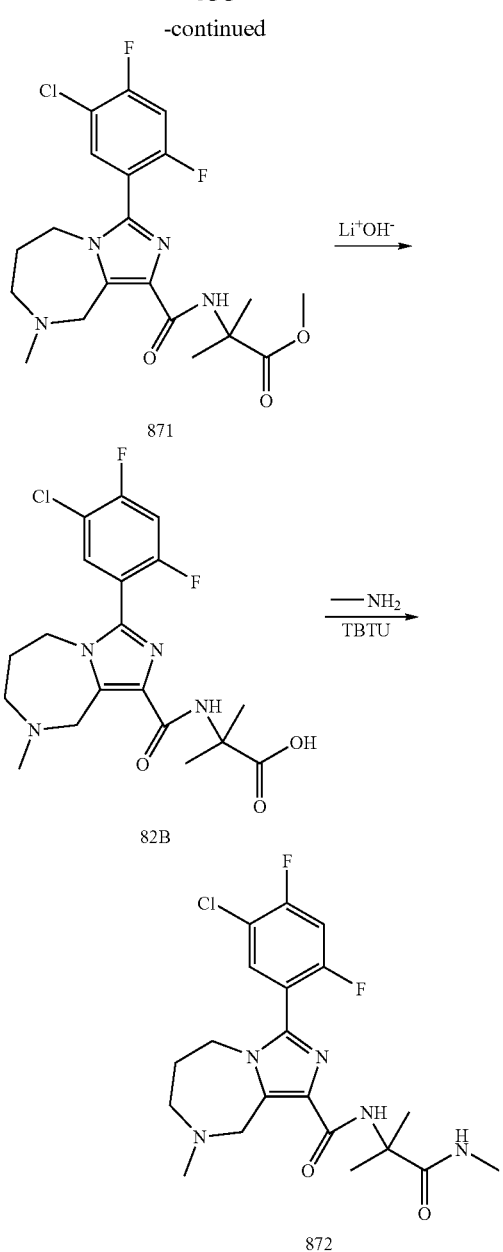

Step 2 Preparation of 2-(3-(5-chloro-2,4-difluorophenyl)-8-methyl-6,7,8,9-tetrahydro-5H-imidazo[1,5-a][1,4]diazepine-1-carboxamido)-2-methylpropanoic acid (Intermediate 82B). To compound 871 (30 mg, 0.068 mmol) in methanol (3 mL) was added lithium hydroxide monohydrate (17 mg, 0.405 mmol) and water (3 mL). The reaction mixture stirred at room temperature for 2 hours. The reaction mixture was concentrated and the residue was used in next step without further purification.

Step 3 Preparation of 3-(5-chloro-2,4-difluorophenyl)-8-methyl-N-(2-methyl-1-(methylamino)-1-oxopropan-2-yl)-6,7,8,9-tetrahydro-5H-imidazo[1,5-a][1,4]diazepine-1-carboxamide (Compound 872). To 82B (38.8 mg, 0.068 mmol) in DMF (2 mL) was added methylamine hydrochloride (30 mg, 0.444 mmol), TBTU (24 mg, 0.075 mmol), and DIEA (100 µL, 0.573 mmol). The reaction mixture stirred for 2 hours. The reaction mixture was concentrated and the residue was purified by preparative LC-MS. Pure fractions were evaporated to give 22 mg of compound 872. LCMS (+ESI) m/z 440.2 [M+H]$^+$.

Compounds 873 and 905 were prepared in the same manner as 872 except that ethyl 1-aminocyclopropanecarboxylate hydrochloride was used in place of α-aminoisobutyric acid methyl ester hydrochloride.

Compound 903 was prepared in the same manner as 871 except that ethyl 1-aminocyclopropanecarboxylate hydrochloride was used in place of α-aminoisobutyric acid methyl ester hydrochloride.

Example 83

Preparation of (S)-3-(5-chloro-2,4-difluorophenyl)-N-(2,2-dimethyl-1-(5-methyl-1,3,4-oxadiazol-2-yl)propyl)-8-methyl-6,7,8,9-tetrahydro-5H-imidazo[1,5-a][1,4]diazepine-1-carboxamide (Compound 889)

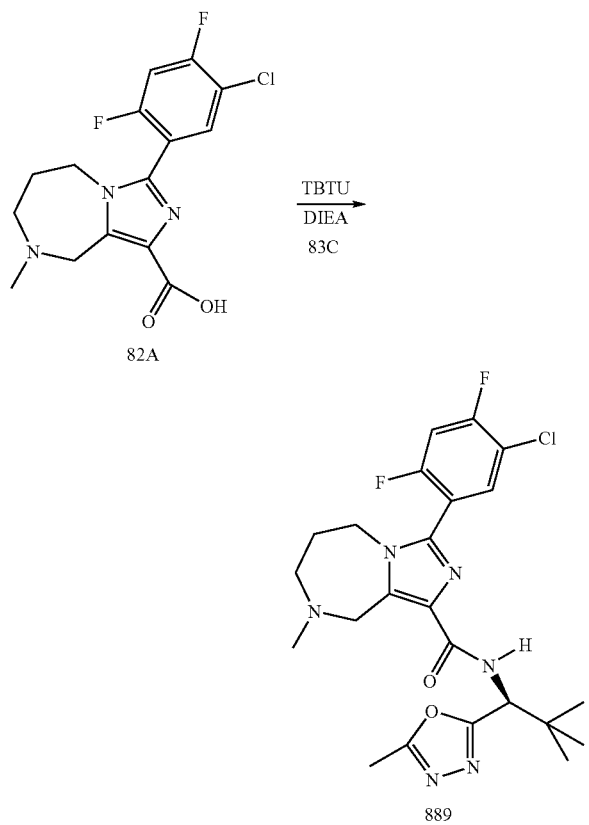

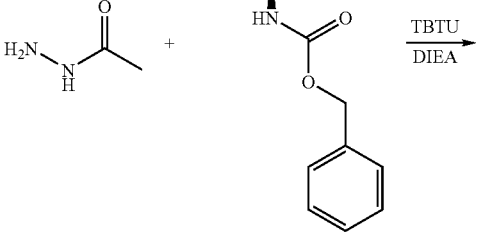

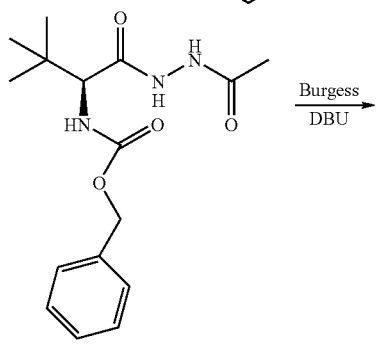

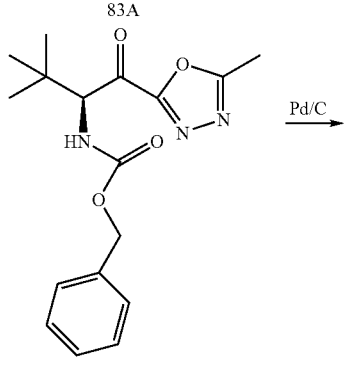

Preparation of (S)-2-amino-3,3-dimethyl-1-(5-methyl-1,3,4-oxadiazol-2-yl)butan-1-one (Intermediate 83C).

Step 1 To a solution of acetohydrazide (36.5 mg, 0.493 mmol) in DMF (1 mL) was added dicyclohexylamine (S)-2-(benzyloxycarbonylamino)-3,3-dimethyl-butanoate (200 mg, 0.448 mmol) and DIEA (116 mg, 0.896 mmol). The reaction mixture stirred at room temperature for 24 hours. The reaction mixture was diluted with water and extracted with ethyl acetate. The organic layer was dried over sodium sulfate, filtered and concentrated under reduced pressure to provide 83A which was used in the next step without further purification.

To 83A (0.22 g, 0.696 mmol) was added Burgess reagent (1 g, 4.20 mmol) and DBU (0.16 mL, 1.062 mmol) in THF (1 mL). The reaction mixture was heated in the microwave at 160° C. for 10 minutes. The reaction mixture was diluted with saturated sodium bicarbonate solution and extracted with ethyl acetate, dried over sodium sulfate, filtered and concentrated to provide 0.22 g of crude 83B which was used in the next step without further purification.

In a Parr reactor vessel was added 83B (0.055 g, 0.183 mmol), palladium on carbon (0.039 g, 0.037 mmol) and methanol. The vessel was put on a Parr shaker for 24 hours at 50 psi. The reaction was filtered through Celite, dried over sodium sulfate, filtered and concentrated to provide 7 mgs of 83C.

Step 2: Preparation of (S)-3-(5-chloro-2,4-difluorophenyl)-N-(2,2-dimethyl-1-(5-methyl-1,3,4-oxadiazol-2-yl)propyl)-8-methyl-6,7,8,9-tetrahydro-5H-imidazo[1,5-a][1,4]diazepine-1-carboxamide (Compound 889). To 82A (10.4 mg, 0.030 mmol prepared in the same manner as compound 18D using 33D in place of 18A and the appropriate boronic acid) in DMF (1 mL) was added 83C (7 mg, 0.033 mmol), DIEA (8 mg, 0.061 mmol) and TBTU (11 mg, 0.033 mmol). The reaction mixture was stirred for 4 hours at room temperature and was then concentrated. The residue was purified by preparative LC-MS. Pure fractions were evaporated to give 6.7 mg of compound 889. LCMS (+ESI) m/z 493.2 [M+H]+.

Compounds 893 and 894 were prepared in a similar manner to 889 except that isobutyrohydrazide and pivalohydrazide respectively, was used in place of acetohyrazide.

Example 84

Preparation of (S)-3-(2,5-difluorophenyl)-N-(3,3-dimethyl-1-(methylamino)-1-oxobutan-2-yl)-8-ethyl-6,7,8,9-tetrahydro-5H-imidazo[1,5-a][1,4]diazepine-1-carboxamide (Compound 906)

Step 1 Preparation of (S)-3-bromo-N-(3,3-dimethyl-1-(methylamino)-1-oxobutan-2-yl)-6,7,8,9-tetrahydro-5H-imidazo[1,5-a][1,4]diazepine-1-carboxamide (Intermediate 84A). Product 33F (1.89 g, 3.89 mmol) was dissolved in DCM (10 mL) and TFA (3 mL) was added. The resulting mixture was stirred at room temperature for 1 hour. The mixture was concentrated, toluene (20 mL) was added and the mixture was evaporated to remove traces of TFA. The resulting material was dried under vacuum overnight and was used in the next step without purification. LCMS (+ESI) m/z 388.1 [M+H]+.

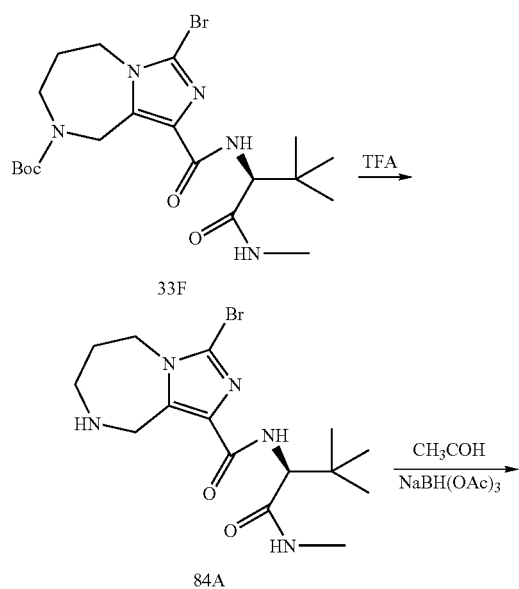

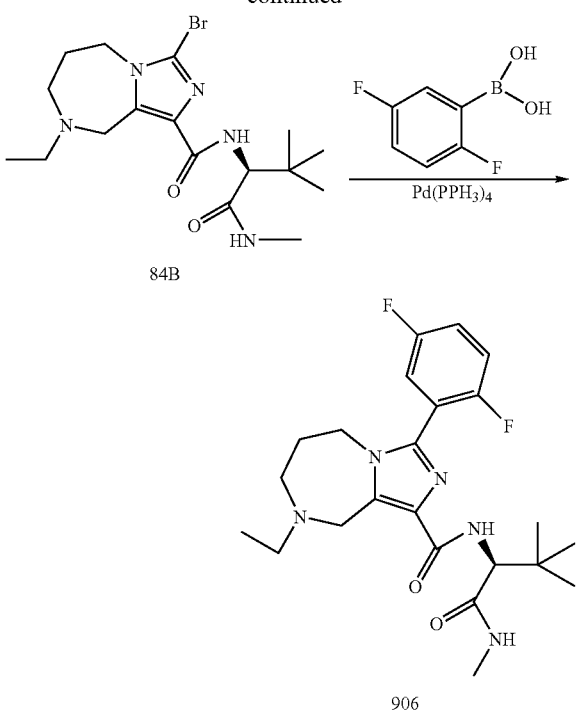

Step 2 Preparation of (S)-3-bromo-N-(3,3-dimethyl-1-(methylamino)-1-oxobutan-2-yl)-8-ethyl-6,7,8,9-tetrahydro-5H-imidazo[1,5-a][1,4]diazepine-1-carboxamide (Intermediate 84B). Intermediate 84A (0.36 g, 0.93 mmol) was dissolved in THF/water and acetic acid (0.056 g, 0.93 mmol) was added. The resulting mixture was cooled to 0° C., then acetaldehyde (0.205 g, 4.66 mmol) was added followed by NaBH(OAc)$_3$ (0.29 g, 1.39 mmol). The resulting mixture was stirred at room temperature for 2 hours and quenched with saturated NaHCO$_3$ solution and concentrated. The residue was dissolved in DCM, washed with brine, dried over Na$_2$SO$_4$ and concentrated. The resulting material was purified by normal phase chromatography eluting with 0-10% MeOH/DCM to provide 0.24 g (62%) of 84B. LCMS (+ESI) m/z 414.1 [M+H]+.

Step 3 Preparation of (S)-3-(2,5-difluorophenyl)-N-(3,3-dimethyl-1-(methylamino)-1-oxobutan-2-yl)-8-ethyl-6,7,8,9-tetrahydro-5H-imidazo[1,5-a][1,4]diazepine-1-carboxamide (Compound 906). Intermediate 84B (0.10 g, 0.24 mmol) was dissolved in dioxane (2 mL) and 2,5-difluorophenylboronic acid (0.053 g, 0.34 mmol) was added, followed by potassium carbonate (0.067 g, 0.48 mmol) and water (0.5 mL). To the resulting mixture was added tetrakis(triphenylphosphine)palladium(0) (0.028 g, 0.024 mmol). The mixture was heated in a microwave reactor at 165° C. for 25 minutes, diluted with methanol and filtered through a Phenomenex thiol SPE tube. The mixture was concentrated and purified by preparative LCMS to provide 0.058 g (48%) of compound 906. $^1$H-NMR (400 MHz, CDCl$_3$) δ: 1.06 (s, 9H), 1.35 (t, 3H), 2.11 (s, 2H), 2.82 (d, 3H), 2.87 (m, 2H), 3.51 (m, 2H), 4.11 (m, 2H), 4.33 (d, 1H), 4.90 (m, 2H), 6.20 (m, 1H), 7.19 (m, 2H), 7.37 (m, 1H), 7.93 (d, 1H). LCMS (+ESI) m/z 448.2 [2M+H]+.

Compound 907 was synthesized in the same manner as compound 906 except that 3,4-difluorophenyl boronic acid was used in place of 2,5-difluorophenylboronic acid. ¹H-NMR (400 MHz, CDCl₃) δ: 1.06 (s, 9H), 1.35 (t, 3H), 2.08 (s, 2H), 2.82 (d, 3H), 2.93 (m, 2H), 3.54 (m, 2H), 4.29 (m, 2H), 4.32 (d, 1H), 4.94 (m, 2H), 6.29 (m, 1H), 7.30 (m, 2H), 7.41 (m, 1H), 7.93 (d, 1H). LCMS (+ESI) m/z 448.2 [2M+H]⁺.

Table 2 below shows the structures and chemical names of compounds 608-914 synthesized as described above.

TABLE 2

| Cmpd No. | Structure | m/z | Chemical Name | Example No. |
|---|---|---|---|---|
| 608 | 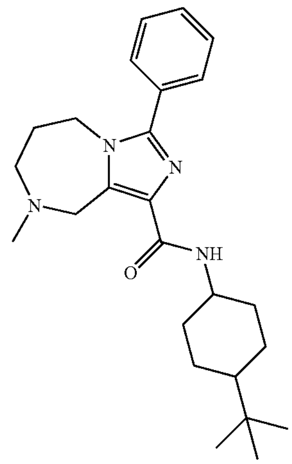 [SMILES: CN1CCCn2c(-c3ccccc3)nc(C(=O)NC3CCC(C(C)(C)C)CC3)c2C1] | 409.2 | N-(4-tert-butylcyclohexyl)-8-methyl-3-phenyl-6,7,8,9-tetrahydro-5H-imidazo[1,5-a][1,4]diazepine-1-carboxamide | 64 |
| 609 | 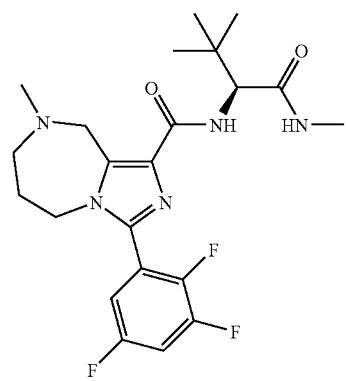 [SMILES: CNC(=O)[C@@H](NC(=O)c1nc(-c2cc(F)cc(F)c2F)n2c1CN(C)CCC2)C(C)(C)C] | 452 | (S)-N-(3,3-dimethyl-1-(methylamino)-1-oxobutan-2-yl)-8-methyl-3-(2,3,5-trifluorophenyl)-6,7,8,9-tetrahydro-5H-imidazo[1,5-a][1,4]diazepine-1-carboxamide | 37 |
| 610 | 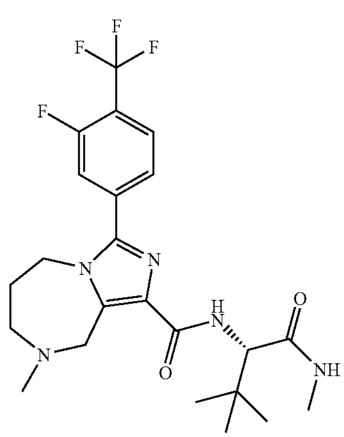 [SMILES: CNC(=O)[C@@H](NC(=O)c1nc(-c2ccc(C(F)(F)F)c(F)c2)n2c1CN(C)CCC2)C(C)(C)C] | 484 | (S)-N-(3,3-dimethyl-1-(methylamino)-1-oxobutan-2-yl)-3-(3-fluoro-4-(trifluoromethyl)phenyl)-8-methyl-6,7,8,9-tetrahydro-5H-imidazo[1,5-a][1,4]diazepine-1-carboxamide | 37 |

TABLE 2-continued

| Cmpd No. | Structure | m/z | Chemical Name | Example No. |
|---|---|---|---|---|
| 611 | 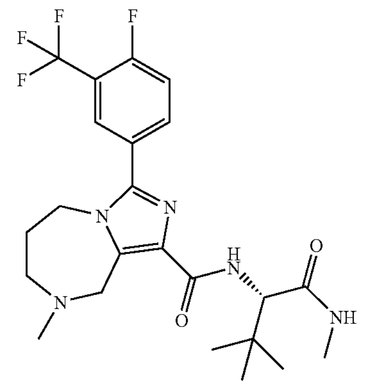 [SMILES: CNC(=O)[C@@H](NC(=O)c1nc(-c2ccc(F)c(C(F)(F)F)c2)n2c1CN(C)CCC2)C(C)(C)C] | 484 | (S)-N-(3,3-dimethyl-1-(methylamino)-1-oxobutan-2-yl)-3-(4-fluoro-3-(trifluoromethyl)phenyl)-8-methyl-6,7,8,9-tetrahydro-5H-imidazo[1,5-a][1,4]diazepine-1-carboxamide | 37 |
| 612 | 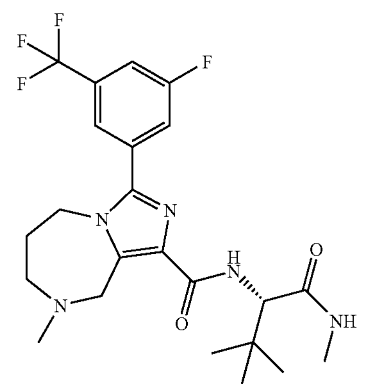 [SMILES: CNC(=O)[C@@H](NC(=O)c1nc(-c2cc(F)cc(C(F)(F)F)c2)n2c1CN(C)CCC2)C(C)(C)C] | 484 | (S)-N-(3,3-dimethyl-1-(methylamino)-1-oxobutan-2-yl)-3-(3-fluoro-5-(trifluoromethyl)phenyl)-8-methyl-6,7,8,9-tetrahydro-5H-imidazo[1,5-a][1,4]diazepine-1-carboxamide | 37 |
| 613 | 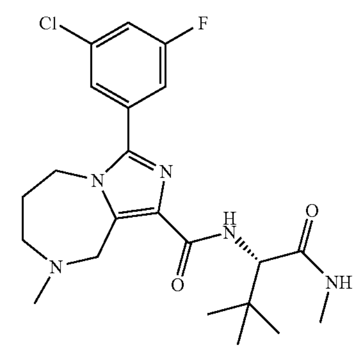 [SMILES: CNC(=O)[C@@H](NC(=O)c1nc(-c2cc(F)cc(Cl)c2)n2c1CN(C)CCC2)C(C)(C)C] | 450 | (S)-3-(3-chloro-5-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 614 | 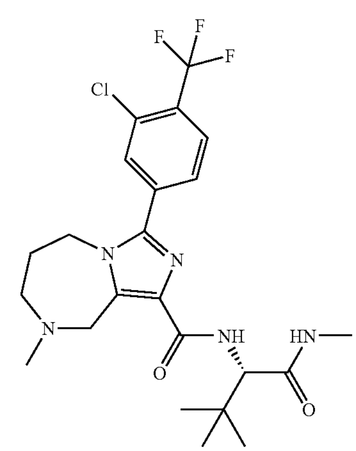 [SMILES: CNC(=O)[C@@H](NC(=O)c1nc(-c2ccc(C(F)(F)F)c(Cl)c2)n2c1CN(C)CCC2)C(C)(C)C] | 500 | (S)-3-(3-chloro-4-(trifluoromethyl)phenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |

TABLE 2-continued

| Cmpd No. | Structure | m/z | Chemical Name | Example No. |
|---|---|---|---|---|
| 615 | 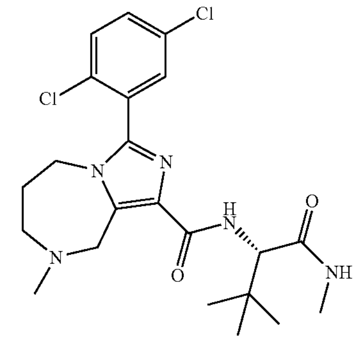 [SMILES: CNC(=O)[C@@H](NC(=O)c1nc(-c2cc(Cl)ccc2Cl)n2c1CN(C)CCC2)C(C)(C)C] | 467 | (S)-3-(2,5-dichlorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 616 | 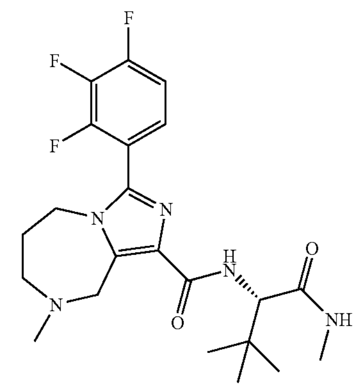 [SMILES: CNC(=O)[C@@H](NC(=O)c1nc(-c2ccc(F)c(F)c2F)n2c1CN(C)CCC2)C(C)(C)C] | 452 | (S)-N-(3,3-dimethyl-1-(methylamino)-1-oxobutan-2-yl)-8-methyl-3-(2,3,4-trifluorophenyl)-6,7,8,9-tetrahydro-5H-imidazo[1,5-a][1,4]diazepine-1-carboxamide | 37 |
| 617 | 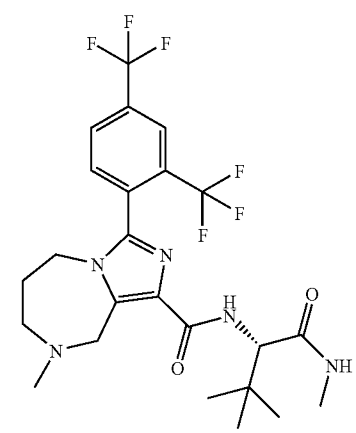 [SMILES: CNC(=O)[C@@H](NC(=O)c1nc(-c2ccc(C(F)(F)F)cc2C(F)(F)F)n2c1CN(C)CCC2)C(C)(C)C] | 534 | (S)-3-(2,4-bis(trifluoromethyl)phenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 618 | 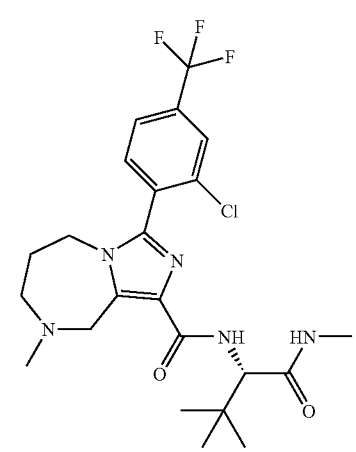 [SMILES: CNC(=O)[C@@H](NC(=O)c1nc(-c2ccc(C(F)(F)F)cc2Cl)n2c1CN(C)CCC2)C(C)(C)C] | 500 | (S)-3-(2-chloro-4-(trifluoromethyl)phenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |

TABLE 2-continued

| Cmpd No. | Structure | m/z | Chemical Name | Example No. |
|---|---|---|---|---|
| 619 | 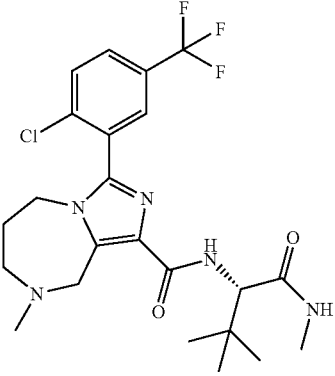 [SMILES: CNC(=O)[C@@H](NC(=O)c1nc(-c2cc(C(F)(F)F)ccc2Cl)n2c1CN(C)CCC2)C(C)(C)C] | 500 | (S)-3-(2-chloro-5-(trifluoromethyl)phenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 620 | 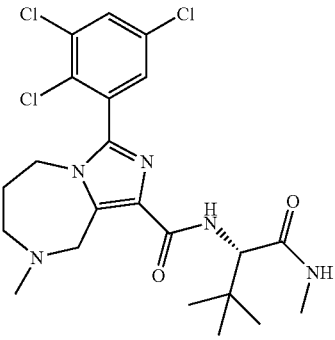 [SMILES: CNC(=O)[C@@H](NC(=O)c1nc(-c2cc(Cl)cc(Cl)c2Cl)n2c1CN(C)CCC2)C(C)(C)C] | 501 | (S)-N-(3,3-dimethyl-1-(methylamino)-1-oxobutan-2-yl)-8-methyl-3-(2,3,5-trichlorophenyl)-6,7,8,9-tetrahydro-5H-imidazo[1,5-a][1,4]diazepine-1-carboxamide | 37 |
| 621 | 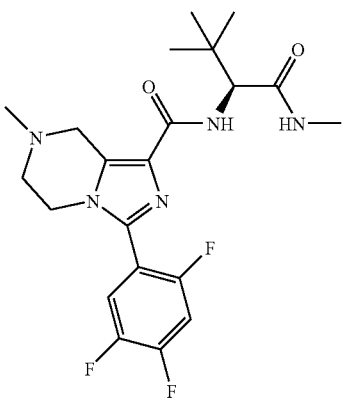 | 438.1 | (S)-N-(3,3-dimethyl-1-(methylamino)-1-oxobutan-2-yl)-7-methyl-3-(2,4,5-trifluorophenyl)-5,6,7,8-tetrahydroimidazo[1,5-a]pyrazine-1-carboxamide | 19 |
| 622 | 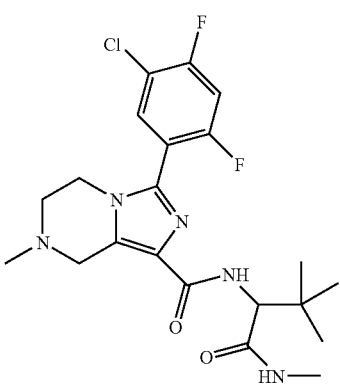 [SMILES: CNC(=O)C(NC(=O)c1nc(-c2cc(Cl)c(F)cc2F)n2c1CN(C)CC2)C(C)(C)C] | 454.1 | (S)-3-(5-chloro-2,4-difluorophenyl)-N-(3,3-dimethyl-1-(methylamino)-1-oxobutan-2-yl)-7-methyl-5,6,7,8-tetrahydroimidazo[1,5-a]pyrazine-1-carboxamide | 19 |

TABLE 2-continued

| Cmpd No. | Structure | m/z | Chemical Name | Example No. |
|---|---|---|---|---|
| 623 | 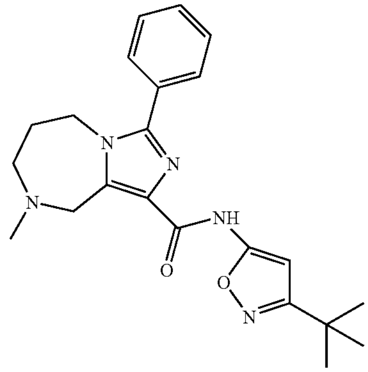 [SMILES: CN1CCCn2c(-c3ccccc3)nc(C(=O)Nc3cc(C(C)(C)C)no3)c2C1] | 394.2 | N-(3-tert-butylisoxazol-5-yl)-8-methyl-3-phenyl-6,7,8,9-tetrahydro-5H-imidazo[1,5-a][1,4]diazepine-1-carboxamide | 64 |
| 624 | 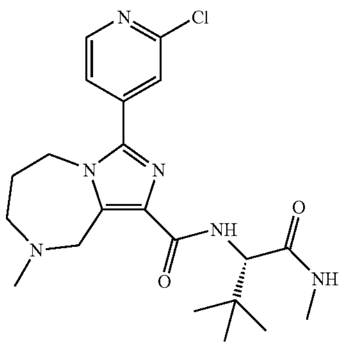 [SMILES: CNC(=O)[C@@H](NC(=O)c1nc(-c2ccnc(Cl)c2)n2c1CN(C)CCC2)C(C)(C)C] | 433.1 | (S)-3-(2-chloropyridin-4-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 625 | 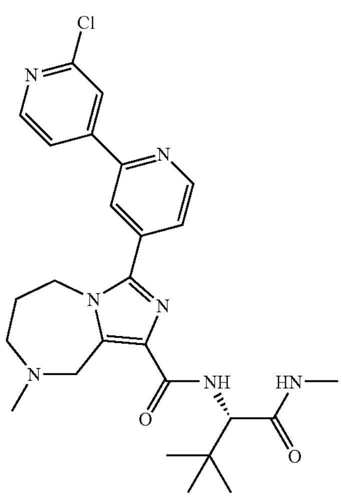 [SMILES: CNC(=O)[C@@H](NC(=O)c1nc(-c2ccnc(-c3ccnc(Cl)c3)c2)n2c1CN(C)CCC2)C(C)(C)C] | 510.0 | (S)-3-(2'-chloro-2,4'-bipyridin-4-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 626 | 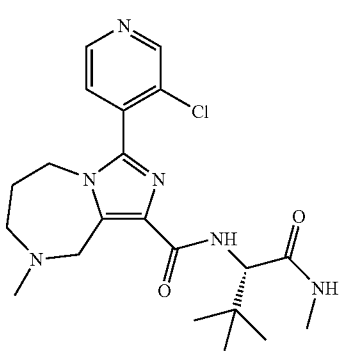 [SMILES: CNC(=O)[C@@H](NC(=O)c1nc(-c2ccncc2Cl)n2c1CN(C)CCC2)C(C)(C)C] | 433.1 | (S)-3-(3-chloropyridin-4-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |

TABLE 2-continued

| Cmpd No. | Structure | m/z | Chemical Name | Example No. |
|---|---|---|---|---|
| 627 | 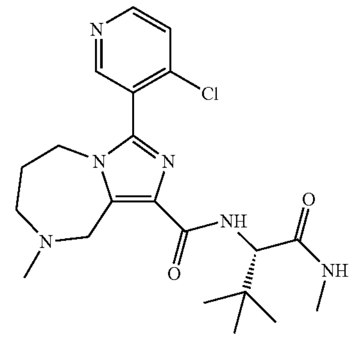 [SMILES: CNC(=O)[C@@H](NC(=O)c1nc(-c2cnccc2Cl)n2c1CN(C)CCC2)C(C)(C)C] | 433.1 | (S)-3-(4-chloropyridin-3-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 628 | 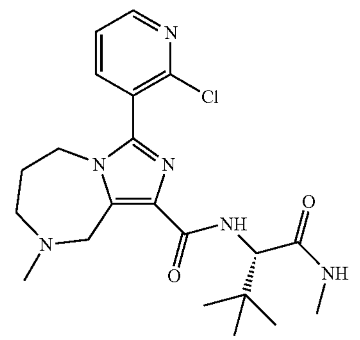 [SMILES: CNC(=O)[C@@H](NC(=O)c1nc(-c2cccnc2Cl)n2c1CN(C)CCC2)C(C)(C)C] | 433.1 | (S)-3-(2-chloropyridin-3-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 629 | 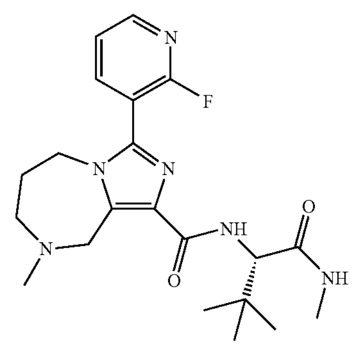 [SMILES: CNC(=O)[C@@H](NC(=O)c1nc(-c2cccnc2F)n2c1CN(C)CCC2)C(C)(C)C] | 417.1 | (S)-N-(3,3-dimethyl-1-(methylamino)-1-oxobutan-2-yl)-3-(2-fluoropyridin-3-yl)-8-methyl-6,7,8,9-tetrahydro-5H-imidazo[1,5-a][1,4]diazepine-1-carboxamide | 37 |
| 630 | 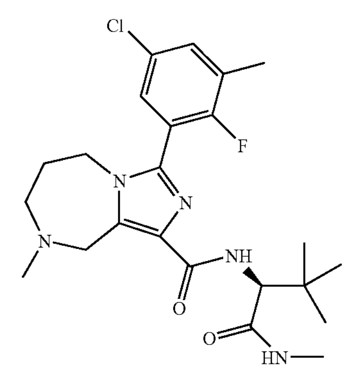 [SMILES: CNC(=O)[C@@H](NC(=O)c1nc(-c2cc(Cl)cc(C)c2F)n2c1CN(C)CCC2)C(C)(C)C] | 464.1 | (S)-3-(5-chloro-2-fluoro-3-methylphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |

TABLE 2-continued

| Cmpd No. | Structure | m/z | Chemical Name | Example No. |
|---|---|---|---|---|
| 631 | 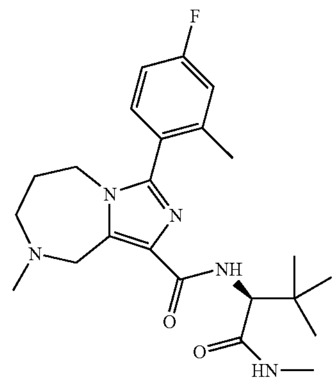 [SMILES: CNC(=O)[C@@H](NC(=O)c1nc(-c2ccc(F)cc2C)n2c1CN(C)CCC2)C(C)(C)C] | 430.2 | (S)-N-(3,3-dimethyl-1-(methylamino)-1-oxobutan-2-yl)-3-(4-fluoro-2-methylphenyl)-8-methyl-6,7,8,9-tetrahydro-5H-imidazo[1,5-a][1,4]diazepine-1-carboxamide | 37 |
| 632 | 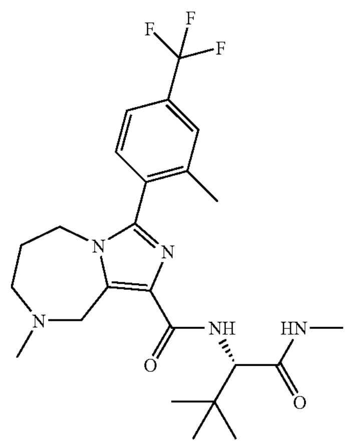 [SMILES: CNC(=O)[C@@H](NC(=O)c1nc(-c2ccc(C(F)(F)F)cc2C)n2c1CN(C)CCC2)C(C)(C)C] | 480.2 | (S)-N-(3,3-dimethyl-1-(methylamino)-1-oxobutan-2-yl)-8-methyl-3-(2-methyl-4-(trifluoromethyl)phenyl)-6,7,8,9-tetrahydro-5H-imidazo[1,5-a][1,4]diazepine-1-carboxamide | 37 |
| 633 | 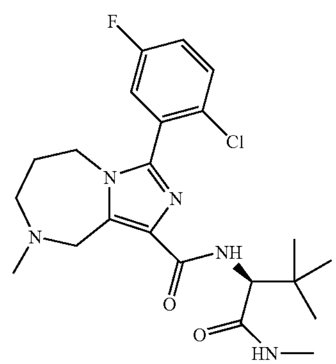 [SMILES: CNC(=O)[C@@H](NC(=O)c1nc(-c2cc(F)ccc2Cl)n2c1CN(C)CCC2)C(C)(C)C] | 450.1 | (S)-3-(2-chloro-5-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 634 | 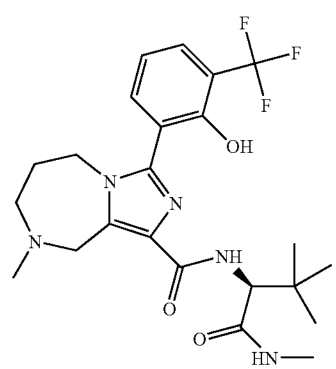 [SMILES: CNC(=O)[C@@H](NC(=O)c1nc(-c2cccc(C(F)(F)F)c2O)n2c1CN(C)CCC2)C(C)(C)C] | 482.1 | (S)-N-(3,3-dimethyl-1-(methylamino)-1-oxobutan-2-yl)-3-(2-hydroxy-3-(trifluoromethyl)phenyl)-8-methyl-6,7,8,9-tetrahydro-5H-imidazo[1,5-a][1,4]diazepine-1-carboxamide | 37 |

TABLE 2-continued

| Cmpd No. | Structure | m/z | Chemical Name | Example No. |
|---|---|---|---|---|
| 635 | 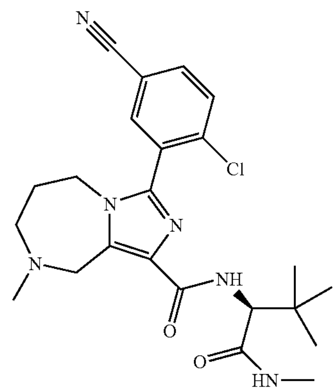 [SMILES: CNC(=O)[C@@H](NC(=O)c1nc(-c2cc(C#N)ccc2Cl)n2c1CN(C)CCC2)C(C)(C)C] | 457.1 | (S)-3-(2-chloro-5-cyanophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 636 | 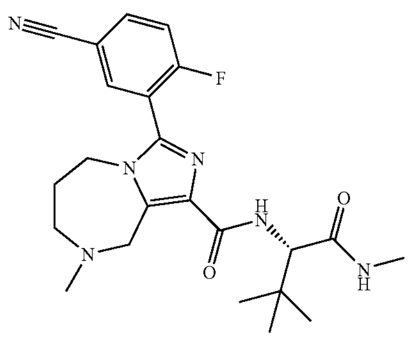 [SMILES: CNC(=O)[C@@H](NC(=O)c1nc(-c2cc(C#N)ccc2F)n2c1CN(C)CCC2)C(C)(C)C] | 441 | (S)-3-(5-cyano-2-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 637 | 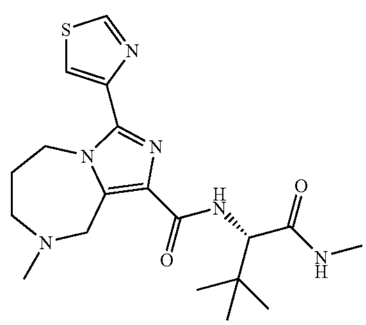 [SMILES: CNC(=O)[C@@H](NC(=O)c1nc(-c2cscn2)n2c1CN(C)CCC2)C(C)(C)C] | 405 | (S)-N-(3,3-dimethyl-1-(methylamino)-1-oxobutan-2-yl)-8-methyl-3-(thiazol-4-yl)-6,7,8,9-tetrahydro-5H-imidazo[1,5-a][1,4]diazepine-1-carboxamide | 37 |
| 638 | 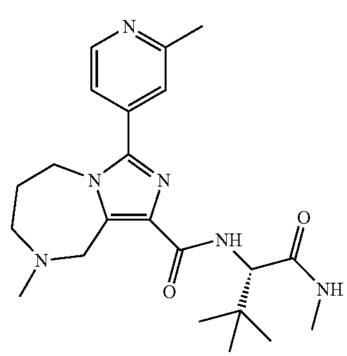 [SMILES: CNC(=O)[C@@H](NC(=O)c1nc(-c2ccnc(C)c2)n2c1CN(C)CCC2)C(C)(C)C] | 413.2 | (S)-N-(3,3-dimethyl-1-(methylamino)-1-oxobutan-2-yl)-8-methyl-3-(2-methylpyridin-4-yl)-6,7,8,9-tetrahydro-5H-imidazo[1,5-a][1,4]diazepine-1-carboxamide | 37 |

TABLE 2-continued

| Cmpd No. | Structure | m/z | Chemical Name | Example No. |
|---|---|---|---|---|
| 639 | 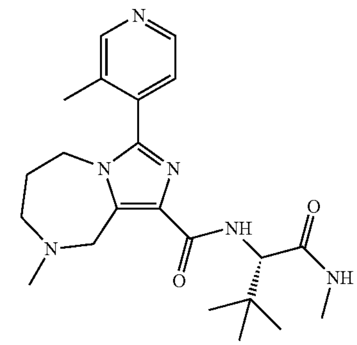 [SMILES: CNC(=O)[C@@H](NC(=O)c1nc(-c2ccncc2C)n2c1CN(C)CCC2)C(C)(C)C] | 413.2 | (S)-N-(3,3-dimethyl-1-(methylamino)-1-oxobutan-2-yl)-8-methyl-3-(4-methylpyridin-3-yl)-6,7,8,9-tetrahydro-5H-imidazo[1,5-a][1,4]diazepine-1-carboxamide | 37 |
| 640 | 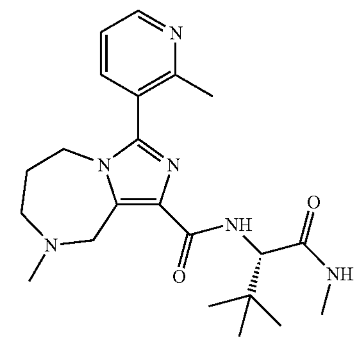 [SMILES: CNC(=O)[C@@H](NC(=O)c1nc(-c2cccnc2C)n2c1CN(C)CCC2)C(C)(C)C] | 413.2 | (S)-N-(3,3-dimethyl-1-(methylamino)-1-oxobutan-2-yl)-8-methyl-3-(2-methylpyridin-3-yl)-6,7,8,9-tetrahydro-5H-imidazo[1,5-a][1,4]diazepine-1-carboxamide | 37 |
| 641 | 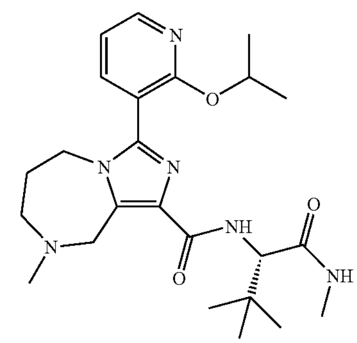 [SMILES: CNC(=O)[C@@H](NC(=O)c1nc(-c2cccnc2OC(C)C)n2c1CN(C)CCC2)C(C)(C)C] | 457.2 | (S)-N-(3,3-dimethyl-1-(methylamino)-1-oxobutan-2-yl)-3-(2-isopropoxypyridin-3-yl)-8-methyl-6,7,8,9-tetrahydro-5H-imidazo[1,5-a][1,4]diazepine-1-carboxamide | 37 |
| 642 | 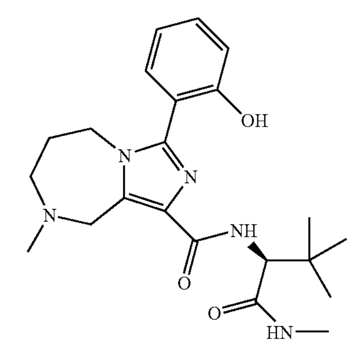 [SMILES: CNC(=O)[C@@H](NC(=O)c1nc(-c2ccccc2O)n2c1CN(C)CCC2)C(C)(C)C] | 414.2 | (S)-N-(3,3-dimethyl-1-(methylamino)-1-oxobutan-2-yl)-3-(2-hydroxyphenyl)-8-methyl-6,7,8,9-tetrahydro-5H-imidazo[1,5-a][1,4]diazepine-1-carboxamide | 37 |

TABLE 2-continued

| Cmpd No. | Structure | m/z | Chemical Name | Example No. |
|---|---|---|---|---|
| 643 | 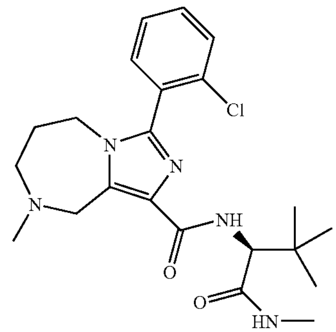 [SMILES: CNC(=O)[C@@H](NC(=O)c1nc(-c2ccccc2Cl)n2c1CN(C)CCC2)C(C)(C)C] | 432.1 | (S)-3-(2-chlorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 644 | 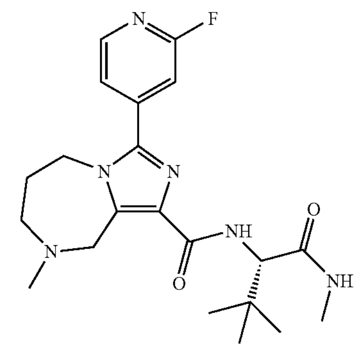 [SMILES: CNC(=O)[C@@H](NC(=O)c1nc(-c2ccnc(F)c2)n2c1CN(C)CCC2)C(C)(C)C] | 417.2 | (S)-N-(3,3-dimethyl-1-(methylamino)-1-oxobutan-2-yl)-3-(2-fluoropyridin-4-yl)-8-methyl-6,7,8,9-tetrahydro-5H-imidazo[1,5-a][1,4]diazepine-1-carboxamide | 37 |
| 645 | 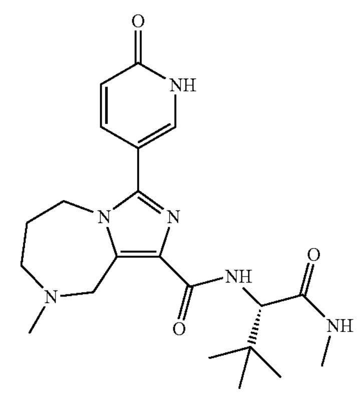 [SMILES: CNC(=O)[C@@H](NC(=O)c1nc(-c2ccc(=O)[nH]c2)n2c1CN(C)CCC2)C(C)(C)C] | 415.1 | (S)-N-(3,3-dimethyl-1-(methylamino)-1-oxobutan-2-yl)-8-methyl-3-(6-oxo-1,6-dihydropyridin-3-yl)-6,7,8,9-tetrahydro-5H-imidazo[1,5-a][1,4]diazepine-1-carboxamide | 37 |
| 646 | 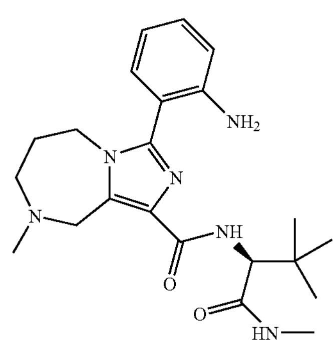 [SMILES: CNC(=O)[C@@H](NC(=O)c1nc(-c2ccccc2N)n2c1CN(C)CCC2)C(C)(C)C] | 413.2 | (S)-3-(2-aminophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |

TABLE 2-continued

| Cmpd No. | Structure | m/z | Chemical Name | Example No. |
|---|---|---|---|---|
| 647 | 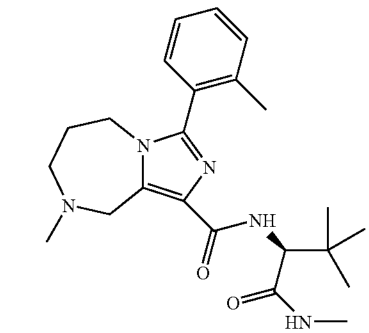 [SMILES: CNC(=O)[C@@H](NC(=O)c1nc(-c2ccccc2C)n2c1CN(C)CCC2)C(C)(C)C] | 412.2 | (S)-N-(3,3-dimethyl-1-(methylamino)-1-oxobutan-2-yl)-8-methyl-3-o-tolyl-6,7,8,9-tetrahydro-5H-imidazo[1,5-a][1,4]diazepine-1-carboxamide | 37 |
| 648 | 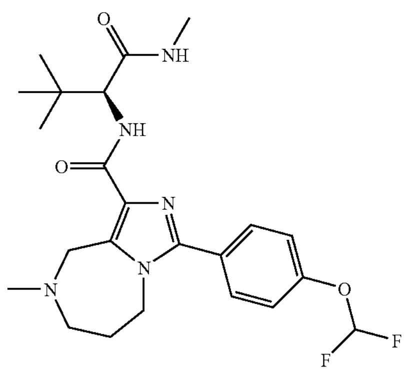 [SMILES: CNC(=O)[C@@H](NC(=O)c1nc(-c2ccc(OC(F)F)cc2)n2c1CN(C)CCC2)C(C)(C)C] | 464.2 | (S)-3-(4-(difluoromethoxy)phenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 649 | 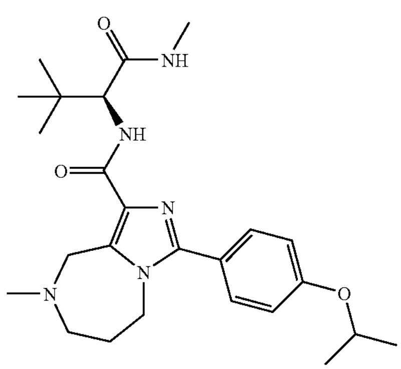 [SMILES: CNC(=O)[C@@H](NC(=O)c1nc(-c2ccc(OC(C)C)cc2)n2c1CN(C)CCC2)C(C)(C)C] | 456.2 | (S)-N-(3,3-dimethyl-1-(methylamino)-1-oxobutan-2-yl)-3-(4-isopropoxyphenyl)-8-methyl-6,7,8,9-tetrahydro-5H-imidazo[1,5-a][1,4]diazepine-1-carboxamide | 37 |
| 650 | 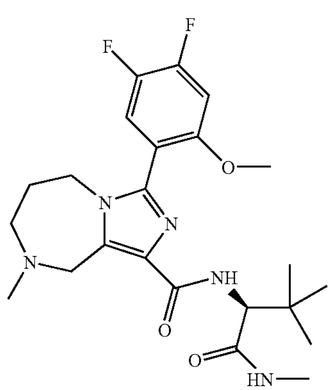 [SMILES: CNC(=O)[C@@H](NC(=O)c1nc(-c2cc(F)c(F)cc2OC)n2c1CN(C)CCC2)C(C)(C)C] | 464.2 | (S)-3-(4,5-difluoro-2-methoxyphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |

TABLE 2-continued

| Cmpd No. | Structure | m/z | Chemical Name | Example No. |
|---|---|---|---|---|
| 651 | 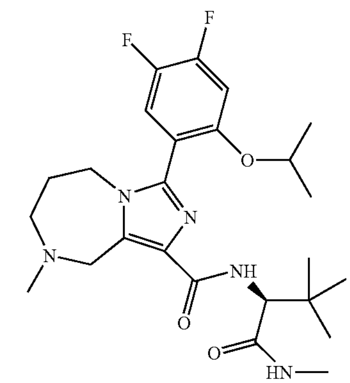 [SMILES: CNC(=O)[C@@H](NC(=O)c1nc(-c2cc(F)c(F)cc2OC(C)C)n2c1CN(C)CCC2)C(C)(C)C] | 492.2 | (S)-3-(4,5-difluoro-2-isopropoxyphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 652 | 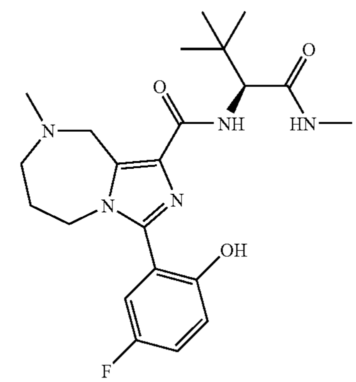 [SMILES: CNC(=O)[C@@H](NC(=O)c1nc(-c2cc(F)ccc2O)n2c1CN(C)CCC2)C(C)(C)C] | 432.2 | (S)-N-(3,3-dimethyl-1-(methylamino)-1-oxobutan-2-yl)-3-(5-fluoro-2-hydroxyphenyl)-8-methyl-6,7,8,9-tetrahydro-5H-imidazo[1,5-a][1,4]diazepine-1-carboxamide | 37 |
| 653 | 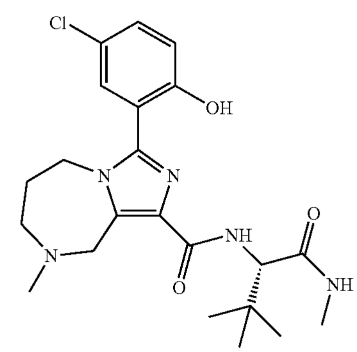 [SMILES: CNC(=O)[C@@H](NC(=O)c1nc(-c2cc(Cl)ccc2O)n2c1CN(C)CCC2)C(C)(C)C] | 448.1 | (S)-3-(5-chloro-2-hydroxyphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 654 | 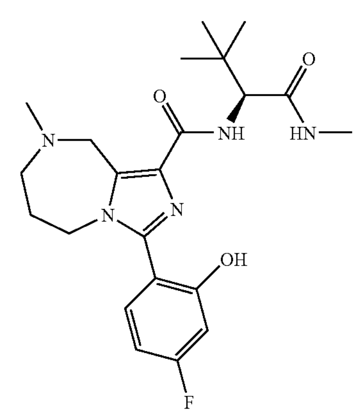 [SMILES: CNC(=O)[C@@H](NC(=O)c1nc(-c2ccc(F)cc2O)n2c1CN(C)CCC2)C(C)(C)C] | 432.1 | (S)-N-(3,3-dimethyl-1-(methylamino)-1-oxobutan-2-yl)-3-(4-fluoro-2-hydroxyphenyl)-8-methyl-6,7,8,9-tetrahydro-5H-imidazo[1,5-a][1,4]diazepine-1-carboxamide | 37 |

TABLE 2-continued

| Cmpd No. | Structure | m/z | Chemical Name | Example No. |
|---|---|---|---|---|
| 655 | 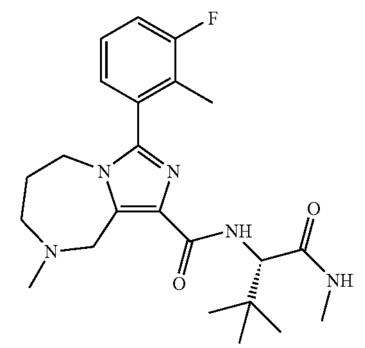 [SMILES: CNC(=O)[C@@H](NC(=O)c1nc(-c2cccc(F)c2C)n2c1CN(C)CCC2)C(C)(C)C] | 430.2 | (S)-N-(3,3-dimethyl-1-(methylamino)-1-oxobutan-2-yl)-3-(3-fluoro-2-methylphenyl)-8-methyl-6,7,8,9-tetrahydro-5H-imidazo[1,5-a][1,4]diazepine-1-carboxamide | 37 |
| 656 | 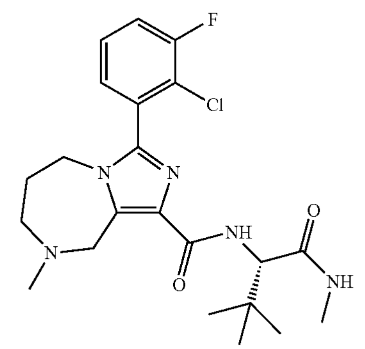 [SMILES: CNC(=O)[C@@H](NC(=O)c1nc(-c2cccc(F)c2Cl)n2c1CN(C)CCC2)C(C)(C)C] | 450.1 | (S)-3-(2-chloro-3-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 657 | 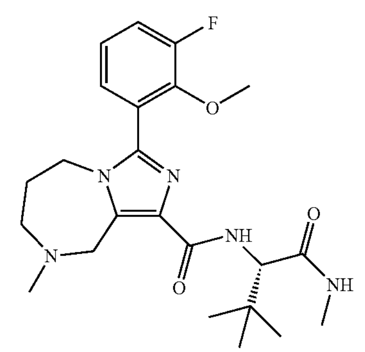 [SMILES: CNC(=O)[C@@H](NC(=O)c1nc(-c2cccc(F)c2OC)n2c1CN(C)CCC2)C(C)(C)C] | 446.2 | (S)-N-(3,3-dimethyl-1-(methylamino)-1-oxobutan-2-yl)-3-(3-fluoro-2-methoxyphenyl)-8-methyl-6,7,8,9-tetrahydro-5H-imidazo[1,5-a][1,4]diazepine-1-carboxamide | 37 |
| 658 | 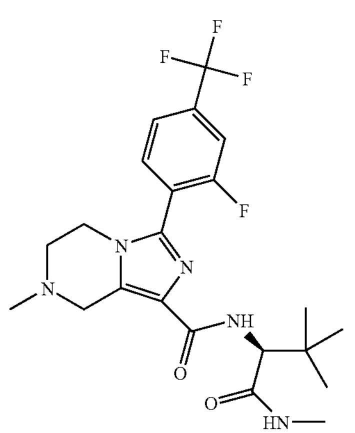 [SMILES: CNC(=O)[C@@H](NC(=O)c1nc(-c2ccc(C(F)(F)F)cc2F)n2c1CN(C)CC2)C(C)(C)C] | 470.1 | (S)-N-(3,3-dimethyl-1-(methylamino)-1-oxobutan-2-yl)-3-(2-fluoro-4-(trifluoromethyl)phenyl)-7-methyl-5,6,7,8-tetrahydroimidazo[1,5-a]pyrazine-1-carboxamide | 19 |

TABLE 2-continued

| Cmpd No. | Structure | m/z | Chemical Name | Example No. |
|---|---|---|---|---|
| 659 | 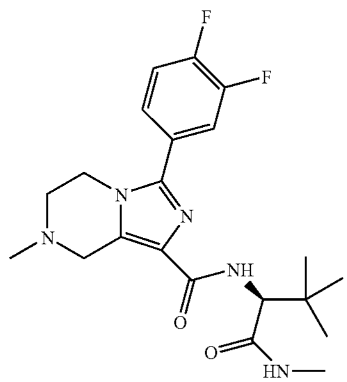 [SMILES: CNC(=O)[C@@H](NC(=O)c1nc(-c2ccc(F)c(F)c2)n2c1CN(C)CC2)C(C)(C)C] | 420.1 | (S)-3-(3,4-difluorophenyl)-N-(3,3-dimethyl-1-(methylamino)-1-oxobutan-2-yl)-7-methyl-5,6,7,8-tetrahydroimidazo[1,5-a]pyrazine-1-carboxamide | 19 |
| 660 | 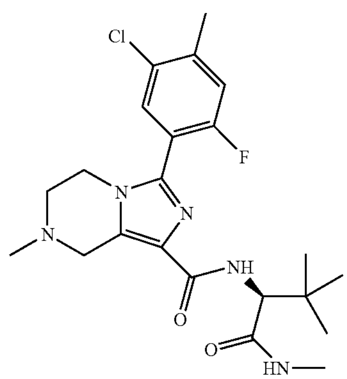 [SMILES: CNC(=O)[C@@H](NC(=O)c1nc(-c2cc(Cl)c(C)cc2F)n2c1CN(C)CC2)C(C)(C)C] | 450.1 | (S)-3-(5-chloro-2-fluoro-4-methylphenyl)-N-(3,3-dimethyl-1-(methylamino)-1-oxobutan-2-yl)-7-methyl-5,6,7,8-tetrahydroimidazo[1,5-a]pyrazine-1-carboxamide | 19 |
| 661 | 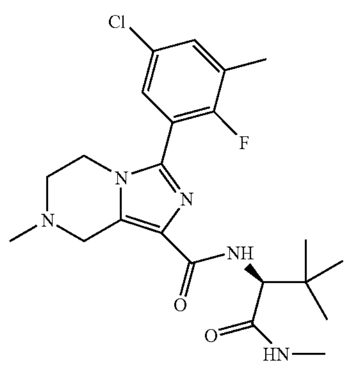 [SMILES: CNC(=O)[C@@H](NC(=O)c1nc(-c2cc(Cl)cc(C)c2F)n2c1CN(C)CC2)C(C)(C)C] | 450.1 | (S)-3-(5-chloro-2-fluoro-3-methylphenyl)-N-(3,3-dimethyl-1-(methylamino)-1-oxobutan-2-yl)-7-methyl-5,6,7,8-tetrahydroimidazo[1,5-a]pyrazine-1-carboxamide | 19 |
| 662 | 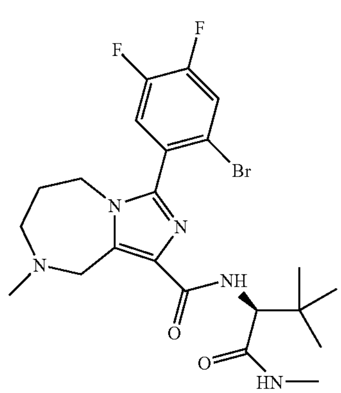 [SMILES: CNC(=O)[C@@H](NC(=O)c1nc(-c2cc(F)c(F)cc2Br)n2c1CN(C)CCC2)C(C)(C)C] | 512.1 | (S)-3-(2-bromo-4,5-difluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |

TABLE 2-continued

| Cmpd No. | Structure | m/z | Chemical Name | Example No. |
|---|---|---|---|---|
| 663 | 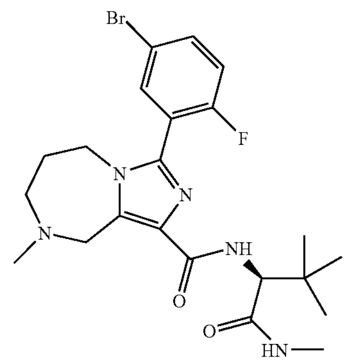 [SMILES: CNC(=O)[C@@H](NC(=O)c1nc(-c2cc(Br)ccc2F)n2c1CN(C)CCC2)C(C)(C)C] | 494.1 | (S)-3-(5-bromo-2-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 664 | 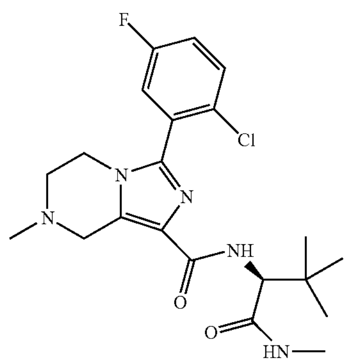 [SMILES: CNC(=O)[C@@H](NC(=O)c1nc(-c2cc(F)ccc2Cl)n2c1CN(C)CC2)C(C)(C)C] | 436.1 | (S)-3-(2-chloro-5-fluorophenyl)-N-(3,3-dimethyl-1-(methylamino)-1-oxobutan-2-yl)-7-methyl-5,6,7,8-tetrahydroimidazo[1,5-a]pyrazine-1-carboxamide | 19 |
| 665 | 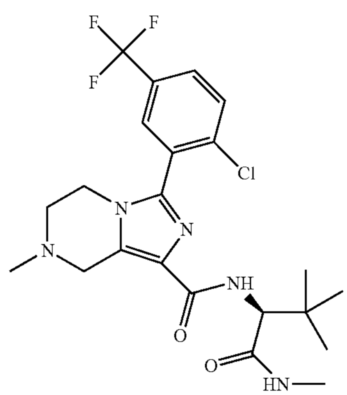 [SMILES: CNC(=O)[C@@H](NC(=O)c1nc(-c2cc(C(F)(F)F)ccc2Cl)n2c1CN(C)CC2)C(C)(C)C] | 486.1 | (S)-3-(2-chloro-5-(trifluoromethyl)phenyl)-N-(3,3-dimethyl-1-(methylamino)-5,6,7,8-tetrahydroimidazo[1,5-a]pyrazine-1-carboxamide | 19 |
| 666 | 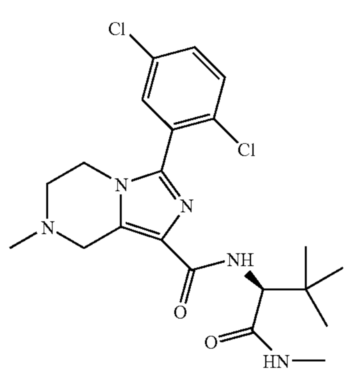 [SMILES: CNC(=O)[C@@H](NC(=O)c1nc(-c2cc(Cl)ccc2Cl)n2c1CN(C)CC2)C(C)(C)C] | 452.1 | (S)-3-(2,5-dichlorophenyl)-N-(3,3-dimethyl-1-(methylamino)-1-oxobutan-2-yl)-7-methyl-5,6,7,8-tetrahydroimidazo[1,5-a]pyrazine-1-carboxamide | 19 |

TABLE 2-continued

| Cmpd No. | Structure | m/z | Chemical Name | Example No. |
|---|---|---|---|---|
| 667 | 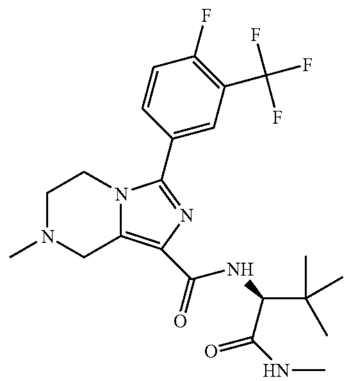 [SMILES: CNC(=O)[C@@H](NC(=O)c1nc(-c2ccc(F)c(C(F)(F)F)c2)n2c1CN(C)CC2)C(C)(C)C] | 470.1 | (S)-N-(3,3-dimethyl-1-(methylamino)-1-oxobutan-2-yl)-3-(4-fluoro-3-(trifluoromethyl)phenyl)-7-methyl-5,6,7,8-tetrahydroimidazo[1,5-a]pyrazine-1-carboxamide | 19 |
| 668 | 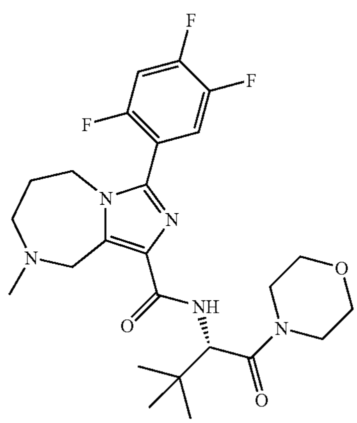 [SMILES: CN1CCCn2c(-c3cc(F)c(F)cc3F)nc(C(=O)N[C@H](C(=O)N3CCOCC3)C(C)(C)C)c2C1] | 508 | (S)-N-(3,3-dimethyl-1-morpholino-1-oxobutan-2-yl)-8-methyl-3-(2,4,5-trifluorophenyl)-6,7,8,9-tetrahydro-5H-imidazo[1,5-a][1,4]diazepine-1-carboxamide | 67 |
| 669 | 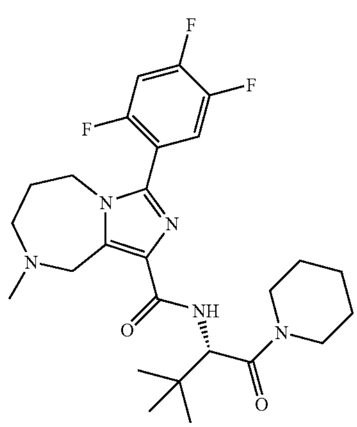 [SMILES: CN1CCCn2c(-c3cc(F)c(F)cc3F)nc(C(=O)N[C@H](C(=O)N3CCCCC3)C(C)(C)C)c2C1] | 506 | (S)-N-(3,3-dimethyl-1-oxo-1-(piperidin-1-yl)butan-2-yl)-8-methyl-3-(2,4,5-trifluorophenyl)-6,7,8,9-tetrahydro-5H-imidazo[1,5-a][1,4]diazepine-1-carboxamide | 67 |

TABLE 2-continued

| Cmpd No. | Structure | m/z | Chemical Name | Example No. |
|---|---|---|---|---|
| 670 | 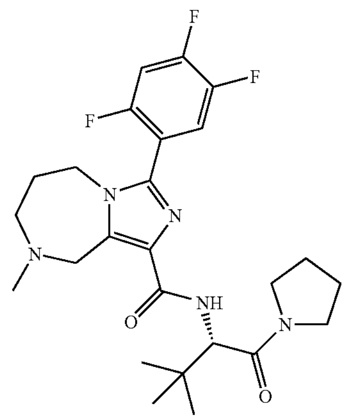 [SMILES: CN1CCCn2c(-c3cc(F)c(F)cc3F)nc(C(=O)N[C@H](C(=O)N3CCCC3)C(C)(C)C)c2C1] | 492 | (S)-N-(3,3-dimethyl-1-oxo-1-(pyrrolidin-1-yl)butan-2-yl)-8-methyl-3-(2,4,5-trifluorophenyl)-6,7,8,9-tetrahydro-5H-imidazo[1,5-a][1,4]diazepine-1-carboxamide | 67 |
| 671 | 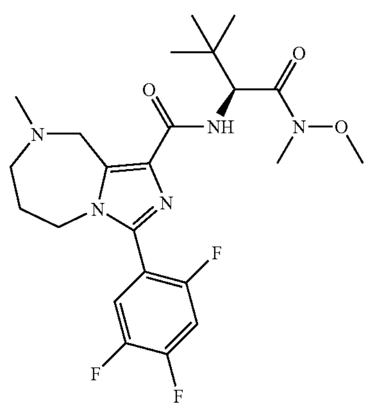 [SMILES: CON(C)C(=O)[C@@H](NC(=O)c1nc(-c2cc(F)c(F)cc2F)n2c1CN(C)CCC2)C(C)(C)C] | 482 | (S)-N-(1-(methoxy(methyl)amino)-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide | 67 |
| 672 | 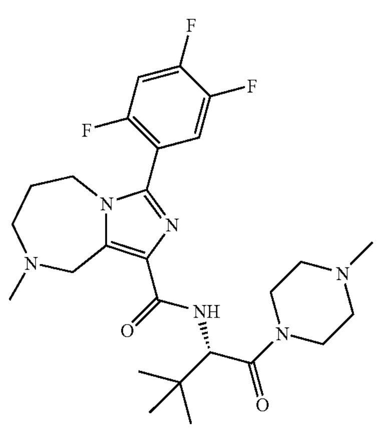 | 521 | (S)-N-(3,3-dimethyl-1-(4-methylpiperazin-1-yl)-1-oxobutan-2-yl)-8-methyl-3-(2,4,5-trifluorophenyl)-6,7,8,9-tetrahydro-5H-imidazo[1,5-a][1,4]diazepine-1-carboxamide | 67 |

TABLE 2-continued

| Cmpd No. | Structure | m/z | Chemical Name | Example No. |
|---|---|---|---|---|
| 673 | 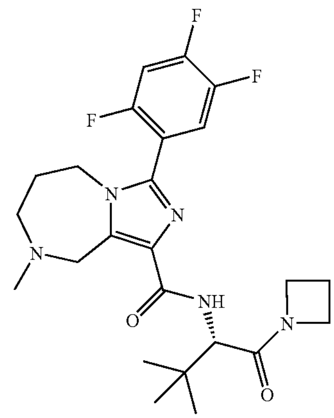 [SMILES: CN1CCCn2c(-c3cc(F)c(F)cc3F)nc(C(=O)N[C@H](C(=O)N3CCC3)C(C)(C)C)c2C1] | 478 | (S)-N-(1-(azetidin-1-yl)-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide | 67 |
| 674 | 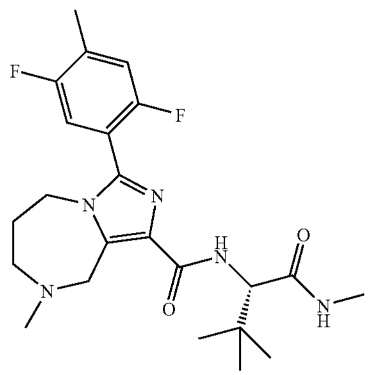 [SMILES: CNC(=O)[C@@H](NC(=O)c1nc(-c2cc(F)c(C)cc2F)n2c1CN(C)CCC2)C(C)(C)C] | 448.2 | (S)-3-(2,5-difluoro-4-methylphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 675 | 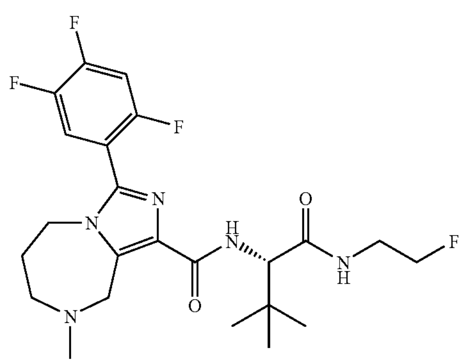 [SMILES: CN1CCCn2c(-c3cc(F)c(F)cc3F)nc(C(=O)N[C@H](C(=O)NCCF)C(C)(C)C)c2C1] | 484 | (S)-N-(1-(2-fluoroethylamino)-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide | 67 |
| 676 | 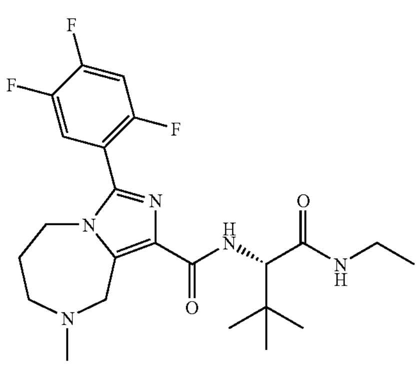 [SMILES: CCNC(=O)[C@@H](NC(=O)c1nc(-c2cc(F)c(F)cc2F)n2c1CN(C)CCC2)C(C)(C)C] | 466.3 | (S)-N-(1-(ethylamino)-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide | 67 |

TABLE 2-continued

| Cmpd No. | Structure | m/z | Chemical Name | Example No. |
|---|---|---|---|---|
| 677 | 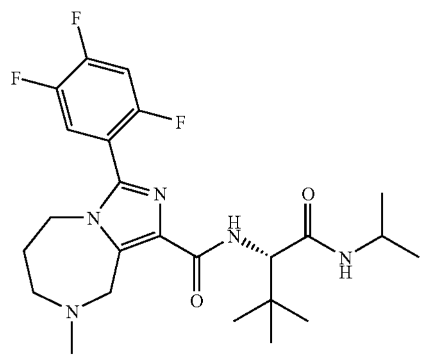 [SMILES: CC(C)NC(=O)[C@@H](NC(=O)c1nc(-c2cc(F)c(F)cc2F)n2c1CN(C)CCC2)C(C)(C)C] | 480 | (S)-N-(1-(isopropylamino)-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide | 67 |
| 678 | 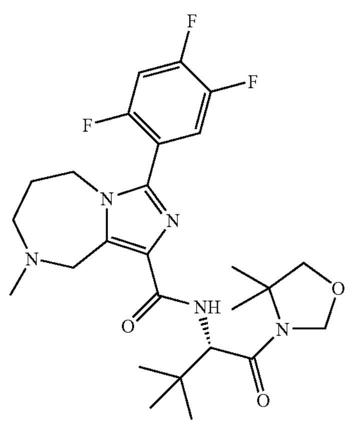 [SMILES: CN1CCCn2c(-c3cc(F)c(F)cc3F)nc(C(=O)N[C@H](C(=O)N3COCC3(C)C)C(C)(C)C)c2C1] | 522 | (S)-N-(1-(4,4-dimethyloxazolidin-3-yl)-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide | 67 |
| 679 | 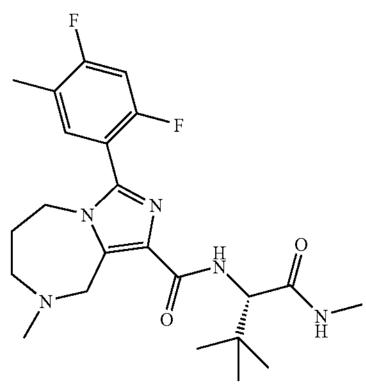 [SMILES: CNC(=O)[C@@H](NC(=O)c1nc(-c2cc(C)c(F)cc2F)n2c1CN(C)CCC2)C(C)(C)C] | 448 | (S)-3-(2,4-difluoro-5-methylphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |

TABLE 2-continued

| Cmpd No. | Structure | m/z | Chemical Name | Example No. |
|---|---|---|---|---|
| 680 | 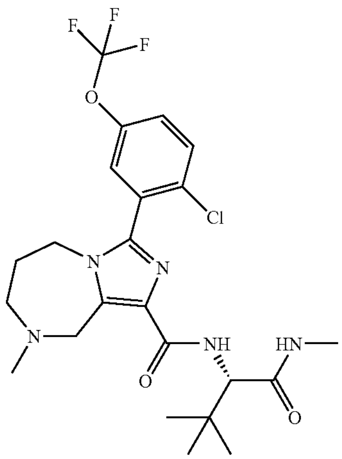 [SMILES: CNC(=O)[C@@H](NC(=O)c1nc(-c2cc(OC(F)(F)F)ccc2Cl)n2c1CN(C)CCC2)C(C)(C)C] | 516.1 | (S)-3-(2-chloro-5-(trifluoromethoxy)phenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 681 | 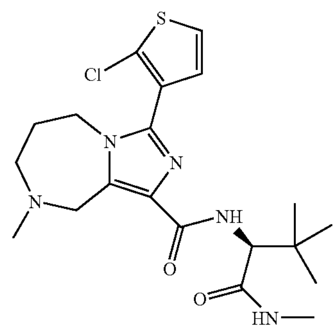 [SMILES: CNC(=O)[C@@H](NC(=O)c1nc(-c2ccsc2Cl)n2c1CN(C)CCC2)C(C)(C)C] | 438.1 | (S)-3-(2-chlorothiophen-3-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 682 | 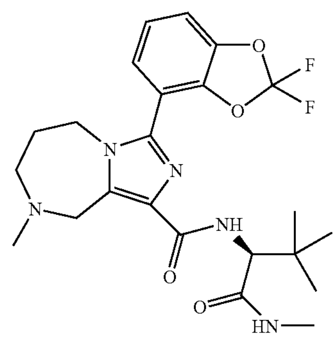 [SMILES: CNC(=O)[C@@H](NC(=O)c1nc(-c2cccc3c2OC(F)(F)O3)n2c1CN(C)CCC2)C(C)(C)C] | 478.2 | (S)-3-(2,2-difluorobenzo[d][1,3]dioxol-4-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 683 | 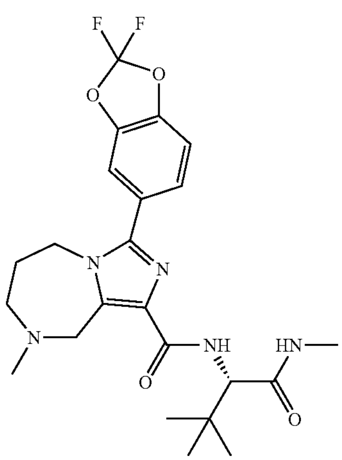 [SMILES: CNC(=O)[C@@H](NC(=O)c1nc(-c2ccc3c(c2)OC(F)(F)O3)n2c1CN(C)CCC2)C(C)(C)C] | 478.1 | (S)-3-(2,2-difluorobenzo[d][1,3]dioxol-5-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |

TABLE 2-continued

| Cmpd No. | Structure | m/z | Chemical Name | Example No. |
|---|---|---|---|---|
| 684 | 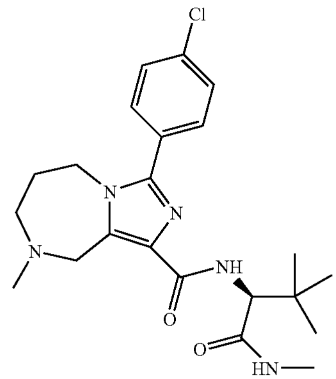 [SMILES: CNC(=O)[C@@H](NC(=O)c1nc(-c2ccc(Cl)cc2)n2c1CN(C)CCC2)C(C)(C)C] | 432.1 | (S)-3-(4-chlorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 685 | 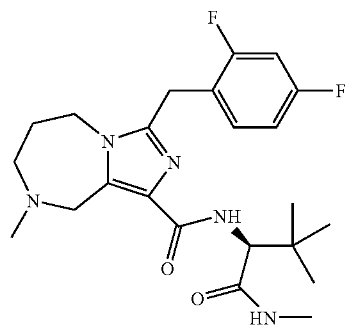 [SMILES: CNC(=O)[C@@H](NC(=O)c1nc(Cc2ccc(F)cc2F)n2c1CN(C)CCC2)C(C)(C)C] | 448.2 | (S)-3-(2,4-difluorobenzyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 68 |
| 686 | 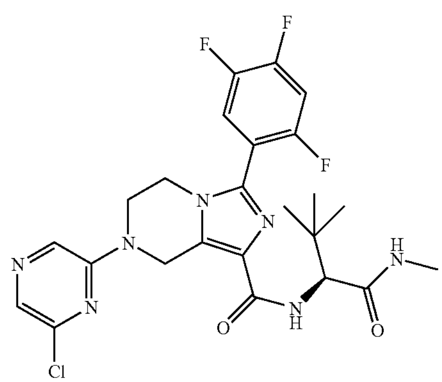 [SMILES: CNC(=O)[C@@H](NC(=O)c1nc(-c2cc(F)c(F)cc2F)n2c1CN(c1cncc(Cl)n1)CC2)C(C)(C)C] | 536 | (S)-7-(6-chloropyrazin-2-yl)-N-(3,3-dimethyl-1-(methylamino)-1-oxobutan-2-yl)-3-(2,4,5-trifluorophenyl)-5,6,7,8-tetrahydroimidazo[1,5-a]pyrazine-1-carboxamide | 29 |
| 687 | 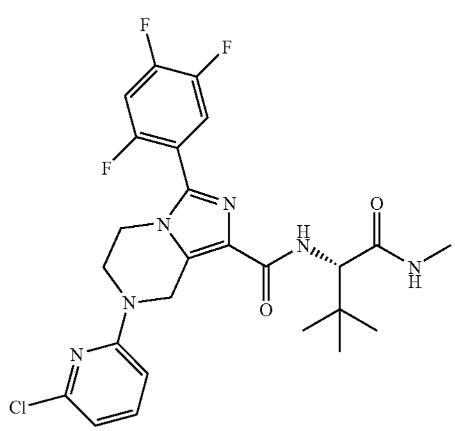 [SMILES: CNC(=O)[C@@H](NC(=O)c1nc(-c2cc(F)c(F)cc2F)n2c1CN(c1cccc(Cl)n1)CC2)C(C)(C)C] | 535 | (S)-7-(6-chloropyridin-2-yl)-N-(3,3-dimethyl-1-(methylamino)-1-oxobutan-2-yl)-3-(2,4,5-trifluorophenyl)-5,6,7,8-tetrahydroimidazo[1,5-a]pyrazine-1-carboxamide | 29 |

TABLE 2-continued

| Cmpd No. | Structure | m/z | Chemical Name | Example No. |
|---|---|---|---|---|
| 688 | 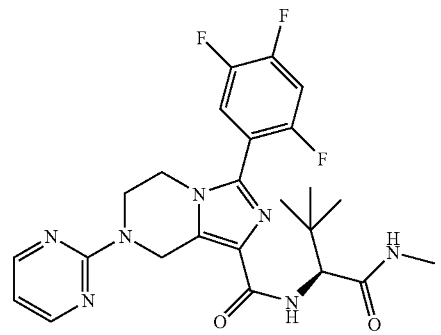 [SMILES: CNC(=O)[C@@H](NC(=O)c1nc(-c2cc(F)c(F)cc2F)n2c1CN(c1ncccn1)CC2)C(C)(C)C] | 502 | (S)-N-(3,3-dimethyl-1-(methylamino)-1-oxobutan-2-yl)-7-(pyrimidin-2-yl)-3-(2,4,5-trifluorophenyl)-5,6,7,8-tetrahydroimidazo[1,5-a]pyrazine-1-carboxamide | 29 |
| 689 | 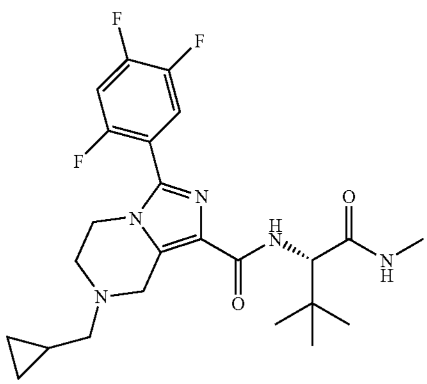 [SMILES: CNC(=O)[C@@H](NC(=O)c1nc(-c2cc(F)c(F)cc2F)n2c1CN(CC1CC1)CC2)C(C)(C)C] | 478 | (S)-7-(cyclopropylmethyl)-N-(3,3-dimethyl-1-(methylamino)-1-oxobutan-2-yl)-3-(2,4,5-trifluorophenyl)-5,6,7,8-tetrahydroimidazo[1,5-a]pyrazine-1-carboxamide | 5 |
| 690 | 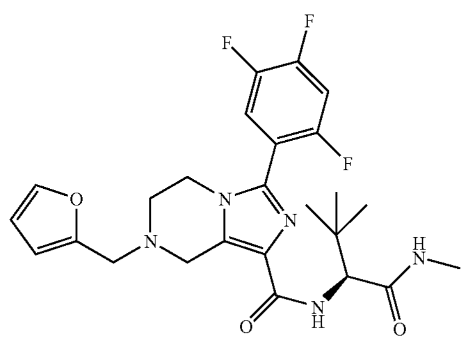 [SMILES: CNC(=O)[C@@H](NC(=O)c1nc(-c2cc(F)c(F)cc2F)n2c1CN(Cc1ccco1)CC2)C(C)(C)C] | 504 | (S)-N-(3,3-dimethyl-1-(methylamino)-1-oxobutan-2-yl)-7-(furan-2-ylmethyl)-3-(2,4,5-trifluorophenyl)-5,6,7,8-tetrahydroimidazo[1,5-a]pyrazine-1-carboxamide | 5 |
| 691 | 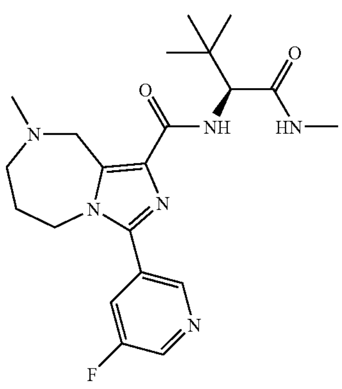 [SMILES: CNC(=O)[C@@H](NC(=O)c1nc(-c2cncc(F)c2)n2c1CN(C)CCC2)C(C)(C)C] | 417.15 | (S)-N-(3,3-dimethyl-1-(methylamino)-1-oxobutan-2-yl)-3-(5-fluoropyridin-3-yl)-8-methyl-6,7,8,9-tetrahydro-5H-imidazo[1,5-a][1,4]diazepine-1-carboxamide | 37 |

TABLE 2-continued

| Cmpd No. | Structure | m/z | Chemical Name | Example No. |
|---|---|---|---|---|
| 692 | 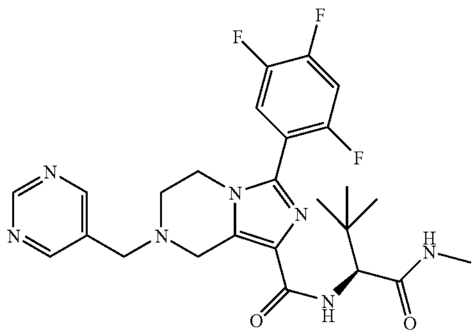 [SMILES: CNC(=O)[C@@H](NC(=O)c1nc(-c2cc(F)c(F)cc2F)n2c1CN(Cc1cncnc1)CC2)C(C)(C)C] | 516 | (S)-N-(3,3-dimethyl-1-(methylamino)-1-oxobutan-2-yl)-7-(pyrimidin-5-ylmethyl)-3-(2,4,5-trifluorophenyl)-5,6,7,8-tetrahydroimidazo[1,5-a]pyrazine-1-carboxamide | 5 |
| 693 | 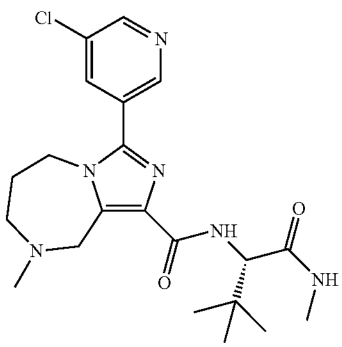 [SMILES: CNC(=O)[C@@H](NC(=O)c1nc(-c2cncc(Cl)c2)n2c1CN(C)CCC2)C(C)(C)C] | 433.1 | (S)-3-(5-chloropyridin-3-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 694 | 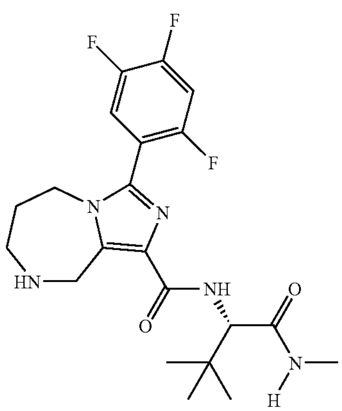 [SMILES: CNC(=O)[C@@H](NC(=O)c1nc(-c2cc(F)c(F)cc2F)n2c1CNCCC2)C(C)(C)C] | 438.1 | (S)-N-(3,3-dimethyl-1-(methylamino)-1-oxobutan-2-yl)-3-(2,4,5-trifluorophenyl)-6,7,8,9-tetrahydro-5H-imidazo[1,5-a][1,4]diazepine-1-carboxamide | 39 |
| 695 | 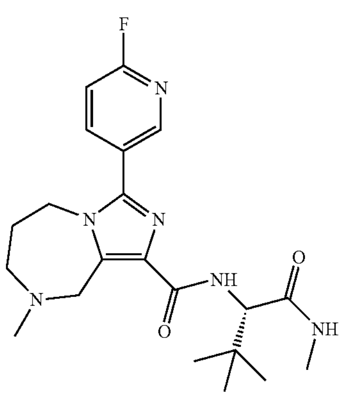 [SMILES: CNC(=O)[C@@H](NC(=O)c1nc(-c2ccc(F)nc2)n2c1CN(C)CCC2)C(C)(C)C] | 471.2 | (S)-N-(3,3-dimethyl-1-(methylamino)-1-oxobutan-2-yl)-3-(6-fluoropyridin-3-yl)-8-methyl-6,7,8,9-tetrahydro-5H-imidazo[1,5-a][1,4]diazepine-1-carboxamide | 37 |

TABLE 2-continued

| Cmpd No. | Structure | m/z | Chemical Name | Example No. |
|---|---|---|---|---|
| 696 | 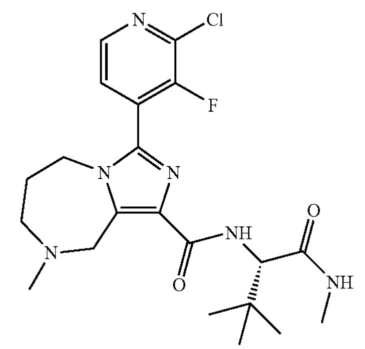 [SMILES: CNC(=O)[C@@H](NC(=O)c1nc(-c2ccnc(Cl)c2F)n2c1CN(C)CCC2)C(C)(C)C] | 451.1 | (S)-3-(2-chloro-3-fluoropyridin-4-yl)-N-(3,3-dimethyl-1-(methylamino)-1-oxobutan-2-yl)-8-methyl-6,7,8,9-tetrahydro-5H-imidazo[1,5-a][1,4 diazepine-1-carboxamide | 37 |
| 697 | 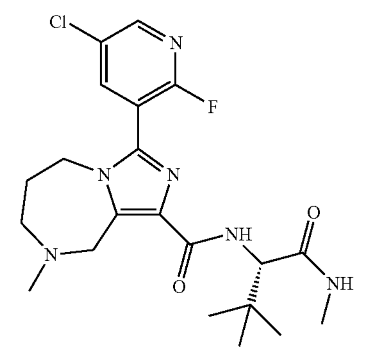 [SMILES: CNC(=O)[C@@H](NC(=O)c1nc(-c2cc(Cl)cnc2F)n2c1CN(C)CCC2)C(C)(C)C] | 451.1 | (S)-3-(5-chloro-2-fluoropyridin-3-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 698 | 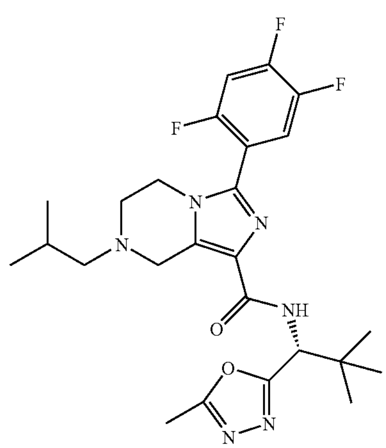 [SMILES: Cc1nnc([C@H](NC(=O)c2nc(-c3cc(F)c(F)cc3F)n3c2CN(CC(C)C)CC3)C(C)(C)C)o1] | 505.2 | (R)-N-(2,2-dimethyl-1-(5-methyl-1,3,4-oxadiazol-2-yl)propyl)-7-isobutyl-3-(2,4,5-trifluorophenyl)-5,6,7,8-tetrahydroimidazo[1,5-a]pyrazine-1-carboxamide | 14 |
| 699 | 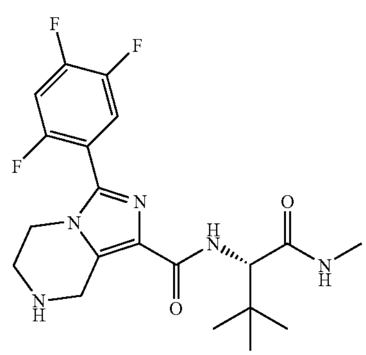 [SMILES: CNC(=O)[C@@H](NC(=O)c1nc(-c2cc(F)c(F)cc2F)n2c1CNCC2)C(C)(C)C] | 424 | (S)-N-(3,3-dimethyl-1-(methylamino)-1-oxobutan-2-yl)-3-(2,4,5-trifluorophenyl)-5,6,7,8-tetrahydroimidazo[1,5-a]pyrazine-1-carboxamide | 2 |

TABLE 2-continued

| Cmpd No. | Structure | m/z | Chemical Name | Example No. |
|---|---|---|---|---|
| 700 | 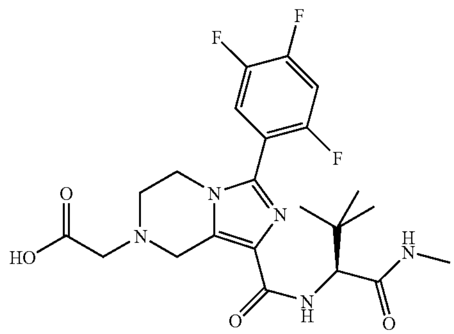 [SMILES: CNC(=O)[C@@H](NC(=O)c1nc(-c2cc(F)c(F)cc2F)n2c1CN(CC(=O)O)CC2)C(C)(C)C] | 482 | (S)-2-(1-(3,3-dimethyl-1-(methylamino)-1-oxobutan-2-ylcarbamoyl)-3-(2,4,5-trifluorophenyl)-5,6-dihydroimidazo[1,5-a]pyrazin-7(8H)-yl)acetic acid | 69 |
| 701 | 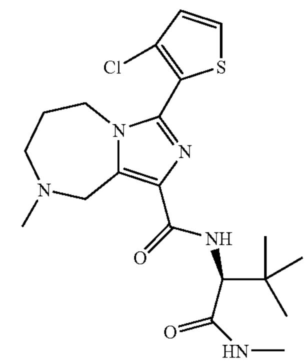 [SMILES: CNC(=O)[C@@H](NC(=O)c1nc(-c2sccc2Cl)n2c1CN(C)CCC2)C(C)(C)C] | 438.1 | (S)-3-(3-chlorothiophen-2-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 702 | 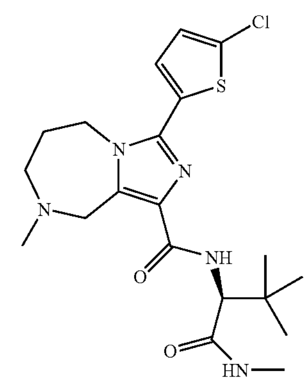 [SMILES: CNC(=O)[C@@H](NC(=O)c1nc(-c2ccc(Cl)s2)n2c1CN(C)CCC2)C(C)(C)C] | 438.1 | (S)-3-(5-chlorothiophen-2-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 703 | 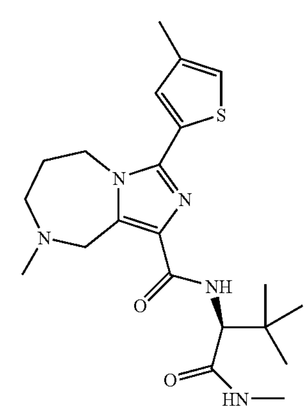 [SMILES: CNC(=O)[C@@H](NC(=O)c1nc(-c2cc(C)cs2)n2c1CN(C)CCC2)C(C)(C)C] | 418.2 | (S)-N-(3,3-dimethyl-1-(methylamino)-1-oxobutan-2-yl)-8-methyl-3-(4-methylthiophen-2-yl)-6,7,8,9-tetrahydro-5H-imidazo[1,5-a][1,4]diazepine-1-carboxamide | 37 |

TABLE 2-continued

| Cmpd No. | Structure | m/z | Chemical Name | Example No. |
|---|---|---|---|---|
| 704 | 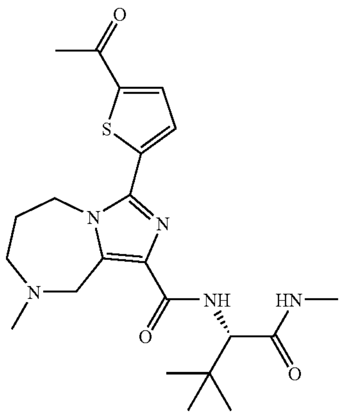 [SMILES: CNC(=O)[C@@H](NC(=O)c1nc(-c2ccc(C(C)=O)s2)n2c1CN(C)CCC2)C(C)(C)C] | 446.1 | (S)-3-(5-acetylthiophen-2-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 705 | 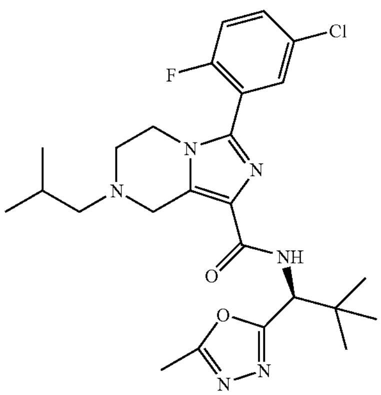 [SMILES: Cc1nnc([C@@H](NC(=O)c2nc(-c3cc(Cl)ccc3F)n3c2CN(CC(C)C)CC3)C(C)(C)C)o1] | 503.1 | (S)-3-(5-chloro-2-fluorophenyl)-N-(2,2-dimethyl-1-(5-methyl-1,3,4-oxadiazol-2-yl)propyl)-7-isobutyl-5,6,7,8-tetrahydroimidazo[1,5-a]pyrazine-1-carboxamide | 14 |
| 706 | 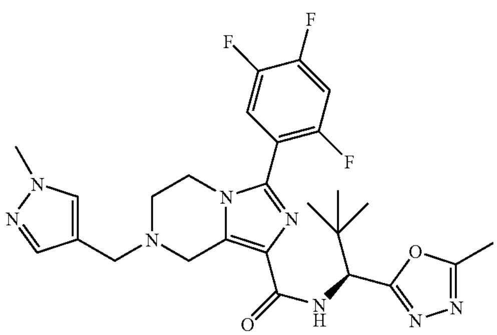 [SMILES: Cc1nnc([C@@H](NC(=O)c2nc(-c3cc(F)c(F)cc3F)n3c2CN(Cc2cnn(C)c2)CC3)C(C)(C)C)o1] | 543.1 | (S)-N-(2,2-dimethyl-1-(5-methyl-1,3,4-oxadiazol-2-yl)propyl)-7-((1-methyl-1H-pyrazol-4-yl)methyl)-3-(2,4,5-trifluorophenyl)-5,6,7,8-tetrahydroimidazo[1,5-a]pyrazine-1-carboxamide | 14 |
| 707 | 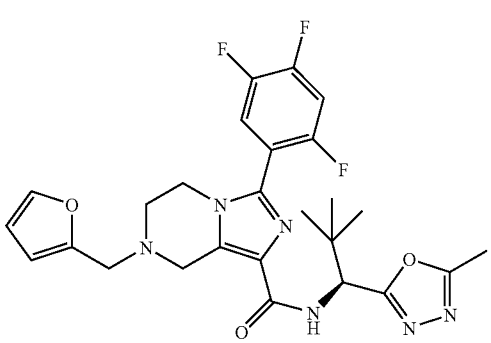 [SMILES: Cc1nnc([C@@H](NC(=O)c2nc(-c3cc(F)c(F)cc3F)n3c2CN(Cc2ccco2)CC3)C(C)(C)C)o1] | 529.1 | (S)-N-(2,2-dimethyl-1-(5-methyl-1,3,4-oxadiazol-2-yl)propyl)-7-(furan-2-ylmethyl)-3-(2,4,5-trifluorophenyl)-5,6,7,8-tetrahydroimidazo[1,5-a]pyrazine-1-carboxamide | 14 |

TABLE 2-continued

| Cmpd No. | Structure | m/z | Chemical Name | Example No. |
|---|---|---|---|---|
| 708 | 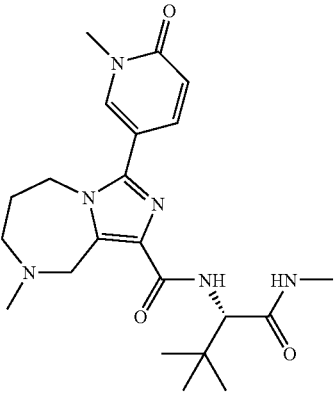 [SMILES: CNC(=O)[C@@H](NC(=O)c1nc(-c2ccc(=O)n(C)c2)n2c1CN(C)CCC2)C(C)(C)C] | 429.2 | (S)-N-(3,3-dimethyl-1-(methylamino)-1-oxobutan-2-yl)-8-methyl-3-(1-methyl-6-oxo-1,6-dihydropyridin-3-yl)-6,7,8,9-tetrahydro-5H-imidazo[1,5-a][1,4]diazepine-1-carboxamide | 37 |
| 709 | 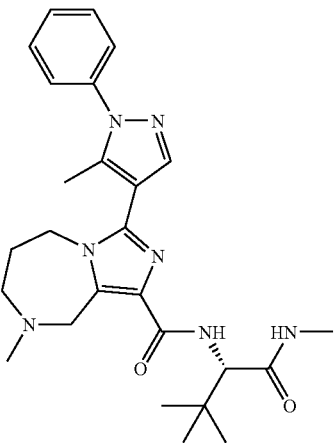 [SMILES: CNC(=O)[C@@H](NC(=O)c1nc(-c2cnn(-c3ccccc3)c2C)n2c1CN(C)CCC2)C(C)(C)C] | 478.2 | (S)-N-(3,3-dimethyl-1-(methylamino)-1-oxobutan-2-yl)-8-methyl-3-(5-methyl-1-phenyl-1H-pyrazol-4-yl)-6,7,8,9-tetrahydro-5H-imidazo[1,5-a][1,4]diazepine-1-carboxamide | 37 |
| 710 | 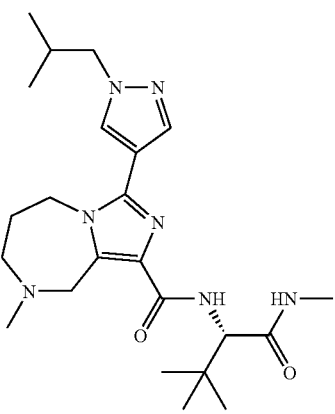 [SMILES: CNC(=O)[C@@H](NC(=O)c1nc(-c2cnn(CC(C)C)c2)n2c1CN(C)CCC2)C(C)(C)C] | 444.2 | (S)-N-(3,3-dimethyl-1-(methylamino)-1-oxobutan-2-yl)-3-(1-isobutyl-1H-pyrazol-4-yl)-8-methyl-6,7,8,9-tetrahydro-5H-imidazo[1,5-a][1,4]diazepine-1-carboxamide | 37 |

TABLE 2-continued

| Cmpd No. | Structure | m/z | Chemical Name | Example No. |
|---|---|---|---|---|
| 711 | 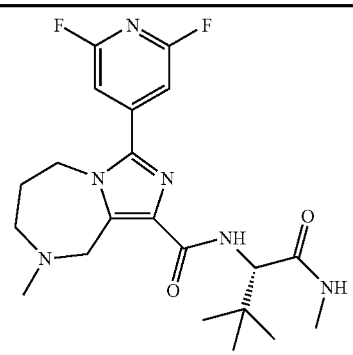 | 435.2 | (S)-3-(2,6-difluoropyridin-4-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 37 |
| 712 | 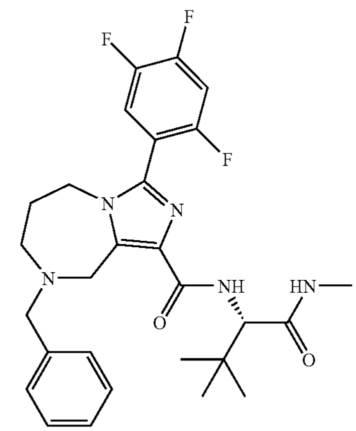 [SMILES: CNC(=O)[C@@H](NC(=O)c1nc(-c2cc(F)c(F)cc2F)n2c1CN(Cc1ccccc1)CCC2)C(C)(C)C] | 528 | (S)-8-benzyl-N-(3,3-dimethyl-1-(methylamino)-1-oxobutan-2-yl)-3-(2,4,5-trifluorophenyl)-6,7,8,9-tetrahydro-5H-imidazo[1,5-a][1,4]diazepine-1-carboxamide | 35 |
| 713 | 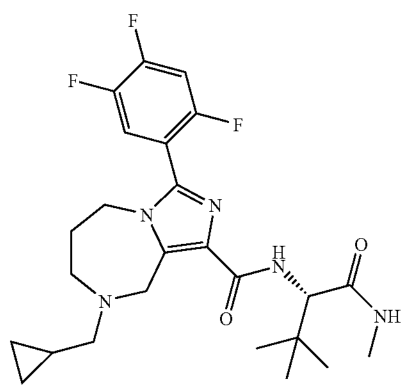 [SMILES: CNC(=O)[C@@H](NC(=O)c1nc(-c2cc(F)c(F)cc2F)n2c1CN(CC1CC1)CCC2)C(C)(C)C] | 492 | (S)-8-(cyclopropylmethyl)-N-(3,3-dimethyl-1-(methylamino)-1-oxobutan-2-yl)-3-(2,4,5-trifluorophenyl)-6,7,8,9-tetrahydro-5H-imidazo[1,5-a][1,4]diazepine-1-carboxamide | 35 |
| 714 | 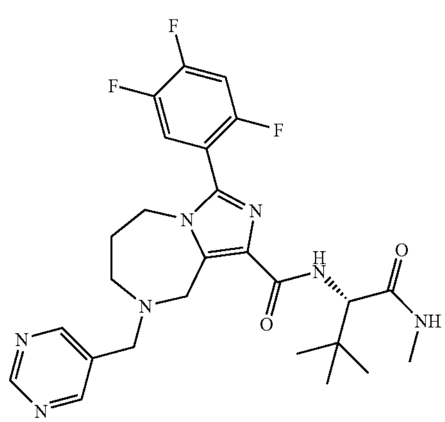 [SMILES: CNC(=O)[C@@H](NC(=O)c1nc(-c2cc(F)c(F)cc2F)n2c1CN(Cc1cncnc1)CCC2)C(C)(C)C] | 530 | (S)-N-(3,3-dimethyl-1-(methylamino)-1-oxobutan-2-yl)-8-(pyrimidin-5-ylmethyl)-3-(2,4,5-trifluorophenyl)-6,7,8,9-tetrahydro-5H-imidazo[1,5-a][1,4]diazepine-1-carboxamide | 35 |

TABLE 2-continued

| Cmpd No. | Structure | m/z | Chemical Name | Example No. |
|---|---|---|---|---|
| 715 | 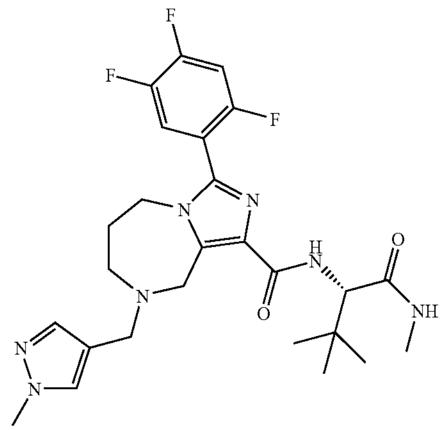 [SMILES: CNC(=O)[C@@H](NC(=O)c1nc(-c2cc(F)c(F)cc2F)n2c1CN(Cc1cnn(C)c1)CCC2)C(C)(C)C] | 532 | (S)-N-(3,3-dimethyl-1-(methylamino)-1-oxobutan-2-yl)-8-((1-methyl-1H-pyrazol-4-yl)methyl)-3-(2,4,5-trifluorophenyl)-6,7,8,9-tetrahydro-5H-imidazo[1,5-a][1,4]diazepine-1-carboxamide | 35 |
| 716 | 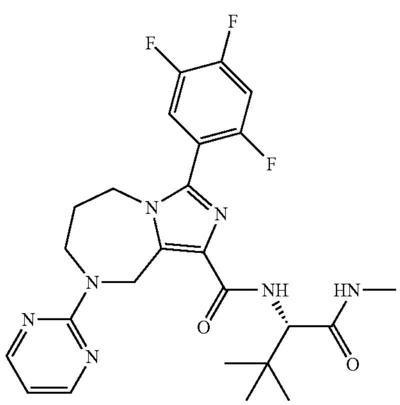 [SMILES: CNC(=O)[C@@H](NC(=O)c1nc(-c2cc(F)c(F)cc2F)n2c1CN(c1ncccn1)CCC2)C(C)(C)C] | 516 | (S)-N-(3,3-dimethyl-1-(methylamino)-1-oxobutan-2-yl)-8-(pyrimidin-2-yl)-3-(2,4,5-trifluorophenyl)-6,7,8,9-tetrahydro-5H-imidazo[1,5-a][1,4]diazepine-1-carboxamide | 44 |
| 717 | 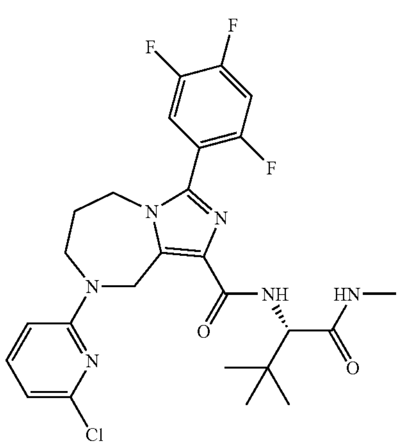 [SMILES: CNC(=O)[C@@H](NC(=O)c1nc(-c2cc(F)c(F)cc2F)n2c1CN(c1cccc(Cl)n1)CCC2)C(C)(C)C] | 549 | (S)-8-(6-chloropyridin-2-yl)-N-(3,3-dimethyl-1-(methylamino)-1-oxobutan-2-yl)-3-(2,4,5-trifluorophenyl)-6,7,8,9-tetrahydro-5H-imidazo[1,5-a][1,4]diazepine-1-carboxamide | 44 |

TABLE 2-continued

| Cmpd No. | Structure | m/z | Chemical Name | Example No. |
|---|---|---|---|---|
| 718 | 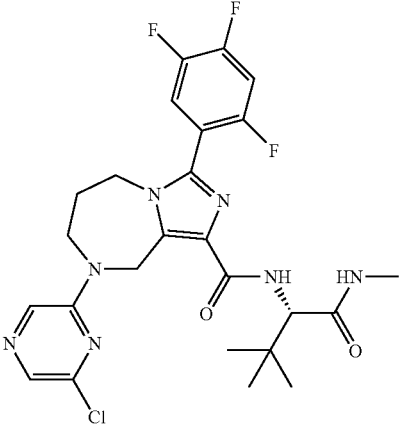 [SMILES: CNC(=O)[C@@H](NC(=O)c1nc(-c2cc(F)c(F)cc2F)n2c1CN(c1cncc(Cl)n1)CCC2)C(C)(C)C] | 550 | (S)-8-(6-chloropyrazin-2-yl)-N-(3,3-dimethyl-1-(methylamino)-1-oxobutan-2-yl)-3-(2,4,5-trifluorophenyl)-6,7,8,9-tetrahydro-5H-imidazo[1,5-a][1,4]diazepine-1-carboxamide | 44 |
| 719 | 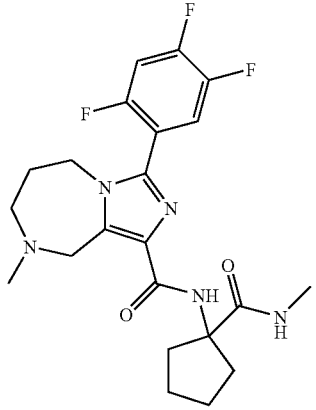 | 450 | 8-methyl-N-(1-(methylcarbamoyl)cyclopentyl)-3-(2,4,5-trifluorophenyl)-6,7,8,9-tetrahydro-5H-imidazo[1,5-a][1,4]diazepine-1-carboxamide | 40 |
| 720 | 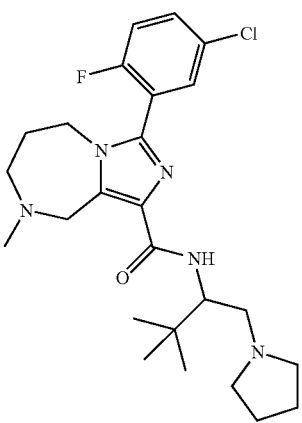 [SMILES: CN1CCCn2c(-c3cc(Cl)ccc3F)nc(C(=O)NC(CN3CCCC3)C(C)(C)C)c2C1] | 476.19 | 3-(5-chloro-2-fluorophenyl)-N-(3,3-dimethyl-1-(pyrrolidin-1-yl)butan-2-yl)-8-methyl-6,7,8,9-tetrahydro-5H-imidazo[1,5-a][1,4]diazepine-1-carboxamide | 40 |

TABLE 2-continued

| Cmpd No. | Structure | m/z | Chemical Name | Example No. |
|---|---|---|---|---|
| 721 | 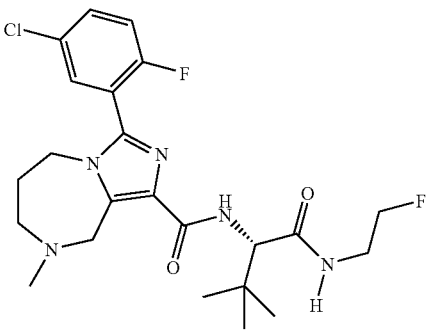 [SMILES: CN1CCCn2c(-c3cc(Cl)ccc3F)nc(C(=O)N[C@H](C(=O)NCCF)C(C)(C)C)c2C1] | 482.2 | (S)-3-(5-chloro-2-fluorophenyl)-N-(1-(2-fluoroethylamino)-3,3-dimethyl-1-oxobutan-2-yl)-8-methyl-6,7,8,9-tetrahydro-5H-imidazo[1,5-a][1,4]diazepine-1-carboxamide | 67 |
| 722 | 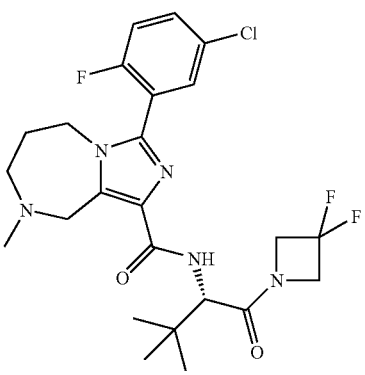 [SMILES: CN1CCCn2c(-c3cc(Cl)ccc3F)nc(C(=O)N[C@H](C(=O)N3CC(F)(F)C3)C(C)(C)C)c2C1] | 512.1 | (S)-3-(5-chloro-2-fluorophenyl)-N-(1-(3,3-difluoroazetidin-1-yl)-3,3-dimethyl-1-oxobutan-2-yl)-8-methyl-6,7,8,9-tetrahydro-5H-imidazo[1,5-a][1,4]diazepine-1-carboxamide | 67 |
| 723 | 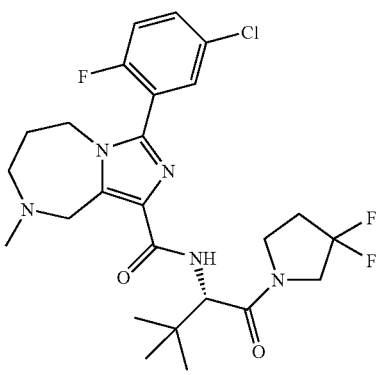 | 526.1 | (S)-3-(5-chloro-2-fluorophenyl)-N-(1-(3,3-difluoropyrrolidin-1-yl)-3,3-dimethyl-1-oxobutan-2-yl)-8-methyl-6,7,8,9-tetrahydro-5H-imidazo[1,5-a][1,4]diazepine-1-carboxamide | 67 |
| 724 | 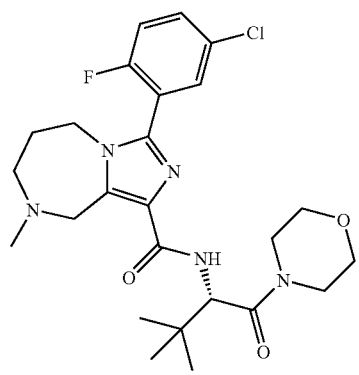 | 506.1 | (S)-3-(5-chloro-2-fluorophenyl)-N-(3,3-dimethyl-1-morpholino-1-oxobutan-2-yl)-8-methyl-6,7,8,9-tetrahydro-5H-imidazo[1,5-a][1,4]diazepine-1-carboxamide | 67 |

TABLE 2-continued

| Cmpd No. | Structure | m/z | Chemical Name | Example No. |
|---|---|---|---|---|
| 725 | 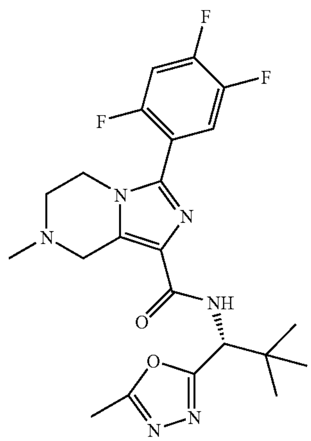 [SMILES: Cc1nnc([C@H](NC(=O)c2nc(-c3cc(F)c(F)cc3F)n3c2CN(C)CC3)C(C)(C)C)o1] | 463.1 | (R)-N-(2,2-dimethyl-1-(5-methyl-1,3,4-oxadiazol-2-yl)propyl)-7-methyl-3-(2,4,5-trifluorophenyl)-5,6,7,8-tetrahydroimidazo[1,5-a]pyrazine-1-carboxamide | 14 |
| 726 | 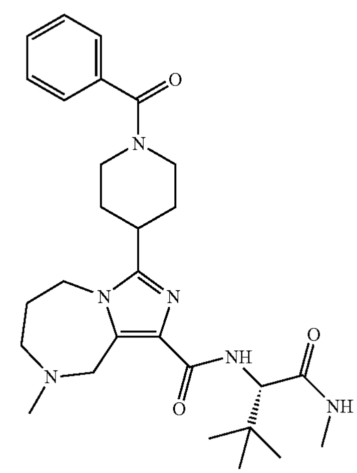 [SMILES: CNC(=O)[C@@H](NC(=O)c1nc(C2CCN(C(=O)c3ccccc3)CC2)n2c1CN(C)CCC2)C(C)(C)C] | 509.4 | (S)-3-(1-benzoylpiperidin-4-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide | 70 |
| 727 | 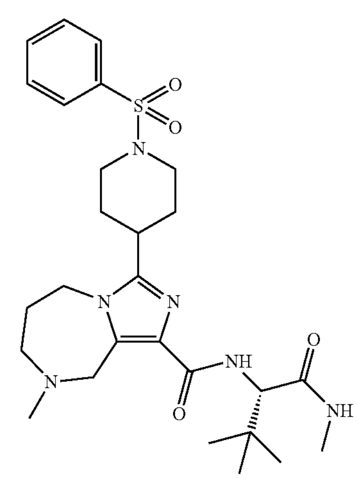 [SMILES: CNC(=O)[C@@H](NC(=O)c1nc(C2CCN(S(=O)(=O)c3ccccc3)CC2)n2c1CN(C)CCC2)C(C)(C)C] | 545.4 | (S)-N-(3,3-dimethyl-1-(methylamino)-1-oxobutan-2-yl)-8-methyl-3-(1-(phenylsulfonyl)piperidin-4-yl)-6,7,8,9-tetrahydro-5H-imidazo[1,5-a][1,4]diazepine-1-carboxamide | 70 |

TABLE 2-continued

| Cmpd No. | Structure | m/z | Chemical Name | Example No. |
|---|---|---|---|---|
| 728 | 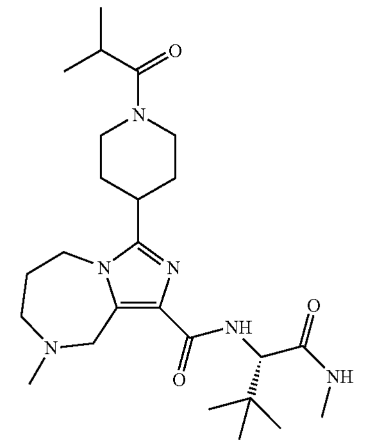 [SMILES: CNC(=O)[C@@H](NC(=O)c1nc(C2CCN(C(=O)C(C)C)CC2)n2c1CN(C)CCC2)C(C)(C)C] | 475.4 | (S)-N-(3,3-dimethyl-1-(methylamino)-1-oxobutan-2-yl)-3-(1-isobutyrylpiperidin-4-yl)-8-methyl-6,7,8,9-tetrahydro-5H-imidazo[1,5-a][1,4]diazepine-1-carboxamide | 70 |
| 729 | 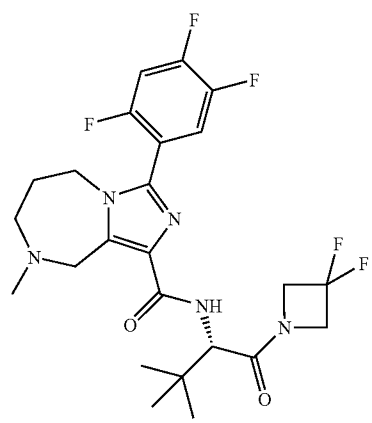 [SMILES: CN1CCCn2c(-c3cc(F)c(F)cc3F)nc(C(=O)N[C@H](C(=O)N3CC(F)(F)C3)C(C)(C)C)c2C1] | 514 | (S)-N-(1-(3,3-difluoroazetidin-1-yl)-3,3-dimethyl-1-oxobutan-2-yl)-8-methyl-3-(2,4,5-trifluorophenyl)-6,7 8,9-tetrahydro-5H-imidazo[1,5-a][1,4]diazepine-1-carboxamide | 67 |
| 730 | 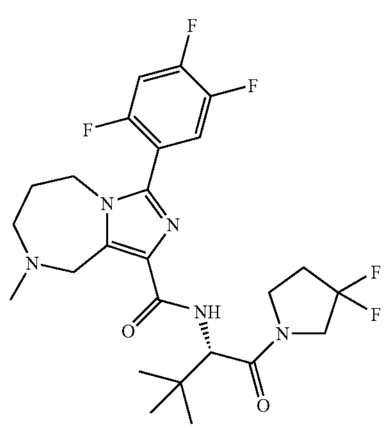 [SMILES: CN1CCCn2c(-c3cc(F)c(F)cc3F)nc(C(=O)N[C@H](C(=O)N3CCC(F)(F)C3)C(C)(C)C)c2C1] | 528 | (S)-N-(1-(3,3-difluoropyrrolidin-1-yl)-3,3-dimethyl-1-oxobutan-2-yl)-8-methyl-3-(2,4,5-trifluorophenyl)-6,7,8,9-tetrahydro-5H-imidazo[[1,5-a][1,4]diazepine-1-carboxamide | 67 |

TABLE 2-continued

| Cmpd No. | Structure | m/z | Chemical Name | Example No. |
|---|---|---|---|---|
| 731 | 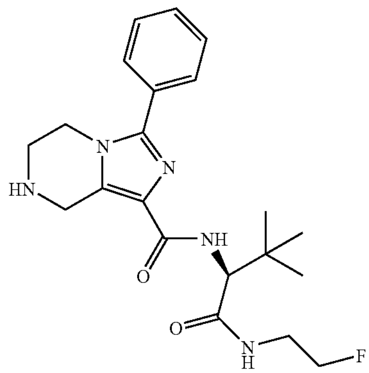 [SMILES: CC(C)(C)[C@H](NC(=O)c1nc(-c2ccccc2)n2c1CNCC2)C(=O)NCCF] | 402.3 | (S)-N-(1-(2-fluoroethylamino)-3,3-dimethyl-1-oxobutan-2-yl)-3-phenyl-5,6,7,8-tetrahydroimidazo[1,5-a]pyrazine-1-carboxamide | 71 |
| 732 | 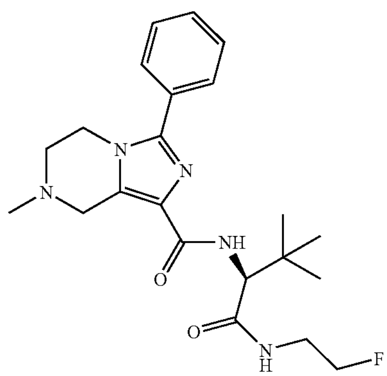 [SMILES: CN1CCn2c(-c3ccccc3)nc(C(=O)N[C@H](C(=O)NCCF)C(C)(C)C)c2C1] | 416.3 | (S)-N-(1-(2-fluoroethylamino)-3,3-dimethyl-1-oxobutan-2-yl)-7-methyl-3-phenyl-5,6,7,8-tetrahydroimidazo[1,5-a]pyrazine-1-carboxamide | 71 |
| 733 | 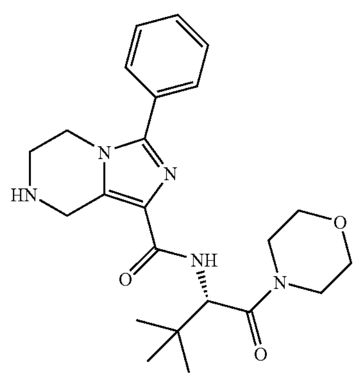 [SMILES: CC(C)(C)[C@H](NC(=O)c1nc(-c2ccccc2)n2c1CNCC2)C(=O)N1CCOCC1] | 426.3 | (S)-N-(3,3-dimethyl-1-morpholino-1-oxobutan-2-yl)-3-phenyl-5,6,7,8-tetrahydroimidazo[1,5-a]pyrazine-1-carboxamide | 71 |
| 734 | 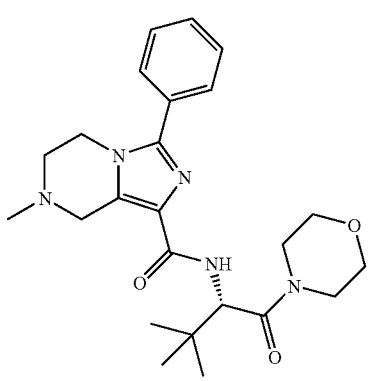 [SMILES: CN1CCn2c(-c3ccccc3)nc(C(=O)N[C@H](C(=O)N3CCOCC3)C(C)(C)C)c2C1] | 440.3 | (S)-N-(3,3-dimethyl-1-morpholino-1-oxobutan-2-yl)-7-methyl-3-phenyl-5,6,7,8-tetrahydroimidazo[1,5-a]pyrazine-1-carboxamide | 71 |

TABLE 2-continued

| Cmpd No. | Structure | m/z | Chemical Name | Example No. |
|---|---|---|---|---|
| 735 | 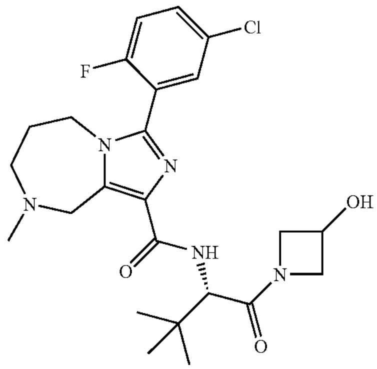 [SMILES: CN1CCCn2c(-c3cc(Cl)ccc3F)nc(C(=O)N[C@H](C(=O)N3CC(O)C3)C(C)(C)C)c2C1] | 492.3 | (S)-3-(5-chloro-2-fluorophenyl)-N-(1-(3-hydroxyazetidin-1-yl)-3,3-dimethyl-1-oxobutan-2-yl)-8-methyl-6,7,8,9-tetrahydro-5H-imidazo[1,5-a][1,4]diazepine-1-carboxamide | 67 |
| 736 | 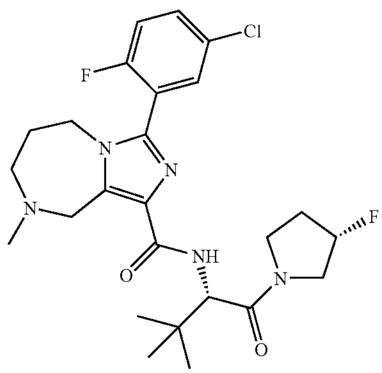 [SMILES: CN1CCCn2c(-c3cc(Cl)ccc3F)nc(C(=O)N[C@H](C(=O)N3CC[C@H](F)C3)C(C)(C)C)c2C1] | 508.3 | 3-(5-chloro-2-fluorophenyl)-N-((S)-1-((S)-3-fluoropyrrolidin-1-yl)-3,3-dimethyl-1-oxobutan-2-yl)-8-methyl-6,7,8,9-tetrahydro-5H-imidazo[1,5-a][1,4]diazepine-1-carboxamide | 67 |
| 737 | 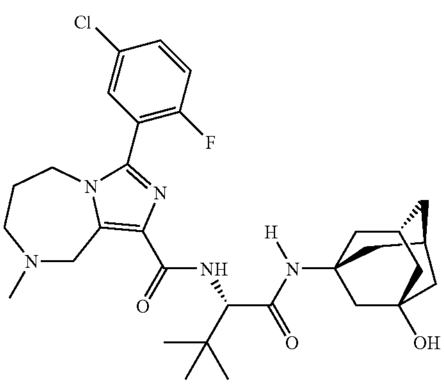 [SMILES: CN1CCCn2c(-c3cc(Cl)ccc3F)nc(C(=O)N[C@H](C(=O)N[C@]34C[C@@H]5C[C@@H](C[C@@](O)(C5)C3)C4)C(C)(C)C)c2C1] | 586.4 | (S)-3-(5-chloro-2-fluorophenyl)-N-(3,3-dimethyl-1-{1-hydroxy-tricyclo[3.3.1.1$^{3,7}$]decan-3-ylamino)}-1-oxobutan-2-yl)-8-methyl-6,7,8,9-tetrahydro-5H-imidazo[1,5-a][1,4]diazepine-1-carboxamide | 67 |
| 738 | 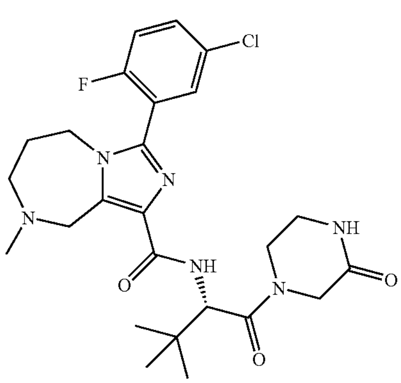 [SMILES: CN1CCCn2c(-c3cc(Cl)ccc3F)nc(C(=O)N[C@H](C(=O)N3CCNC(=O)C3)C(C)(C)C)c2C1] | 519.3 | (S)-3-(5-chloro-2-fluorophenyl)-N-(3,3-dimethyl-1-oxo-1-(3-oxopiperazin-1-yl)butan-2-yl)-8-methyl-6,7,8,9-tetrahydro-5H-imidazo[1,5-a][1,4]diazepine-1-carboxamide | 67 |

TABLE 2-continued

| Cmpd No. | Structure | m/z | Chemical Name | Example No. |
|---|---|---|---|---|
| 739 | 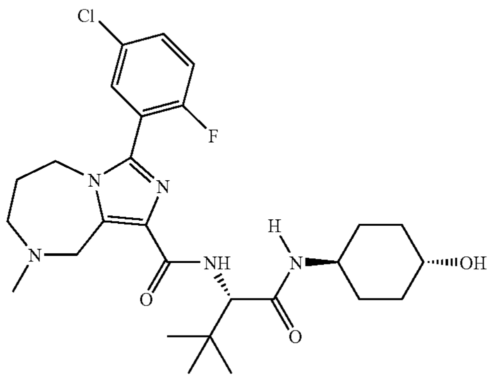 [SMILES: CN1CCCn2c(-c3cc(Cl)ccc3F)nc(C(=O)N[C@H](C(=O)N[C@H]3CC[C@H](O)CC3)C(C)(C)C)c2C1] | 534.3 | 3-(5-chloro-2-fluorophenyl)-N-((S)-1-((1r,4S)-4-hydroxycyclohexylamino)-3,3-dimethyl-1-oxobutan-2-yl)-8-methyl-6,7,8,9-tetrahydro-5H-imidazo[1,5-a][1,4]diazepine-1-carboxamide | 67 |
| 740 | 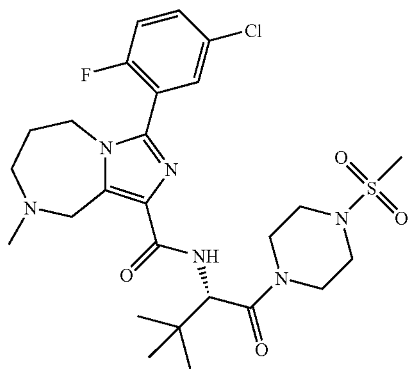 [SMILES: CN1CCCn2c(-c3cc(Cl)ccc3F)nc(C(=O)N[C@H](C(=O)N3CCN(S(C)(=O)=O)CC3)C(C)(C)C)c2C1] | 583.3 | (S)-3-(5-chloro-2-fluorophenyl)-N-(3,3-dimethyl-1-(4-(methylsulfonyl)piperazin-1-yl)-1-oxobutan-2-yl)-8-methyl-6,7,8,9-tetrahydro-5H-imidazo[1,5-a][1,4]diazepine-1-carboxamide | 67 |
| 741 | 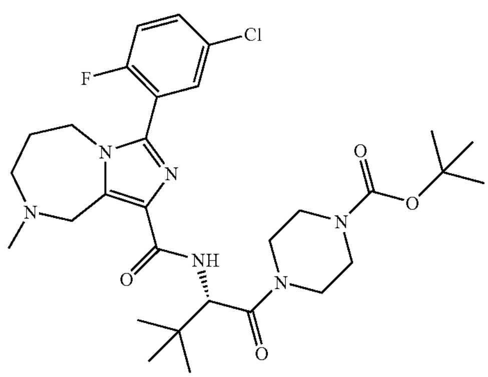 [SMILES: CN1CCCn2c(-c3cc(Cl)ccc3F)nc(C(=O)N[C@H](C(=O)N3CCN(C(=O)OC(C)(C)C)CC3)C(C)(C)C)c2C1] | 605.4 | (S)-tert-butyl 4-(2-(3-(5-chloro-2-fluorophenyl)-8-methyl-6,7,8,9-tetrahydro-5H-imidazo[1,5-a][1,4]diazepine-1-carboxamido)-3,3-dimethylbutanoyl)piperazine-1-carboxylate | 67 |
| 742 | 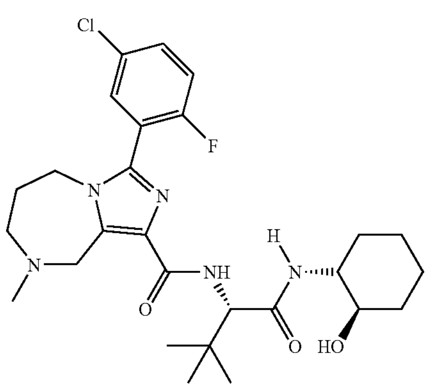 | 534.3 | 3-(5-chloro-2-fluorophenyl)-N-((S)-1-((1R,2R)-2-hydroxycyclohexylamino)-3,3-dimethyl-1-oxobutan-2-yl)-8-methyl-6,7,8,9-tetrahydro-5H-imidazo[1,5-a][1,4]diazepine-1-carboxamide | 67 |

TABLE 2-continued

| Cmpd No. | Structure | m/z | Chemical Name | Example No. |
|---|---|---|---|---|
| 743 | 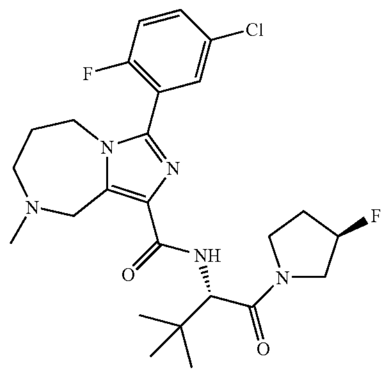 [SMILES: CN1CCCn2c(-c3cc(Cl)ccc3F)nc(C(=O)N[C@H](C(=O)N3CC[C@@H](F)C3)C(C)(C)C)c2C1] | 508.3 | 3-(5-chloro-2-fluorophenyl)-N-((S)-1-((R)-3-fluoropyrrolidin-1-yl)-3,3-dimethyl-1-oxobutan-2-yl)-8-methyl-6,7,8,9-tetrahydro-5H-imidazo[1,5-a][1,4]diazepine-1-carboxamide | 67 |
| 744 | 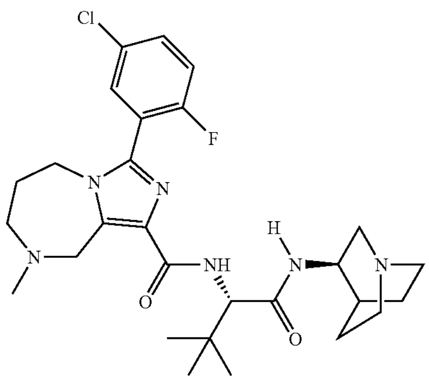 [SMILES: CN1CCCn2c(-c3cc(Cl)ccc3F)nc(C(=O)N[C@H](C(=O)N[C@H]3CN4CCC3CC4)C(C)(C)C)c2C1] | 545.3 | 3-(5-chloro-2-fluorophenyl)-N-((S)-3,3-dimethyl-1-oxo-1-((R)-quinuclidin-3-ylamino)butan-2-yl)-8-methyl-6,7,8,9-tetrahydro-5H-imidazo[1,5-a][1,4]diazepine-1-carboxamide | 67 |
| 745 | 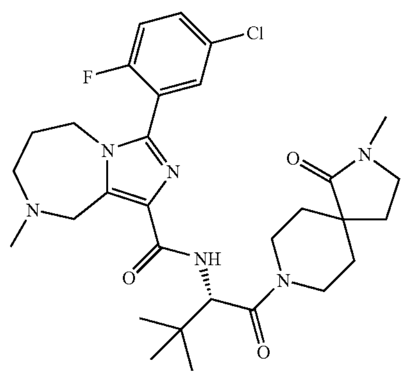 [SMILES: CN1CCCn2c(-c3cc(Cl)ccc3F)nc(C(=O)N[C@H](C(=O)N3CCC4(CCN(C)C4=O)CC3)C(C)(C)C)c2C1] | 587.4 | (S)-3-(5-chloro-2-fluorophenyl)-N-(3,3-dimethyl-1-(2-methyl-1-oxo-2,8-diazaspiro[4.5]decan-8-yl)-1-oxobutan-2-yl)-8-methyl-6,7,8,9-tetrahydro-5H-imidazo[1,5-a][1,4]diazepine-1-carboxamide | 67 |
| 746 | 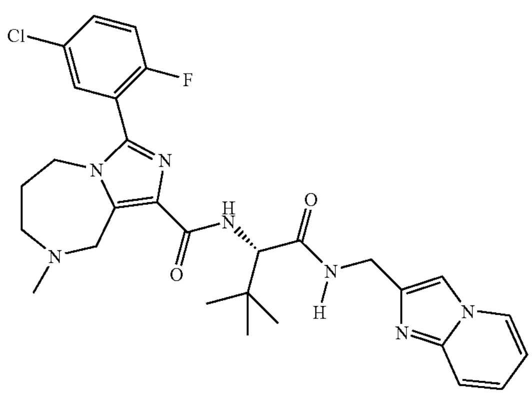 [SMILES: CN1CCCn2c(-c3cc(Cl)ccc3F)nc(C(=O)N[C@H](C(=O)NCc3cn4ccccc4n3)C(C)(C)C)c2C1] | 588.3 | (S)-3-(5-chloro-2-fluorophenyl)-N-(1-(imidazo[1,2-a]pyridin-2-ylmethylamino)-3,3-dimethyl-1-oxobutan-2-yl)-8-methyl-6,7,8,9-tetrahydro-5H-imidazo[1,5-a][1,4]diazepine-1-carboxamide | 67 |

TABLE 2-continued

| Cmpd No. | Structure | m/z | Chemical Name | Example No. |
|---|---|---|---|---|
| 747 | 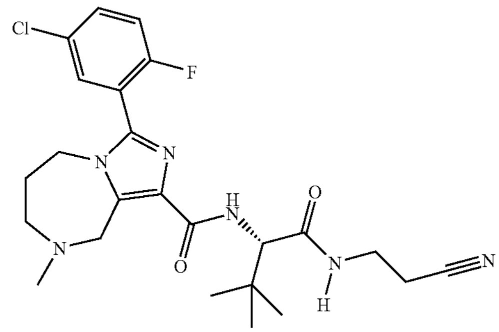 [SMILES: CN1CCCn2c(-c3cc(Cl)ccc3F)nc(C(=O)N[C@H](C(=O)NCCC#N)C(C)(C)C)c2C1] | 489.3 | (S)-3-(5-chloro-2-fluorophenyl)-N-(1-(2-cyanoethylamino)-3,3-dimethyl-1-oxobutan-2-yl)-8-methyl-6,7,8,9-tetrahydro-5H-imidazo[1,5-a][1,4]diazepine-1-carboxamide | 67 |
| 748 | 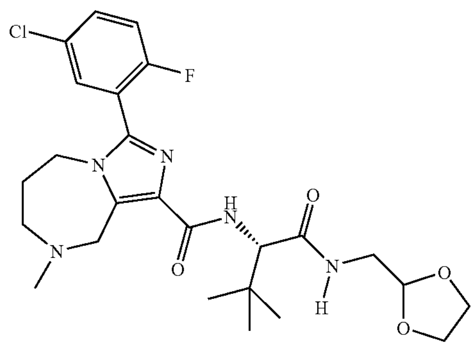 [SMILES: CN1CCCn2c(-c3cc(Cl)ccc3F)nc(C(=O)N[C@H](C(=O)NCC3OCCO3)C(C)(C)C)c2C1] | 522.3 | (S)-N-(1-((1,3-dioxolan-2-yl)methylamino)-3,3-dimethyl-1-oxobutan-2-yl)-3-(5-chloro-2-fluorophenyl)-8-methyl-6,7,8,9-tetrahydro-5H-imidazo[1,5-a][1,4]diazepine-1-carboxamide | 67 |
| 749 | 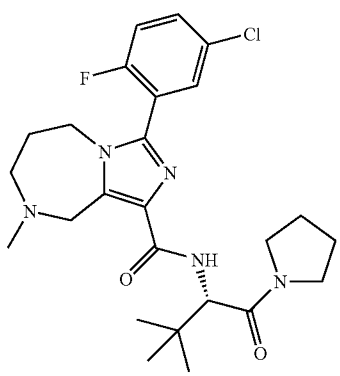 [SMILES: CN1CCCn2c(-c3cc(Cl)ccc3F)nc(C(=O)N[C@H](C(=O)N3CCCC3)C(C)(C)C)c2C1] | 490.3 | (S)-3-(5-chloro-2-fluorophenyl)-N-(3,3-dimethyl-1-oxo-1-(pyrrolidin-1-yl)butan-2-yl)-8-methyl-6,7,8,9-tetrahydro-5H-imidazo[1,5-a][1,4]diazepine-1-carboxamide | 67 |
| 750 | 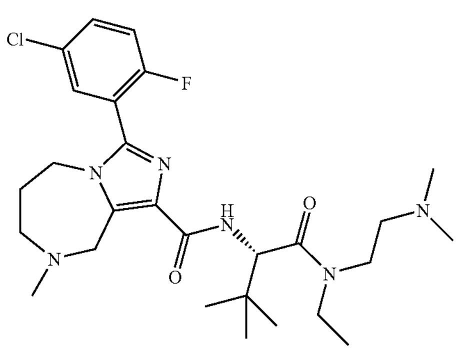 [SMILES: CCN(CCN(C)C)C(=O)[C@@H](NC(=O)c1nc(-c2cc(Cl)ccc2F)n2c1CN(C)CCC2)C(C)(C)C] | 536 | (S)-3-(5-chloro-2-fluorophenyl)-N-(1-((2-(dimethylamino)ethyl)(ethyl)amino)-3,3-dimethyl-1-oxobutan-2-yl)-8-methyl-6,7,8,9-tetrahydro-5H-imidazo[1,5-a][1,4]diazepine-1-carboxamide | 67 |

TABLE 2-continued

| Cmpd No. | Structure | m/z | Chemical Name | Example No. |
|---|---|---|---|---|
| 751 | 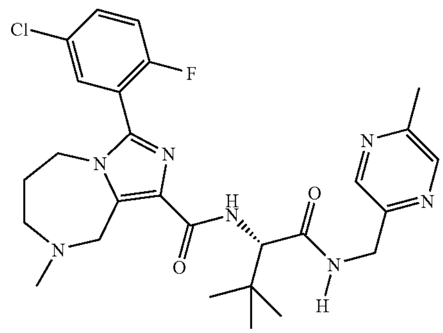 [SMILES: Cc1cnc(CNC(=O)[C@@H](NC(=O)c2nc(-c3cc(Cl)ccc3F)n3c2CN(C)CCC3)C(C)(C)C)cn1] | 542.3 | (S)-3-(5-chloro-2-fluorophenyl)-N-(3,3-dimethyl-1-((5-methylpyrazin-2-yl)methylamino)-1-oxobutan-2-yl)-8-methyl-6,7,8,9-tetrahydro-5H-imidazo[1,5-a][1,4]diazepine-1-carboxamide | 67 |
| 752 | 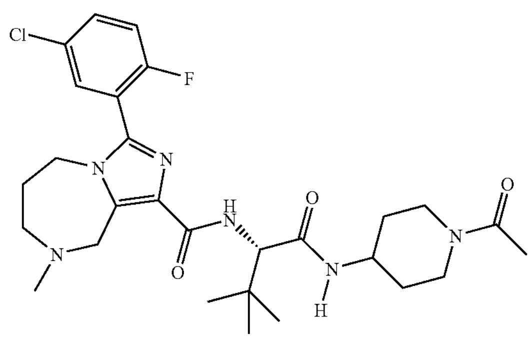 [SMILES: CC(=O)N1CCC(NC(=O)[C@@H](NC(=O)c2nc(-c3cc(Cl)ccc3F)n3c2CN(C)CCC3)C(C)(C)C)CC1] | 561.3 | (S)-N-(1-(1-acetylpiperidin-4-ylamino)-3,3-dimethyl-1-oxobutan-2-yl)-3-(5-chloro-2-fluorophenyl)-8-methyl-6,7,8,9-tetrahydro-5H-imidazo[1,5-a][1,4]diazepine-1-carboxamide | 67 |
| 753 | 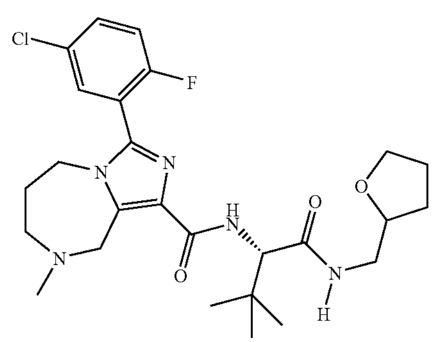 [SMILES: CN1CCCn2c(-c3cc(Cl)ccc3F)nc(C(=O)N[C@H](C(=O)NCC3CCCO3)C(C)(C)C)c2C1] | 520.3 | 3-(5-chloro-2-fluorophenyl)-N-((2S)-3,3-dimethyl-1-oxo-1-((tetrahydrofuran-2-yl)methylamino)butan-2-yl)-8-methyl-6,7,8,9-tetrahydro-5H-imidazo[1,5-a][1,4]diazepine-1-carboxamide | 67 |
| 754 | 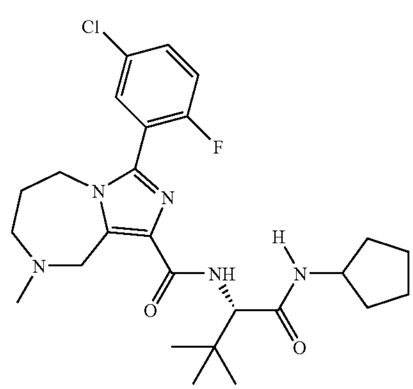 [SMILES: CN1CCCn2c(-c3cc(Cl)ccc3F)nc(C(=O)N[C@H](C(=O)NC3CCCC3)C(C)(C)C)c2C1] | 504.3 | (S)-3-(5-chloro-2-fluorophenyl)-N-(1-(cyclopentylamino)-3,3-dimethyl-1-oxobutan-2-yl)-8-methyl-6,7,8,9-tetrahydro-5H-imidazo[1,5-a][1,4]diazepine-1-carboxamide | 67 |

TABLE 2-continued

| Cmpd No. | Structure | m/z | Chemical Name | Example No. |
|---|---|---|---|---|
| 755 | 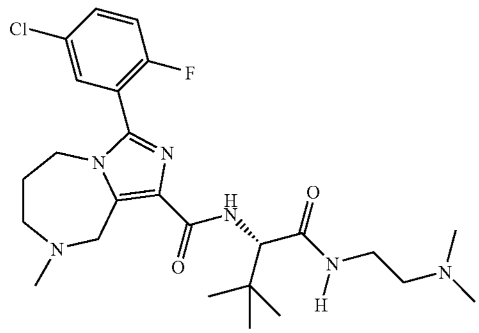 [SMILES: CN(C)CCNC(=O)[C@@H](NC(=O)c1nc(-c2cc(Cl)ccc2F)n2c1CN(C)CCC2)C(C)(C)C] | 508 | (S)-3-(5-chloro-2-fluorophenyl)-N-(1-(2-(dimethylamino)ethylamino)-3,3-dimethyl-1-oxobutan-2-yl)-8-methyl-6,7,8,9-tetrahydro-5H-imidazo[1,5-a][1,4]diazepine-1-carboxamide | 67 |
| 756 | 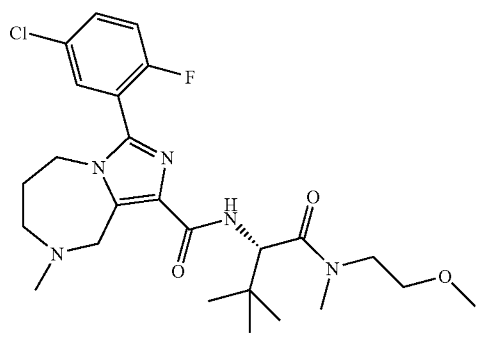 [SMILES: COCCN(C)C(=O)[C@@H](NC(=O)c1nc(-c2cc(Cl)ccc2F)n2c1CN(C)CCC2)C(C)(C)C] | 508.3 | (S)-3-(5-chloro-2-fluorophenyl)-N-(1-((2-methoxyethyl)(methyl)amino)-3,3-dimethyl-1-oxobutan-2-yl)-8-methyl-6,7,8,9-tetrahydro-5H-imidazo[1,5-a][1,4]diazepine-1-carboxamide | 67 |
| 757 | 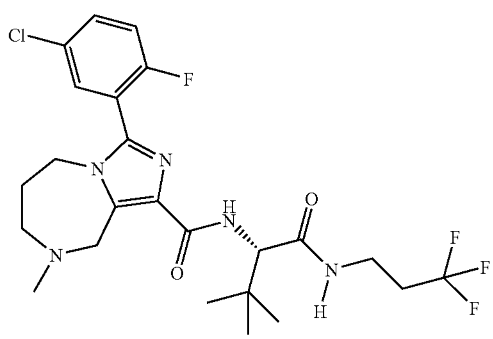 [SMILES: CN1CCCn2c(-c3cc(Cl)ccc3F)nc(C(=O)N[C@H](C(=O)NCCC(F)(F)F)C(C)(C)C)c2C1] | 532.3 | (S)-3-(5-chloro-2-fluorophenyl)-N-(3,3-dimethyl-1-oxo-1-(3,3,3-trifluoropropylamino)butan-2-yl)-8-methyl-6,7,8,9-tetrahydro-5H-imidazo[1,5-a][1,4]diazepine-1-carboxamide | 67 |
| 758 | 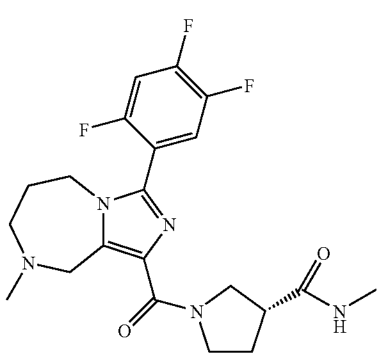 | 436.2 | (R)-N-methyl-1-(8-methyl-3-(2,4,5-trifluorophenyl)-6,7,8,9-tetrahydro-5H-imidazo[1,5-a][1,4]diazepine-1-carbonyl)pyrrolidine-3-carboxamide | 72 |

TABLE 2-continued

| Cmpd No. | Structure | m/z | Chemical Name | Example No. |
|---|---|---|---|---|
| 759 | 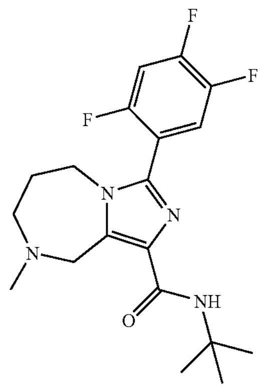 [SMILES: CN1CCCn2c(-c3cc(F)c(F)cc3F)nc(C(=O)NC(C)(C)C)c2C1] | 381 | N-tert-butyl-8-methyl-3-(2,4,5-trifluorophenyl)-6,7,8,9-tetrahydro-5H-imidazo[1,5-a][1,4]diazepine-1-carboxamide | 72 |
| 760 | 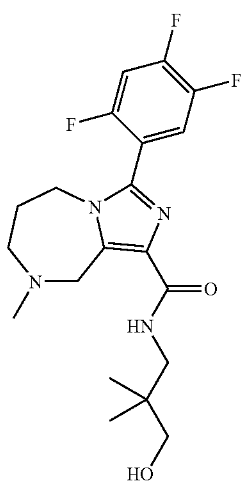 [SMILES: CN1CCCn2c(-c3cc(F)c(F)cc3F)nc(C(=O)NCC(C)(C)CO)c2C1] | 411 | N-(3-hydroxy-2,2-dimethylpropyl)-8-methyl-3-(2,4,5-trifluorophenyl)-6,7,8,9-tetrahydro-5H-imidazo[1,5-a][1,4]diazepine-1-carboxamide | 72 |
| 761 | 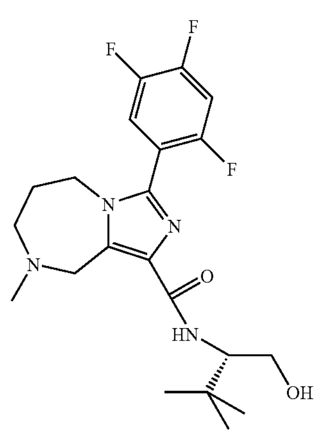 [SMILES: CN1CCCn2c(-c3cc(F)c(F)cc3F)nc(C(=O)N[C@H](CO)C(C)(C)C)c2C1] | 425.3 | (S)-N-(1-hydroxy-3,3-dimethylbutan-2-yl)-8-methyl-3-(2,4,5-trifluorophenyl)-6,7,8,9-tetrahydro-5H-imidazo[1,5-a][1,4]diazepine-1-carboxamide | 72 |

TABLE 2-continued

| Cmpd No. | Structure | m/z | Chemical Name | Example No. |
|---|---|---|---|---|
| 762 | 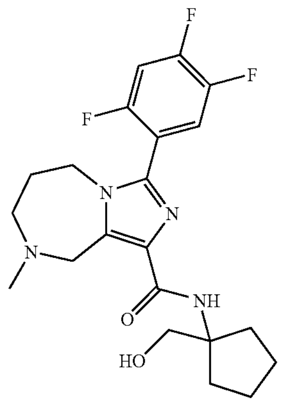 [SMILES: CN1CCCn2c(-c3cc(F)c(F)cc3F)nc(C(=O)NC3(CO)CCCC3)c2C1] | 423 | N-(1-(hydroxymethyl)cyclopentyl)-8-methyl-3-(2,4,5-trifluorophenyl)-6,7,8,9-tetrahydro-5H-imidazo[1,5-a][1,4]diazepine-1-carboxamide | 72 |
| 763 | 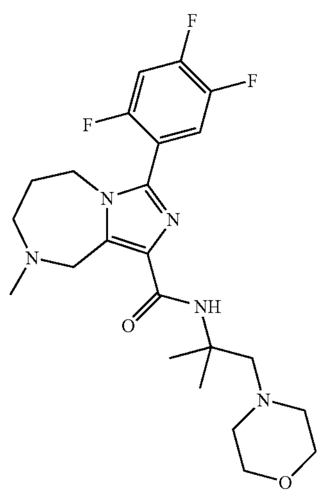 [SMILES: CN1CCCn2c(-c3cc(F)c(F)cc3F)nc(C(=O)NC(C)(C)CN3CCOCC3)c2C1] | 466 | 8-methyl-N-(2-methyl-1-morpholinopropan-2-yl)-3-(2,4,5-trifluorophenyl)-6,7,8,9-tetrahydro-5H-imidazo[1,5-a][1,4]diazepine-1-carboxamide | 72 |
| 764 | 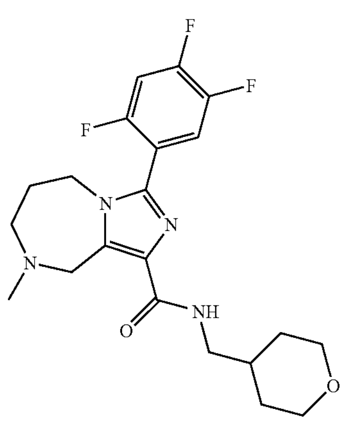 [SMILES: CN1CCCn2c(-c3cc(F)c(F)cc3F)nc(C(=O)NCC3CCOCC3)c2C1] | 423 | 8-methyl-N-((tetrahydro-2H-pyran-4-yl)methyl)-3-(2,4,5-trifluorophenyl)-6,7,8,9-tetrahydro-5H-imidazo[1,5-a][1,4]diazepine-1-carboxamide | 72 |

TABLE 2-continued

| Cmpd No. | Structure | m/z | Chemical Name | Example No. |
|---|---|---|---|---|
| 765 | 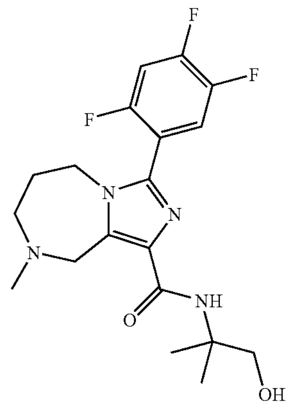 [SMILES: CN1CCCn2c(-c3cc(F)c(F)cc3F)nc(C(=O)NC(C)(C)CO)c2C1] | 397 | N-(1-hydroxy-2-methylpropan-2-yl)-8-methyl-3-(2,4,5-trifluorophenyl)-6,7,8,9-tetrahydro-5H-imidazo[1,5-a][1,4]diazepine-1-carboxamide | 72 |
| 766 | 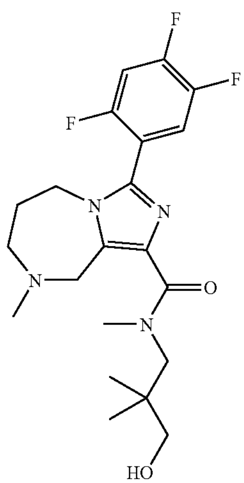 [SMILES: CN1CCCn2c(-c3cc(F)c(F)cc3F)nc(C(=O)N(C)CC(C)(C)CO)c2C1] | 425 | N-(3-hydroxy-2,2-dimethylpropyl)-N,8-dimethyl-3-(2,4,5-trifluorophenyl)-6,7,8,9-tetrahydro-5H-imidazo[1,5-a][1,4]diazepine-1-carboxamide | 72 |
| 767 | 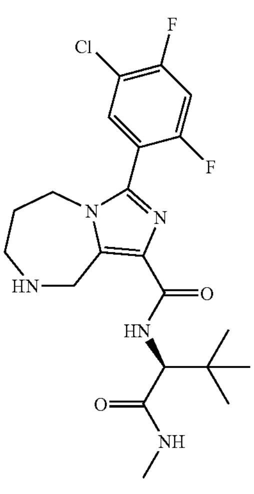 [SMILES: CNC(=O)[C@@H](NC(=O)c1nc(-c2cc(Cl)c(F)cc2F)n2c1CNCCC2)C(C)(C)C] | 454 | (S)-3-(5-chloro-2,4-difluorophenyl)-N-(3,3-dimethyl-1-(methylamino)-1-oxobutan-2-yl)-6,7,8,9-tetrahydro-5H-imidazo[1,5-a][1,4]diazepine-1-carboxamide | 34 |

TABLE 2-continued

| Cmpd No. | Structure | m/z | Chemical Name | Example No. |
|---|---|---|---|---|
| 768 | 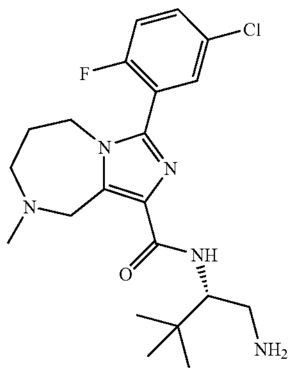 [SMILES: CN1CCCn2c(-c3cc(Cl)ccc3F)nc(C(=O)N[C@H](CN)C(C)(C)C)c2C1] | 422 | (S)-N-(1-amino-3,3-dimethylbutan-2-yl)-3-(5-chloro-2-fluorophenyl)-8-methyl-6,7,8,9-tetrahydro-5H-imidazol[1,5-a][1,4]diazepine-1-carboxamide | 73 |
| 769 | 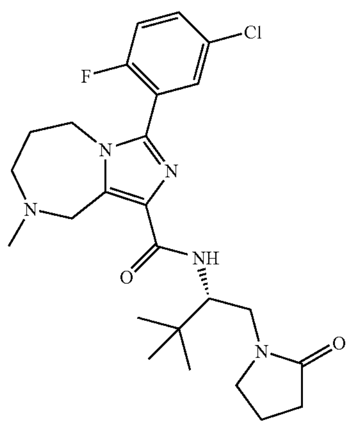 [SMILES: CN1CCCn2c(-c3cc(Cl)ccc3F)nc(C(=O)N[C@H](CN3CCCC3=O)C(C)(C)C)c2C1] | 490.32 | (S)-3-(5-chloro-2-fluorophenyl)-N-(3,3-dimethyl-1-(2-oxopyrrolidin-1-yl)butan-2-yl)-8-methyl-6,7,8,9-tetrahydro-5H-imidazo[1,5-a][1,4]diazepine-1-carboxamide | 74 |
| 770 | 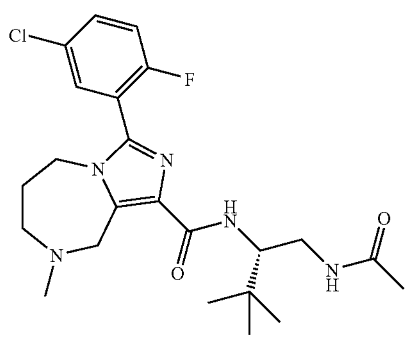 [SMILES: CC(=O)NC[C@@H](NC(=O)c1nc(-c2cc(Cl)ccc2F)n2c1CN(C)CCC2)C(C)(C)C] | 464.2 | (S)-N-(1-acetamido-3,3-dimethylbutan-2-yl)-3-(5-chloro-2-fluorophenyl)-8-methyl-6,7,8,9-tetrahydro-5H-imidazo[1,5-a][1,4]diazepine-1-carboxamide | 75 |
| 771 | 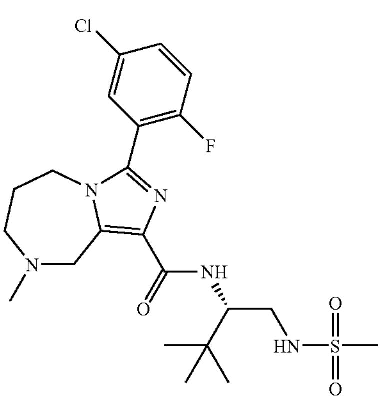 [SMILES: CN1CCCn2c(-c3cc(Cl)ccc3F)nc(C(=O)N[C@H](CNS(C)(=O)=O)C(C)(C)C)c2C1] | 500.2 | (S)-3-(5-chloro-2-fluorophenyl)-N-(3,3-dimethyl-1-(methylsulfonamido)butan-2-yl)-8-methyl-6,7,8,9-tetrahydro-5H-imidazo[1,5-a][1,4]diazepine-1-carboxamide | 75 |

TABLE 2-continued

| Cmpd No. | Structure | m/z | Chemical Name | Example No. |
|---|---|---|---|---|
| 772 | 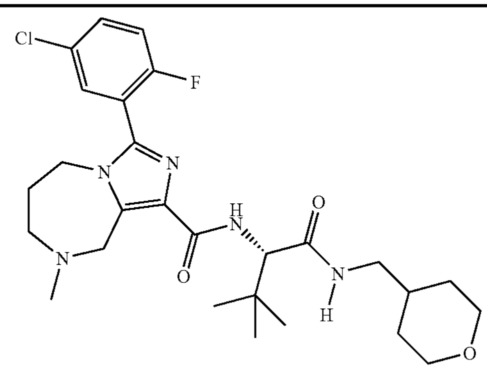 | 534.3 | (S)-3-(5-chloro-2-fluorophenyl)-N-(3,3-dimethyl-1-oxo-1-((tetrahydro-2H-pyran-4-yl)methylamino)butan-2-yl)-8-methyl-6,7,8,9-tetrahydro-5H-imidazo[1,5-a][1,4]diazepine-1-carboxamide | 67 |
| 773 | 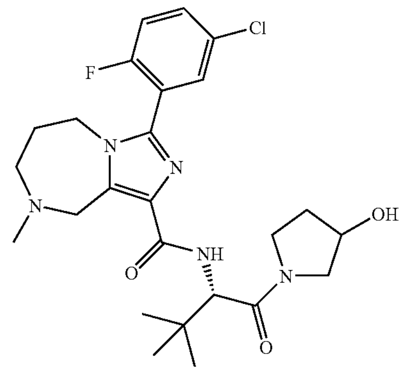 | 506.2 | 3-(5-chloro-2-fluorophenyl)-N-((2S)-1-(3-hydroxypyrrolidin-1-yl)-3,3-dimethyl-1-oxobutan-2-yl)-8-methyl-6,7,8,9-tetrahydro-5H-imidazo[1,5-a][1,4]diazepine-1-carboxamide | 67 |
| 774 | 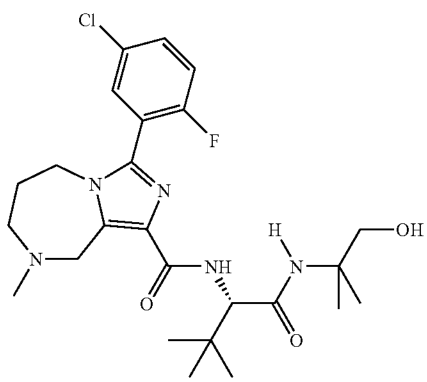 [SMILES: CN1CCCn2c(-c3cc(Cl)ccc3F)nc(C(=O)N[C@H](C(=O)NC(C)(C)CO)C(C)(C)C)c2C1] | 510.29 | (S)-3-(5-chloro-2-fluorophenyl)-N-(1-(1-hydroxy-2-methylpropan-2-ylamino)-3,3-dimethyl-1-oxobutan-2-yl)-8-methyl-6,7,8,9-tetrahydro-5H-imidazo[1,5-a][1,4]diazepine-1-carboxamide | 67 |
| 775 | 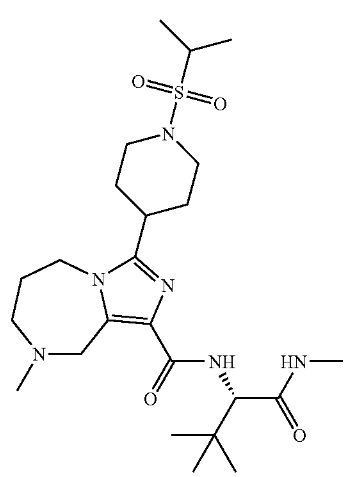 [SMILES: CNC(=O)[C@@H](NC(=O)c1nc(C2CCN(S(=O)(=O)C(C)C)CC2)n2c1CN(C)CCC2)C(C)(C)C] | 511.4 | (S)-N-(3,3-dimethyl-1-(methylamino)-1-oxobutan-2-yl)-3-(1-(isopropylsulfonyl)piperidin-4-yl)-8-methyl-6,7,8,9-tetrahydro-5H-imidazo[1,5-a][1,4]diazepine-1-carboxamide | 70 |

TABLE 2-continued

| Cmpd No. | Structure | m/z | Chemical Name | Example No. |
|---|---|---|---|---|
| 776 | 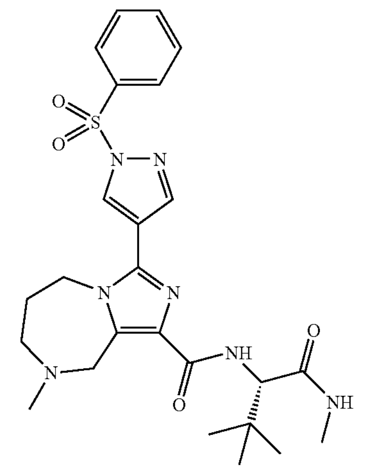 [SMILES: CNC(=O)[C@@H](NC(=O)c1nc(-c2cnn(S(=O)(=O)c3ccccc3)c2)n2c1CN(C)CCC2)C(C)(C)C] | 528.3 | (S)-N-(3,3-dimethyl-1-(methylamino)-1-oxobutan-2-yl)-8-methyl-3-(1-(phenylsulfonyl)-1H-pyrazol-4-yl)-6,7,8,9-tetrahydro-5H-imidazo[1,5-a][1,4]diazepine-1-carboxamide | 76 |
| 777 | 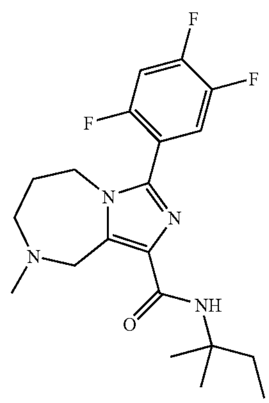 [SMILES: CCC(C)(C)NC(=O)c1nc(-c2cc(F)c(F)cc2F)n2c1CN(C)CCC2] | 395 | 8-methyl-N-tert-pentyl-3-(2,4,5-trifluorophenyl)-6,7,8,9-tetrahydro-5H-imidazo[1,5-a][1,4]diazepine-1-carboxamide | 72 |
| 778 | 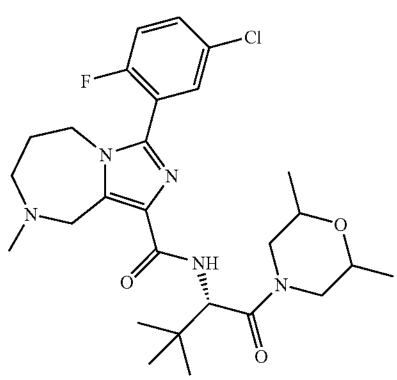 | 419.2 | 3-(5-chloro-2-fluorophenyl)-N-((2S)-1-(2,6-dimethylmorpholino)-3,3-dimethyl-1-oxobutan-2-yl)-8-methyl-6,7,8,9-tetrahydro-5H-imidazo[1,5-a][1,4]diazepine-1-carboxamide | 67 |

TABLE 2-continued

| Cmpd No. | Structure | m/z | Chemical Name | Example No. |
|---|---|---|---|---|
| 779 | 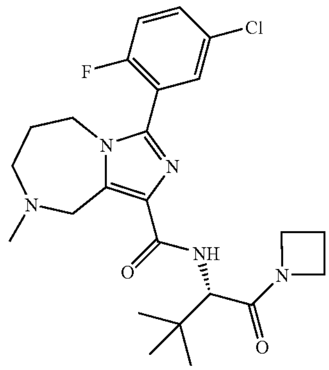 [SMILES: CN1CCCn2c(-c3cc(Cl)ccc3F)nc(C(=O)N[C@H](C(=O)N3CCC3)C(C)(C)C)c2C1] | 476.2 | (S)-N-(1-(azetidin-1-yl)-3,3-dimethyl-1-oxobutan-2-yl)-3-(5-chloro-2-fluorophenyl)-8-methyl-6,7,8,9-tetrahydro-5H-imidazo[1,5-a][1,4]diazepine-1-carboxamide | 67 |
| 780 | 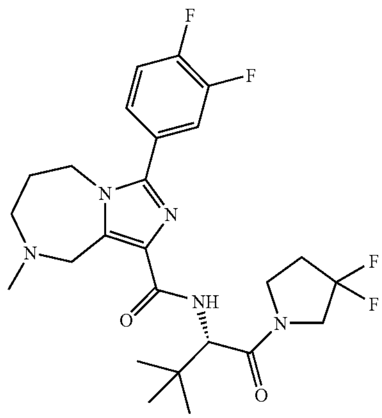 [SMILES: CN1CCCn2c(-c3ccc(F)c(F)c3)nc(C(=O)N[C@H](C(=O)N3CCC(F)(F)C3)C(C)(C)C)c2C1] | 510 | (S)-3-(3,4-difluorophenyl)-N-(1-(3,3-difluoropyrrolidin-1-yl)-3,3-dimethyl-1-oxobutan-2-yl)-8-methyl-6,7,8,9-tetrahydro-5H-imidazo[1,5-a][1,4]diazepine-1-carboxamide | 77 |
| 781 | 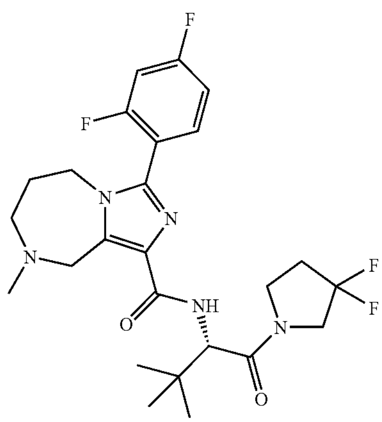 [SMILES: CN1CCCn2c(-c3ccc(F)cc3F)nc(C(=O)N[C@H](C(=O)N3CCC(F)(F)C3)C(C)(C)C)c2C1] | 510 | (S)-3-(2,4-difluorophenyl)-N-(1-(3,3-difluoropyrrolidin-1-yl)-3,3-dimethyl-1-oxobutan-2-yl)-8-methyl-6,7,8,9-tetrahydro-5H-imidazo[1,5-a][1,4]diazepine-1-carboxamide | 77 |
| 782 | 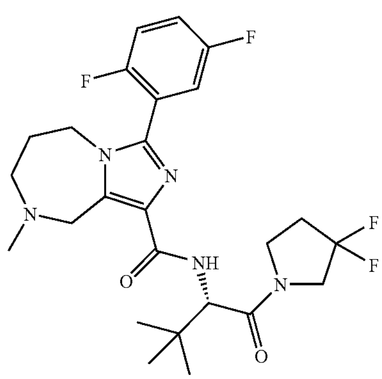 [SMILES: CN1CCCn2c(-c3cc(F)ccc3F)nc(C(=O)N[C@H](C(=O)N3CCC(F)(F)C3)C(C)(C)C)c2C1] | 510 | (S)-3-(2,5-difluorophenyl)-N-(1-(3,3-difluoropyrrolidin-1-yl)-3,3-dimethyl-1-oxobutan-2-yl)-8-methyl-6,7,8,9-tetrahydro-5H-imidazo[1,5-a][1,4]diazepine-1-carboxamide | 77 |

TABLE 2-continued

| Cmpd No. | Structure | m/z | Chemical Name | Example No. |
|---|---|---|---|---|
| 783 | 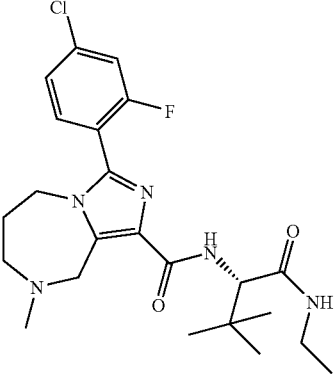 [SMILES: CCNC(=O)[C@@H](NC(=O)c1nc(-c2ccc(Cl)cc2F)n2c1CN(C)CCC2)C(C)(C)C] | 464 | (S)-3-(4-chloro-2-fluorophenyl)-N-(1-(ethylamino)-3,3-dimethyl-1-oxobutan-2-yl)-8-methyl-6,7,8,9-tetrahydro-5H-imidazo[1,5-a][1,4]diazepine-1-carboxamide | 77 |
| 784 | 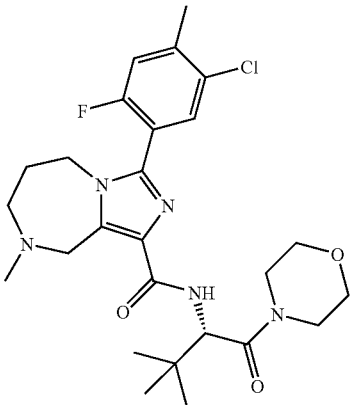 [SMILES: Cc1cc(F)c(-c2nc(C(=O)N[C@H](C(=O)N3CCOCC3)C(C)(C)C)c3n2CCCN(C)C3)cc1Cl] | 521 | (S)-3-(5-chloro-2-fluoro-4-methylphenyl)-N-(3,3-dimethyl-1-morpholino-1-oxobutan-2-yl)-8-methyl-6,7,8,9-tetrahydro-5H-imidazo[1,5-a][1,4]diazepine-1-carboxamide | 77 |
| 785 | 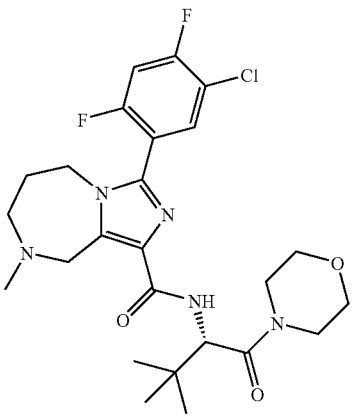 [SMILES: CN1CCCn2c(-c3cc(Cl)c(F)cc3F)nc(C(=O)N[C@H](C(=O)N3CCOCC3)C(C)(C)C)c2C1] | 525 | (S)-3-(5-chloro-2,4-difluorophenyl)-N-(3,3-dimethyl-1-morpholino-1-oxobutan-2-yl)-8-methyl-6,7,8,9-tetrahydro-5H-imidazo[1,5-a][1,4]diazepine-1-carboxamide | 77 |

TABLE 2-continued

| Cmpd No. | Structure | m/z | Chemical Name | Example No. |
|---|---|---|---|---|
| 786 | 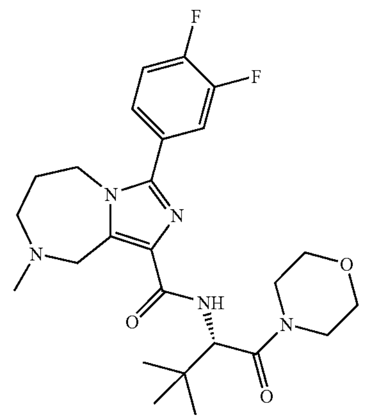 [SMILES: CN1CCCn2c(-c3ccc(F)c(F)c3)nc(C(=O)N[C@H](C(=O)N3CCOCC3)C(C)(C)C)c2C1] | 490 | (S)-3-(3,4-difluorophenyl)-N-(3,3-dimethyl-1-morpholino-1-oxobutan-2-yl)-8-methyl-6,7,8,9-tetrahydro-5H-imidazo[1,5-a][1,4]diazepine-1-carboxamide | 77 |
| 787 | 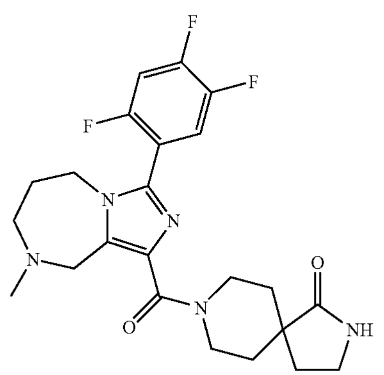 [SMILES: CN1CCCn2c(-c3cc(F)c(F)cc3F)nc(C(=O)N3CCC4(CCNC4=O)CC3)c2C1] | 462.2 | 8-(8-methyl-3-(2,4,5-trifluorophenyl)-6,7,8,9-tetrahydro-5H-imidazo[1,5-a][1,4]diazepine-1-carbonyl)-2,8-diazaspiro[4.5]decan-1-one | 72 |
| 788 | 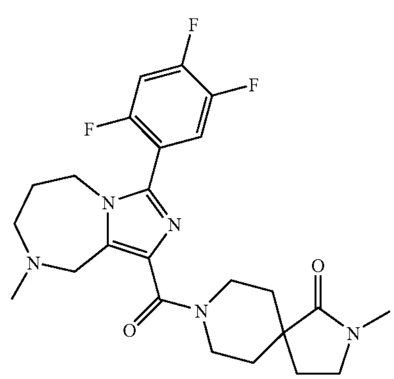 | 476.2 | 2-methyl-8-(8-methyl-3-(2,4,5-trifluorophenyl)-6,7,8,9-tetrahydro-5H-imidazo[1,5-a][1,4]diazepine-1-carbonyl)-2,8-diazaspiro[4.5]decan-1-one | 72 |

TABLE 2-continued

| Cmpd No. | Structure | m/z | Chemical Name | Example No. |
|---|---|---|---|---|
| 789 | 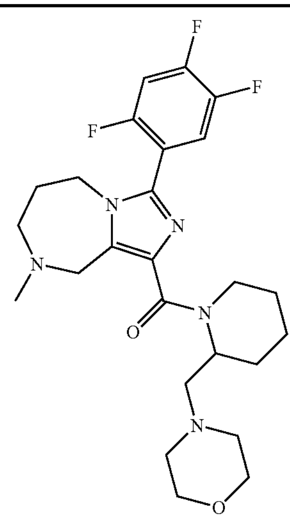 | 492.3 | (8-methyl-3-(2,4,5-trifluorophenyl)-6,7,8,9-tetrahydro-5H-imidazo[1,5-a][1,4]diazepin-1-yl)(2-(morpholinomethyl)piperidin-1-yl)methanone | 72 |
| 790 | 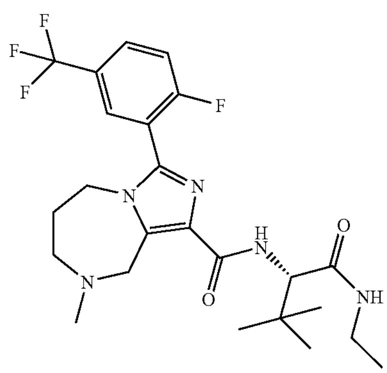 [SMILES: CCNC(=O)[C@@H](NC(=O)c1nc(-c2cc(C(F)(F)F)ccc2F)n2c1CN(C)CCC2)C(C)(C)C] | 498 | (S)-N-(1-(ethylamino)-3,3-dimethyl-1-oxobutan-2-yl)-3-(2-fluoro-5-(trifluoromethyl)phenyl)-8-methyl-6,7,8,9-tetrahydro-5H-imidazo[1,5-a][1,4]diazepine-1-carboxamide | 77 |
| 791 | 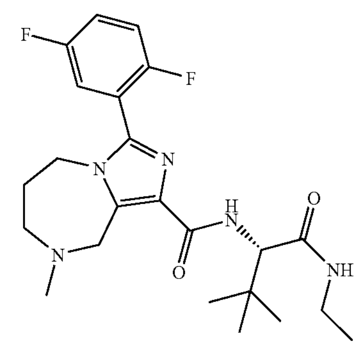 [SMILES: CCNC(=O)[C@@H](NC(=O)c1nc(-c2cc(F)ccc2F)n2c1CN(C)CCC2)C(C)(C)C] | 448 | (S)-3-(2,5-difluorophenyl)-N-(1-(ethylamino)-3,3-dimethyl-1-oxobutan-2-yl)-8-methyl-6,7,8,9-tetrahydro-5H-imidazo[1,5-a][1,4]diazepine-1-carboxamide | 77 |
| 792 | 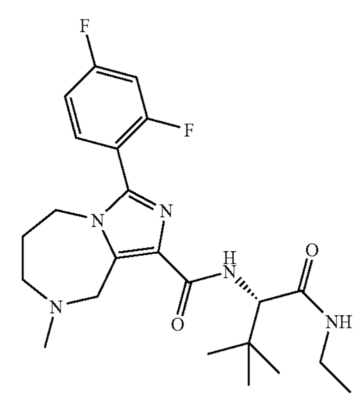 [SMILES: CCNC(=O)[C@@H](NC(=O)c1nc(-c2ccc(F)cc2F)n2c1CN(C)CCC2)C(C)(C)C] | 448 | (S)-3-(2,4-difluorophenyl)-N-(1-(ethylamino)-3,3-dimethyl-1-oxobutan-2-yl)-8-methyl-6,7,8,9-tetrahydro-5H-imidazo[1,5-a][1,4]diazepine-1-carboxamide | 77 |

TABLE 2-continued

| Cmpd No. | Structure | m/z | Chemical Name | Example No. |
|---|---|---|---|---|
| 793 | 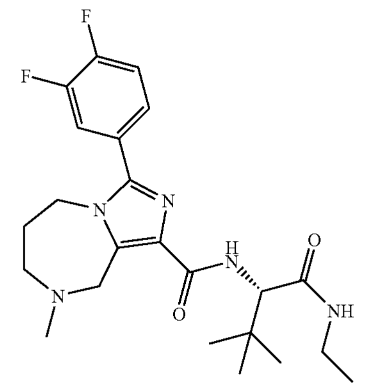 [SMILES: CCNC(=O)[C@@H](NC(=O)c1nc(-c2ccc(F)c(F)c2)n2c1CN(C)CCC2)C(C)(C)C] | 448 | (S)-3-(3,4-difluorophenyl)-N-(1-(ethylamino)-3,3-dimethyl-1-oxobutan-2-yl)-8-methyl-6,7,8,9-tetrahydro-5H-imidazo[1,5-a][1,4]diazepine-1-carboxamide | 77 |
| 794 | 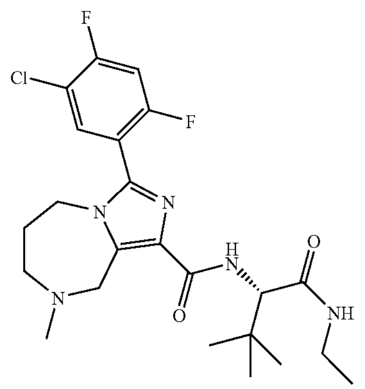 [SMILES: CCNC(=O)[C@@H](NC(=O)c1nc(-c2cc(Cl)c(F)cc2F)n2c1CN(C)CCC2)C(C)(C)C] | 482 | (S)-3-(5-chloro-2,4-difluorophenyl)-N-(1-(ethylamino)-3,3-dimethyl-1-oxobutan-2-yl)-8-methyl-6,7,8,9-tetrahydro-5H-imidazo[1,5-a][1,4]diazepine-1-carboxamide | 77 |
| 795 | 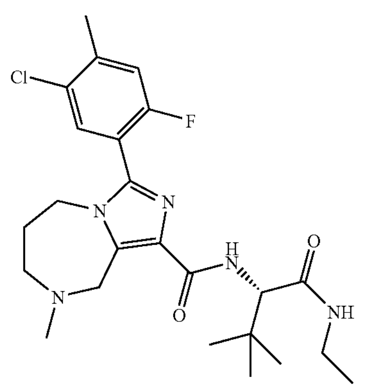 [SMILES: CCNC(=O)[C@@H](NC(=O)c1nc(-c2cc(Cl)c(C)cc2F)n2c1CN(C)CCC2)C(C)(C)C] | 479 | (S)-3-(5-chloro-2-fluoro-4-methylphenyl)-N-(1-(ethylamino)-3,3-dimethyl-1-oxobutan-2-yl)-8-methyl-6,7,8,9-tetrahydro-5H-imidazo[1,5-a][1,4]diazepine-1-carboxamide | 77 |
| 796 | 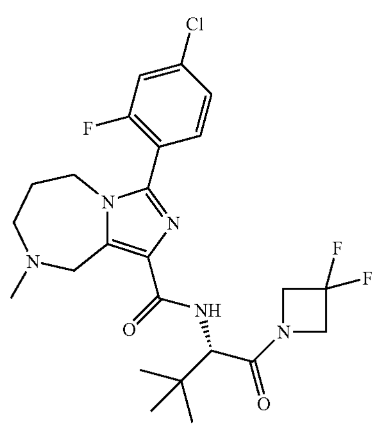 | 512 | (S)-3-(4-chloro-2-fluorophenyl)-N-(1-(3,3-difluoroazetidin-1-yl)-3,3-dimethyl-1-oxobutan-2-yl)-8-methyl-6,7,8,9-tetrahydro-5H-imidazo[1,5-a][1,4]diazepine-1-carboxamide | 77 |

TABLE 2-continued

| Cmpd No. | Structure | m/z | Chemical Name | Example No. |
|---|---|---|---|---|
| 797 | 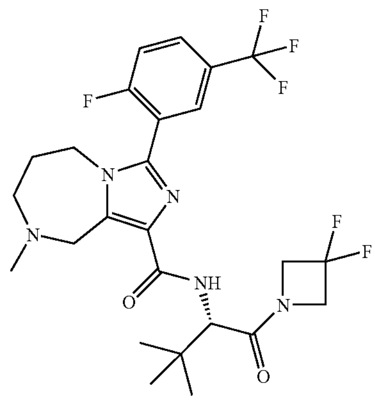 [SMILES: CN1CCCn2c(-c3cc(C(F)(F)F)ccc3F)nc(C(=O)N[C@H](C(=O)N3CC(F)(F)C3)C(C)(C)C)c2C1] | 546 | (S)-N-(1-(3,3-difluoroazetidin-1-yl)-3,3-dimethyl-1-oxobutan-2-yl)-3-(2-fluoro-5-(trifluoromethyl)phenyl)-8-methyl-6,7,8,9-tetrahydro-5H-imidazo[1,5-a][1,4]diazepine-1-carboxamide | 77 |
| 798 | 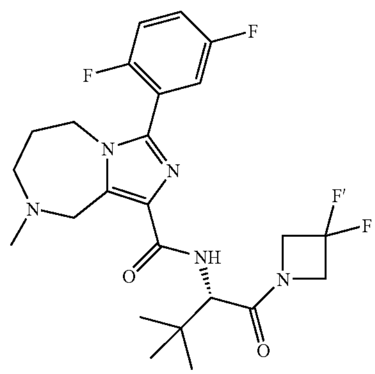 | 496 | (S)-N-(1-(3,3-difluoroazetidin-1-yl)-3,3-dimethyl-1-oxobutan-2-yl)-3-(2,5-difluorophenyl)-8-methyl-6,7,8,9-tetrahydro-5H-imidazo[1,5-a][1,4]diazepine-1-carboxamide | 77 |
| 799 | 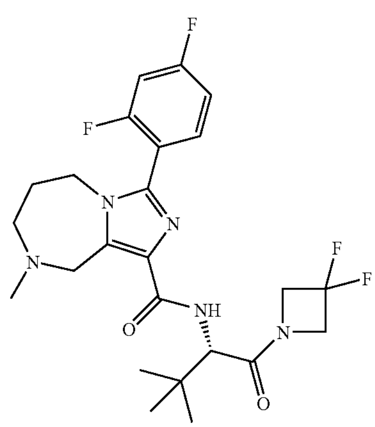 [SMILES: CN1CCCn2c(-c3ccc(F)cc3F)nc(C(=O)N[C@H](C(=O)N3CC(F)(F)C3)C(C)(C)C)c2C1] | 496 | (S)-N-(1-(3,3-difluoroazetidin-1-yl)-3,3-dimethyl-1-oxobutan-2-yl)-3-(2,4-difluorophenyl)-8-methyl-6,7,8,9-tetrahydro-5H-imidazo[1,5-a][1,4]diazepine-1-carboxamide | 77 |

TABLE 2-continued

| Cmpd No. | Structure | m/z | Chemical Name | Example No. |
|---|---|---|---|---|
| 800 | 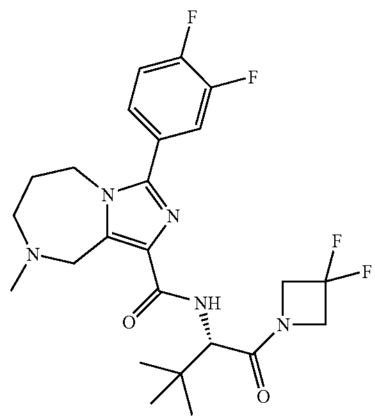 [SMILES: CN1CCCn2c(-c3ccc(F)c(F)c3)nc(C(=O)N[C@H](C(=O)N3CC(F)(F)C3)C(C)(C)C)c2C1] | 496 | (S)-N-(1-(3,3-difluoroazetidin-1-yl)-3,3-dimethyl-1-oxobutan-2-yl)-3-(3,4-difluorophenyl)-8-methyl-6,7,8,9-tetrahydro-5H-imidazo[1,5-a][1,4]diazepine-1-carboxamide | 77 |
| 801 | 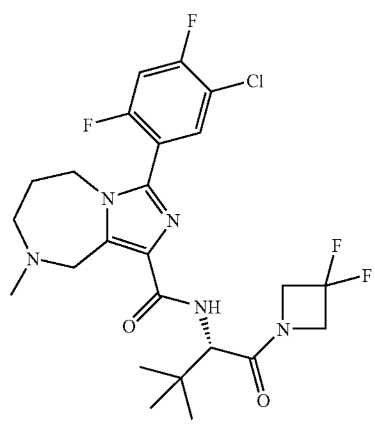 [SMILES: CN1CCCn2c(-c3cc(Cl)c(F)cc3F)nc(C(=O)N[C@H](C(=O)N3CC(F)(F)C3)C(C)(C)C)c2C1] | 530 | (S)-3-(5-chloro-2,4-difluorophenyl)-N-(1-(3,3-difluoroazetidin-1-yl)-3,3-dimethyl-1-oxobutan-2-yl)-8-methyl-6,7,8,9-tetrahydro-5H-imidazo[1,5-a][1,4]diazepine-1-carboxamide | 77 |
| 802 | 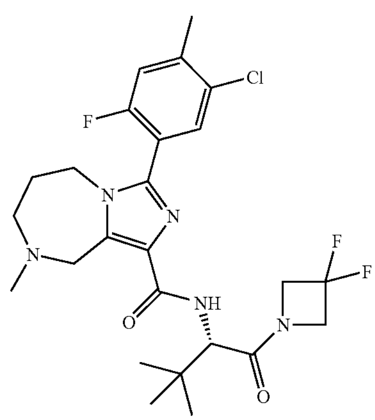 [SMILES: Cc1cc(F)c(-c2nc(C(=O)N[C@H](C(=O)N3CC(F)(F)C3)C(C)(C)C)c3n2CCCN(C)C3)cc1Cl] | 526 | (S)-3-(5-chloro-2-fluoro-4-methylphenyl)-N-(1-(3,3-difluoroazetidin-1-yl)-3,3-dimethyl-1-oxobutan-2-yl)-8-methyl-6,7,8,9-tetrahydro-5H-imidazo[1,5-a][1,4]diazepine-1-carboxamide | 77 |

TABLE 2-continued

| Cmpd No. | Structure | m/z | Chemical Name | Example No. |
|---|---|---|---|---|
| 803 | 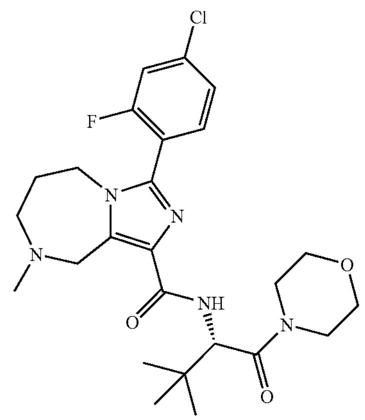 | 507 | (S)-3-(4-chloro-2-fluorophenyl)-N-(3,3-dimethyl-1-morpholino-1-oxobutan-2-yl)-8-methyl-6,7,8,9-tetrahydro-5H-imidazo[1,5-a][1,4]diazepine-1-carboxamide | 77 |
| 804 | 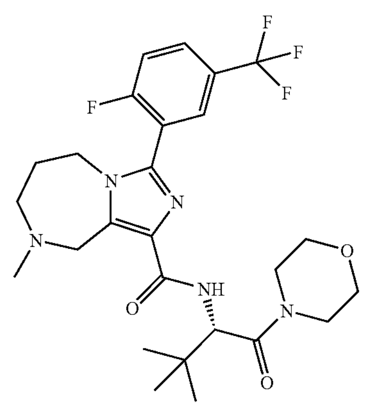 [SMILES: CN1CCCn2c(-c3cc(C(F)(F)F)ccc3F)nc(C(=O)N[C@H](C(=O)N3CCOCC3)C(C)(C)C)c2C1] | 540 | (S)-N-(3,3-dimethyl-1-morpholino-1-oxobutan-2-yl)-3-(2-fluoro-5-(trifluoromethyl)phenyl)-8-methyl-6,7,8,9-tetrahydro-5H-imidazo[1,5-a][1,4]diazepine-1-carboxamide | 77 |
| 805 | 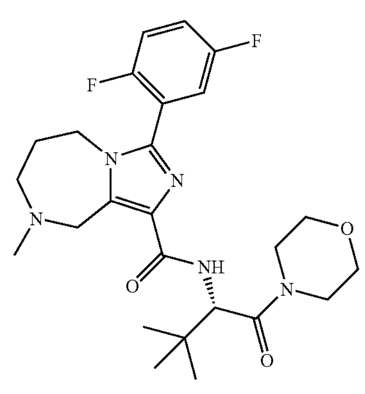 [SMILES: CN1CCCn2c(-c3cc(F)ccc3F)nc(C(=O)N[C@H](C(=O)N3CCOCC3)C(C)(C)C)c2C1] | 490 | (S)-3-(2,5-difluorophenyl)-N-(3,3-dimethyl-1-morpholino-1-oxobutan-2-yl)-8-methyl-6,7,8,9-tetrahydro-5H-imidazo[1,5-a][1,4]diazepine-1-carboxamide | 77 |

TABLE 2-continued

| Cmpd No. | Structure | m/z | Chemical Name | Example No. |
|---|---|---|---|---|
| 806 | 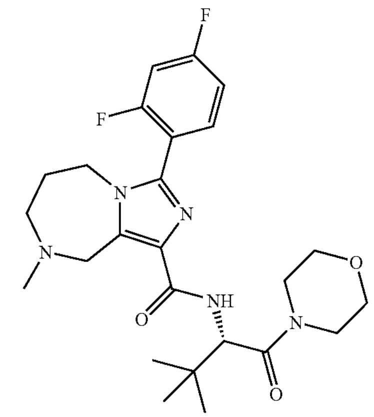 [SMILES: CN1CCCn2c(-c3ccc(F)cc3F)nc(C(=O)N[C@H](C(=O)N3CCOCC3)C(C)(C)C)c2C1] | 490 | (S)-3-(2,4-difluorophenyl)-N-(3,3-dimethyl-1-morpholino-1-oxobutan-2-yl)-8-methyl-6,7,8,9-tetrahydro-5H-imidazo[1,5-a][1,4]diazepine-1-carboxamide | 77 |
| 807 | 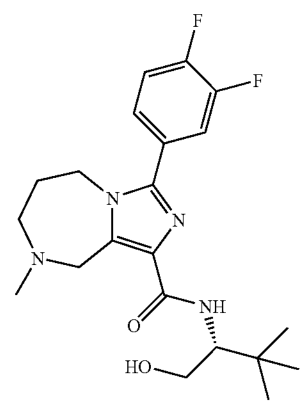 [SMILES: CN1CCCn2c(-c3ccc(F)c(F)c3)nc(C(=O)N[C@@H](CO)C(C)(C)C)c2C1] | 407.2 | (R)-3-(3,4-difluorophenyl)-N-(1-hydroxy-3,3-dimethylbutan-2-yl)-8-methyl-6,7,8,9-tetrahydro-5H-imidazo[1,5-a][1,4]diazepine-1-carboxamide | 72 |
| 808 | 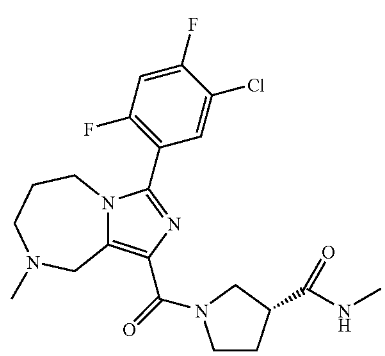 | 452.2 | (R)-1-(3-(5-chloro-2,4-difluorophenyl)-8-methyl-6,7,8,9-tetrahydro-5H-imidazo[1,5-a][1,4]diazepine-1-carbonyl)-N-methylpyrrolidine-3-carboxamide | 72 |
| 809 | 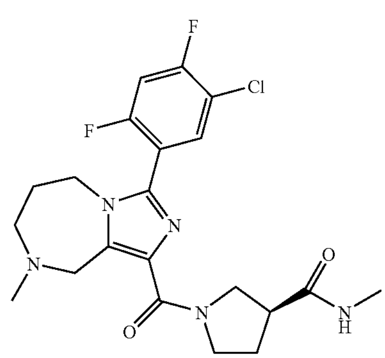 | 452.2 | (S)-1-(3-(5-chloro-2,4-difluorophenyl)-8-methyl-6,7,8,9-tetrahydro-5H-imidazo[1,5-a][1,4]diazepine-1-carbonyl)-N-methylpyrrolidine-3-carboxamide | 72 |

TABLE 2-continued

| Cmpd No. | Structure | m/z | Chemical Name | Example No. |
|---|---|---|---|---|
| 810 | 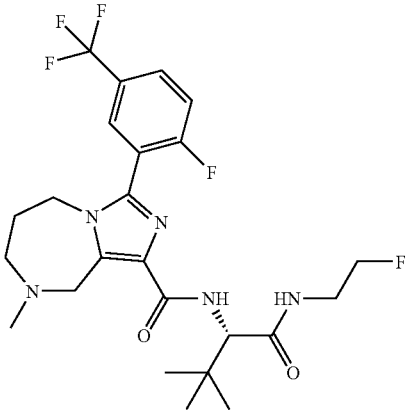 [SMILES: CN1CCCn2c(-c3cc(C(F)(F)F)ccc3F)nc(C(=O)N[C@H](C(=O)NCCF)C(C)(C)C)c2C1] | 516 | (S)-3-(2-fluoro-5-(trifluoromethyl)phenyl)-N-(1-(2-fluoroethylamino)-3,3-dimethyl-1-oxobutan-2-yl)-8-methyl-6,7,8,9-tetrahydro-5H-imidazo[1,5-a][1,4]diazepine-1-carboxamide | 77 |
| 811 | 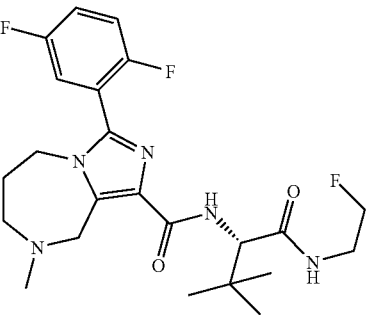 [SMILES: CN1CCCn2c(-c3cc(F)ccc3F)nc(C(=O)N[C@H](C(=O)NCCF)C(C)(C)C)c2C1] | 466 | (S)-3-(2,5-difluorophenyl)-N-(1-(2-fluoroethylamino)-3,3-dimethyl-1-oxobutan-2-yl)-8-methyl-6,7,8,9-tetrahydro-5H-imidazo[1,5-a][1,4]diazepine-1-carboxamide | 77 |
| 812 | 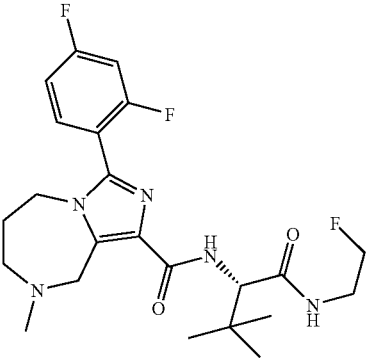 [SMILES: CN1CCCn2c(-c3ccc(F)cc3F)nc(C(=O)N[C@H](C(=O)NCCF)C(C)(C)C)c2C1] | 466 | (S)-3-(2,4-difluorophenyl)-N-(1-(2-fluoroethylamino)-3,3-dimethyl-1-oxobutan-2-yl)-8-methyl-6,7,8,9-tetrahydro-5H-imidazo[1,5-a][1,4]diazepine-1-carboxamide | 77 |
| 813 | 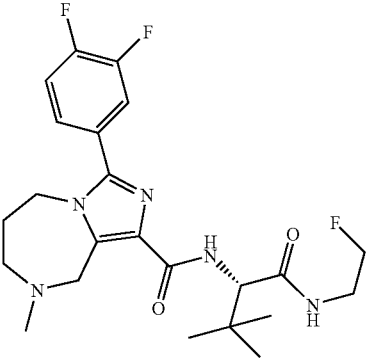 [SMILES: CN1CCCn2c(-c3ccc(F)c(F)c3)nc(C(=O)N[C@H](C(=O)NCCF)C(C)(C)C)c2C1] | 943 | (S)-3-(3,4-difluorophenyl)-N-(1-(2-fluoroethylamino)-3,3-dimethyl-1-oxobutan-2-yl)-8-methyl-6,7,8,9-tetrahydro-5H-imidazo[1,5-a][1,4]diazepine-1-carboxamide | 77 |

TABLE 2-continued

| Cmpd No. | Structure | m/z | Chemical Name | Example No. |
|---|---|---|---|---|
| 814 | 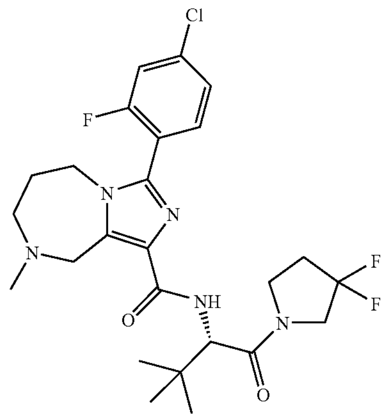 | 526 | (S)-3-(4-chloro-2-fluorophenyl)-N-(1-(3,3-difluoropyrrolidin-1-yl)-(3,3-dimethyl-1-oxobutan-2-yl)-8-methyl-6,7,8,9-tetrahydro-5H-imidazo[1,5-a][1,4]diazepine-1-carboxamide | 77 |
| 815 | 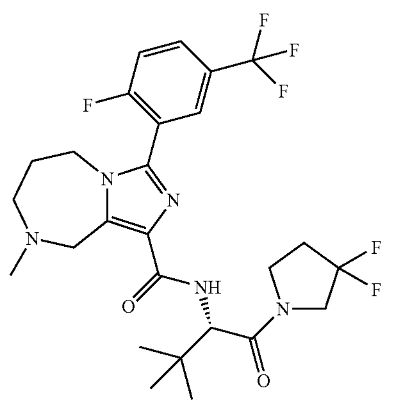 [SMILES: CN1CCCn2c(-c3cc(C(F)(F)F)ccc3F)nc(C(=O)N[C@H](C(=O)N3CCC(F)(F)C3)C(C)(C)C)c2C1] | 560 | (S)-N-(1-(3,3-difluoropyrrolidin-1-yl)-3,3-dimethyl-1-oxobutan-2-yl)-3-(2-fluoro-5-(trifluoromethyl)phenyl)-8-methyl-6,7,8,9-tetrahydro-5H-imidazo[1,5-a][1,4]diazepine-1-carboxamide | 77 |
| 816 | 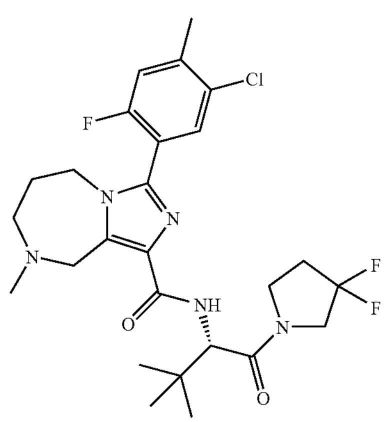 [SMILES: Cc1cc(F)c(-c2nc(C(=O)N[C@H](C(=O)N3CCC(F)(F)C3)C(C)(C)C)c3n2CCCN(C)C3)cc1Cl] | 541 | (S)-3-(5-chloro-2-fluoro-4-methylphenyl)-N-(1-(3,3-difluoropyrrolidin-1-yl)-3,3-dimethyl-1-oxobutan-2-yl)-8-methyl-6,7,8,9-tetrahydro-5H-imidazo[1,5-a][1,4]diazepine-1-carboxamide | 77 |

TABLE 2-continued

| Cmpd No. | Structure | m/z | Chemical Name | Example No. |
|---|---|---|---|---|
| 817 | 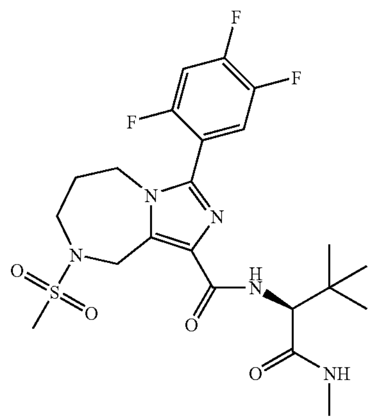 [SMILES: CNC(=O)[C@@H](NC(=O)c1nc(-c2cc(F)c(F)cc2F)n2c1CN(S(C)(=O)=O)CCC2)C(C)(C)C] | 516.2 | (S)-N-(3,3-dimethyl-1-(methylamino)-1-oxobutan-2-yl)-8-(methylsulfonyl)-3-(2,4,5-trifluorophenyl)-6,7,8,9-tetrahydro-5H-imidazo[1,5-a][1,4]diazepine-1-carboxamide | 38 |
| 818 | 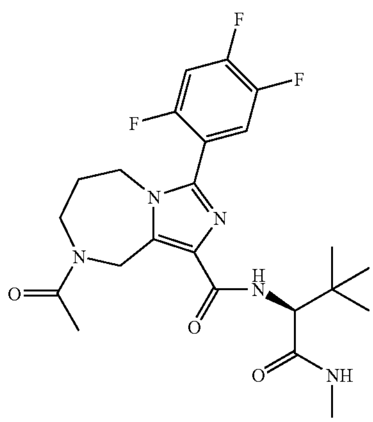 [SMILES: CNC(=O)[C@@H](NC(=O)c1nc(-c2cc(F)c(F)cc2F)n2c1CN(C(C)=O)CCC2)C(C)(C)C] | 480.2 | (S)-8-acetyl-N-(3,3-dimethyl-1-(methylamino)-1-oxobutan-2-yl)-3-(2,4,5-trifluorophenyl)-6,7,8,9-tetrahydro-5H-imidazo[1,4]diazepine-1-carboxamide | 38 |
| 819 | 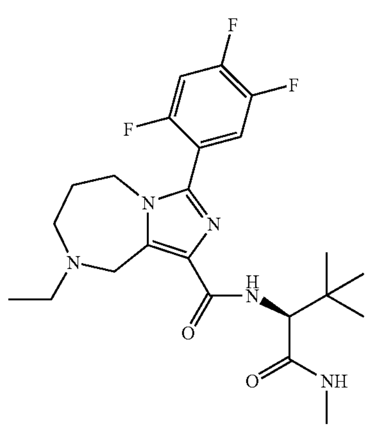 [SMILES: CCN1CCCn2c(-c3cc(F)c(F)cc3F)nc(C(=O)N[C@H](C(=O)NC)C(C)(C)C)c2C1] | 466.3 | (S)-N-(3,3-dimethyl-1-(methylamino)-1-oxobutan-2-yl)-8-ethyl-3-(2,4,5-trifluorophenyl)-6,7,8,9-tetrahydro-5H-imidazo[1,5-a][1,4]diazepine-1-carboxamide | 35 |

TABLE 2-continued

| Cmpd No. | Structure | m/z | Chemical Name | Example No. |
|---|---|---|---|---|
| 820 | 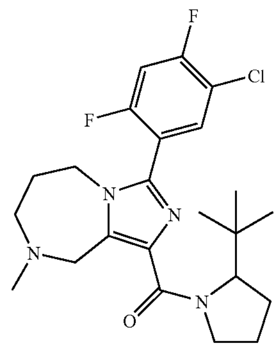 [SMILES: CN1CCCn2c(-c3cc(Cl)c(F)cc3F)nc(C(=O)N3CCCC3C(C)(C)C)c2C1] | 451 | (2-tert-butylpyrrolidin-1-yl)(3-(5-chloro-2,4-difluorophenyl)-8-methyl-6,7,8,9-tetrahydro-5H-imidazo[1,5-a][1,4]diazepin-1-yl)methanone | 72 |
| 821 | 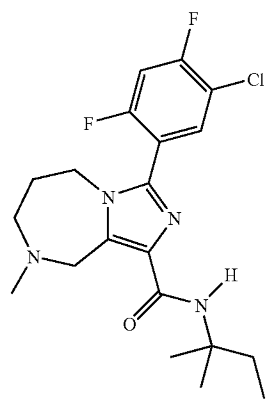 [SMILES: CCC(C)(C)NC(=O)c1nc(-c2cc(Cl)c(F)cc2F)n2c1CN(C)CCC2] | 411 | 3-(5-chloro-2,4-difluorophenyl)-8-methyl-N-tert-pentyl-6,7,8,9-tetrahydro-5H-imidazo[1,5-a][1,4]diazepine-1-carboxamide | 72 |
| 822 | 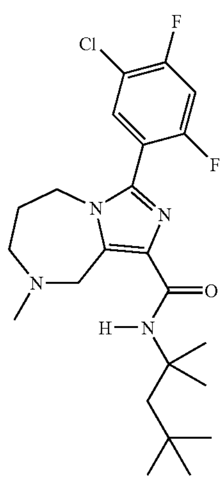 [SMILES: CN1CCCn2c(-c3cc(Cl)c(F)cc3F)nc(C(=O)NC(C)(C)CC(C)(C)C)c2C1] | 452 | 3-(5-chloro-2,4-difluorophenyl)-8-methyl-N-(2,4,4-trimethylpentan-2-yl)-6,7,8,9-tetrahydro-5H-imidazo[1,5-a][1,4]diazepine-1-carboxamide | 72 |
| 823 | 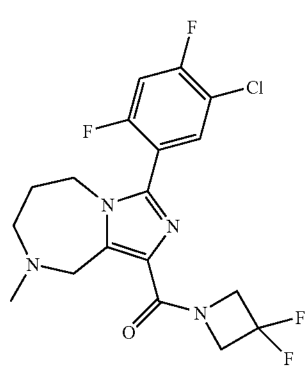 [SMILES: CN1CCCn2c(-c3cc(Cl)c(F)cc3F)nc(C(=O)N3CC(F)(F)C3)c2C1] | 417 | (3-(5-chloro-2,4-difluorophenyl)-8-methyl-6,7,8,9-tetrahydro-5H-imidazo[1,5-a][1,4]diazepin-1-yl)(3,3-difluoroazetidin-1-yl)methanone | 72 |

TABLE 2-continued

| Cmpd No. | Structure | m/z | Chemical Name | Example No. |
|---|---|---|---|---|
| 824 | 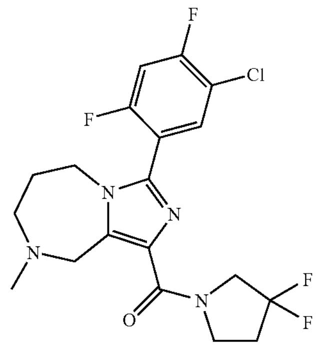 [SMILES: CN1CCCn2c(-c3cc(Cl)c(F)cc3F)nc(C(=O)N3CCC(F)(F)C3)c2C1] | 431 | (3-(5-chloro-2,4-difluorophenyl)-8-methyl-6,7,8,9-tetrahydro-5H-imidazo[1,5-a][1,4]diazepin-1-yl)(3,3-difluoropyrrolidin-1-yl)methanone | 72 |
| 825 | 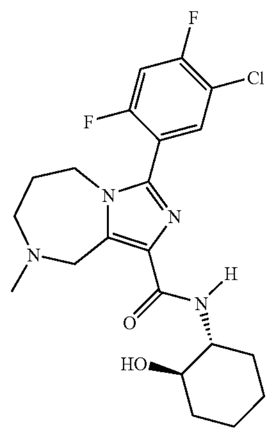 [SMILES: CN1CCCn2c(-c3cc(Cl)c(F)cc3F)nc(C(=O)N[C@@H]3CCCC[C@H]3O)c2C1] | 439 | 3-(5-chloro-2,4-difluorophenyl)-N-((1R,2R)-2-hydroxycyclohexyl)-8-methyl-6,7,8,9-tetrahydro-5H-imidazo[1,5-a][1,4]diazepine-1-carboxamide | 72 |
| 826 | 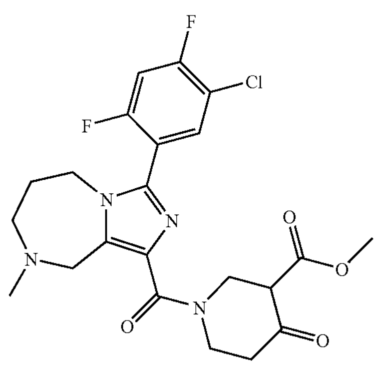 | 481 | methyl 1-(3-(5-chloro-2,4-difluorophenyl)-8-methyl-6,7,8,9-tetrahydro-5H-imidazo[1,5-a][1,4]diazepine-1-carbonyl)-4-oxopiperidine-3-carboxylate | 72 |
| 827 | 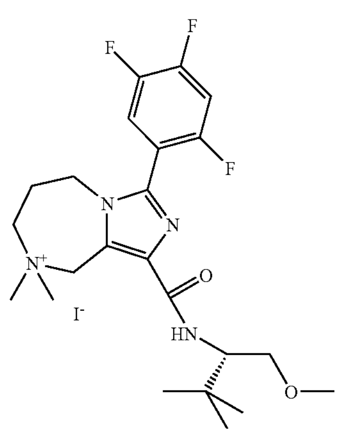 | 454.2 | (S)-N-(1-methoxy-3,3-dimethylbutan-2-yl)-8-methyl-3-(2,4,5-trifluorophenyl)-6,7,8,9-tetrahydro-5H-imidazo[1,5-a][1,4]diazepine-1-carboxamide methiodide | 78 |

TABLE 2-continued

| Cmpd No. | Structure | m/z | Chemical Name | Example No. |
|---|---|---|---|---|
| 828 | 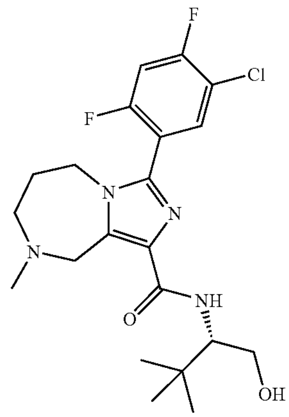 [SMILES: CN1CCCn2c(-c3cc(Cl)c(F)cc3F)nc(C(=O)N[C@H](CO)C(C)(C)C)c2C1] | 441 | (S)-3-(5-chloro-2,4-difluorophenyl)-N-(1-hydroxy-3,3-dimethylbutan-2-yl)-8-methyl-6,7,8,9-tetrahydro-5H-imidazo[1,5-a][1,4]diazepine-1-carboxamide | 72 |
| 829 | 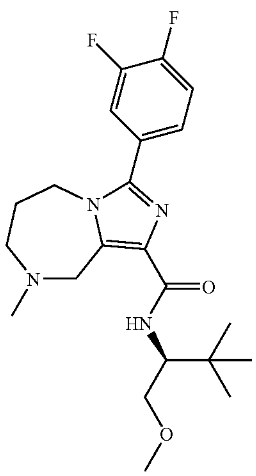 [SMILES: COC[C@@H](NC(=O)c1nc(-c2ccc(F)c(F)c2)n2c1CN(C)CCC2)C(C)(C)C] | 421.2 | (S)-3-(3,4-difluorophenyl)-N-(1-methoxy-3,3-dimethylbutan-2-yl)-8-methyl-6,7,8,9-tetrahydro-5H-imidazo[1,5-a][1,4]diazepine-1-carboxamide | 79 |
| 830 | 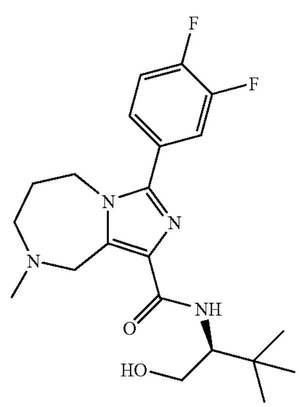 [SMILES: CN1CCCn2c(-c3ccc(F)c(F)c3)nc(C(=O)N[C@H](CO)C(C)(C)C)c2C1] | 407.2 | (S)-3-(3,4-difluorophenyl)-N-(1-hydroxy-3,3-dimethylbutan-2-yl)-8-methyl-6,7,8,9-tetrahydro-5H-imidazo[1,5-a][1,4]diazepine-1-carboxamide | 72 |

TABLE 2-continued

| Cmpd No. | Structure | m/z | Chemical Name | Example No. |
|---|---|---|---|---|
| 831 | 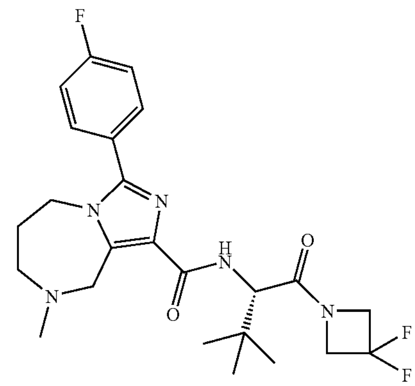 [SMILES: CN1CCCn2c(-c3ccc(F)cc3)nc(C(=O)N[C@H](C(=O)N3CC(F)(F)C3)C(C)(C)C)c2C1] | 478 | (S)-N-(1-(3,3-difluoroazetidin-1-yl)-3,3-dimethyl-1-oxobutan-2-yl)-3-(4-fluorophenyl)-8-methyl-6,7,8,9-tetrahydro-5H-imidazo[1,5-a][1,4]diazepine-1-carboxamide | 77 |
| 832 | 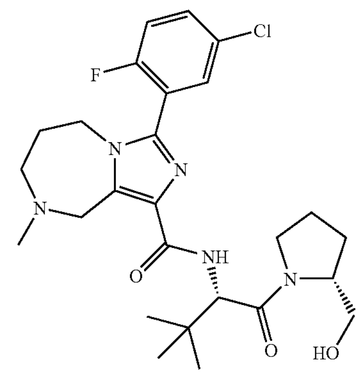 [SMILES: CN1CCCn2c(-c3cc(Cl)ccc3F)nc(C(=O)N[C@H](C(=O)N3CCC[C@@H]3CO)C(C)(C)C)c2C1] | 419.2 | 3-(5-chloro-2-fluorophenyl)-N-((S)-1-((R)-2-(hydroxymethyl)pyrrolidin-1-yl)-3,3-dimethyl-1-oxobutan-2-yl)-8-methyl-6,7,8,9-tetrahydro-5H-imidazo[1,5-a][1,4]diazepine-1-carboxamide | 67 |
| 833 | 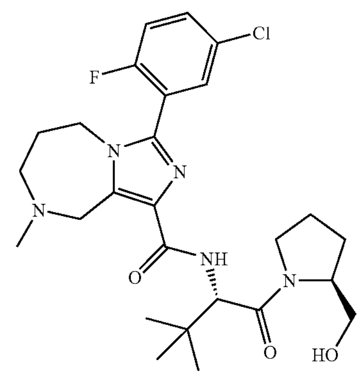 [SMILES: CN1CCCn2c(-c3cc(Cl)ccc3F)nc(C(=O)N[C@H](C(=O)N3CCC[C@H]3CO)C(C)(C)C)c2C1] | 419.2 | 3-(5-chloro-2-fluorophenyl)-N-((S)-1-((R)-2-(hydroxymethyl)pyrrolidin-1-yl)-3,3-dimethyl-1-oxobutan-2-yl)-8-methyl-6,7,8,9-tetrahydro-5H-imidazo[1,5-a][1,4]diazepine-1-carboxamide | 67 |
| 834 | 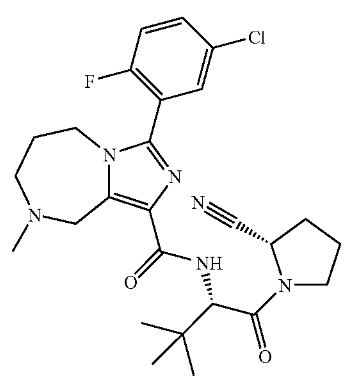 [SMILES: CN1CCCn2c(-c3cc(Cl)ccc3F)nc(C(=O)N[C@H](C(=O)N3CCC[C@H]3C#N)C(C)(C)C)c2C1] | 515.2 | 3-(5-chloro-2-fluorophenyl)-N-((S)-1-((S)-2-cyanopyrrolidin-1-yl)-3,3-dimethyl-1-oxobutan-2-yl)-8-methyl-6,7,8,9-tetrahydro-5H-imidazo[1,5-a][1,4]diazepine-1-carboxamide | 67 |

TABLE 2-continued

| Cmpd No. | Structure | m/z | Chemical Name | Example No. |
|---|---|---|---|---|
| 835 | 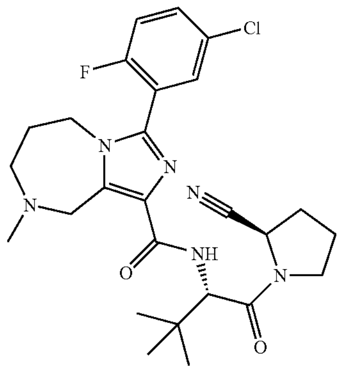 [SMILES: CN1CCCn2c(-c3cc(Cl)ccc3F)nc(C(=O)N[C@H](C(=O)N3CCC[C@@H]3C#N)C(C)(C)C)c2C1] | 515.2 | 3-(5-chloro-2-fluorophenyl)-N-((S)-1-((R)-2-cyanopyrrolidin-1-yl)-3,3-dimethyl-1-oxobutan-2-yl)-8-methyl-6,7,8,9-tetrahydro-5H-imidazo[1,5-a][1,4]diazepine-1-carboxamide | 67 |
| 836 | 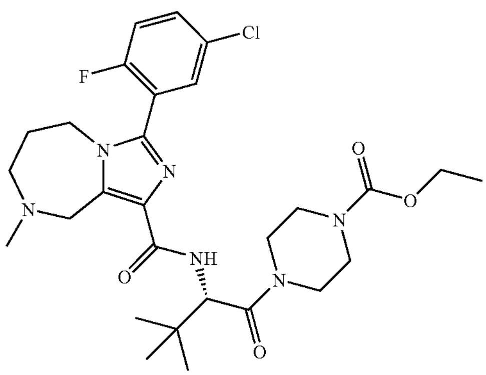 [SMILES: CCOC(=O)N1CCN(C(=O)[C@@H](NC(=O)c2nc(-c3cc(Cl)ccc3F)n3c2CN(C)CCC3)C(C)(C)C)CC1] | 577.3 | (S)-ethyl 4-(2-(3-(5-chloro-2-fluorophenyl)-8-methyl-6,7,8,9-tetrahydro-5H-imidazo[1,5-a][1,4]diazepine-1-carboxamido)-3,3-dimethylbutanoyl)piperazine-1-carboxylate | 67 |
| 837 | 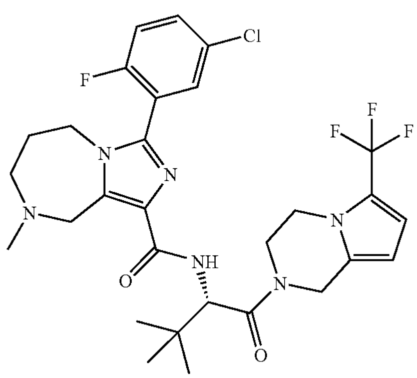 [SMILES: CN1CCCn2c(-c3cc(Cl)ccc3F)nc(C(=O)N[C@H](C(=O)N3CCn4c(ccc4C(F)(F)F)C3)C(C)(C)C)c2C1] | 611.3 | (S)-3-(5-chloro-2-fluorophenyl)-N-(3,3-dimethyl-1-oxo-1-(3-(trifluoromethyl)-5,6-dihydro-[1,2,4]triazolo[4,3-a]pyrazin-7(8H)-yl)butan-2-yl)-8-methyl-6,7,8,9-tetrahydro-5H-imidazo[1,5-a][1,4]diazepine-1-carboxamide | 67 |
| 838 | 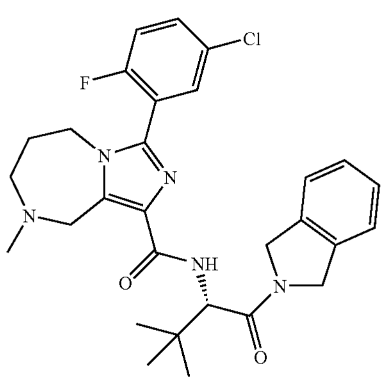 [SMILES: CN1CCCn2c(-c3cc(Cl)ccc3F)nc(C(=O)N[C@H](C(=O)N3Cc4ccccc4C3)C(C)(C)C)c2C1] | 539 | (S)-3-(5-chloro-2-fluorophenyl)-N-(1-(isoindolin-2-yl)-3,3-dimethyl-1-oxobutan-2-yl)-8-methyl-6,7,8,9-tetrahydro-5H-imidazo[1,5-a][1,4]diazepine-1-carboxamide | 67 |

TABLE 2-continued

| Cmpd No. | Structure | m/z | Chemical Name | Example No. |
|---|---|---|---|---|
| 839 | 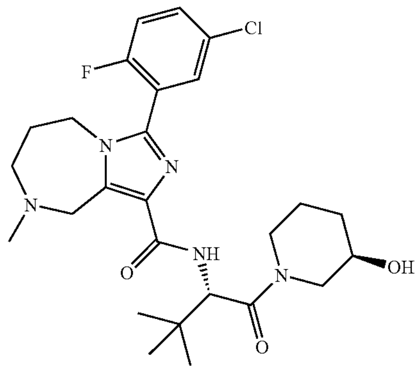 [SMILES: CN1CCCn2c(-c3cc(Cl)ccc3F)nc(C(=O)N[C@H](C(=O)N3CCC[C@@H](O)C3)C(C)(C)C)c2C1] | 419.2 | 3-(5-chloro-2-fluorophenyl)-N-((S)-1-((R)-3-hydroxypiperidin-1-yl)-3,3-dimethyl-1-oxobutan-2-yl)-8-methyl-6,7,8,9-tetrahydro-5H-imidazo[1,5-a][1,4]diazepine-1-carboxamide | 67 |
| 840 | 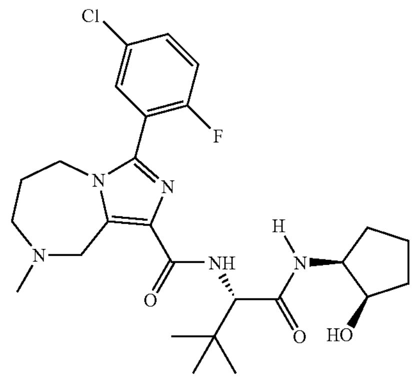 [SMILES: CN1CCCn2c(-c3cc(Cl)ccc3F)nc(C(=O)N[C@H](C(=O)N[C@H]3CCC[C@H]3O)C(C)(C)C)c2C1] | 520.3 | 3-(5-chloro-2-fluorophenyl)-N-((S)-1-((1S,2R)-2-hydroxycyclopentylamino)-3,3-dimethyl-1-oxobutan-2-yl)-8-methyl-6,7,8,9-tetrahydro-5H-imidazo[1,5-a][1,4]diazepine-1-carboxamide | 67 |
| 841 | 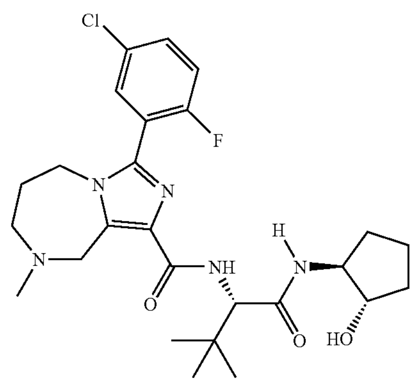 [SMILES: CN1CCCn2c(-c3cc(Cl)ccc3F)nc(C(=O)N[C@H](C(=O)N[C@H]3CCC[C@@H]3O)C(C)(C)C)c2C1] | 520.3 | 3-(5-chloro-2-fluorophenyl)-N-((S)-1-((1S,2S)-2-hydroxycyclopentylamino)-3,3-dimethyl-1-oxobutan-2-yl)-8-methyl-6,7,8,9-tetrahydro-5H-imidazo[1,5-a][1,4]diazepine-1-carboxamide | 67 |
| 842 | 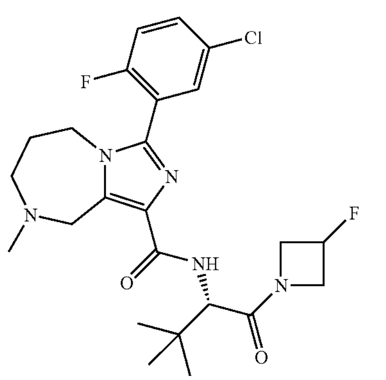 [SMILES: CN1CCCn2c(-c3cc(Cl)ccc3F)nc(C(=O)N[C@H](C(=O)N3CC(F)C3)C(C)(C)C)c2C1] | 494.2 | (S)-3-(5-chloro-2-fluorophenyl)-N-(1-(3-fluoroazetidin-1-yl)-3,3-dimethyl-1-oxobutan-2-yl)-8-methyl-6,7,8,9-tetrahydro-5H-imidazo[1,5-a][1,4]diazepine-1-carboxamide | 67 |

TABLE 2-continued

| Cmpd No. | Structure | m/z | Chemical Name | Example No. |
|---|---|---|---|---|
| 843 | 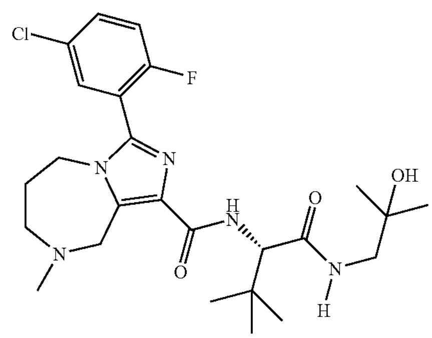 [SMILES: CN1CCCn2c(-c3cc(Cl)ccc3F)nc(C(=O)N[C@H](C(=O)NCC(C)(C)O)C(C)(C)C)c2C1] | 508.2 | (S)-3-(5-chloro-2-fluorophenyl)-N-(1-(2-hydroxy-2-methylpropylamino)-3,3-dimethyl-1-oxobutan-2-yl)-8-methyl-6,7,8,9-tetrahydro-5H-imidazo[1,5-a][1,4]diazepine-1-carboxamide | 67 |
| 844 | 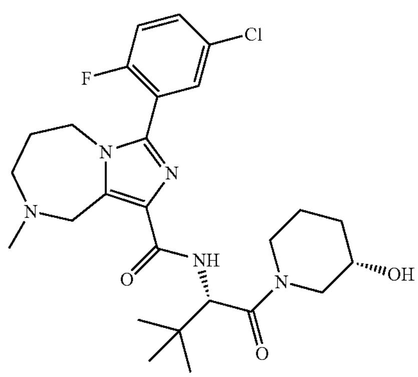 [SMILES: CN1CCCn2c(-c3cc(Cl)ccc3F)nc(C(=O)N[C@H](C(=O)N3CCC[C@H](O)C3)C(C)(C)C)c2C1] | 419.2 | 3-(5-chloro-2-fluorophenyl)-N-((S)-1-((S)-3-hydroxypiperidin-1-yl)-3,3-dimethyl-1-oxobutan-2-yl)-8-methyl-6,7,8,9-tetrahydro-5H-imidazo[1,5-a][1,4]diazepine-1-carboxamide | 67 |
| 845 | 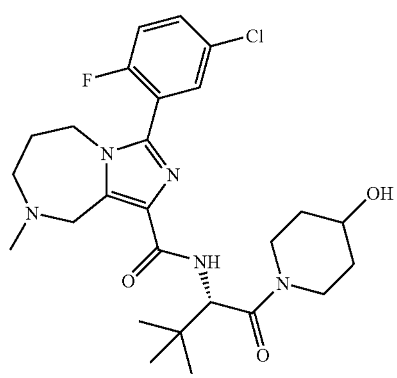 [SMILES: CN1CCCn2c(-c3cc(Cl)ccc3F)nc(C(=O)N[C@H](C(=O)N3CCC(O)CC3)C(C)(C)C)c2C1] | 419.2 | (S)-3-(5-chloro-2-fluorophenyl)-N-(1-(4-hydroxypiperidin-1-yl)-3,3-dimethyl-1-oxobutan-2-yl)-8-methyl-6,7,8,9-tetrahydro-5H-imidazo[1,5-a][1,4]diazepine-1-carboxamide | 67 |
| 846 | 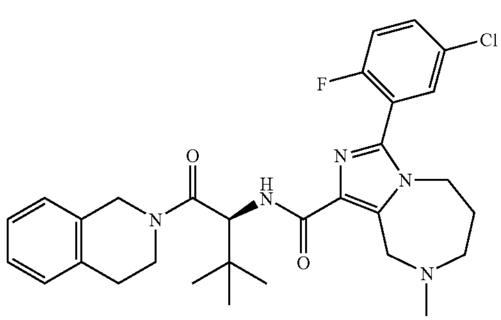 [SMILES: CN1CCCn2c(-c3cc(Cl)ccc3F)nc(C(=O)N[C@H](C(=O)N3CCc4ccccc4C3)C(C)(C)C)c2C1] | | (S)-3-(5-chloro-2-fluorophenyl)-N-(1-(3,4-dihydroisoquinolin-2(1H)-yl)-3,3-dimethyl-1-oxobutan-2-yl)-8-methyl-6,7,8,9-tetrahydro-5H-imidazo[1,5-a][1,4]diazepine-1-carboxamide | 67 |

TABLE 2-continued

| Cmpd No. | Structure | m/z | Chemical Name | Example No. |
|---|---|---|---|---|
| 847 | 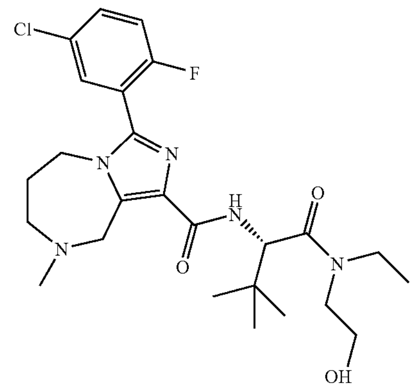 [SMILES: CCN(CCO)C(=O)[C@@H](NC(=O)c1nc(-c2cc(Cl)ccc2F)n2c1CN(C)CCC2)C(C)(C)C] | 508.3 | (S)-3-(5-chloro-2-fluorophenyl)-N-(1-(ethyl(2-hydroxyethyl)amino)-3,3-dimethyl-1-oxobutan-2-yl)-8-methyl-6,7,8,9-tetrahydro-5H-imidazo[1,5-a][1,4]diazepine-1-carboxamide | 67 |
| 848 | 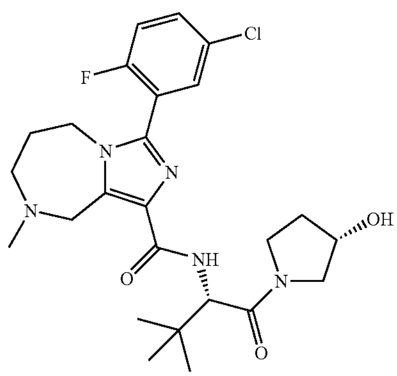 [SMILES: CN1CCCn2c(-c3cc(Cl)ccc3F)nc(C(=O)N[C@H](C(=O)N3CC[C@H](O)C3)C(C)(C)C)c2C1] | 507 | 3-(5-chloro-2-fluorophenyl)-N-((S)-1-((S)-3-hydroxypyrrolidin-1-yl)-3,3-dimethyl-1-oxobutan-2-yl)-8-methyl-6,7,8,9-tetrahydro-5H-imidazo[1,5-a][1,4]diazepine-1-carboxamide | 67 |
| 849 | 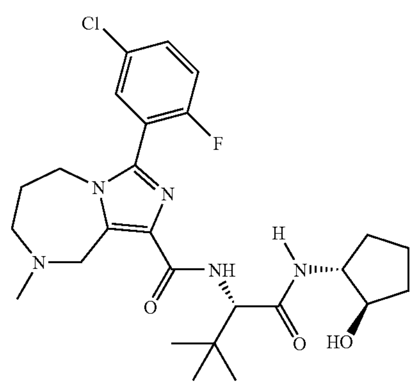 [SMILES: CN1CCCn2c(-c3cc(Cl)ccc3F)nc(C(=O)N[C@H](C(=O)N[C@@H]3CCC[C@H]3O)C(C)(C)C)c2C1] | 520.3 | 3-(5-chloro-2-fluorophenyl)-N-((S)-1-((1R,2R)-2-hydroxycyclopentylamino)-3,3-dimethyl-1-oxobutan-2-yl)-8-methyl-6,7,8,9-tetrahydro-5H-imidazo[1,5-a][1,4]diazepine-1-carboxamide | 67 |
| 850 | 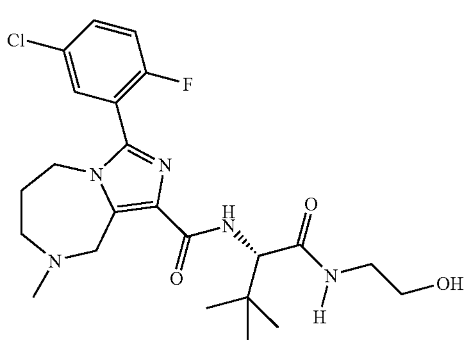 [SMILES: CN1CCCn2c(-c3cc(Cl)ccc3F)nc(C(=O)N[C@H](C(=O)NCCO)C(C)(C)C)c2C1] | 480.2 | (S)-3-(5-chloro-2-fluorophenyl)-N-(1-(2-hydroxyethylamino)-3,3-dimethyl-1-oxobutan-2-yl)-8-methyl-6,7,8,9-tetrahydro-5H-imidazo[1,5-a][1,4]diazepine-1-carboxamide | 67 |

TABLE 2-continued

| Cmpd No. | Structure | m/z | Chemical Name | Example No. |
|---|---|---|---|---|
| 851 | 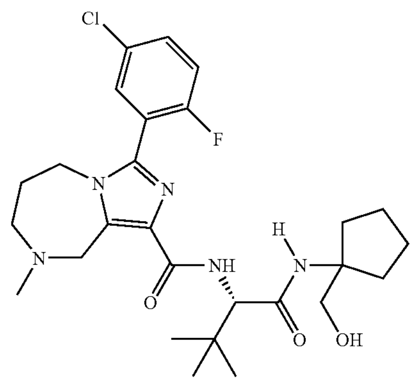 [SMILES: CN1CCCn2c(-c3cc(Cl)ccc3F)nc(C(=O)N[C@H](C(=O)NC3(CO)CCCC3)C(C)(C)C)c2C1] | 534.3 | (S)-3-(5-chloro-2-fluorophenyl)-N-(1-(1-(hydroxymethyl)cyclopentylamino)-3,3-dimethyl-1-oxobutan-2-yl)-8-methyl-6,7,8,9-tetrahydro-5H-imidazo[1,5-a][1,4]diazepine-1-carboxamide | 67 |
| 852 | 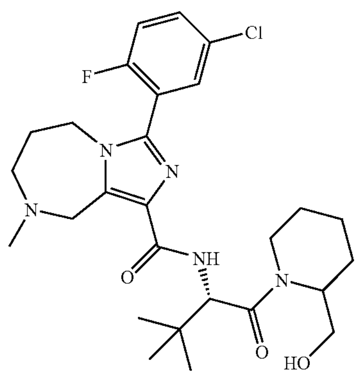 [SMILES: CN1CCCn2c(-c3cc(Cl)ccc3F)nc(C(=O)N[C@H](C(=O)N3CCCCC3CO)C(C)(C)C)c2C1] | 534.3 | 3-(5-chloro-2-fluorophenyl)-N-((2S)-1-(2-(hydroxymethyl)piperidin-1-yl)-3,3-dimethyl-1-oxobutan-2-yl)-8-methyl-6,7,8,9-tetrahydro-5H-imidazo[1,5-a][1,4]diazepine-1-carboxamide | 67 |
| 853 | 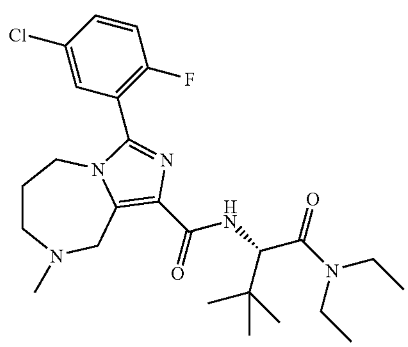 [SMILES: CCN(CC)C(=O)[C@@H](NC(=O)c1nc(-c2cc(Cl)ccc2F)n2c1CN(C)CCC2)C(C)(C)C] | 492.3 | (S)-3-(5-chloro-2-fluorophenyl)-N-(1-(diethylamino)-3,3-dimethyl-1-oxobutan-2-yl)-8-methyl-6,7,8,9-tetrahydro-5H-imidazo[1,5-a][1,4]diazepine-1-carboxamide | 67 |
| 854 | 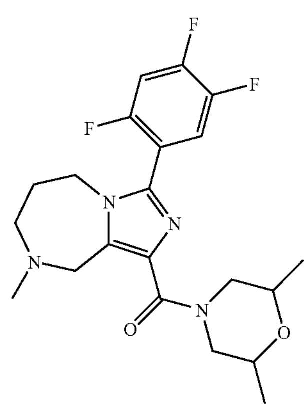 | 423.2 | (2,6-dimethylmorpholino)(8-methyl-3-(2,4,5-trifluorophenyl)-6,7,8,9-tetrahydro-5H-imidazo[1,5-a][1,4]diazepin-1-yl)methanone | 72 |

TABLE 2-continued

| Cmpd No. | Structure | m/z | Chemical Name | Example No. |
|---|---|---|---|---|
| 855 | 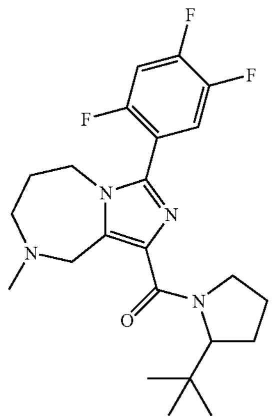 [SMILES: CN1CCCn2c(-c3cc(F)c(F)cc3F)nc(C(=O)N3CCCC3C(C)(C)C)c2C1] | 435.1 | (2-tert-butylpyrrolidin-1-yl)(8-methyl-3-(2,4,5-trifluorophenyl)-6,7,8,9-tetrahydro-5H-imidazo[1,5-a][1,4]diazepin-1-yl)methanone | 72 |
| 856 | 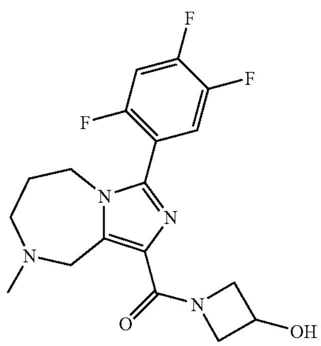 [SMILES: CN1CCCn2c(-c3cc(F)c(F)cc3F)nc(C(=O)N3CC(O)C3)c2C1] | 381.2 | (3-hydroxyazetidin-1-yl)(8-methyl-3-(2,4,5-trifluorophenyl)-6,7,8,9-tetrahydro-5H-imidazo[1,5-a][1,4]diazepin-1-yl)methanone | 72 |
| 857 | 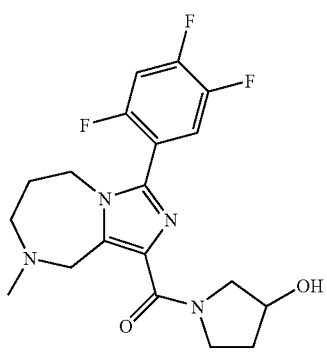 [SMILES: CN1CCCn2c(-c3cc(F)c(F)cc3F)nc(C(=O)N3CCC(O)C3)c2C1] | 395.2 | (3-hydroxypyrrolidin-1-yl)(8-methyl-3-(2,4,5-trifluorophenyl)-6,7,8,9-tetrahydro-5H-imidazo[1,5-a][1,4]diazepin-1-yl)methanone | 72 |
| 858 | 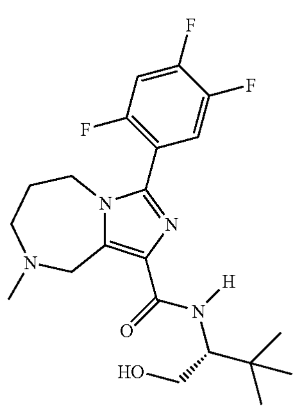 [SMILES: CN1CCCn2c(-c3cc(F)c(F)cc3F)nc(C(=O)N[C@@H](CO)C(C)(C)C)c2C1] | 425.3 | (R)-N-(1-hydroxy-3,3-dimethylbutan-2-yl)-8-methyl-3-(2,4,5-trifluorophenyl)-6,7,8,9-tetrahydro-5H-imidazo[1,5-a][1,4]diazepine-1-carboxamide | 72 |

TABLE 2-continued

| Cmpd No. | Structure | m/z | Chemical Name | Example No. |
|---|---|---|---|---|
| 859 | 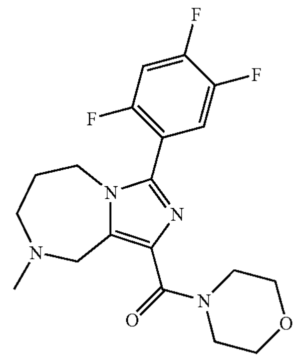 [SMILES: CN1CCCn2c(-c3cc(F)c(F)cc3F)nc(C(=O)N3CCOCC3)c2C1] | 395.2 | (8-methyl-3-(2,4,5-trifluorophenyl)-6,7,8,9-tetrahydro-5H-imidazo[1,5-a][1,4]diazepin-1-yl)(morpholino)methanone | 72 |
| 860 | 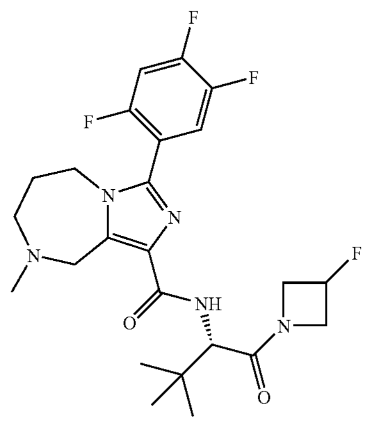 [SMILES: CN1CCCn2c(-c3cc(F)c(F)cc3F)nc(C(=O)N[C@H](C(=O)N3CC(F)C3)C(C)(C)C)c2C1] | 496.2 | (S)-N-(1-(3-fluoroazetidin-1-yl)-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide | 67 |
| 861 | 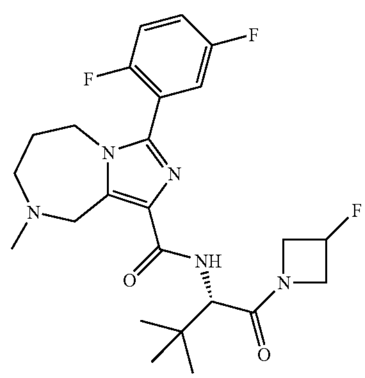 [SMILES: CN1CCCn2c(-c3cc(F)ccc3F)nc(C(=O)N[C@H](C(=O)N3CC(F)C3)C(C)(C)C)c2C1] | 478.3 | (S)-3-(2,5-difluorophenyl)-N-(1-(3-fluoroazetidin-1-yl)-3,3-dimethyl-1-oxobutan-2-yl)-8-methyl-6,7,8,9-tetrahydro-5H-imidazo[1,5-a][1,4]diazepine-1-carboxamide | 67 |
| 862 | 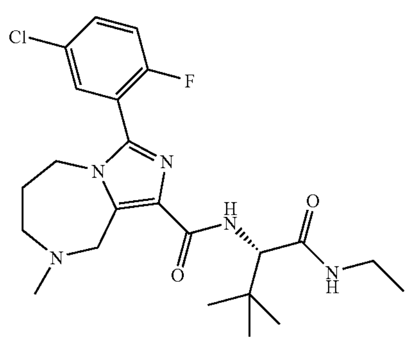 [SMILES: CCNC(=O)[C@@H](NC(=O)c1nc(-c2cc(Cl)ccc2F)n2c1CN(C)CCC2)C(C)(C)C] | 464 | (S)-3-(5-chloro-2-fluorophenyl)-N-(1-(ethylamino)-3,3-dimethyl-1-oxobutan-2-yl)-8-methyl-6,7,8,9-tetrahydro-5H-imidazo[1,5-a][1,4]diazepine-1-carboxamide | 67 |

TABLE 2-continued

| Cmpd No. | Structure | m/z | Chemical Name | Example No. |
|---|---|---|---|---|
| 863 | 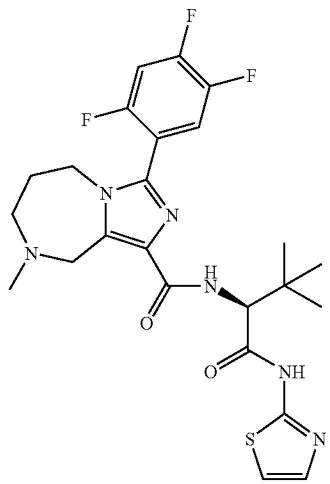 [SMILES: CN1CCCn2c(-c3cc(F)c(F)cc3F)nc(C(=O)N[C@H](C(=O)Nc3nccs3)C(C)(C)C)c2C1] | 521.2 | (S)-N-(3,3-dimethyl-1-oxo-1-(thiazol-2-ylamino)butan-2-yl)-8-methyl-3-(2,4,5-trifluorophenyl)-6,7,8,9-tetrahydro-5H-imidazo[1,5-a][1,4]diazepine-1-carboxamide | 67 |
| 864 | 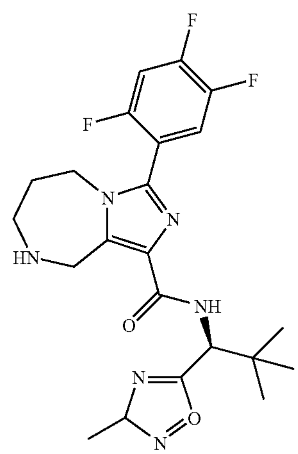 | 463.2 | (S)-N-(2,2-dimethyl-1-(3-methyl-1,2,4-oxadiazol-5-yl)propyl)-3-(2,4,5-trifluorophenyl)-6,7,8,9-tetrahydro-5H-imidazo[1,5-a][1,4]diazepine-1-carboxamide | 81 |
| 865 | 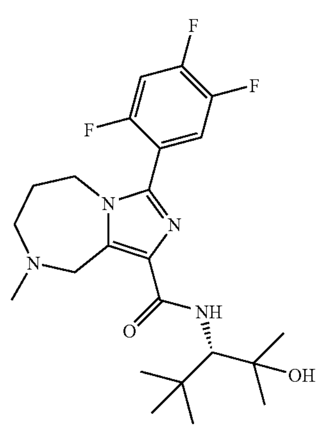 [SMILES: CN1CCCn2c(-c3cc(F)c(F)cc3F)nc(C(=O)N[C@@H](C(C)(C)C)C(C)(C)O)c2C1] | 453.3 | (S)-N-(2-hydroxy-2,4,4-trimethylpentan-3-yl)-8-methyl-3-(2,4,5-trifluorophenyl)-6,7,8,9-tetrahydro-5H-imidazo[1,5-a][1,4]diazepine-1-carboxamide | 80 |

TABLE 2-continued

| Cmpd No. | Structure | m/z | Chemical Name | Example No. |
|---|---|---|---|---|
| 866 | 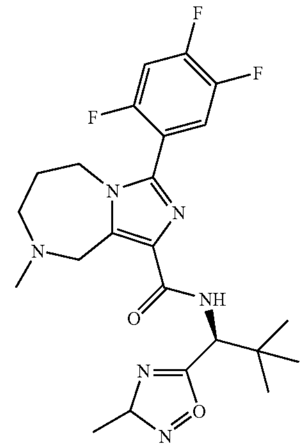 | 477.2 | (S)-N-(2,2-dimethyl-1-(3-methyl-1,2,4-oxadiazol-5-yl)propyl)-8-methyl-3-(2,4,5-trifluorophenyl)-6,7,8,9-tetrahydro-5H-imidazo[1,5-a][1,4]diazepine-1-carboxamide | 81 |
| 867 | 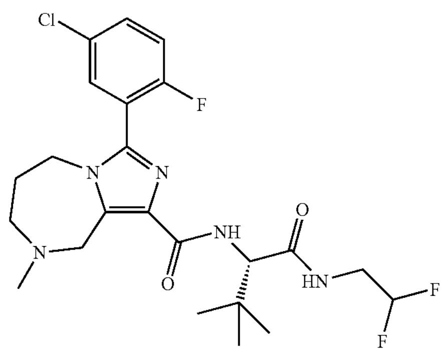 [SMILES: CN1CCCn2c(-c3cc(Cl)ccc3F)nc(C(=O)N[C@H](C(=O)NCC(F)F)C(C)(C)C)c2C1] | 500 | (S)-3-(5-chloro-2-fluorophenyl)-N-(1-(2,2-difluoroethylamino)-3,3-dimethyl-1-oxobutan-2-yl)-8-methyl-6,7,8,9-tetrahydro-5H-imidazo[1,5-a][1,4]diazepine-1-carboxamide | 67 |
| 868 | 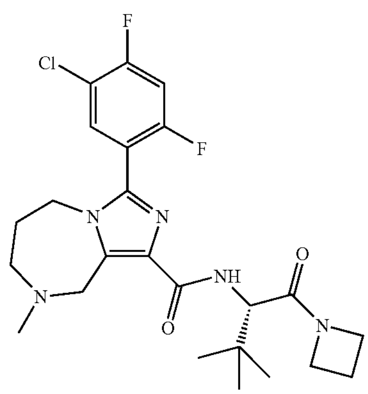 [SMILES: CN1CCCn2c(-c3cc(Cl)c(F)cc3F)nc(C(=O)N[C@H](C(=O)N3CCC3)C(C)(C)C)c2C1] | 494 | (S)-N-(1-(azetidin-1-yl)-3,3-dimethyl-1-oxobutan-2-yl)-3-(5-chloro-2,4-difluorophenyl)-8-methyl-6,7,8,9-tetrahydro-5H-imidazo[1,5-a][1,4]diazepine-1-carboxamide | 77 |
| 869 | 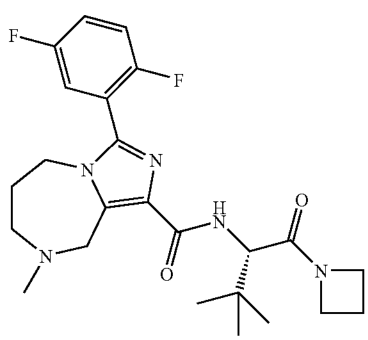 [SMILES: CN1CCCn2c(-c3cc(F)ccc3F)nc(C(=O)N[C@H](C(=O)N3CCC3)C(C)(C)C)c2C1] | 460 | (S)-N-(1-(azetidin-1-yl)-3,3-dimethyl-1-oxobutan-2-yl)-3-(2,5-difluorophenyl)-8-methyl-6,7,8,8-tetrahydro-5H-imidazo[1,5-a][1,4]diazepine-1-carboxamide | 77 |

TABLE 2-continued

| Cmpd No. | Structure | m/z | Chemical Name | Example No. |
|---|---|---|---|---|
| 870 | 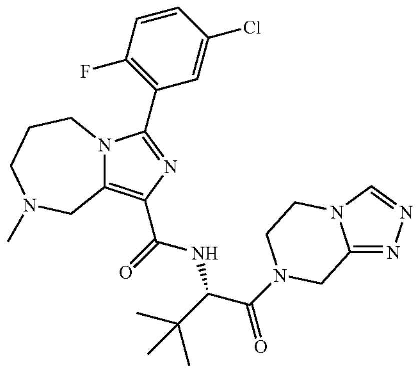 [SMILES: CN1CCCn2c(-c3cc(Cl)ccc3F)nc(C(=O)N[C@H](C(=O)N3CCn4cnnc4C3)C(C)(C)C)c2C1] | 544 | (S)-3-(5-chloro-2-fluorophenyl)-N-(1-(5,6-dihydro-[1,2,4]triazolo[4,3-a]pyrazin-7(8H)-yl)-3,3-dimethyl-1-oxobutan-2-yl)-8-methyl-6,7,8,9-tetrahydro-5H-imidazo[1,5-a][1,4]diazepine-1-carboxamide | 67 |
| 871 | 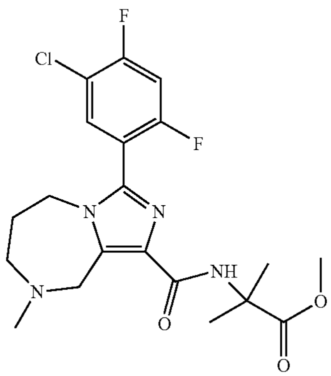 [SMILES: COC(=O)C(C)(C)NC(=O)c1nc(-c2cc(Cl)c(F)cc2F)n2c1CN(C)CCC2] | 441.2 | methyl 2-(3-(5-chloro-2,4-difluorophenyl)-8-methyl-6,7,8,9-tetrahydro-5H-imidazo[1,5-a][1,4]diazepine-1-carboxamido)-2-methylpropanoate | 82 |
| 872 | 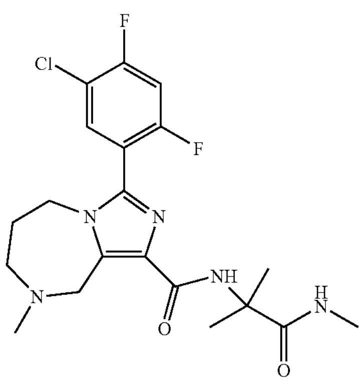 [SMILES: CNC(=O)C(C)(C)NC(=O)c1nc(-c2cc(Cl)c(F)cc2F)n2c1CN(C)CCC2] | 440.2 | 3-(5-chloro-2,4-difluorophenyl)-8-methyl-N-(2-methyl-1-(methylamino)-1-oxopropan-2-yl)-6,7,8,9-tetrahydro-5H-imidazo[1,5-a][1,4]diazepine-1-carboxamide | 82 |
| 873 | 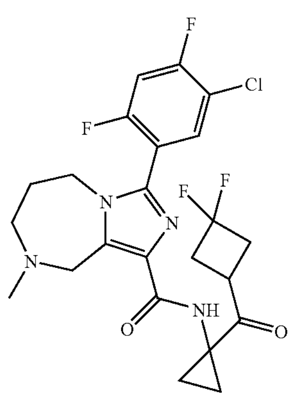 [SMILES: CN1CCCn2c(-c3cc(Cl)c(F)cc3F)nc(C(=O)NC3(C(=O)C4CC(F)(F)C4)CC3)c2C1] | 500.1 | 3-(5-chloro-2,4-difluorophenyl)-N-(1-(3,3-difluoroazetidine-1-carbonyl)cyclopropyl)-8-methyl-6,7,8,9-tetrahydro-5H-imidazo[1,5-a][1,4]diazepine-1-carboxamide | 82 |

TABLE 2-continued

| Cmpd No. | Structure | m/z | Chemical Name | Example No. |
|---|---|---|---|---|
| 874 | 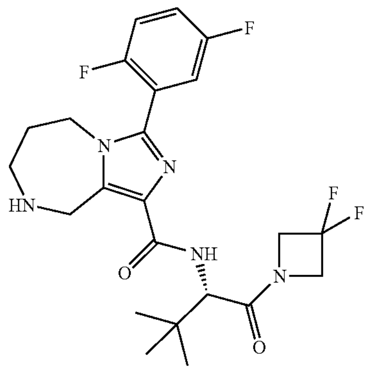 [SMILES: CC(C)(C)[C@H](NC(=O)c1nc(-c2cc(F)ccc2F)n2c1CNCCC2)C(=O)N1CC(F)(F)C1] | 482 | (S)-N-(1-(3,3-difluoroazetidin-1-yl)-3,3-dimethyl-1-oxobutan-2-yl)-3-(2,5-difluorophenyl)-6,7,8,9-tetrahydro-5H-imidazo[1,5-a][1,4]diazepine-1-carboxamide | 67 |
| 875 | 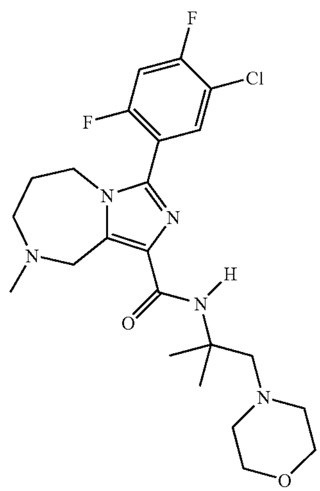 [SMILES: CN1CCCn2c(-c3cc(Cl)c(F)cc3F)nc(C(=O)NC(C)(C)CN3CCOCC3)c2C1] | 482.2 | 3-(5-chloro-2,4-difluorophenyl)-8-methyl-N-(2-methyl-1-morpholinopropan-2-yl)-6,7,8,9-tetrahydro-5H-imidazo[1,5-a][1,4]diazepine-1-carboxamide | 72 |
| 876 | 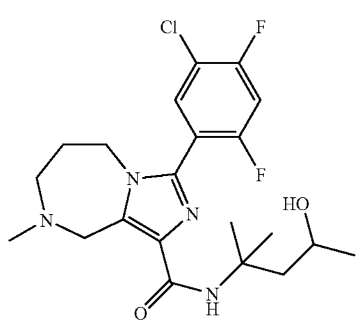 [SMILES: CC(O)CC(C)(C)NC(=O)c1nc(-c2cc(Cl)c(F)cc2F)n2c1CN(C)CCC2] | 441.2 | 3-(5-chloro-2,4-difluorophenyl)-N-(4-hydroxy-2-methylpentan-2-yl)-8-methyl-6,7,8,9-tetrahydro-5H-imidazo[1,5-a][1,4]diazepine-1-carboxamide | 72 |

TABLE 2-continued

| Cmpd No. | Structure | m/z | Chemical Name | Example No. |
|---|---|---|---|---|
| 877 | 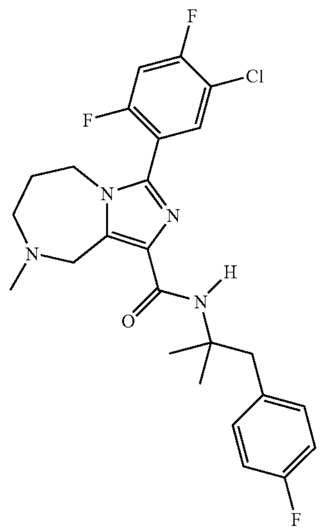 [SMILES: CN1CCCn2c(-c3cc(Cl)c(F)cc3F)nc(C(=O)NC(C)(C)Cc3ccc(F)cc3)c2C1] | 491.2 | 3-(5-chloro-2,4-difluorophenyl)-N-(1-(4-fluorophenyl)-2-methylpropan-2-yl)-8-methyl-6,7,8,9-tetrahydro-5H-imidazo[1,5-a][1,4]diazepine-1-carboxamide | 72 |
| 878 | 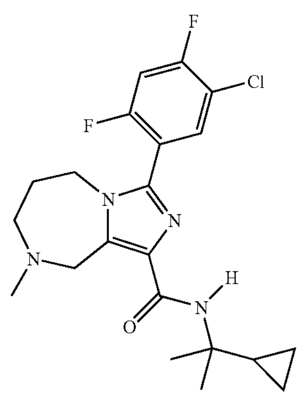 [SMILES: CN1CCCn2c(-c3cc(Cl)c(F)cc3F)nc(C(=O)NC(C)(C)C3CC3)c2C1] | 423.2 | 3-(5-chloro-2,4-difluorophenyl)-N-(2-cyclopropylpropan-2-yl)-8-methyl-6,7,8,9-tetrahydro-5H-imidazo[1,5-a][1,4]diazepine-1-carboxamide | 72 |
| 879 | 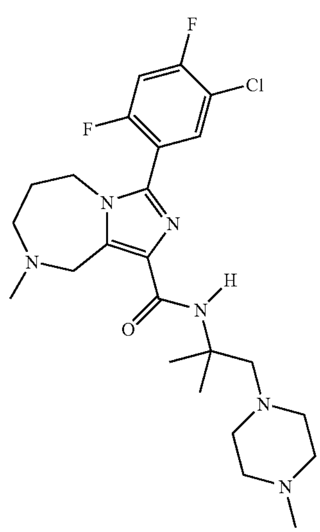 [SMILES: CN1CCN(CC(C)(C)NC(=O)c2nc(-c3cc(Cl)c(F)cc3F)n3c2CN(C)CCC3)CC1] | 495.25 | 3-(5-chloro-2,4-difluorophenyl)-8-methyl-N-(2-methyl-1-(4-methylpiperazin-1-yl)propan-2-yl)-6,7,8,9-tetrahydro-5H-imidazo[1,5-a][1,4]diazepine-1-carboxamide | 72 |

TABLE 2-continued

| Cmpd No. | Structure | m/z | Chemical Name | Example No. |
|---|---|---|---|---|
| 880 | 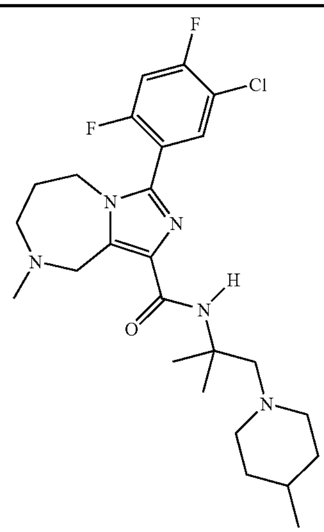 | 494.24 | 3-(5-chloro-2,4-difluorophenyl)-8-methyl-N-(2-methyl-1-(4-methylpiperidin-1-yl)propan-2-yl)-6,7,8,9-tetrahydro-5H-imidazo[1,5-a][1,4]diazepine-1-carboxamide | 72 |
| 881 | 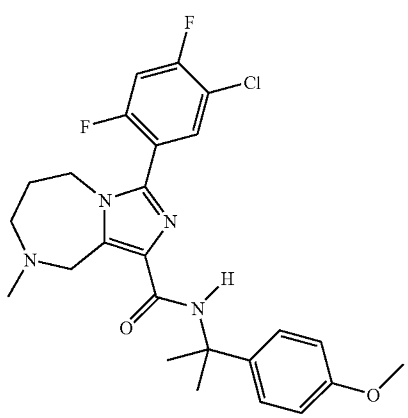 | 489.17 | 3-(5-chloro-2,4-difluorophenyl)-N-(2-(4-methoxyphenyl)propan-2-yl)-8-methyl-6,7,8,9-tetrahydro-5H-imidazo[1,5-a][1,4]diazepine-1-carboxamide | 72 |
| 882 | 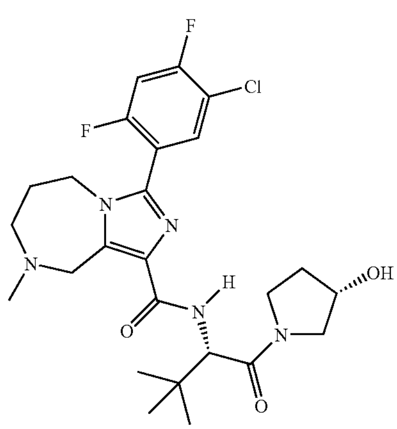 [SMILES: CN1CCCn2c(-c3cc(Cl)c(F)cc3F)nc(C(=O)N[C@H](C(=O)N3CC[C@H](O)C3)C(C)(C)C)c2C1] | 524.2 | 3-(5-chloro-2,4-difluorophenyl)-N-((S)-1-((S)-3-hydroxypyrrolidin-1-yl)-3,3-dimethyl-1-oxobutan-2-yl)-8-methyl-6,7,8,9-tetrahydro-5H-imidazo[1,5-a][1,4]diazepine-1-carboxamide | 67 |

TABLE 2-continued

| Cmpd No. | Structure | m/z | Chemical Name | Example No. |
|---|---|---|---|---|
| 883 | 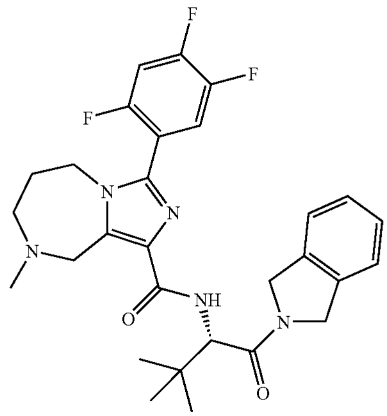 [SMILES: CN1CCCn2c(-c3cc(F)c(F)cc3F)nc(C(=O)N[C@H](C(=O)N3Cc4ccccc4C3)C(C)(C)C)c2C1] | 540 | (S)-N-(1-(isoindolin-2-yl)-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide | 67 |
| 884 | 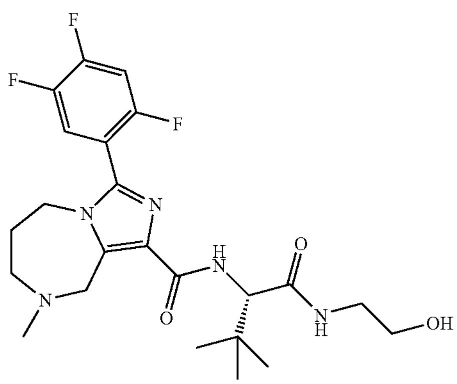 [SMILES: CN1CCCn2c(-c3cc(F)c(F)cc3F)nc(C(=O)N[C@H](C(=O)NCCO)C(C)(C)C)c2C1] | 482 | (S)-N-(1-(2-hydroxyethylamino)-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide | 67 |
| 885 | 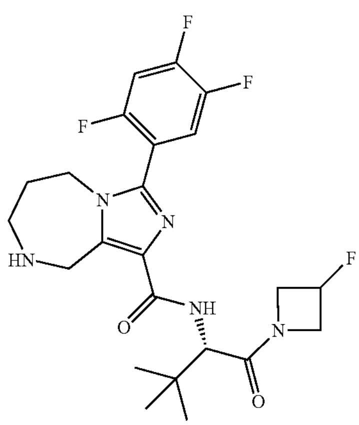 [SMILES: CC(C)(C)[C@H](NC(=O)c1nc(-c2cc(F)c(F)cc2F)n2c1CNCCC2)C(=O)N1CC(F)C1] | 482 | (S)-N-(1-(3-fluoroazetidin-1-yl)-3,3-dimethyl-1-oxobutan-2-yl)-3-(2,4,5-trifluorophenyl)-6,7,8,9-tetrahydro-5H-imidazo[1,5-a][1,4]diazepine-1-carboxamide | 67 |
| 886 | 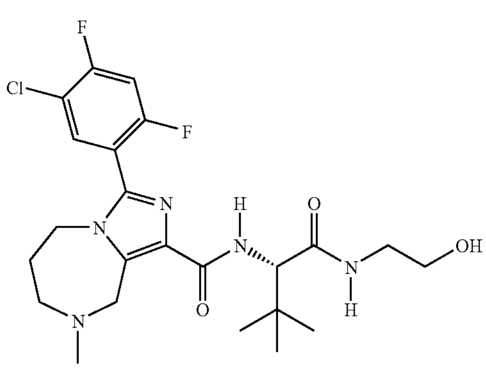 [SMILES: CN1CCCn2c(-c3cc(Cl)c(F)cc3F)nc(C(=O)N[C@H](C(=O)NCCO)C(C)(C)C)c2C1] | 498.2 | (S)-3-(5-chloro-2,4-difluorophenyl)-N-(1-(2-hydroxyethylamino)-3,3-dimethyl-1-oxobutan-2-yl)-8-methyl-6,7,8,9-tetrahydro-5H-imidazo[1,5-a][1,4]diazepine-1-carboxamide | 67 |

TABLE 2-continued

| Cmpd No. | Structure | m/z | Chemical Name | Example No. |
|---|---|---|---|---|
| 887 | 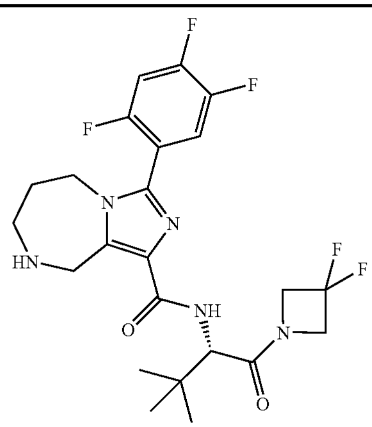 | 500 | (S)-N-(1-(3,3-difluoroazetidin-1-yl)-3,3-dimethyl-1-oxobutan-2-yl)-3-(2,4,5-trifluorophenyl)-6,7,8,9-tetrahydro-5H-imidazo[1,5-a][1,4]diazepine-1-carboxamide | 67 |
| 888 | 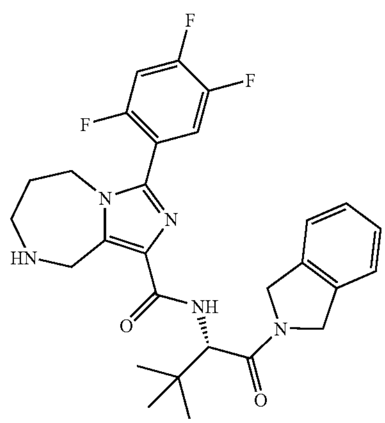 [SMILES: CC(C)(C)[C@H](NC(=O)c1nc(-c2cc(F)c(F)cc2F)n2c1CNCCC2)C(=O)N1Cc2ccccc2C1] | 526 | (S)-N-(1-(isoindolin-2-yl)-3,3-dimethyl-1-oxobutan-2-yl)-3-(2,4,5-trifluorophenyl)-6,7,8,9-tetrahydro-5H-imidazo[1,5-a][1,4]diazepine-1-carboxamide | 67 |
| 889 | 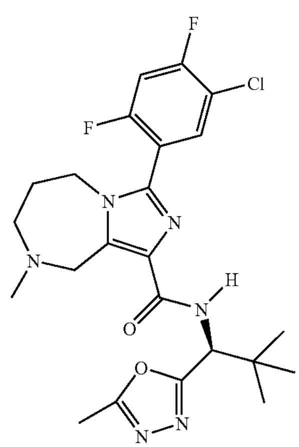 [SMILES: Cc1nnc([C@@H](NC(=O)c2nc(-c3cc(Cl)c(F)cc3F)n3c2CN(C)CCC3)C(C)(C)C)o1] | 493.2 | (S)-3-(5-chloro-2,4-difluorophenyl)-N-(2,2-dimethyl-1-(5-methyl-1,3,4-oxadiazol-2-yl)propyl)-8-methyl-6,7,8,9-tetrahydro-5H-imidazo[1,5-a][1,4]diazepine-1-carboxamide | 83 |

TABLE 2-continued

| Cmpd No. | Structure | m/z | Chemical Name | Example No. |
|---|---|---|---|---|
| 890 | 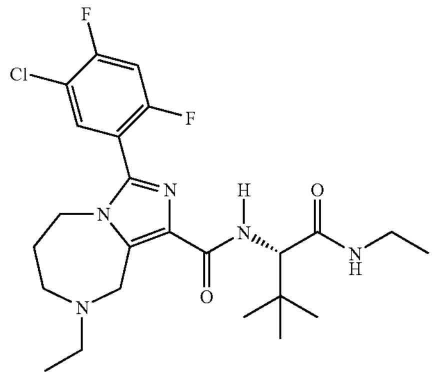 [SMILES: CCNC(=O)[C@@H](NC(=O)c1nc(-c2cc(Cl)c(F)cc2F)n2c1CN(CC)CCC2)C(C)(C)C] | 496.2 | (S)-3-(5-chloro-2,4-difluorophenyl)-8-ethyl-N-(1-(ethylamino)-3,3-dimethyl-1-oxobutan-2-yl)-6,7,8,9-tetrahydro-5H-imidazo[1,5-a][1,4]diazepine-1-carboxamide | 77 |
| 891 | 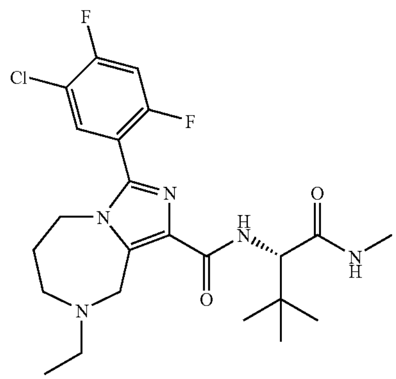 [SMILES: CCN1CCCn2c(-c3cc(Cl)c(F)cc3F)nc(C(=O)N[C@H](C(=O)NC)C(C)(C)C)c2C1] | 482 | (S)-3-(5-chloro-2,4-difluorophenyl)-N-(3,3-dimethyl-1-(methylamino)-1-oxobutan-2-yl)-8-ethyl-6,7,8,9-tetrahydro-5H-imidazo[1,5-a][1,4]diazepine-1-carboxamide | 35 |
| 892 | 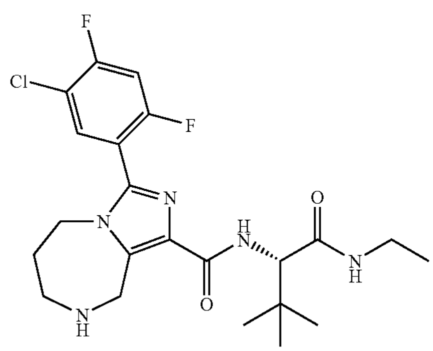 [SMILES: CCNC(=O)[C@@H](NC(=O)c1nc(-c2cc(Cl)c(F)cc2F)n2c1CNCCC2)C(C)(C)C] | 468.2 | (S)-3-(5-chloro-2,4-difluorophenyl)-N-(1-(ethylamino)-3,3-dimethyl-1-oxobutan-2-yl)-6,7,8,9-tetrahydro-5H-imidazo[1,5-a][1,4]diazepine-1-carboxamide | 34 |
| 893 | 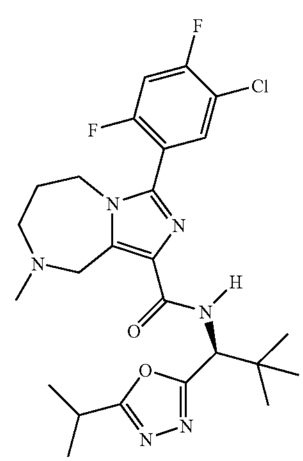 [SMILES: CC(C)c1nnc([C@@H](NC(=O)c2nc(-c3cc(Cl)c(F)cc3F)n3c2CN(C)CCC3)C(C)(C)C)o1] | 521.2 | (S)-3-(5-chloro-2,4-difluorophenyl)-N-(1-(5-isopropyl-1,3,4-oxadiazol-2-yl)-2,2-dimethylpropyl)-8-methyl-6,7,8,9-tetrahydro-5H-imidazo[1,5-a][1,4]diazepine-1-carboxamide | 83 |

TABLE 2-continued

| Cmpd No. | Structure | m/z | Chemical Name | Example No. |
|---|---|---|---|---|
| 894 | 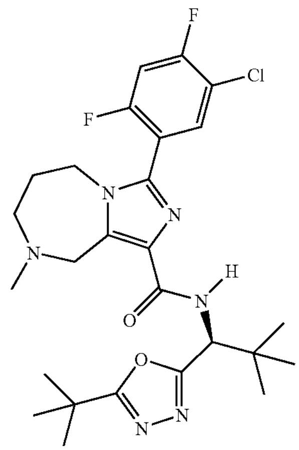 [SMILES: CN1CCCn2c(-c3cc(Cl)c(F)cc3F)nc(C(=O)N[C@H](c3nnc(C(C)(C)C)o3)C(C)(C)C)c2C1] | 535.3 | (S)-N-(1-(5-tert-butyl-1,3,4-oxadiazol-2-yl)-2,2-dimethylpropyl)-3-(5-chloro-2,4-difluorophenyl)-8-methyl-6,7,8,9-tetrahydro-5H-imidazo[1,5-a][1,4]diazepine-1-carboxamide | 83 |
| 895 | 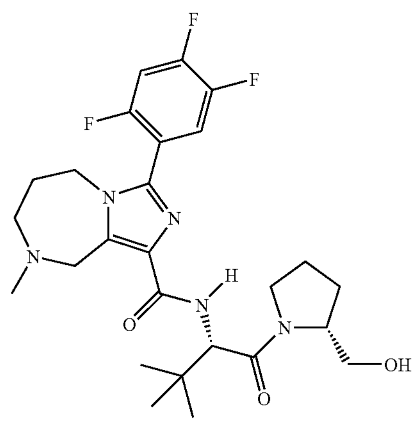 [SMILES: CN1CCCn2c(-c3cc(F)c(F)cc3F)nc(C(=O)N[C@H](C(=O)N3CCC[C@@H]3CO)C(C)(C)C)c2C1] | 522.3 | N-((S)-1-((R)-2-(hydroxymethyl)pyrrolidin-1-yl)-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide | 67 |
| 896 | 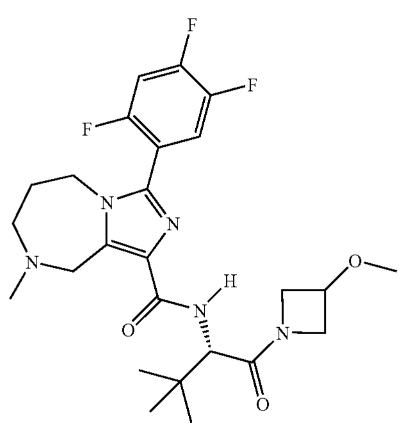 | 508.3 | (S)-N-(1-(3-methoxyazetidin-1-yl)-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide | 67 |

TABLE 2-continued

| Cmpd No. | Structure | m/z | Chemical Name | Example No. |
|---|---|---|---|---|
| 897 | 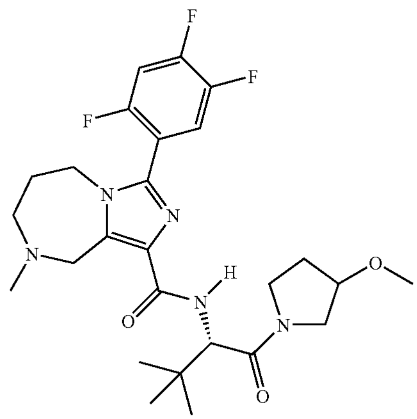 | 522.5 | N-((2S)-1-(3-methoxypyrrolidin-1-yl)-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide | 67 |
| 898 | 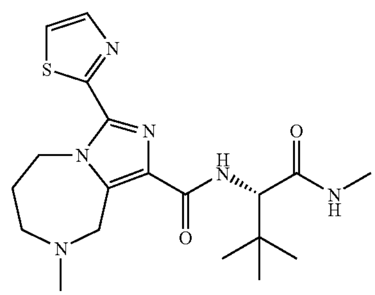 [SMILES: CNC(=O)[C@@H](NC(=O)c1nc(-c2nccs2)n2c1CN(C)CCC2)C(C)(C)C] | 405 | (S)-N-(3,3-dimethyl-1-(methylamino)-1-oxobutan-2-yl)-8-methyl-3-(thiazol-2-yl)-imidazo[1,5-a][1,4]diazepine-1-carboxamide | 28 |
| 899 | 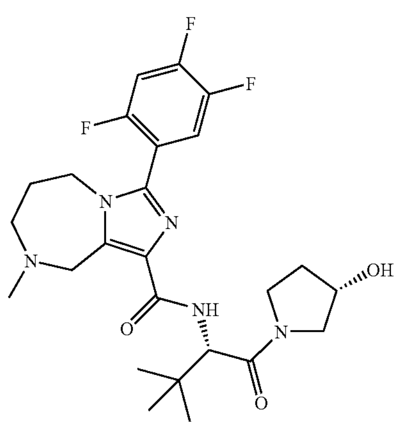 [SMILES: CN1CCCn2c(-c3cc(F)c(F)cc3F)nc(C(=O)N[C@H](C(=O)N3CC[C@H](O)C3)C(C)(C)C)c2C1] | 508 | N-((S)-1-((S)-3-hydroxypyrrolidin-1-yl)-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide | 67 |
| 900 | 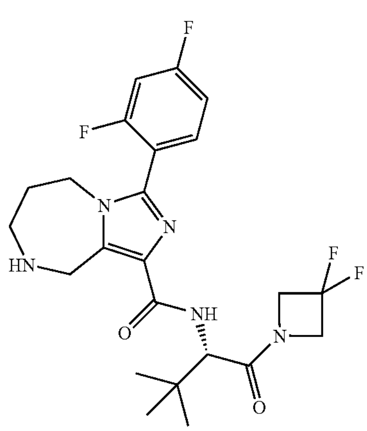 [SMILES: CC(C)(C)[C@H](NC(=O)c1nc(-c2ccc(F)cc2F)n2c1CNCCC2)C(=O)N1CC(F)(F)C1] | 482.2 | (S)-N-(1-(3,3-difluoroazetidin-1-yl)-3,3-dimethyl-1-oxobutan-2-yl)-3-(2,4-difluorophenyl)-6,7,8,9-tetrahydro-5H-imidazo[1,5-a][1,4]diazepine-1-carboxamide | 67 |

TABLE 2-continued

| Cmpd No. | Structure | m/z | Chemical Name | Example No. |
|---|---|---|---|---|
| 901 | 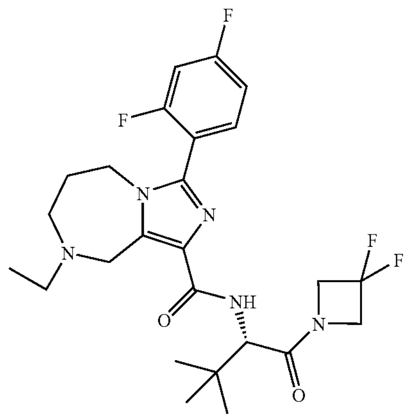 [SMILES: CCN1CCCn2c(-c3ccc(F)cc3F)nc(C(=O)N[C@H](C(=O)N3CC(F)(F)C3)C(C)(C)C)c2C1] | 510.2 | (S)-N-(1-(3,3-difluoroazetidin-1-yl)-3,3-dimethyl-1-oxobutan-2-yl)-3-(2,4-difluorophenyl)-8-ethyl-6,7,8,9-tetrahydro-5H-imidazo[1,5-a][1,4]diazepine-1-carboxamide | 67 |
| 902 | 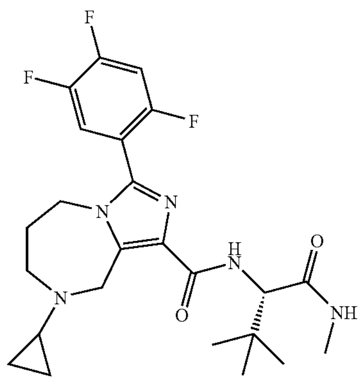 [SMILES: CNC(=O)[C@@H](NC(=O)c1nc(-c2cc(F)c(F)cc2F)n2c1CN(C1CC1)CCC2)C(C)(C)C] | 478.3 | (S)-8-cyclopropyl-N-(3,3-dimethyl-1-(methylamino)-1-oxobutan-2-yl)-3-(2,4,5-trifluorophenyl)-6,7,8,9-tetrahydro-5H-imidazo[1,5-a][1,4]diazepine-1-carboxamide | 13 |
| 903 | 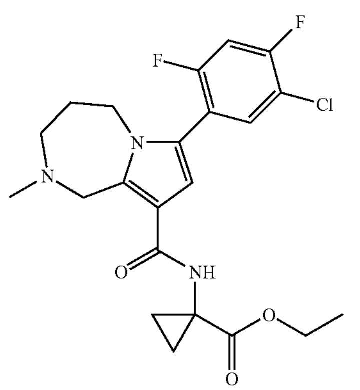 [SMILES: CCOC(=O)C1(NC(=O)c2cc(-c3cc(Cl)c(F)cc3F)n3c2CN(C)CCC3)CC1] | 453.1 | ethyl 1-(3-(5-chloro-2,4-difluorophenyl)-8-methyl-6,7,8,9-tetrahydro-5H-imidazo[1,5-a][1,4]diazepine-1-carboxamido)cyclopropanecarboxylate | 82 |
| 904 | 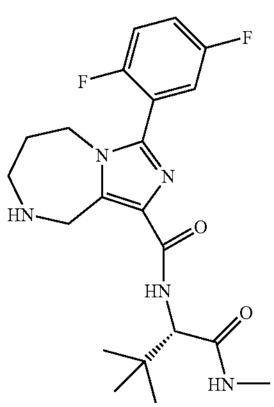 [SMILES: CNC(=O)[C@@H](NC(=O)c1nc(-c2cc(F)ccc2F)n2c1CNCCC2)C(C)(C)C] | 420.2 | (S)-3-(2,5-difluorophenyl)-N-(3,3-dimethyl-1-(methylamino)-1-oxobutan-2-yl)-6,7,8,9-tetrahydro-5H-imidazo[1,5-a][1,4]diazepine-1-carboxamide | 39 |

TABLE 2-continued

| Cmpd No. | Structure | m/z | Chemical Name | Example No. |
|---|---|---|---|---|
| 905 | 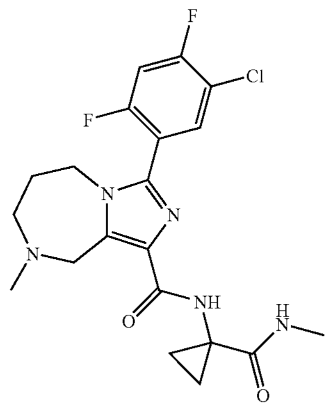 | 438.1 | 3-(5-chloro-2,4-difluorophenyl)-8-methyl-N-(1-(methylcarbamoyl)cyclopropyl)-6,7,8,9-tetrahydro-5H-imidazo[1,5-a][1,4]diazepine-1-carboxamide | 82 |
| 906 | 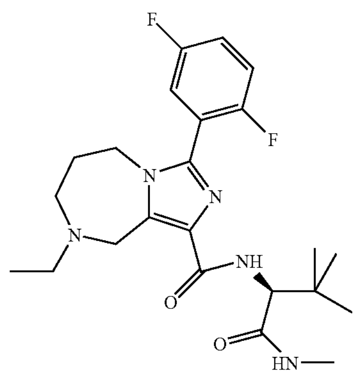 [SMILES: CCN1CCCn2c(-c3cc(F)ccc3F)nc(C(=O)N[C@H](C(=O)NC)C(C)(C)C)c2C1] | 448.2 | (S)-3-(2,5-difluorophenyl)-N-(3,3-dimethyl-1-(methylamino)-1-oxobutan-2-yl)-8-ethyl-6,7,8,9-tetrahydro-5H-imidazo[1,5-a][1,4]diazepine-1-carboxamide | 84 |
| 907 | 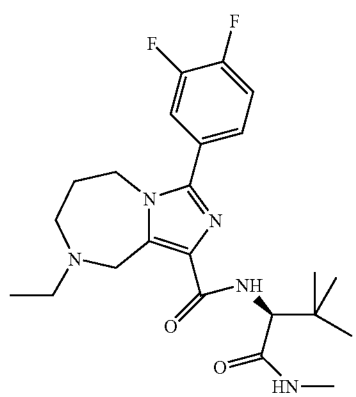 [SMILES: CCN1CCCn2c(-c3ccc(F)c(F)c3)nc(C(=O)N[C@H](C(=O)NC)C(C)(C)C)c2C1] | 448.2 | (S)-3-(3,4-difluorophenyl)-N-(3,3-dimethyl-1-(methylamino)-1-oxobutan-2-yl)-8-ethyl-6,7,8,9-tetrahydro-5H-imidazo[1,5-a][1,4]diazepine-1-carboxamide | 84 |
| 908 | 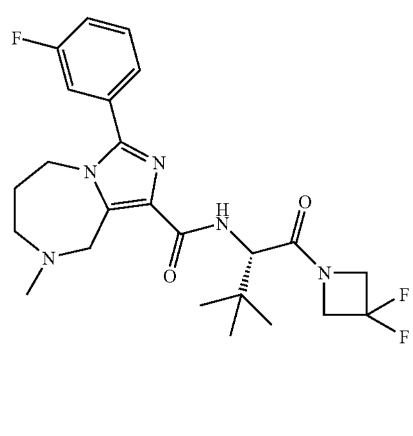 [SMILES: CN1CCCn2c(-c3cccc(F)c3)nc(C(=O)N[C@H](C(=O)N3CC(F)(F)C3)C(C)(C)C)c2C1] | 478 | (S)-N-(1-(3,3-difluoroazetidin-1-yl)-3,3-dimethyl-1-oxobutan-2-yl)-3-(3-fluorophenyl)-8-methyl-6,7,8,9-tetrahydro-5H-imidazo[1,5-a][1,4]diazipine-1-carboxamide | 77 |

TABLE 2-continued

| Cmpd No. | Structure | m/z | Chemical Name | Example No. |
|---|---|---|---|---|
| 909 | 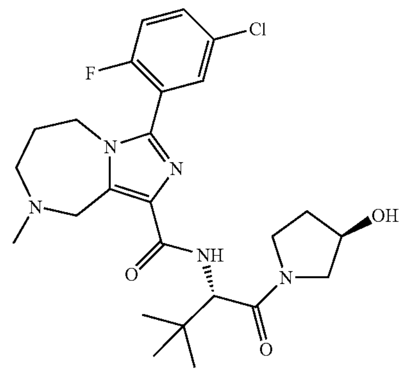 [SMILES: CN1CCCn2c(-c3cc(Cl)ccc3F)nc(C(=O)N[C@H](C(=O)N3CC[C@@H](O)C3)C(C)(C)C)c2C1] | 506 | 3-(5-chloro-2-fluorophenyl)-N-((S)-1-((R)-3-hydroxypyrrolidin-1-yl)-3,3-dimethyl-1-oxobutan-2-yl)-8-methyl-6,7,8,9-tetrahydro-5H-imidazo[1,5-a][1,4]diazepine-1-carboxamide | 67 |
| 910 | 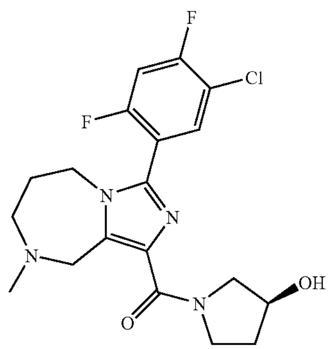 [SMILES: CN1CCCn2c(-c3cc(Cl)c(F)cc3F)nc(C(=O)N3CC[C@H](O)C3)c2C1] | 411.2 | (S)-(3-(5-chloro-2,4-difluorophenyl)-8-methyl-6,7,8,9-tetrahydro-5H-imidazo[1,5-a][1,4]diazepin-1-yl)(3-hydroxypyrrolidin-1-yl)methanone | 72 |
| 911 | 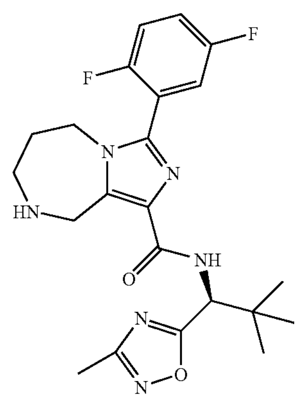 [SMILES: Cc1noc([C@@H](NC(=O)c2nc(-c3cc(F)ccc3F)n3c2CNCCC3)C(C)(C)C)n1] | 445.3 | (S)-3-(2,5-difluorophenyl)-N-(2,2-dimethyl-1-(3-methyl-1,2,4-oxadiazol-5-yl)propyl)-6,7,8,9-tetrahydro-5H-imidazo[1,5-a][1,4]diazepine-1-carboxamide | 81 |
| 912 | 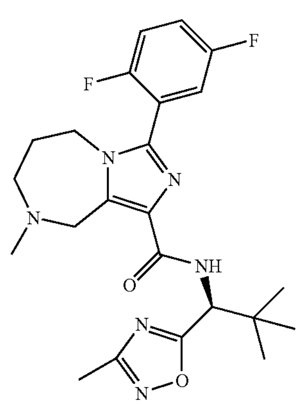 [SMILES: Cc1noc([C@@H](NC(=O)c2nc(-c3cc(F)ccc3F)n3c2CN(C)CCC3)C(C)(C)C)n1] | 459.3 | (S)-3-(2,5-difluorophenyl)-N-(2,2-dimethyl-1-(3-methyl-1,2,4-oxadiazol-5-yl)propyl)-8-methyl-6,7,8,9-tetrahydro-5H-imidazo[1,5-a][1,4]diazepine-1-carboxamide | 81 |

TABLE 2-continued

| Cmpd No. | Structure | m/z | Chemical Name | Example No. |
|---|---|---|---|---|
| 913 | 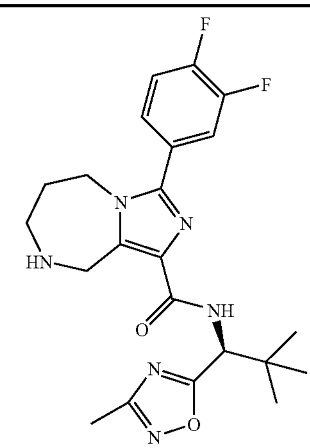 | 445.3 | (S)-3-(3,4-difluorophenyl)-N-(2,2-dimethyl-1-(3-methyl-1,2,4-oxadiazol-5-yl)propyl)-6,7,8,9-tetrahydro-5H-imidazo[1,5-a][1,4]diazepine-1-carboxamide | 81 |
| 914 | 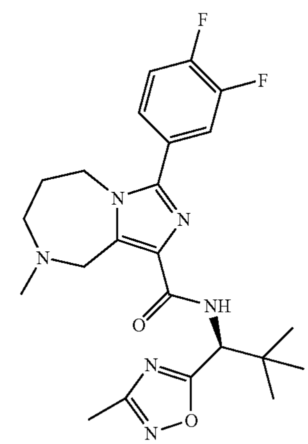 [SMILES: Cc1noc([C@@H](NC(=O)c2nc(-c3ccc(F)c(F)c3)n3c2CN(C)CCC3)C(C)(C)C)n1] | 459.3 | (S)-3-(3,4-difluorophenyl)-N-(2,2-dimethyl-1-(3-methyl-1,2,4-oxadiazol-5-yl)propyl)-8-methyl-6,7,8,9-tetrahydro-5H-imidazo[1,5-a][1,4]diazepine-1-carboxamide | 81 |

Screening Methods

The ability of compounds to act as agonists or inverse agonists at human CB2 and CB1 receptors (hCB2, hCB1, respectively) and at the rat CB2 receptor (rCB2) was determined by measuring changes in intracellular cAMP levels. Chinese Hamster Ovary (CHO-K1) cell lines stably expressing hCB2 (Genebank: X74328) or hCB1 (Genebank: X54937) were purchased from Euroscreen (Gosselies, Belgium). The rat CB2 receptor was expressed from genomic DNA (provided by M. Abood, Calif. Pacific Medical Center) in CHO-K1 cells from expression plasmid vector, pcDNA3.1.

Cell lines were grown in suspension in EX-CELL 302 CHO Serum-free medium (Sigma, cat #14324C) supplemented with 1% Fetal Bovine Serum, glutamine and non-essential amino-acids under 0.4 mg/mL G418 selection.

Receptor mediated responses were determined by measuring changes in intracellular cAMP using LANCE cAMP detection kit (cat #AD0264, Perkin Elmer, Wellesley, Mass.) based on time-resolved fluorescence resonance energy transfer (TR-FRET). Changes in cAMP were determined in cells pre-incubated with IBMX (isobutyl methylxanthine) and pre-stimulated with NKH-477 (a water soluble forskolin derivative, cat #1603, Tocris, Ellisville, Mo.) to increase basal cAMP levels as detailed below.

On the day of the experiment, cells were spun at low speed for 5 min at room temperature. The supernatant was removed and cells were resuspended in stimulation buffer (Hanks Buffered Salt Solution/5 mM HEPES, containing 0.5 mM IBMX (cat #17018, Sigma) and 0.02% BSA (Perkin-Elmer, cat #CR84-100)). Cell clumps were removed by filtering through cell strainer 40 μm (BD Falcon, Discovery Labware, Bedford, Mass.) and diluted to $2 \times 10^5$ cells/mL. Antibody supplied with the LANCE cAMP immunoassay kit was then added according to the manufacturer's instructions. An aliquot of cells was taken for un-induced controls. To the remaining cells was added NKH-477 (a water soluble forskolin derivative, Tocris cat #1603) to a final concentration of 2-8 μM. Cells were then incubated for 30 min at room temperature prior to adding to Proxiplates containing test compounds (final DMSO concentration was less than 0.5%) with a Multidrop bulk dispenser, followed by a sixty minute incubation at room temperature. The response was stopped by addition of the detection mix supplied with the LANCE kit. The reagents were allowed to equilibrate for three hours prior to reading on an Envision multi-mode detector (Perkin-Elmer). TR-FRET was measured using a 330-380 nm excitation filter, a 665 nm emission filter, dichroic mirror 380 nm and Z=1 mm. Cyclic AMP concentrations in each well were back-calculated from a cAMP standard curve run concurrently during each assay. Each plate contained 16 wells of forskolin stimulated cells and 16 wells of forskolin plus CP55,940-treated cells. Cells were treated with 1 μM CP55,940 (Tocris cat. #0949). Concentrations of cAMP were expressed as a percent of the difference of these two groups of wells. Concentration-response data including $EC_{50}$ (the concentration of compound producing 50% of the maximal response) and intrinsic activity (the percent maximal activation compared to full activation by CP55,940) were determined using a four-parameter non-linear regression algorithm (Xlfit equation 251, IDBS).

Example 85

Determination of $EC_{50}$ Values for Compounds at Human and Rat Cannabinoid Receptors Tables IIA, IIB and IIC, below show compounds (1)-(607) and Tables IIIA and IIIB show compounds (608)-(914) grouped by $EC_{50}$ ranges. For convenience, the ranges were chosen as follows: The most potent group of compounds was classified in an $EC_{50}$ range from 0.1 nM to 10 nM. The second most potent group was classified in an $EC_{50}$ range from greater than 10 nM to 100 nM. The third most potent group was classified in an $EC_{50}$ range from greater than 100 nM to 10 μM. Finally, the fourth group classified by potency had an $EC_{50}$ of greater than 10 μM as determined by the above method.

The $EC_{50}$ range for each of the compounds 1-607 determined against the human CB2 receptor (hCB2 $EC_{50}$) is shown in Table IIA.

Table IIIA shows the hCB2 $EC_{50}$ ranges for compounds 608-914.

The $EC_{50}$ range for each of the compounds 1-607 determined against the rat CB2 receptor is shown in Table IIB.

The $EC_{50}$ range for each of the compounds 1-607 determined against the human CB1 receptor (hCB1 $EC_{50}$) is shown in Table IIC.

Table 111B shows the hCB1 $EC_{50}$ ranges for compounds 608-914.

TABLE IIA

| CB | $EC_{50}$ | +/− | (CMPD NO.) |
|---|---|---|---|
| HCB2 | 0.1 nM–10 nM | + | 6, 241, 245, 246, 250, 268, 271, 303, 359, 361, 363, 366, 370, 371, 373, 373, 448, 451, 459, 469, 484, 487, 503, 555, 560, 561, 574, 578, 579 |
| | | − | |
| | >10 nM–100 nM | + | 4, 7, 8, 9, 13, 18, 39, 48, 49, 52, 53, 72, 73, 111, 119, 142, 144, 163, 165, 178, 238, 240, 243, 244, 247, 248, 249, 251, 256, 258, 263, 266, 269, 272, 276, 277, 278, 279, 298, 305, 306, 315, 317, 329, 345, 355, 357, 360, 362, 368, 372, 375, 396, 397, 398, 400, 424, 425, 432, 433, 434, 435, 436, 437, 439, 441, 442, 449, 450, 456, 467, 468, 482, 485, 486, 494, 507, 522, 531, 535, 538, 539, 541, 542, 544, 545, 548, 551, 552, 554, 558, 563, 568, 569, 571, 572, 573, 575, 576, 577, 580, 581, 583, 584, 585, 588, 589, 590, 591, 600 |
| | | − | 88 |
| | >100 nM–10 μM | + | 2, 10, 11, 12, 14, 15, 16, 20, 21, 23, 24, 26, 27, 40, 43, 45, 47, 50, 51, 57, 59, 64, 66, 67, 75, 76, 79, 81, 87, 91, 92, 112, 118, 121, 140, 141, 143, 149, 153, 161, 164, 168, 170, 171, 172, 173, 174, 175, 177, 189, 192, 194, 196, 197, 198, 199, 200, 201, 202, 203, 206, 207, 239, 252, 253, 254, 257, 260, 261, 262, 264, 267, 273, 275, 280, 282, 283, 284, 285, 286, 287, 289, 295, 296, 301, 302, 304, 307, 308, 311, 314, 318, 319, 324, 325, 327, 328, 330, 331, 332, 333, 334, 335, 336, 337, 338, 339, 340, 341, 342, 347, 348, 349, 351, 352, 353, 354, 356, 358, 365, 367, 369, 376, 377, 380, 384, 387, 393, 395, 399, 402, 404, 415, 416, 418, 429, 430, 431, 438, 440, 444, 446, 447, 452, 454, 455, 460, 465, 472, 473, 474, 475, 476, 477, 478, 480, 488, 489, 491, 492, 495, 496, 497, 498, 499, 501, 502, 504, 505, 506, 510, 511, 513, 514, 519, 521, 524, 528, 529, 530, 532, 533, 534, 536, 537, 540, 543, 546, 547, 549, 556, 557, 559, 562, 564, 565, 566, 567, 570, 582, 586, 587, 593, 594, 596, 598, 601, 604, 605, 607 |
| | | − | 1, 30, 31, 32, 33, 34, 35, 36, 37, 38, 54, 55, 56, 62, 65, 93, 95, 96, 97, 98, 99, 101, 104, 125, 128, 145, 148, 157, 183, 190, 191, 274, 288, 294, 299, 300, 310, 445, 458, 462, 493, 517 |
| | >10 μM | | 3, 5, 17, 19, 22, 25, 28, 29, 41, 42, 44, 46, 58, 60, 61, 63, 68, 69, 70, 71, 74, 77, 78, 80, 82, 83, 84, 85, 86, 89, 90, 94, 100, 102, 103, 105, 106, 107, 108, 109, 110, 113, 114, 115, 116, 117, 120, 122, 123, 124, 126, 127, 129, 130, 131, 132, 133, 134, 135, 136, 137, 138, 139, 146, 147, 150, 151, 152, 154, 155, 156, 158, 159, 160, 162, 166, 167, 169, 176, 179, 180, 181, 182, 184, 185, 186, 187, 188, 193, 195, 204, 205, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 242, 255, 259, 265, 270, 281, 290, 291, 292, 293, 297, 309, 312, 313, 316, 320, 321, 322, 323, 326, 343, 344, 346, 350, 364, 378, 379, 381, 382, 383, 385, 386, 388, 389, 390, 391, 392, 394, 401, 403, 405, 406, 407, 408, 409, 410, 411, 412, 413, 414, 417, 419, 420, 421, 422, 423, 426, 427, 428, 443, 453, 457, 461, 463, 464, 466, 470, 471, 479, 481, 483, 490, 500, 508, 509, 512, 515, 516, 518, 520, 523, 525, 526, 527, 550, 553, 592, 595, 597, 599, 602, 603, 606 |

TABLE IIB

| CB | $EC_{50}$ | +/− | (CMPD NO.) |
|---|---|---|---|
| RCB2 | 0.1 nM–10 nM | + | 10, 73, 75, 86, 244, 247, 263, 271, 279, 303, 305, 361, 366, 370, 371, 372, 373, 373, 396, 406, 424, 441, 448, 451, 459, 460, 482, 486, 487, 495, 507, 531, 535, 541, 542, 547, 552, 554, 555, 558, 560, 561, 572, 574, 578, 579, 583, 584, 585, 589, 590 |
| | | − | 52, 68, 89, 90, 144, 155, 160, 163, 165, 198, 241, 284, 288 |
| | >10 nM–100 nM | + | 11, 15, 21, 39, 48, 76, 81, 120, 172, 174, 189, 199, 200, 203, 243, 253, 255, 256, 264, 269, 272, 275, 278, 280, 281, 297, 298, 306, 311, 328, 329, 331, 337, 340, 345, 351, 352, 355, 359, 362, 368, 375, 376, 377, 397, 398, 400, 403, 425, 432, 434, 435, 436, 439, 440, 446, 447, 449, 450, 456, 465, 467, 485, 496, 498, 499, 503, 510, 511, 514, 521, 529, 530, 533, 534, 537, 538, 539, 544, 545, 546, 548, 551, 557, 563, 564, 565, 566, 567, 568, 569, 571, 573, 575, 576, 577, 580, 581, 586, 587, 588, 591, 593, 594, 598 |
| | | − | 3, 5, 7, 30, 34, 36, 37, 49, 53, 54, 56, 58, 60, 64, 71, 74, 80, 84, 85, 87, 88, 91, 92, 93, 94, 95, 97, 98, 100, 103, 104, 106, 107, 108, 109, 112, 119, 123, 131, 132, 133, 139, 141, 142, 143, 145, 148, 149, 150, 154, 157, 158, 161, 164, 167, 168, 178, 179, 183, 184, 185, 190, 191, 197, 202, 240, 245, 246, 249, 251, 265, 270, 274, 276, 277, 299, 300, 310, 313, 322, 326, 380, 414, 438, 458, 466, 470, 494, 518, 520, 522, 523 |
| | >100 nM–10 μM | + | 2, 14, 16, 20, 23, 40, 66, 110, 201, 206, 207, 234, 252, 257, 261, 262, 267, 286, 287, 296, 304, 307, 317, 318, 324, 325, 327, 333, 348, 349, 353, 365, 369, 393, 395, 399, 402, 416, 417, 429, 430, 442, 452, 453, 455, 463, 472, 473, 474, 475, 476, 477, 478, 479, 488, 489, 490, 491, 497, 501, 502, 504, 505, 506, 519, 528, 536, 540, 543, 570, 582, 597, 601, 604, 605, 606, 607 |

TABLE IIB-continued

| CB | EC$_{50}$ | +/− | (CMPD NO.) |
|---|---|---|---|
| | | − | 1, 8, 9, 12, 18, 22, 29, 31, 32, 33, 35, 38, 42, 43, 44, 45, 46, 55, 62, 69, 70, 78, 79, 83, 96, 99, 101, 102, 105, 113, 114, 115, 116, 117, 118, 121, 122, 124, 125, 126, 128, 129, 130, 134, 136, 137, 138, 140, 146, 147, 151, 152, 153, 156, 159, 162, 166, 169, 170, 171, 177, 180, 181, 182, 186, 187, 188, 192, 193, 195, 196, 208, 212, 214, 215, 216, 219, 224, 227, 228, 242, 254, 260, 266, 283, 289, 290, 291, 292, 293, 294, 308, 312, 314, 316, 320, 321, 323, 330, 336, 339, 341, 346, 350, 354, 358, 363, 364, 378, 381, 382, 383, 384, 390, 394, 409, 418, 420, 421, 443, 444, 445, 454, 457, 461, 464, 468, 483, 492, 493, 513, 515, 516, 517, 524, 525, 526, 527, 532, 550, 562, 595 |
| | >10 μM | | 4, 6, 13, 17, 19, 24, 25, 26, 27, 28, 41, 47, 50, 51, 57, 59, 61, 63, 65, 67, 72, 77, 82, 111, 127, 135, 173, 175, 176, 194, 204, 205, 209, 210, 211, 213, 217, 218, 220, 221, 222, 223, 225, 226, 229, 230, 231, 232, 233, 235, 236, 237, 238, 239, 248, 250, 258, 259, 268, 273, 282, 285, 295, 301, 302, 309, 315, 319, 332, 334, 335, 338, 342, 343, 344, 347, 356, 357, 360, 367, 379, 385, 386, 387, 388, 389, 391, 392, 401, 404, 405, 407, 408, 410, 411, 412, 413, 415, 419, 422, 423, 426, 427, 428, 431, 433, 437, 462, 469, 471, 480, 481, 484, 500, 508, 509, 512, 549, 553, 556, 559, 592, 596, 599, 600, 602, 603 |

TABLE IIC

| CB | EC$_{50}$ | +/− | (CMPD NO.) |
|---|---|---|---|
| HCB1 | 0.1 nM−10 nM | + | 371 |
| | | − | |
| | >10 nM−100 nM | + | 355, 361, 366, 558, 561, 573, 574, 578, 579, 590 |
| | | − | |
| | >100 nM−10 μM | + | 238, 268, 269, 271, 272, 274, 279, 298, 299, 300, 368, 397, 436, 441, 442, 447, 448, 449, 450, 451, 454, 458, 460, 482, 483, 498, 503, 505, 506, 507, 508, 514, 538, 539, 541, 542, 544, 545, 547, 548, 551, 552, 554, 555, 556, 559, 560, 563, 564, 568, 569, 570, 571, 572, 575, 576, 577, 580, 581, 583, 584, 585, 586, 587, 588, 589, 591, 593, 594, 600, 601 |
| | | − | 602 |
| | >10 μM | | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 239, 240, 241, 242, 243, 244, 245, 246, 247, 248, 249, 250, 251, 252, 253, 254, 255, 256, 257, 258, 259, 260, 261, 262, 263, 264, 265, 266, 267, 270, 273, 275, 276, 277, 278, 280, 281, 282, 283, 284, 285, 286, 287, 288, 289, 290, 291, 292, 293, 294, 295, 296, 297, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 356, 357, 358, 359, 360, 362, 363, 364, 365, 367, 369, 370, 372, 373, 375, 376, 377, 378, 379, 380, 381, 382, 383, 384, 385, 386, 387, 388, 389, 390, 391, 392, 393, 394, 395, 396, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 437, 438, 439, 440, 443, 444, 445, 446, 452, 453, 455, 456, 457, 459, 461, 462, 463, 464, 465, 466, 467, 468, 469, 470, 471, 472, 473, 474, 475, 476, 477, 478, 479, 480, 481, 484, 485, 486, 487, 488, 489, 490, 491, 492, 493, 494, 495, 496, 499, 500, 501, 502, 504, 509, 510, 511, 512, 513, 515, 516, 517, 518, 519, 520, 521, 522, 523, 524, 525, 526, 527, 528, 529, 530, 531, 532, 533, 534, 535, 536, 537, 540, 543, 546, 549, 550, 553, 557, 562, 565, 566, 567, 582, 592, 595, 596, 597, 598, 599, 603, 604, 605, 606, 607 |

TABLE IIIA

| CB | EC50 | +/− | COMPOUND NUMBER. |
|---|---|---|---|
| HCB2 | 0.1 nM−10 nM | + | 619, 621, 622, 659, 660, 663, 669, 670, 671, 673, 674, 675, 676, 677, 685, 690, 694, 699, 702, 721, 722, 729, 735, 749, 754, 761, 767, 777, 779, 791, 794, 797, 798, 801, 802, 815, 821, 822, 842, 850, 853, 860, 861, 866, 867, 868, 869, 891 |
| | | − | 686, 688, 689, 712 |
| | >10 nM−100 nM | + | 615, 624, 633, 635, 637, 644, 658, 662, 664, 665, 666, 667, 668, 672, 678, 679, 684, 695, 697, 706, 711, 723, 724, 725, 730, 737, 738, 741, 742, 743, 753, 756, 757, 759, 762, 773, 778, 780, 781, 782, 783, 784, 785, 786, 790, 792, 793, 795, 796, 799, 800, 803, 804, 805, 806, 811, 813, 814, 816, 817, 819, 820, 828, 829, 832, 833, 834, 835, 836, 838, 839, 844, 845, 846, 847, 848, 851, 852, 862, 863, 864, 865, 871, 874, 878, 882, 883, 884, 885, 886, 887, 888, 889, 892, 895, 896, 897, 898, 899, 900, 901, 903, 904, 906, 907, 908, 909 |
| | | − | 687, 692, 698, 705, 713, 714, 715, 716 |
| | >100 nM−10 μM | + | 608, 609, 610, 611, 612, 613, 614, 616, 618, 620, 625, 626, 627, 628, 629, 630, 631, 634, 636, 638, 639, 642, 643, 645, 646, 647, 648, 650, 651, 652, 653, 654, 655, 656, 661, 680, 681, 682, 683, 691, 693, 696, 700, 701, 703, 704, 708, 719, 720, 726, 727, 731, 732, 733, 734, 736, 739, 740, 745, 746, |

TABLE IIIA-continued

| CB | EC50 | +/- | COMPOUND NUMBER. |
|---|---|---|---|
| | | | 747, 748, 750, 751, 752, 755, 760, 763, 764, 765, 766, 769, 770, 771, 772, 774, 807, 812, 823, 825, 830, 831, 837, 840, 841, 843, 849, 855, 858, 870, 872, 873, 875, 876, 877, 881, 893, 894, 905 |
| | | − | 818 |
| | >10 µM | | 617, 623, 632, 640, 641, 649, 657, 707, 709, 710, 717, 718, 728, 744, 758, 768, 775, 776, 787, 788, 789, 808, 809, 810, 824, 826, 827, 854, 856, 857, 859, 879, 880, 890, 902, 910 |

TABLE IIIB

| CB | EC50 | +/- | COMPOUND NUMBER. |
|---|---|---|---|
| HCB1 | 0.1 nM-10 nM | + | 663, 671, 673, 675, 676, 688, 689, 690, 712, 794, 801, 819, 860, 867, 868, 891, 902 |
| | | − | |
| | >10 nM-100 nM | + | 615, 619, 621, 622, 659, 660, 665, 668, 670, 674, 679, 685, 686, 687, 692, 694, 697, 699, 702, 707, 713, 714, 716, 717, 721, 722, 723, 729, 737, 741, 749, 754, 757, 767, 778, 779, 785, 790, 791, 795, 797, 798, 799, 802, 804, 815, 816, 822, 833, 838, 842, 844, 847, 848, 850, 853, 861, 862, 864, 866, 869, 882, 884, 886, 889, 890, 892, 899, 906, 907 |
| | | − | |
| | >100 nM-10 µM | + | 609, 610, 611, 612, 613, 614, 616, 618, 620, 624, 626, 629, 630, 631, 633, 634, 635, 636, 637, 642, 643, 644, 648, 650, 652, 653, 654, 655, 656, 658, 661, 662, 664, 666, 667, 669, 672, 677, 678, 680, 681, 683, 684, 691, 693, 695, 696, 698, 700, 701, 703, 705, 706, 711, 715, 724, 725, 730, 732, 734, 735, 736, 738, 739, 740, 742, 743, 745, 746, 747, 748, 750, 751, 752, 753, 755, 756, 759, 760, 761, 762, 763, 766, 772, 773, 774, 777, 780, 781, 782, 783, 784, 786, 792, 793, 796, 800, 803, 805, 806, 807, 811, 812, 813, 814, 817, 820, 821, 825, 828, 829, 830, 831, 832, 834, 835, 836, 837, 839, 841, 843, 845, 846, 849, 851, 852, 855, 858, 863, 865, 870, 871, 872, 874, 875, 876, 877, 878, 881, 883, 885, 887, 888, 893, 894, 895, 896, 897, 898, 900, 901, 903, 904, 908, 909 |
| | | − | 608, 623, 827, 857 |
| | >10 µM | | 617, 625, 627, 628, 632, 638, 639, 640, 641, 645, 646, 647, 649, 651, 657, 682, 704, 708, 709, 710, 718, 719, 720, 726, 727, 728, 731, 733, 744, 758, 764, 765, 768, 769, 770, 771, 775, 776, 787, 788, 789, 808, 809, 810, 818, 823, 824, 826, 840, 854, 856, 859, 873, 879, 880, 905, 910 |

"+" or "−" in Tables II and III identify the compound as an agonist or an inverse agonist, respectively. ND: Not determined.

Example 86

Anti-Hyperalgesia in an Inflammatory Pain Model

The anti-hyperalgesic effects of test compounds in the Complete Freund's Adjuvant (CFA) model of inflammatory pain was examined as described below. Male Sprague-Dawley rats (Hsd:Sprague-Dawley®™ SD®™, Harlan, Indianapolis, Ind.) weighing 201±1 grams, were housed three per cage. Animals had free access to food and water and were maintained on a twelve hour light/dark schedule for the entire duration of the experiment. Approximately 12 hours prior to behavioral testing, animals were placed on wire mesh bottom cages with free access to water but no access to food. Test compounds were prepared in 50% PEG-400 (Sigma-Aldrich, cat. P3265). Indomethacin (Fluka, cat 57413) was suspended in 0.5% methylcellulose (Sigma-Aldrich, cat. 274429). Groups of eight animals were anesthetized with 2-3% isoflurane and local inflammation induced by 50 µl CFA (Sigma-Aldrich, cat F5881, *Mycobacterium tuberculosis* 1 mg/ml) injected subcutaneously into the plantar surface of the left paw.

Assessment of mechanical hyperalgesia: Baseline and post-treatment withdrawal thresholds to a noxious mechanical stimulus were measured using the Randall-Selitto paw pressure apparatus (Ugo Basile Analgesymeter, model 7200). This apparatus generates a linearly increasing mechanical force. The stimulus was applied to the plantar surface of the hind paws by a dome-shaped plastic tip placed between the third and fourth metatarsus. To avoid tissue damage, a cut-off pressure was set at 390 grams. Mechanical thresholds were defined as the force in grams at the first pain behavior, which includes paw withdrawal, struggle, and/or vocalization. Indomethacin (30 mg/kg, p.o.) served as the positive control. Mechanical hyperalgesia was measured using the Randall-Selitto paw pressure device before CFA injection and after intraperitoneal (i.p.) compound administration over a twenty-four-hour period. The mean and standard error of the mean (SEM) were determined for the injured and normal paws for each treatment group. The results for Compound 91 as compared with vehicle alone are shown in FIG. 1. No side effects were observed during the course of the experiment.

Example 87

Inhibition of Acetic Acid-Induced Writhing in Mice

This test identifies compounds which exhibit analgesic activity against visceral pain or pain associated with activation of low pH-sensitive nociceptors [see Barber and Gottschlich (1986) Med. Res. Rev. 12: 525-562; Ramabadran and Bansinath (1986) Pharm. Res. 3: 263-270]. Intraperitoneal administration of dilute acetic acid solution causes a writhing behavior in mice. A writhe is defined as a contraction of the abdominal muscles accompanied by an extension of the forelimbs and elongation of the body. The number of writhes observed in the presence and absence of test compounds is counted to determine the analgesic activity of the compounds.

Male ICR mice, 20-40 grams in weight, were weighed and placed in individual observation chambers (usually a 4000 ml beaker) with a fine layer of rodent bedding at the bottom. To determine the activity and potency of test compounds, different doses of the compound solution or vehicle were injected subcutaneously in the back of the neck 30 minutes prior to administration of acetic acid solution. After administration of the compound or vehicle control, mice were returned to their individual observation chambers awaiting the intraperitoneal administration of acetic acid solution. Thirty minutes later, 10 ml/kg of a 0.6% (v/v) acetic acid solution was then injected into the right lower quadrant of the abdomen. Immediately after the injection, the mouse was returned to its observation chamber and the recording of the number of writhes begun immediately. The number of writhes was counted over a 15-min period starting from the time of acetic acid injection. Raw data were analyzed using a one-way ANOVA followed by Dunnett's post-tests. For dose-response analysis, raw data were converted to % maximum possible effect (% MPE) using the formula: % MPE=((Wc−Wv)/(0−Wv))*100, where Wc is the number of writhes in compound-treated mice and Wv is the mean number of writhes in vehicle-treated mice. The dose which elicited 50% attenuation of hypersensitivity (ED50) was determined using linear regression analysis. (Tallarida & Murray, 1987).

Figure 2:
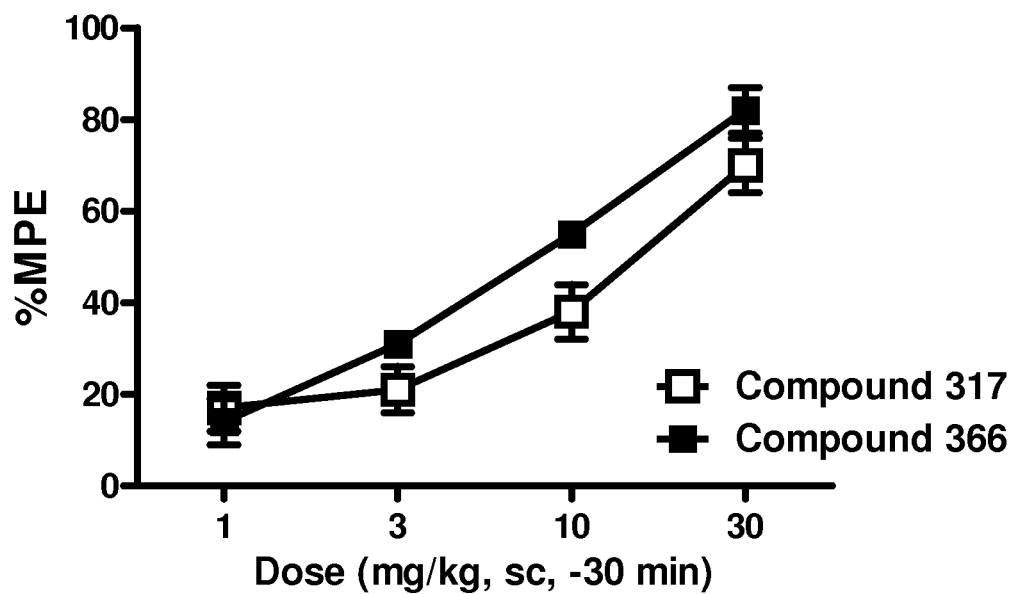
FIG. 2 shows a dose response in the inhibition of acetic acid-induced writhing in mice, for compounds 317 and 366 administered subcutaneously at doses of 3 mg/kg, 10 mg/kg and 30 mg/kg.

Dose response relationships were established for compounds 317 and 366 by subcutaneous injection of doses equivalent to 3, 10 and 30 mg/kg given 30 minutes before intraperitoneal injection of the acetic acid solution. The number of writhes observed in treated an untreated animals were compared and the results are shown in FIG. 2.

Example 88

Carrageenan Model of Acute Inflammation

Acute inflammation was produced in rats by injecting 0.1 mL of 2% λ-carrageenan (type IV; Sigma, St. Louis, Mo.) into one hind paw. Carrageenan treatment elicited a marked hind paw swelling (edema) relative to the non-injected paw. At various time points following carrageenan injection, paw volume measurements were taken for both hind paws using a plethysmometer (Stoelting). Briefly, the rat was gently held under the arms with one hand, and its ankle was stabilized with the other hand, each paw was dipped (for a duration of ~sec, i.e., sufficient time to get a stable reading) into a known volume of fluid and total fluid displacement was recorded. Animals were administered vehicle or test compounds prior to carrageenan administration. A statistically significant reduction in hind paw volume relative to the vehicle-treated control group was interpreted as an anti-inflammatory effect.

Figure 3A:
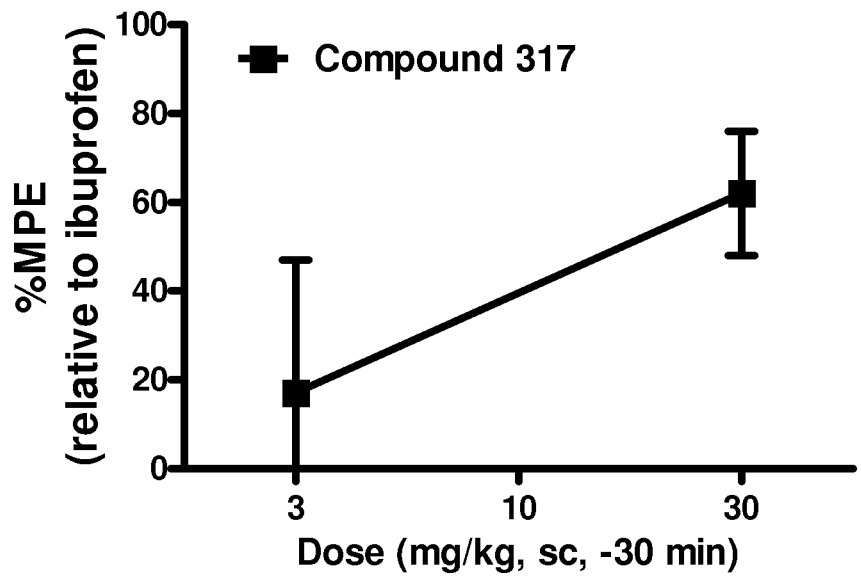
FIG. 3 shows a dose response in the inhibition of carrageenan-induced hyper-sensitivity in rat for (A) compound 317 administered sub-cutaneously at doses of 3 mg/kg, 10 mg/kg and 30 mg/kg; and (B) compound 366 administered orally at doses of 1 mg/kg, 3 mg/kg and 10 mg/kg.
Figure 3B:
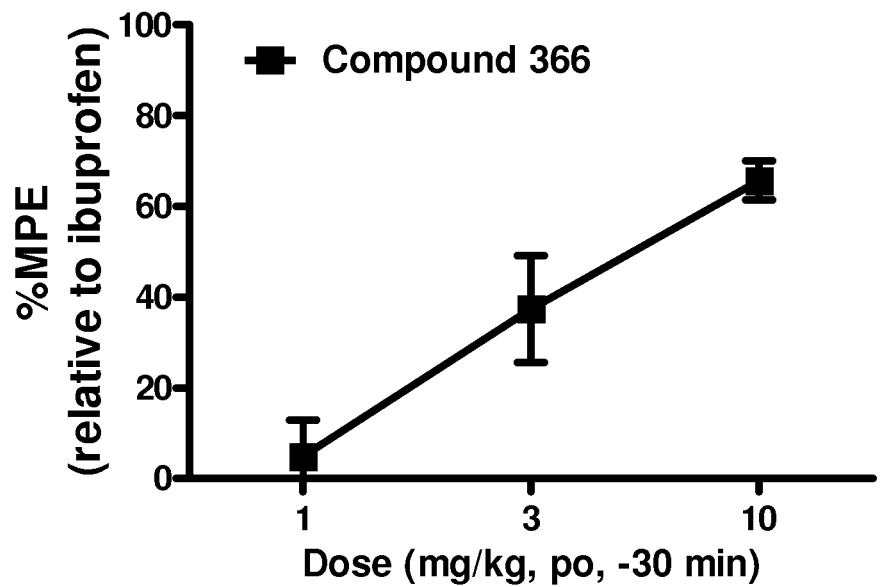

FIG. 3A shows the results obtained when compound 317 was administered subcutaneously at a dose of 3 or 30 mg/kg thirty minutes before carrageenan treatment. FIG. 3B shows the results obtained with compound 366 administered orally at doses of 1, 3 and 10 mg/kg, thirty minutes before carrageenan treatment.

Example 89

Spinal Nerve Ligation (SNL) Model

Figure 4:
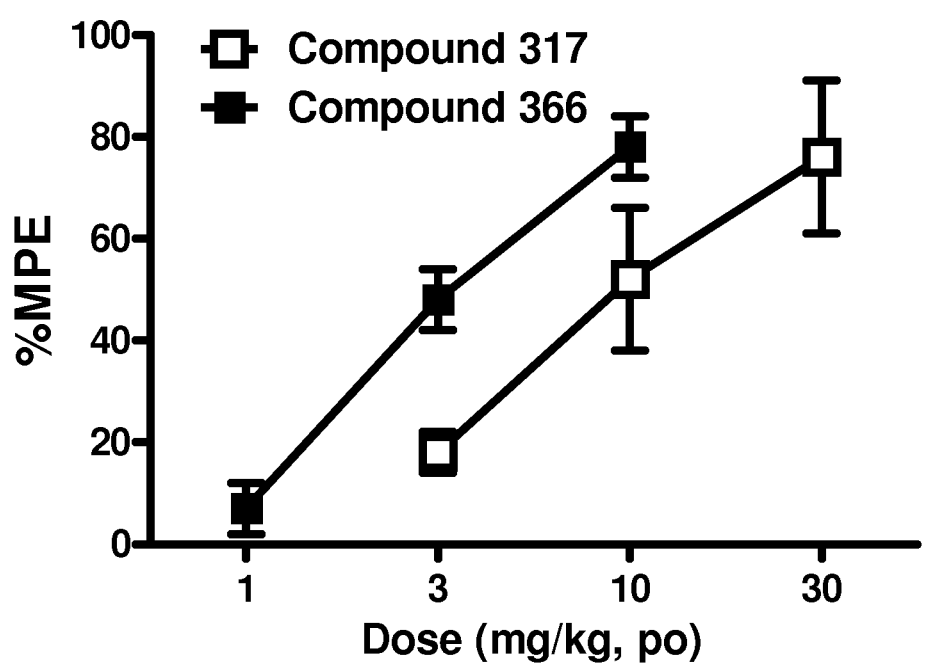
FIG. 4 shows a dose response in the neuropathic pain model in rat for compounds 317 and 366 administered orally at 3 mg/kg, 10 mg/kg and 30 mg/kg.

The SNL model (Kim and Chung 1992) was used to induce chronic neuropathic pain in rats. The rats were anesthetized with isoflurane, the left L5 transverse process was removed, and the L5 and L6 spinal nerves were tightly ligated with 6-0 silk suture. The wound was then closed with internal sutures and external staples. Following at least seven days post SNL, baseline, post-injury and post-treatment values for non-noxious mechanical sensitivity were evaluated using eight Semmes-Weinstein filaments (Stoelting, Wood Dale, Ill., USA) with varying stiffness (0.4, 0.7, 1.2, 2.0, 3.6, 5.5, 8.5, and 15 g) according to the up-down method (Chaplan et al. 1994). Animals were placed on a perforated metallic platform and allowed to acclimate to their surroundings for a minimum of thirty minutes before testing. The mean and standard error of the mean (SEM) were determined for the injured paw in each treatment group. Since this stimulus is normally not considered painful, significant injury-induced increases in responsiveness in this test are interpreted as a measure of mechanical allodynia. The dose which elicited 50% attenuation of mechanical hypersensitivity ($ED_{50}$) was determined using linear regression analysis. Results obtained after oral administration of compound 317 at 3, 10 and 30 mg/kg and with compound 366 at 1, 3 and 10 mg/kg are shown in FIG. 4.

The texts of the references cited in this specification are herein incorporated by reference in their entireties. In the event that a definition of a term as incorporated by reference differs from the meaning defined herein, then the meaning provided herein is intended. The examples provided herein are for illustration purposes only and are not to be interpreted as limiting the scope of the invention, the full scope of which will be immediately recognized by those of skill in the art.

We claim:

1. A method of prophylaxis or treatment of pain in a mammal, the method comprising administering to the mammal an effective amount of a compound having the structure of formula I:

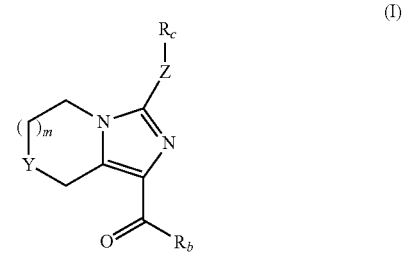

(I)

or a pharmaceutically acceptable salt, acid salt, or stereoisomer thereof, wherein:

Y is selected from the group consisting of $NR_a$ and $N^+R_1R_2X^-$;

Z is selected from the group consisting of a bond, $-(CH_2)_p-$, $-CH=CH-$, $-C\equiv C-$, $-CONH-$ and $-CO-$;

$R_a$ is selected from the group consisting of —H, $C_1$-$C_8$ alkyl, $C_3$-$C_6$ alkenyl, $C_3$-$C_6$ alkynyl, aryl, $C_3$-$C_8$ cycloalkyl, $C_3$-$C_8$ cycloalkenyl, —$SO_2R_3$, —$COR_3$, —$CONR_3R_4$, —$CSNR_3R_4$, —$COOR_3$ and —$(CH_2)_q$heterocyclyl, wherein the alkyl, cycloalkyl, cycloalkenyl, aryl and heterocyclyl of $R_a$ are each optionally substituted with one to four substituents independently selected from the group consisting of halo, —OH, oxo, —$NH_2$, —$NO_2$, —CN, —COOH, —$COR_3$, —$OCF_3$, —$CF_3$, $C_1$-$C_6$ alkyl, $C_1$-$C_4$ alkoxy, $C_3$-$C_8$ cycloalkyl, and phenyl;

$R_b$ is selected from the group consisting of $C_1$-$C_8$ alkyl, $C_2$-$C_8$ alkenyl, aryl, —$NR_5R_6$,

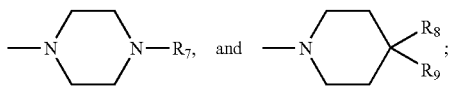

wherein the alkyl, alkenyl and aryl of $R_b$ are each optionally substituted with one to three substituents independently selected from the group consisting of $C_1$-$C_4$ alkyl, $C_2$-$C_4$ alkenyl, $C_3$-$C_6$ cycloalkyl, $C_1$-$C_4$ alkoxy, aryl, 5-, 6-, and 7-membered heterocyclyl, halo, —OH, —$NH_2$, —CN and —$NO_2$;

$R_c$ is selected from the group consisting of halo, $C_1$-$C_6$ alkyl, $C_2$-$C_6$ alkenyl, $C_2$-$C_6$ alkynyl, $C_3$-$C_{10}$ cycloalkyl, $C_3$-$C_8$ cycloalkenyl, $C_1$-$C_4$ alkoxy, aryl, 5-, 6-, 7-, 8-membered monocyclic heterocyclyl, 9-, and 10-membered bicyclic heterocyclyl; wherein the $C_2$-$C_6$ alkenyl, $C_2$-$C_6$ alkynyl, $C_3$-$C_{10}$ cycloalkyl, $C_3$-$C_8$ cycloalkenyl, aryl, 5-, 6-, 7-, 8-membered monocyclic heterocyclyl, 9- and 10-membered bicyclic heterocyclyl of $R_c$ are optionally substituted with one to five substituents independently selected from the group consisting of $C_1$-$C_4$ alkyl, $C_1$-$C_4$ alkoxy, $C_1$-$C_4$ haloalkyl, $C_1$-$C_4$ haloalkoxy, $C_3$-$C_6$ cycloalkyl, $C_4$-$C_8$ cycloalkenyl, halo, —OH, —$NH_2$, (A)(A')(A'')(A''')aryl, (A)(A')(A'')(A''')heterocyclyl, $NR_{14}R_{15}$, $(CH_2)_pNR_{14}R_{15}$, —CN, —$NO_2$, oxo, —$COOR_{14}$, $SOR_{14}$, $SO_2R_{14}$, $SO_2NR_{14}R_{15}$, $NR_{15}SO_2R_{16}$, $COR_{14}$, $CONR_{14}R_{15}$ and $NR_{15}COR_{16}$; wherein (A), (A'), (A'') and (A''') are each an independently selected from the group consisting of —H and $C_1$-$C_4$ alkyl and each heterocyclyl of (A)(A')(A'')(A''')heterocyclyl is independently selected from the group consisting of 5-, 6-, 7-, 8-membered monocyclic heterocyclyl, 9- and 10-membered bicyclic heterocyclyl;

$R_1$ and $R_2$ are each independently $C_1$-$C_4$ alkyl;

$R_3$ and $R_4$, when either or both are present, are each independently selected from the group consisting of —H, $C_1$-$C_6$ alkyl, $C_3$-$C_6$ alkenyl, $C_3$-$C_6$ alkynyl, $C_3$-$C_8$ cycloalkyl, $C_3$-$C_8$ cycloalkenyl, aryl, 4-, 5-, 6-, 7- and 8-membered heterocyclyl; wherein $R_3$ and $R_4$ that are not H are each independently optionally substituted with one to three substituents independently selected from the group consisting of $C_1$-$C_6$ alkyl, $C_1$-$C_6$ haloalkyl, $C_3$-$C_8$ cycloalkyl, $C_1$-$C_4$ alkoxy, $C_1$-$C_4$ acyl, aryl, 5-, 6-, 7-, 8-membered monocyclic heterocyclyl, 9- and 10-membered bicyclic heterocyclyl, —$NH_2$, —$NO_2$, —CN, —OH, —COOH, oxo, and halo; provided that if $R_a$ is $SO_2R_3$, then $R_3$ is not —H; alternatively, $R_3$ and $R_4$ taken together with the nitrogen atom to which they are bonded form a heterocyclyl selected from the group consisting of 4-, 5-, 6-, 7- and 8-membered heterocyclyl;

$R_5$ is selected from the group consisting of —H, $C_1$-$C_4$ alkyl and $C_1$-$C_4$ haloalkyl; wherein the alkyl and haloalkyl of $R_5$ are optionally substituted with one to four substituents independently selected from the group consisting of $C_1$-$C_4$ alkoxy, —OH, —$NH_2$ and —CN;

$R_6$ is selected from the group consisting of —H, —$CR_{10}R_{11}R_{12}$, —$CR_{10}R_{11}COR_{13}$, $C_1$-$C_8$ alkyl, $C_3$-$C_{10}$ cycloalkyl, aryl, 5-, 6-, 7-, 8-membered monocyclic heterocyclyl, 9- and 10-membered bicyclic heterocyclyl; wherein the alkyl, cycloalkyl, aryl, and heterocyclyl of $R_6$ are optionally substituted with one to three substituents independently selected from the group consisting of $C_1$-$C_4$ alkyl, aryl, halo, —OH, $C_1$-$C_4$ alkoxy, $C_1$-$C_4$ hydroxyalkyl, —$COR_{13}$, —$SO_2R_{11}$, —$SO_2NR_8R_9$, —$NH_2$, —CN, and —$NO_2$; alternatively, $R_5$ and $R_6$ taken together with the nitrogen atom to which they are bonded form a heterocyclyl selected from the group consisting of 5-, 6-, 7-, 8-membered monocyclic heterocyclyl, 9- and 10-membered bicyclic heterocyclyl, which heterocyclyl substituent of $R_6$ is optionally substituted with one to two substituents independently selected from the group consisting of $C_1$-$C_4$ alkyl, $C_1$-$C_4$ haloalkyl, —$COOR_1$, —$CONR_1R_2$, and oxo;

$R_7$ is selected from the group consisting of —$COR_3$, —$COOR_3$, —$SO_2R_3$, and 5-, 6- and 7-membered heterocyclyl;

$R_8$ and $R_9$ are independently selected from the group consisting of —H, $C_1$-$C_4$ alkyl, $C_1$-$C_4$ haloalkyl, $C_1$-$C_4$ alkoxy, $C_3$-$C_6$ cycloalkyl, aryl, 5-, 6-, 7-, 8-membered monocyclic heterocyclyl, 9- and 10-membered bicyclic heterocyclyl, halo, —OH, $C_1$-$C_4$ alkoxy, $C_1$-$C_4$ alkyl, —$CONH_2$, —$NH_2$, —CN and —$NO_2$; alternatively: (i) $R_8$ and $R_9$, taken together with the nitrogen atom to which they are bonded form a heterocyclyl moiety which is optionally substituted with one to three substituents selected from the group consisting of $C_1$-$C_4$ alkyl, halo, oxo, and aryl; or (ii) $R_8$ and $R_9$, taken together with the carbon atom to which they are bonded form a cycloalkyl which is optionally substituted with one to three substituents selected from the group consisting of $C_1$-$C_4$ alkyl, $C_1$-$C_4$ haloalkyl, halo, oxo and aryl;

$R_{10}$ is selected from the group consisting of —H and $C_1$-$C_4$ alkyl;

$R_{11}$ is selected from the group consisting of —H, $C_1$-$C_8$ alkyl, $C_2$-$C_6$ alkenyl, $C_2$-$C_4$ alkynyl, $C_3$-$C_{10}$ cycloalkyl, aryl, 5-, 6-, 7-, 8-membered monocyclic heterocyclyl, 9- and 10-membered bicyclic heterocyclyl; wherein the alkyl, alkenyl, alkynyl, cycloalkyl, aryl and 5-, 6-, 7-, 8-membered monocyclic heterocyclyl, 9- and 10-membered bicyclic heterocyclyl of $R_{11}$ are optionally substituted with one to three substituents independently selected from the group consisting of $C_1$-$C_4$ alkyl, $C_3$-$C_6$ cycloalkyl, haloaryl, aryl, and 5-, 6-, 7-, 8-membered monocyclic heterocyclyl, 9- and 10-membered bicyclic heterocyclyl, halo, —OH, $C_1$-$C_4$ alkoxy, —$NH_2$, -guanidino, —CN, —$NO_2$, oxo, —$COOR_{10}$, —$CONR_8R_9$, —$SO_2NR_8R_9$, —$SR_{10}$, —$SOR_1$ and —$SO_2R_{11}$;

$R_{12}$ is selected from the group consisting of —H, $C_1$-$C_4$ alkyl and $C_1$-$C_4$ hydroxyalkyl;

$R_{13}$ is selected from the group consisting of —$OR_{10}$ and —$NR_8R_9$;

$R_{14}$, $R_{15}$ and $R_{16}$ are each independently selected from the group consisting of —H, and $C_1$-$C_4$ alkyl; alternatively, $R_{14}$ and $R_{15}$ taken together with the nitrogen atom to which they are bonded form a heterocyclyl selected from the group consisting of 5-, 6-, 7-, 8-membered monocyclic heterocyclyl, 9- and 10-membered bicyclic heterocyclyl;

$X^-$ is an anionic counterion; and m is 2; each instance of p is independently an integer from 1 to 6; and q is independently zero or an integer from 1 to 4;

provided that when $R_c$ is heterocyclyl, the heterocyclyl is directly bonded through a carbon atom of a ring of the heterocyclyl.

2. The method according to claim 1, wherein:
Y is $NR_a$ and Z is selected from the group consisting of a bond, $-(CH_2)_p$ and $-CO-$; and
each p is independently an integer from 1 to 3; and each q is independently zero or an integer from 1 to 2.

3. The method according to claim 1, wherein:
$R_a$ is selected from the group consisting of —H, $C_1$-$C_8$ alkyl, $C_3$-$C_6$ alkenyl, $C_3$-$C_6$ alkynyl, $C_3$-$C_8$ cycloalkyl, $C_3$-$C_8$ cycloalkenyl, $-SO_2R_3$, $-COR_3$, $-CONR_3R_4$, $-CSNR_3R_4$, $-COOR_3$ and $-(CH_2)_q$heterocyclyl, wherein the alkyl, cycloalkyl, cycloalkenyl and heterocyclyl of $R_a$ are each optionally substituted with one to four substituents independently selected from the group consisting of halo, —OH, oxo, $-NH_2$, $-NO_2$, —CN, —COOH, $-COR_3$, $-OCF_3$, $-CF_3$, $C_1$-$C_6$ alkyl, $C_1$-$C_4$ alkoxy and $C_3$-$C_8$ cycloalkyl; and $R_3$ and $R_4$, when either or both are present, are each independently selected from the group consisting of —H, $C_1$-$C_6$ alkyl, and $C_3$-$C_6$ cycloalkyl; wherein the alkyl and cycloalkyl of $R_3$ and $R_4$ that are not H are each independently optionally substituted with one to three substituents independently selected from the group consisting of $C_1$-$C_4$ alkyl, $C_1$-$C_4$ haloalkyl, $C_3$-$C_6$ cycloalkyl, $C_1$-$C_4$ alkoxy, 5-, 6-, 7- and 8-membered heterocyclyl, $-NH_2$, —CN, —OH, oxo, and halo; alternatively, $R_3$ and $R_4$ taken together with the nitrogen atom to which they are bonded form a heterocyclyl selected from the group consisting of 4-, 5- and 6-membered heterocyclyl.

4. The method according to claim 1, wherein:
$R_b$ is selected from the group consisting of $C_1$-$C_8$ alkyl, $C_2$-$C_8$ alkenyl, and $-NR_5R_6$, wherein the alkyl and alkenyl of $R_b$ are each optionally substituted with one to three substituents independently selected from the group consisting of $C_1$-$C_4$ alkyl, $C_3$-$C_6$ cycloalkyl, $C_1$-$C_4$ alkoxy, aryl, 5-, 6-, and 7-membered heterocyclyl, halo, —OH and $-NH_2$.

5. The method according to claim 1, wherein:
$R_c$ is selected from the group consisting of $C_1$-$C_6$ alkyl, $C_3$-$C_6$ cycloalkyl, aryl and 5-, 6-, 7-, 8-, 9-, and 10-membered heterocyclyl; wherein the $C_3$-$C_6$ cycloalkyl, aryl and heterocyclyl of $R_c$ are optionally substituted with one to three substituents independently selected from the group consisting of $C_1$-$C_4$ alkyl, $C_1$-$C_4$ alkoxy, $C_1$-$C_4$ haloalkyl, $C_1$-$C_4$ haloalkoxy, halo, —OH, $-NH_2$, $NR_{14}R_{15}$, $(CH_2)_pNR_{14}R_{15}$, —CN, $-NO_2$, oxo, $-COOR_{14}$, $SO_2R_{14}$, $SO_2NR_{14}R_{15}$, $NR_{15}SO_2R_{16}$, $COR_{14}$, $CONR_{14}R_{15}$ and $NR_{15}COR_{16}$.

6. The method according to claim 1, wherein:
Z is selected from the group consisting of a bond, $-(CH_2)_p$, $-CONH-$ and $-CO-$;
$R_a$ is selected from the group consisting of $C_1$-$C_8$ alkyl, $C_3$-$C_6$ alkenyl, $C_3$-$C_6$ alkynyl, $C_3$-$C_8$ cycloalkyl, $-SO_2R_3$, $-COR_3$, $-CONR_3R_4$, $-CSNR_3R_4$, $-COOR_3$ and $-(CH_2)_q$heterocyclyl, wherein the alkyl, cycloalkyl, and heterocyclyl of $R_a$ are each optionally substituted with one to three substituents independently selected from the group consisting of halo, —OH, oxo, $-NH_2$, $-NO_2$, —CN, —COOH, $-COR_3$, $-OCF_3$, $-CF_3$, $C_1$-$C_6$ alkyl, $C_1$-$C_4$ alkoxy and $C_3$-$C_8$ cycloalkyl;

$R_b$ is selected from the group consisting of $C_1$-$C_8$ alkyl, $C_2$-$C_8$ alkenyl, aryl, $NR_5N_6$,

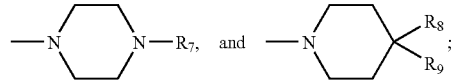

wherein the alkyl, alkenyl and aryl of $R_b$ are each optionally substituted with one or two substituents independently selected from the group consisting of $C_1$-$C_4$ alkyl, $C_3$-$C_6$ cycloalkyl, $C_1$-$C_4$ alkoxy, aryl, 5-, 6-, and 7-membered heterocyclyl, halo, —OH, $-NH_2$, —CN and $-NO_2$;

$R_c$ is selected from the group consisting of $C_1$-$C_6$ alkyl, $C_3$-$C_6$ cycloalkyl, aryl, 5-, 6-, 7-, 8-membered monocyclic heterocyclyl, 9- and 10-membered bicyclic heterocyclyl; wherein the alkyl, cycloalkyl, aryl, and heterocyclyl of $R_c$ are optionally substituted with one to three substituents independently selected from the group consisting of $C_1$-$C_4$ alkyl, $C_1$-$C_4$ alkoxy, $C_1$-$C_4$ haloalkyl, $C_1$-$C_4$ haloalkoxy, halo, —OH, $-NH_2$, $(CH_2)_pNR_{14}R_{15}$, —CN, oxo, $-COOR_{14}$, $CR_{14}$, $CONR_{14}R_{15}$ and $NR_{15}COR_{16}$; and
each q is independently 1 or 2.

7. The method according to claim 1, wherein:
Y is $NR_a$;
Z is selected from the group consisting of a bond and $-(CH_2)-$;
$R_a$ is selected from the group consisting of —H, $C_1$-$C_8$ alkyl, and $C_3$-$C_8$ cycloalkyl;
$R_c$ is selected from the group consisting of aryl, 5-, 6-, 7-, 8-membered monocyclic heterocyclyl, 9- and 10-membered bicyclic heterocyclyl; wherein the aryl, and heterocyclyl of $R_c$ are optionally substituted with one to three substituents independently selected from the group consisting of $C_1$-$C_4$ alkyl, $C_1$-$C_4$ alkoxy, $C_1$-$C_4$ haloalkyl, $C_1$-$C_4$ haloalkoxy, halo, —OH, $-NH_2$, $-NR_{14}R_{15}$, $-CH_2NR_{14}R_{15}$, —CN, -oxo, $-COOR_{14}$, $CR_{14}$, $CONR_{14}R_{15}$ and $NR_{15}COR_{16}$.

8. The method according to claim 1, wherein:
$R_b$ is selected from the group consisting of $-NR_5R_6$,

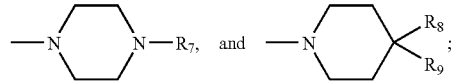

$R_5$ is selected from the group consisting of —H and $C_1$-$C_8$ alkyl;
$R_6$ is selected from the group consisting of $-CR_{10}R_{11}R_{12}$ and $-CR_{10}R_{11}COR_{13}$; alternatively, $R_5$ and $R_6$ taken together with the nitrogen atom to which they are bonded form a heterocyclyl selected from the group consisting of 6-, 7-, 8-membered monocyclic heterocyclyl, 9- and 10-membered bicyclic heterocyclyl, which heterocyclyl substituent of the $R_5R_6$ heterocycle is optionally substituted with one to two substituents independently selected from the group consisting of $C_1$-$C_4$ alkyl, $C_1$-$C_4$ haloalkyl, $-COOR_1$, $-CONR_1R_2$ and oxo;

$R_{10}$ is —H;

$R_{11}$ is selected from the group consisting of $C_1$-$C_8$ alkyl, $C_3$-$C_{10}$ cycloalkyl, aryl, 5-, 6-, 7-, 8-membered monocyclic heterocyclyl, 9- and 10-membered bicyclic heterocyclyl; wherein the alkyl, cycloalkyl, aryl and 5-6-, 7-, 8-, 9- and 10-membered heterocyclyl of $R_{11}$ are optionally substituted with one to three substituents independently selected from the group consisting of $C_1$-$C_4$ alkyl, $C_3$-$C_6$ cycloalkyl, aryl, and 5-, 6-, 7- and 8-membered heterocyclyl, halo, —OH, $C_1$-$C_4$ alkoxy, —$NH_2$, -guanidino, —CN, oxo, —$COOR_{10}$, —$CONR_8R_9$, —$SO_2NR_8R_9$, —$SR_{10}$, —$SOR_1$ and —$SO_2R_1$; and each q is independently zero or an integer from 1 to 3.

9. The method according to claim 8, wherein:

Y is $NR_a$;

Z is selected from the group consisting of a bond and —($CH_2$)—;

$R_a$ is $C_1$-$C_8$ alkyl; and $R_c$ is selected from the group consisting of aryl, 5- and 6-membered heterocyclyl; wherein the aryl, and heterocyclyl of $R_c$ are optionally substituted with one to three substituents independently selected from the group consisting of $C_1$-$C_4$ alkyl, $C_1$-$C_4$ alkoxy, $C_1$-$C_4$ haloalkoxy, $C_1$-$C_4$ haloalkoxy, halo, —OH, —$NH_2$, $NR_{14}R_{15}$, $CH_2NR_{14}R_{15}$, —CN, $NO_2$, oxo, —$COOR_{14}$, $SOR_{14}$, $SO_2R_{14}$, $SO_2NR_{14}R_{15}$, $NR_{15}SO_2R_{16}$, $COR_{14}$, $CONR_{14}R_{15}$ and $NR_{15}COR_{16}$.

10. The method according to claim 9, wherein:

$R_b$ is $NR_5R_6$, $R_5$ is —H;

$R_6$ is —$CR_{10}R_{11}COR_{13}$;

$R_{11}$ is $C_1$-$C_8$ alkyl;

$R_{13}$ is $NR_8R_9$; and

Each q is independently zero, 1 or 2.

11. The method according to claim 1, wherein:

Y is $NR_a$;

Z is selected from the group consisting of a bond, —($CH_2$)$_p$, and —CONH— and —CO—; and $R_a$ is selected from the group consisting of —H, $C_1$-$C_8$ alkyl, $C_3$-$C_8$ cycloalkyl —$SO_2R_3$, —$COR_3$, —$CONR_3R_4$, —$CSNR_3R_4$— and —($CH_2$)$_q$heterocyclyl, wherein the alkyl, cycloalkyl and heterocyclyl of $R_a$ are each optionally substituted with one to three substituents independently selected from the group consisting of halo, —OH, oxo, —$NH_2$, —$NO_2$, —CN, —$COR_3$, —$OCF_3$, —$CF_3$, $C_1$-$C_6$ alkyl.

12. The method according to claim 11, wherein:

Y is $NR_a$ and Z is a bond;

$R_a$ is $C_1$-$C_8$ alkyl; $R_b$ is $NR_5R_6$;

$R_5$ is —H and $R_6$ is —$CR_{10}R_{11}COR_{13}$;

$R_8$ and $R_9$ are independently selected from the group consisting of —H and $C_1$-$C_6$ alkyl;

$R_{10}$ $R_{11}$ and $R_{12}$ are each independently selected from the group consisting of —H and $C_1$-$C_4$ alkyl; and $R_{13}$ is $NR_8R_9$.

13. The method according to claim 12, wherein:

$R_a$ is $C_1$-$C_4$ alkyl; $R_c$ is halophenyl; and $R_8$ is —H and $R_9$ is $C_1$-$C_6$ alkyl.

14. The method according to claim 12, wherein:

$R_a$ is methyl or ethyl, and $R_{10}$ is tertbutyl.

15. The method according to claim 1, wherein: $R_a$ is selected from the group consisting of —H, methyl, ethyl, isobutyl, cyclopropyl, cyclopropylmethyl; methylsulfonyl; furan-2-ylmethyl, pyrimidin-2-yl, pyrimidin-5-ylmethyl, 6-chloro-pyridin-2-yl, 6-chloro-pyrazin-2-yl, (1-methyl-1H-pyrazol-4-yl)methyl, benzyl, and acetyl.

16. The method according to claim 1, wherein $R_b$ is selected from the group consisting of 3,3-dimethyl-1-(methylamino)-1-oxobutan2-ylamino, 1-(ethylamino)-3,3-dimethyl-1-oxobutan-2-yl amino, 1-(isopropylamino)-3,3-dimethyl-1-oxobutan-2-ylamino, 4-tert-butylcyclohexylamino, 3-tertbutylisoxazol-5-ylamino, 3,3-dimethyl-1-morpholino-1-oxobutan-2-ylamino, 3,3-dimethyl-1-oxo-(piperidin-1-yl)butan-2-ylamino, 3,3-dimethyl-1-oxo-1-(pyrrolidin-1-yl)butan-2-ylamino, 1-(methoxy(methyl)amino)-3,3-dimethyl-1-oxobutan-2-yl amino, 1-(2-fluoroethylamino)-3,3-dimethyl-1-oxobutan-2-ylamino, 1-(azetidin-1-yl)-3,3-dimethyl-1-oxobutan-2-ylamino, 3,3-dimethyl-1-(4-methylpiperazin-1-yl)-1-oxobutan-2-ylamino, 1-(4,4-dimethyloxazolidin-3-yl)-3,3-dimethyl-1-oxobutan-2-ylamino, 2,2-dimethyl-1-(5-methyl-1,3,4-oxadiazol-2-yl)propyl-amino, 1-(methylcarbamoyl)cyclopentylamino, 3,3-dimethyl-1-(pyrrolidin-1-yl)butan-2-ylamino, 1-(3,3-difluoroazetidin-1-yl)-3,3-dimethyl-1-oxobutan-2-ylamino, 1-(3,3-difluoropyrolidin-1-yl)-3,3-dimethyl-1-oxobutan-2-ylamino, 1-(3-hydroxyazetidin-1-yl)-3,3-dimethyl-1-oxobutan-2-ylamino, 1-(-3-fluoropyrrolidin-1-yl)-3,3-dimethyl-1-oxobutan-2-ylamino, 3,3-dimethyl-1-{1-hydroxy-tricyclo[3.3.1.13,7]decan-3-ylamino)}-1-oxobutan-2-ylamino, 3,3-dimethyl-1-oxo-1-(3-oxopiperazin-1-yl)butan-2-ylamino, 1-(4-hydroxycyclohexylamino)-3,3-dimethyl-1-oxobutan-2-ylamino, 3,3-dimethyl-1-(4-(methylsulfonyl)piperazin-1-ylamino, 3,3-dimethyl-1-(4-(tert-butyl-carboxyl)-piperazin-1-yl)-1-oxobutan-2-ylamino, 1-(2-hydroxycyclohexylamino)-3,3-dimethyl-1-oxobutan-2-ylamino, 3,3-dimethyl-1-oxo-1-(quinuclidin-3-ylamino)butan-2-ylamino, 3,3-dimethyl-1-(2-methyl-1-oxo-2,8-diazaspiro-[4.5]decan-8-yl)-1-oxobutan-2-ylamino, 1-(imidazo[1,2-a]pyridin-2-ylmethylamino)-3,3-dimethyl-1-oxobutan-2-ylamino, 1-(2-yanoethylamino)-3,3-dimethyl-1-oxobutan-2-ylamino, 1-((1,3-dioxolan-2-yl)methylamino)-3,3-dimethyl-1-oxobutan-2-ylamino, 1-((2-(dimethylamino)ethyl)(ethyl)amino)-3,3-dimethyl-1-oxobutan-2-ylamino, 3,3-dimethyl-1-((5-methylpyrazin-2-yl)methylamino)-1-oxobutan-2-ylamino, 1-(1-acetylpiperidin-4-ylamino)-3,3-dimethyl-1-oxobutan-2-ylamino, 3,3-dimethyl-1-oxo-1-((tetrahydrofuran-2-yl)methylamino)-butan-2-ylamino, 1-(cyclopentylamino)-3,3-dimethyl-1-oxobutan-2-yl, 1-(2-(dimethylamino)ethylamino)-3,3-dimethyl-1-oxobutan-2-ylamino, 1-((2-methoxyethyl)(methyl)amino)-3,3-dimethyl-1-oxobutan-2-ylamino, 3,3-dimethyl-1-oxo-1-(3,3,3-trifluoropropylamino)butan-2-ylamino, 1-N-methyl-pyrrolidine-3-carboxamide, tert-butylamino, 3-hydroxy-2,2-dimethylpropylamine, 1-hydroxy-3,3-dimethylbutan-2-ylamino, 1-(hydroxymethyl)cyclopentylamine, 2-methyl-1-morpholinopropan-2-ylamino, (tetrahydro-2H-pyran-4-yl)methylamino, 1-hydroxy-2-methylpropan-2-ylamino, 1-amino-3,3-dimethylbutan-2-ylamino, 3,3-dimethyl-1-(2-oxopyrrolidin-1-yl)butan-2-ylamino, 1-acetamido-3,3-dimethylbutan-2-ylamino, 3,3-dimethyl-1-(methylsulfonamido)butan-2-ylamino, 3,3-dimethyl-1-oxo-1-((tetrahydro-2H-pyran-4-yl)methylamino)butan-2-ylamino, 1-(3-hydroxypyrrolidin-1-yl)-3,3-dimethyl-1-oxobutan-2-ylamino, 1-(1-hydroxy-2-methylpropan-2-ylamino)-3,3-dimethyl-1-oxobutan-2-ylamino, tert-pentylamino, 1-(2,6-dimethylmorpholino)-3,3-dimethyl-1-oxobutan-2-ylamino, 2-(morpholinomethyl)piperidin-1-yl, 1-hydroxy-3,3-dimethylbutan-2-ylamino, 2-tert-butylpyrrolidin-1-yl, 2,4,4-trimethylpentan-2-ylamino, 2-hydroxycyclohexylamine, 1-(4-oxopiperidine)-3-methyl carboxylate, 1-methoxy-3,3-dimethylbutan-2-ylamino, 1-hydroxy-3,3-dimethylbutan-2-ylamino, 1-2-cyanopyrrolidin-1-yl)-3,3-dimethyl-1- oxobutan-2-ylamino, 4-carboxyethylpiperid-1-yl, 3,3-dimethyl-1-oxo-1-(3-(trifluoromethyl)-5,6-dihydro-[1,2,4]triazolo[4,3-a]pyrazin-7(8H)-yl)butan-2-ylamino, 1-(isoindolin-2-yl)-3,3-dimethyl-1-oxobutan-2-ylamino, 1-(3-hydroxypiperidin-1-yl)-3,3-dimethyl-1-oxobutan-2-ylamino, 1-(2-hydroxycyclopentylamino)-3,3-dimethyl-1-oxobutan-2-ylamino, 1-(3-fluoroazetidin-1-yl)-3,3-dimethyl-1-oxobutan-2-ylamino, 1-(2-hydroxy-2-methylpropylamino)-3,3-dimethyl-1-oxobutan-2-ylamino, 4-hydroxypiperidin-1-yl, 1-(3,4-dihydroisoquinolin-2(1H)-yl, 1-(ethyl(2-hydroxyethyl)amino)-3,3-dimethyl-1-oxobutan-2-ylamino, 1-(diethylamino)-3,3-dimethyl-1-oxobutan-2-ylamino, 1-(2,6-dimethylmorpholino), 3,3-dimethyl-1-oxo-1-(thiazol-2-ylamino)butan-2-ylamino, 2,2-dimethyl-1-(3-methyl-1,2,4-oxadiazol-5-yl)propylamino, 2-hydroxy-2,4,4-trimethylpentan-3-ylamino, 1-(2,2-difluoroethylamino)-3,3-dimethyl-1-oxobutan-2-ylamino, 2-(carboxymethyl)propan-2-ylamino, 2-(N-methylcarboxamido)-propan-2-ylamino, 1-(3,3-difluoroazetidine-1-carbonyl)-cyclopropylamino, 4-hydroxy-2-methylpentan-2-ylamino, 1-(4-fluorophenyl)-2-methylpropan-2-ylamino, 2-cyclopropylpropan-2-ylamino, 2-methyl-1-(4-methylpiperazin-1-yl)propan-2-ylamino, 2-methyl-1-(4-methylpiperidin-1-yl)propan-2-yl, 2-(4-methoxyphenyl)propan-2-ylamino, 1-(2-hydroxyethylamino)-3,3-dimethyl-1-oxobutan-2-ylamino, 1-(5-isopropyl-1,3,4-oxadiazol-2-yl)-2,2-dimethylpropylamino, 1-(5-tert-butyl-1,3,4-oxadiazol-2-yl)-2,2-dimethylpropylamino, 1-(2-(hydroxymethyl)pyrrolidin-1-yl)-3,3-dimethyl-1-oxobutan-2-ylamino, 1-(3-methoxyazetidin-1-yl)-3,3-dimethyl-1-oxobutan-2-ylamino, 1-(3-methoxypyrrolidin-1-yl)-3,3-dimethyl-1-oxobutan-2-ylamino, 2-(carboxymethyl)-cyclopropan-2-ylamino, and 2-(N-methylcarboxamido)cyclopropan-2-ylamino, and 3-hydroxypyrrolidin-1-ylamino.

17. The method according to claim 1, wherein: $R_c$ is selected from the group consisting of phenyl, 2-hydroxyphenyl, 5-chloro-2-hydroxyphenyl, 5-bromo-2-fluorophenyl, 4-fluoro-2-hydroxyphenyl, 3-fluoro-2-methylphenyl, 2-aminophenyl, 2-chlorophenyl, 2-chloro-3-fluorophenyl, 3-fluoro-2-methoxyphenyl, 3,4-difluorophenyl, 2-bromo-4,5-difluoro-phenyl, 2,3,5-trifluorophenyl, 2,4,5-trifluorophenyl, 2,3,4-trifluorophenyl, 3-fluoro-4-(trifluoromethyl)phenyl, 4-fluoro-3-(trifluoromethyl)phenyl, 2-fluoro-4-(trifluoromethyl)phenyl, 3-fluoro-5-(trifluoromethyl)phenyl, 3-chloro-5-fluorophenyl, 2-chloro-4-(trifluoromethyl)-phenyl, 2-chloro-5-(trifluoromethyl)-phenyl, 3-chloro-4-(trifluoromethyl)-phenyl, 2,5-dichlorophenyl, 2,4-bis(trifluoromethyl)phenyl, 2,3,5-trichlorophenyl, 5-chloro-2,4-difluorophenyl, 5-chloro-2-fluoro-4-methylphenyl, 2-chloropyridin-4-yl, 2-chloro-pyridin-4-yl, 3-chloro-pyridin-4-yl, 2-chloro-2,4-bipyridin-4-yl, 4-chloro-pyridin-3-yl, 2-chloropyridin-3-yl, 2-fluoro-pyridin-3-yl, 6-oxo-1,6-dihydro-pyridin-3-yl, 5-chloro-2-fluoro-3-methylphenyl, 4-fluoro-2-methylphenyl, 2-methyl-4-(trifluoromethyl)phenyl, 2-chloro-5-fluoromethyl-phenyl, 2-hydroxy-3-trifluorophenyl, 2-chloro-5-cyanophenyl, 2-fluoro-5-cyanophenyl, 3-(thiazol-4-yl), 2-methylpyridin-4-yl, 4-methylpyridin-3-yl, 2-methylpyridin-3-yl, 2-isopropoxypyridin-3-yl, 3-o-tolyl, 4-(difluoro-methoxy)phenyl, 4-isopropoxyphenyl, 4,5-difluoro-2-methoxyphenyl, and 4,5-difluoro-2-isopropoxyphenyl.

18. The method according to claim 1, wherein the compound of formula I is selected from the group consisting of:
(S)-tert-butyl 1-(3,3-dimethyl-1-(methylamino)-1-oxobutan-2-ylcarbamoyl)-3-phenyl-5,6-dihydroimidazo[1,5-a]pyrazine-7(8H)-carboxylate;

(S)—N-(3,3-dimethyl-1-(methylamino)-1-oxobutan-2-yl)-3-phenyl-5,6,7,8-tetrahydro-imidazo[1,5-a]pyrazine-1-carboxamide;
(S)—N-(3,3-dimethyl-1-(methylamino)-1-oxobutan-2-yl)-3-(3-(trifluoromethyl)-phenyl)-5,6,7,8-tetrahydroimidazo[1,5-a]pyrazine-1-carboxamide;
(S)—N-(3,3-dimethyl-1-(methylamino)-1-oxobutan-2-yl)-3-(3-fluorophenyl)-5,6,7,8-tetrahydroimidazo[1,5-a]pyrazine-1-carboxamide;
(S)—N-(3,3-dimethyl-1-(methylamino)-1-oxobutan-2-yl)-3-(4-(trifluoromethyl)-phenyl)-5,6,7,8-tetrahydroimidazo[1,5-a]pyrazine-1-carboxamide;
(S)—N-(3,3-dimethyl-1-(methylamino)-1-oxobutan-2-yl)-3-(4-fluorophenyl)-5,6,7,8-tetrahydroimidazo[1,5-a]pyrazine-1-carboxamide;
(S)—N-(3,3-dimethyl-1-(methylamino)-1-oxobutan-2-yl)-3-(4-fluoro-3-methyl-phenyl)-5,6,7,8-tetrahydroimidazo[1,5-a]pyrazine-1-carboxamide;
(S)—N-(3,3-dimethyl-1-(methylamino)-1-oxobutan-2-yl)-3-m-tolyl-5,6,7,8-tetrahydro-imidazo[1,5-a]pyrazine-1-carboxamide;
(S)-3-(4-chlorophenyl)-N-(3,3-dimethyl-1-(methylamino)-1-oxobutan-2-yl)-5,6,7,8-tetrahydroimidazo[1,5-a]pyrazine-1-carboxamide;
(S)-3-(2-chlorophenyl)-N-(3,3-dimethyl-1-(methylamino)-1-oxobutan-2-yl)-5,6,7,8-tetrahydroimidazo[1,5-a]pyrazine-1-carboxamide;
(S)—N-(3,3-dimethyl-1-(methylamino)-1-oxobutan-2-yl)-3-(thiophen-3-yl)-5,6,7,8-tetrahydroimidazo[1,5-a]pyrazine-1-carboxamide;
(S)—N-(3,3-dimethyl-1-(methylamino)-1-oxobutan-2-yl)-3-(furan-3-yl)-5,6,7,8-tetrahydroimidazo[1,5-a]pyrazine-1-carboxamide;
(S)-3-benzyl-N-(3,3-dimethyl-1-(methylamino)-1-oxobutan-2-yl)-5,6,7,8-tetrahydroimidazo[1,5-a]pyrazine-1-carboxamide;
(S)—N-(3,3-dimethyl-1-(methylamino)-1-oxobutan-2-yl)-3-(pyridin-3-yl)-5,6,7,8-tetrahydroimidazo[1,5-a]pyrazine-1-carboxamide;
(S)—N-(3,3-dimethyl-1-(methylamino)-1-oxobutan-2-yl)-3-(furan-2-yl)-5,6,7,8-tetrahydroimidazo[1,5-a]pyrazine-1-carboxamide;
(S)—N-(3,3-dimethyl-1-(methylamino)-1-oxobutan-2-yl)-3-(thiophen-2-yl)-5,6,7,8-tetrahydroimidazo[1,5-a]pyrazine-1-carboxamide;
(S)—N-(3,3-dimethyl-1-(methylamino)-1-oxobutan-2-yl)-3-(1-methyl-1H-pyrazol-4-yl)-5,6,7,8-tetrahydroimidazo[1,5-a]pyrazine-1-carboxamide;
(S)-3-(3-chlorophenyl)-N-(3,3-dimethyl-1-(methylamino)-1-oxobutan-2-yl)-5,6,7,8-tetrahydroimidazo[1,5-a]pyrazine-1-carboxamide;
(S)—N-(3,3-dimethyl-1-(methylamino)-1-oxobutan-2-yl)-3-(pyrimidin-5-yl)-5,6,7,8-tetrahydroimidazo[1,5-a]pyrazine-1-carboxamide;
(S)-3-(benzo[b]thiophen-3-yl)-N-(3,3-dimethyl-1-(methylamino)-1-oxobutan-2-yl)-5,6,7,8-tetrahydroimidazo[1,5-a]pyrazine-1-carboxamide;
(S)—N-(3,3-dimethyl-1-(methylamino)-1-oxobutan-2-yl)-3-(4-methylthiophen-3-yl)-5,6,7,8-tetrahydroimidazo[1,5-a]pyrazine-1-carboxamide;
(S)—N-(1-hydroxy-3,3-dimethylbutan-2-yl)-3-phenyl-5,6,7,8-tetrahydroimidazo-[1,5-a]pyrazine-1-carboxamide;
(R)—N-(1-hydroxy-3,3-dimethylbutan-2-yl)-3-phenyl-5,6,7,8-tetrahydroimidazo-[1,5-a]pyrazine-1-carboxamide;

N-neopentyl-3-phenyl-5,6,7,8-tetrahydroimidazo[1,5-a]pyrazine-1-carboxamide, morpholino(3-phenyl-5,6,7,8-tetrahydroimidazo[1,5-a]pyrazin-1-yl)methanone;
(R)—N-(3,3-dimethylbutan-2-yl)-3-phenyl-5,6,7,8-tetrahydroimidazo[1,5-a]-pyrazine-1-carboxamide;
(S)—N-(3,3-dimethylbutan-2-yl)-3-phenyl-5,6,7,8-tetrahydroimidazo[1,5-a]-pyrazine-1-carboxamide;
(S)—N-(1-(methylamino)-1-oxopropan-2-yl)-3-phenyl-5,6,7,8-tetrahydroimidazo-[1,5-a]pyrazine-1-carboxamide;
N-(3-hydroxy-2,2-dimethylpropyl)-3-phenyl-5,6,7,8-tetrahydroimidazo[1,5-a]-pyrazine-1-carboxamide;
tert-butyl 3-phenyl-1-(1,3,3-trimethylbicyclo[2.2.1]heptan-2-ylcarbamoyl)-5,6-dihydroimidazo[1,5-a]pyrazine-7(8H)-carboxylate;
(S)-tert-butyl 3-phenyl-1-(1-phenylethylcarbamoyl)-5,6-dihydroimidazo[1,5a]pyrazine-7(8H)-carboxylate; tert-butyl 3-phenyl-1-(phenylcarbamoyl)-5,6-dihydroimidazo[1,5-a]pyrazine-7(8H)-carboxylate;
tert-butyl 3-(4-chlorophenyl)-1-(isopentylcarbamoyl)-5,6-dihydroimidazo[1,5-a]pyrazine-7(8H)-carboxylate;
(S)-tert-butyl 3-(4-chlorophenyl)-1-(1-hydroxy-3,3-dimethylbutan-2-ylcarbamoyl)-5,6-dihydroimidazo[1,5-a]pyrazine-7(8H)-carboxylate;
tert-butyl 3-phenyl-1-(piperidin-1-ylcarbamoyl)-5,6-dihydroimidazo[1,5-a]-pyrazine-7(8H)-carboxylate;
tert-butyl 1-(cyclohexylcarbamoyl)-3-phenyl-5,6-dihydroimidazo[1,5-a]pyrazine-7(8H)-carboxylate;
(R)-tert-butyl 1-(1-cyclohexylethylcarbamoyl)-3-phenyl-5,6-dihydroimidazo[1,5-a]pyrazine-7(8H)-carboxylate;
tert-butyl 3-phenyl-1-((tetrahydro-2H-pyran-4-yl)methylcarbamoyl)-5,6-dihydro-imidazo[1,5-a]pyrazine-7(8H)-carboxylate;
3-phenyl-N-(1,3,3-trimethylbicyclo[2.2.1]heptan-2-yl)-5,6,7,8-tetrahydroimidazo-[1,5-a]pyrazine-1-carboxamide;
(S)-3-phenyl-N-(1-phenylethyl)-5,6,7,8-tetrahydroimidazo[1,5-a]pyrazine-1-carboxamide;
N,3-diphenyl-5,6,7,8-tetrahydroimidazo[1,5-a]pyrazine-1-carboxamide,
3-(4-chlorophenyl)-N-isopentyl-5,6,7,8-tetrahydroimidazo[1,5-a]pyrazine-1-carboxamide;
(S)-3-(4-chlorophenyl)-N-(1-hydroxy-3,3-dimethylbutan-2-yl)-5,6,7,8-tetrahydroimidazo[1,5-a]pyrazine-1-carboxamide;
3-phenyl-N-(piperidin-1-yl)-5,6,7,8-tetrahydroimidazo[1,5-a]pyrazine-1-carboxamide;
(R)—N-(1-cyclohexylethyl)-3-phenyl-5,6,7,8-tetrahydroimidazo[1,5-a]pyrazine-1-carboxamide;
3-phenyl-N-((tetrahydro-2H-pyran-4-yl)methyl)-5,6,7,8-tetrahydroimidazo[1,5-a]-pyrazine-1-carboxamide;
N-cyclohexyl-3-phenyl-5,6,7,8-tetrahydroimidazo[1,5-a]pyrazine-1-carboxamide;
(S)—N-(3,3-dimethyl-1-(methylamino)-1-oxobutan-2-yl)-7-methyl-3-phenyl-5,6,7,8-tetrahydroimidazo[1,5-a]pyrazine-1-carboxamide;
(S)-3-(4-chlorophenyl)-N-(3,3-dimethyl-1-(methylamino)-1-oxobutan-2-yl)-7-methyl-5,6,7,8-tetrahydroimidazo[1,5-a]pyrazine-1-carboxamide;
(R)—N-(3,3-dimethylbutan-2-yl)-7-methyl-3-phenyl-5,6,7,8-tetrahydroimidazo-[1,5-a]pyrazine-1-carboxamide;
(S)—N-(3,3-dimethylbutan-2-yl)-7-methyl-3-phenyl-5,6,7,8-tetrahydroimidazo-[1,5-a]pyrazine-1-carboxamide;
(R)—N-(3,3-dimethylbutan-2-yl)-7-isobutyl-3-phenyl-5,6,7,8-tetrahydroimidazo-[1,5-a]pyrazine-1-carboxamide;
(S)—N-(3,3-dimethylbutan-2-yl)-7-isobutyl-3-phenyl-5,6,7,8-tetrahydroimidazo-[1,5-a]pyrazine-1-carboxamide;
(S)—N-(3,3-dimethyl-1-(methylamino)-1-oxobutan-2-yl)-7-(3,3-dimethylbutyl)-3-phenyl-5,6,7,8-tetrahydroimidazo[1,5-a]pyrazine-1-carboxamide;
(S)—N-(3,3-dimethyl-1-(methylamino)-1-oxobutan-2-yl)-7-neopentyl-3-phenyl-5,6,7,8-tetrahydroimidazo[1,5-a]pyrazine-1-carboxamide;
(S)-7-(cyclopropylmethyl)-N-(3,3-dimethyl-1-(methylamino)-1-oxobutan-2-yl)-3-phenyl-5,6,7,8-tetrahydroimidazo[1,5-a]pyrazine-1-carboxamide;
7-methyl-N-neopentyl-3-phenyl-5,6,7,8-tetrahydroimidazo[1,5-a]pyrazine-1-carboxamide;
7-isobutyl-N-neopentyl-3-phenyl-5,6,7,8-tetrahydroimidazo[1,5-a]pyrazine-1-carboxamide;
(S)—N-(1-hydroxy-3,3-dimethylbutan-2-yl)-7-methyl-3-phenyl-5,6,7,8-tetrahydro-imidazo[1,5-a]pyrazine-1-carboxamide;
(S)—N-(1-hydroxy-3,3-dimethylbutan-2-yl)-7-isobutyl-3-phenyl-5,6,7,8-tetrahydro-imidazo[1,5-a]pyrazine-1-carboxamide;
(S)-7-benzyl-N-(3,3-dimethyl-1-(methylamino)-1-oxobutan-2-yl)-3-phenyl-5,6,7,8-tetrahydroimidazo[1,5-a]pyrazine-1-carboxamide;
(S)—N-(3,3-dimethyl-1-(methylamino)-1-oxobutan-2-yl)-3-phenyl-7-(pyrimidin-5-ylmethyl)-5,6,7,8-tetrahydroimidazo[1,5-a]pyrazine-1-carboxamide;
(S)—N-(3,3-dimethyl-1-(methylamino)-1-oxobutan-2-yl)-3-phenyl-7-(pyridin-3-ylmethyl)-5,6,7,8-tetrahydroimidazo[1,5-a]pyrazine-1-carboxamide;
(S)—N-(3,3-dimethyl-1-(methylamino)-1-oxobutan-2-yl)-7-(furan-2-ylmethyl)-3-phenyl-5,6,7,8-tetrahydroimidazo[1,5-a]pyrazine-1-carboxamide;
(S)—N-(3,3-dimethyl-1-(methylamino)-1-oxobutan-2-yl)-7-((1-methyl-1H-pyrazol-5-yl)methyl)-3-phenyl-5,6,7,8-tetrahydroimidazo[1,5-a]pyrazine-1-carboxamide;
(S)—N-(3,3-dimethyl-1-(methylamino)-1-oxobutan-2-yl)-7-((1-methyl-1H-pyrazol-4-yl)methyl)-3-phenyl-5,6,7,8-tetrahydroimidazo[1,5-a]pyrazine-1-carboxamide;
(R)—N-(1-hydroxy-3,3-dimethylbutan-2-yl)-7-methyl-3-phenyl-5,6,7,8-tetrahydro-imidazo[1,5-a]pyrazine-1-carboxamide;
(R)—N-(1-hydroxy-3,3-dimethylbutan-2-yl)-7-isobutyl-3-phenyl-5,6,7,8-tetrahydro-imidazo[1,5-a]pyrazine-1-carboxamide;
(7-methyl-3-phenyl-5,6,7,8-tetrahydroimidazo[1,5-a]pyrazin-1-yl)(morpholino)-methanone;
(7-isobutyl-3-phenyl-5,6,7,8-tetrahydroimidazo[1,5-a]pyrazin-1-yl)(morpholino)-methanone;
(S)—N-(3,3-dimethyl-1-(methylamino)-1-oxobutan-2-yl)-7-((1-methyl-1H-pyrrol-2-yl)methyl)-3-phenyl-5,6,7,8-tetrahydroimidazo[1,5-a]pyrazine-1-carboxamide;
(S)—N-(3,3-dimethyl-1-(methylamino)-1-oxobutan-2-yl)-3-phenyl-7-(thiazol-2-ylmethyl)-5,6,7,8-tetrahydroimidazo[1,5-a]pyrazine-1-carboxamide;
(S)—N-(3,3-dimethyl-1-(methylamino)-1-oxobutan-2-yl)-7-methyl-3-(thiophen-3-yl)-5,6,7,8-tetrahydroimidazo[1,5-a]pyrazine-1-carboxamide;
(S)-7-(cyclopropylmethyl)-N-(3,3-dimethyl-1-(methylamino)-1-oxobutan-2-yl)-3-(thiophen-3-yl)-5,6,7,8-tetrahydroimidazo[1,5-a]pyrazine-1-carboxamide;
(S)-3-(benzo[b]thiophen-3-yl)-N-(3,3-dimethyl-1-(methylamino)-1-oxobutan-2-yl)-7-methyl-5,6,7,8-tetrahydroimidazo[1,5-a]pyrazine-1-carboxamide;

(S)—N-(3,3-dimethyl-1-(methylamino)-1-oxobutan-2-yl)-7-(pyrimidin-5-ylmethyl)-3-(thiophen-3-yl)-5,6,7,8-tetrahydroimidazo[1,5-a]pyrazine-1-carboxamide;

(S)—N-(1-(methylamino)-1-oxopropan-2-yl)-3-phenyl-7-(pyrimidin-5-ylmethyl)-5,6,7,8-tetrahydroimidazo[1,5-a]pyrazine-1-carboxamide;

(S)-7-methyl-N-(1-(methylamino)-1-oxopropan-2-yl)-3-phenyl-5,6,7,8-tetra-hydroimidazo[1,5-a]pyrazine-1-carboxamide;

(S)—N-(1-(dimethylamino)-3,3-dimethyl-1-oxobutan-2-yl)-7-methyl-3-phenyl-5,6,7,8-tetrahydroimidazo[1,5-a]pyrazine-1-carboxamide;

(S)—N-(1-(dimethylamino)-3,3-dimethyl-1-oxobutan-2-yl)-7-isobutyl-3-phenyl-5,6,7,8-tetrahydroimidazo[1,5-a]pyrazine-1-carboxamide;

(S)—N-(3,3-dimethyl-1-(methylamino)-1-oxobutan-2-yl)-7-methyl-3-(4-methyl-thiophen-3-yl)-5,6,7,8-tetrahydroimidazo[1,5-a]pyrazine-1-carboxamide;

N-(3-hydroxy-2,2-dimethylpropyl)-7-methyl-3-phenyl-5,6,7,8-tetrahydroimidazo-[1,5-a]pyrazine-1-carboxamide;

7-(cyclopropylmethyl)-N-(3-hydroxy-2,2-dimethylpropyl)-3-phenyl-5,6,7,8-tetra-hydroimidazo[1,5-a]pyrazine-1-carboxamide;

(S)-7-(cyclopropylmethyl)-N-(1-hydroxy-3,3-dimethylbutan-2-yl)-3-phenyl-5,6,7,8-tetrahydroimidazo[1,5-a]pyrazine-1-carboxamide;

(S)—N-(3,3-dimethyl-1-(methylamino)-1-oxobutan-2-yl)-7-isopropyl-3-phenyl-5,6,7,8-tetrahydroimidazo[1,5-a]pyrazine-1-carboxamide;

(S)-methyl 3,3-dimethyl-2-(7-methyl-3-phenyl-5,6,7,8-tetrahydroimidazo[1,5-a]pyrazine-1-carboxamido)butanoate;

(S)—N-(2,2-dimethyl-1-(3-methyl-1,2,4-oxadiazol-5-yl)propyl)-7-methyl-3-phenyl-5,6,7,8-tetrahydroimidazo[1,5-a]pyrazine-1-carboxamide;

(S)-7-(cyclopropylmethyl)-N-(2,2-dimethyl-1-(3-methyl-1,2,4-oxadiazol-5-yl)propyl)-3-phenyl-5,6,7,8-tetrahydroimidazo[1,5-a]pyrazine-1-carboxamide;

(S)—N-(2,2-dimethyl-1-(3-methyl-1,2,4-oxadiazol-5-yl)propyl)-7-isopropyl-3-phenyl-5,6,7,8-tetrahydroimidazo[1,5-a]pyrazine-1-carboxamide;

(S)—N-(2,2-dimethyl-1-(3-methyl-1,2,4-oxadiazol-5-yl)propyl)-7-isobutyl-3-phenyl-5,6,7,8-tetrahydroimidazo[1,5-a]pyrazine-1-carboxamide;

(S)—N-(3,3-dimethyl-1-(methylamino)-1-oxobutan-2-yl)-7-(ethylsulfonyl)-3-phenyl-5,6,7,8-tetrahydroimidazo[1,5-a]pyrazine-1-carboxamide;

(S)—N-(3,3-dimethyl-1-(methylamino)-1-oxobutan-2-yl)-7-(methylsulfonyl)-3-phenyl-5,6,7,8-tetrahydroimidazo[1,5-a]pyrazine-1-carboxamide;

(S)—N-(3,3-dimethyl-1-(methylamino)-1-oxobutan-2-yl)-7-(4-fluorophenyl-sulfonyl)-3-phenyl-5,6,7,8-tetrahydroimidazo[1,5-a]pyrazine-1-carboxamide;

(S)—N-(3,3-dimethyl-1-(methylamino)-1-oxobutan-2-yl)-7-(isopropylsulfonyl)-3-phenyl-5,6,7,8-tetrahydroimidazo[1,5-a]pyrazine-1-carboxamide;

(S)—N-(3,3-dimethyl-1-(methylamino)-1-oxobutan-2-yl)-7-(isobutylsulfonyl)-3-phenyl-5,6,7,8-tetrahydroimidazo[1,5-a]pyrazine-1-carboxamide;

(S)—N-(3,3-dimethyl-1-(methylamino)-1-oxobutan-2-yl)-3-phenyl-7-(phenyl-sulfonyl)-5,6,7,8-tetrahydroimidazo[1,5-a]pyrazine-1-carboxamide;

(S)—N-(3,3-dimethyl-1-(methylamino)-1-oxobutan-2-yl)-7-(2-nitrophenylsulfonyl)-3-phenyl-5,6,7,8-tetrahydroimidazo[1,5-a]pyrazine-1-carboxamide;

(S)—N-(3,3-dimethyl-1-(methylamino)-1-oxobutan-2-yl)-7-(2-fluorophenyl-sulfonyl)-3-phenyl-5,6,7,8-tetrahydroimidazo[1,5-a]pyrazine-1-carboxamide;

(S)—N-(3,3-dimethyl-1-(methylamino)-1-oxobutan-2-yl)-7-(3-fluorophenyl-sulfonyl)-3-phenyl-5,6,7,8-tetrahydroimidazo[1,5-a]pyrazine-1-carboxamide;

(S)-7-(cyclopropylsulfonyl)-N-(3,3-dimethyl-1-(methylamino)-1-oxobutan-2-yl)-3-phenyl-5,6,7,8-tetrahydroimidazo[1,5-a]pyrazine-1-carboxamide;

(S)-7-(4-fluorophenylsulfonyl)-N-(1-hydroxy-3,3-dimethylbutan-2-yl)-3-phenyl-5,6,7,8-tetrahydroimidazo[1,5-a]pyrazine-1-carboxamide;

(S)—N-(1-hydroxy-3,3-dimethylbutan-2-yl)-3-phenyl-7-(phenylsulfonyl)-5,6,7,8-tetrahydroimidazo[1,5-a]pyrazine-1-carboxamide;

7-(4-fluorophenylsulfonyl)-N-neopentyl-3-phenyl-5,6,7,8-tetrahydroimidazo[1,5-a]-pyrazine-1-carboxamide;

N-neopentyl-3-phenyl-7-(phenylsulfonyl)-5,6,7,8-tetrahydroimidazo[1,5-a]-pyrazine-1-carboxamide;

(7-(4-fluorophenylsulfonyl)-3-phenyl-5,6,7,8-tetrahydroimidazo[1,5-a]pyrazin-1-yl)(morpholino)methanone;

(S)-7-(4-chlorophenylsulfonyl)-N-(3,3-dimethyl-1-(methylamino)-1-oxobutan-2-yl)-3-phenyl-5,6,7,8-tetrahydroimidazo[1,5-a]pyrazine-1-carboxamide;

(S)—N-(3,3-dimethyl-1-(methylamino)-1-oxobutan-2-yl)-3-phenyl-7-(4-(trifluoro-methyl)phenylsulfonyl)-5,6,7,8-tetrahydroimidazo[1,5-a]pyrazine-1-carboxamide;

(S)-7-(4-cyanophenylsulfonyl)-N-(3,3-dimethyl-1-(methylamino)-1-oxobutan-2-yl)-3-phenyl-5,6,7,8-tetrahydroimidazo[1,5-a]pyrazine-1-carboxamide;

(S)—N-(3,3-dimethyl-1-(methylamino)-1-oxobutan-2-yl)-7-(4-fluorophenyl-sulfonyl)-3-(thiophen-3-yl)-5,6,7,8-tetrahydroimidazo[1,5-a]pyrazine-1-carboxamide;

(S)-7-(4-fluorophenylsulfonyl)-N-(1-(methylamino)-1-oxopropan-2-yl)-3-phenyl-5,6,7,8-tetrahydroimidazo[1,5-a]pyrazine-1-carboxamide;

(R)—N-(1-cyclohexylethyl)-7-(ethylsulfonyl)-3-phenyl-5,6,7,8-tetrahydroimidazo-[1,5-a]pyrazine-1-carboxamide;

7-(ethylsulfonyl)-3-phenyl-N-(1,3,3-trimethylbicyclo[2.2.1]heptan-2-yl)-5,6,7,8-tetrahydroimidazo[1,5-a]pyrazine-1-carboxamide;

(S)-7-(ethylsulfonyl)-3-phenyl-N-(1-phenylethyl)-5,6,7,8-tetrahydroimidazo[1,5-a]-pyrazine-1-carboxamide 7-(ethylsulfonyl)-N,3-diphenyl-5,6,7,8-tetrahydroimidazo[1,5-a]pyrazine-1-carboxamide;

7-(ethylsulfonyl)-3-phenyl-N-(piperidin-1-yl)-5,6,7,8-tetrahydroimidazo[1,5-a]-pyrazine-1-carboxamide;

3-(4-chlorophenyl)-7-(ethylsulfonyl)-N-isopentyl-5,6,7,8-tetrahydroimidazo[1,5-a]-pyrazine-1-carboxamide;

7-(ethylsulfonyl)-3-phenyl-N-((tetrahydro-2H-pyran-4-yl)methyl)-5,6,7,8-tetrahydro-imidazo[1,5-a]pyrazine-1-carboxamide;

N-cyclohexyl-7-(ethylsulfonyl)-3-phenyl-5,6,7,8-tetrahydroimidazo[1,5-a]-pyrazine-1-carboxamide;

7-(cyclopropanecarbonyl)-3-phenyl-N-(1,3,3-trimethylbicyclo[2.2.1]heptan-2-yl)-5,6,7,8-tetrahydroimidazo[1,5-a]pyrazine-1-carboxamide;

7-benzoyl-3-phenyl-N-(1,3,3-trimethylbicyclo[2.2.1]heptan-2-yl)-5,6,7,8-tetrahydro-imidazo[1,5-a]pyrazine-1-carboxamide;

3-phenyl-7-(tetrahydrofuran-3-carbonyl)-N-(1,3,3-trimethylbicyclo[2.2.1]heptan-2-yl)-5,6,7,8-tetrahydroimidazo[1,5-a]pyrazine-1-carboxamide;

7-(furan-2-carbonyl)-3-phenyl-N-(1,3,3-trimethylbicyclo[2.2.1]heptan-2-yl)-5,6,7,8-tetrahydroimidazo[1,5-a]pyrazine-1-carboxamide;
3-phenyl-7-pivaloyl-N-(1,3,3-trimethylbicyclo[2.2.1]heptan-2-yl)-5,6,7,8-tetrahydro-imidazo[1,5-a]pyrazine-1-carboxamide;
(S)-7-(cyclopropanecarbonyl)-3-phenyl-N-(1-phenylethyl)-5,6,7,8-tetrahydro-imidazo[1,5-a]pyrazine-1-carboxamide;
(S)-7-benzoyl-3-phenyl-N-(1-phenylethyl)-5,6,7,8-tetrahydroimidazo[1,5-a]-pyrazine-1-carboxamide;
(S)-7-(cyclopropanecarbonyl)-N-(3,3-dimethyl-1-(methylamino)-1-oxobutan-2-yl)-3-phenyl-5,6,7,8-tetrahydroimidazo[1,5-a]pyrazine-1-carboxamide;
(S)-7-benzoyl-N-(3,3-dimethyl-1-(methylamino)-1-oxobutan-2-yl)-3-phenyl-5,6,7,8-tetrahydroimidazo[1,5-a]pyrazine-1-carboxamide;
(S)—N-(3,3-dimethyl-1-(methylamino)-1-oxobutan-2-yl)-7-(furan-2-carbonyl)-3-phenyl-5,6,7,8-tetrahydroimidazo[1,5-a]pyrazine-1-carboxamide;
7-(cyclopropanecarbonyl)-N,3-diphenyl-5,6,7,8-tetrahydroimidazo[1,5-a]pyrazine-1-carboxamide;
7-benzoyl-3-(4-chlorophenyl)-N-isopentyl-5,6,7,8-tetrahydroimidazo[1,5-a]-pyrazine-1-carboxamide;
3-(4-chlorophenyl)-7-(cyclopropanecarbonyl)-N-isopentyl-5,6,7,8-tetrahydro-imidazo[1,5-a]pyrazine-1-carboxamide;
(R)—N-(1-cyclohexylethyl)-7-(cyclopropanecarbonyl)-3-phenyl-5,6,7,8-tetra-hydroimidazo[1,5-a]pyrazine-1-carboxamide;
(R)—N-(1-cyclohexylethyl)-3-phenyl-7-pivaloyl-5,6,7,8-tetrahydroimidazo[1,5-a]-pyrazine-1-carboxamide;
7-(cyclopropanecarbonyl)-3-phenyl-N-((tetrahydro-2H-pyran-4-yl)methyl)-5,6,7,8-tetrahydroimidazo[1,5-a]pyrazine-1-carboxamide;
3-phenyl-N-((tetrahydro-2H-pyran-4-yl)methyl)-7-(tetrahydrofuran-3-carbonyl)-5,6,7,8-tetrahydroimidazo[1,5-a]pyrazine-1-carboxamide;
N-cyclohexyl-7-(cyclopropanecarbonyl)-3-phenyl-5,6,7,8-tetrahydroimidazo[1,5-a]-pyrazine-1-carboxamide;
N-cyclohexyl-3-phenyl-7-pivaloyl-5,6,7,8-tetrahydroimidazo[1,5-a]pyrazine-1-carboxamide;
N-cyclohexyl-7-(furan-3-carbonyl)-3-phenyl-5,6,7,8-tetrahydroimidazo[1,5-a]-pyrazine-1-carboxamide;
N—((R)-1-cyclohexylethyl)-3-phenyl-7-(tetrahydrofuran-3-carbonyl)-5,6,7,8-tetrahydroimidazo[1,5-a]pyrazine-1-carboxamide;
(R)—N-(1-cyclohexylethyl)-7-(2-hydroxyethyl)-3-phenyl-5,6,7,8-tetrahydroimidazo-[1,5-a]pyrazine-1-carboxamide;
N-cyclohexyl-3-phenyl-7-((tetrahydrofuran-3-yl)methyl)-5,6,7,8-tetrahydroimidazo-[1,5-a]pyrazine-1-carboxamide;
7-isobutyl-3-phenyl-N-(1,3,3-trimethylbicyclo[2.2.1]heptan-2-yl)-5,6,7,8-tetrahydro-imidazo[1,5-a]pyrazine-1-carboxamide;
7-(2-hydroxyethyl)-3-phenyl-N-(1,3,3-trimethylbicyclo[2.2.1]heptan-2-yl)-5,6,7,8-tetrahydroimidazo[1,5-a]pyrazine-1-carboxamide;
7-ethyl-3-phenyl-N-(1,3,3-trimethylbicyclo[2.2.1]heptan-2-yl)-5,6,7,8-tetrahydro-imidazo[1,5-a]pyrazine-1-carboxamide;
(S)-7-isobutyl-3-phenyl-N-(1-phenylethyl)-5,6,7,8-tetrahydroimidazo[1,5-a]-pyrazine-1-carboxamide;
(S)-7-(2-hydroxyethyl)-3-phenyl-N-(1-phenylethyl)-5,6,7,8-tetrahydroimidazo-[1,5-a]pyrazine-1-carboxamide;
(S)-7-ethyl-3-phenyl-N-(1-phenylethyl)-5,6,7,8-tetrahydroimidazo[1,5-a]pyrazine-1-carboxamide;
(S)—N-(3,3-dimethyl-1-(methylamino)-1-oxobutan-2-yl)-7-isobutyl-3-phenyl-5,6,7,8-tetrahydroimidazo[1,5-a]pyrazine-1-carboxamide;
(S)—N-(3,3-dimethyl-1-(methylamino)-1-oxobutan-2-yl)-7-ethyl-3-phenyl-5,6,7,8-tetrahydroimidazo[1,5-a]pyrazine-1-carboxamide;
7-isobutyl-N,3-diphenyl-5,6,7,8-tetrahydroimidazo[1,5-a]pyrazine-1-carboxamide;
7-(2-hydroxyethyl)-N,3-diphenyl-5,6,7,8-tetrahydroimidazo[1,5-a]pyrazine-1-carboxamide;
7-ethyl-N,3-diphenyl-5,6,7,8-tetrahydroimidazo[1,5-a]pyrazine-1-carboxamide;
(S)—N-(3,3-dimethyl-1-(methylamino)-1-oxobutan-2-yl)-7-(2-hydroxyethyl)-3-phenyl-5,6,7,8-tetrahydroimidazo[1,5-a]pyrazine-1-carboxamide;
N,3-diphenyl-7-propyl-5,6,7,8-tetrahydroimidazo[1,5-a]pyrazine-1-carboxamide;
7-isobutyl-3-phenyl-N-(piperidin-1-yl)-5,6,7,8-tetrahydroimidazo[1,5-a]pyrazine-1-carboxamide;
7-(2-hydroxyethyl)-3-phenyl-N-(piperidin-1-yl)-5,6,7,8-tetrahydroimidazo[1,5-a]-pyrazine-1-carboxamide;
3-(4-chlorophenyl)-7-isobutyl-N-isopentyl-5,6,7,8-tetrahydroimidazo[1,5-a]-pyrazine-1-carboxamide;
3-(4-chlorophenyl)-7-ethyl-N-isopentyl-5,6,7,8-tetrahydroimidazo[1,5-a]pyrazine-1-carboxamide;
3-(4-chlorophenyl)-7-(2-hydroxyethyl)-N-isopentyl-5,6,7,8-tetrahydroimidazo[1,5-a]-pyrazine-1-carboxamide;
(S)-3-(4-chlorophenyl)-N-(1-hydroxy-3,3-dimethylbutan-2-yl)-7-isobutyl-5,6,7,8-tetrahydroimidazo[1,5-a]pyrazine-1-carboxamide;
(S)-3-(4-chlorophenyl)-7-ethyl-N-(1-hydroxy-3,3-dimethylbutan-2-yl)-5,6,7,8-tetrahydroimidazo[1,5-a]pyrazine-1-carboxamide;
(S)-3-(4-chlorophenyl)-N-(1-hydroxy-3,3-dimethylbutan-2-yl)-7-(2-hydroxyethyl)-5,6,7,8-tetrahydroimidazo[1,5-a]pyrazine-1-carboxamide;
(R)—N-(1-cyclohexylethyl)-7-isobutyl-3-phenyl-5,6,7,8-tetrahydroimidazo[1,5-a]-pyrazine-1-carboxamide;
(R)—N-(1-cyclohexylethyl)-7-ethyl-3-phenyl-5,6,7,8-tetrahydroimidazo[1,5-a]-pyrazine-1-carboxamide;
N-cyclohexyl-7-isobutyl-3-phenyl-5,6,7,8-tetrahydroimidazo[1,5-a]-pyrazine-1-carboxamide;
N-cyclohexyl-7-(2-hydroxyethyl)-3-phenyl-5,6,7,8-tetrahydroimidazo[1,5-a]-pyrazine-1-carboxamide;
7-isobutyl-3-phenyl-N-((tetrahydro-2H-pyran-4-yl)methyl)-5,6,7,8-tetrahydro-imidazo[1,5-a]pyrazine-1-carboxamide;
7-ethyl-3-phenyl-N-((tetrahydro-2H-pyran-4-yl)methyl)-5,6,7,8-tetrahydro-imidazo[1,5-a]pyrazine-1-carboxamide;
7-(2-hydroxyethyl)-3-phenyl-N-((tetrahydro-2H-pyran-4-yl)methyl)-5,6,7,8-tetrahydroimidazo[1,5-a]pyrazine-1-carboxamide;
(R)-7-acetyl-N-(1-cyclohexylethyl)-3-phenyl-5,6,7,8-tetrahydroimidazo[1,5-a]-pyrazine-1-carboxamide;
N7-isopropyl-3-phenyl-N-(1,3,3-trimethylbicyclo[2.2.1]heptan-2-yl)-5,6-dihydro-imidazo[1,5-a]pyrazine-1,7(8H)-dicarboxamide;
(S)-7-acetyl-3-phenyl-N-(1-phenylethyl)-5,6,7,8-tetrahydroimidazo[1,5-a]-pyrazine-1-carboxamide;
7-acetyl-N,3-diphenyl-5,6,7,8-tetrahydroimidazo[1,5-a]pyrazine-1-carboxamide;
(S)-7-acetyl-N-(3,3-dimethyl-1-(methylamino)-1-oxobutan-2-yl)-3-phenyl-5,6,7,8-tetrahydroimidazo[1,5-a]pyrazine-1-carboxamide;

7-acetyl-3-phenyl-N-(piperidin-1-yl)-5,6,7,8-tetrahydroimidazo[1,5-a]pyrazine-1-carboxamide;
7-acetyl-3-phenyl-N-((tetrahydro-2H-pyran-4-yl)methyl)-5,6,7,8-tetrahydro-imidazo[1,5-a]pyrazine-1-carboxamide;
7-acetyl-N-cyclohexyl-3-phenyl-5,6,7,8-tetrahydroimidazo[1,5-a]pyrazine-1-carboxamide;
methyl 3-phenyl-1-(1,3,3-trimethylbicyclo[2.2.1]heptan-2-ylcarbamoyl)-5,6-dihydroimidazo[1,5-a]pyrazine-7(8H)-carboxylate;
(S)-methyl 3-phenyl-1-(1-phenylethylcarbamoyl)-5,6-dihydroimidazo[1,5-a]-pyrazine-7(8H)-carboxylate;
(S)-methyl 1-(3,3-dimethyl-1-(methylamino)-1-oxobutan-2-ylcarbamoyl)-3-phenyl-5,6-dihydroimidazo[1,5-a]pyrazine-7(8H)-carboxylate;
methyl 3-phenyl-1-(phenylcarbamoyl)-5,6-dihydroimidazo[1,5-a]pyrazine-7(8H)-carboxylate;
methyl 3-phenyl-1-(piperidin-1-ylcarbamoyl)-5,6-dihydroimidazo[1,5-a]pyrazine-7(8H)-carboxylate;
methyl 3-(4-chlorophenyl)-1-(isopentylcarbamoyl)-5,6-dihydroimidazo[1,5-a]-pyrazine-7(8H)-carboxylate;
(S)-methyl 3-(4-chlorophenyl)-1-(1-hydroxy-3,3-dimethylbutan-2-ylcarbamoyl)-5,6-dihydroimidazo[1,5-a]pyrazine-7(8H)-carboxylate;
(R)-methyl 1-(1-cyclohexylethylcarbamoyl)-3-phenyl-5,6-dihydroimidazo[1,5-a]-pyrazine-7(8H)-carboxylate;
methyl 3-phenyl-1-((tetrahydro-2H-pyran-4-yl)methylcarbamoyl)-5,6-dihydro-imidazo[1,5-a]pyrazine-7(8H)-carboxylate;
methyl 1-(cyclohexylcarbamoyl)-3-phenyl-5,6-dihydroimidazo[1,5-a]pyrazine-7(8H)-carboxylate;
(S)—N-(3,3-dimethyl-1-(methylamino)-1-oxobutan-2-yl)-7-(3,3-dimethylbutanoyl)-3-phenyl-5,6,7,8-tetrahydroimidazo[1,5-a]pyrazine-1-carboxamide;
(S)—N-(3,3-dimethyl-1-(methylamino)-1-oxobutan-2-yl)-3-phenyl-7-propionyl-5,6,7,8-tetrahydroimidazo[1,5-a]pyrazine-1-carboxamide;
(S)—N-(3,3-dimethyl-1-(methylamino)-1-oxobutan-2-yl)-3-phenyl-7-pivaloyl-5,6,7,8-tetrahydroimidazo[1,5-a]pyrazine-1-carboxamide;
(S)—N-(3,3-dimethyl-1-(methylamino)-1-oxobutan-2-yl)-7-isobutyryl-3-phenyl-5,6,7,8-tetrahydroimidazo[1,5-a]pyrazine-1-carboxamide;
(S)—N-7-tert-butyl-N-1-(3,3-dimethyl-1-(methylamino)-1-oxobutan-2-yl)-3-phenyl-5,6-dihydroimidazo[1,5-a]pyrazine-1,7(8H)-dicarboxamide;
(S)—N1-(3,3-dimethyl-1-(methylamino)-1-oxobutan-2-yl)-3-phenyl-N-7-propyl-5,6-dihydroimidazo[1,5-a]pyrazine-1,7(8H)-dicarboxamide;
(S)—N1-(3,3-dimethyl-1-(methylamino)-1-oxobutan-2-yl)-N7,3-diphenyl-5,6-dihydroimidazo[1,5-a]pyrazine-1,7(8H)-dicarboxamide;
(S)—N-(3,3-dimethyl-1-(methylamino)-1-oxobutan-2-yl)-3-phenyl-7-(propyl-carbamothioyl)-5,6,7,8-tetrahydroimidazo[1,5-a]pyrazine-1-carboxamide;
(S)—N-(1-(dimethylamino)-3,3-dimethyl-1-oxobutan-2-yl)-3-phenyl-5,6,7,8-tetrahydroimidazo[1,5-a]pyrazine-1-carboxamide;
(S)-7-cyclopropyl-N-(3,3-dimethyl-1-(methylamino)-1-oxobutan-2-yl)-3-phenyl-5,6,7,8-tetrahydroimidazo[1,5-a]pyrazine-1-carboxamide;
(S)-7-cyclopropyl-N-(2,2-dimethyl-1-(3-methyl-1,2,4-oxadiazol-5-yl)propyl)-3-phenyl-5,6,7,8-tetrahydroimidazo[1,5-a]pyrazine-1-carboxamide;
(S)-8-cyclopropyl-N-(3,3-dimethyl-1-(methylamino)-1-oxobutan-2-yl)-3-phenyl-6,7,8,9-tetrahydro-5H-imidazo[1,5-a][1,4]diazepine-1-carboxamide;
(S)—N-(2,2-dimethyl-1-(5-methyl-1,3,4-oxadiazol-2-yl)propyl)-3-phenyl-5,6,7,8-tetrahydroimidazo[1,5-a]pyrazine-1-carboxamide;
(S)—N-(2,2-dimethyl-1-(5-methyl-1,3,4-oxadiazol-2-yl)propyl)-7-methyl-3-phenyl-5,6,7,8-tetrahydroimidazo[1,5-a]pyrazine-1-carboxamide;
(S)—N-(2,2-dimethyl-1-(5-methyl-1,3,4-oxadiazol-2-yl)propyl)-7-isobutyl-3-phenyl-5,6,7,8-tetrahydroimidazo[1,5-a]pyrazine-1-carboxamide;
(S)-3-bromo-N-(3,3-dimethyl-1-(methylamino)-1-oxobutan-2-yl)-7-methyl-5,6,7,8-tetrahydroimidazo[1,5-a]pyrazine-1-carboxamide;
(S)—N-(3,3-dimethyl-1-(methylamino)-1-oxobutan-2-yl)-7-methyl-3-(phenyl-ethynyl)-5,6,7,8-tetrahydroimidazo[1,5-a]pyrazine-1-carboxamide;
(S)—N-(3,3-dimethyl-1-(methylamino)-1-oxobutan-2-yl)-7-methyl-3-(pyridin-3-ylethynyl)-5,6,7,8-tetrahydroimidazo[1,5-a]pyrazine-1-carboxamide;
(S)-7-methyl-N-(3-methyl-1-(methylamino)-1-oxobutan-2-yl)-3-phenyl-5,6,7,8-tetrahydroimidazo[1,5-a]pyrazine-1-carboxamide;
(S)-7-methyl-N-(2-(methylamino)-2-oxo-1-phenylethyl)-3-phenyl-5,6,7,8-tetra-hydroimidazo[1,5-a]pyrazine-1-carboxamide;
3-(4-chloro-2-fluorophenyl)-7-methyl-N-(4-sulfamoylphenyl)-5,6,7,8-tetrahydro-imidazo[1,5-a]pyrazine-1-carboxamide;
tert-butyl 4-(3-(4-chloro-2-fluorophenyl)-7-methyl-5,6,7,8-tetrahydroimidazo-[1,5-a]pyrazine-1-carboxamido)piperidine-1-carboxylate;
(4-benzoylpiperazin-1-yl)(3-(4-chloro-2-fluorophenyl)-7-methyl-5,6,7,8-tetrahydro-imidazo[1,5-a]pyrazin-1-yl)methanone;
(3-(4-chloro-2-fluorophenyl)-7-methyl-5,6,7,8-tetrahydroimidazo[1,5-a]pyrazin-1-yl)(4-(pyrimidin-2-yl)piperazin-1-yl)methanone;
5-chloro-1-(1-(3-(4-chloro-2-fluorophenyl)-7-methyl-5,6,7,8-tetrahydro-imidazo[1,5-a]pyrazine-1-carbonyl)piperidin-4-yl)-1H-benzo[d]imidazol-2(3H)-one;
3-(4-chloro-2-fluorophenyl)-7-methyl-N-(1-(methylsulfonyl)piperidin-4-yl)-5,6,7,8-tetrahydroimidazo[1,5-a]pyrazine-1-carboxamide;
8-(3-(4-chloro-2-fluorophenyl)-7-methyl-5,6,7,8-tetrahydroimidazo[1,5-a]-pyrazine-1-carbonyl)-1-phenyl-1,3,8-triazaspiro[4.5]decan-4-one;
1-(1-(3-(4-chloro-2-fluorophenyl)-7-methyl-5,6,7,8-tetrahydroimidazo[1,5-a]-pyrazine-1-carbonyl)piperidin-4-yl)-1H-benzo[d]imidazol-2(3H)-one;
3-(4-chloro-2-fluorophenyl)-7-methyl-N-(3-(methylcarbamoyl)phenyl)-5,6,7,8-tetrahydroimidazo[1,5-a]pyrazine-1-carboxamide;
3-(4-chloro-2-fluorophenyl)-7-methyl-N-(2-(methylcarbamoyl)phenyl)-5,6,7,8-tetrahydroimidazo[1,5-a]pyrazine-1-carboxamide;
3-(4-chloro-2-fluorophenyl)-7-methyl-N-(4-(methylcarbamoyl)phenyl)-5,6,7,8-tetrahydroimidazo[1,5-a]pyrazine-1-carboxamide;
3-(4-chloro-2-fluorophenyl)-7-methyl-N-(4-(morpholinosulfonyl)phenyl)-5,6,7,8-tetrahydroimidazo[1,5-a]pyrazine-1-carboxamide;
8-(3-(4-chloro-2-fluorophenyl)-7-methyl-5,6,7,8-tetrahydroimidazo[1,5-a]-pyrazine-1-carbonyl)-2,8-diazaspiro[4.5]decan-1-one;
8-(3-(4-chloro-2-fluorophenyl)-7-methyl-5,6,7,8-tetrahydroimidazo[1,5-a]-pyrazine-1-carbonyl)-2-methyl-2,8-diazaspiro[4.5]decan-1-one;

1-(1-(3-(4-chloro-2-fluorophenyl)-7-methyl-5,6,7,8-tetrahydroimidazo[1,5-a]-pyrazine-1-carbonyl)piperidin-4-yl)indolin-2-one;

(3-(4-chloro-2-fluorophenyl)-7-methyl-5,6,7,8-tetrahydroimidazo[1,5-a]pyrazin-1-yl)(4-(3,5-dimethyl-4H-1,2,4-triazol-4-yl)piperidin-1-yl)methanone;

methyl 3-((3-(4-chloro-2-fluorophenyl)-7-methyl-5,6,7,8-tetrahydroimidazo[1,5-a]-pyrazine-1-carboxamido)methyl)benzoate;

1-(3-(4-chloro-2-fluorophenyl)-7-methyl-5,6,7,8-tetrahydroimidazo[1,5-a]-pyrazine-1-carbonyl)-4-morpholinopiperidine-4-carboxamide.

(3-(4-chloro-2-fluorophenyl)-7-methyl-5,6,7,8-tetrahydroimidazo[1,5-a]pyrazin-1-yl)(4-(morpholine-4-carbonyl)piperidin-1-yl)methanone;

1-(1-(3-(4-chloro-2-fluorophenyl)-7-methyl-5,6,7,8-tetrahydroimidazo[1,5-a]-pyrazine-1-carbonyl)piperidin-4-yl)-4-phenyl-1H-imidazol-2(3H)-one;

3-(4-chloro-2-fluorophenyl)-7-methyl-N-((2-oxo-2,3-dihydro-1H-benzo-[d]imidazol-5-yl)methyl)-5,6,7,8-tetrahydroimidazo[1,5-a]pyrazine-1-carboxamide;

N-(3-hydroxypropyl)-7-methyl-3-phenyl-5,6,7,8-tetrahydroimidazo[1,5-a]-pyrazine-1-carboxamide;

N-(1-hydroxy-2-methylpropan-2-yl)-7-methyl-3-phenyl-5,6,7,8-tetrahydro-imidazo[1,5-a]pyrazine-1-carboxamide;

N-(1-hydroxypropan-2-yl)-7-methyl-3-phenyl-5,6,7,8-tetrahydroimidazo[1,5-a]-pyrazine-1-carboxamide;

N-(1-hydroxybutan-2-yl)-7-methyl-3-phenyl-5,6,7,8-tetrahydroimidazo[1,5-a]-pyrazine-1-carboxamide;

N-(1-hydroxypentan-2-yl)-7-methyl-3-phenyl-5,6,7,8-tetrahydroimidazo[1,5-a]-pyrazine-1-carboxamide;

N-((1,3-dioxolan-2-yl)methyl)-7-methyl-3-phenyl-5,6,7,8-tetrahydroimidazo[1,5-a]-pyrazine-1-carboxamide;

N-(1-(hydroxymethyl)cyclopentyl)-7-methyl-3-phenyl-5,6,7,8-tetrahydroimidazo-[1,5-a]pyrazine-1-carboxamide;

7-methyl-3-phenyl-N-((tetrahydro-2H-pyran-4-yl)methyl)-5,6,7,8-tetrahydro-imidazo[1,5-a]pyrazine-1-carboxamide;

7-methyl-N-((5-methylpyrazin-2-yl)methyl)-3-phenyl-5,6,7,8-tetrahydro-imidazo[1,5-a]pyrazine-1-carboxamide;

(S)-3-cyclopentenyl-N-(3,3-dimethyl-1-(methylamino)-1-oxobutan-2-yl)-7-methyl-5,6,7,8-tetrahydroimidazo[1,5-a]pyrazine-1-carboxamide;

(S)—N-(3,3-dimethyl-1-(methylamino)-1-oxobutan-2-yl)-7-methyl-3-(pyrimidin-5-yl)-5,6,7,8-tetrahydroimidazo[1,5-a]pyrazine-1-carboxamide;

(S)—N-(3,3-dimethyl-1-(methylamino)-1-oxobutan-2-yl)-3-(3-fluoro-4-methyl-phenyl)-7-methyl-5,6,7,8-tetrahydroimidazo[1,5-a]pyrazine-1-carboxamide;

(S)-3-(4-chloro-2-fluorophenyl)-N-(3,3-dimethyl-1-(methylamino)-1-oxobutan-2-yl)-7-methyl-5,6,7,8-tetrahydroimidazo[1,5-a]pyrazine-1-carboxamide;

(S)—N-(3,3-dimethyl-1-(methylamino)-1-oxobutan-2-yl)-7-methyl-3-(quinolin-8-yl)-5,6,7,8-tetrahydroimidazo[1,5-a]pyrazine-1-carboxamide;

(S,E)-N-(3,3-dimethyl-1-(methylamino)-1-oxobutan-2-yl)-7-methyl-3-(prop-1-enyl)-5,6,7,8-tetrahydroimidazo[1,5-a]pyrazine-1-carboxamide;

(S)—N-(3,3-dimethyl-1-(methylamino)-1-oxobutan-2-yl)-3-(3-fluorophenyl)-7-methyl-5,6,7,8-tetrahydroimidazo[1,5-a]pyrazine-1-carboxamide;

(S)—N-(3,3-dimethyl-1-(methylamino)-1-oxobutan-2-yl)-3-(2-fluoro-5-(trifluoromethyl)phenyl)-7-methyl-5,6,7,8-tetrahydroimidazo[1,5-a]pyrazine-1-carboxamide;

(S)-3-(5-chloro-2-fluorophenyl)-N-(3,3-dimethyl-1-(methylamino)-1-oxobutan-2-yl)-7-methyl-5,6,7,8-tetrahydroimidazo[1,5-a]pyrazine-1-carboxamide;

(S)—N-(3,3-dimethyl-1-(methylamino)-1-oxobutan-2-yl)-3-(4-fluorophenyl)-7-methyl-5,6,7,8-tetrahydroimidazo[1,5-a]pyrazine-1-carboxamide;

(S)-3-(2,4-difluorophenyl)-N-(3,3-dimethyl-1-(methylamino)-1-oxobutan-2-yl)-7-methyl-5,6,7,8-tetrahydroimidazo[1,5-a]pyrazine-1-carboxamide;

(S)—N-(3,3-dimethyl-1-(methylamino)-1-oxobutan-2-yl)-3-(2-fluoro-4-methylphenyl)-7-methyl-5,6,7,8-tetrahydroimidazo[1,5-a]pyrazine-1-carboxamide;

(S)-3-(2,5-difluorophenyl)-N-(3,3-dimethyl-1-(methylamino)-1-oxobutan-2-yl)-7-methyl-5,6,7,8-tetrahydroimidazo[1,5-a]pyrazine-1-carboxamide;

(S)—N-(3,3-dimethyl-1-(methylamino)-1-oxobutan-2-yl)-3-(2-fluoro-5-methyl-phenyl)-7-methyl-5,6,7,8-tetrahydroimidazo[1,5-a]pyrazine-1-carboxamide;

(S)—N-(3,3-dimethyl-1-(methylamino)-1-oxobutan-2-yl)-7-methyl-3-(pyridin-3-yl)-5,6,7,8-tetrahydroimidazo[1,5-a]pyrazine-1-carboxamide;

(S)-3-(2-chlorophenyl)-N-(3,3-dimethyl-1-(methylamino)-1-oxobutan-2-yl)-7-methyl-5,6,7,8-tetrahydroimidazo[1,5-a]pyrazine-1-carboxamide;

(S)-3-(4-cyanophenyl)-N-(3,3-dimethyl-1-(methylamino)-1-oxobutan-2-yl)-7-methyl-5,6,7,8-tetrahydroimidazo[1,5-a]pyrazine-1-carboxamide;

(S)—N-(3,3-dimethyl-1-(methylamino)-1-oxobutan-2-yl)-7-methyl-3-(2-(trifluoro-methyl)phenyl)-5,6,7,8-tetrahydroimidazo[1,5-a]pyrazine-1-carboxamide;

(S)-3-cyclohexenyl-N-(3,3-dimethyl-1-(methylamino)-1-oxobutan-2-yl)-7-methyl-5,6,7,8-tetrahydroimidazo[1,5-a]pyrazine-1-carboxamide;

(S)—N-(3,3-dimethyl-1-(methylamino)-1-oxobutan-2-yl)-7-methyl-3-(2-methyl-prop-1-enyl)-5,6,7,8-tetrahydroimidazo[1,5-a]pyrazine-1-carboxamide;

(S)—N-(3,3-dimethyl-1-(methylamino)-1-oxobutan-2-yl)-3-(2-fluorophenyl)-7-methyl-5,6,7,8-tetrahydroimidazo[1,5-a]pyrazine-1-carboxamide;

(S)-3-(2-cyanophenyl)-N-(3,3-dimethyl-1-(methylamino)-1-oxobutan-2-yl)-7-methyl-5,6,7,8-tetrahydroimidazo[1,5-a]pyrazine-1-carboxamide;

(S)-3-(3-cyanophenyl)-N-(3,3-dimethyl-1-(methylamino)-1-oxobutan-2-yl)-7-methyl-5,6,7,8-tetrahydroimidazo[1,5-a]pyrazine-1-carboxamide;

(S)-3-(2,3-difluorophenyl)-N-(3,3-dimethyl-1-(methylamino)-1-oxobutan-2-yl)-7-methyl-5,6,7,8-tetrahydroimidazo[1,5-a]pyrazine-1-carboxamide;

(S)-3-(3,5-difluorophenyl)-N-(3,3-dimethyl-1-(methylamino)-1-oxobutan-2-yl)-7-methyl-5,6,7,8-tetrahydroimidazo[1,5-a]pyrazine-1-carboxamide;

(S,E)-N-(3,3-dimethyl-1-(methylamino)-1-oxobutan-2-yl)-3-(3,3-dimethylbut-1-enyl)-7-methyl-5,6,7,8-tetrahydroimidazo[1,5-a]pyrazine-1-carboxamide;

(S,E)-N-(3,3-dimethyl-1-(methylamino)-1-oxobutan-2-yl)-3-(3-methoxyprop-1-enyl)-7-methyl-5,6,7,8-tetrahydroimidazo[1,5-a]pyrazine-1-carboxamide;

(S)-3-(biphenyl-4-yl)-N-(3,3-dimethyl-1-(methylamino)-1-oxobutan-2-yl)-7-methyl-5,6,7,8-tetrahydroimidazo[1,5-a]pyrazine-1-carboxamide;

(S)—N-(3,3-dimethyl-1-(methylamino)-1-oxobutan-2-yl)-7-methyl-3-vinyl-5,6,7,8-tetrahydroimidazo[1,5-a]pyrazine-1-carboxamide;

(S)—N-(3,3-dimethyl-1-(methylamino)-1-oxobutan-2-yl)-7-methyl-3-(prop-1-en-2-yl)-5,6,7,8-tetrahydroimidazo[1,5-a]pyrazine-1-carboxamide;

(S,E)-N-(3,3-dimethyl-1-(methylamino)-1-oxobutan-2-yl)-7-methyl-3-(pent-1-enyl)-5,6,7,8-tetrahydroimidazo[1,5-a]pyrazine-1-carboxamide;

(S)-3-cyclopropyl-N-(3,3-dimethyl-1-(methylamino)-1-oxobutan-2-yl)-7-methyl-5,6,7,8-tetrahydroimidazo[1,5-a]pyrazine-1-carboxamide;

N—((S)-3,3-dimethyl-1-(methylamino)-1-oxobutan-2-yl)-7-methyl-3-(4-methyl-cyclohex-1-enyl)-5,6,7,8-tetrahydroimidazo[1,5-a]pyrazine-1-carboxamide;

3-(4-tert-butylcyclohex-1-enyl)-N—((S)-3,3-dimethyl-1-(methylamino)-1-oxobutan-2-yl)-7-methyl-5,6,7,8-tetrahydroimidazo[1,5-a]pyrazine-1-carboxamide;

(S,E)-3-cycloheptenyl-N-(3,3-dimethyl-1-(methylamino)-1-oxobutan-2-yl)-7-methyl-5,6,7,8-tetrahydroimidazo[1,5-a]pyrazine-1-carboxamide;

(S,E)-3-(2-cyclopropylvinyl)-N-(3,3-dimethyl-1-(methylamino)-1-oxobutan-2-yl)-7-methyl-5,6,7,8-tetrahydroimidazo[1,5-a]pyrazine-1-carboxamide;

(S)—N-(3,3-dimethyl-1-(methylamino)-1-oxobutan-2-yl)-7-methyl-3-(1,2,3,6-tetra-hydropyridin-4-yl)-5,6,7,8-tetrahydroimidazo[1,5-a]pyrazine-1-carboxamide;

(S)-7-methyl-N-(4-methyl-1-(methylamino)-1-oxopentan-2-yl)-3-phenyl-5,6,7,8-tetrahydroimidazo[1,5-a]pyrazine-1-carboxamide;

(S)-3-(4-chloro-2-fluorophenyl)-7-methyl-N-(4-methyl-1-(methylamino)-1-oxopentan-2-yl)-5,6,7,8-tetrahydroimidazo[1,5-a]pyrazine-1-carboxamide;

(S)-3-(4-chloro-3-fluorophenyl)-7-methyl-N-(4-methyl-1-(methylamino)-1-oxopentan-2-yl)-5,6,7,8-tetrahydroimidazo[1,5-a]pyrazine-1-carboxamide;

(S)-3-(3,4-difluorophenyl)-7-methyl-N-(4-methyl-1-(methylamino)-1-oxopentan-2-yl)-5,6,7,8-tetrahydroimidazo[1,5-a]pyrazine-1-carboxamide;

(S)-3-cyclopentenyl-7-methyl-N-(4-methyl-1-(methylamino)-1-oxopentan-2-yl)-5,6,7,8-tetrahydroimidazo[1,5-a]pyrazine-1-carboxamide;

(S)-3-(3,4-dihydro-2H-pyran-6-yl)-7-methyl-N-(4-methyl-1-(methylamino)-1-oxopentan-2-yl)-5,6,7,8-tetrahydroimidazo[1,5-a]pyrazine-1-carboxamide;

(S)-3,3-dimethyl-2-(7-methyl-3-phenyl-5,6,7,8-tetrahydroimidazo[1,5-a]pyrazine-1-carboxamido)butanoic acid;

(S)—N-(2,2-dimethyl-1-(3-methyl-1,2,4-oxadiazol-5-yl)propyl)-3-phenyl-5,6,7,8-tetrahydroimidazo[1,5-a]pyrazine-1-carboxamide;

(S)—N-(1-(3-tert-butyl-1,2,4-oxadiazol-5-yl)-2,2-dimethylpropyl)-7-methyl-3-phenyl-5,6,7,8-tetrahydroimidazo[1,5-a]pyrazine-1-carboxamide;

(S)—N-(1-(3-tert-butyl-1,2,4-oxadiazol-5-yl)-2,2-dimethylpropyl)-7-cyclopropyl-3-phenyl-5,6,7,8-tetrahydroimidazo[1,5-a]pyrazine-1-carboxamide;

(S)—N-(1-amino-3,3-dimethyl-1-oxobutan-2-yl)-7-methyl-3-phenyl-5,6,7,8-tetrahydroimidazo[1,5-a]pyrazine-1-carboxamide;

(S,E)-N-(3,3-dimethyl-1-(methylamino)-1-oxobutan-2-yl)-7-methyl-3-(3-morpholinoprop-1-enyl)-5,6,7,8-tetrahydroimidazo[1,5-a]pyrazine-1-carboxamide;

(S,E)-N-(3,3-dimethyl-1-(methylamino)-1-oxobutan-2-yl)-7-methyl-3-(3-(piperidin-1-yl)prop-1-enyl)-5,6,7,8-tetrahydroimidazo[1,5-a]pyrazine-1-carboxamide;

(S,E)-N-(3,3-dimethyl-1-(methylamino)-1-oxobutan-2-yl)-7-methyl-3-(3-(pyrrolidin-1-yl)prop-1-enyl)-5,6,7,8-tetrahydroimidazo[1,5-a]pyrazine-1-carboxamide;

(S)-3-benzoyl-N-(3,3-dimethyl-1-(methylamino)-1-oxobutan-2-yl)-7-methyl-5,6,7,8-tetrahydroimidazo[1,5-a]pyrazine-1-carboxamide;

(S)—N1-(3,3-dimethyl-1-(methylamino)-1-oxobutan-2-yl)-7-methyl-N-3-phenyl-5,6,7,8-tetrahydroimidazo[1,5-a]pyrazine-1,3-dicarboxamide;

3,3-dimethyl-1-(3-phenyl-5,6,7,8-tetrahydroimidazo[1,5-a]pyrazin-1-yl)butan-1-one;

3,3-dimethyl-1-(7-methyl-3-phenyl-5,6,7,8-tetrahydroimidazo[1,5-a]pyrazin-1-yl)butan-1-one;

3-methyl-1-(7-methyl-3-phenyl-5,6,7,8-tetrahydroimidazo[1,5-a]pyrazin-1-yl)but-2-en-1-one;

1-(7-methyl-3-phenyl-5,6,7,8-tetrahydroimidazo[1,5-a]pyrazin-1-yl)-4-phenyl-butan-1-one;

N—((S)-3,3-dimethyl-1-(methylamino)-1-oxobutan-2-yl)-3-(hydroxy(phenyl)-methyl)-7-methyl-5,6,7,8-tetrahydroimidazo[1,5-a]pyrazine-1-carboxamide;

3-(cyclopropyl(hydroxy)methyl)-N—((S)-3,3-dimethyl-1-(methylamino)-1-oxobutan-2-yl)-7-methyl-5,6,7,8-tetrahydroimidazo[1,5-a]pyrazine-1-carboxamide;

(S)—N-(3,3-dimethyl-1-(methylamino)-1-oxobutan-2-yl)-7-methyl-3-(thiazol-2-yl)-5,6,7,8-tetrahydroimidazo[1,5-a]pyrazine-1-carboxamide;

(S)—N-(3,3-dimethyl-1-(methylamino)-1-oxobutan-2-yl)-3-phenyl-7-(pyrimidin-2-yl)-5,6,7,8-tetrahydroimidazo[1,5-a]pyrazine-1-carboxamide;

(S)-7-(6-chloropyridin-2-yl)-N-(3,3-dimethyl-1-(methylamino)-1-oxobutan-2-yl)-3-phenyl-5,6,7,8-tetrahydroimidazo[1,5-a]pyrazine-1-carboxamide;

(S)-7-(6-chloropyrazin-2-yl)-N-(3,3-dimethyl-1-(methylamino)-1-oxobutan-2-yl)-3-phenyl-5,6,7,8-tetrahydroimidazo[1,5-a]pyrazine-1-carboxamide;

(S)—N-(3,3-dimethyl-1-(methylamino)-1-oxobutan-2-yl)-3-phenyl-7-(pyrazin-2-yl)-5,6,7,8-tetrahydroimidazo[1,5-a]pyrazine-1-carboxamide;

(R)—N-(3,3-dimethyl-1-(methylamino)-1-oxobutan-2-yl)-7-methyl-3-phenyl-5,6,7,8-tetrahydroimidazo[1,5-a]pyrazine-1-carboxamide;

(S)-3-cyclopentyl-N-(3,3-dimethyl-1-(methylamino)-1-oxobutan-2-yl)-7-methyl-5,6,7,8-tetrahydroimidazo[1,5-a]pyrazine-1-carboxamide;

(S)—N-(3,3-dimethyl-1-(methylamino)-1-oxobutan-2-yl)-7-methyl-3-propyl-5,6,7,8-tetrahydroimidazo[1,5-a]pyrazine-1-carboxamide;

(S)-3-cyclohexyl-N-(3,3-dimethyl-1-(methylamino)-1-oxobutan-2-yl)-7-methyl-5,6,7,8-tetrahydroimidazo[1,5-a]pyrazine-1-carboxamide;

(S)—N-(3,3-dimethyl-1-(methylamino)-1-oxobutan-2-yl)-3-isobutyl-7-methyl-5,6,7,8-tetrahydroimidazo[1,5-a]pyrazine-1-carboxamide;

(S)—N-(3,3-dimethyl-1-(methylamino)-1-oxobutan-2-yl)-7-methyl-3-(3-(piperidin-1-yl)propyl)-5,6,7,8-tetrahydroimidazo[1,5-a]pyrazine-1-carboxamide;

(S)—N-(3,3-dimethyl-1-(methylamino)-1-oxobutan-2-yl)-7-methyl-3-(3-(pyrrolidin-1-yl)propyl)-5,6,7,8-tetrahydroimidazo[1,5-a]pyrazine-1-carboxamide;

(S)—N-(3,3-dimethyl-1-(methylamino)-1-oxobutan-2-yl)-7-methyl-3-(3-morpholinopropyl)-5,6,7,8-tetrahydroimidazo[1,5-a]pyrazine-1-carboxamide;

(S)—N-(3,3-dimethyl-1-(methylamino)-1-oxobutan-2-yl)-3-ethyl-7-methyl-5,6,7,8-tetrahydroimidazo[1,5-a]pyrazine-1-carboxamide;

(S)-1-(3,3-dimethyl-1-(methylamino)-1-oxobutan-2-ylcarbamoyl)-7,7-dimethyl-3-phenyl-5,6,7,8-tetrahydroimidazo[1,5-a]pyrazin-7-ium;

(S)-tert-butyl 1-(3,3-dimethyl-1-(methylamino)-1-oxobutan-2-ylcarbamoyl)-3-phenyl-6,7-dihydro-5H-imidazo[1,5-a][1,4]diazepine-8(9H)-carboxylate;

(S)-tert-butyl 3-(4-chloro-2-fluorophenyl)-1-(3,3-dimethyl-1-(methylamino)-1-oxobutan-2-ylcarbamoyl)-6,7-dihydro-5H-imidazo[1,5-a][1,4]diazepine-8(9H)-carboxylate;

(S)—N-(3,3-dimethyl-1-(methylamino)-1-oxobutan-2-yl)-3-phenyl-6,7,8,9-tetrahydro-5H-imidazo[1,5-a][1,4]diazepine-1-carboxamide;

(S)-3-(4-chloro-2-fluorophenyl)-N-(3,3-dimethyl-1-(methylamino)-1-oxobutan-2-yl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(2-fluoro-4-methyl-phenyl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-phenyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-ethyl-3-phenyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-isopropyl-3-phenyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-isobutyl-3-phenyl-6,7,8,9-tetrahydro-5H-imidazo[1,5-a][1,4]diazepine-1-carboxamide;

(S)-8-(cyclopropylmethyl)-N-(3,3-dimethyl-1-(methylamino)-1-oxobutan-2-yl)-3-phenyl-6,7,8,9-tetrahydro-5H-imidazo[1,5-a][1,4]diazepine-1-carboxamide;

(S)-3-(4-chloro-2-fluorophenyl)-N-(3,3-dimethyl-1-(methylamino)-1-oxobutan-2-yl)-8-isobutyl-6,7,8,9-tetrahydro-5H-imidazo[1,5-a][1,4]diazepine-1-carboxamide;

(S)-8-(cyclopropylmethyl)-N-(3,3-dimethyl-1-(methylamino)-1-oxobutan-2-yl)-3-(2-fluoro-4-methylphenyl)-6,7,8,9-tetrahydro-H-imidazo[1,5-a][1,4]diazepine-1-carboxamide;

(S)-3-bromo-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(2-methoxyphenyl)-8-methyl-6,7,8,9-tetrahydro-5H-imidazo[1,5-a][1,4]diazepine-1-carboxamide;

(S)-3-(2,3-dihydrobenzo[b][1,4]dioxin-6-yl)-N-(3,3-dimethyl-1-(methylamino)-1-oxobutan-2-yl)-8-methyl-6,7,8,9-tetrahydro-5H-imidazo[1,5-a][1,4]-diazepine-1-carboxamide;

(S)-3-(5-chloro-2-methoxyphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)-3-(3-cyanophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(thiophen-3-yl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(4-(trifluoromethyl)phenyl)-6,7,8,9-tetrahydro-5H-imidazo[1,5-a][1,4]diazepine-1-carboxamide;

(S)-3-(3,5-difluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-p-tolyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(2-(trifluoro-methoxy)phenyl)-6,7,8,9-tetrahydro-5H-imidazo[1,5-a][1,4]diazepine-1-carboxamide;

(S)-3-(3-chloro-4-methylphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)-3-(2-chloro-5-methylphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S,E)-N-(3,3-dimethyl-1-(methylamino)-1-oxobutan-2-yl)-8-methyl-3-styryl-6,7,8,9-tetrahydro-5H-imidazo[1,5-a][1,4]diazepine-1-carboxamide;

(S)-3-(2-chloro-4-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(3-(trifluoro-methoxy)phenyl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(4-(trifluoro-methoxy)phenyl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(2-fluoro-4-methyl-phenyl)-8-methyl-6,7,8,9-tetrahydro-5H-imidazo[1,5-a][1,4]diazepine-1-carboxamide;

(S)-3-(benzo[d][1,3]dioxol-5-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)-3-(4-cyanophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(4-methoxy-2-methylphenyl)-8-methyl-6,7,8,9-tetrahydro-5H-imidazo[1,5-a][1,4]-diazepine-1-carboxamide;

(S)-3-(2,4-dimethoxypyrimidin-5-yl)-N-(3,3-dimethyl-1-(methylamino)-1-oxobutan-2-yl)-8-methyl-6,7,8,9-tetrahydro-5H-imidazo[1,5-a][1,4]-diazepine-1-carboxamide;

(S)—N-(3,3-dimethyl-1-(methylamino)-1-oxobutan-2-yl)-3-(3-fluorophenyl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(2-fluoro-3-methoxyphenyl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(4-fluoro-3-methylphenyl)-8-methyl-6,7,8,9-tetrahydro-5H-imidazo[1,5-a][1,4]-diazepine-1-carboxamide;

(S)—N-(3,3-dimethyl-1-(methylamino)-1-oxobutan-2-yl)-8-methyl-3-(pyridin-3-yl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(thiophen-2-yl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(4-methoxy-3-methylphenyl)-8-methyl-6,7,8,9-tetrahydro-5H-imidazo[1,5-a][1,4]diazepine-1-carboxamide;

(S)-3-(benzofuran-2-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(4-methylthiophen-3-yl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(2-fluorophenyl)-8-methyl-6,7,8,9-tetrahydro-5H-imidazo[1,5-a][1,4]diazepine-1-carboxamide;

(S)-3-(benzo[b]thiophen-3-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)-3-(2,4-difluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)-3-(3-chloro-2-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)-3-(5-chloro-2-fluoro-4-methylphenyl)-N-(3,3-dimethyl-1-(methylamino)-1-oxobutan-2-yl)-8-methyl-6,7,8,9-tetrahydro-5H-imidazo[1,5-a][1,4]-diazepine-1-carboxamide;

(S)—N-(3,3-dimethyl-1-(methylamino)-1-oxobutan-2-yl)-3-(2-fluoro-4-methoxyphenyl)-8-methyl-6,7,8,9-tetrahydro-5H-imidazo[1,5-a][1,4]-diazepine-1-carboxamide;

(S)-3-(2,5-difluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(3-fluoro-4-methylphenyl)-8-methyl-6,7,8,9-tetrahydro-5H-imidazo[1,5-a][1,4]diazepine-1-carboxamide;

(S)-3-(5-chloro-2-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(2-fluoro-5-methylphenyl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(2-fluoro-5-(trifluoromethyl)phenyl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(2-fluoro-3-(trifluoro-methyl)phenyl)-8-methyl-6,7,8,9-tetrahydro-5H-imidazo[1,5-a]-[1,4]diazepine-1-carboxamide;

N—((S)-3,3-dimethyl-1-(methylamino)-1-oxobutan-2-yl)-3-(2-fluoro-6-methoxy-phenyl)-8-methyl-6,7,8,9-tetrahydro-5H-imidazo[1,5-a][1,4]diazepine-1-carboxamide;

(S)-3-(4-chloro-2-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)-3-(2-chloro-4-methylphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(2-fluoro-4-(trifluoro-methyl)phenyl)-8-methyl-6,7,8,9-tetrahydro-5H-imidazo[1,5-a][1,4]-diazepine-1-carboxamide;

(S)-3-(2,3-difluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)-3-(5-chloro-2,4-difluorophenyl)-N-(3,3-dimethyl-1-(methylamino)-1-oxobutan-2-yl)-8-methyl-6,7,8,9-tetrahydro-5H-imidazo[1,5-a][1,4]-diazepine-1-carboxamide;

(S)—N-(3,3-dimethyl-1-(methylamino)-1-oxobutan-2-yl)-8-methyl-3-(2,4,5-trifluoro-phenyl)-6,7,8,9-tetrahydro-5H-imidazo[1,5-a][1,4]diazepine-1-carboxamide;

(S)-3-(3-chloro-4-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)-3-(4-chloro-3-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)-3-(3,4-difluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(3,4,5-trifluoro-phenyl)-6,7,8,9-tetrahydro-5H-imidazo[1,5-a][1,4]diazepine-1-carboxamide;

(S,E)-N-(3,3-dimethyl-1-(methylamino)-1-oxobutan-2-yl)-8-methyl-3-(prop-1-enyl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(2-methyl-prop-1-enyl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(4-morpholino-phenyl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(4-(methyl-sulfonyl)phenyl)-6,7,8,9-tetrahydro-5H-imidazo[1,5-a][1,4]-diazepine-1-carboxamide;

(S)—N-(3,3-dimethyl-1-(methylamino)-1-oxobutan-2-yl)-8-methyl-3-(naphthalen-2-yl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(4-(dimethylamino)-phenyl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(3-(dimethylamino)-phenyl)-8-methyl-6,7,8,9-tetrahydro-5H-imidazo[1,5-a][1,4]diazepine-1-carboxamide;

(S)-3-(biphenyl-3-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(3-fluoro-5-methoxy-phenyl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(3-(pyrrolidin-1-ylsulfonyl)phenyl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(3-(morpholine-4-carbonyl)phenyl)-6,7,8,9-tetrahydro-5H-imidazo[1,5-a][1,4]diazepine-1-carboxamide;

(S)-methyl 4-(1-(3,3-dimethyl-1-(methylamino)-1-oxobutan-2-ylcarbamoyl)-8-methyl-6,7,8,9-tetrahydro-5H-imidazo[1,5-a][1,4]diazepin-3-yl)-3-fluoro-benzoate;

(S)-tert-butyl 4-(1-(3,3-dimethyl-1-(methylamino)-1-oxobutan-2-ylcarbamoyl)-8-methyl-6,7,8,9-tetrahydro-5H-imidazo[1,5-a][1,4]diazepin-3-yl)-5,6-dihydro-pyridine-1(2H)-carboxylate;

(S)—N-(3,3-dimethyl-1-(methylamino)-1-oxobutan-2-yl)-3-(4-fluoro-3-(morpholine-4-carbonyl)phenyl)-8-methyl-6,7,8,9-tetrahydro-5H-imidazo[1,5-a][1,4]-diazepine-1-carboxamide;

(S)-3-(4-(1H-pyrazol-1-yl)phenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(3-(methylcarbamoyl)phenyl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(4-(4-methyl-piperazine-1-carbonyl)phenyl)-6,7,8,9-tetrahydro-5H-imidazo[1,5-a][1,4]-diazepine-1-carboxamide;

(S)—N-(3,3-dimethyl-1-(methylamino)-1-oxobutan-2-yl)-3-(4-fluoro-3-methoxy-phenyl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(4-(dimethylcarbamoyl)-phenyl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(pyridin-2-yl)-6,7,8,9-tetrahydro-5H-imidazo[1,5-a][1,4]diazepine-1-carboxamide;

(S)-3-cyclohexenyl-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S,E)-N-(3,3-dimethyl-1-(methylamino)-1-oxobutan-2-yl)-3-(3,3-dimethylbut-1-enyl)-8-methyl-6,7,8,9-tetrahydro-5H-imidazo[1,5-a][1,4]diazepine-1-carboxamide;

(S,E)-N-(3,3-dimethyl-1-(methylamino)-1-oxobutan-2-yl)-3-(3-methoxyprop-1-enyl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(2-(trifluoro-methyl)phenyl)-6,7,8,9-tetrahydro-5H-imidazo[1,5-a][1,4]diazepine-1-carboxamide;

(S,E)-N-(3,3-dimethyl-1-(methylamino)-1-oxobutan-2-yl)-3-(hex-1-enyl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(4-(morpholine-4-carbonyl)phenyl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(pyridin-4-yl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(2-isopropylphenyl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(3-fluoro-4-methoxy-phenyl)-8-methyl-6,7,8,9-tetrahydro-5H-imidazo[1,5-a][1,4]diazepine-1-carboxamide;

(S)-3-(5-carbamoyl-2-fluorophenyl)-N-(3,3-dimethyl-1-(methylamino)-1-oxo-butan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(4-fluoro-3-(methyl-carbamoyl)phenyl)-8-methyl-6,7,8,9-tetrahydro-5H-imidazo[1,5-a][1,4]-diazepine-1-carboxamide;

(S)—N-(3,3-dimethyl-1-(methylamino)-1-oxobutan-2-yl)-8-methyl-3-(3-(5-methyl-1,3,4-oxadiazol-2-yl)phenyl)-6,7,8,9-tetrahydro-5H-imidazo[1,5-a][1,4]-diazepine-1-carboxamide;

(S)—N-(3,3-dimethyl-1-(methylamino)-1-oxobutan-2-yl)-8-methyl-3-(4-(methyl-carbamoyl)phenyl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(3-(methyl-sulfonyl)phenyl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(4-(N,N-dimethyl-sulfamoyl)phenyl)-8-methyl-6,7,8,9-tetrahydro-5H-imidazo[1,5-a][1,4]-diazepine-1-carboxamide;

(S)-5-(1-(3,3-dimethyl-1-(methylamino)-1-oxobutan-2-ylcarbamoyl)-8-methyl-6,7,8,9-tetrahydro-5H-imidazo[1,5-a][1,4]diazepin-3-yl)-2-fluorobenzoic acid;

(S)—N-(3,3-dimethyl-1-(methylamino)-1-oxobutan-2-yl)-3-(3-(dimethyl-carbamoyl)-phenyl)-8-methyl-6,7,8,9-tetrahydro-5H-imidazo[1,5-a]-[1,4]diazepine-1-carboxamide;

(S)-3-(biphenyl-2-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)-3-(4-tert-butylphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)-3-(4-acetylphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)-3-(3-carbamoyl-5-fluorophenyl)-N-(3,3-dimethyl-1-(methylamino)-1-oxobutan-2-yl)-8-methyl-6,7,8,9-tetrahydro-5H-imidazo[1,5-a][1,4]-diazepine-1-carboxamide;

(S)—N-(3,3-dimethyl-1-(methylamino)-1-oxobutan-2-yl)-8-methyl-3-(naphthalen-1-yl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(3-methoxy-5-(trifluoro-methyl)phenyl)-8-methyl-6,7,8,9-tetrahydro-5H-imidazo[1,5-a][1,4]diaz-epine-1-carboxamide;

(S)—N-(3,3-dimethyl-1-(methylamino)-1-oxobutan-2-yl)-3-(2-fluorobiphenyl-4-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(4-(methyl-sulfonamido)phenyl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(3-(methyl-sulfonamido)phenyl)-6,7,8,9-tetrahydro-5H-imidazo[1,5-a][1,4]diazepine-1-carboxamide;

(S)-3-(3-carbamoylphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)-3-(4-carbamoylphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)-3-(2,5-difluoro-4-methoxyphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)-3-(3-cyano-4-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(4-(dimethyl-carbamoyl)-3-fluorophenyl)-8-methyl-6,7,8,9-tetrahydro-5H-imidazo[1,5-a][1,4]diazepine-1-carboxamide;

(S)-3-(4-carbamoyl-3-fluorophenyl)-N-(3,3-dimethyl-1-(methylamino)-1-oxobutan-2-yl)-8-methyl-6,7,8,9-tetrahydro-5H-imidazo[1,5-a][1,4]-diazepine-1-carboxamide;

N—((S)-3,3-dimethyl-1-(methylamino)-1-oxobutan-2-yl)-8-methyl-3-(4-(5-oxopyrazolidin-3-yl)phenyl)-6,7,8,9-tetrahydro-5H-imidazo[1,5-a][1,4]-diazepine-1-carboxamide;

(S)-3-(3-carbamoyl-4-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-vinyl-6,7,8,9-tetrahydro-5H-imidazo[1,5-a][1,4]diazepine-1-carboxamide;

(S)-3-(2-carbamoylphenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(1H-pyrazol-4-yl)-6,7,8,9-tetrahydro-5H-imidazo[1,5-a][1,4]diazepine-1-carboxamide;

(S)-3-(3-chlorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S,E)-N-(3,3-dimethyl-1-(methylamino)-1-oxobutan-2-yl)-8-methyl-3-(pent-1-enyl)-6,7,8,9-tetrahydro-5H-imidazo[1,5-a][1,4]diazepine-1-carboxamide;

(S)-3-cyclopropyl-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S,E)-3-(2-cyclopropylvinyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(4-fluorophenyl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(3-(trifluoro-methyl)phenyl)-6,7,8,9-tetrahydro-5H-imidazo[1,5-a][1,4]-diazepine-1-carboxamide;

(S,E)-3-(2-cyclohexylvinyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(furan-3-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(prop-1-en-2-yl)-6,7,8,9-tetrahydro-5H-imidazo[1,5-a][1,4]diazepine-1-carboxamide;

N—((S)-3,3-dimethyl-1-(methylamino)-1-oxobutan-2-yl)-3-(3,5-dimethylisoxazol-4-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(5-methylfuran-2-yl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(quinolin-8-yl)-6,7,8,9-tetrahydro-5H-imidazo[1,5-a][1,4]diazepine-1-carboxamide;

(S,E)-3-(3-cyclopentylprop-1-enyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S,E)-N-(3,3-dimethyl-1-(methylamino)-1-oxobutan-2-yl)-8-methyl-3-(2-(thiophen-3-yl)vinyl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(1-methyl-1H-pyrazol-4-yl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(1,4-dioxaspiro-[4.5]dec-7-en-8-yl)-6,7,8,9-tetrahydro-5H-imidazo[1,5-a][1,4]diazepine-1-carboxamide;

N—((S)-3,3-dimethyl-1-(methylamino)-1-oxobutan-2-yl)-8-methyl-3-(4-methyl-cyclohex-1-enyl)-6,7,8,9-tetrahydro-5H-imidazo[1,5-a][1,4]diazepine-1-carboxamide;

3-(4-tert-butylcyclohex-1-enyl)-N—((S)-3,3-dimethyl-1-(methylamino)-1-oxobutan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(3-fluoropyridin-4-yl)-8-methyl-6,7,8,9-tetrahydro-5H-imidazo[1,5-a][1,4]diazepine-1-carboxamide;

(S)-3-(3,4-dihydro-2H-pyran-6-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(3,3,3-trifluoro-prop-1-en-2-yl)-6,7,8,9-tetrahydro-5H-imidazo[1,5-a][1,4]-diazepine-1-carboxamide;

(S)—N-(3,3-dimethyl-1-(methylamino)-1-oxobutan-2-yl)-8-methyl-3-(3-methylbut-2-en-2-yl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(1-phenyl-vinyl)-6,7,8,9-tetrahydro-5H-imidazo[1,5-a][1,4]diazepine-1-carboxamide;

(S)-3-cyclopentenyl-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S,E)-3-cycloheptenyl-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S,E)-N-(3,3-dimethyl-1-(methylamino)-1-oxobutan-2-yl)-8-methyl-3-(3-phenylprop-1-enyl)-6,7,8,9-tetrahydro-5H-imidazo[1,5-a][1,4]diazepine-1-carboxamide;

(S)-3-benzyl-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(1,2,3,6-tetrahydropyridin-4-yl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-(ethylsulfonyl)-3-phenyl-6,7,8,9-tetrahydro-5H-imidazo[1,5-a][1,4]diazepine-1-carboxamide;

(S)-8-benzoyl-N-(3,3-dimethyl-1-(methylamino)-1-oxobutan-2-yl)-3-phenyl-6,7,8,9-tetrahydro-5H-imidazo[1,5-a][1,4]diazepine-1-carboxamide;

(S)-8-acetyl-N-(3,3-dimethyl-1-(methylamino)-1-oxobutan-2-yl)-3-phenyl-6,7,8,9-tetrahydro-5H-imidazo[1,5-a][1,4]diazepine-1-carboxamide;
(S)—N-(3,3-dimethyl-1-(methylamino)-1-oxobutan-2-yl)-8-(4-fluoro-phenylsulfonyl)-3-phenyl-6,7,8,9-tetrahydro-5H-imidazo[1,5-a][1,4]-diazepine-1-carboxamide;
(S)-methyl 3,3-dimethyl-2-(3-phenyl-6,7,8,9-tetrahydro-5H-imidazo[1,5-a][1,4]-diazepine-1-carboxamido)butanoate;
(S)-methyl 2-(3-(2-fluoro-4-methylphenyl)-6,7,8,9-tetrahydro-5H-imidazo[1,5-a]-[1,4]diazepine-1-carboxamido)-3,3-dimethylbutanoate;
(S)-methyl 3,3-dimethyl-2-(8-methyl-3-phenyl-6,7,8,9-tetrahydro-5H-imidazo-[1,5a][1,4]diazepine-1-carboxamido)butanoate;
(S)-methyl 2-(8-isopropyl-3-phenyl-6,7,8,9-tetrahydro-5H-imidazo[1,5-a]-[1,4]diazepine-1-carboxamido)-3,3-dimethylbutanoate;
(S)-methyl 2-(3-(2-fluoro-4-methylphenyl)-8-methyl-6,7,8,9-tetrahydro-5H-imidazo[1,5-a][1,4]diazepine-1-carboxamido)-3,3-dimethylbutanoate;
(S)-methyl 2-(8-(cyclopropylmethyl)-3-(2-fluoro-4-methylphenyl)-6,7,8,9-tetrahydro-5H-imidazo[1,5-a][1,4]diazepine-1-carboxamido)-3,3-dimethylbutanoate;
(S)-3,3-dimethyl-2-(8-methyl-3-phenyl-6,7,8,9-tetrahydro-5H-imidazo[1,5-a][1,4]diazepine-1-carboxamido)butanoic acid;
(S)—N-(1-(isopropylamino)-3,3-dimethyl-1-oxobutan-2-yl)-8-methyl-3-phenyl-6,7,8,9-tetrahydro-5H-imidazo[1,5-a][1,4]diazepine-1-carboxamide;
(S)—N-(3,3-dimethyl-1-oxo-1-(propylamino)butan-2-yl)-8-methyl-3-phenyl-6,7,8,9-tetrahydro-5H-imidazo[1,5-a][1,4]diazepine-1-carboxamide;
(S)—N-(1-(isobutylamino)-3,3-dimethyl-1-oxobutan-2-yl)-8-methyl-3-phenyl-6,7,8,9-tetrahydro-5H-imidazo[1,5-a][1,4]diazepine-1-carboxamide;
(S)—N-(1-(2-methoxyethylamino)-3,3-dimethyl-1-oxobutan-2-yl)-8-methyl-3-phenyl-6,7,8,9-tetrahydro-5H-imidazo[1,5-a][1,4]diazepine-1-carboxamide;
(S)—N-(1-(2-fluoroethylamino)-3,3-dimethyl-1-oxobutan-2-yl)-8-methyl-3-phenyl-6,7,8,9-tetrahydro-5H-imidazo[1,5-a][1,4]diazepine-1-carboxamide;
(S)—N-(1-(cyclopropylamino)-3,3-dimethyl-1-oxobutan-2-yl)-8-methyl-3-phenyl-6,7,8,9-tetrahydro-5H-imidazo[1,5-a][1,4]diazepine-1-carboxamide;
(S)—N-(1-(ethylamino)-3,3-dimethyl-1-oxobutan-2-yl)-8-methyl-3-phenyl-6,7,8,9-tetrahydro-5H-imidazo[1,5-a][1,4]diazepine-1-carboxamide;
(S)—N-(3,3-dimethyl-1-oxo-1-((tetrahydro-2H-pyran-4-yl)methylamino)butan-2-yl)-8-methyl-3-phenyl-6,7,8,9-tetrahydro-5H-imidazo[1,5-a][1,4]diazepine-1-carboxamide;
(S)—N-(1-(cyclobutylamino)-3,3-dimethyl-1-oxobutan-2-yl)-8-methyl-3-phenyl-6,7,8,9-tetrahydro-5H-imidazo[1,5-a][1,4]diazepine-1-carboxamide;
(S)-1-(3,3-dimethyl-1-(methylamino)-1-oxobutan-2-ylcarbamoyl)-8,8-dimethyl-3-phenyl-6,7,8,9-tetrahydro-5H-imidazo[1,5-a][1,4]diazepin-8-ium;
(S)-3-(4-chloro-2-fluorophenyl)-N-(3,3-dimethyl-1-(methylamino)-1-oxobutan-2-yl)-8-(pyrimidin-2-yl)-6,7,8,9-tetrahydro-5H-imidazo[1,5-a][1,4]diazepine-1-carboxamide;
(S)—N-(3,3-dimethyl-1-(methylamino)-1-oxobutan-2-yl)-3-phenyl-8-(pyrimidin-2-yl)-6,7,8,9-tetrahydro-5H-imidazo[1,5-a][1,4]diazepine-1-carboxamide;
(S)—N-(3,3-dimethyl-1-(methylamino)-1-oxobutan-2-yl)-8-methyl-3-pentyl-6,7,8,9-tetrahydro-5H-imidazo[1,5-a][1,4]diazepine-1-carboxamide;
(S)—N-(3,3-dimethyl-1-(methylamino)-1-oxobutan-2-yl)-8-methyl-3-propyl-6,7,8,9-tetrahydro-5H-imidazo[1,5-a][1,4]diazepine-1-carboxamide;
(S)—N-(3,3-dimethyl-1-(methylamino)-1-oxobutan-2-yl)-3-isobutyl-8-methyl-6,7,8,9-tetrahydro-5H-imidazo[1,5-a][1,4]diazepine-1-carboxamide;
(S)-3-cyclohexyl-N-(3,3-dimethyl-1-(methylamino)-1-oxobutan-2-yl)-8-methyl-6,7,8,9-tetrahydro-5H-imidazo[1,5-a][1,4]diazepine-1-carboxamide;
(S)—N-(3,3-dimethyl-1-(methylamino)-1-oxobutan-2-yl)-3-(3,3-dimethylbutyl)-8-methyl-6,7,8,9-tetrahydro-5H-imidazo[1,5-a][1,4]diazepine-1-carboxamide;
(S)—N-(3,3-dimethyl-1-(methylamino)-1-oxobutan-2-yl)-3-(3-methoxypropyl)-8-methyl-6,7,8,9-tetrahydro-5H-imidazo[1,5-a][1,4]diazepine-1-carboxamide;
(S)-3-(2-cyclopropylethyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;
(S)—N-(3,3-dimethyl-1-(methylamino)-1-oxobutan-2-yl)-3-hexyl-8-methyl-6,7,8,9-tetrahydro-5H-imidazo[1,5-a][1,4]diazepine-1-carboxamide;
(S)—N-(3,3-dimethyl-1-(methylamino)-1-oxobutan-2-yl)-3-ethyl-8-methyl-6,7,8,9-tetrahydro-5H-imidazo[1,5-a][1,4]diazepine-1-carboxamide;
(S)-3-(2-cyclohexylethyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;
(S)-3-(3-cyclopentylpropyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;
(S)—N-(3,3-dimethyl-1-(methylamino)-1-oxobutan-2-yl)-8-methyl-3-(2-(thiophen-3-yl)ethyl)-6,7,8,9-tetrahydro-5H-imidazo[1,5-a][1,4]diazepine-1-carboxamide;
(S)—N-(3,3-dimethyl-1-(methylamino)-1-oxobutan-2-yl)-3-isopropyl-8-methyl-6,7,8,9-tetrahydro-5H-imidazo[1,5-a][1,4]diazepine-1-carboxamide;
(S)-3-cyclopentyl-N-(3,3-dimethyl-1-(methylamino)-1-oxobutan-2-yl)-8-methyl-6,7,8,9-tetrahydro-5H-imidazo[1,5-a][1,4]diazepine-1-carboxamide;
(S)-3-cycloheptyl-N-(3,3-dimethyl-1-(methylamino)-1-oxobutan-2-yl)-8-methyl-6,7,8,9-tetrahydro-5H-imidazo[1,5-a][1,4]diazepine-1-carboxamide;
(S)—N-(3,3-dimethyl-1-(methylamino)-1-oxobutan-2-yl)-8-methyl-3-(4-methyl-cyclohexyl)-6,7,8,9-tetrahydro-5H-imidazo[1,5-a][1,4]diazepine-1-carboxamide;
(S)—N-(3,3-dimethyl-1-(methylamino)-1-oxobutan-2-yl)-8-methyl-3-(3-morpholino-propyl)-6,7,8,9-tetrahydro-5H-imidazo[1,5-a][1,4]diazepine-1-carboxamide;
(S)—N-(3,3-dimethyl-1-(methylamino)-1-oxobutan-2-yl)-8-methyl-3-(3-(piperidin-1-yl)propyl)-6,7,8,9-tetrahydro-5H-imidazo[1,5-a][1,4]diazepine-1-carboxamide;
(S)—N-(3,3-dimethyl-1-(methylamino)-1-oxobutan-2-yl)-8-methyl-3-(3-(pyrrolidin-1-yl)propyl)-6,7,8,9-tetrahydro-5H-imidazo[1,5-a][1,4]diazepine-1-carboxamide;
(S)—N-(3,3-dimethyl-1-(methylamino)-1-oxobutan-2-yl)-8-methyl-3-(piperidin-4-yl)-6,7,8,9-tetrahydro-5H-imidazo[1,5-a][1,4]diazepine-1-carboxamide;
N—((S)-3,3-dimethyl-1-(methylamino)-1-oxobutan-2-yl)-8-methyl-3-(tetrahydro-2H-pyran-2-yl)-6,7,8,9-tetrahydro-5H-imidazo[1,5-a][1,4]diazepine-1-carboxamide;

N—((S)-3,3-dimethyl-1-(methylamino)-1-oxobutan-2-yl)-8-methyl-3-(1,1,1-trifluoro-propan-2-yl)-6,7,8,9-tetrahydro-5H-imidazo[1,5-a][1,4]diazepine-1-carboxamide;

N—((S)-3,3-dimethyl-1-(methylamino)-1-oxobutan-2-yl)-8-methyl-3-(1-phenylethyl)-6,7,8,9-tetrahydro-5H-imidazo[1,5-a][1,4]diazepine-1-carboxamide;

N—((S)-3,3-dimethyl-1-(methylamino)-1-oxobutan-2-yl)-8-methyl-3-(3-methylbutan-2-yl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-3-(4-hydroxybutyl)-8-methyl-6,7,8,9-tetrahydro-5H-imidazo[1,5-a][1,4]diazepine-1-carboxamide;

(S,E)-N-(3,3-dimethyl-1-(methylamino)-1-oxobutan-2-yl)-8-methyl-3-(3-morpholino-prop-1-enyl)-6,7,8,9-tetrahydro-5H-imidazo[1,5-a]-[1,4]diazepine-1-carboxamide;

(S,E)-N-(3,3-dimethyl-1-(methylamino)-1-oxobutan-2-yl)-8-methyl-3-(3-(piperidin-1-yl)prop-1-enyl)-6,7,8,9-tetrahydro-5H-imidazo[1,5-a][1,4]diazepine-1-carboxamide;

(S,E)-N-(3,3-dimethyl-1-(methylamino)-1-oxobutan-2-yl)-8-methyl-3-(3-(pyrrolidin-1-yl)prop-1-enyl)-6,7,8,9-tetrahydro-5H-imidazo[1,5-a][1,4]diazepine-1-carboxamide;

(S,E)-3-(3-(diethylamino)prop-1-enyl)-N-(3,3-dimethyl-1-(methylamino)-1-oxobutan-2-yl)-8-methyl-6,7,8,9-tetrahydro-5H-imidazo[1,5-a]-[1,4]diazepine-1-carboxamide;

(S,E)-N-(3,3-dimethyl-1-(methylamino)-1-oxobutan-2-yl)-3-(3-(dimethylamino)prop-1-enyl)-8-methyl-6,7,8,9-tetrahydro-5H-imidazo[1,5-a][1,4]diazepine-1-carboxamide;

(S,E)-N-(3,3-dimethyl-1-(methylamino)-1-oxobutan-2-yl)-3-(4-hydroxybut-1-enyl)-8-methyl-6,7,8,9-tetrahydro-5H-imidazo[1,5-a][1,4]diazepine-1-carboxamide;

(S)-2-(8-(tert-butoxycarbonyl)-3-phenyl-6,7,8,9-tetrahydro-5H-imidazo[1,5-a][1,4]diazepine-1-carboxamido)-3,3-dimethylbutanoic acid;

(S)-2-(8-(tert-butoxycarbonyl)-3-(2-fluoro-4-methylphenyl)-6,7,8,9-tetrahydro-5H-imidazo[1,5-a][1,4]diazepine-1-carboxamido)-3,3-dimethylbutanoic acid;

(S)-tert-butyl 1-(2,2-dimethyl-1-(3-methyl-1,2,4-oxadiazol-5-yl)propylcarbamoyl)-3-phenyl-6,7-dihydro-5H-imidazo[1,5-a][1,4]diazepine-8(9H)-carboxylate;

(S)-tert-butyl 1-(2,2-dimethyl-1-(3-methyl-1,2,4-oxadiazol-5-yl)propylcarbamoyl)-3-(2-fluoro-4-methylphenyl)-6,7-dihydro-5H-imidazo[1,5-a][1,4]diazepine-8(9H)-carboxylate;

(S)—N-(2,2-dimethyl-1-(3-methyl-1,2,4-oxadiazol-5-yl)propyl)-3-phenyl-6,7,8,9-tetrahydro-5H-imidazo[1,5-a][1,4]diazepine-1-carboxamide;

(S)—N-(2,2-dimethyl-1-(3-methyl-1,2,4-oxadiazol-5-yl)propyl)-3-(2-fluoro-4-methylphenyl)-6,7,8,9-tetrahydro-5H-imidazo[1,5-a][1,4]diazepine-1-carboxamide;

(S)—N-(2,2-dimethyl-1-(3-methyl-1,2,4-oxadiazol-5-yl)propyl)-8-methyl-3-phenyl-6,7,8,9-tetrahydro-5H-imidazo[1,5-a][1,4]diazepine-1-carboxamide;

(S)—N-(2,2-dimethyl-1-(3-methyl-1,2,4-oxadiazol-5-yl)propyl)-3-(2-fluoro-4-methyl-phenyl)-8-methyl-6,7,8,9-tetrahydro-5H-imidazo[1,5-a][1,4]diazepine-1-carboxamide;

(S)—N-(2,2-dimethyl-1-(3-methyl-1,2,4-oxadiazol-5-yl)propyl)-3-(2-fluoro-4-methyl-phenyl)-8-isopropyl-6,7,8,9-tetrahydro-5H-imidazo[1,5-a][1,4]diazepine-1-carboxamide;

(S)—N-(2,2-dimethyl-1-(3-methyl-1,2,4-oxadiazol-5-yl)propyl)-8-ethyl-3-phenyl-6,7,8,9-tetrahydro-5H-imidazo[1,5-a][1,4]diazepine-1-carboxamide;

(S)—N-(2,2-dimethyl-1-(3-methyl-1,2,4-oxadiazol-5-yl)propyl)-8-isopropyl-3-phenyl-6,7,8,9-tetrahydro-5H-imidazo[1,5-a][1,4]diazepine-1-carboxamide;

(S)-3-(4-chloro-2-fluorophenyl)-N-(3,3-dimethyl-1-(methylamino)-1-oxobutan-2-yl)-8-(piperidin-4-yl)-6,7,8,9-tetrahydro-5H-imidazo[1,5-a][1,4]diazepine-1-carboxamide;

(S)-8-(1-acetylpiperidin-4-yl)-3-(4-chloro-2-fluorophenyl)-N-(3,3-dimethyl-1-(methylamino)-1-oxobutan-2-yl)-6,7,8,9-tetrahydro-5H-imidazo[1,5-a][1,4]diazepine-1-carboxamide;

(S)-3-(4,4-difluorocyclohexyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;

(S)-3-(4-chloro-2-fluorophenyl)-8-methyl-N-(4-methyl-1-(methylamino)-1-oxopentan-2-yl)-6,7,8,9-tetrahydro-5H-imidazo[1,5-a][1,4]diazepine-1-carboxamide;

(S)-3-(4-fluorophenyl)-8-methyl-N-(4-methyl-1-(methylamino)-1-oxopentan-2-yl)-6,7,8,9-tetrahydro-5H-imidazo[1,5-a][1,4]diazepine-1-carboxamide;

(S)-3-(3-fluorophenyl)-8-methyl-N-(4-methyl-1-(methylamino)-1-oxopentan-2-yl)-6,7,8,9-tetrahydro-5H-imidazo[1,5-a][1,4]diazepine-1-carboxamide;

(S)-3-(2,5-difluorophenyl)-8-methyl-N-(4-methyl-1-(methylamino)-1-oxopentan-2-yl)-6,7,8,9-tetrahydro-5H-imidazo[1,5-a][1,4]diazepine-1-carboxamide;

(S)-3-(2-fluoro-4-(trifluoromethyl)phenyl)-8-methyl-N-(4-methyl-1-(methyl-amino)-1-oxopentan-2-yl)-6,7,8,9-tetrahydro-5H-imidazo[1,5-a][1,4]-diazepine-1-carboxamide;

(S)-3-(2,4-difluorophenyl)-8-methyl-N-(4-methyl-1-(methylamino)-1-oxopentan-2-yl)-6,7,8,9-tetrahydro-5H-imidazo[1,5-a][1,4]diazepine-1-carboxamide;

(S)-3-(3,4-difluorophenyl)-8-methyl-N-(4-methyl-1-(methylamino)-1-oxopentan-2-yl)-6,7,8,9-tetrahydro-5H-imidazo[1,5-a][1,4]diazepine-1-carboxamide;

(S)-3-(5-chloro-2-fluorophenyl)-8-methyl-N-(4-methyl-1-(methylamino)-1-oxo-pentan-2-yl)-6,7,8,9-tetrahydro-5H-imidazo[1,5-a][1,4]diazepine-1-carboxamide;

(S)-3-(3-chloro-4-fluorophenyl)-8-methyl-N-(4-methyl-1-(methylamino)-1-oxo-pentan-2-yl)-6,7,8,9-tetrahydro-5H-imidazo[1,5-a][1,4]diazepine-1-carboxamide;

(S)-8-methyl-N-(4-methyl-1-(methylamino)-1-oxopentan-2-yl)-3-(2,4,5-trifluoro-phenyl)-6,7,8,9-tetrahydro-5H-imidazo[1,5-a][1,4]diazepine-1-carboxamide;

(S)-3-(5-chloro-2,4-difluorophenyl)-8-methyl-N-(4-methyl-1-(methylamino)-1-oxo-pentan-2-yl)-6,7,8,9-tetrahydro-5H-imidazo[1,5-a][1,4]diazepine-1-carboxamide;

(S)-3-cyclohexyl-8-methyl-N-(4-methyl-1-(methylamino)-1-oxopentan-2-yl)-6,7,8,9-tetrahydro-5H-imidazo[1,5-a][1,4]diazepine-1-carboxamide (S)—N-(1-cyclohexyl-2-(methylamino)-2-oxoethyl)-8-methyl-3-(2,4,5-trifluoro-phenyl)-6,7,8,9-tetrahydro-5H-imidazo[1,5-a][1,4]diazepine-1-carboxamide;

(S)-3-(5-chloro-2,4-difluorophenyl)-N-(1-cyclohexyl-2-(methylamino)-2-oxoethyl)-8-methyl-6,7,8,9-tetrahydro-5H-imidazo[1,5-a][1,4]diazepine-1-carboxamide;

(S)-8-methyl-N-(2-(methylamino)-2-oxo-1-phenylethyl)-3-phenyl-6,7,8,9-tetrahydro-5H-imidazo[1,5-a][1,4]diazepine-1-carboxamide;

- (S)-3-(4-chloro-2-fluorophenyl)-N-(4,4-dimethyl-1-(methylamino)-1-oxopentan-2-yl)-8-methyl-6,7,8,9-tetrahydro-5H-imidazo[1,5-a][1,4]diazepine-1-carboxamide;
- (S)-3-(5-chloro-2-fluorophenyl)-N-(4,4-dimethyl-1-(methylamino)-1-oxopentan-2-yl)-8-methyl-6,7,8,9-tetrahydro-5H-imidazo[1,5-a][1,4]diazepine-1-carboxamide;
- (S)-3-(3-chloro-4-fluorophenyl)-N-(4,4-dimethyl-1-(methylamino)-1-oxopentan-2-yl)-8-methyl-6,7,8,9-tetrahydro-5H-imidazo[1,5-a][1,4]diazepine-1-carboxamide;
- (S)—N-(4,4-dimethyl-1-(methylamino)-1-oxopentan-2-yl)-3-(4-fluorophenyl)-8-methyl-6,7,8,9-tetrahydro-5H-imidazo[1,5-a][1,4]diazepine-1-carboxamide;
- (S)—N-(4,4-dimethyl-1-(methylamino)-1-oxopentan-2-yl)-3-(3-fluorophenyl)-8-methyl-6,7,8,9-tetrahydro-5H-imidazo[1,5-a][1,4]diazepine-1-carboxamide;
- (S)-3-(2,4-difluorophenyl)-N-(4,4-dimethyl-1-(methylamino)-1-oxopentan-2-yl)-8-methyl-6,7,8,9-tetrahydro-5H-imidazo[1,5-a][1,4]diazepine-1-carboxamide;
- (S)-3-(4-chloro-3-fluorophenyl)-N-(4,4-dimethyl-1-(methylamino)-1-oxopentan-2-yl)-8-methyl-6,7,8,9-tetrahydro-5H-imidazo[1,5-a][1,4]diazepine-1-carboxamide;
- (S)—N-(4,4-dimethyl-1-(methylamino)-1-oxopentan-2-yl)-3-(2-fluoro-4-(trifluoromethyl)phenyl)-8-methyl-6,7,8,9-tetrahydro-5H-imidazo[1,5-a][1,4]diazepine-1-carboxamide;
- (S)-3-(3,4-difluorophenyl)-N-(4,4-dimethyl-1-(methylamino)-1-oxopentan-2-yl)-8-methyl-6,7,8,9-tetrahydro-5H-imidazo[1,5-a][1,4]diazepine-1-carboxamide;
- (S)-3-(2,5-difluorophenyl)-N-(4,4-dimethyl-1-(methylamino)-1-oxopentan-2-yl)-8-methyl-6,7,8,9-tetrahydro-5H-imidazo[1,5-a][1,4]diazepine-1-carboxamide;
- (S)-3-(5-chloro-2,4-difluorophenyl)-N-(4,4-dimethyl-1-(methylamino)-1-oxopentan-2-yl)-8-methyl-6,7,8,9-tetrahydro-5H-imidazo[1,5-a][1,4]-diazepine-1-carboxamide;
- (S)—N-(4,4-dimethyl-1-(methylamino)-1-oxopentan-2-yl)-8-methyl-3-(2,4,5-trifluorophenyl)-6,7,8,9-tetrahydro-5H-imidazo[1,5-a][1,4]diazepine-1-carboxamide;
- (S)-3-(4-chloro-2-fluorophenyl)-N-(1-(dimethylamino)-3,3-dimethyl-1-oxobutan-2-yl)-8-methyl-6,7,8,9-tetrahydro-5H-imidazo[1,5-a][1,4]diazepine-1-carboxamide;
- (S)—N-(1-(dimethylamino)-3,3-dimethyl-1-oxobutan-2-yl)-8-methyl-3-phenyl-6,7,8,9-tetrahydro-5H-imidazo[1,5-a][1,4]diazepine-1-carboxamide;
- (S)-3-(3-chloro-4-fluorophenyl)-N-(1-(dimethylamino)-3,3-dimethyl-1-oxobutan-2-yl)-8-methyl-6,7,8,9-tetrahydro-5H-imidazo[1,5-a][1,4]diazepine-1-carboxamide;
- (S)-3-(5-chloro-2-fluorophenyl)-N-(1-(dimethylamino)-3,3-dimethyl-1-oxobutan-2-yl)-8-methyl-6,7,8,9-tetrahydro-5H-imidazo[1,5-a][1,4]diazepine-1-carboxamide;
- (S)-3-(4-chloro-3-fluorophenyl)-N-(1-(dimethylamino)-3,3-dimethyl-1-oxobutan-2-yl)-8-methyl-6,7,8,9-tetrahydro-5H-imidazo[1,5-a][1,4]diazepine-1-carboxamide;
- (S)-3-(3,4-difluorophenyl)-N-(1-(dimethylamino)-3,3-dimethyl-1-oxobutan-2-yl)-8-methyl-6,7,8,9-tetrahydro-5H-imidazo[1,5-a][1,4]diazepine-1-carboxamide;
- (S)-3-(2,5-difluorophenyl)-N-(1-(dimethylamino)-3,3-dimethyl-1-oxobutan-2-yl)-8-methyl-6,7,8,9-tetrahydro-5H-imidazo[1,5-a][1,4]diazepine-1-carboxamide;
- (S)-3-(2,4-difluorophenyl)-N-(1-(dimethylamino)-3,3-dimethyl-1-oxobutan-2-yl)-8-methyl-6,7,8,9-tetrahydro-5H-imidazo[1,5-a][1,4]diazepine-1-carboxamide;
- (S)—N-(1-amino-4-methyl-1-oxopentan-2-yl)-3-(4-chloro-2-fluorophenyl)-8-methyl-6,7,8,9-tetrahydro-5H-imidazo[1,5-a][1,4]diazepine-1-carboxamide;
- (S)—N-(1-amino-4-methyl-1-oxopentan-2-yl)-3-(4-fluorophenyl)-8-methyl-6,7,8,9-tetrahydro-5H-imidazo[1,5-a][1,4]diazepine-1-carboxamide;
- (S)—N-(1-amino-4-methyl-1-oxopentan-2-yl)-3-(3-fluorophenyl)-8-methyl-6,7,8,9-tetrahydro-5H-imidazo[1,5-a][1,4]diazepine-1-carboxamide;
- (S)—N-(1-amino-4-methyl-1-oxopentan-2-yl)-3-(2,5-difluorophenyl)-8-methyl-6,7,8,9-tetrahydro-5H-imidazo[1,5-a][1,4]diazepine-1-carboxamide;
- (S)—N-(1-amino-4-methyl-1-oxopentan-2-yl)-3-(2,4-difluorophenyl)-8-methyl-6,7,8,9-tetrahydro-5H-imidazo[1,5-a][1,4]diazepine-1-carboxamide;
- (S)—N-(1-amino-4-methyl-1-oxopentan-2-yl)-3-(5-chloro-2-fluorophenyl)-8-methyl-6,7,8,9-tetrahydro-5H-imidazo[1,5-a][1,4]diazepine-1-carboxamide;
- (S)—N-(1-amino-4-methyl-1-oxopentan-2-yl)-3-cyclohexyl-8-methyl-6,7,8,9-tetrahydro-5H-imidazo[1,5-a][1,4]diazepine-1-carboxamide;
- (S)—N-(1-amino-4-methyl-1-oxopentan-2-yl)-3-(5-chloro-2,4-difluorophenyl)-8-methyl-6,7,8,9-tetrahydro-5H-imidazo[1,5-a][1,4]diazepine-1-carboxamide;
- (S)—N-(1-amino-4-methyl-1-oxopentan-2-yl)-8-methyl-3-(2,4,5-trifluorophenyl)-6,7,8,9-tetrahydro-5H-imidazo[1,5-a][1,4]diazepine-1-carboxamide;
- (S)—N-(1-amino-3,3-dimethyl-1-oxobutan-2-yl)-3-(4-chloro-2-fluorophenyl)-8-methyl-6,7,8,9-tetrahydro-5H-imidazo[1,5-a][1,4]diazepine-1-carboxamide;
- (S)—N-(1-amino-3,3-dimethyl-1-oxobutan-2-yl)-3-(5-chloro-2-fluorophenyl)-8-methyl-6,7,8,9-tetrahydro-5H-imidazo[1,5-a][1,4]diazepine-1-carboxamide;
- (S)—N-(1-amino-3,3-dimethyl-1-oxobutan-2-yl)-3-(2,5-difluorophenyl)-8-methyl-6,7,8,9-tetrahydro-5H-imidazo[1,5-a][1,4]diazepine-1-carboxamide;
- (S)—N-(1-amino-3,3-dimethyl-1-oxobutan-2-yl)-3-(3-chloro-4-fluorophenyl)-8-methyl-6,7,8,9-tetrahydro-5H-imidazo[1,5-a][1,4]diazepine-1-carboxamide;
- (S)—N-(1-amino-3,3-dimethyl-1-oxobutan-2-yl)-3-(4-chloro-3-fluorophenyl)-8-methyl-6,7,8,9-tetrahydro-5H-imidazo[1,5-a][1,4]diazepine-1-carboxamide;
- (S)—N-(1-amino-3,3-dimethyl-1-oxobutan-2-yl)-3-(2,4-difluorophenyl)-8-methyl-6,7,8,9-tetrahydro-5H-imidazo[1,5-a][1,4]diazepine-1-carboxamide;
- (S)—N-(1-amino-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide;
- (S)—N-(1-amino-3,3-dimethyl-1-oxobutan-2-yl)-3-(5-chloro-2,4-difluorophenyl)-8-methyl-6,7,8,9-tetrahydro-5H-imidazo[1,5-a][1,4]diazepine-1-carboxamide;
- (S)—N-(1-amino-3,3-dimethyl-1-oxobutan-2-yl)-3-(3,4-difluorophenyl)-8-methyl-6,7,8,9-tetrahydro-5H-imidazo[1,5-a][1,4]diazepine-1-carboxamide;
- (S)—N-(1-amino-3,3-dimethyl-1-oxobutan-2-yl)-8-methyl-3-phenyl-6,7,8,9-tetrahydro-5H-imidazo[1,5-a][1,4]diazepine-1-carboxamide;
- (S)—N-(1-amino-4,4-dimethyl-1-oxopentan-2-yl)-3-(2,5-difluorophenyl)-8-methyl-6,7,8,9-tetrahydro-5H-imidazo[1,5-a][1,4]diazepine-1-carboxamide;
- (S)—N-(1-amino-4,4-dimethyl-1-oxopentan-2-yl)-3-(4-chloro-2-fluorophenyl)-8-methyl-6,7,8,9-tetrahydro-5H-imidazo[1,5-a][1,4]diazepine-1-carboxamide;

(S)—N-(1-amino-4,4-dimethyl-1-oxopentan-2-yl)-3-(5-chloro-2-fluorophenyl)-8-methyl-6,7,8,9-tetrahydro-5H-imidazo[1,5-a][1,4]diazepine-1-carboxamide;
(S)—N-(1-amino-4,4-dimethyl-1-oxopentan-2-yl)-3-(3,4-difluorophenyl)-8-methyl-6,7,8,9-tetrahydro-5H-imidazo[1,5-a][1,4]diazepine-1-carboxamide;
(S)—N-(1-amino-4,4-dimethyl-1-oxopentan-2-yl)-3-(3-chloro-4-fluorophenyl)-8-methyl-6,7,8,9-tetrahydro-5H-imidazo[1,5-a][1,4]diazepine-1-carboxamide;
(S)—N-(1-amino-4,4-dimethyl-1-oxopentan-2-yl)-3-(4-chloro-3-fluorophenyl)-8-methyl-6,7,8,9-tetrahydro-5H-imidazo[1,5-a][1,4]diazepine-1-carboxamide;
(S)—N-(1-amino-4,4-dimethyl-1-oxopentan-2-yl)-3-(2,4-difluorophenyl)-8-methyl-6,7,8,9-tetrahydro-5H-imidazo[1,5-a][1,4]diazepine-1-carboxamide;
(S)—N-(1-amino-4,4-dimethyl-1-oxopentan-2-yl)-8-methyl-3-(2,4,5-trifluoro-phenyl)-6,7,8,9-tetrahydro-5H-imidazo[1,5-a][1,4]diazepine-1-carboxamide;
(S)—N-(1-amino-4,4-dimethyl-1-oxopentan-2-yl)-3-(5-chloro-2,4-difluorophenyl)-8-methyl-6,7,8,9-tetrahydro-5H-imidazo[1,5-a][1,4]diazepine-1-carboxamide;
(S)-8-methyl-N-(1-(methylamino)-1-oxo-3-(thiazol-4-yl)propan-2-yl)-3-(2,4,5-trifluorophenyl)-6,7,8,9-tetrahydro-5H-imidazo[1,5-a][1,4]diazepine-1-carboxamide;
(S)-3-(5-chloro-2,4-difluorophenyl)-8-methyl-N-(1-(methylamino)-1-oxo-3-(thiazol-4-yl)propan-2-yl)-6,7,8,9-tetrahydro-5H-imidazo[1,5-a][1,4]-diazepine-1-carboxamide;
(S)-3-(3,6-dihydro-2H-pyran-4-yl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;
N-(5-tert-butylisoxazol-3-yl)-8-methyl-3-phenyl-6,7,8,9-tetrahydro-5H-imidazo[1,5-a][1,4]diazepine-1-carboxamide;
N-(4-tert-butylthiazol-2-yl)-8-methyl-3-phenyl-6,7,8,9-tetrahydro-5H-imidazo[1,5-a][1,4]diazepine-1-carboxamide;
(S)-3-chloro-N-(3,3-dimethyl-1-(methylamino)-1-oxobutan-2-yl)-6,7,8,9-tetrahydro-5H-imidazo[1,5-a][1,4]diazepine-1-carboxamide;
(S)-3-chloro-N-(3,3-dimethyl-1-(methylamino)-1-oxobutan-2-yl)-8-methyl-6,7,8,9-tetrahydro-5H-imidazo[1,5-a][1,4]diazepine-1-carboxamide;
(S)-3-(3,5-bis(trifluoromethyl)phenyl)-N-(3,3-dimethyl-1-(methylamino)-1-oxobutan-2-yl)-8-methyl-6,7,8,9-tetrahydro-5H-imidazo[1,5-a][1,4]-diazepine-1-carboxamide;
(S)-3-(4-bromo-2-fluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide;
(S)-3-(2,6-difluorophenyl)-N-(3,3-dimethyl-1-(methylamino)-1-oxobutan-2-yl)-8-methyl-6,7,8,9-tetrahydro-5H-imidazo[1,5-a][1,4]diazepine-1-carboxamide
(S)—N-methyl-1-(3-phenyl-6,7,8,9-tetrahydro-5H-imidazo[1,5-a][1,4]diazepine-1-carbonyl)pyrrolidine-2-carboxamide;
(S)—N-methyl-1-(8-methyl-3-phenyl-6,7,8,9-tetrahydro-5H-imidazo[1,5-a][1,4]-diazepine-1-carbonyl)pyrrolidine-2-carboxamide;
N-(3-fluoro-3-methyl-1-(methylamino)-1-oxobutan-2-yl)-3-phenyl-6,7,8,9-tetrahydro-5H-imidazo[1,5-a][1,4]diazepine-1-carboxamide;
N-(3-fluoro-3-methyl-1-(methylamino)-1-oxobutan-2-yl)-8-methyl-3-phenyl-6,7,8,9-tetrahydro-5H-imidazo[1,5-a][1,4]diazepine-1-carboxamide;
(S)—N-(3-hydroxy-3-methyl-1-(methylamino)-1-oxobutan-2-yl)-3-phenyl-6,7,8,9-tetrahydro-5H-imidazo[1,5-a][1,4]diazepine-1-carboxamide;
3-(5-chloro-2-fluorophenyl)-N—((S)-1-((1S,2S)-2-hydroxycyclopentylamino)-3,3-dimethyl-1-oxobutan-2-yl)-8-methyl-6,7,8,9-tetrahydro-5H-imidazo[1,5-a][1,4]diazepine-1-carboxamide;
(S)-3-(5-chloro-2-fluorophenyl)-N-(1-(3-fluoroazetidin-1-yl)-3,3-dimethyl-1-oxobutan-2-yl)-8-methyl-6,7,8,9-tetrahydro-5H-imidazo[1,5-a][1,4]diazepine-1-carboxamide;
(S)-3-(5-chloro-2-fluorophenyl)-N-(1-(2-hydroxy-2-methylpropylamino)-3,3-dimethyl-1-oxobutan-2-yl)-8-methyl-6,7,8,9-tetrahydro-5H-imidazo[1,5-a][1,4]diazepine-1-carboxamide;
3-(5-chloro-2-fluorophenyl)-N—((S)-1-((S)-3-hydroxypiperidin-1-yl)-3,3-dimethyl-1-oxobutan-2-yl)-8-methyl-6,7,8,9-tetrahydro-5H-imidazo[1,5-a][1,4]diazepine-1-carboxamide;
(S)-3-(5-chloro-2-fluorophenyl)-N-(1-(4-hydroxypiperidin-1-yl)-3,3-dimethyl-1-oxobutan-2-yl)-8-methyl-6,7,8,9-tetrahydro-5H-imidazo[1,5-a][1,4]diazepine-1-carboxamide;
(S)-3-(5-chloro-2-fluorophenyl)-N-(1-(3,4-dihydroisoquinolin-2(1H)-yl)-3,3-dimethyl-1-oxobutan-2-yl)-8-methyl-6,7,8,9-tetrahydro-5H-imidazo[1,5-a][1,4]diazepine-1-carboxamide;
(S)-3-(5-chloro-2-fluorophenyl)-N-(1-(ethyl(2-hydroxyethyl)amino)-3,3-dimethyl-1-oxobutan-2-yl)-8-methyl-6,7,8,9-tetrahydro-5H-imidazo[1,5-a][1,4]diazepine-1-carboxamide;
3-(5-chloro-2-fluorophenyl)-N—((S)-1-((S)-3-hydroxypyrrolidin-1-yl)-3,3-dimethyl-1-oxobutan-2-yl)-8-methyl-6,7,8,9-tetrahydro-5H-imidazo[1,5-a][1,4]diazepine-1-carboxamide;
3-(5-chloro-2-fluorophenyl)-N—((S)-1-((1R,2R)-2-hydroxycyclopentylamino)-3,3-dimethyl-1-oxobutan-2-yl)-8-methyl-6,7,8,9-tetrahydro-5H-imidazo[1,5-a][1,4]diazepine-1-carboxamide;
(S)-3-(5-chloro-2-fluorophenyl)-N-(1-(2-hydroxyethylamino)-3,3-dimethyl-1-oxobutan-2-yl)-8-methyl-6,7,8,9-tetrahydro-5H-imidazo[1,5-a][1,4]diazepine-1-carboxamide;
(S)-3-(5-chloro-2-fluorophenyl)-N-(1-(1-(hydroxymethyl)cyclopentylamino)-3,3-dimethyl-1-oxobutan-2-yl)-8-methyl-6,7,8,9-tetrahydro-5H-imidazo[1,5-a][1,4]diazepine-1-carboxamide;
3-(5-chloro-2-fluorophenyl)-N-((2S)-1-(2-(hydroxymethyl)piperidin-1-yl)-3,3-dimethyl-1-oxobutan-2-yl)-8-methyl-6,7,8,9-tetrahydro-5H-imidazo[1,5-a][1,4]diazepine-1-carboxamide;
(S)-3-(5-chloro-2-fluorophenyl)-N-(1-(diethylamino)-3,3-dimethyl-1-oxobutan-2-yl)-8-methyl-6,7,8,9-tetrahydro-5H-imidazo[1,5-a][1,4]diazepine-1-carboxamide;
(2,6-dimethylmorpholino)(8-methyl-3-(2,4,5-trifluorophenyl)-6,7,8,9-tetrahydro-5H-imidazo[1,5-a][1,4]diazepin-1-yl)methanone;
(2-tert-butylpyrrolidin-1-yl)(8-methyl-3-(2,4,5-trifluorophenyl)-6,7,8,9-tetrahydro-5H-imidazo[1,5-a][1,4]diazepin-1-yl)methanone;
(3-hydroxyazetidin-1-yl)(8-methyl-3-(2,4,5-trifluorophenyl)-6,7,8,9-tetrahydro-5H-imidazo[1,5-a][1,4]diazepin-1-yl)methanone;
(3-hydroxypyrrolidin-1-yl)(8-methyl-3-(2,4,5-trifluorophenyl)-6,7,8,9-tetrahydro-5H-imidazo[1,5-a][1,4]diazepin-1-yl)methanone;

(R)—N-(1-hydroxy-3,3-dimethylbutan-2-yl)-8-methyl-3-(2,4,5-trifluorophenyl)-6,7,8,9-tetrahydro-5H-imidazo[1,5-a][1,4]diazepine-1-carboxamide;

(8-methyl-3-(2,4,5-trifluorophenyl)-6,7,8,9-tetrahydro-5H-imidazo[1,5-a][1,4]diazepin-1-yl)(morpholino)methanone;

(S)—N-(1-(3-fluoroazetidin-1-yl)-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide;

(S)-3-(2,5-difluorophenyl)-N-(1-(3-fluoroazetidin-1-yl)-3,3-dimethyl-1-oxobutan-2-yl)-8-methyl-6,7,8,9-tetrahydro-5H-imidazo[1,5-a][1,4]diazepine-1-carboxamide;

(S)-3-(5-chloro-2-fluorophenyl)-N-(1-(ethylamino)-3,3-dimethyl-1-oxobutan-2-yl)-8-methyl-6,7,8,9-tetrahydro-5H-imidazo[1,5-a][1,4]diazepine-1-carboxamide;

(S)—N-(3,3-dimethyl-1-oxo-1-(thiazol-2-ylamino)butan-2-yl)-8-methyl-3-(2,4,5-trifluorophenyl)-6,7,8,9-tetrahydro-5H-imidazo[1,5-a][1,4]diazepine-1-carboxamide;

(S)—N-(2,2-dimethyl-1-(3-methyl-1,2,4-oxadiazol-5-yl)propyl)-3-(2,4,5-trifluorophenyl)-6,7,8,9-tetrahydro-5H-imidazo[1,5-a][1,4]diazepine-1-carboxamide;

(S)—N-(2-hydroxy-2,4,4-trimethylpentan-3-yl)-8-methyl-3-(2,4,5-trifluorophenyl)-6,7,8,9-tetrahydro-5H-imidazo[1,5-a][1,4]diazepine-1-carboxamide;

(S)—N-(2,2-dimethyl-1-(3-methyl-1,2,4-oxadiazol-5-yl)propyl)-8-methyl-3-(2,4,5-trifluorophenyl)-6,7,8,9-tetrahydro-5H-imidazo[1,5-a][1,4]diazepine-1-carboxamide;

(S)-3-(5-chloro-2-fluorophenyl)-N-(1-(2,2-difluoroethylamino)-3,3-dimethyl-1-oxobutan-2-yl)-8-methyl-6,7,8,9-tetrahydro-5H-imidazo[1,5-a][1,4]diazepine-1-carboxamide;

(S)—N-(1-(azetidin-1-yl)-3,3-dimethyl-1-oxobutan-2-yl)-3-(5-chloro-2,4-difluorophenyl)-8-methyl-6,7,8,9-tetrahydro-5H-imidazo[1,5-a][1,4]diazepine-1-carboxamide;

(S)—N-(1-(azetidin-1-yl)-3,3-dimethyl-1-oxobutan-2-yl)-3-(2,5-difluorophenyl)-8-methyl-6,7,8,9-tetrahydro-5H-imidazo[1,5-a][1,4]diazepine-1-carboxamide;

(S)-3-(5-chloro-2-fluorophenyl)-N-(1-(5,6-dihydro-[1,2,4]triazolo[4,3-a]pyrazin-7(8H)-yl)-3,3-dimethyl-1-oxobutan-2-yl)-8-methyl-6,7,8,9-tetrahydro-5H-imidazo[1,5-a][1,4]diazepine-1-carboxamide;

methyl 2-(3-(5-chloro-2,4-difluorophenyl)-8-methyl-6,7,8,9-tetrahydro-5H-imidazo[1,5-a][1,4]diazepine-1-carboxamido)-2-methylpropanoate;

3-(5-chloro-2,4-difluorophenyl)-8-methyl-N-(2-methyl-1-(methylamino)-1-oxopropan-2-yl)-6,7,8,9-tetrahydro-5H-imidazo[1,5-a][1,4]diazepine-1-carboxamide;

3-(5-chloro-2,4-difluorophenyl)-N-(1-(3,3-difluoroazetidine-1-carbonyl)cyclopropyl)-8-methyl-6,7,8,9-tetrahydro-5H-imidazo[1,5-a][1,4]diazepine-1-carboxamide;

(S)—N-(1-(3,3-difluoroazetidin-1-yl)-3,3-dimethyl-1-oxobutan-2-yl)-3-(2,5-difluorophenyl)-6,7,8,9-tetrahydro-5H-imidazo[1,5-a][1,4]diazepine-1-carboxamide;

3-(5-chloro-2,4-difluorophenyl)-8-methyl-N-(2-methyl-1-morpholinopropan-2-yl)-6,7,8,9-tetrahydro-5H-imidazo[1,5-a][1,4]diazepine-1-carboxamide;

3-(5-chloro-2,4-difluorophenyl)-N-(4-hydroxy-2-methylpentan-2-yl)-8-methyl-6,7,8,9-tetrahydro-5H-imidazo[1,5-a][1,4]diazepine-1-carboxamide;

3-(5-chloro-2,4-difluorophenyl)-N-(1-(4-fluorophenyl)-2-methylpropan-2-yl)-8-methyl-6,7,8,9-tetrahydro-5H-imidazo[1,5-a][1,4]diazepine-1-carboxamide;

3-(5-chloro-2,4-difluorophenyl)-N-(2-cyclopropylpropan-2-yl)-8-methyl-6,7,8,9-tetrahydro-5H-imidazo[1,5-a][1,4]diazepine-1-carboxamide;

3-(5-chloro-2,4-difluorophenyl)-8-methyl-N-(2-methyl-1-(4-methylpiperazin-1-yl)propan-2-yl)-6,7,8,9-tetrahydro-5H-imidazo[1,5-a][1,4]diazepine-1-carboxamide;

3-(5-chloro-2,4-difluorophenyl)-8-methyl-N-(2-methyl-1-(4-methylpiperidin-1-yl)propan-2-yl)-6,7,8,9-tetrahydro-5H-imidazo[1,5-a][1,4]diazepine-1-carboxamide;

3-(5-chloro-2,4-difluorophenyl)-N-(2-(4-methoxyphenyl)propan-2-yl)-8-methyl-6,7,8,9-tetrahydro-5H-imidazo[1,5-a][1,4]diazepine-1-carboxamide;

3-(5-chloro-2,4-difluorophenyl)-N—((S)-1-((S)-3-hydroxypyrrolidin-1-yl)-3,3-dimethyl-1-oxobutan-2-yl)-8-methyl-6,7,8,9-tetrahydro-5H-imidazo[1,5-a][1,4]diazepine-1-carboxamide;

(S)—N-(1-(isoindolin-2-yl)-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide;

(S)—N-(1-(2-hydroxyethylamino)-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide;

(S)—N-(1-(3-fluoroazetidin-1-yl)-3,3-dimethyl-1-oxobutan-2-yl)-3-(2,4,5-trifluorophenyl)-6,7,8,9-tetrahydro-5H-imidazo[1,5-a][1,4]diazepine-1-carboxamide;

(S)-3-(5-chloro-2,4-difluorophenyl)-N-(1-(2-hydroxyethylamino)-3,3-dimethyl-1-oxobutan-2-yl)-8-methyl-6,7,8,9-tetrahydro-5H-imidazo[1,5-a][1,4]diazepine-1-carboxamide;

(S)—N-(1-(3,3-difluoroazetidin-1-yl)-3,3-dimethyl-1-oxobutan-2-yl)-3-(2,4,5-trifluorophenyl)-6,7,8,9-tetrahydro-5H-imidazo[1,5-a][1,4]diazepine-1-carboxamide;

(S)—N-(1-(isoindolin-2-yl)-3,3-dimethyl-1-oxobutan-2-yl)-3-(2,4,5-trifluorophenyl)-6,7,8,9-tetrahydro-5H-imidazo[1,5-a][1,4]diazepine-1-carboxamide;

(S)-3-(5-chloro-2,4-difluorophenyl)-N-(2,2-dimethyl-1-(5-methyl-1,3,4-oxadiazol-2-yl)propyl)-8-methyl-6,7,8,9-tetrahydro-5H-imidazo[1,5-a][1,4]diazepine-1-carboxamide;

(S)-3-(5-chloro-2,4-difluorophenyl)-8-ethyl-N-(1-(ethylamino)-3,3-dimethyl-1-oxobutan-2-yl)-6,7,8,9-tetrahydro-5H-imidazo[1,5-a][1,4]diazepine-1-carboxamide;

(S)-3-(5-chloro-2,4-difluorophenyl)-N-(3,3-dimethyl-1-(methylamino)-1-oxobutan-2-yl)-8-ethyl-6,7,8,9-tetrahydro-5H-imidazo[1,5-a][1,4]diazepine-1-carboxamide;

(S)-3-(5-chloro-2,4-difluorophenyl)-N-(1-(ethylamino)-3,3-dimethyl-1-oxobutan-2-yl)-6,7,8,9-tetrahydro-5H-imidazo[1,5-a][1,4]diazepine-1-carboxamide;

(S)-3-(5-chloro-2,4-difluorophenyl)-N-(1-(5-isopropyl-1,3,4-oxadiazol-2-yl)-2,2-dimethylpropyl)-8-methyl-6,7,8,9-tetrahydro-5H-imidazo[1,5-a][1,4]diazepine-1-carboxamide;

(S)—N-(1-(5-tert-butyl-1,3,4-oxadiazol-2-yl)-2,2-dimethylpropyl)-3-(5-chloro-2,4-difluorophenyl)-8-methyl-6,7,8,9-tetrahydro-5H-imidazo[1,5-a][1,4]diazepine-1-carboxamide;

N—((S)-1-((R)-2-(hydroxymethyl)pyrrolidin-1-yl)-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide;

(S)—N-(1-(3-methoxyazetidin-1-yl)-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide;

N-((2S)-1-(3-methoxypyrrolidin-1-yl)-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide;

(S)—N-(3,3-dimethyl-1-(methylamino)-1-oxobutan-2-yl)-8-methyl-3-(thiazol-2-yl)-6,7,8,9-tetrahydro-5H-imidazo[1,5-a][1,4]diazepine-1-carboxamide;

N—((S)-1-((S)-3-hydroxypyrrolidin-1-yl)-3,3-dimethyl-1-oxobutan-2-yl)-8-methyl-3-(2,4,5-trifluorophenyl)-6,7,8,9-tetrahydro-5H-imidazo[1,5-a][1,4]diazepine-1-carboxamide;

(S)—N-(1-(3,3-difluoroazetidin-1-yl)-3,3-dimethyl-1-oxobutan-2-yl)-3-(2,4-difluorophenyl)-6,7,8,9-tetrahydro-5H-imidazo[1,5-a][1,4]diazepine-1-carboxamide;

(S)—N-(1-(3,3-difluoroazetidin-1-yl)-3,3-dimethyl-1-oxobutan-2-yl)-3-(2,4-difluorophenyl)-8-ethyl-6,7,8,9-tetrahydro-5H-imidazo[1,5-a][1,4]diazepine-1-carboxamide;

(S)-8-cyclopropyl-N-(3,3-dimethyl-1-(methylamino)-1-oxobutan-2-yl)-3-(2,4,5-trifluorophenyl)-6,7,8,9-tetrahydro-5H-imidazo[1,5-a][1,4]diazepine-1-carboxamide;

ethyl 1-(3-(5-chloro-2,4-difluorophenyl)-8-methyl-6,7,8,9-tetrahydro-5H-imidazo[1,5-a][1,4]diazepine-1-carboxamido)cyclopropanecarboxylate;

(S)-3-(2,5-difluorophenyl)-N-(3,3-dimethyl-1-(methylamino)-1-oxobutan-2-yl)-6,7,8,9-tetrahydro-5H-imidazo[1,5-a][1,4]diazepine-1-carboxamide;

3-(5-chloro-2,4-difluorophenyl)-8-methyl-N-(1-(methylcarbamoyl)cyclopropyl)-6,7,8,9-tetrahydro-5H-imidazo[1,5-a][1,4]diazepine-1-carboxamide;

(S)-3-(2,5-difluorophenyl)-N-(3,3-dimethyl-1-(methylamino)-1-oxobutan-2-yl)-8-ethyl-6,7,8,9-tetrahydro-5H-imidazo[1,5-a][1,4]diazepine-1-carboxamide;

(S)-3-(3,4-difluorophenyl)-N-(3,3-dimethyl-1-(methylamino)-1-oxobutan-2-yl)-8-ethyl-6,7,8,9-tetrahydro-5H-imidazo[1,5-a][1,4]diazepine-1-carboxamide;

(S)—N-(1-(3,3-difluoroazetidin-1-yl)-3,3-dimethyl-1-oxobutan-2-yl)-3-(3-fluorophenyl)-8-methyl-6,7,8,9-tetrahydro-5H-imidazo[1,5-a][1,4]diazepine-1-carboxamide;

3-(5-chloro-2-fluorophenyl)-N—((S)-1-((R)-3-hydroxypyrrolidin-1-yl)-3,3-dimethyl-1-oxobutan-2-yl)-8-methyl-6,7,8,9-tetrahydro-5H-imidazo[1,5-a][1,4]diazepine-1-carboxamide;

(S)-(3-(5-chloro-2,4-difluorophenyl)-8-methyl-6,7,8,9-tetrahydro-5H-imidazo[1,5-a][1,4]diazepin-1-yl)(3-hydroxypyrrolidin-1-yl)methanone;

(S)-3-(2,5-difluorophenyl)-N-(2,2-dimethyl-1-(3-methyl-1,2,4-oxadiazol-5-yl)propyl)-6,7,8,9-tetrahydro-5H-imidazo[1,5-a][1,4]diazepine-1-carboxamide;

(S)-3-(2,5-difluorophenyl)-N-(2,2-dimethyl-1-(3-methyl-1,2,4-oxadiazol-5-yl)propyl)-8-methyl-6,7,8,9-tetrahydro-5H-imidazo[1,5-a][1,4]diazepine-1-carboxamide;

(S)-3-(3,4-difluorophenyl)-N-(2,2-dimethyl-1-(3-methyl-1,2,4-oxadiazol-5-yl)propyl)-6,7,8,9-tetrahydro-5H-imidazo[1,5-a][1,4]diazepine-1-carboxamide; and (S)-3-(3,4-difluorophenyl)-N-(2,2-dimethyl-1-(3-methyl-1,2,4-oxadiazol-5-yl)propyl)-8-methyl-6,7,8,9-tetrahydro-5H-imidazo[1,5-a][1,4]diazepine-1-carboxamide.

19. A method of prophylaxis, inhibition or treatment of a cannabinoid receptor-associated disease, disorder or condition in a mammal, wherein the disease, disorder or condition is selected from the group consisting of pain and inflammation, the method comprising administering to the mammal an effective amount of a compound having the structure of formula I:

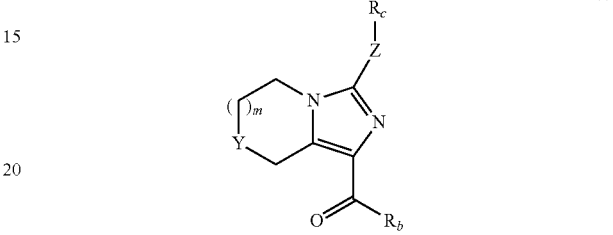

or a pharmaceutically acceptable salt, acid salt, or stereoisomer thereof, wherein:

Y is selected from the group consisting of $NR_a$ and $N^+R_1R_2X^-$;

Z is selected from the group consisting of a bond, —$(CH_2)_p$—, —CH=CH—, —C≡C—, —CONH— and —CO—;

$R_a$ is selected from the group consisting of —H, $C_1$-$C_8$ alkyl, $C_3$-$C_6$ alkenyl, $C_3$-$C_6$ alkynyl, aryl, $C_3$-$C_8$ cycloalkyl, $C_3$-$C_8$ cycloalkenyl, —$SO_2R_3$, —$COR_3$, —$CONR_3R_4$, —$CSNR_3R_4$, —$COOR_3$ and —$(CH_2)_q$heterocyclyl, wherein the alkyl, cycloalkyl, cycloalkenyl, aryl and heterocyclyl of $R_a$ are each optionally substituted with one to four substituents independently selected from the group consisting of halo, —OH, oxo, —$NH_2$, —$NO_2$, —CN, —COOH, —$COR_3$, —$OCF_3$, —$CF_3$, $C_1$-$C_6$ alkyl, $C_1$-$C_4$ alkoxy, $C_3$-$C_8$ cycloalkyl, and phenyl;

$R_b$ is selected from the group consisting of $C_1$-$C_8$ alkyl, $C_2$-$C_8$ alkenyl, aryl, —$NR_5R_6$,

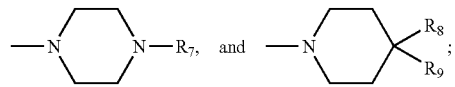

wherein the alkyl, alkenyl and aryl of $R_b$ are each optionally substituted with one to three substituents independently selected from the group consisting of $C_1$-$C_4$ alkyl, $C_2$-$C_4$ alkenyl, $C_3$-$C_6$ cycloalkyl, $C_1$-$C_4$ alkoxy, aryl, 5-, 6-, and 7-membered heterocyclyl, halo, —OH, —$NH_2$, —CN and —$NO_2$;

$R_c$ is selected from the group consisting of halo, $C_1$-$C_6$ alkyl, $C_2$-$C_6$ alkenyl, $C_2$-$C_6$ alkynyl, $C_3$-$C_{10}$ cycloalkyl, $C_3$-$C_8$ cycloalkenyl, $C_1$-$C_4$ alkoxy, aryl, 5-, 6-, 7-, 8-membered monocyclic heterocyclyl, 9-, and 10-membered bicyclic heterocyclyl; wherein the $C_2$-$C_6$ alkenyl, $C_2$-$C_6$ alkynyl, $C_3$-$C_{10}$ cycloalkyl, $C_3$-$C_8$ cycloalkenyl, aryl, 5-, 6-, 7-, 8-membered monocyclic heterocyclyl, 9- and 10-membered bicyclic heterocyclyl of $R_c$ are optionally substituted with one to five substituents independently selected from the group consisting of $C_1$-$C_4$ alkyl, $C_1$-$C_4$ alkoxy, $C_1$-$C_4$ haloalkyl, $C_1$-$C_4$ haloalkoxy, $C_3$-$C_6$ cycloalkyl, $C_4$-$C_8$ cycloalkenyl, halo, —OH, —NH$_2$, (A)(A')(A'')(A''')aryl, (A)(A')(A'')(A''')heterocyclyl, NR$_{14}$R$_{15}$, (CH$_2$)$_p$NR$_{14}$R$_{15}$, —CN, —NO$_2$, oxo, —COOR$_{14}$, SOR$_{14}$, SO$_2$R$_{14}$, SO$_2$NR$_{14}$R$_{15}$, NR$_{15}$SO$_2$R$_{16}$, COR$_{14}$, CONR$_{14}$R$_{15}$ and NR$_{15}$COR$_{16}$; wherein (A), (A'), (A'') and (A''') are each an independently selected from the group consisting of —H and $C_1$-$C_4$ alkyl and each heterocyclyl of (A)(A')(A'')(A''')heterocyclyl is independently selected from the group consisting of 5-, 6-, 7-, 8-membered monocyclic heterocyclyl, 9- and 10-membered bicyclic heterocyclyl;

R$_1$ and R$_2$ are each independently $C_1$-$C_4$ alkyl;

R$_3$ and R$_4$, when either or both are present, are each independently selected from the group consisting of —H, $C_1$-$C_6$ alkyl, $C_3$-$C_6$ alkenyl, $C_3$-$C_6$ alkynyl, $C_3$-$C_8$ cycloalkyl, $C_3$-$C_8$ cycloalkenyl, aryl, 4-, 5-, 6-, 7- and 8-membered heterocyclyl; wherein R$_3$ and R$_4$ that are not H are each independently optionally substituted with one to three substituents independently selected from the group consisting of $C_1$-$C_6$ alkyl, $C_1$-$C_6$ haloalkyl, $C_3$-$C_8$ cycloalkyl, $C_1$-$C_4$ alkoxy, $C_1$-$C_4$ acyl, aryl, 5-, 6-, 7-, 8-membered monocyclic heterocyclyl, 9- and 10-membered bicyclic heterocyclyl, —NH$_2$, —NO$_2$, —CN, —OH, —COOH, oxo, and halo; provided that if R$_a$ is SO$_2$R$_3$, then R$_3$ is not —H; alternatively, R$_3$ and R$_4$ taken together with the nitrogen atom to which they are bonded form a heterocyclyl selected from the group consisting of 4-, 5-, 6-, 7- and 8-membered heterocyclyl;

R$_5$ is selected from the group consisting of —H, $C_1$-$C_4$ alkyl and $C_1$-$C_4$ haloalkyl; wherein the alkyl and haloalkyl of R$_5$ are optionally substituted with one to four substituents independently selected from the group consisting of $C_1$-$C_4$ alkoxy, —OH, —NH$_2$ and —CN;

R$_6$ is selected from the group consisting of —H, —CR$_{10}$R$_{11}$R$_{12}$, —CR$_{10}$R$_{11}$COR$_{13}$, $C_1$-$C_8$ alkyl, $C_3$-$C_{10}$ cycloalkyl, aryl, 5-, 6-, 7-, 8-membered monocyclic heterocyclyl, 9- and 10-membered bicyclic heterocyclyl; wherein the alkyl, cycloalkyl, aryl, and heterocyclyl of R$_6$ are optionally substituted with one to three substituents independently selected from the group consisting of $C_1$-$C_4$ alkyl, aryl, halo, —OH, $C_1$-$C_4$ alkoxy, $C_1$-$C_4$ hydroxyalkyl, —COR$_{13}$, —SO$_2$R$_{11}$, —SO$_2$NR$_8$R$_9$, —NH$_2$, —CN, —NO$_2$; alternatively, R$_5$ and R$_6$ taken together with the nitrogen atom to which they are bonded form a heterocyclyl selected from the group consisting of 5-, 6-, 7-, 8-membered monocyclic heterocyclyl, 9- and 10-membered bicyclic heterocyclyl, which heterocyclyl substituent of R$_6$ is optionally substituted with one to two substituents independently selected from the group consisting of $C_1$-$C_4$ alkyl, $C_1$-$C_4$ haloalkyl, —COOR$_1$, —CONR$_1$R$_2$, and oxo;

R$_7$ is selected from the group consisting of —COR$_3$, —COOR$_3$, —SO$_2$R$_3$, and 5-, 6- and 7-membered heterocyclyl;

R$_8$ and R$_9$ are independently selected from the group consisting of —H, $C_1$-$C_4$ alkyl, $C_1$-$C_4$ haloalkyl, $C_1$-$C_4$ alkoxy, $C_3$-$C_6$ cycloalkyl, aryl, 5-, 6-, 7-, 8-membered monocyclic heterocyclyl, 9- and 10-membered bicyclic heterocyclyl, halo, —OH, $C_1$-$C_4$ alkoxy, $C_1$-$C_4$ alkyl, —CONH$_2$, —NH$_2$, —CN and —NO$_2$; alternatively: (i) R$_8$ and R$_9$, taken together with the nitrogen atom to which they are bonded form a heterocyclyl moiety which is optionally substituted with one to three substituents selected from the group consisting of $C_1$-$C_4$ alkyl, halo, oxo and aryl; or (ii) R$_8$ and R$_9$, taken together with the carbon atom to which they are bonded form a cycloalkyl which is optionally substituted with one to three substituents selected from the group consisting of $C_1$-$C_4$ alkyl, $C_1$-$C_4$ haloalkyl, halo, oxo and aryl;

R$_{10}$ is selected from the group consisting of —H and $C_1$-$C_4$ alkyl;

R$_{11}$ is selected from the group consisting of —H, $C_1$-$C_8$ alkyl, $C_2$-$C_6$ alkenyl, $C_2$-$C_4$ alkynyl, $C_3$-$C_{10}$ cycloalkyl, aryl, 5-, 6-, 7-, 8-membered monocyclic heterocyclyl, 9- and 10-membered bicyclic heterocyclyl; wherein the alkyl, alkenyl, alkynyl, cycloalkyl, aryl and 5-, 6-, 7-, 8-membered monocyclic heterocyclyl, 9- and 10-membered bicyclic heterocyclyl of R$_{11}$ are optionally substituted with one to three substituents independently selected from the group consisting of $C_1$-$C_4$ alkyl, $C_3$-$C_6$ cycloalkyl, haloaryl, aryl, and 5-, 6-, 7-, 8-membered monocyclic heterocyclyl, 9- and 10-membered bicyclic heterocyclyl, halo, —OH, $C_1$-$C_4$ alkoxy, —NH$_2$, -guanidino, —CN, —NO$_2$, oxo, —COOR$_{10}$, —CONR$_8$R$_9$, —SO$_2$NR$_8$R$_9$, —SR$_{10}$, —SOR$_1$ and —SO$_2$R$_1$;

R$_{12}$ is selected from the group consisting of —H, $C_1$-$C_4$ alkyl and $C_1$-$C_4$ hydroxyalkyl;

R$_{13}$ is selected from the group consisting of —OR$_{10}$ and —NR$_8$R$_9$;

R$_{14}$, R$_{15}$ and R$_{16}$ are each independently selected from the group consisting of —H, and $C_1$-$C_4$ alkyl; alternatively, R$_{14}$ and R$_{15}$ taken together with the nitrogen atom to which they are bonded form a heterocyclyl selected from the group consisting of 5-, 6-, 7-, 8-membered monocyclic heterocyclyl, 9- and 10-membered bicyclic heterocyclyl;

X$^-$ is an anionic counterion; and m is 2; each instance of p is independently an integer from 1 to 6; and q is independently zero or an integer from 1 to 4;

provided that when R$_c$ is heterocyclyl, the heterocyclyl is directly bonded through a carbon atom of a ring of the heterocyclyl.

20. The method according to claim 19, wherein the cannabinoid receptor-associated disease, disorder or condition is inflammation.

21. The method according to claim 19, wherein the compound of formula I is administered intravenously, transdermally, transmucosally, intranasally, subcutaneously, intramuscularly, orally or topically.

22. The method according to claim 21, wherein the compound of formula I is administered topically to the eye.

* * * * *